(12) United States Patent
Boyle et al.

(10) Patent No.: US 8,039,430 B2
(45) Date of Patent: Oct. 18, 2011

(54) PEPTIDIC COMPOUNDS

(75) Inventors: Timothy Patrick Boyle, Kirrawee (AU);
John Barnard Bremner, Balgownie (AU); Zinka Brkic, Wollongong (AU);
Jonathan Alan Victor Coates, Beaumaris (AU); Neal Kevin Dalton, Caringbah (AU); John Joseph Deadman, Carlton (AU); Paul Anthony Keller, Kiama (AU); Jody Morgan, Thirroul (AU); Stephen Geoffrey Pyne, Mt. Keira (AU); David Ian Rhodes, Heidelberg Heights (AU); Mark James Robertson, Keiraville (AU)

(73) Assignee: University of Wollongong, New South Wales (AU)

( * ) Notice: Subject to any disclaimer, the term of this patent is extended or adjusted under 35 U.S.C. 154(b) by 903 days.

(21) Appl. No.: 11/813,782

(22) PCT Filed: Sep. 21, 2005

(86) PCT No.: PCT/AU2005/001444
§ 371 (c)(1),
(2), (4) Date: Feb. 28, 2008

(87) PCT Pub. No.: WO2006/074501
PCT Pub. Date: Jul. 20, 2006

(65) Prior Publication Data
US 2008/0300287 A1 Dec. 4, 2008

(30) Foreign Application Priority Data
Jan. 13, 2005 (AU) ............................. 2005900134

(51) Int. Cl.
*A61K 38/06* (2006.01)
(52) U.S. Cl. ............................. 514/2.4; 514/21.9
(58) Field of Classification Search .................. None
See application file for complete search history.

(56) References Cited

U.S. PATENT DOCUMENTS
5,811,515 A 9/1998 Grubbs et al.

FOREIGN PATENT DOCUMENTS
JP 60116700 6/1985
WO WO-03002545 1/2003

OTHER PUBLICATIONS

K. Abiraj et al., "Synthesis of shorter active analogues of Bactenecin7: The effect of change of N-terminal configuration on antimicrobial activity." Letters in Peptide Science, 9: 283-290, 2002.
Alessandro Tossi et al., "Design of synthetic antimicrobial peptides based on sequence analogy and amphipathicity." Eur. J. Biochem. 250, 549-558, (1997).
Alfredo Rodriguez-Tebar et al., "Thermochemistry of the interaction between peptides and vancomycin or ristocetin," Journal of Antibiotics, p. 1578-1583, Nov. 1986.
Anderson et al., "Vancomycin, a new antibiotic. IV. Pharmacologic." Antibiotics annual Journal, 1956-1957, p. 75-81.
Dessen et al., "Crystal Structure of PBP2x from a Highly Penicillin-resistant *Streptococcus pneumoniae* Clinical Isolate", The Journal of Biological Chemistry, vol. 276, No. 48, Issue of Nov. 30, pp. 45106-45112, 2001.
Anthony J. Pearson et al., "Studies on the Synthesis of Aryl Ethers Using Arene-Manganese Chemistry", J. Org. Chem. 1991, 56, 7092-7097.
Chandra T. Miller et al., "The Synthesis and Screening of 1,4,5,8-Naphthalenetetracarboxylic Diimide-Peptide Conjugates with Antibacterial Activity", Bioorganic & Medicinal Chemistry 9 (2001) 2015-2024. Charles Ford et al., "In Vivo Activities of U-100592 and U-100766, Novel Oxazolidinone Antimicrobial Agents, against Experimental Bacterial Infections", Antimicrobial Agents and Chemotherapy, Jun. 1996, p. 1508-1513.
David B. Searls et al., "Using bioinformatics in gene and drug discovery", DDT vol. 5, No. 4 Apr. 2000.
Dawei Ma et al., "General and Stereospecific Route to 9-Substituted, 8,9-Disubstituted, and 9,10-Disubstituted Analogues of Benzolactam-V8", J. Org. Chem. 1999, 64, 6366-6373.

(Continued)

*Primary Examiner* — Christina Bradley
(74) *Attorney, Agent, or Firm* — Fish & Richardson P.C.

(57) ABSTRACT

The present invention provides a compound of formula (I), (II), (III) and (IV) as defined herein and pharmaceutically acceptable derivatives thereof. The present invention further provides use of the compounds of the present invention in the treatment of bacterial infection and in the treatment of HIV infection. Also provided are pharmaceutical compositions comprising the compounds of the present invention.

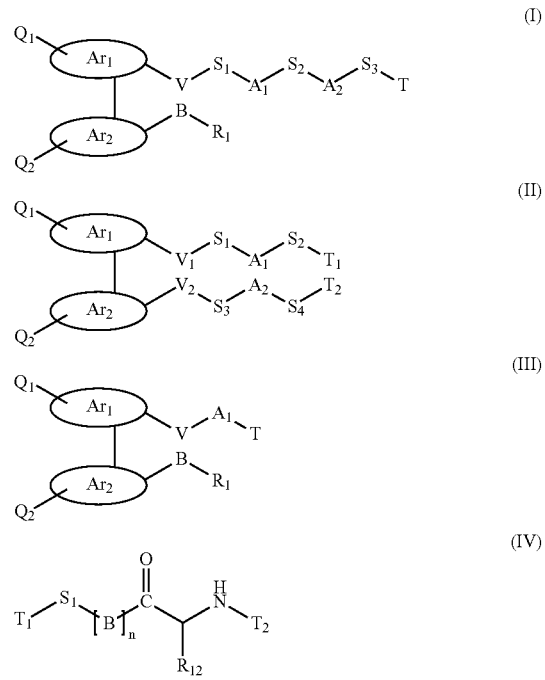

6 Claims, 1 Drawing Sheet

OTHER PUBLICATIONS

Deborah A. Mosca et al., "IB-367, a Protegrin Peptide with in Vitro and in Vivo Activities against the Microflora Associated with Oral Mucositis", Antimicrobial Agents and Chemotherapy, Jul. 2000, p. 1803-1808.

Donald T. Moir et al., "Genomics and Antimicrobial Drug Discovery", Antimicrobial Agents and Chemotherapy, Mar. 1999, p. 439-446.

Williams et al., "Structural and Mode of Action Studies on the Antibiotic Vancomycin. Evidence from 270-MHz Proton Magnetic Resonance", Journal of the American Chemical Society, 99:8, Apr. 13, 1977.

Williams et al., "Detailed Binding Sites of the Antibiotics Vancomycin and Ristocetin A: Determination of Intermolecular Distances in Antibiotic/Substrate Complexes by Use of the Time-Dependent NOE", J. Am. Chem. Soc.. vol. 105. No. 5. 1983.

Eranthie Weerapana et al., "Peptides to peptidomimetics: towards the design and synthesis of bioavailable inhibitors of oligosaccharyl transferase", Org. Biomol. Chem., 2003, 93-99.

Frederick Marshall et al., "Structure Studies on Vancomycin", the Lilly Research Laboratories, Indianapolis 6, Indiana, Apr. 20, 1964.

George Eliopoulos et al., "In Vitro Activities of New Oxazolidinone Antimicrobial Agents against Enterococci", Antimicrobial Agents and Chemotherapy, Jul. 1996, p. 1745-1747.

Wright et al., "D-Alanyl-D-alanine Ligases and the Molecular Mechanism of Vancomycin Resis tance", Acc. Chem. Res. 1992, 25, 468-473.

Griffith et al., "Vancomycin, a new antibiotic." J. Antibiotics annual. 1955-1956, 619-622.

Guiot et al., "Isolation of Vancomycin-Resistant Enterococci in Haematologic Patients", Eur. J. Clin. Microbiol. Infect. Dis., vol. 10, 1991.

Haiyan Lei et al., "Efficient Synthesis of a Phosphinate Bis-Amino Acid and Its Use in the Construction of Amphiphilic Peptides", J. Org. Chem. 1994,59, 4206-4210.

Hyun-Sik Oh et al., "Development of novel lipid-peptide hybrid compounds with antibacterial activity from natural cationic antibacterial peptides", Bioorganic & Medicinal Chemistry Letters 14 (2004) 1109-1113.

Gamet et al., "Etude De La Racemisation Induite Par La Dmap Dans les reactions de couplage peptidique", Tetrahedron vol. 40, No. 11, pp. 1995 to 2001, 1984.

J. Heijenoort et al., "Formation of the glycan chains in the synthesis of bacterial peptidoglycan", Glycobiology vol. 11, No. 3, pp. 25R-36R, 2001.

Jeffrey Kaplan et al., "The Role of Sugar Residues in Molecular Recognition by Vancomycin", J. Med. Chem. 2001, 44, 1837-1840.

Jennifer Daly et al., "Mechanism of Action and in Vitro and in Vivo Activities of S-6123, a New Oxazolidinone Compound", Antimicrobial Agents and Chemotherapy, Sep. 1988, p. 1341-1346.

Jizu Yi et al., "An Inhibitory Monoclonal Antibody Binds at the Turn of the Helix-Turn-Helix Motif in the N-terminal Domain of HIV-1 Integrase", vol. 275, No. 49, Issue of Dec. 8, pp. 38739-38748, 2000.

John B. Bremner et al., "Synthesis of carbazole-linked cyclic and acyclic peptoids with antibacterial activity", Tetrahedron 59 (2003) 8741-8755.

Hoffmann et al., "Phylogenetic perspectives in innate immunity" Science, May 21, 1999, 284, 5418; Academic Research Library p. 1313.

Karen Bush et al., "A Functional Classification Scheme for b-Lactamases and Its Correlation with Molecular Structure", Antimicrobial Agents and Chemotherapy, Jun. 1995, p. 1211-1233.

Konrad Feichtinger et al., "Diprotected Triflylguanidines: A New Class of Guanidinylation Reagents", J. Org. Chem. 1998, 63, 3804-3805.

Harris et al., "Structure of the Glycopeptide Antibiotic Vancomycin. Evidence for an Asparagine Residue in the Peptide", J. Am. Chem., Soc, 1982, 104, 4293-4295.

Makoto Kuroda et al., "Whole genome sequencing of meticillin-resistant *Staphylococcus aureus*", The Lancet, vol. 357, Apr. 21, 2001.

Matthias Schuster et al., "Olefin Metathesis in Organic Chemistry", Angew. Chem. Int. Ed. Engl. 1997, 36, 2036-2056.

McCormick et al., "Vancomycin, A New Antibiotic I. Chemical and Biologic Properties ", Medical Encyclopedia, Inc., New York, NY 1956, p. 606-611.

McGrady et al., "Synthesis of 5-Isopropyl-Substituted Poly(L-proline)s Optically Active cis- and trans-5-lsopropylproline and Poly(cis- and trans-5-Isopropylproline", Polymer Journal, vol. 19(5):539-555, 1987.

Menno Monnee et al., "Bio-inspired Synthetic Receptor Molecules Towards Mimicry of Vancomycin", Bioorg. Med. Chem. Lett. 11 (2001) 1521-1525.

Michael Pirrung et al., "Photoremovable Protecting Groups for Phosphorylation of Chiral Alcohols. Asymmetric Synthesis of Phosphotriesters of (–)-3', 5'- Dimethoxybenzoin", J. Org. Chem. 1994, 59, 3890-3897.

Min Ge et al.,"Vancomycin derivatives that inhibit peptidoglycan biosynthesis without bindin", Academic Research Library; Apr. 16, 1999; 284, 5413.

Morten B. Strom et al., "Antibacterial activity of 15-residue lactoferricin derivatives", J. Peptide Res. 56, 2000, 265-274.

Morten B. Strom et al., "Antimicrobial Activity of Short Arginine- and Tryptophan-rich Peptides", J. Peptide Sci. 8: 431-437 (2002).

Norris E. Allen et al., "Molecular Interactions of a Semisynthetic Glycopeptide Antibiotic with D-Alanyl-D-Alanine and D-Alanyl-D-Lactate Residues", Antimicrobial Agents and Chemotherapy, Jan. 1997, p. 66-71.

David Payne et al., "The impact of genomics on novel antibacterial targets", Current Opinion in Drug Discovery and Development, 3(2):177-190, 2000.

Peter Dineen et al., "43 Years Experience in Diagnosis and Treatment", Tuberculous Peritonitis, Ann. Surg, vol. 184, No. 6, Dec. 1976.

Peter Swaren et al., "X-ray Structure of the Asn276Asp Variant of the *Escherichia coli* TEM-1 b-Lactamase: Direct Observation of Electrostatic Modulation in Resistance to Inactivation by Clavulanic Acid", Biochemistry 1999, 38, 9570-9576.

Robert Kerns et al., "The Role of Hydrophobic Substituents in the Biological Activityof Glycopeptide Antibiotics", J. Am. Chem. Soc. 2000, 122, 12608-12609.

Ronald D Gonzales et al., "Infections due to vancomycinresistant *Enterococcus faecium* resistant to linezolid", The Lancet, vol. 357, Apr. 14, 2001.

Ronald N. Jones et al., "In Vitro Activity and Spectrum of LY333328, a Novel Glycopeptide Derivative", Antimicrobial Agents and Chemotherapy, Feb. 1996, p. 488-493.

Scott J. Miller et al., "Synthesis of Conformationally Restricted Amino Acids and Peptides Employing Olefin Metathesis", J. Am. Chem. Soc. 1995,117, 5855-5856.

D. Scott Wilbur et al., "Synthesis and Radioiodination of N-Boc-p-(tri-n-butylstannyl)- L-phenylalanine Tetrafluorophenyl Ester: Preparation of a Radiolabeled Phenylalanine Derivative for Peptide Synthesis", Bioconjugate Chem. 1993, 4, 574-580.

A. Severin et al., "Separation of Abnormal Cell Wall Composition from Penicillin Resistance through Genetic Transformation of *Streptococcus pneumoniae*", Journal of Bacteriology, Apr. 1996, p. 1788-1792.

Shawn D. Erickson et al., "Practical Synthesis of a Highly Enantioselective Receptor for Peptides", J. Org. Chem. 1993,58, 1305-1308.

A. M. Slee et al., "Oxazolidinones, a New Class of Synthetic Antibacterial Agents: in Vitro and in Vivo Activities of DuP 105 and DuP 721", Antimicrobial Agents and Chemotherapy, Nov. 1987, p. 1791-1797.

Sotirios Tsiodras et al., "Linezolid resistance in a clinical isolate of *Staphylococcus aureus*", The Lancet, vol. 358, Jul. 21, 2001.

C. K. Stover et al., "Complete genome sequence of *Pseudomonas aeruginosa* PAO1, an opportunistic pathogen", Nature, vol. 406, Aug. 31, 2000.

Terrence R. Burke Jr. et al., "Hydroxylated Aromatic Inhibitors of HIV-1 Integrase", J. Med. Chem. 1995, 38, 4171-4178.

Gale et al., "The synthesis and binding of N-terminal derivatives of vancomycin to a bacterial cell wall analogue", J. Chem. Soc., Perkin Trans. 1, 1999, 2267-2270.

Tina M. Trnka et al., "The Development of L$_2$X$_2$Rud=CHR Olefin Metathesis Catalysts: An Organometallic Success Story", Acc. Chem. Res. 2001, 34, 18-29.

Uma N. Sundram et al., "Novel Vancomycin Dimers with Activity against Vancomycin-Resistant Enterococci", J. Am. Chem. Soc. 1996, 118, 13107-13108.

Von John K. Stille et al., "Palladium-katalysierte Kupplungsreaktionen organischer Elektrophile rnit Organozinn-Verbindungen", Angew. Chem. 98 (1986) 504-519.

Yehuda Goldgur et al., "Structure of the HIV-1 integrase catalytic domain complexed with an inhibitor: a platform for antiviral drug design", PNAS, vol. 96, No. 23, 13040-13043, Nov. 9, 1999.

Young Hwang et al., "Rapid microtiter assays for poxvirus topoisomerase, mammalian type IB topoisomerase and HIV-1 integrase: application to ihibitor isolation", Nucleic Acids Research, vol. 28, No. 24, 4884-4892, 2000.

Jh Toney et al., "Iseganan (IntraBiotics Pharmaceuticals)", Current Opinion in Investigational Drugs, 3(2):225-228, 2002.

Hellwinkel, D. Systematic Nomenclature of Organic Chemistry; 1st ed.; Springer: Berlin, 2001.

Tous, G.; Bush, A.; Tous, A.; Jordan, F. "O'(Epoxyalkyl)tyrosines and (Epoxyalky)phenylalanine as Irreversible Inactivators of Serine Proteases: Synthesis and Inhibittion Mechanism" J. Med. Chem. 1990, 33, 1620-34.

Abbott, S. D.; Lane-Bell, P.; Sidhu, K. P. S.; Vederas, J. C. J. Am. Chem. Soc. 1994, 116, 6513-20.

Harold C. Neu et al., "The Crisis in Antibiotic Resistance", Science, New Series, vol. 257, No. 5073 (Aug. 21, 1992), pp. 1064-1073.

Nicolaou et al., "New methods in combinatorial chemistry facilitate the Rapid Design of huge libraries of compounds." Scientific American, May 2001.

Noble et al., "Co-transfer of vancomycin and other resistance genes from *Enterococcus faecalis* NCTC 12201 to *Staphylococcus aureus*", FEMS Microbiology Letters 93 (1992) 195-198.

Sandra Handwerger et al., "Nosocomial Outbreak Due to *Enterococcus faecium* Highly Resistant to Vancomycin, Penicillin, and Gentamicin", Clinical Infectious Diseases, vol. 16, No. 6 (Jun., 1993), pp. 750-755.

Sievert, D.M. Morbid. Mortal. Wkly Rep. 2002, 51, 565-7.

Halls, G. The Complete Guide to Anti-infectives; PJB Publications: Richmond Surrey UK, 1999.

Nicole Perna et al., "Genome sequence of enterohaemorrhagic *Escherichia coli* 0157:H7", Nature. vol. 409, Jan. 25, 2001.

Hannes Loferer et al., "Mining bacterial genomes for antimicrobial targets", Molecular Medicine Today, Dec. 2000 (vol. 6).

Christopher G. Dowson et al., "Horizontal Transfer of Penicillin-Binding Protein Genes in Penicillin-Resistant Clinical Isolates of *Streptococcus pneumoniae*", Proceedings of the Nat. Acad. of Scien. of the U.S.A., vol. 86, No. 22 (Nov. 15, 1989), pp. 8842-8846.

Patrick C. Blanpain et al., "A Multifaceted Approach to the Study of the Side-Chain Conformation in b-Lactamase-Resistant Penicillins", J. Med. Chem. 1980,23, 1283-1292.

Wenlin Lee et al., "A 1.2-Å snapshot of the final step of bacterial cell wall biosynthesis", PNAS, vol. 98, No. 4, Feb 13, 2001.

Sheldrick, G. M.; Jones, P. G.; Kennard, O.; Williams, D. H.; Smith, G. A. Nature 1978, 271, 223-5.

Williams, D. H., Westwell, M. S., Beauregard, D. A., Sharman, G. J., Dancer, R. J., Try, A. C., and Bardsley, B. in Anti-infectives. Recent Advances in Chemistry and Structure Activity Relationships (Bently, P.H.; O'HAnlon, P.J.) Royal Society of Chem., Cambridge., 1997, p. 3-14. "Annual Reports in Medicinal Chemistry", J. Med. Chem. 1998, 41, 258-261.

Howard S. Gold et al., "Antimicrobial-Drug Resistance" The New England Journal of Medicine, vol. 335, Nov. 17, 1996, 1445-1453.

Roderich D. Sussmuth et al., "Vancomycin Resistance: Small Molecule Approaches Targeting the Bacterial Cell Wall Biosynthesis", Chem. Bio. Chem., 2002, 3, 295 -298.

Daniel A. Beauregard et al., "Dimerization and Membrane Anchors in Extracellular Targeting of Vancomycin Group Antibiotics", Antimicrobial Agents and Chemotherapy, Mar. 1995, p. 781-785.

Martin S. Westwell et al., "Two Conformers of the Glycopeptide Antibiotic Teocpplanin with Distinct Ligand Binding Sites", The Journal of Antibiotics, vol. 48, No. 11, Nov. 1995, p. 1292-1298.

Thalia I. Nicas et al., "Beyond vancomycin: new therapies to meet the challenge of glycopeptide resistance", Trends in microbiology, vol. 5, No. 6, Jun. 1997, p. 240-249.

Ford, C. W.; Hamel, J. C.; Stapert, D.; Moerman, J. K.; Hutchinson, D. K.; Barbachyn, M. R.; Zurenko, G. E. Trends Microbiol. 1997, 5, 196-200.

Zelenitsky S.A. et al., "Time-Kill Curves for a Semisynthetic Glycopeptide, LY333328, against Vancomycin-Susceptible and Vancomycin-Resistant *Enterococcus faecium* Strains" Antimicrobial Agents and Chemotherapy, Jun. 1997, p. 1407-1408.

Aldona L. Baltch et al., "Comparison of Inhibitory and Bactericidal Activities and Postantibiotic Effects of LY333328 and Ampicillin Used Singly and in Combination against Vancomycin-Resistant *Enterococcus faecium*", Antimicrobial Agents and Chemotherapy, Oct. 1998, p. 2564-2568.

Q. May Wang et al., "Identification and Characterization of a Monofunctional Glycosyltransferase from *Staphylococcus aureus*", Journal of Bacteriology, Aug. 2001, p. 4779-4785.

Berthold Hinzen et al., "Mimicking the Vancomycin Carboxylate Binding Site: Synthetic Receptors for Sulfonates, Carboxylates, and N-Protected a-Amino Acids in Water", Helvetica Chimica Acta—vol. 79 (1996), 942-960.

Ruo Xu et al., "Combinatorial Library Approach for the Identification of Synthetic Receptors Targeting Vancomycin-Resistant Bacteria", J. Am. Chem. Soc. 1999, 121, 4898-4899.

Gabriela Chiosis et al., "Selective Cleavage of D-Ala-D-Lac by Small Molecules: Re-Sensitizing Resistant Bacteria to Vancomycin", Science; Aug. 24, 2001; 293, 5534; Academic Research Library, p. 1484-7.

S. Thennarasu et al., "Synthetic Peptides Corresponding to the b-Hairpin Loop of Rabbit Defensin NP-2 Show Antimicrobial Activity", Biochemical and Biophysical Research Communications 254, 281-283 (1999).

Hisako Saido-Sakanaka et al., "Synthesis and characterization of bactericidal oligopeptides designed on the basis of an insect antibacterial peptide", Biochem. J. (1993) 338, 29-33.

Bengt Erik Haug et al., "The Role of Tryptophan in the Antibacterial Activity of a 15-Residue Bovine Lactoferricin Peptide", Journal of Peptide Science J. Peptide Sci. 7: 190-196 (2001).

Bengt Erik Haug et al., "Bulky Aromatic Amino Acids Increase the Antibacterial Activity of 15-Residue Bovine Lactoferricin Derivatives", Journal of Peptide Science J. Peptide Sci. 7: 425-432 (2001).

Morten B. Strom et al., "The Pharmacophore of Short Cationic Antibacterial Peptides", Journal of Medicinal Chemistry, 2003, vol. 46, No. 9, 1567-70.

Richard Houghten et al., "Generation and use of synthetic peptide combinatorial libraries for basic research and drug discovery", Nature. vol. 354, Nov. 7, 1991, 84-86.

John B. Bremner et al., "The synthesis of a novel binaphthyl-based cyclic peptoid with anti-bacterial activity" New J. Chem., 2002, 26, 1549-1551.

John Bremner et al., "The Synthesis of a Novel Carbazole-linked Cyclic Peptoid with Antibacterial Activity", The Synthesis of a Novel Carbazole-linked Cyclic Peptoid, 2002, No. 2, 219-222.

Martin Rowlands et al., "Esters of 3-Pyridylacetic Acid that Combine Potent Inhibition of 17α-Hydroxylase/C$_{17,20}$-Lyase (Cytochrome P45017α) with Resistance to Esterase Hydrolysis", J. Med. Chem, 1995, 38, 4191-4197.

Bjorn Luning et al., "Solid Phase Synthesis of Mono- and Di-saccharide-containing Glycopeptides", J. Chem. Soc., Chem. Commun., 1267-8, 1989.

Oliver Brummer et al., "Olefin Cross-Metathesis with Monosubstituted Olefins", Chem. Eur. J. 1997, 3, No. 3, 441-6.

Cacchi, "Palladium-Catalyzed Reaction of Enol Triflates with 1-Alkynes. A New Route to Conjugated Enynes", Synthesis, pp. 320-322 (1985).

Scott J. Miller et al., "Application of Ring-Closing Metathesis to the Synthesis of Rigidified Amino Acids and Peptides", J. Am. Chem. Soc. 1996, 118, 9606-9614.

Morera et al., "An Efficient Synthesis of 4-Aryl and 4-Vinylphenylalanines by Stille Cross-Coupling Reaction", Synlett, Dec. 1997, 1403-5.

Mark D. Andrake et al., "Retroviral Integrase, Putting the Pieces Together", The Journal of Biological Chemistry, vol. 271, No. 33, Issue of Aug. 16, pp. 19633-19636, 1996.

O'Brien, Claire et al., "HIV Integrase Structure Catalyzes Drug Search", Science; Dec. 23, 1994; 266, 5193; Academic Research Library, p. 1946.

Alison B. Hickman et al., "Biophysical and Enzymatic Propertieosf the Catalytic Domain of HIV-1 Integyase" Journal of Biological Chemistry, vol. 269, No. 46, Nov. 18, pp. 29279-29287, 1994.

Modelling studies were performed by AMRAD in collaboration with the Victorian College of Pharmacy. For experimental details and docking procedures see: Wielens, J. PhD Thesis, Victorian College of Pharmacy (Monash University), 2004.

Rolf van Benthem et al., "A Partical Synthesis of Geometrically Pure N-Boc-Protected Primary Allylic Amines", Synlett, May 1994, 368-370.

Pierre Beaulieu et al., " Enantiospecific Synthesis of D-a, w-Diaminoalkanoic Acids", Tetrahedron Letters, vol. 29, No. 17, pp. 2019-2022, 1988.

Zhengxin Dong et al., "An Efficient Asymmetric Synthesis of L-a, w-Diamioalkanoic Acids" Tetrahedron Letters, vol. 33, No. 50, pp. 7725-7726, 1992.

Nieto et al., "Modifictions of the Acyl-D-alanyl-D-alanine Terminus Affecting Complex-Formation with Vancomycin", Biochem. J. (1971) 123, 789-803.

Mackay, J. P.; Gerhard, U.; Beauregard, D. A.; Williams, D. H.; Westwell, M. S.; Searle, M. S. J. Am. Chem. Soc. 1994, 116, 4581-90.

Helen Linsdell et al., "Dimerization of A82846B, Vancomycin and Ristocetin: Influence on Antibiotc Complexation with Cell Wall Model Peptides", the Journal of Antibiotics, vol. 49, No. 2; Nov. 1996, 181-193.

Mark S. Searle et al., "Enthalpic (electrostatic) contribution to the chelate effect: a correlation between ligand binding constant and a specific hydrogen bond strength in complexes of glycopeptide antibiotics with cell wall analogues", J Cliern. Soc., Perkin Truns. 1, 1996.

Robert J. Dancer et al., "Binding of a vancomycin group antibiotic to a cell wall analogue from vancomycin-resistant bacteria", Chem. Commun., 1996, 1445-6.

Jeniffer Barna et al., "Structural Features that affect the Binding of Teicoplanin, Ristocetin A, and their Derivatives to the Bacterial Cell-wall Model N-Acetyl-D-alanyl-D-alanine", J. Chem. Soc., Commun., 1985, 254-6.

Michmil P. Williamson et al., Interactions of vancomycin and ristocetin with peptides as a model for protein binding, Tetrahedron vol. 40, No. 3, pp. 569-577, 1984.

Thomas J. D. Jørgensen et al., "Subtle differences in molecular recognition between modified glycopeptide antibiotics and bacterial receptor peptides identified by electrospray ionization mass spectrometry", J. Chem. Soc., Perkin Trans. 2, 1999, 1859-1863.

Thomas J. D. Jørgensen et al., "Direct Determination of Solution Binding Constants for Noncovalent Complexes between Bacterial Cell Wall Peptide Analogues and Vancomycin Group Antibiotics by Electrospray Ionization Mass Spectrometry", Anal. Chem. 1998, 70, 4427-4432.

Anca van de Kerk-van Hoof et al., "Interactions of a- and b-avoparcin with bacterial cell-wall receptor-mimiching peptides studied by electrospray ionization mass spectrometry," J. of Antimicrobial Chemotherapy (1999), 44, 593-599.

Perrin, D. D. A., W. L. F. Purification of Laboratory Chemicals; 3rd ed.; Pergamon Press Ltd.: Oxford, 1988.

Luc Meyer et al., "Chiral Auxiliaries with a Switching Center: New Tools in Asymmetric Synthesis. Application to the Synthesis of Enantiomerically Pure (R)- and (S)-a-Amino Acids", J. Org. Chem. 1998, 63, 8094-8095.

Min Ge et al.,"Vancomycin derivatives that inhibit peptidoglycan biosynthesis without bindin", Academic Research Library; Apr. 16, 1999; 284, 507-111.

FIGURE 1

| Well Conc. µg/mL | Test Peptoid Compound 1 | | | Test Peptoid Compound 2 | | | Vancomycin Control | | | Compound-Negative Control | | |
|---|---|---|---|---|---|---|---|---|---|---|---|---|
| 125 | T1 | T1 | T1 | T2 | T2 | T2 | VC | VC | VC | NC | NC | NC |
| 62.5 | T1 | T1 | T1 | T2 | T2 | T2 | VC | VC | VC | NC | NC | NC |
| 31.3 | T1 | T1 | T1 | T2 | T2 | T2 | VC | VC | VC | NC | NC | NC |
| 15.6 | T1 | T1 | T1 | T2 | T2 | T2 | VC | VC | VC | NC | NC | NC |
| 7.8 | T1 | T1 | T1 | T2 | T2 | T2 | VC | VC | VC | NC | NC | NC |
| 3.9 | T1 | T1 | T1 | T2 | T2 | T2 | VC | VC | VC | NC | NC | NC |
| 1.9 | T1 | T1 | T1 | T2 | T2 | T2 | VC | VC | VC | NC | NC | NC |
| 1 | T1 | T1 | T1 | T2 | T2 | T2 | VC | VC | VC | NC | NC | NC |

PEPTIDIC COMPOUNDS

FIELD OF THE INVENTION

This invention relates to novel peptidic compounds, methods for preparing them and their use as antibiotics and in the treatment of HIV infections.

BACKGROUND OF THE INVENTION

Bacteria and the bacterial infections that can be treated by antibiotics include, but are not limited to the following:

*Staphylococcus aureus*, (or "staph"), are bacteria commonly found on the skin and in the noses of healthy people, (F) and are one of the most common causes of skin infections and can also cause serious and sometimes fatal infections (such as bloodstream infections including toxic shock syndrome, impetigo, surgical wound infections, infections of plastic implants, osteomyelitis and pneumonia).

Enterococci, which have been known as a cause of infective endocarditis for close to a century, more recently have been recognized as a cause of nosocomial infection and "superinfection" in patients receiving antimicrobial agents.

Other Gram positive bacteria that can be treated by antibiotics include *staphylococcus epidermitis* which causes endocarditis, *clostridium difficile* which causes diarrhea and pseudomembranous colitis, *bacillus anthracis* of anthrax and *streptococcus pneumoniae* which causes pneumonia, meningitis, septicemia, and childhood otitis media (or ear-ache). The family of *streptococcus* bacteria can also be divided into group A or Pyrogenes, which are involved in blood poisoning, glomerularnephritis and fevers such as puerperal, scarlet and rheumatic fever. Group B or *streptococcus agalactiae* cause neonatal meningitis and pneumonia.

Bacterial Resistance to Antibiotics

Bacterial Infections can occur while in hospital (noscomial), but an additional problem is the increase of infections that are acquired while the person is in the community. A recent study (C) identified the antimicrobial susceptibility profile and resistance mechanisms of pretreatment MRSA isolates obtained from adult subjects participating in recent clinical treatment trials of community respiratory infections. Out of 465 *S. aureus* isolates, 43 were identified as MRSA. Antimicrobial susceptibility testing indicated susceptibility rates to: vancomycin (100%), gentamicin (86%), clindamycin (39%), quinolones (49%), and erythromycin (12%). All ciprofloxacin-resistant isolates had an amino acid change in GyrA and GrlA. The results indicate that MRSA from adult subjects with community respiratory infections have similar antimicrobial susceptibility profiles and resistance mechanisms as nosocomial MRSA.

The pathogenic potential of *Staphylococcus aureus* in nosocomial and community-acquired infections is well known. When penicillin was introduced in mid-1940s, *S. aureus* was almost 94% susceptible to this drug. Widespread resistance to penicillin developed in the 1950s, followed by resistance to semi-synthetic penicillins in the 1960s and 1970s. Since then, strains of methicillin-resistant *S. aureus* and methicillin-resistant coagulase-neg. staphylococci have spread worldwide. The prevalence of methicillin-resistant *S. aureus* varies geographically. In Argentina it reaches nearly 50%. Methicillin resistance in staphylococci develops due to the additional. penicillin binding protein PBP2a encoded by gene mecA and is a serious problem both for microbiologists and physicians(A). The high prevalence of methicillin-resistant staphylococci compromises the use of semi-synthetic penicillins for clin. treatments in many institutions, thus increasing the use of vancomycin (a glycopeptide). Until 1996, glycopeptides were almost universally active against *S. aureus* but it was then that the first glycopeptide-intermediate *S. aureus* (GISA) also known as VISA (vancomycin intermediately resistant *S. aureus*) was described and isolated in Japan, followed by France and USA. Infections with *Staphylococcus aureus* with reduced susceptibility to vancomycin continue to be reported, including 2 cases caused by *S. aureus* isolates with full resistance to vancomycin. (A) There is also vancomycin-resistant *S. aureus* (VRSA) The worldwide increase in the incidence of *S. aureus* clinical isolates with reduced susceptibility to vancomycin and teicoplanin means that glycopeptide resistance in *S. aureus* is becoming an important clinical problem.

The exact mechanisms involved have not been elucidated yet, although VISA is associated with increased wall synthesis. Many VISA strains are characterized by increased cell wall biosynthesis and decreased crosslinking of the peptide side chains, leading to accumulation of free D-alanyl-D-alanine termini in the peptidoglycan, which it has been proposed can act as false target sites for vancomycin. (B)

The mechanism of vancomycin resistance in *enterococcus* is well defined and appears to be different to that of VISA.

Vancomycin resistance in enterococci, known as VRE or glycopeptide-resistant enterococci (GRE), exists as either intrinsic resistance where isolates of *Enterococcus gallinarum* and *E. casseliflavus/E. flavescens* demonstrate an inherent, low-level resistance to vancomycin or by acquired resistance where Enterococci become resistant to vancomycin by acquisition of genetic information from another organism. Most commonly, this resistance is seen in *E. faecium* and *E. faecalis*, but also has been recognized in *E. raffinosus, E. avium, E. durans*, and several other enterococcal species.

Several genes, including vanA, vanB, vanC, vanD, and vanE, contribute to resistance to vancomycin in enterococci.

*E. faecium* is the most frequently isolated species of VRE in hospitals and typically produces high vancomycin (>128 µg/ml) and teicoplanin (>16 µg/ml) minimum inhibitory concentrations (MICs). These isolates typically contain vanA genes. The epidemiology of vancomycin-resistant *Enterococcus faecium* (VREF) in Europe is characterized by a large community reservoir. In contrast, nosocomial outbreaks and infections (without a community reservoir) characterize VREF in the United States. (G)

In vancomycin-susceptible enterococci, D-alanyl-D-alanine (formed by an endogenous D-alanine-D-alanine ligase) is added to a tripeptide precursor to form a pentapeptide precursor. The D-Ala-D-Ala terminus is the target of vancomycin; once vancomycin has bound, the use of this pentapeptide precursor for further cell-wall synthesis is prevented. In the VanA phenotype, one of the proteins whose synthesis is induced by exposure of bacterial cells to vancomycin is called VanA; VanA is a ligase and resembles the D-alanine-D-alanine ligase from *Escherichia coli* and other organisms, including vancomycin-susceptible enterococci. VanA generates D-Ala-D-X, where X is usually lactate; the formation of D-lactate is due to the presence of VanH, a dehydrogenase encoded by vanH. The depsipeptide moiety, D-Ala-D-Lac, is then added to a tripeptide precursor, resulting in a depsipentapeptide precursor. Vancomycin does not bind to the D-Ala-D-Lac terminus, so this depsipentapeptide can be used in the remaining steps of cell-wall synthesis. However, when the normal pentapeptide precursor ending in D-Ala-D-Ala is also present, cells are not fully vancomycin resistant, despite the presence of D-Ala-D-Lac containing precursors. This apparent problem is taken care of in large part by vanX, which encodes a dipeptidase, VanX, that cleaves D-Ala-D-Ala, preventing its addition to the tripeptide precursor. Should any D-Ala-D-Ala escape cleavage and result in a normal pentapeptide precursor, vanY encodes an ancillary or back-up function. That is, it codes for a carboxypeptidase, VanY, which cleaves D-alanine and D-lactate from D-Ala-D-Ala and D-Ala-D-Lac termini, respectively, resulting in tetrapeptide precursors, to which vancomycin does not bind. The other genes involved in the VanA resistance complex include vanR and vanS, whose encoded proteins are involved in sensing the presence of extracellular vancomycin or its effect and signaling intracellularly to activate transcription of vanH, vanA, and vanX. A final gene in the vanA cluster is vanZ, which encodes VanZ, the role of which is not known. (J)

VanB, encoded by vanB in the vanB gene cluster, is also a ligase that stimulates the formation of D-Ala-D-Lac. The VanB phenotype is typically associated with moderate to high levels of vancomycin resistance but is without resistance to teicoplanin. This is explained by the observation that vancomycin, but not teicoplanin, can induce the synthesis of VanB and of VanHB and VanXB. However, because mutants resistant to teicoplanin can readily be selected from VanB strains on teicoplanin-containing agar, clinical resistance would likely occur among VanB strains if teicoplanin were widely used. Most of the proteins encoded by the vanA gene cluster have homologues encoded by the vanB gene cluster, except for VanZ. The vanB gene cluster has an additional gene, vanW, of unknown function.

The acquired gene clusters associated with vanA and vanB are found in different genetic surroundings. These elements have in turn been found on both transferable and nontransferable plasmids, as well as on the chromosome of the host strain. VanB type resistance was initially not found to be transferable, but at least in some instances, the vanB gene cluster has been found on large (90 kb to 250 kb) chromosomally located transferable elements, More recently, vanB has been found as part of plasmids. (I)

In addition to being found in different genetic surroundings, the vanA and vanB gene clusters have also been found in a number of different bacterial species. vanA has been found in multiple enterococcal species as well as in lactococci, Orskovia, and Arcanobacteria (H). The distribution of the vanB gene cluster seems somewhat more restricted, having been found primarily in *E. faecium* and *E. faecalis*, although it has recently been found in *Streptococcus bovis* (H).

The VanC phenotype (low-level resistance to vancomycin, susceptible to teicoplanin) is an inherent (naturally occurring) property of *E. gallinarum* and *E. casseliflavus*. This property is not transferable and is related to the presence of species-specific genes vanC-1 and vanC-2, respectively; a third possible species, *E. flavescens* and its gene vanC-3, are so closely related to *E. casseliflavus* and vanC-2 that different names are probably not warranted. These species appear to have two ligases; the cell-wall pentapeptide, at least in *E. gallinarum*, ends in a mix of D-Ala-D-Ala and D-Ala-D-Ser. The genes vanC-1 and vanC-2 apparently lead to the formation of D-Ala-D-Ser containing cell-wall precursors, while D-Ala-D-Ala ligases, also present in these organisms, result in D-Ala-D-Ala. The presence of both D-Ala-D-Ala and D-Ala-D-Ser precursors may explain why many isolates of these species test susceptible to vancomycin and why even those isolates with decreased susceptibility display only low-level resistance. (J)

VanD-type glycopeptide resistance has been recently described in an *E. faecium* isolate from the United States (I). The organism was constitutively resistant to vancomycin (MIC>64 µg/ml) and to low levels (4 µg/ml) of teicoplanin. Following polymerase chain reaction amplification with primers that amplify many D-Ala-D-Ala ligases, a 605-bp fragment was identified whose deduced amino acid sequence showed 69% identity to VanA and VanB and 43% identify to VanC.

Bacterial Resistance to Different Classes of Antibiotics.

As well as resistance to approved beta-lactam, glycopeptide antibiotics (including vancomycin, trade name vancocin), and the macrolide-lincosamide-streptogramins (including quinupristin-dalfopristin, trade name synercid) (D) various recent findings have also underlined the importance of biocide resistance as a clin. relevant phenomenon. (D) Outbreaks of biocide-resistant organisms in hospitals have been described and the genetic mechanism for resistance to quaternary ammonium compds. (QACs) in *Staphylococcus aureus* has now been elucidated.

Some strains of MRSA which have intermediate resistance to glycopeptides were demonstrated to have decreased susceptibility to some biocides including triclosan for which minimal bactericidal concns. (MBCs) increased from 0.002 to 3.12 mg 1-1. Biocide resistance amongst enterococci has also been demonstrated although there was no clear correlation between biocide and antibiotic resistance. The exact mechanisms of resistance in these strains are still being studied but it is clear that biocide resistance is an important clin. phenomenon.

Vancomycin is a cyclic compound. Disclosed herein by reference, WO 03/002545 teaches that 'peptoid compounds' made from a peptide chain covalently linked in a cyclic form through a heterocyclic or aromatic ring system have antibacterial activity. The reaction know to those skilled in the art variously as 'ring closing metathesis', 'Grubbs metathesis' or 'olefin metathesis' is taught in WO 03/00254 to join the ends of the molecule which therefore need to terminate in allyl groups ($-CH_2-CH=CH_2$) that react in that chemical processes described. The literature (J. Bremner et al New J. Chem, 2002, 26, 1549-1551) teaches that cyclic compounds so made based on a 1,1-binaphthyl scaffold linked in a ring through the 3,3'-positions can have antibacterial activity. Further this literature describes cyclic molecules made from 1,1'-binaphthyl linked through the 2,2' positions.

Additionally the prior art (J. Bremner et al Tetrahedron, 2003, 59, 8741-8755) teaches that related cyclic compounds (therein known as 'carbazole linked cyclic peptoids') can have antibacterial activity.

There is a need for new compounds which are useful in the treatment of bacterial infections, especially those caused by vancomycin resistant organisms.

(A) *Staphylococcus aureus* with reduced susceptibility to vancomycin. Cosgrove, S. E.; Carroll, K. C.; Perl, T. M. Clinical Infectious Diseases (2004), 39(4), 539-545.

(B) Morphological and genetic differences in two isogenic *Staphylococcus aureus* strains with decreased susceptibilities to vancomycin. Reipert, A; Ehlert, Kn; Kast, T; Bierbaum, G. Antimicrobial Agents and Chemotherapy (2003), 47(2), 568-576.

(C) Antimicrobial susceptibility and molecular characterization of community-acquired methicillin-resistant *Staphylococcus aureus*. Almer, L. S.; Shortridge, V. D.; Nilius, A. M.; Beyer, Jill M.; Soni, Niru B.; Bui, Mai H.; Stone, G. G.; Flamm, R. K Diagnostic Microbiology and Infectious Disease (2002), 43(3), 225-232.

(D) Methicillin-resistant, quinupristin-dalfopristin-resistant *Staphylococcus aureus* with reduced sensitivity to glycopeptides. Werner, G.; Cuny, C.; Schmitz, F.-J.; Witte, W. Journal of Clinical Microbiology (2001), 39(10), 3586-3590.

(E) Susceptibility of antibiotic-resistant cocci to biocides. Fraise, A. P. Society for Applied Microbiology Symposium Series (2002), 31(Antibiotic and Biocide Resistance in Bacteria).

(F) WWW.CDC.gov VISA/VRSA Vancomycin-Intermediate/Resistant *Staphylococcus aureus*

(G) Epidemic and nonepidemic multidrug-resistant *Enterococcus faecium*. Leavis H L, Willems R J L, Top J, Spalburg E, Mascini E M, Fluit A C, et al. Emerg Infect Dis. 2003 September Available from: URL: http://www.cdc.gov/ncidod/EID/vol9no9/02-0383.htm (H) Power E G M, Abdulla Y H, Talsania H G, Spice W, Aathithan S, French G L. vanA genes in vancomycin-resistant clinical isolates of *Oerskovia turbata* and *Arcanobacterium* (*Corynebacterium*) *haemolyticum*. J Antimicrob Chemother 1995; 36:595-606.

(I) Perichon B, Reynolds P, Courvalin P. VanD-type glycopeptide-resistant *Enterococcus faecium* BM4339. Antimicrob Agents Chemother 1997; 41:2016-8.

(J) Diversity among Multidrug-Resistant Enterococci Barbara E. Murray, M.D. Emerg Infect Dis. 2003 September. Available from: URL: http://www.cdc.gov/ncidod/EID/vol4no1/murray.htm

SUMMARY OF THE INVENTION

In a first aspect, the present invention provides a compound of formula I,

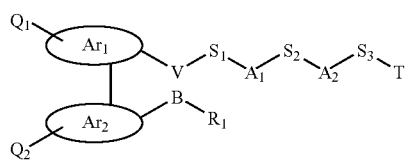

(I)

or pharmaceutically acceptable derivatives thereof, wherein:

$Ar_1$ and $Ar_2$ are each independently selected from an aromatic or heterocyclic ring system or partially or fully reduced derivatives thereof;

$Q_1$ and $Q_2$ are each independently selected from hydrogen, $C_1$-$C_{12}$alkyl, $C_3$-$C_6$cycloalkyl, $C_1$-$C_{12}$alkyloxy, nitro, halogen, hydroxyl, amino, mono or dialkylamino, carboxylic acid or a salt or ester thereof, sulphonic acid or a salt or ester thereof, phosphoric acid or a salt or ester thereof, or a nitrogen containing group such as carboxamide, sulphonamide or phosphoramide wherein each $C_1$-$C_{12}$alkyl, $C_1$-$C_{12}$alkyloxy or $C_3$-$C_6$cycloalkyl is optionally substituted with hydroxyl, amino, carboxylic acid or a salt or ester thereof, sulphonic acid or a salt or ester thereof, phosphoric acid or a salt or ester thereof, or a nitrogen containing group such as carboxamide, sulphonamide or phosphoramide;

B is selected from —O—, —S—, —S(O)—, —S(O)$_2$—, —NH—, and —N(C$_1$-C$_6$alkyl)-;

$R_1$ is selected from hydrogen, $C_1$-$C_{12}$alkyl, $C_1$-$C_6$alkylC$_3$-$C_6$cycloalkyl, $C_1$-$C_6$alkylC$_6$-$C_{10}$aryl, $C_2$-$C_6$alkenyl, $C_2$-$C_6$alkynyl, a polyoxyalkylene having from 2 to 6 carbon atoms, and when B is —S—, —S(O)—, —S(O)$_2$—, —NH— or —N(C$_1$-C$_6$alkyl)- then $R_1$ may be hydroxyl;

V is a linker group selected from —O—, —O-L-C(O), —O-L-NR$_6$—, —C(O), —NR$_6$—, —S(O)—, —S(O)$_2$—, —O-L-S(O)—, —S(O)$_2$-L-C(O)—, —S(O)$_2$-L-NR$_6$—, P(O)$_{2\text{-}0}$—;

wherein L is selected from $C_1$-$C_{12}$alkyl, $C_2$-$C_8$ alkenyl, $C_3$-$C_6$cycloalkyl, polyoxyalkylene having from 2 to 6 carbon atoms, $C_6$-$C_{10}$aryl and $C_1$-$C_6$alkylC$_6$-$C_{10}$aryl and wherein $R_6$ is selected from H, $C_1$-$C_{12}$alkyl;

$A_1$ and $A_2$ are the same or different and are basic amino acid residues;

each of $S_1$, $S_2$ and $S_3$ is either present or absent and is an independently selected amino acid residue;

T is present or absent and is selected from —C(O)R$_8$, —C(O)OR$_8$, —OR$_8$, —NHR$_8$, NHOR$_8$, —NH—C$_6$aryl-CO—R$_8$, —NH—C$_6$aryl-CO—NHR$_8$, —NH—C$_6$aryl-CONHOR$_8$, —NH—C$_6$aryl-CONHOH, —C(O)NHR$_8$, —(NH)—SO$_2$C$_6$aryl, —(NH)COR$_8$;

or T forms a carboxylate isostere, optionally substituted with R$_8$, which replaces the carboxylic acid group of the amino acid to which T is connected;

wherein R$_8$ is selected from hydrogen, $C_1$-$C_{12}$alkyl, $C_1$-$C_6$alkylC$_6$-$C_{10}$aryl, $C_1$-$C_6$alkylC$_3$-$C_6$cycloalkyl, $C_2$-$C_6$alkenyl, and $C_2$-$C_6$alkynyl; and wherein when T is connected to the C-terminus of an amino acid residue then the carbonyl group of the amino acid residue may be reduced to methylene.

In a second aspect, there is provided a compound of formula II,

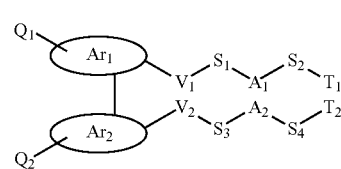

(II)

or pharmaceutically acceptable derivatives thereof, wherein:

$Ar_1$ and $Ar_2$ are each independently selected from an aromatic or heterocyclic ring system or partially or fully reduced derivatives thereof;

$Q_1$ and $Q_2$ are each independently selected from hydrogen, $C_1$-$C_{12}$alkyl, $C_3$-$C_6$cycloalkyl, $C_1$-$C_{12}$alkyloxy, nitro, halogen, hydroxyl, amino, mono or dialkylamino, carboxylic acid or a salt or ester thereof, sulphonic acid or a salt or ester thereof, phosphoric acid or a salt or ester thereof, or a nitrogen containing group such as carboxamide, sulphonamide or phosphoramide wherein each $C_1$-$C_{12}$alkyl, $C_1$-$C_{12}$alkyloxy or $C_3$-$C_6$cycloalkyl is optionally substituted with hydroxyl, amino, carboxylic acid or a salt or ester thereof, sulphonic acid or a salt or ester thereof, phosphoric acid or a salt or ester thereof, or a nitrogen containing group such as carboxamide, sulphonamide or phosphoramide;

each of $V_1$ and $V_2$ is a linker group independently selected from —O—, —O-L-C(O), —O-L-NR—, —C(O)—, —NR$_6$—, —S(O)—, —S(O)$_2$—, —O-L-S(O)—, —S(O)$_2$-L-C(O)—, —S(O)$_2$-L-NR$_6$—, P(O)$_2$O—;

wherein L is selected from $C_1$-$C_{12}$alkyl, $C_2$-$C_8$alkenyl, $C_3$-$C_6$cycloalkyl, polyoxyalkylene having from 2 to 6 carbon atoms, $C_6$-$C_{10}$aryl and C, $C_6$alkylC$_6$-$C_{10}$aryl and wherein $R_6$ is selected from H, $C_1$-$C_{12}$alkyl;

$A_1$ and $A_2$ are the same or different and are basic amino acid residues;

each of $S_1$, $S_2$, $S_3$ and $S_4$ is either present or absent and is an independently selected amino acid residue;

$T_1$ is either present or absent and is independently selected from —C(O)R$_8$, —C(O)OR$_8$, —OR$_8$, —NHR$_8$, —NHOR$_8$, —NH—C$_6$aryl-COR$_8$, —NH—C$_6$aryl- CONHR$_8$, —NH—C$_6$aryl-CONHOR$_8$, —NH—C$_6$aryl-CONHOH, —C(O)NHR$_8$, —(NH)—SO$_2$C$_6$aryl, —(NH)COR$_8$;

or T$_1$ forms a carboxylate isostere, optionally substituted with R$_8$, which replaces the carboxylic acid group of the amino acid to which T1 is connected;

wherein R$_8$ is selected from hydrogen, C$_1$-C$_{12}$alkyl, C$_1$-C$_6$alkylC$_6$-C$_{10}$aryl, C$_1$-C$_6$alkylC$_3$-C$_6$cycloalkyl, C$_2$-C$_6$alkenyl, and C$_2$-C$_6$alkynyl; and wherein when T1 is connected to the C-terminus of an amino acid residue then the carbonyl group of the amino acid residue may be reduced to methylene;

T$_2$ is either present or absent and is independently selected from —C(O)OR$_9$, —OR$_9$, —NHR$_9$, NHOR$_9$, —NH—C$_6$aryl-CO—R$_9$, —NH—C$_6$aryl-CO—NHR$_9$, —NH—C$_6$aryl-CONHOR$_9$, —NH—C$_6$aryl-CONHOH, —C(O)NHR$_8$, —(NH)—SO$_2$C$_6$aryl, —(NH)COR$_8$;

or T$_2$ forms a carboxylate isostere, optionally substituted with R$_9$, which replaces the carboxylic acid group of the amino acid to which T$_2$ is connected;

wherein R$_9$ is selected from hydrogen, C$_1$-C$_{12}$alkyl, C$_1$-C$_6$alkylC$_6$-C$_{10}$aryl, C$_1$-C$_6$alkylC$_3$-C$_6$cycloalkyl, C$_2$-C$_6$alkenyl, and C$_2$-C$_6$alkynyl; and wherein when T$_2$ is connected to the C-terminus of an amino acid residue then the carbonyl group of the amino acid residue may be reduced to methylene.

In a third aspect, there is provided a compound of formula III,

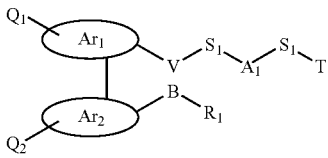

(III)

or pharmaceutically acceptable derivatives thereof, wherein:

Ar$_1$ and Ar$_2$ are each independently selected from an aromatic or heterocyclic ring system or partially or fully reduced derivatives thereof;

Q$_1$ and Q$_2$ are each independently selected from hydrogen, C$_1$-C$_{12}$alkyl, C$_3$-C$_6$cycloalkyl, C$_1$-C$_{12}$alkyloxy, nitro, halogen, hydroxyl, amino, mono or dialkylamino, carboxylic acid or a salt or ester thereof, sulphonic acid or a salt or ester thereof, phosphoric acid or a salt or ester thereof, or a nitrogen containing group such as carboxamide, sulphonamide or phosphoramide wherein each C$_1$-C$_{12}$alkyl, C$_1$-C$_{12}$alkyloxy or C$_3$-C$_6$cycloalkyl is optionally substituted with hydroxyl, amino, carboxylic acid or a salt or ester thereof, sulphonic acid or a salt or ester thereof, phosphoric acid or a salt or ester thereof, or a nitrogen containing group such as carboxamide, sulphonamide or phosphoramide;

B is selected from —O—, —S—, —S(O)—, —S(O)$_2$—, —NH—, and —N(C$_1$-C$_6$alkyl)-;

R$_1$ is selected from hydrogen, C$_1$-C$_{12}$alkyl, C$_1$-C$_6$alkylC$_3$-C$_6$cycloalkyl, C$_1$-C$_6$alkylC$_6$-C$_{10}$aryl, C$_2$-C$_6$alkenyl, C$_2$-C$_6$alkynyl, a polyoxyalkylene having from 2 to 6 carbon atoms, and when B is —S—, —S(O)—, —S(O)$_2$—, —NH— or —N(C$_1$-C$_6$alkyl)- then R$_1$ may be hydroxyl;

V$_1$ is a linker group selected from selected from —O—, —O-L-C(O), —O-L-NR$_6$—, —C(O)—, —NR$_6$—, —S(O)—, —S(O)$_2$—, —O-L-S(O)—, —S(O)$_2$-L-C(O)—, —S(O)$_2$-L-NR$_6$—, —P(O)$_2$O—;

wherein L is selected from C$_1$-C$_{12}$alkyl, C$_2$-C$_8$alkenyl, C$_3$-C$_6$cycloalkyl, polyoxyalkylene having from 2 to 6 carbon atoms, C$_6$-C$_{10}$ aryl and C$_1$-C$_6$alkylC$_6$-C$_{10}$aryl and wherein R$_6$ is selected from H, C$_1$-C$_{12}$ alkyl;

A$_1$ is a basic amino acid residue;

each of S$_1$ and S$_2$ is either present or absent and is an independently selected amino acid residue;

T is present or absent and is selected from —C(O)R$_8$, —C(O)OR$_8$, —OR$_8$, —NHR$_8$, —NHOR$_8$, —NH—C$_6$aryl-COR$_8$, —NH—C$_6$aryl-CONHR$_8$, —NH—C$_6$aryl-CONHOR$_8$, —NH—C$_6$aryl-CONHOH, —C(O)NHR$_8$, —(NH)—SO$_2$C$_6$aryl, —(NH)COR$_8$;

or T forms a carboxylate isostere, optionally substituted with R$_8$, which replaces the carboxylic acid group of the amino acid to which T is connected;

wherein R$_8$ is selected from hydrogen, C$_1$-C$_{12}$alkyl, C$_1$-C$_6$alkylC$_6$-C$_{10}$aryl, C$_1$-C$_6$alkylC$_3$-C$_6$cycloalkyl, C$_2$-C$_6$alkenyl, and C$_2$-C$_6$alkynyl; and wherein when T is connected to the C-terminus of an amino acid residue then the carbonyl group of the amino acid residue may be reduced to methylene.

In a fourth aspect, there is provided a compound of formula IV,

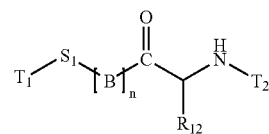

IV or pharmaceutically acceptable derivatives thereof, wherein

R$_{12}$ is an alkylaromatic or alkylpolyaromatic group optionally substituted with —OC$_{1-6}$alkyl or —OC$_{2-6}$alkenyl;

each B is an independently basic amino acid residue;

n=1 or 2;

S$_1$ is present or absent and is an independently selected amino acid residue;

T$_1$ is selected from —NHR$_{13}$, —NHOR$_{13}$, —NH—C$_6$aryl-COR$_{13}$, —NH—C$_6$aryl-CONHR$_{13}$, —NH—C$_6$aryl-CONHOR$_{13}$, —NH—C$_6$aryl-CONHOH, —(NH)—SO$_2$C$_6$aryl, —(NH)COR$_{13}$ or

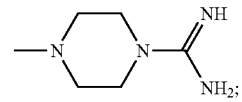

or T1 forms a carboxylate isostere, optionally substituted with R$_{13}$, which replaces the carboxylic acid group of the amino acid to which T$_1$ is connected;

wherein R$_{13}$ is selected from hydrogen, C$_1$-C$_{12}$alkyl, C$_1$-C$_6$alkylC$_6$-C$_{10}$aryl, C$_1$-C$_6$alkylC$_3$-C$_6$cycloalkyl, C$_2$-C$_6$alkenyl, and C$_2$-C$_6$alkynyl; and wherein when T$_1$ is connected to the C-terminus of an amino acid residue then the carbonyl group of the amino acid residue may be reduced to methylene;

T$_2$ is selected from —C(O)R$_{14}$, —C(O)OR$_{14}$, —OR$_{14}$, —C(O)NHR$_{14}$;

wherein $R_{14}$ is selected from hydrogen, $C_1$-$C_{12}$alkyl, $C_1$-$C_6$alkyl$C_6$-$C_{10}$aryl, $C_1$-$C_6$alkyl$C_3$-$C_6$cycloalkyl, $C_2$-$C_6$alkenyl, $C_2$-$C_6$alkynyl, and $CH_2$-fluorene;

wherein the optional substituent of $R_{12}$ and the side-chain of $S_1$ may together form a —$OC_{1-6}$alkylene linking group.

In a fifth aspect, there is a provided a compound of Example 2.

In a sixth aspect, there is provided a composition comprising a compound according to any one of the first to fifth aspects, a salt or a pharmaceutically acceptable derivative thereof together with one or more pharmaceutically acceptable carriers or adjuvants.

In a seventh aspect, there is provided a method of treating a bacterial infection in a mammal comprising administering an effective amount of compound according to any one of the first to fifth aspects, a salt or a pharmaceutically acceptable derivative thereof.

In an eighth aspect, there is provided a method for treatment or prophylaxis of HIV in a subject comprising administering to said subject an effective amount of a compound according to any one of the first to fifth aspects, a salt or a pharmaceutically acceptable derivative thereof.

BRIEF DESCRIPTION OF THE FIGURES

FIG. 1. shows a diagrammatic representation of the antibacterial screening assay design using a 96-well microtitre plate.

DETAILED DESCRIPTION OF THE INVENTION

In a first aspect, the present invention provides a compound of formula I,

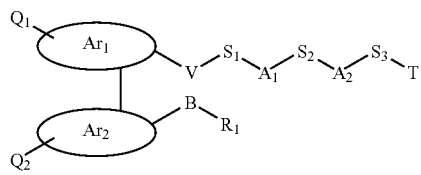

or pharmaceutically acceptable derivatives thereof, wherein:

$Ar_1$ and $Ar_2$ are each independently selected from an aromatic or heterocyclic ring system or partially or fully reduced derivatives thereof;

$Q_1$ and $Q_2$ are each independently selected from hydrogen, $C_1$-$C_{12}$alkyl, $C_3$-$C_6$cycloalkyl, $C_1$-$C_{12}$alkyloxy, nitro, halogen, hydroxyl, amino, mono or dialkylamino, carboxylic acid or a salt or ester thereof, sulphonic acid or a salt or ester thereof, phosphoric acid or a salt or ester thereof, or a nitrogen containing group such as carboxamide, sulphonamide or phosphoramide wherein each $C_1$-$C_{12}$alkyl, $C_1$-$C_{12}$alkyloxy or $C_3$-$C_6$cycloalkyl is optionally substituted with hydroxyl, amino, carboxylic acid or a salt or ester thereof, sulphonic acid or a salt or ester thereof, phosphoric acid or a salt or ester thereof, or a nitrogen containing group such as carboxamide, sulphonamide or phosphoramide;

B is selected from —O—, —S—, —S(O)—, —S(O)$_2$—, —NH—, and —N($C_1$-$C_6$alkyl)-;

$R_1$ is selected from hydrogen, $C_1$-$C_{12}$alkyl, $C_1$-$C_6$alkyl$C_3$-$C_6$cycloalkyl, $C_1$-$C_6$alkyl$C_6$-$C_{10}$aryl, $C_2$-$C_6$alkenyl, $C_2$-$C_6$alkynyl, a polyoxyalkylene having from 2 to 6 carbon atoms, and when B is —S—, —S(O)—, —S(O)$_2$—, —NH— or —N($C_1$-$C_6$alkyl)- then $R_1$ may be hydroxyl;

V is a linker group selected from —O—, —O-L-C(O), —O-L-NR$_6$—, —C(O)—, —NR$_6$—, —S(O)—, —S(O)$_2$—, —O-L-S(O)—, —S(O)$_2$-L-C(O)—, —S(O)$_2$-L-NR$_6$—, P(O)$_2$O—;

wherein L is selected from $C_1$-$C_{12}$alkyl, $C_2$-$C_8$ alkenyl, $C_3$-$C_6$cycloalkyl, polyoxyalkylene having from 2 to 6 carbon atoms, $C_6$-$C_{10}$aryl and $C_1$-$C_6$alkyl$C_6$-$C_{10}$aryl and wherein $R_6$ is selected from H, $C_1$-$C_{12}$alkyl;

$A_1$ and $A_2$ are the same or different and are basic amino acid residues;

each of $S_1$, $S_2$ and $S_3$ is either present or absent and is an independently selected amino acid residue;

T is present or absent and is selected from —C(O)OR$_8$, —OR$_8$, —NHR$_8$, NHOR$_8$, —NH—$C_6$aryl-CO—R$_8$, —NH—$C_6$aryl-CO—NHR$_8$, —NH—$C_6$aryl-CONHOR$_8$, —NH—$C_6$aryl-CONHOH, —C(O)NHR$_8$, —(NH)—SO$_2$C$_6$aryl, —(NH)COR$_8$;

or T forms a carboxylate isostere, optionally substituted with R$_8$, which replaces the carboxylic acid group of the amino acid to which T is connected;

wherein R$_8$ is selected from hydrogen, $C_1$-$C_{12}$alkyl, $C_1$-$C_6$alkyl$C_6$-$C_{10}$aryl, $C_1$-$C_6$alkyl$C_3$-$C_6$cycloalkyl, $C_2$-$C_6$alkenyl, and $C_2$-$C_6$alkynyl; and wherein when T is connected to the C-terminus of an amino acid residue then the carbonyl group of the amino acid residue may be reduced to methylene.

Preferably, $A_1$ and $A_2$ are each independently selected from the group consisting of lysine, arginine and ornithine. More preferably $A_1$ is selected from lysine and ornithine and $A_2$ is selected from arginine.

Preferably, $S_1$ and $S_2$ are absent.

In a preferred embodiment, the compound of formula I is of formula Ia:

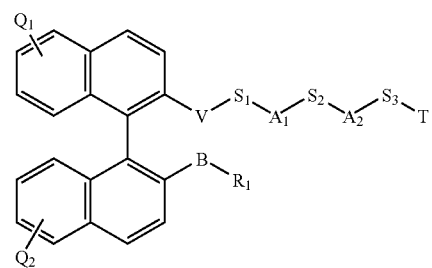

wherein $Q_1$, $Q_2$, V, $S_1$, $A_1$, $S_1$, $A_2$, $S_3$, T, B and $R_1$ are as defined above.

In a further preferred embodiment, the compound of formula I is of formula Ib:

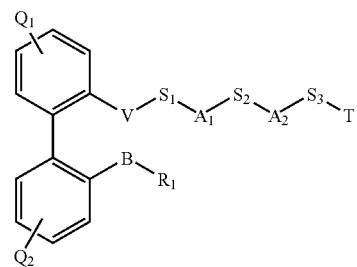

wherein $Q_1$, $Q_2$, V, $S_1$, $A_1$, $S_1$, $A_2$, $S_3$, T, B and $R_1$ are as defined above.

In a second aspect, there is provided a compound of formula II,

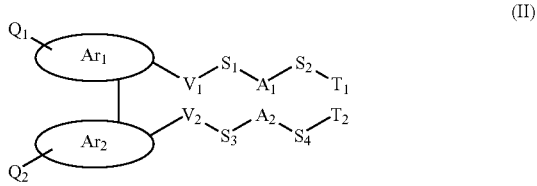

or pharmaceutically acceptable derivatives thereof, wherein:

$Ar_1$ and $Ar_2$ are each independently selected from an aromatic or heterocyclic ring system or partially or fully reduced derivatives thereof;

$Q_1$ and $Q_2$ are each independently selected from hydrogen, $C_1$-$C_{12}$alkyl, $C_3$-$C_6$cycloalkyl, $C_1$-$C_{12}$alkyloxy, nitro, halogen, hydroxyl, amino, mono or dialkylamino, carboxylic acid or a salt or ester thereof, sulphonic acid or a salt or ester thereof, phosphoric acid or a salt or ester thereof, or a nitrogen containing group such as carboxamide, sulphonamide or phosphoramide wherein each $C_1$-$C_{12}$alkyl, $C_1$-$C_{12}$alkyloxy or $C_3$-$C_6$cycloalkyl is optionally substituted with hydroxyl, amino, carboxylic acid or a salt or ester thereof, sulphonic acid or a salt or ester thereof, phosphoric acid or a salt or ester thereof, or a nitrogen containing group such as carboxamide, sulphonamide or phosphoramide;

each of $V_1$ and $V_2$ is a linker group independently selected from —O—, —O-L-C(O), —O-L-$NR_6$—, —C(O)—, —$NR_6$—, —S(O)—, —S(O)$_2$—, —O-L-S(O)—, —S(O)$_2$-L-C(O)—, —S(O)$_2$-L-$NR_6$—, —P(O)$_2$O—;

wherein L is selected from $C_1$-$C_{12}$ alkyl, $C_2$-$C_8$ alkenyl, $C_3$-$C_6$cycloalkyl, polyoxyalkylene having from 2 to 6 carbon atoms, $C_6$-$C_{10}$aryl and $C_1$-$C_{16}$alkyl$C_6$-$C_{10}$aryl and wherein $R_6$ is selected from H, $C_1$-$C_{12}$alkyl;

$A_1$ and $A_2$ are the same or different and are basic amino acid residues;

each of $S_1$, $S_2$, $S_3$ and $S_4$ is either present or absent and is an independently selected amino acid residue;

$T_1$ is either present or absent and is independently selected from —C(O)$OR_8$, —$OR_8$, —$NHR_8$, —$NHOR_8$, —NH—$C_6$aryl-$COR_8$, —NH—$C_6$aryl-$CONHR_8$, —NH—$C_6$aryl-$CONHOR_8$, —NH—$C_6$aryl-CONHOH, —C(O)$NHR_8$, —(NH)—SO$_2$$C_6$aryl, —(NH)$COR_8$;

or T1 forms a carboxylate isostere, optionally substituted with $R_8$, which replaces the carboxylic acid group of the amino acid to which T1 is connected;

wherein $R_8$ is selected from hydrogen, $C_1$-$C_{12}$alkyl, $C_1$-$C_6$alkyl$C_6$-$C_{10}$aryl, $C_1$-$C_6$alkyl$C_3$-$C_6$cycloalkyl, $C_2$-$C_6$alkenyl, and $C_2$-$C_6$alkynyl; and wherein when T1 is connected to the C-terminus of an amino acid residue then the carbonyl group of the amino acid residue may be reduced to methylene;

$T_2$ is either present or absent and is independently selected from —C(O)$OR_9$, —$OR_9$, —$NHR_9$, $NHOR_9$, —NH—$C_6$aryl-CO—$R_9$, —NH—$C_6$aryl-CO—$NHR_9$, —NH—$C_6$aryl-$CONHR_9$, —NH—$C_6$aryl-CONHOH, —C(O)$NHR_8$, —(NH)—SO$_2$$C_6$aryl, —(NH)$COR_8$;

or $T_2$ forms a carboxylate isostere, optionally substituted with $R_9$, which replaces the carboxylic acid group of the amino acid to which $T_2$ is connected;

wherein $R_9$ is selected from hydrogen, $C_1$-$C_{12}$alkyl, $C_1$-$C_6$alkyl$C_6$-$C_{10}$aryl, $C_1$-$C_6$alkyl$C_3$-$C_6$cycloalkyl, $C_2$-$C_6$alkenyl, and $C_2$-$C_6$alkynyl; and wherein when $T_2$ is connected to the C-terminus of an amino acid residue then the carbonyl group of the amino acid residue may be reduced to methylene.

Preferably, $A_1$ and $A_2$ are each independently selected from the group consisting of lysine, arginine and ornithine.

Preferably, $A_1$ and $A_2$ are the same.

Preferably, $S_1$, $S_2$, $S_3$ and $S_4$ are absent.

In a third aspect, there is provided a compound of formula III,

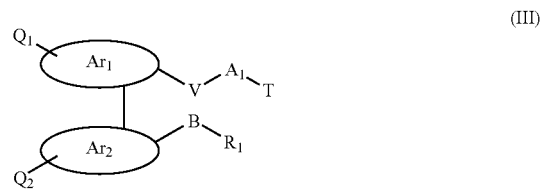

or pharmaceutically acceptable derivatives thereof, wherein:

$Ar_1$ and $Ar_2$ are each independently selected from an aromatic or heterocyclic ring system or partially or fully reduced derivatives thereof;

$Q_1$ and $Q_2$ are each independently selected from hydrogen, $C_1$-$C_{12}$alkyl, $C_3$-$C_6$cycloalkyl, $C_1$-$C_{12}$alkyloxy, nitro, halogen, hydroxyl, amino, mono or dialkylamino, carboxylic acid or a salt or ester thereof, sulphonic acid or a salt or ester thereof, phosphoric acid or a salt or ester thereof, or a nitrogen containing group such as carboxamide, sulphonamide or phosphoramide wherein each $C_1$-$C_{12}$alkyl, $C_1$-$C_{12}$alkyloxy or $C_3$-$C_6$cycloalkyl is optionally substituted with hydroxyl, amino, carboxylic acid or a salt or ester thereof, sulphonic acid or a salt or ester thereof, phosphoric acid or a salt or ester thereof, or a nitrogen containing group such as carboxamide, sulphonamide or phosphoramide;

B is selected from —O—, —S—, —S(O)—, —S(O)$_2$—, —NH—, and —N($C_1$-$C_6$alkyl)-;

$R_1$ is selected from hydrogen, $C_1$-$C_{12}$alkyl, $C_1$-$C_6$alkyl$C_3$-$C_6$cycloalkyl, $C_1$-$C_6$alkyl$C_6$-$C_{10}$aryl, $C_2$-$C_6$alkenyl, $C_2$-$C_6$alkynyl, a polyoxyalkylene having from 2 to 6 carbon atoms, and when B is —S—, —S(O)—, —S(O)$_2$—, —NH— or —N($C_1$-$C_6$alkyl)- then $R_1$ may be hydroxyl;

$V_1$ is a linker group selected from selected from —O—, —O-L-C(O), —O-L-$NR_6$—, —C(O)— —$NR_6$—, —S(O)—, —S(O)$_2$—, —O-L-S(O)—, —S(O)$_2$-L-C(O)—, —S(O)$_2$-L-$NR_6$—, P(O)$_2$O— wherein L is selected from $C_1$-$C_{12}$alkyl, $C_2$-$C_8$alkenyl, $C_3$-$C_6$cycloalkyl, polyoxyalkylene having from 2 to 6 carbon atoms, $C_6$-$C_{10}$ aryl and $C_1$-$C_6$alkyl$C_6$-$C_{10}$aryl and wherein $R_6$ is selected from H, $C_1$-$C_{12}$ alkyl;

$A_1$ is a is a basic amino acid residue;

each of $S_1$ and $S_2$ is either present or absent and is an independently selected amino acid residue;

T is present or absent and is selected from —C(O)$OR_8$, —$OR_8$, —$NHR_8$, —$NHOR_8$, —NH—$C_6$aryl-$COR_8$, —NH—$C_6$aryl-$CONHR_8$, —NH—$C_6$aryl-$CONHOR_8$, —NH—$C_6$aryl-CONHOH, —C(O)$NHR_8$, —(NH)—SO$_2$$C_6$aryl, —(NH)$COR_8$;

or T forms a carboxylate isostere, optionally substituted with $R_8$, which replaces the carboxylic acid group of the amino acid to which T is connected;
wherein $R_8$ is selected from hydrogen, $C_1$-$C_{12}$alkyl, $C_1$-$C_6$alkyl$C_6$-$C_{10}$aryl, $C_1$-$C_6$alkyl$C_3$-$C_6$cycloalkyl, $C_2$-$C_6$alkenyl, and $C_2$-$C_6$alkynyl; and
wherein when T is connected to the C-terminus of an amino acid residue then the carbonyl group of the amino acid residue may be reduced to methylene.

Preferably, $A_1$ is selected from lysine, arginine and ornithine.

In a fourth aspect, there is provided a compound of formula IV,

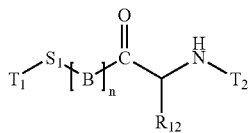

IV or pharmaceutically derivatives thereof, wherein
$R_{12}$ is an alkylaromatic or alkylpolyaromatic group optionally substituted with —$OC_{1-6}$alkyl or —$OC_{2-6}$alkenyl;
each B is an independently selected basic amino acid residue;
n=1 or 2;
$S_1$ is present or absent and is an independently selected amino acid residue;
$T_1$ is selected from —$NHR_{13}$, —$NHOR_{13}$, —NH—$C_6$aryl-$COR_{13}$, —NH—$C_6$aryl-$CONHR_{13}$, —NH—$C_6$aryl-CONHOR$_{13}$, —NH—$C_6$aryl-CONHOH, —(NH)—$SO_2C_6$aryl, —(NH)$COR_{13}$ or

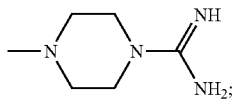

or $T_1$ forms a carboxylate isostere, optionally substituted with $R_{13}$, which replaces the carboxylic acid group of the amino acid to which $T_1$ is connected;
wherein $R_{13}$ is selected from hydrogen, $C_1$-$C_{12}$alkyl, $C_1$-$C_6$alkyl$C_6$-$C_{10}$aryl, $C_1$-$C_6$alkyl$C_3$-$C_6$cycloalkyl, $C_2$-$C_6$alkenyl, and $C_2$-$C_6$alkynyl; and
wherein when $T_1$ is connected to the C-terminus of an amino acid residue then the carbonyl group of the amino acid residue may be reduced to methylene;
$T_2$ is selected from —$C(O)R_{14}$, —$C(O)OR_{14}$, —$OR_{14}$, —$C(O)NBR_{14}$;
wherein $R_{14}$ is selected from hydrogen, $C_1$-$C_{12}$alkyl, $C_1$-$C_6$alkyl$C_6$-$C_{10}$aryl, $C_1$-$C_6$alkyl$C_3$-$C_6$cycloalkyl, $C_2$-$C_6$alkenyl, $C_2$-$C_6$alkynyl, and $CH_2$-fluorene;
wherein the optional substituent of $R_{12}$ and the side-chain of Si may together form a —$OC_{1-6}$alkylene linking group.

Preferably, $R_{12}$ is selected from —$CH_2$-phenyl-$OCH_2CH$=$CH_2$ and —$CH_2$-phenylanthracene. Preferably, $S_1$ is selected from allylglycine. Preferably, $T_2$ is —$C(O)CH_3$. Preferably, $T_1$ is $CH_3O$—. Preferably, B is arginine or lysine.

In a fifth aspect, there is provided a compound of Example 2.

Preferably the compound of Example 2 is selected from 69, 70, 71, 72, 73, 74, 75, 76, 83, 32, 37, 65, 56, 118, 119, 120, 121, 132, 90, 134, 135, 136, 137, 139, 140, 141, 159, 160, 163, 164, 78, 81, 88, 87, 89, 165, 166, 167, and 168.

It would be understood by the person skilled in the art the peptide chain formed by the combination of the amino acid residues of the compounds of the present invention could be a peptide or a reverse peptide depending on the nature of the linker group V: for example, where the group V is of the form O-L-C(O)— then the peptide will be a peptide chain with its N-terminus bound to V whereas if the group V is of the form —O-L-NH— then the peptide will be a reverse peptide chain with its C-terminus bound to V.

As is well known to those skilled in the art, the term carboxylate isostere includes any moiety capable of replacing the carboxylate group of an amino acid. Suitable carboxylate isosteres include tetrazole (ref: e.g JOC 1992, 57, 202-209; JACS 1998, 110, 5875-5880 or Tet. Lett, 1993, 34, 1757-1760.), isoxazole, oxazole and thiazole.

As used herein, the term "halo" or "halogen" refers to fluorine (fluoro), chlorine (chloro), bromine (bromo) or iodine (iodo).

As used herein, the term "alkyl" either used alone, having 1 to 12, preferably 1 to 8, more preferably 1 to 6, carbon atoms, or in compound terms such as NH(alkyl) or N(alkyl)$_2$, refers to monovalent straight chain or branched hydrocarbon groups having 1 to 12 carbon atoms, including their stereoisomeric forms if applicable. For example, suitable alkyl groups include, but are not limited to methyl, ethyl, propyl, isopropyl, n-butyl, sec-butyl, tert-butyl, pentyl, 2-methylbutyl, 3-methylbutyl, n-hexyl, 2-, 3- or 4-methylpentyl, 2-ethylbutyl, n-hexyl, and 2-, 3-, 4- or 5-methylpentyl.

As used herein, the term "alkenyl" refers to straight chain or branched hydrocarbon groups having one or more double bonds between carbon atoms. Suitable alkenyl groups include, but are not limited to ethenyl, propenyl, isopropenyl, butenyl, pentenyl and hexenyl.

The term "alkynyl" as used herein, refers to straight chain or branched hydrocarbon groups containing one or more triple bonds. Suitable alkynyl groups include, but are not limited to ethynyl, propynyl, butynyl, pentynyl and hexenyl.

The term "cycloalkyl" as used herein, refers to cyclic hydrocarbon groups. Suitable cycloalkyl groups include, but are not limited to cyclopropyl, cyclobutyl, cyclopentyl and cyclohexyl.

The term "aryl" as used herein, refers to a $C_6$-$C_{10}$ aromatic hydrocarbon group, for example phenyl or naphthyl.

The term "heterocycle" when used alone or in compound words includes monocyclic, polycyclic, fused or conjugated hydrocarbon residues, preferably $C_{3-6}$, wherein one or more carbon atoms (and where appropriate, hydrogen atoms attached thereto) are replaced by a heteroatom so as to provide a non-aromatic or aromatic residue. Suitable heteroatoms include, O, N and S. Where two or more carbon atoms are replaced, this may be by two or more of the same heteroatom or by different heteroatoms. Suitable examples of heterocyclic groups may include pyrrolidinyl, pyrrolinyl, piperidyl, piperazinyl, morpholino, indolinyl, indazolyl, quinolinyl, isoquinolinyl, imidazolidinyl, pyrazolidinyl, thiomorpholino, dioxanyl, tetrahydrofuranyl, tetrahydropyranyl, tetrahydropyrrolyl etc.

Each alkyl, alkenyl, alkynyl, cycloalkyl, aryl or heterocyclyl group may be optionally substituted with $C_1$-$C_6$alkyl, OH, $OC_1$-$C_6$alkyl, halo, CN, $NO_2$, $CO_2H$, $CO_2C_1$-$C_6$alkyl, $CONH_2$, $CONH(C_1$-$C_6$alkyl), $CON(C_1$-$C_6$alkyl)$_2$, trifluoromethyl, $C_6$aryl, $C_3$-$C_6$cycloalkyl, hetrocyclyl, $NH_2$, $NH(C_1$-$C_6$alkyl) or $N(C_1$-$C_6$alkyl)$_2$. For example, an optionally substituted aryl group may be 4-methylphenyl or 4-hydroxyphenyl group, and an optionally substituted alkyl group may be 2-hydroxyethyl, trifluoromethyl, or difluoromethyl. Further, methyl substituents ($C_1$alkyl) may be substituted with an optionally substituted aryl to form a benzyl substituent.

As used herein, the term "amino acid residue" refers to an amino acid which is bound by means of amide bonds or suitable replacements thereof to one or more of the linker group V, other amino acid residues and the terminal group T. The amino acid may be an α-amino acid or a β-amino acid. A suitable replacement for the amide bond can be any replacement that is known in the art as it is well known that where two amino acids or a combination of natural and unnatural amino acids are joined together to form an amide bond between them the bond can be replaced by a suitable link, which may be called a peptoid (discussion of this may be found in P M Fischer 'The design, synthesis and application of stereochemical and directional peptide isosteres a critical review' Curr. Protein and Peptide Science, 2003, 4(5), 339-356 and references therein). Examples of suitable replacements include, but are not limited to:

- reduced amide: amino methylene: $CH_2NH$; (Szelke, M., Leckie, B.; Hallet A., Jones, D. M., Sueiras, J.; Atrash. B.; Lever, A., Nature, 19821982, 299, 555-557.; Ambo A, Adachi T, Sasaki Y. Synthesis and opioid activities of [D-Leu-8]Dynorphin(1-8) analogs containing a reduced peptide bond, psi($CH_2$—NH). Chem Pharm Bull (Tokyo). 1995, 43(9), 1547-50)
- ether bond: $CH_2O$; (Hedenstrom M, Yuan Z, Brickmann K, Carlsson J, Ekholm K, Johansson B, Kreutz E, Nilsson A, Sethson I, Kihlberg j. Conformations and receptor activity of desmopressin analogues, which contain gamma-turn mimetics or a psi[$CH(_2)O$] isostere. J Med Chem. 2002, 45(12), 2501-11)
- hydroxy ethylene $CHOHCH_2$— and ketomethylene $COCH_2$; (Harbeson S L, Rich D H. Inhibition of aminopeptidases by peptides containing ketomethylene and hydroxyethylene amide bond replacements. J Med Chem. 1989, 32(6), 1378-92)
- urea NHCONH; (Dales N A, Bohacek R S, Satyshur K A, Rich D H. Design and synthesis of unsymmetrical peptidyl urea inhibitors of aspartic peptidases Org Lett. 2001, 3(15), 2313-6)

The amino acid may be a L- or D-isomer and may have a naturally occurring side chain or a non-naturally occurring side chain. The amino acid may also be further substituted in the α-position or the β-position with a group selected from —$C_1$-$C_{12}$alkyl, —$C_2$-$C_6$alkenyl, —$C_2$-$C_6$alkynyl, —$(CH_2)_n$$COR_a$, —$(CH_2)_n$$R_b$, —$PO_3H$, —$(CH_2)_n$heterocyclyl or —$(CH_2)_n$aryl where $R_a$ is —OH, —$NH_2$, —$NHC_1$-$C_6$alkyl, —$OC_1$-$C_{12}$alkyl$C_1$-$C_{12}$alkyl and $R_b$ is —OH, —SH, —$SC_1$-$C_6$alkyl, —$OC_1$-$C_{12}$alkyl, —$C_3$-$C_6$cycloalkyl, —$C_3$-$C_6$cycloalkenyl, —$NH_2$, —$NHC_1$-$C_6$alkyl or —NHC(C=NH)$NH_2$, n is 0 or an integer from 1 to 6 and where each alkyl, alkenyl, alkynyl, cycloalkyl, cycloalkenyl, aryl or heterocyclyl group may be substituted with one or more groups selected from —OH, —$NH_2$, —$NHC_1$-$C_6$alkyl, —$OC_1$-$C_{12}$alkyl, —SH, —$SC_1$-$C_6$alkyl, —$CO_2H$, —$CO_2C_1$-$C_6$alkyl, —$CONH_2$ or —$CONHC_1$-$C_6$alkyl.

The term "α-amino acid" as used herein, refers to a compound having an amino group and a carboxyl group in which the amino group and the carboxyl group are separated by a single carbon atom, the α-carbon atom. An α-amino acid includes naturally occurring and non-naturally occurring L-amino acids and their D-isomers and derivatives thereof such as salts or derivatives where functional groups are protected by suitable protecting groups. The α-amino acid may also be further substituted in the α-position with a group selected from —$C_1$-$C_{12}$alkyl, —$C_2$-$C_{10}$alkenyl, —$C_2$-$C_{12}$alkynyl, —$(CH_2)_n$$COR_1$, —$(CH_2)_n$$R_2$, —$PO_3H$, —$(CH_2)_n$heterocyclyl or —$(CH_2)_n$aryl where $R_1$ is —OH, —$NH_2$, —$NHC_1$-$C_{12}$alkyl, —$OC_1$-$C_{12}$alkyl or $C_1$-$C_{12}$alkyl and $R_2$ is —OH, —SH, —$SC_1$-$C_6$alkyl, —$OC_1$-$C_{12}$alkyl, —$C_3$-$C_6$cycloalkyl$C_3$-$C_6$cycloalkenyl, $OC_1$-$C_{12}$alkyl, —$NH_2$, —$NHC_1$-$C_3$alkyl or —NHC(C=NH)$NH_2$, n is 0 or an integer from 1 to 10 and where each alkyl, alkenyl, alkynyl, cycloalkyl, cycloalkenyl, aryl or heterocyclyl group may be substituted with one or more groups selected from —OH, —$NH_2$, —$NHC_1$-$C_6$alkyl, —$OC_1$-$C_{12}$alkyl, —SH, —$SC_1$-$C_6$alkyl, —$CO_2H$, —$CO_2C_1$-$C_6$alkyl, —$CONH_2$ or —$CONHC_1$-$C_6$alkyl.

As used herein, the term "β-amino acid" refers to an amino acid that differs from an α-amino acid in that there are two (2) carbon atoms separating the carboxyl terminus and the amino terminus. As such, β-amino acids with a specific side chain can exist as the R or S enantiomers at either of the α (C2) carbon or the β (C3) carbon, resulting in a total of 4 possible isomers for any given side chain. The side chains may be the same as those of naturally occurring α-amino acids or may be the side chains of non-naturally occurring amino acids.

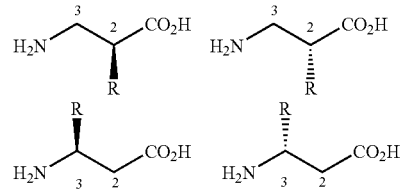

Furthermore, the β-amino acids may have mono-, di-, tri- or tetra-substitution at the C2 and C3 carbon atoms. Mono-substitution may be at the C2 or C3 carbon atom. Di-substitution includes two substituents at the C2 carbon atom, two substituents at the C3 carbon atom or one substituent at each of the C2 and C3 carbon atoms. Tri-substitution includes two substituents at the C2 carbon atom and one substituent at the C3 carbon atom or two substituents at the C3 carbon atom and one substituent at the C2 carbon atom. Tetra-substitution provides for two substituents at the C2 carbon atom and two substituents at the C3 carbon atom. Suitable substituents include —$C_1$-$C_{12}$alkyl, —$C_2$-$C_6$alkenyl, —$C_2$-$C_6$alkynyl, —$(CH_2)_n$$COR_a$, —$(CH_2)_n$$R_b$, —$PO_3H$, —$(CH_2)_n$heterocyclyl or —$(CH_2)_n$aryl where $R_a$ is —OH, —$NH_2$, —NHCl—$C_6$alkyl, —$OC_1$-$C_{12}$alkyl or —$C_1$-$C_{12}$alkyl and $R_b$ is —OH, —SH, —$SC_1$-$C_6$alkyl, —$OC_1$-$C_{12}$alkyl, —$C_3$-$C_6$cycloalkyl, —$C_3$-$C_6$cycloalkenyl, —$NH_2$, —$NHC_1$-$C_6$alkyl or —NHC(C=NH)$NH_2$, n is 0 or an integer from 1 to 6 and where each alkyl, alkenyl, alkynyl cycloalkyl, cycloalkenyl, aryl or heterocyclyl group may be substituted with one or more groups selected from —OH, —$NH_2$, —$NHC_1$-$C_6$alkyl, —$OC_1$-$C_{12}$alkyl, —SH, —$SC_1$-$C_6$alkyl, —$CO_2H$, —$CO_2C_1$-$C_6$alkyl, —$CONH_2$ or —$CONHC_1$-$C_6$alkyl.

The term "non-naturally occurring amino acid" as used herein, refers to amino acids having a side chain that does not occur in the naturally occurring L-α-amino acids. Examples of non-natural amino acids and derivatives include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

The term "basic amino acid" includes any amino acid having a side chain that can act as a base and generally includes amino acids having a side chain bearing one or more nitrogen atoms. Included within the definition are the naturally occurring basic L-amino acids lysine, arginine, and histidine and their D-isomers. Further included are the L- and D-forms of ornithine; 2-, 3- and 4-amidinophenylglycine; 2, 3, and 4 amidinophenylalanine; 2-, 3- and 4-guanidinophenylglycine; pyridylalanine; cysteic- and homocysteic acid-S-(aminoiminomethyl) amides; and amidinopiperidinylalanine. Preferably, the side-chain comprises an amino group ($NH_2$) or an amino group substituted on the nitrogen atom with up to two substituents. Examples of optional substituents include $C_1$-$C_{12}$alkyl, $C_3$-$C_7$cycloalkyl, $C_6$-$C_{10}$aryl, benzyl, and suitable nitrogen protecting groups (see "Protective Groups in Organic Synthesis" Theodora Greene and Peter Wuts, third edition, Wiley Interscience, 1999). Preferably, the amino group is capable of carrying a positive charge at physiological pH. In a preferred form of the invention, the side chain comprises a substituent selected from a group consisting of: —N($R_{10}$)$_2$, —N($R_{10}$)—CO$R_{11}$, —N$R_{10}$C(=N$R_{10}$)N($R_{10}$)$_2$, —C(=N$R_{10}$)N($R_{10}$)$_2$, —N$R_{10}$C(=O)N($R_{10}$)$_2$, —N=NC(=N$R_{10}$)N($R_{10}$)$_2$, N$R_{10}$N$R_{10}$C(=O)NHN($R_{10}$)$_2$, —N$R_{10}$CC=NHN($R_{10}$)$_2$ wherein each $R_{10}$ is independently selected from hydrogen and $C_1$-$C_6$alkyl and R11 is selected from hydrogen, hydroxy, $C_1$-$C_{12}$alkyl, $C_1$-$C_6$alkoxy and N$R_{10}$; and 3-8-membered N-containing heterocyclic group such as piperidinyl, pyrrollodinyl, imidazolinyl, pyrazolidinyl or piperazinyl, wherein the 3-8-membered N-containing heterocyclic group can be attached via a nitrogen or carbon atom. Preferred substituents include optionally substituted guanidine [—NHC(=NH)$NH_2$], amidino [—C(=NH)$NH_2$], ureido [—NHC(=O)$NH_2$], carbazono [—N=NC(=)NH$NH_2$], carbazido [—NHNHC(=O)NH$NH_2$] and semicarbazido [—NHC(=O)NH$NH_2$] and amino ([$NH_2$].

The compounds of the present invention include binaphthyl derivatives. Substituted binaphthyl derivatives are chiral compounds. The present invention encompassed both enantiomeric forms. Preferably, when the compound of the present invention is a 2,2'-binapthyl derivative then the binapthyl group is in the S configuration.

The term "pharmaceutically acceptable derivative" may include any pharmaceutically acceptable salt, hydrate or prodrug, or any other compound which upon administration to a subject, is capable of providing (directly or indirectly) a compound of the present invention or a pharmaceutically active metabolite or residue thereof.

The salts of the compound of formulae (I) to (IV) are preferably pharmaceutically acceptable, but it will be appreciated that non-pharmaceutically acceptable salts also fall within the scope of the present invention, since these are useful as intermediates in the preparation of pharmaceutically acceptable salts.

Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids. Base salts include, but are not limited to, those formed with pharmaceutically acceptable cations, such as sodium, potassium, lithium, calcium, magnesium, zinc, ammonium, alkylammonium such as salts formed from triethylamine, alkoxyammonium such as those formed with ethanolamine and salts formed from ethylenediamine, choline or amino acids such as arginine, lysine or histidine. General information on types of pharmaceutically acceptable salts and their formation is known to those skilled in the art and is as described in general texts such as "Handbook of Pharmaceutical salts" P. H. Stahl, C. G. Wermuth, 1$^{st}$ edition, 2002, Wiley-VCH.

Basic nitrogen-containing groups may be quaternised with such agents as lower alkyl halide, such as methyl, ethyl, propyl, and butyl chlorides, bromides and iodides; dialkyl sulfates like dimethyl and diethyl sulfate; and others.

The term "prodrug" is used in its broadest sense and encompasses those derivatives that are converted in vivo to the compounds of the invention. Such derivatives would readily occur to those skilled in the art, and include, for example, compounds in which a free hydroxy group is converted into a group, such as an ester, carbonate or carbamate, which is capable of being converted in vivo back to a hydroxy group. A prodrug may include modifications of one or more of the functional groups of a compound of formula (I). In particular, compounds of formula I having free amino, amido, hydroxy or carboxylic groups can be converted into prodrugs. Prodrugs include compounds wherein an amino acid residue, or a polypeptide chain of two or more (eg, two, three or four) amino acid residues which are covalently joined through peptide bonds to free amino, hydroxy and carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methioine sulfone. Prodrugs also include compounds wherein carbonates, carbamates, amides and alkyl esters which are covalently bonded to the above substituents of formula I through the carbonyl carbon prodrug sidechain. Prodrugs also include phosphate derivatives of compounds of the present invention (such as acids, salts of acids, or esters) joined through a phosphorus-oxygen bond to a free hydroxyl of the compound I.

It will also be recognised that the compounds of the first to fifth aspects may possess asymmetric centres and are therefore capable of existing in more than one stereoisomeric form. The invention thus also relates to compounds in substantially pure isomeric form at one or more asymmetric centres e.g., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution.

In a sixth aspect, there is provided a composition comprising a compound according to any one of the first to fifth aspects, a salt or a pharmaceutically acceptable derivative thereof together with one or more pharmaceutically acceptable carriers or adjuvants.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

In a seventh aspect, there is provided a method of treating a bacterial infection in a mammal comprising administering an effective amount of compound according to any one of the first to fifth aspects, a salt or a pharmaceutically acceptable derivative thereof.

Yet another aspect of the present invention provides a use of a compound of the first to fifth aspects in the preparation of a medicament for treating or preventing bacterial infection. They are particularly useful for treating infections caused by Gram positive bacteria such as *enterococcus faecium, Staphylococcus aureus, Staphylococcus epidermis, Klebsiella pneumoniae, Streptococcus pneumoniae*, including multi-resistant strains such as vancomycin resistant *Staphylococcus aureus* and methicillin-resistant *Staphylococcus aureus.*

Accordingly the invention provides the use of a compound of the first to fifth aspects for treatment or prophylaxis of bacterial infections and provides method comprising of administering an suitable amount of a compound according to one of the first to fifth aspects.

Suitable dosages may lie within the range of about 0.1 ng per kg of body weight to 1 g per kg of body weight per dosage. The dosage is preferably in the range of 1 μg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another preferred embodiment, the dosage is in the range of 1 mg to 100 mg per kg of body weight per dosage, such as up to 50 mg per kg of body weight per dosage. In yet another embodiment, the dosage is in the range of 1 μg to 1 mg per kg of body weight per dosage.

Suitable dosage amounts and dosing regimens can be determined by the attending physician and may depend on the severity of the condition as well as the general age, health and weight of the subject.

The active ingredient may be administered in a single dose or a series of doses. While it is possible for the active ingredient to be administered alone, it is preferable to present it as a composition, preferably as a pharmaceutical formulation.

This invention thus further provides pharmaceutical formulation comprising a compound of the invention or a pharmaceutically acceptable salt or derivative thereof together with one or more pharmaceutically acceptable carriers thereof and, optionally, other therapeutic and/or prophylactic ingredients. The carriers(s) must be "acceptable' in the sense of being compatible with other ingredients of the formulation and not deleterious to the recipient thereof.

Pharmaceutical formulations include those for oral, rectal, nasal, topical (including buccal and sub-lingual), vaginal or parenteral (including intramuscular, sub-cutaneous and intravenous) administration or in a form suitable for administration by inhalation or insufflation. The compounds of the invention, together with a conventional adjuvant, carrier or diluent, may thus be placed into the form of pharmaceutical compositions and unit dosages thereof, and in such form may be employed as solids, such as tablets or filled capsules, or liquids as solutions, suspensions, emulsions, elixirs or capsules filled with the same, all for oral use, in the form of suppositories for rectal administration; or in the form of sterile injectable solutions for parenteral (including subcutaneous) use.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The subjects treated in the above method are mammals, including, but not limited to, cows, sheep, goats, horses, dogs, cats, guinea pigs, rats or other bovine, ovine, equine, canine, feline, rodent or murine species, and preferably a human being, male or female.

As used herein, the term "effective amount" relates to an amount of compound which, when administered according to a desired dosing regimen, provides the desired treatment of the bacterial infection or therapeutic activity, or disease prevention. Dosing may occur at intervals of minutes, hours, days, weeks, months or years or continuously over any one of these periods. A therapeutic, or treatment, effective amount is an amount of the compound which, when administered according to a desired dosing regimen, is sufficient to at least partially attain the desired therapeutic effect, or delay the onset of, or inhibit the progression of or halt or partially or fully reverse the onset or progression of the bacterial infection. A prevention effective amount is an amount of compound which when administered according to the desired dosing regimen is sufficient to at least partially prevent or delay the onset of a particular disease or condition.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The pharmaceutical composition and method of the present invention may further comprise other therapeutically active compounds which are usually applied in the treatment of the above mentioned pathological conditions. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

When other therapeutic agents are employed in combination with the compounds of the present invention they may be used for example in amounts as noted in the Physician Desk Reference (PDR) or as otherwise determined by one of ordinary skill in the art.

In addition to the antibacterial properties of compounds of the present invention, the present inventors have also found that compounds of the present invention are also effective in treating HIV. Accordingly, in an eighth aspect the present invention provides a method for treatment or prophylaxis of HIV in a subject comprising administering to said subject an effective amount of a compound according to any one of the first to fourth aspects, a salt or a pharmaceutically acceptable derivative thereof.

Preferably, the compound is selected from one or more of the following compounds of Example 2: 78, 81, 88, 89, 165, 166, 167, 168, 83, 119, 164, 163, 158.

In order that the nature of the present invention may be more clearly understood, preferred forms thereof will now be described with reference to the following non-limiting examples.

EXPERIMENTAL

Compounds of Formulae (I) to (III) may be prepared using the methods depicted or described herein or known in the art for the preparation of compounds of analogous structure. It will be understood that minor modifications to methods described herein or known in the art may be required to synthesise particular compounds of Formula (I). General synthetic procedures applicable to the synthesis of compounds may be found in standard references such as *Comprehensive Organic Transformations*, R. C. Larock, 1989, VCH Publishers, *Advanced Organic Chemistry*, J. March, 4th edition, 1992, Wiley InterScience, *Amino Acid and Peptide Synthesis*, J. Jones, (Oxford Chemistry Primers) 2$^{nd}$ edition 2002, Oxford university press, *The practice of peptide synthesis*, 2003, 2nd edition, M. Bodansky and A. Bodansky, Springer-Verlag, New York and references therein. It will also be recognised that certain reactive groups may require protection and deprotection during the synthetic process. Suitable protecting and deprotecting methods for reactive functional groups are known in the art for example in *Protective Groups in Organic Synthesis*, T. W. Greene & P. Wutz, John Wiley & Son, 3$^{rd}$ Edition, 1999.

Compounds of formula (I) as described above, may be prepared by reacting a compound of formula (A):

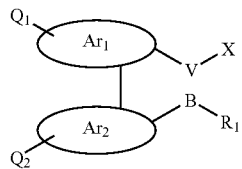

A wherein X is OH or an activating group; with a compound of formula (B) under appropriate conditions.

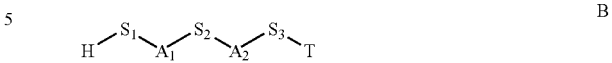

B wherein B, $R_1$, $Ar_1$, $Ar_2$, V, $Q_1$, $Q_2$, $S_1$, $A_1$, $S_2$, $A_2$, $S_3$, T are as defined in formula (I).

Conveniently the reaction between compounds formulae (A) and (B) is based upon forming an amide bond and may be conducted using approaches routinely used in peptide synthesis. For example, the coupling reaction of an amine with a carboxylic acid (X=OH) or an activated carbonyl carbon such as an acyl chloride, acyl azide, acyl-succinimide or an anhydride (X=Cl, N3, O-succinimde, OC(O)R).

Compounds of the formula (A) may be conveniently prepared from an aromatic or heteroaromatic ring system carrying any of;

desired substituents functional groups which may be converted into desired substituents using conventional approaches known to those skilled in the art; or appropriately activated positions on the nucleus of the ring system such that desired substituents may be placed on the ring system using conventional approaches known to those skilled in the art.

In addition the ring system $Ar_1$—$Ar_2$ includes a position that may be converted into the group BR1. This position may be a functional group or may be an appropriately activated position on the ring to allow conversion into functional groups using conventional approaches known to those skilled in the art. For example functional groups include hydroxyl, amino and suitably protected derivatives of these. Examples of suitably activated positions include those which may be alkylated or acylated such as phenoxide.

The compound of formula (B) can be prepared using any suitable approach readily ascertainable to those skilled in the art. Preferably compound (B) can be formed by reactions of suitably protected amino acids in a suitable sequence. In one preferred approach this is based upon formation of amide bonds and may be conducted using approaches routinely used in peptide synthesis, for example, the reaction of an amine with an appropriately activated carbonyl group. Preferably compound (B) may have a protecting group on the amino terminus of S1 or S2 which is removed once the group S1A1S2A2S3T has been formed to allow coupling of S1 or A1 to V of compound (A). Those skilled in the art can readily determine the appropriate methodology to build the desired group (B).

Where appropriate, protecting groups may be used to mask certain positions on the compounds of formulae (A) and (B) so as to avoid or limit unwanted side reactions.

Suitable aromatic or heteroaromatic ring systems may be commercially available or be readily prepared from commercially available ring systems or ring system precursors.

The compounds of the present invention may be prepared according to the general procedure of Scheme 1. Although this process is illustrated using specific reagents and compounds, it will be appreciated by one of skill in the art that suitable analogous reagents may be used to prepare analogous products, as depicted, for example, in scheme 1.

As would be understood by persons skilled in the art compounds of formulae II and III can be prepared by similar methods (after appropriate modification) to those used to produce compounds of formula I.

Example 1

Preparation and Biological Activity of Compounds According to the Present Invention General Synthetic Procedures Protocol 1: Peptide Coupling To a stirred solution of an acid (1 equiv.) and an amine (1 equiv.) in dry acetonitrile or DMF (5-10 mls) was added EDCI (1.2 equiv.) and HObt (1.2 equiv.). If the amine was a HCl salt then 1 equivalent of DIPEA was also added. The reaction mixture was stirred overnight before the solvent was removed and the resultant residue subjected to flash silica gel column chromatography (normally using 2% MeOH/DCM as the eluant) to afford the desired compound Protocol 2: N-Fmoc Deprotection To a stirring solution of the Fmoc-protected peptide in dry acetonitrile (5-10 mls) was added piperidine (0.1 ml). The resultant solution was then stirred at room temperature for 3 hours. The solvent was then removed and the resultant residue subjected to flash silica gel chromatography using a short column (using 2% MeOH/DCM then 5% MeOH/DCM upon removal of Fmoc byproducts) to afford the desired compound.

Protocol 3: N-Boc & PMC/PBF Deprotection

To a stirring solution of the protected peptide in DCM (2 mls) was added TFA (2 mls). The reaction mixture was stirred at room temperature for three hours before the solvent was removed. After triturating twice more with DCM (2 mls), the residue was taken up in DCM (2 ml) and treated with a HCl/ether solution (2 ml, 1M), stirred for a minute and evaporated to dryness. This treatment with HCl was repeated twice more. For BOC-deprotection this is the final step, for PMC/PBF-deprotection the following is completed. The residue is taken up in DCM (or dry MeOH if insoluble in DCM), precipitated by the addition of ether and the solid collected by centrifugation. This step is repeated once more to remove the protecting group byproduct. The resultant solid is then dried to yield the desired compound as its hydrochloride salt.

Protocol 4

To a stirring solution of the acid, alcohol, and triphenylphosphine in THF at 0° C. under a nitrogen atmosphere was added DIAD dropwise. The solution was allowed to warm to room temperature and stirred overnight. The solvent was then removed in vacuo and the resulting residue purified by flash column chromatography over silica to yield the desired product.

Protecting Groups

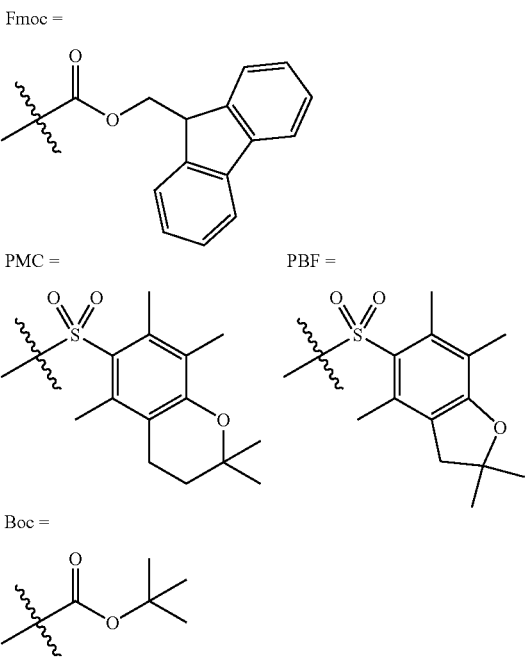

General Notes

Melting point determinations were carried out on a Gallenkamp melting point apparatus. Chemical ionization (CI) and electron impact (EI) mass spectra were obtained on a Shimadzu QP-5000 mass spectrometer by a direct insertion technique with an electron beam energy of 70 eV. Electrospray (ES) m/z mass spectra were obtained on a VG Autospec spectrometer. High-resolution mass spectra (HRMS) were determined on a micromass QT of 2 spectrometer using polyethylene glycol or polypropylene glycol as the internal standard. The m/z values are stated with their peak intensity as a percentage in parentheses. Proton and carbon nuclear magnetic resonance (NMR) spectra were obtained as specified on a Varian Mercury 300 MHz or Varian Inova 500 MHz spectrometer. Spectra were recorded in the specified deuterated solvent, and referenced to the residual non-deuterated solvent signal. Chemical shifts (δ) in ppm were measured relative to the internal standard. Multiplet (m) signals are reported from the centre of the peak. Analytical thin layer chromatography (TLC) was carried out on Merck silica gel 60 $F_{254}$ pre-coated aluminium plates with a thickness of 0.2 mm. All column chromatography was performed under 'flash' conditions on Merck silica gel 60 (230-400 mesh). Chromatography solvent mixtures were measured by volume. All compounds were judged to be of greater than 95% purity based upon $^1$H NMR and TLC analysis. Starting materials and reagents were purchased from Sigma-Aldrich Pty Ltd or Auspep Pty Ltd and were used as received.

General Synthetic Scheme (Example - Compound 1)

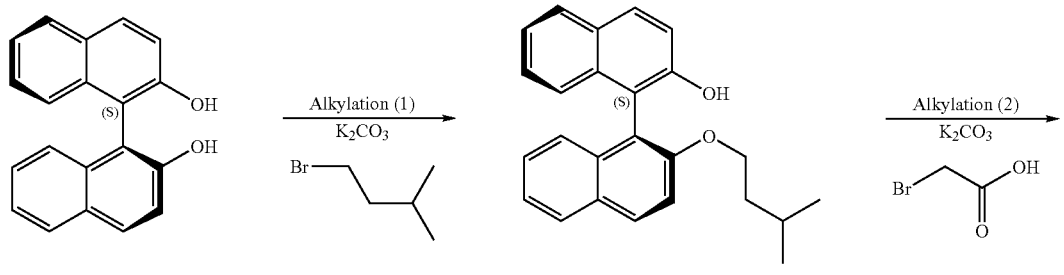

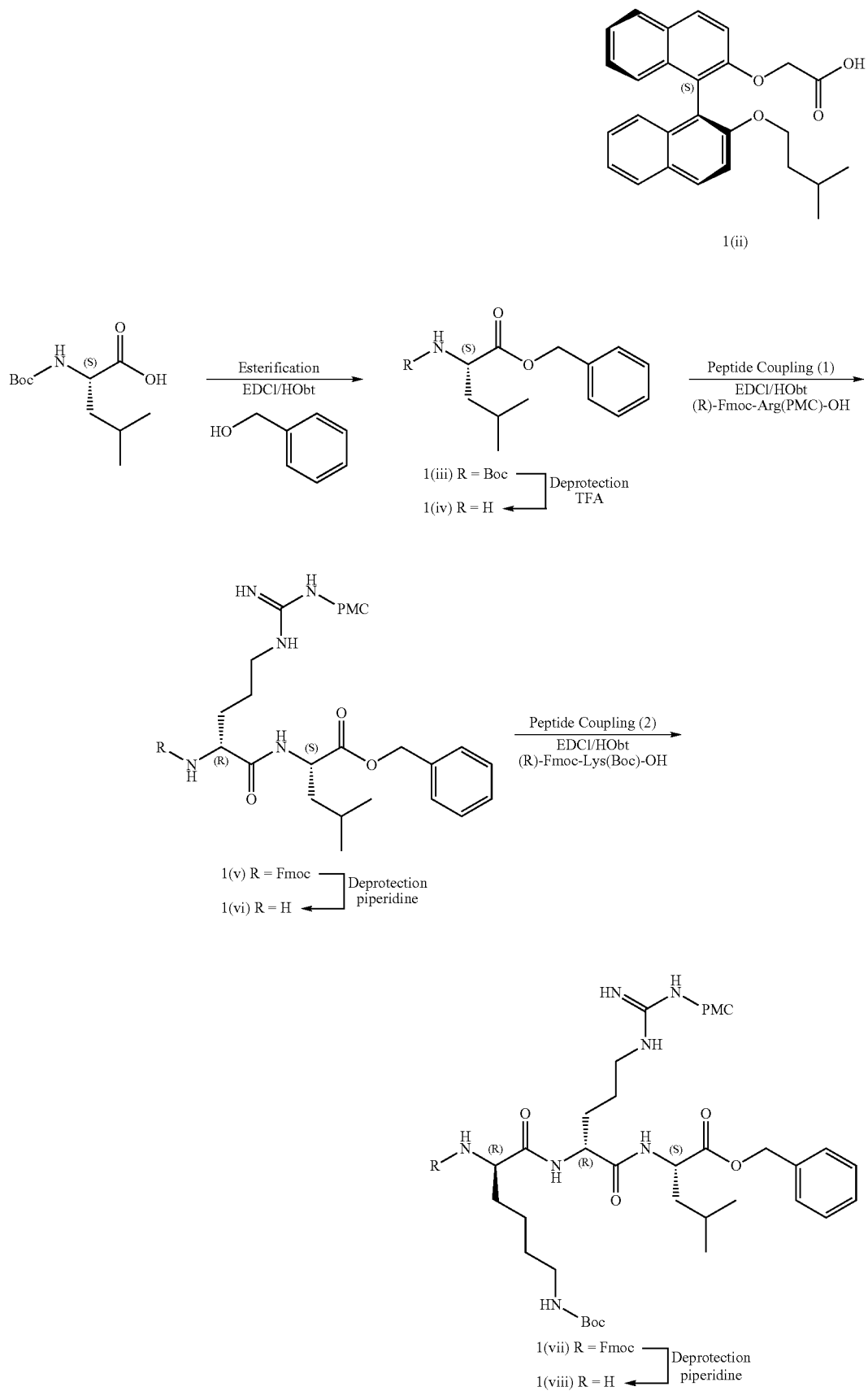

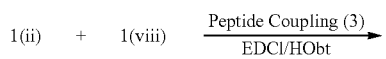

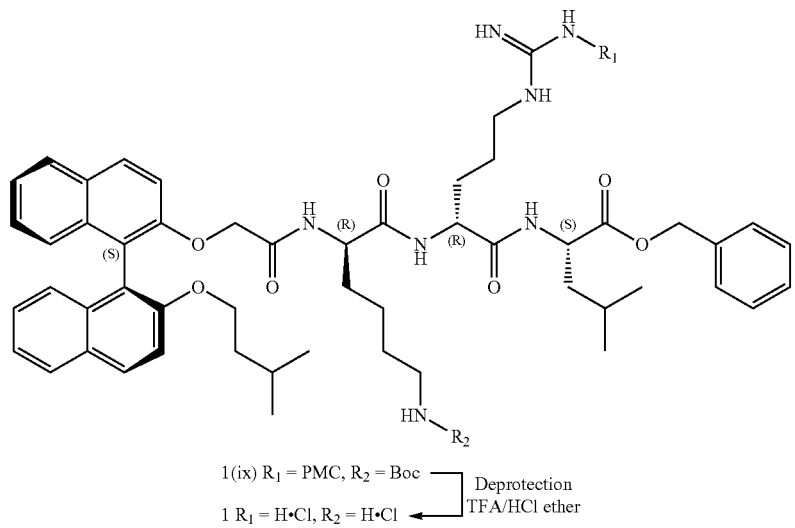

1(ix) R$_1$ = PMC, R$_2$ = Boc ⎤ Deprotection
1 R$_1$ = H·Cl, R$_2$ = H·Cl ⎦ TFA/HCl ether Compounds of Formula I
Synthesis of Compound 1

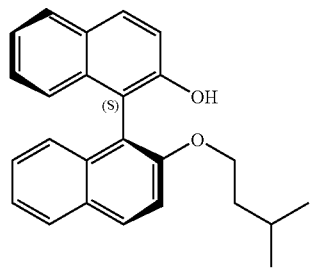

1(i)

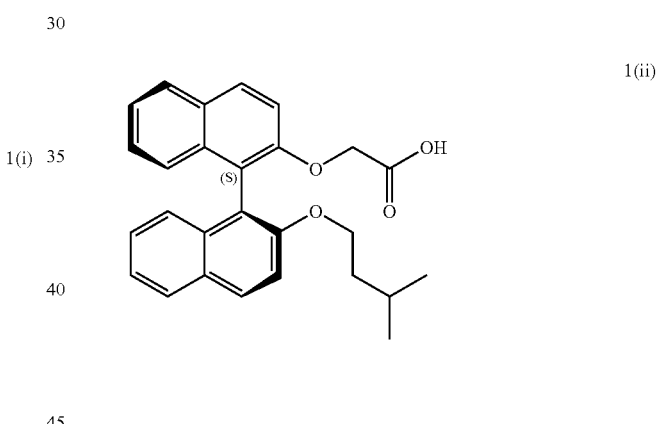

1(ii)

To a solution of 1,1'-binaphth-2,2'-diol (1 g, 3.49 mmol) in dry acetone (100 ml) was added anhydrous potassium carbonate (5 g). A solution of 1-bromo-3-methylbutane (0.52 ml, 4.19 mmol) in acetone (30 ml) was added dropwise over a 90 min period. The mixture was then heated at reflux for 3 hrs and left to sit overnight before being cooled and filtered. The solid residue was then washed twice more with acetone (10 ml) before the combined organic extracts were evaporated to dryness to yield a honey coloured oil. Subsequent flash column chromatography with 1:1 DCM/Hexane as the eluant affords the desired product 1(i) as a yellow oil (705 mg, 57%). R$_f$=0.64 (1:1 hexane/DCM). Starting diol was also recovered (357 mg, 36%) indicating the reaction had not gone to completion.

$^1$H NMR (300 MHz, CDCl$_3$) δ 0.61, d, J=6.5 Hz, 3H, 0.65, d, J=6.5 Hz, 3H, 1.32, m, 3H, 3.98, m, 2H, 4.95, s, OH; 7.04, dist d, J=7.8 Hz, 1H, 7.25, m, 7H, 7.42, d, J=9.1 Hz, 1H, 7.84, d, J=7.8 Hz, 1H, 7.87, d, J=8.7 Hz, 1H, 7.99, d, J=9.0, Hz, 1H.

To 1(i) (532 mg, 1.49 mmol) in dry MeOH (25 ml) was added potassium carbonate (2.06 g, 14.9 mmol) and bromoacetic acid (1.03 g, 7.45 mmol). The resultant solution was then heated at reflux for 8 hrs over which time a white ppte had fallen out of solution. The reaction mixture was then evaporated to dryness and the residue dissolved in water (50 ml). This was then washed with ether (3×30 ml) before the aqueous layer was acidified with 3M HCl. This acidified solution was then extracted with DCM (3×30 ml) to yield a yellow solution. This yellow solution was then dried (MgSO$_4$) and evaporated to dryness to yield the product 1(ii) as a yellow oil (325 mg, 53%). Starting material was also recovered (135 mg, 25%) indicating the reaction had not gone to completion.

$^1$H NMR (300 MHz, CDCl$_3$) δ 0.54, d, J=6.5 Hz, 3H, 0.64, d, J=6.5 Hz, 3H, 1.19, m, 1H, 1.30, m, 2H, 3.94, m, 1H, 4.13, m, 1H, 4.57, ABq, J=16.8 Hz, 1H, 4.69, ABq, J=16.8 Hz, 1H, 7.26, m, 4H, 7.37, m, 3H, 7.48, d, J=8.8 Hz, 1H, 7.90, d, J=8.2 Hz, 2H, 7.97, d, J=8.8 Hz, 1H, 8.00, d, J=8.8, Hz, 1H, 8.06, br s, COOH. MS (EI +ve) 414 (100%) [M+H]$^+$.

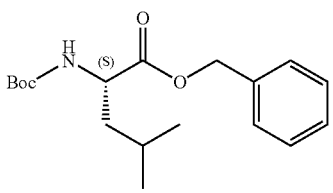

1(iii)

This compound was prepared via Protocol 1, using BOC-(L)-leu-OH (600 mg, 2.59 mmol) and BzOH (0.41 ml, 4.0 mmol) to yield the desired product 1(iii) as an off white solid (512 mg, 62%). $R_f$=0.78 (5% MeOH/DCM), staining with Mo dip.

$^1$H NMR (300 MHz, CDCl$_3$) δ 0.91, d, J=6.5 Hz, 6H, 1.44, m, 2H, 1.45, s, 9H, 1.66, m, 1H, 4.36, m, 1H, 5.08, ABq, J=12.3 Hz, 1H, 5.17, ABq, J=12.3 Hz, 1H, 5.27, d, J=8.4 Hz, NH; 7.31, m, 5H. MS (ES +ve) m/z 322 (100%) [M+H]$^+$.

1(iv)

To 1(iii) (510 mg, 1.59 mmol) dissolved in DCM (2 ml) was added TFA (2 ml) and the resulting solution stirred at room temperature for 1 hr. Ethyl acetate (15 ml) was then added and the solution washed with sat. sodium bicarbonate solution until the washings were basic. The organic layer was then dried (MgSO$_4$) and evaporated to dryness to yield the desired product 1(iv) as a colourless oil (172 mg, 49%). $R_f$=0.37 (5% MeOH/DCM), staining with Mo dip.

$^1$H NMR (300 MHz, CDCl$_3$) δ 0.88, d, J=6.4 Hz, 3H, 0.90, d, J=6.4 Hz, 3H, 1.43, m, 2H, 1.54, m, 1H, 1.72, m, 1H, 1.74, m, NH$_2$; 3.48, m, 1H, 5.12, s, 2H, 7.32, m, 5H. MS (ES +ve) m/z 222 (100%) [M+H]$^+$.

1(v)

This compound was prepared via Protocol 1 using 1(iv) (160 mg, 0.723 mmol) and Fmoc-(D)-arg(Pmc)-OH (662.8 mg, 1.00 mmol) to yield the desired product 1(v) as an off white solid (460 mg, 73%).

$^1$H NMR (300 MHz, CDCl$_3$) δ 0.81, m, 6H, 1.21, s, 6H, 1.58, m, 5H, 1.67, m, 3H, 1.85, m, 1H, 2.04, s, 3H, 2.49, m, 2H, 2.54, s, 3H, 2.58, s, 3H, 3.21, m, 2H, 4.04, m, 1H, 4.23, m, 3H, 4.52, m, 1H, 5.02, ABq, J=12.3 Hz, 1H, 5.08, ABq, J=12.3 Hz, 1H, 6.22, br s, NH; 6.36, bs, NH; 7.25, m, 9H, 7.50, d, J=7.3 Hz, 2H, 7.69, d, J=7.3 Hz, 2H. MS (ES +ve) m/z 888 (100%) [M+Na]$^+$; 866 (10) [M+H]$^+$.

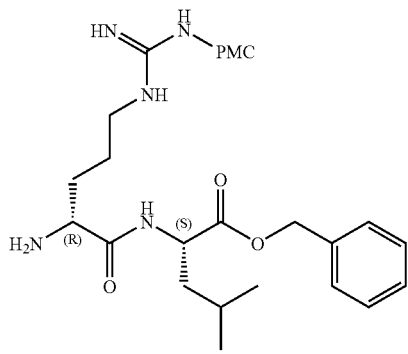

1(vi)

This compound was prepared via Protocol 2, using 1(v) (450 mg, 0.520 mmol) to yield the desired product 1(vi) as an off white solid (244 mg, 73%). $R_f$=0.07 (5% MeOH/DCM).

$^1$H NMR (300 MHz, CDCl$_3$) δ 0.88, m, 6H, 1.28, s, 6H, 1.57, m, 5H, 1.77, m, 2H, 1.86, m, 2H, 2.08, s, 3H, 2.54, s, 3H, 2.58, s, 3H, 2.60, m, 2H, 3.14, m, 2H, 3.38, m, 1H, 4.51, m, 1H, 5.05, ABq, J=12.3 Hz, 1H, 5.13, ABq, J=12.3 Hz, 1H, 6.33, br s, NH; 6.38, br s, NH; 7.29, m, 5H, 7.78, d, J=7.6 Hz, NH. MS (ES +ve) m/z 644 (100%) [M+H]$^+$.

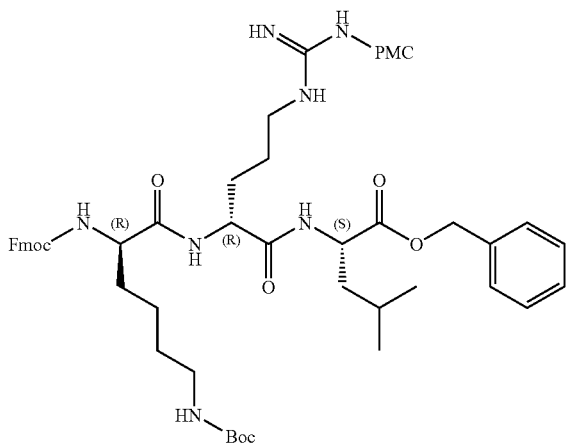

1(vii)

This compound was prepared via Protocol 1, using 1(vi) (240 mg, 0.373 mmol) and Fmoc-(D)-lys(BOC)-OH (187 mg, 0.4 mmol) to yield the desired product 1(vii) as an off white solid (336 mg, 82%). $R_f$=0.28 (5% MeOH/DCM).

$^1$H NMR (300 MHz, CDCl$_3$) δ 0.83, m, 6H, 1.17, m, 2H, 1.18, s, 6H, 1.40, s, 9H, 1.40, m, 2H, 1.60, m, 11H, 2.02, s, 3H, 2.51, m, 2H, 2.52, s, 3H, 2.55, s, 3H, 3.02, m, 2H, 3.18, m, 2H, 3.91, m, 1H, 4.18, m, 3H, 4.52, m, 1H, 5.00, m, 2H, 6.48, br s, NH; 7.25, m, 9H, 7.43, d, J=7.6 Hz, NH; 7.52, m, 2H, 7.69, d, J=7.6 Hz, 2H. MS (ES +ve) m/z 1116 (80%) [M+Na]$^+$; 1094 (100) [M+H]$^+$.

1(viii)

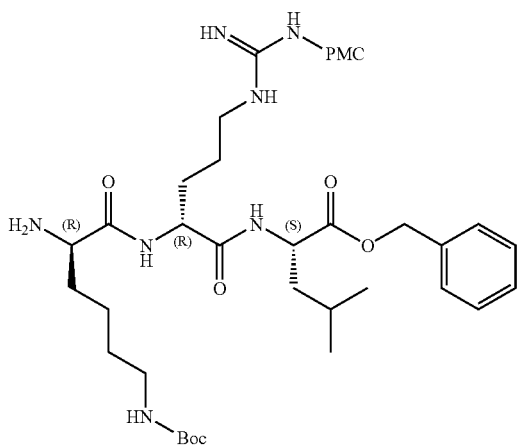

This compound was prepared via Protocol 2, using 1(vii) (330 mg, 0.302 mmol) to yield the desired product 1(viii) as an off white solid (239 mg, 91%). $R_f$=baseline (5% MeOH/DCM).

$^1$H NMR (300 MHz, CDCl$_3$) δ 0.82, d, J=5.8 Hz, 3H, 0.84, d, J=5.8 Hz, 3H, 1.23, m, 2H, 1.27, s, 6H, 1.38, s, 9H, 1.40, m, 2H, 1.60, m, 11H, 2.07, s, 3H, 2.52, s, 3H, 2.54, s, 3H, 2.58, m, 2H, 3.01, m, 2H, 3.19, m, 2H, 3.29, m, 1H, 4.52, m, 2H, 4.92, m, NH; 5.03, ABq, J=12.3 Hz, 1H, 5.09, ABq, J=12.3 Hz, 1H, 6.39, br s, NH; 7.28, m, 5H, 7.58, d, J=7.9 Hz, NH; 7.95, d, J=7.3 Hz, NH. MS (ES +ve) m/z 872 (100%) [M+H]$^+$.

1(ix)

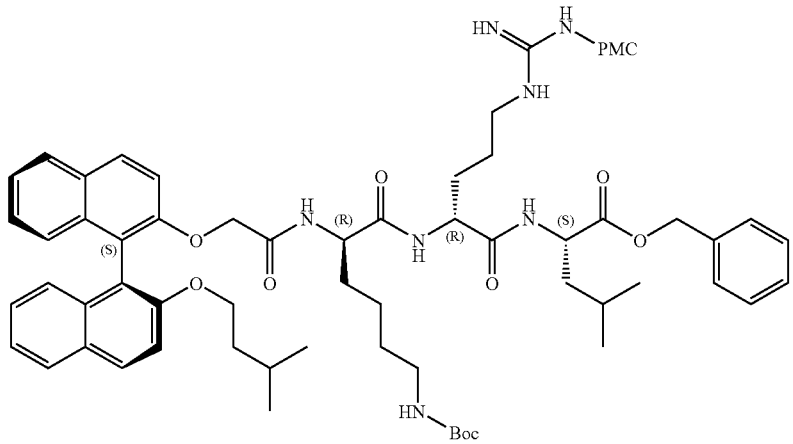

This compound was prepared via Protocol 1, using 1(ii) (50 mg, 0.121 mmol) and 1(viii) (110 mg, 0.126 mmol) to yield the product 1(ix) as a white solid (114 mg, 74%). $R_f$=0.16 (5% MeOH/DCM).

$^1$H NMR (300 MHz, CDCl$_3$) δ 0.46, d, J=6.2 Hz, 3H, 0.52, d, J=6.2 Hz, 3H, 0.89, m, 9H, 1.20, m, 5H, 1.28, s, 6H, 1.39, m, 2H, 1.41, s, 9H, 1.70, m, 7H, 2.09, s, 3H, 2.55, s, 3H, 2.57, s, 3H, 2.61, m, 2H, 2.89, m, 2H, 3.10, m, 2H, 3.86, m, 1H, 4.04, m, 2H, 4.48, m, 4H, 4.82, m, NH; 5.07, ABq, J=12.6 Hz, 1H, 5.16, ABq, J=12.6 Hz, 1H, 6.18, d, J=7.0 Hz, NH; 6.29, br s, NH; 6.48, br s, NH; 7.20, m, 4H, 7.31, m, 7H, 7.45, d, J=9.1 Hz, 2H, 7.85, m, 2H, 7.95, m, 2H, 8.06, d, J=8.8 Hz, NH. MS (ES +ve) m/z 1291 (70%) [M+Na]$^+$; 1268 (100) [M+H]$^+$.

Compound 1

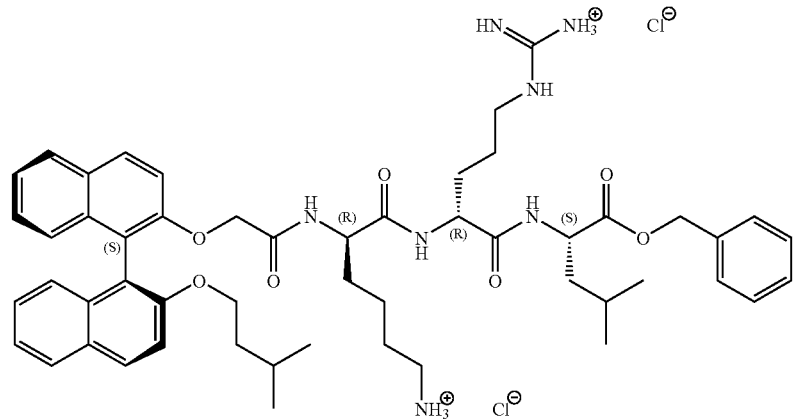

This compound was prepared via Protocol 3, using 1(ix) (104 mg, 0.082 mmol) to yield the desired compound 1 as a white solid (78 mg, 98%).

$^1$H NMR (300 MHz, CD$_3$OD) δ 0.38, d, J=6.2 Hz, 3H, 0.43, d, J=6.2 Hz, 3H, 0.80, m, 9H, 1.07, m, 3H, 1.52, m, 10H; 2.69, m, 2H, 3.05, m, 2H, 3.82, m, H, 4.01, m, 2H, 4.35, m, 4H, 5.03, m, 2H, 6.94, m, 2H, 7.06, m, 2H, 7.21, m, 7H, 7.34, d, J=9.1 Hz, 1H, 7.42, d, J=9.1 Hz, 1H, 7.85, m, 4H. MS (ES +ve) m/z 902 (10%) [M+H]$^+$; 452 (100) [M+H]$^{2+}$.

Synthesis of Compound 2

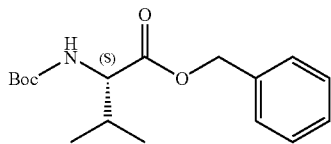

2(i)

To BOC-(L)-val-OH (100 mg, 0.48 mmol) and potassium carbonate (160 mg, 1.16 mmol) in acetone (10 ml) was added benzyl bromide (0.1 ml, 0.84 mmol). The resulting solution was heated at reflux overnight before being cooled, filtered and evaporated to dryness. The resultant residue was then subjected to flash column chromatography over silica, using initially 1:1 hexane/DCM to remove benzyl bromide, then DCM to yield the product 2(i) as a colourless oil (110 mg, 75%). R$_f$=0.38 (DCM) staining with Mo dip.

$^1$H NMR (300 MHz, CDCl$_3$) δ 0.84, d, J=7.0 Hz, 3H, 0.93, d, J=7.0 Hz, 3H, 1.43, s, 9H, 2.14, m, 1H, 4.27, dd, J$_1$=9.1 Hz, J$_2$=4.7 Hz, 1H, 5.05, obscured d, NH; 5.07, ABq, J=12.3 Hz, 1H, 5.20, ABq, J=12.3 Hz, 1H, 7.34, m, 5H. MS (ES +ve) m/z 308 (60%) [M+H]$^+$; 208 (100) [M+H-Boc]$^+$.

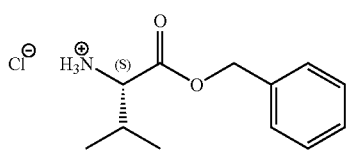

2(ii)

This compound was prepared via Protocol 3 using 2(i) (105 mg, 0.34 mmol) to give the product 2(ii) as an off white solid (65 mg, 92%).

$^1$H NMR (300 MHz, CDCl$_3$) δ 1.06, m, 6H, 2.44, m, 1H, 4.09, m, 1H, 5.13, ABq, J=12.0 Hz, 1H, 5.26, ABq, J=12.0 Hz, 1H, 7.32, m, 5H, 8.51, br s, NH$_3$$^+$.

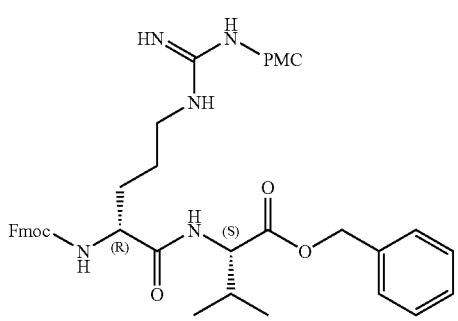

2(iii)

This compound was prepared via Protocol 1 using 2(ii) (136 mg, 0.800 mmol) and Fmoc-(D)-arg(Pmc)-OH (530 mg, 0.800 mmol) to yield the desired product 2(iii) as an off white solid (659 mg, 97%). R$_f$=0.40 (5% MeOH/DCM).

$^1$H NMR (300 MHz, CDCl$_3$) δ 0.79, d, J=7.0 Hz, 3H, 0.83, d, J=7.0 Hz, 3H, 1.23, s, 6H, 1.60, m, 2H, 1.68, m, 3H, 1.87, m, 1H, 2.04, s, 3H, 2.11, m, 1H, 2.52, m, 2H, 2.53, s, 3H, 2.56, s, 3H, 3.20, m, 2H, 4.05, m, 1H, 4.25, m, 3H, 4.45, dd, J=8.5 Hz, J$_2$=5.6 Hz, 1H, 5.00, ABq, J=12.3 Hz, 1H, 5.10, ABq, J=12.3 Hz, 1H, 6.27, m, NH; 7.21, m, 2H, 7.26, m, 5H, 7.31, m, 2H, 7.50, d, J=7.3 Hz, 2H, 7.69, d, J=7.6 Hz, 2H. MS (ES +ve) m/z 852 (100%) [M+H]$^+$.

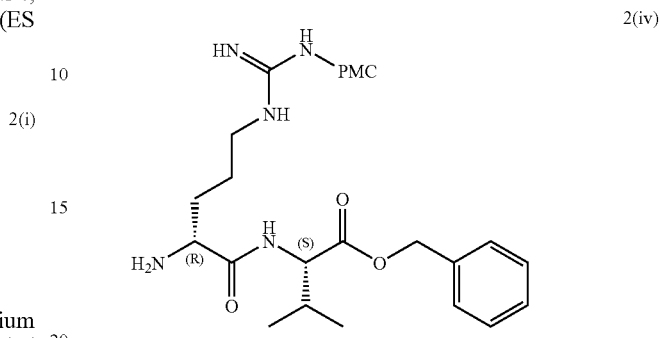

2(iv)

This compound was prepared via Protocol 2, using 2(iii) (604 mg, 0.709 mmol) to yield the desired product 2(iv) as a colourless oil (361 mg, 81%). R$_f$=baseline (5% MeOH/DCM).

$^1$H NMR (300 MHz, CDCl$_3$) δ 0.85, d, J=7.0 Hz, 3H, 0.88, d, J=7.0 Hz, 3H, 1.28, s, 6H, 1.53, m, 3H, 1.77, m, 3H/NH$_2$; 2.08, s, 3H, 2.17, m, 1H, 2.53, s, 3H, 2.55, s, 3H, 2.59, m, 2H, 3.13, m, 2H, 3.38, m, 1H, 4.40, dd, J=8.5 Hz, J$_2$=5.3 Hz, 1H, 5.15, ABq, J=12.3 Hz, 1H, 5.15, ABq, J=12.3 Hz, 1H, 6.38, br s, NH; 7.30, m, 5H, 7.87, d, J=8.5 Hz, NH. MS (ES +ve) m/z 630 (100%) [M+H]$^+$.

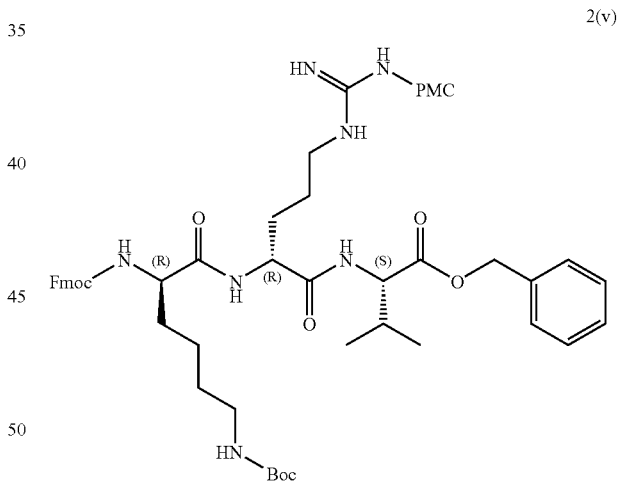

2(v)

This compound was prepared via Protocol 1, using 2(iv) (350 mg, 0.556 mmol) and Fmoc-(D)-lys(BOC)-OH (260 mg, 0.555 mmol) to yield the desired product 2(v) as an off white solid (592 mg, 99%). R$_f$=0.25 (5% MeOH/DCM).

$^1$H NMR (300 MHz, CDCl$_3$) δ 0.87, m, 6H, 1.21, s, 3H, 1.22, s, 3H, 1.41, m, 13H, 1.67, m, 4H, 1.75, m, 3H, 1.88, m, 1H, 2.05, s, 3H, 2.18, m, 1H, 2.52, m, 2H, 2.54, s, 3H, 2.57, s, 3H, 3.03, m, 2H, 3.19, m, 2H, 4.01, m, 1H, 4.28, m, 3H, 4.52, m, 1H, 4.61, m, 1H, 4.98, ABq, J=12.3 Hz, 1H, 5.04, m, NH; 5.12, ABq, J=12.3 Hz, 1H, 6.48, br m, NH; 7.27, m, 7H, 7.33, m, 2H, 7.45, d, J=8.2 Hz, NH; 7.55, m, 2H, 7.70, d, J=7.0 Hz, 2H, 7.89, m, NH. MS (ES +ve) m/z 1080 (20%) [M+H]$^+$; 559.8 (100) [M+H+K]$^{2+}$.

2(vi)

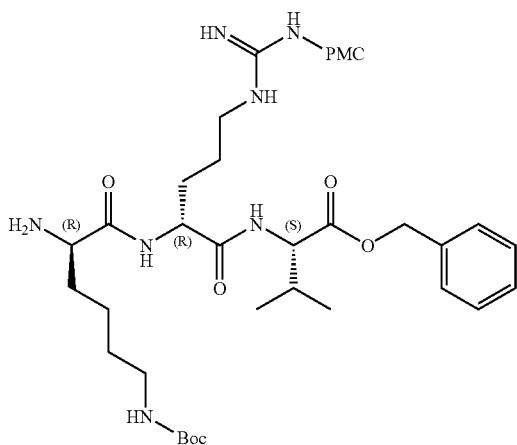

This compound was prepared via Protocol 2, using 2(v) (350 mg, 0.324 mmol) to yield the desired product 2(vi) as an off white solid (204 mg, 79%). $R_f$=baseline (5% MeOH/DCM).

$^1$H NMR (300 MHz, CDCl$_3$) δ 0.82, δ, J=6.7 Hz, 3H, 0.86, d, J=6.7 Hz, 3H, 1.27, s, 6H, 1.30, m, 4H, 1.38, s, 9H, 1.52, m, 2H, 1.69, m, 2H, 1.76, dist t, 2H, 1.85, m, 2H, 2.07, s, 3H, 2.12, m, 1H, 2.52, s, 3H, 2.54, s, 3H, 2.58, m, 2H, 3.01, m, 2H, 3.18, m, 2H, 3.30, m, 1H, 4.46, m, 1H, 4.61, m, NH; 5.02, ABq, J=12.3 Hz, 1H, 5.12, ABq, J=12.3 Hz, 1H, 6.40, br s, NH; 7.28, m, 5H, 7.52, d, J=8.5 Hz, NH; 7.99, d, J=7.0 Hz, NH. MS (ES +ve) m/z 858 (100%) [M+H]$^+$.

2(vii)

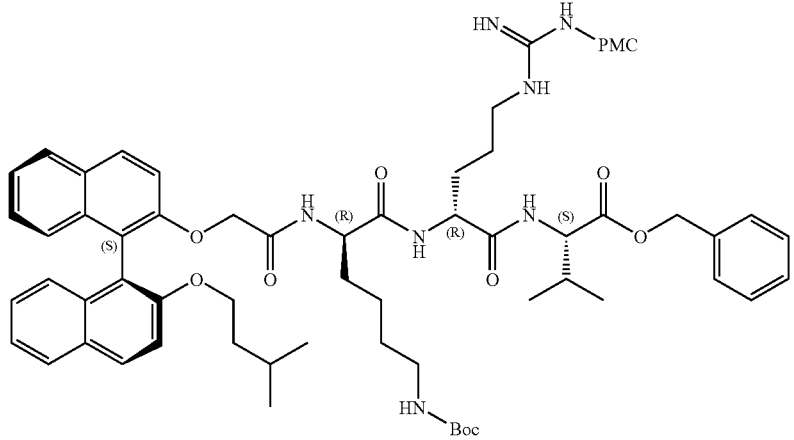

This compound was prepared via Protocol 1, using 1(ii) (92 mg, 0.222 mmol) and 2(vi) (190 mg, 0.222 mmol) to yield the product 2(vii) as a white solid (180 mg, 65%). $R_f$=0.11 (5% MeOH/DCM).

$^1$H NMR (300 MHz, CDCl$_3$) δ 0.48, d, J=6.4 Hz, 3H, 0.53, d, J=6.4 Hz, 3H, 0.82, m, 2H, 0.87, t, J=7.0 Hz, 6H, 1.18, m, 6H, 1.28, s, 6H, 1.41, s, 9H, 1.60, m, 1H, 1.76, dist t, 2H, 1.85, m, 1H, 2.08, s, 3H, 2.20, m, 1H, 2.54, s, 3H, 2.56, s, 3H, 2.58, m, 2H, 2.89, m, 2H, 3.14, m, 2H, 3.87, m, 1H, 4.06, m, 2H, 4.45, m, 4H, 4.82, m, NH; 5.08, ABq, J=12.3 Hz, H, 5.19, ABq, J=12.3 Hz, 1H, 6.22, m, NH; 7.13, m, 2H, 7.25, m, 2H, 7.35, m, 8H, 7.46, d, J=9.1 Hz, 1H, 7.83, d, J=7.6 Hz, 1H, 7.85, d, J=7.9 Hz, 1H, 7.93, d, J=8.8 Hz, 1H, 7.94, d, J=9.1 Hz, 1H. MS (ES +ve) m/z 1255 (100%) [M+H]$^+$.

Compound 2

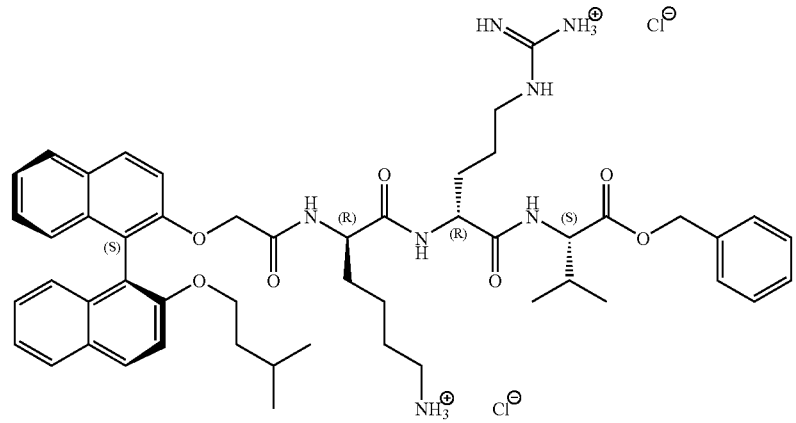

This compound was prepared via Protocol 3, using 2(vii) (100 mg, 0.080 mmol) to yield the product 2 as a white solid (49 mg, 64%).

$^1$H NMR (300 MHz, CD$_3$OD) δ 0.51, d, J=6.5 Hz, 3H, 0.56, d, J=6.5 Hz, 3H, 0.92, d, J=6.7 Hz, 6H, 0.94, m, 1H, 1.18, m, 3H, 1.61, m, 6H, 2.18, m, 1H, 2.79, m, 2H, 3.16, m, 2H, 3.94, m, 1H, 4.10, m, 2H, 4.48, m, 4H, 5.13, ABq, J=12.3 Hz, 1H, 5.20, ABq, J=12.3 Hz, 1H, 7.06, m, 2H, 7.20, dist t, 2H, 7.35, m, 7H, 7.46, d, J=8.8 Hz, 1H, 7.55, d, J=9.1 Hz, 1H, 7.89, d, J=7.9 Hz, 1H, 7.91, d, J=8.2 Hz, 1H, 8.00, d, J=9.1 Hz, 2H. MS (ES +ve) m/z 888 (10%) [M+H]$^+$; 445 (100) [M+2H]$^{2+}$.

Synthesis of Compound 3

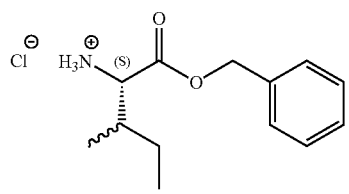

3(i)

To BOC-(L)-Ile-OH (200 mg, 0.86 mmol) and potassium carbonate (300 mg, 2.16 mmol) in acetone (20 ml) was added benzyl bromide (0.2 ml, 1.72 mmol). The resulting solution was heated at reflux overnight before being cooled, filtered and evaporated to dryness. The resultant residue was subjected to flash column chromatography over silica, eluting first with 1:1 hexane/DCM to remove benzyl bromide, then with DCM. The product 3(i) was isolated as a colourless oil (253 mg, 91%). R$_f$=0.28 (DCM) using Mo stain.

$^1$H NMR (300 MHz, CDCl$_3$) δ 0.88, m, 6H, 1.12, m, 1H, 1.38, m, 1H, 1.43, s, 9H, 1.86, m, 1H, 4.31, m, 1H, 5.05, m, NH; 5.10, ABq, J=12.3 Hz, 1H, 5.20, ABq, J=12.3 Hz, 1H, 7.33, m, 5H.

3(ii)

This compound was prepared via Protocol 3, using 3(i) (115 mg, 0.358 mmol) to yield the desired product 3(ii) as an off white solid hydrochloride salt (80 mg, 87%).

$^1$H NMR (300 MHz, CDCl$_3$) δ 0.90, t, J=7.1 Hz, 3H, 1.03, d, J=6.8 Hz, 3H, 1.43, m, 2H, 2.16, m, 1H, 4.14, m, 1H, 5.13, ABq, J=12.0 Hz, 1H, 5.26, ABq, J=12.0 Hz, 1H, 7.33, m, 5H, 8.62, br s, NH$_3^+$.

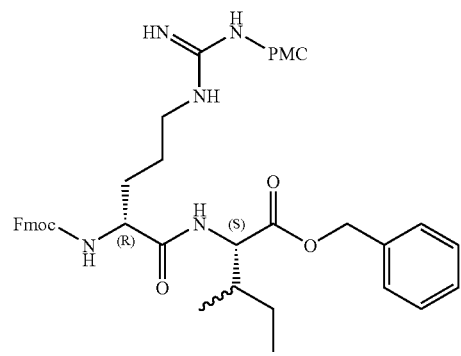

3(iii)

This compound was prepared via Protocol 1 using 3(ii) (173 mg, 0.778 mmol) and Fmoc-(D)-arg(Pmc)-OH (520 mg, 0.785 mmol) to yield the desired product 3(iii) as an off white solid (452 mg, 79%). R$_f$=0.40 (5% MeOH/DCM).

$^1$H NMR (300 MHz, CDCl$_3$) δ 0.75, m, 6H, 1.11, m, 1H, 1.23, s, 6H, 1.30, m, 1H, 1.60, m, 2H, 1.70, dist t, 2H, 1.86, m, 2H, 1.99, m, 1H, 2.05, s, 3H, 2.50, m, 2H, 2.53, s, 3H, 2.56, s, 3H, 3.20, m, 2H, 4.06, dist t, 1H, 4.25, m, 3H, 4.50, dd, J=8.3 Hz, J$_2$=5.3 Hz, 1H, 5.01, ABq, J=12.0 Hz, 1H, 5.12, ABq, J=12.3 Hz, 1H, 6.13, br s, NH; 6.27, s, NH; 7.19, dist t, 2H, 7.26, m, 5H, 7.33, dist t, 2H, 7.51, d, J=7.5 Hz, 2H, 7.6, dist t, NH; 7.70, d, J=7.8 Hz, 2H. MS (ES +ve) m/z 866 (100%) [M+H]$^+$.

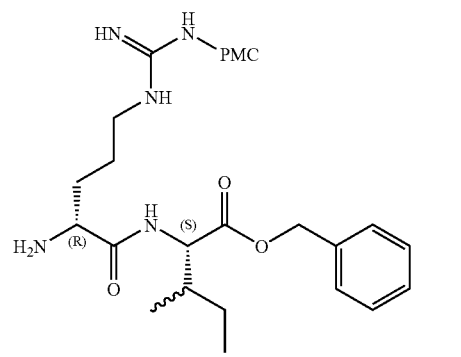

3(iv)

This compound was prepared via Protocol 2, using 3(iii) (540 mg, 0.623 mmol) to yield the desired product 3(iv) as a white solid (338 mg, 84%). R$_f$=baseline (5% MeOH/DCM).

$^1$H NMR (300 MHz, CDCl$_3$) δ 0.85, m, 6H, 1.13, m, 1H, 1.28, s, 6H, 1.34, m, 1H, 1.54, m, 3H, 1.66, m, 1H, 1.77, dist t, 2H, 1.90, m, 1H, 2.08, s, 3H, 2.54, s, 3H, 2.56, s, 3H, 2.60, dist t, 2H, 3.13, m, 2H, 3.37, m, 1H, 4.45, dd, J=8.5 Hz, J$_2$=5.3 Hz, 1H, 5.04, ABq, J=12.3 Hz, 1H, 5.16, ABq, J=12.3 Hz, 1H, 6.31, br s, NH; 6.38, br s, NH; 7.30, m, 5H, 7.87, d, J=8.5 Hz, NH. MS (ES +ve) m/z 644 (100%) [M+H]$^+$.

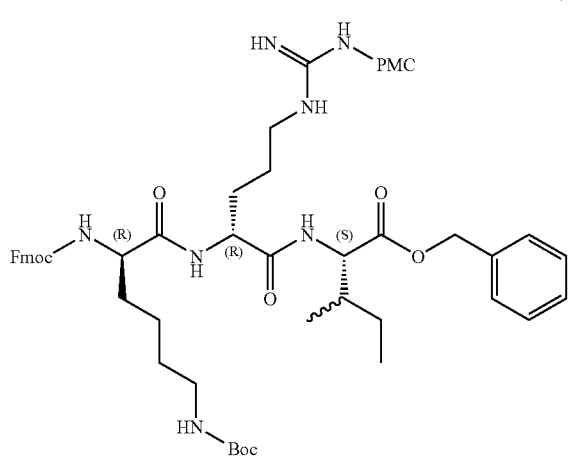

3(v)

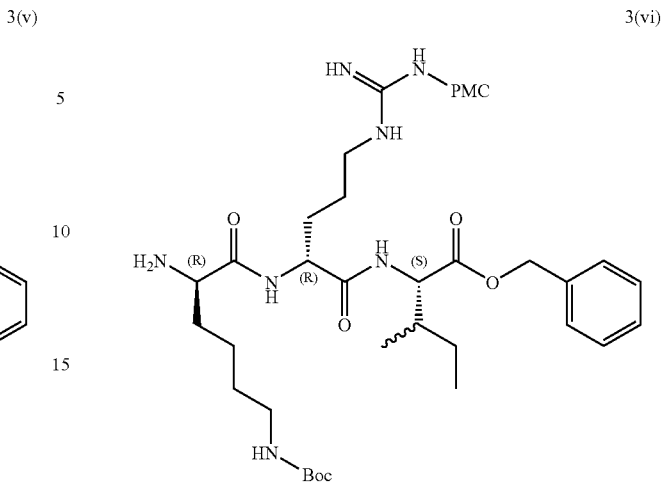

3(vi)

This compound was prepared via Protocol 1, using 3(iv) (300 mg, 0.466 mmol) and Fmoc-(D)-lys(BOC)-OH (218 mg, 0.465 mmol) to yield the desired product 3(v) as an off white solid (388 mg, 76%). $R_f$=0.25 (5% MeOH/DCM).

$^1$H NMR (300 MHz, CDCl$_3$) δ 0.83, m, 6H, 1.16, m, 1H, 1.21, s, 3H, 1.22, s, 3H, 1.38, m, 4H, 1.40, s, 9H, 1.67, m, 8H, 1.92, m, 2H, 2.04, s, 3H, 2.52, m, 2H, 2.53, s, 3H, 2.56, s, 3H, 3.03, m, 2H, 3.18, m, 2H, 4.01, dist t, 1H, 4.26, m, 3H, 4.54, m, 2H, 4.95, m, NH; 4.98, ABq, J=12.3 Hz, 1H, 5.13, ABq, J=12.3 Hz, 1H, 6.20, br s, NH; 6.41, br s, NH; 7.27, m, 9H, 7.54, m, 2H, 7.70, d, J=7.3 Hz, 2H. MS (ES +ve) m/z 1116 (80%) [M+Na]$^+$; 1094 (100) [M+H]$^+$.

This compound was prepared via Protocol 2, using 3(v) (388 mg, 0.355 mmol) to yield the desired product 3(vi) as an off white solid (268 mg, 87%). $R_f$=baseline (5% MeOH/DCM).

$^1$H NMR (300 MHz, CDCl$_3$) δ 0.82, m, 6H, 1.15, m, 1H, 1.26, s, 6H, 1.31, m, 2H, 1.37, m, 2H, 1.38, s, 9H, 1.51, m, 2H, 1.71, m, 6H, 1.86, m, 2H, 2.07, s, 3H, 2.52, s, 3H, 2.54, s, 3H, 2.59, m, 2H, 3.02, m, 2H, 3.18, m, 2H, 3.30, m, 1H, 4.51, m, 1H, 4.58, m, 1H, 4.93, m, NH; 5.01, ABq, J=12.3 Hz, 1H, 5.13, ABq, J=12.3 Hz, 1H, 6.39, br s, NH; 7.28, m, 5H, 7.49, d, J=8.5 Hz, NH; 7.98, d, J=7.9 Hz, NH. MS (ES +ve) m/z 872 (100%) [M+H]$^+$.

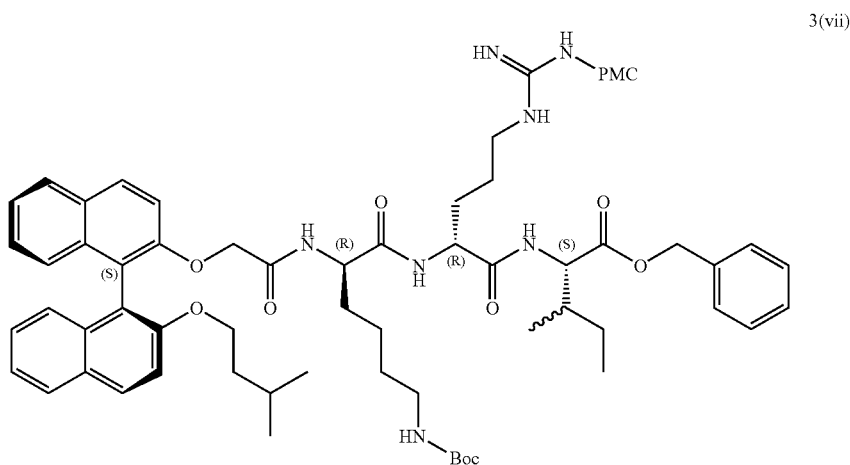

3(vii)

This compound was prepared via Protocol 1, using 1(ii) (119 mg, 0.287 mmol) and 3(vi) (250 mg, 0.287 mmol) to yield the product 3(vii) as a white solid (171 mg, 47%). $R_f$=0.07 (5% MeOH/DCM).

$^1$H NMR (300 MHz, CDCl$_3$) δ 0.48, d, J=6.4 Hz, 3H, 0.53, d, J=6.4 Hz, 3H, 0.87, m, 7H, 0.96, m, 1H, 1.20, m, 11H, 1.27, s, 6H, 1.41, s, 9H, 1.59, m, 1H, 1.75, m, 2H, 1.84, m, 1H, 1.92, m, 1H, 2.08, s, 3H, 2.54, s, 3H, 2.56, s, 3H, 2.57, m, 2H, 2.88, m, 2H, 3.11, m, 2H, 3.87, m, 1H, 4.09, m, 2H, 4.49, m, 4H, 5.07, ABq, J=12.3 Hz, 1H, 5.19, ABq, J=12.3 Hz, 1H, 6.24, br s, NH; 7.31, m, 12H, 7.44, d, J=9.1 Hz, 1H, 7.84, m, 2H, 7.92, m, 2H. MS (ES +ve) m/z 1269 (100%) [M+H]$^+$.

Compound 3

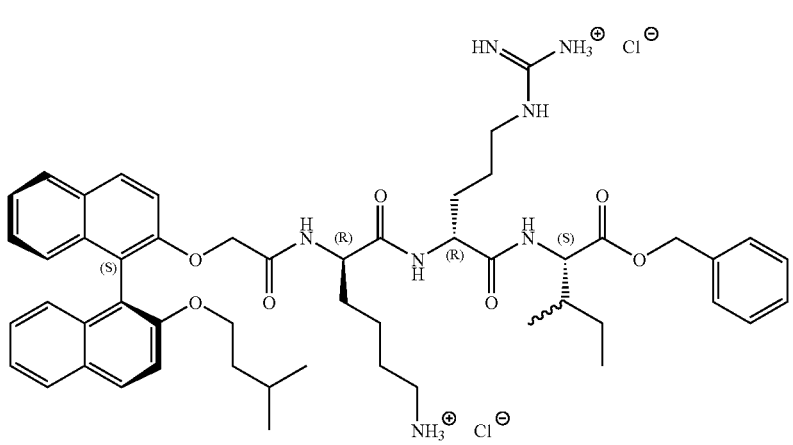

This compound was prepared via Protocol 3, using 3(vii) (170 mg, 0.134 mmol) to yield the product 3 as a white solid (127 mg, 97%).

$^1$H NMR (300 MHz, CD$_3$OD) δ 0.48, d, J=6.2 Hz, 3H, 0.53, d, J=6.2 Hz, 3H, 0.87, m, 7H, 0.96, m, 1H, 1.17, m, 5H, 1.57, m, 8H, 1.79, m, 1H, 1.91, m, 1H, 2.81, m, 2H, 3.16, m, 2H, 3.92, m, 1H, 4.10, m, 1H, 4.19, m, 1H, 4.43, m, 4H, 5.10, ABq, J=12.3 Hz, 1H, 5.19, ABq, J=12.3 Hz, 1H, 7.05, m, 2H, 7.16, m, 2H, 7.33, m, 7H, 7.43, d, J=9.1 Hz, 1H, 7.53, d, J=9.1 Hz, 1H, 7.85, m, 2H, 7.99, m, 2H. MS (ES +ve) m/z 902 (10%) [M+H]$^+$; 452.0 (100) [M+2H]$^{2+}$.

Synthesis of Compound 4

4(i)

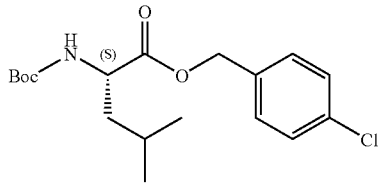

To BOC(L)-Leu-OH (250 mg, 1.08 mmol) and potassium carbonate (747 mg, 5.40 mmol) in acetone (50 ml) was added 4-chlorobenzyl bromide (333 mg, 1.62 mmol). The resulting solution was heated at reflux overnight before being cooled, filtered and evaporated to dryness. The resultant residue was subjected to flash column chromatography over silica, eluting with 1:4 hexane/DCM to first remove 4-chlorobenzyl bromide, then with DCM to yield the product 4(i) as a colourless oil (366 mg, 95%). R$_f$=0.55 (DCM) using Mo dip.

$^1$H NMR (300 MHz, CDCl$_3$) δ 0.89, d, J=6.4 Hz, 3H, 0.90, d, J=6.4 Hz, 3H, 1.41, s, 9H, 1.48, m, 2H, 1.64, m, 1H, 4.31, m, 1H, 4.95, d, J=8.2 Hz, NH; 5.06, ABq, J=12.3 Hz, 1H, 5.13, ABq, J=12.3 Hz, 1H, 7.25, ABq, J=8.4 Hz, 2H, 7.30, ABq, J=8.2 Hz, 2H. MS (ES +ve) m/z 356 (100%) [M+H]$^+$.

4(ii)

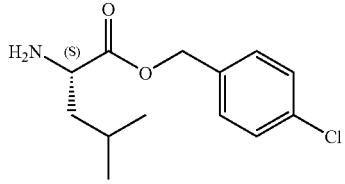

This compound was prepared via Protocol 4, using 4(i) (366 mg, 1.03 mmol) to yield the desired product 4(ii) as a colourless oil (235 mg, 89%).

$^1$H NMR (300 MHz, CDCl$_3$) δ 0.88, d, J=6.4 Hz, 3H, 0.91, d, J=6.4 Hz, 3H, 1.43, m, 1H, 1.55, m, 1H, 1.56, m, NH$_2$; 1.74, m, 1H, 3.48, m, 1H, 5.09, s, 2H, 7.27, ABq, J=8.5 Hz, 2H, 7.32, ABq, J=8.5 Hz, 2H. MS (ES +ve) m/z 256 (100%) [M+H]$^+$.

4(iii)

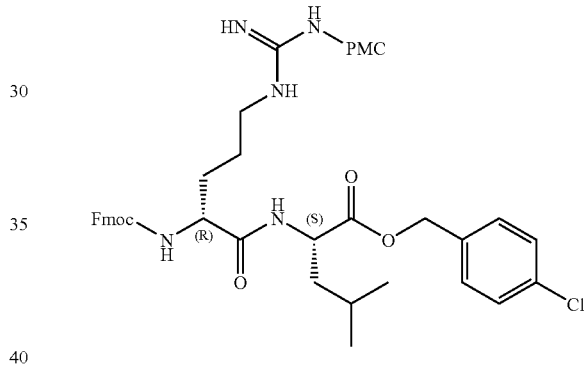

This compound was prepared via Protocol 1 using 4(ii) (235 mg, 0.919 mmol) and Fmoc-(D)-arg(Pmc)-OH (609 mg, 0.919 mmol) to yield the desired product 4(iii) as an off white solid (806 mg, 97%).

$^1$H NMR (500 MHz, CDCl$_3$) δ 0.79, dist d, 6H, 1.28, s, 6H, 1.65, m, 8H, 1.89, m, 1H, 2.03, s, 3H, 2.49, m, 2H, 2.53, s, 3H, 2.56, s, 3H, 3.23, m, 2H, 4.03, m, 1H, 4.28, m, 3H, 4.51, m, 1H, 4.96, ABq, J=12.2 Hz, 1H, 5.02, ABq, J=12.2 Hz, 1H, 6.42, br s, NH; 7.19, m, 6H, 7.31, dist t, 2H, 7.49, dist d, 2H, 7.54, d, J=7.8 Hz, NH; 7.68, ABq, J=7.8 Hz, 2H. MS (ES +ve) m/z 900 (100%) [M+H]$^+$.

4(iv)

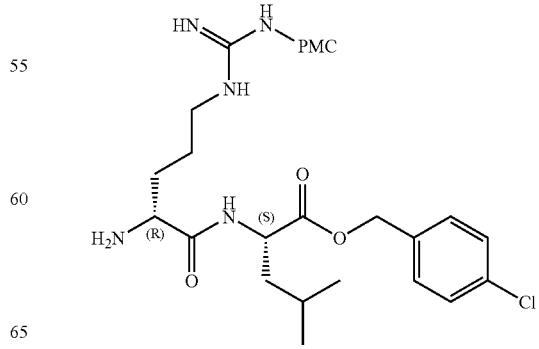

This compound was prepared via Protocol 2, using 4(iii) (798 mg, 0.887 mmol) to yield the desired product 4(iv) as an off white solid (532 mg, 88%).

¹H NMR (500 MHz, CDCl₃) δ 0.76, d, J=6.1 Hz, 3H, 0.88, d, J=6.1 Hz, 3H, 1.28, s, 6H, 1.57, m, 5H/NH₂; 1.77, m, 3H, 2.02, m, 1H, 2.08, s, 3H, 2.53, s, 3H, 2.55, s, 3H, 2.59, m, 2H, 3.15, m, 2H, 3.41, m, 1H, 4.49, m, 1H, 5.01, ABq, J=12.2 Hz, 1H, 5.07, ABq, J=12.2 Hz, 1H, 6.45, br s, NH; 7.22, ABq, J=8.5 Hz, 2H, 7.26, ABq, J=8.5 Hz, 2H, 7.83, d, J=7.9 Hz, NH. MS (ES +ve) m/z 678 (100%) [M+H]⁺.

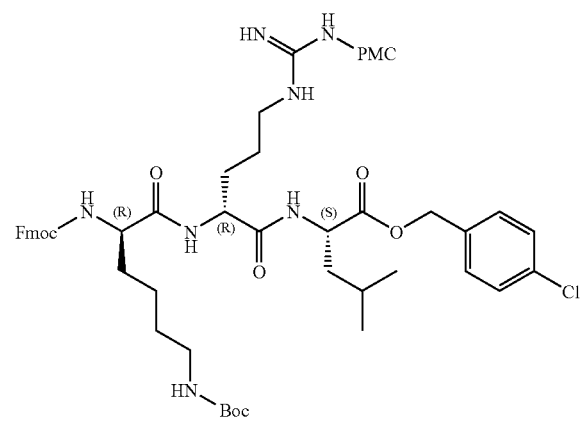

4(v)

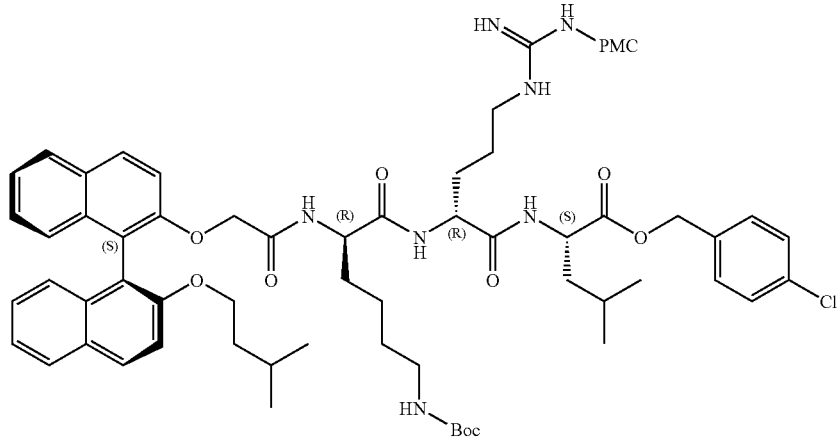

4(vi)

This compound was prepared via Protocol 2, using 4(v) (330 mg, 0.292 mmol) to yield the desired product 4(vi) as an off white solid (236 mg, 89%).

¹H NMR (500 MHz, CDCl₃) δ 0.85, d, J=5.9 Hz, 3H, 0.87, d, J=5.9 Hz, 3H, 1.29, s, 6H, 1.48, s, 9H, 1.57, m, 14H/NH₂; 2.09, s, 3H, 2.13, m, 1H, 2.54, s, 3H, 2.56, s, 3H, 2.60, m, 2H, 3.04, m, 2H, 3.22, m, 2H, 3.35, m, 1H, 4.52, m, 1H, 4.59, m, 1H, 4.98, m, NH; 5.02, ABq, J=12.2 Hz, 1H, 5.07, ABq, J=12.2 Hz, 1H, 6.45, br s, NH; 7.23, ABq, J=8.5 Hz, 2H, 7.28, ABq, J=8.5 Hz, 2H, 7.71, m, NH; 8.00, m, NH. MS (ES +ve) m/z 906 (100%) [M+H]+.

4(vii)

This compound was prepared via Protocol 1, using 4(iv) (519 mg, 0.765 mmol) and Fmoc-(D)-lys(BOC)-OH (359 mg, 0.766 mmol) to yield the desired product 4(v) as an off white solid (785 mg, 91%).

¹H NMR (500 MHz, CDCl₃) δ 0.82, d, J=5.5 Hz, 3H, 0.84, d, J=5.9 Hz, 3H, 1.19, br s, 6H, 1.39, s, 9H, 1.63, m, 14H, 2.02, s, 3H, 2.05, m, 1H, 2.51, m, 2H, 2.52, s, 3H, 2.55, s, 3H, 3.02, m, 2H, 3.19, m, 2H, 3.94, m, 1H, 4.14, m, 3H, 4.53, m, 2H, 4.95, m, 2H/NH; 6.47, br m, NH; 7.19, m, 4H, 7.32, m, 2H, 7.54, m, 4H, 7.69, m, 2H. MS (ES +ve) m/z 1128 (100%) [M+H]⁺.

This compound was prepared via Protocol 1, using 1(ii) (105 mg, 0.254 mmol) and 4(vi) (230 mg, 0.254 mmol) to yield the product 4(vii) as a white solid (144 mg, 44%).

¹H NMR (500 MHz, CDCl₃) δ 0.46, d, J=5.3 Hz, 3H, 0.52, d, J=5.3 Hz, 3H, 0.79, m, 2H, 0.87, d, J=5.9 Hz, 3H, 0.89, d, J=5.9 Hz, 3H, 0.94, m, 1H, 1.19, m, 6H, 1.28, s, 6H, 1.29, m, 2H, 1.41, s, 9H, 1.64, m, 4H, 1.76, m, 2H, 1.84, m, 1H, 2.09, s, 3H, 2.54, s, 3H, 2.56, s, 3H, 2.58, m, 2H, 2.90, m, 2H, 3.15, m, 2H, 3.87, m, 1H, 4.04, m, 2H, 4.41, m, 2H, 4.45, m, 3H, 4.82, m, NH; 5.04, ABq, J=12.2 Hz, 1H, 5.11, ABq, J=12.2 Hz, 1H, 6.19, d, J=6.8 Hz, NH; 6.29, br s, NH; 7.26, m, 11H, 7.44, d, J=9.1 Hz, 1H, 7.83, d, J=8.3 Hz, 1H, 7.85, d, J=8.3 Hz, 1H, 7.93, d, J=9.0 Hz, 1H, 7.94, d, J=8.9 Hz, 1H. MS (ES +ve) m/z 1302 (60%) [M+H]⁺; 602 (100) [M+2H-BOC]⁺.

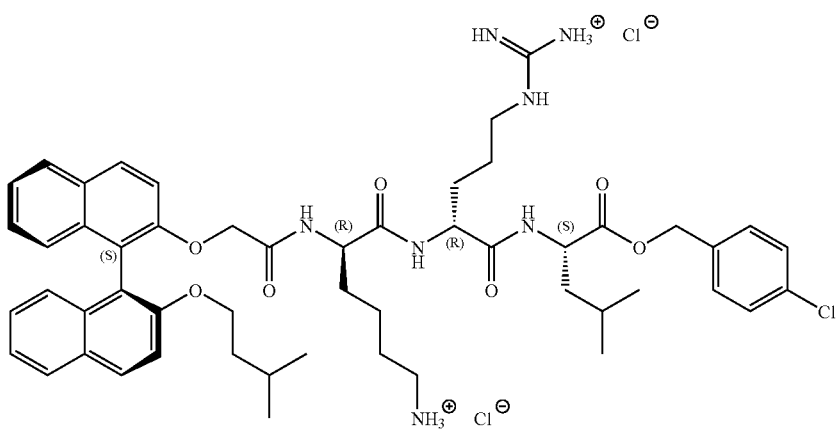

Compound 4

This compound was prepared via Protocol 3, using 4(vii) (140 mg, 0.107 mmol) to yield the desired product 4 as a white solid (101 mg, 93%).

$^1$H NMR (500 MHz, CD$_3$OD) δ 0.40, d, J=6.3 Hz, 3H, 0.45, d, J=6.3 Hz, 3H, 0.78, d, J=4.8 Hz, 3H, 0.83, d, J=4.8 Hz, 3H, 0.84, m, 2H, 1.05, m, 2H, 1.13, m, 2H, 1.53, m, 9H, 1.72, m, 1H, 2.70, m, 2H, 3.06, m, 2H, 3.84, m, 1H, 4.03, m, 2H, 4.36, m, 4H, 5.02, s, 2H, 7.06, dist t, 2H, 7.18, m, 2H, 7.33, m, 6H, 7.45, d, J=9.3 Hz, 1H, 7.54, d, J=8.8 Hz, 1H, 7.88, d, J=7.8 Hz, 1H, 7.91, d, J=8.3 Hz, 1H, 8.00, dist t, 2H. MS (ES +ve) m/z 936 (15%) [M+H]$^+$; 469 (100) [M+2H]$^{2+}$.

Synthesis of Compound 5

5(i)

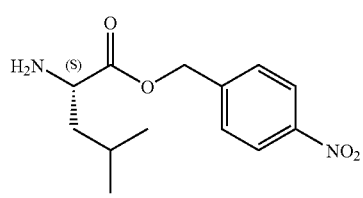

To BOC(L)-Leu-OH (250 mg, 1.08 mmol) and potassium carbonate (747 mg, 5.40 mmol) in acetone (50 ml) was added 4-nitrobenzyl bromide (350 mg, 1.62 mmol). The resulting solution was heated at reflux overnight before being cooled, filtered and evaporated to dryness. The resultant residue was subjected to flash column chromatography over silica, eluting with 1:4 hexane/DCM to first remove 4-nitrobenzyl bromide, then with DCM to yield the product 5(i) as a colourless oil.

$^1$H NMR (500 MHz, CDCl$_3$) δ 0.95, d, J=6.8 Hz, 6H, 1.44, s, 9H, 1.53, m, 1H, 1.63, m, 1H, 1.71, m, 1H, 4.38, m, 1H, 4.99, d, J=8.3 Hz, NH; 5.27, s, 2H, 7.53, ABq, J=8.3 Hz, 2H, 8.22, ABq, J=8.3 Hz, 2H. MS (EI) m/z 265 (100%) [M-BOC]$^+$.

5(ii)

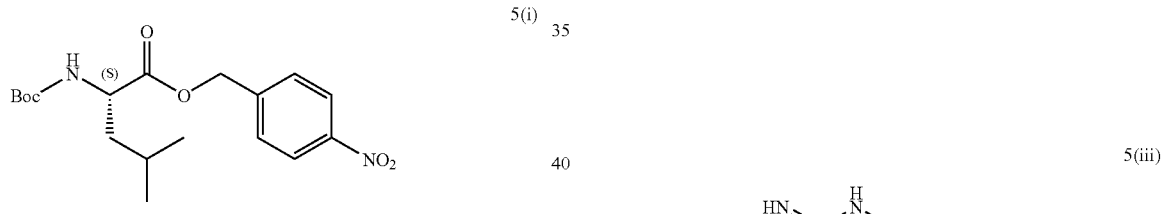

To 5(i) (215 mg, 0.59 mmol) in DCM (2 ml) was added TFA (2 ml) and the resulting solution stirred at room temperature for 3 hrs. The solution was then diluted with DCM (5 ml) and washed with sat. sodium bicarbonate solution until the washings were basic. The organic layer was then dried (MgSO$_4$), filtered and evaporated to dryness to yield the desired product 5(ii) as a white solid (131 mg, 84%).

$^1$H NMR (500 MHz, CDCl$_3$) δ 0.93, d, J=8.8 Hz, 3H, 0.95, d, J=8.8 Hz, 3H, 1.50, m, 1H, 1.62, m, 1H, 1.54, m, 1H, 1.79, m, 1H, 2.37, br s, NH$_2$; 3.61, m, 1H, 5.26, s, 2H, 7.54, ABq, J=8.8 Hz, 2H, 8.22, ABq, J=8.8 Hz, 2H. MS (ES +ve) m/z 267 (100%) [M+H]$^+$.

5(iii)

This compound was prepared via Protocol 1 using 5(ii) (130 mg, 0.488 mmol) and Fmoc-(D)-arg(Pmc)-OH (323 mg, 0.488 mmol) to yield the desired product 5(iii) as a white solid (414 mg, 93%).

$^1$H NMR (500 MHz, CDCl$_3$) δ 0.83, br s, 6H, 1.21, s, 6H, 1.61, m, 4H, 1.66, m, 3H, 1.75, m, 2H, 2.03, s, 3H, 2.49, m, 2H, 2.53, s, 3H, 2.57, s, 3H, 3.23, m, 2H, 4.01, m, 1H, 4.23, m, 2H, 4.36, m, 1H, 4.56, m, 1H, 5.09, s, 2H, 6.45, br s, NH; 7.17, m, 2H, 7.29, m, 5H (inc NH); 7.48, ABq, J=8.8 Hz, 2H, 7.66, m, 2H, 7.70, m, NH; 8.04, ABq, J=8.8 Hz, 2H. MS (ES +ve) m/z 911 (100%) [M+H]$^+$.

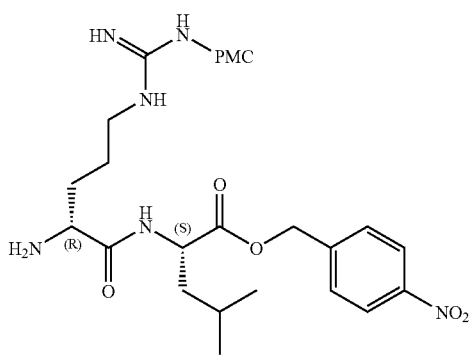

5(iv)

This compound was prepared via Protocol 2, using 5(iii) (400 mg, 0.439 mmol) to yield the desired product 5(iv) as an off white solid (210 mg, 69%).

$^1$H NMR (500 MHz, CDCl$_3$) δ 0.90, dist d, 6H, 1.28, s, 6H, 1.57, m, 4H, 1.65, m, 2H, 1.78, m, 3H, 2.07, s, 3H, 2.52, s, 3H, 2.54, s, 3H, 2.59, m, 2H, 3.17, m, 2H, 3.49, m, 1H, 4.53, m, 1H, 5.20, s, 2H, 6.45, br s, NH; 7.47, ABq, J=8.3 Hz, 2H, 7.90, d, J=5.4 Hz, NH. 8.22, ABq, J=8.3 Hz, 2H. $^{13}$C NMR (125 MHz, CDCl$_3$) δ 12.0, 17.3, 18.4, 21.2, 21.5, 22.6, 22.9, 24.8, 25.2, 26.6, 31.6, 32.6, 40.2, 50.7, 54.0, 65.2, 73.5, 117.9, 123.6, 123.9, 128.2, 133.1, 134.6, 135.2, 142.7, 147.5, 153.5, 156.3, 172.4, 175.3. MS (ES +ve) m/z 689 (100%) [M+H]$^+$.

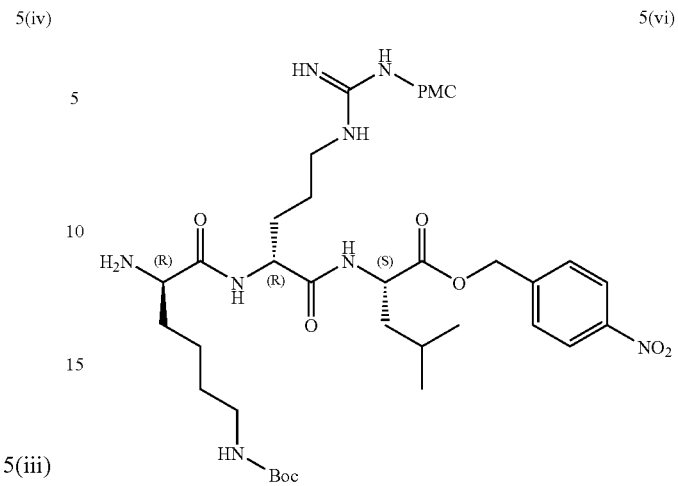

5(vi)

The Fmoc-protected precursor to this compound was prepared via Protocol 4, using 5(iv) (200 mg, 0.290 mmol) and Fmoc-(D)-lys(BOC)-OH (136 mg, 0.290 mmol) to yield the Fmoc-protected derivative 5(v) as an off white solid. The desired deprotected compound was prepared via Protocol 2, to yield the product 5(vi) as an off white solid (201 mg, 76%).

$^1$H NMR (500 MHz, CDCl$_3$) δ 0.87, d, J=5.8 Hz, 3H, 0.90, d, J=5.8 Hz, 3H, 1.29, s, 6H, 1.40, s, 9H, 1.60, m, 15H, 2.08, s, 3H, 2.54, s, 3H, 2.56, s, 3H, 2.60, m, 2H, 3.04, m, 2H, 3.23, m, 2H, 3.51, m, 1H, 4.58, m, 2H, 4.93, m, NH; 5.19, s, 2H, 6.44, br s, NH; 7.48, ABq, J=8.8 Hz, 2H, 7.77, m, NH; 8.01, m, NH; 8.16, ABq, J=8.8 Hz, 2H. MS (ES +ve) m/z 917 (10%) [M+H]$^+$; 431.5 (100) [M+H-C$_4$H$_8$]$^+$.

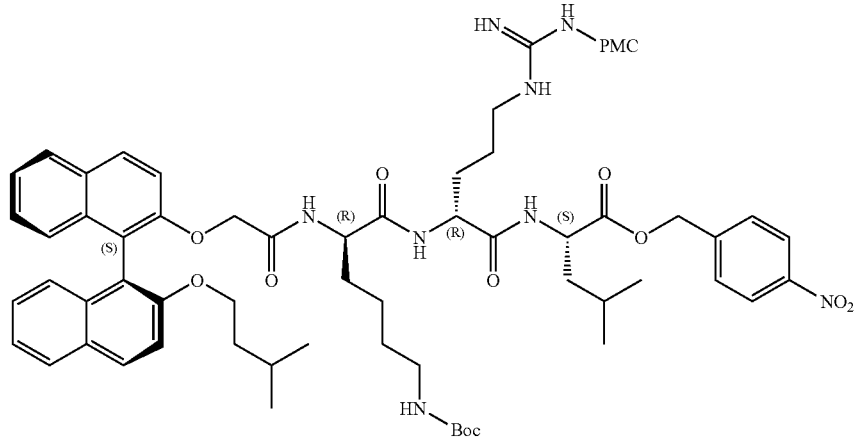

5(vii)

This compound was prepared via Protocol 1, using 1(ii) (91 mg, 0.022 mmol) and 5(vi) (190 mg, 0.021 mmol) to yield the product 5(vii) as a white solid (194 mg, 71%).

$^1$H NMR (500 MHz, CDCl$_3$) δ 0.46, d, J=6.3 Hz, 3H, 0.51, d, J=6.3 Hz, 3H, 0.89, d, J=5.8 Hz, 3H, 0.90, m, 2H, 0.92, d, J=5.8 Hz, 3H, 1.25, m, 4H, 1.26, s, 6H, 1.40, s, 9H, 1.56, m, 10H; 1.83, m, 1H, 2.07, s, 3H, 2.53, s, 3H, 2.56, s, 3H, 2.58, m, 2H, 2.90, m, 2H, 3.15, m, 2H, 3.93, m, 3H, 4.51, m, 4H, 5.22, s, 2H, 6.20, d, J=7.0 Hz, NH; 6.29, br s, NH; 7.04, d, J=7.3 Hz, H, 7.06, d, J=8.3 Hz, 1H, 7.17, m, 2H, 7.31, t, J=7.3 Hz, 2H, 7.45, d, J=9.3 Hz, 1H, 7.53, d, J=9.3 Hz, 1H, 7.58, ABq, J=8.8 Hz, 2H, 7.87, d, J=8.3 Hz, 1H, 7.89, d, J=8.3 Hz, H, 7.99, d, J=8.8 Hz, 1H, 8.00, d, J=9.3 Hz, 1H, 8.19, ABq, J=8.8 Hz, 2H. MS (ES +ve) m/z 1313 (100%) [M+H]$^+$.

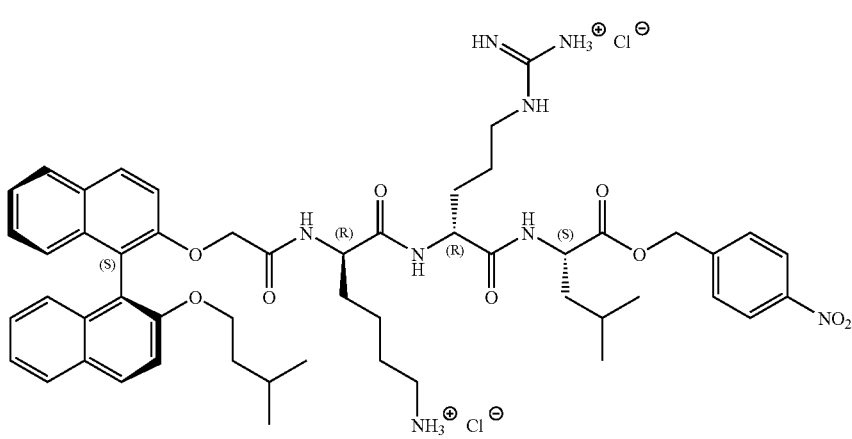

Compound 5

This compound was prepared via Protocol 3, using 5(vii) (194 mg, 0.015 mmol) to yield an impure product. Protocol 3 was repeated on 130 mg of this product to yield the desired product 5 as an off white solid (110 mg, 84%).

$^1$H NMR (500 MHz, CD$_3$OD) δ 0.38, d, J=6.4 Hz, 3H, 0.44, d, J=6.4 Hz, 3H, 0.80, d, J=5.5 Hz, 3H, 0.85, d, J=5.5 Hz, 3H, 0.90, m, 2H, 1.10, m, 4H, 1.56, m, 9H, 1.74, m, 1H, 2.70, m, 2H, 3.06, m, 2H, 3.83, m, 1H, 4.02, m, 2H, 4.27, m, 1H, 4.36, ABq, J=14.5 Hz, 1H, 4.40, m, 1H, 4.46, ABq, J=14.5 Hz, 1H, 5.26, s, 2H, 7.04, d, J=7.3 Hz, 1H, 7.06, d, J=8.3 Hz, 1H, 7.17, m, 2H, 7.31, t, J=7.3 Hz, 2H, 7.45, d, J=9.3 Hz, H, 7.53, d, J=9.3 Hz, 1H, 7.58, ABq, J=8.8 Hz, 2H, 7.87, d, J=8.3 Hz, 1H, 7.89, d, J=8.3 Hz, 1H, 7.99, d, J=8.8 Hz, 1H, 8.00, d, J=9.3 Hz, 1H, 8.19, ABq, J=8.8 Hz, 2H. MS (ES +ve) m/z 947 (10%) [M+H]$^+$; 474.5 (100) [M+2H]$^{2+}$.

Synthesis of Compound 6

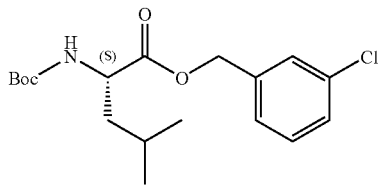

6(i)

To BOC-(L)-leu-OH (250 mg, 1.08 mmol) and potassium carbonate (1.00 g, 7.24 mmol) in acetone (25 ml) was added 2-chlorobenzyl bromide (0.16 ml, 1.22 mmol). The resulting solution was heated at reflux overnight before being cooled, filtered and evaporated to dryness. The resultant residue was subjected to flash column chromatography over silica, eluting with 5% ethyl acetate/hexane to first remove 2-chlorobenzyl bromide, then with DCM to yield the product 6(i) as a white solid (370 mg, 96%).

$^1$H NMR (500 MHz, CDCl$_3$) δ 0.92, d, J=6.3 Hz, 3H, 0.93, d, J=6.3 Hz, 3H, 1.43, s, 9H, 1.54, m, 1H, 1.68, m, 2H, 4.36, m, 1H, 5.08, m, NH; 5.13, m, 2H, 7.22, m, 1H, 7.27, m, 2H, 7.34, s, 1H. MS (ES +ve), m/z 357 (100%) [M+H]$^+$; 257 (70) [M+H-BOC]$^+$.

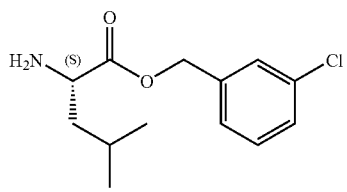

6(ii)

To 6(i) (360 mg, 1.01 mmol) in DCM (2 ml) was added TFA (2 ml) and the resulting solution stirred at room temperature for 3 hrs. The solution was then diluted with DCM (5 ml) and washed with sat. sodium bicarbonate solution until the washings were basic. The organic layer was then dried (MgSO$_4$), filtered and evaporated to dryness to yield the desired product 6(ii) as a pale yellow oil (179 mg, 69%).

$^1$H NMR (500 MHz, CDCl$_3$) δ 0.85, d, J=6.8 Hz, 3H, 0.87, d, J=6.8 Hz, 3H, 1.41, m, 1H, 1.52, m, 1H, 1.71, m, 1H, 2.41, br s NH$_2$; 3.50, m, 1H, 5.05, s, 2H, 7.18, m, 1H, 7.23, m, 2H, 7.28, s, 1H. MS (ES +ve) m/z 256.0 (100%) [M+H]$^+$.

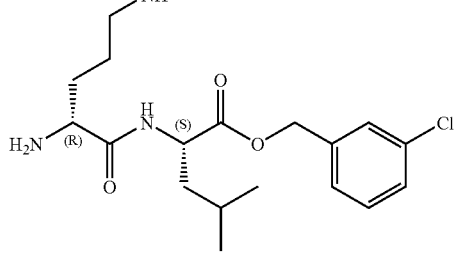

6(iv)

This compound was prepared in two steps. The first step via Protocol 1, using 6(ii) (170 mg, 0.67 mmol) and Fmoc-(D)-arg(Pmc)-OH (398 mg, 0.60 mmol) to yield the Fmoc protected precursor 6(iii) as an off white foamy solid (529 mg, MS (ES +ve) m/z 900.0 (100%) [M+H]$^+$). The desired product was then prepared via Protocol 2, using precursor 6(iii) (230 mg, 0.26 mmol) to afford the product 6(iv) as a colourless oil (150 mg, 85% two steps).

¹H NMR (500 MHz, CDCl₃) δ 0.80, d, J=6.4 Hz, 3H, 0.82, d, J=6.4 Hz, 3H, 1.21, s, 6H, 1.51, m, 5H, 1.70, m, 3H, 2.01, s, 3H, 2.03, m, 1H, 2.46, s, 3H, 2.48, s, 3H, 2.52, m, 2H, 3.08, m, 2H, 3.36, m, 1H, 4.42, m, 1H, 4.95, ABq, J=12.3 Hz, 1H, 5.01, ABq, J=12.3 Hz, H, 6.32, br s, NH; 7.15, m, 4H, 7.76, d, J=6.8 Hz, NH. MS (ES +ve) m/z 678.0 (100%) [M+H]⁺. HRMS for C₃₃H₄₈ClN₅O₆S, calculated 678.3092, found 678.3094.

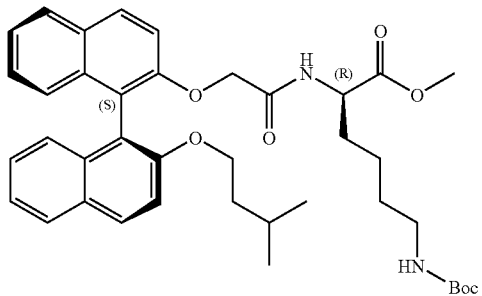

6(v)

This compound was prepared via Protocol 1, using 1(ii) (642 mg, 1.55 mmol) and (D)-lys(BOC)-OMe (400 mg, 1.54 mmol) to yield the desired compound 6(v) as a off white sticky solid (898 mg, 89%). R_f=0.53 (5% MeOH/DCM).

¹H NMR (500 MHz, CDCl₃) δ 0.54, d, J=6.4 Hz, 3H, 0.58, d, J=6.4 Hz, 3H, 0.78, m, 2H, 1.00, m, 1H, 1.22, m, 6H, 1.42, s, 9H, 2.91, m, 2H, 3.59, s, 3H, 3.95, m, 1H, 4.06, m, 1H, 4.29, m, 1H, 4.45, ABq, J=14.3 Hz, 1H, 4.51, ABq, J=14.3 Hz, 1H, 4.64, br s, NH; 6.15, d, J=8.5 Hz, NH; 7.17, m, 4H, 7.30, m, 3H, 7.46, d, J=8.9 Hz, 1H, 7.83, d, J=7.5 Hz, 1H, 7.84, d, J=7.8 Hz, 1H, 7.92, d, J=10.2 Hz, 1H, 7.94, d, J=10.2 Hz, 1H. MS (ES) m/z 657.1 (100%) [M+H]⁺; 557.1 (90) [M+H-BOC]⁺.

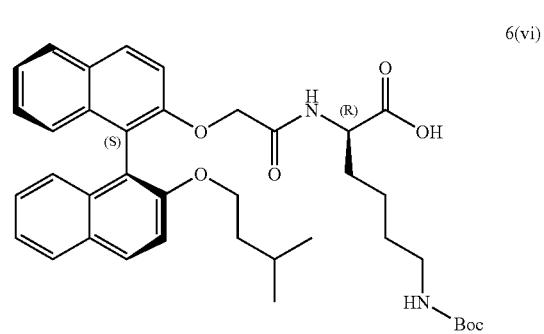

6(vi)

To a solution of 6(v) (898 mg, 1.37 mmol) in THF (20 ml) was added a solution of LiOH.H₂O (1260 mg, 30.1 mmol) in water (10 ml). The resultant solution was stirred at RT for 1 hr before diethyl ether (20 ml) was added and the layer separated. The aqueous layer was extracted with sat. sodium bicarbonate solution and the aqueous extracts combined then acidified to pH ~2-3 using 1M potassium bisulphate. The aqueous layer was then extracted with DCM (3×20 ml). A TLC of the initial and final organic layers was completed and showed the product was in both layers. As a result, all of the organic fractions were combined, dried (MgSO₄) and evaporated to dryness to yield the product 6(vi) as an off white foamy solid (854, 97%).

¹H NMR (300 MHz, CDCl₃) δ 0.53, d, J=6.3 Hz, 3H, 0.57, d, J=6.3 Hz, 3H, 0.82, m, 2H, 1.24, m, 5H, 1.40, m, 2H (obscured by BOC-CH₃); 1.44, s, 9H, 2.92, m, 2H, 3.95, m, 1H, 4.05, m, 1H, 4.31, m, 1H, 4.49, ABq, J=14.6 Hz, 1H, 4.57, ABq, J=14.6 Hz, 1H, 4.60, br s, NH (obscured by ABq); 6.15, m, NH; 7.19, m, 4H, 7.32, m, 3H, 7.44, d, J=9.1 Hz, 1H, 7.85, d, J=8.0 Hz, 1H, 7.86, d, J=8.1 Hz, 1H, 7.94, d, J=9.0 Hz, 1H, 7.96, d, J=9.1 Hz, 1H. MS (ES+ve) 643.1 (100%) [M+H]⁺; 543.1 (30) [M+H-BOC]⁺.

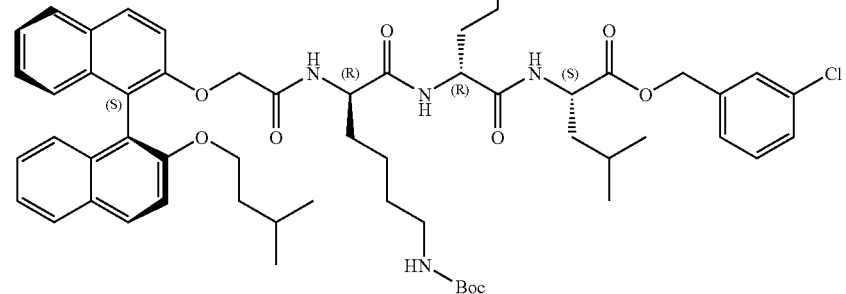

6(vii)

This compound was prepared via Protocol 1, using 6(vi) (122 mg, 0.186 mmol) and 6(iv) (145 mg, 0.199 mmol) to yield 6(vii) as a white solid (198 mg, 82%).

¹H NMR (500 MHz, CDCl₃) δ 0.39, d, J=6.5 Hz, 3H, 0.44, d, J=6.5 Hz, 3H, 0.70, m, 2H, 0.80, d, J=5.6 Hz, 3H, 0.82, d, J=5.6 Hz, 3H, 0.89, m, 1H, 1.12, m, 6H, 1.19, s, 6H, 1.29, m, 2H, 1.33, s, 9H, 1.55, m, 4H, 1.68, m, 2H, 1.71, m, 1H, 2.00, s, 3H, 2.48, s, 3H, 2.48, s, 3H, 2.50, m, 2H, 2.82, m, 2H, 3.07, m, 2H, 3.79, m, 1H, 3.96, m, 2H, 4.33, m, 2H, 4.44, m, 3H, 4.73, m, NH; 4.97, ABq, J=12.7 Hz, 1H, 5.03, ABq, J=12.7 Hz, 1H, 6.12, d, J=6.9 Hz, NH; 6.22, br s, NH; 7.26, m, 11H, 7.36, d, J=9.1 Hz, 1H, 7.75, d, J=10.1 Hz, 1H, 7.77, d, J=8.7 Hz, 1H, 7.84, d, J=8.7 Hz, 1H, 7.86, d, J=7.6 Hz, 1H. MS (ES +ve) m/z 1301.9 (100%) [M+H]⁺; 602.6 (30) [M+2H-BOC]²⁺.

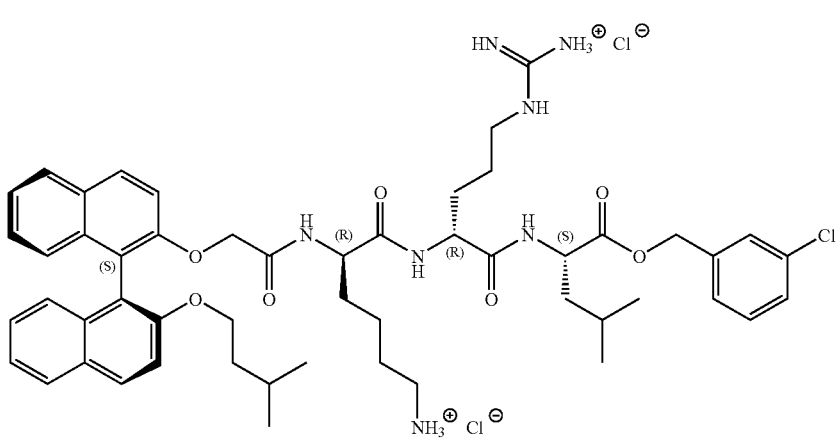

Compound 6

This compound was prepared via Protocol 3, using 6(vii) (180 mg, 0.138 mmol) to yield 6 as an off white solid (130 mg, 93%).

$^1$H NMR (500 MHz, CD$_3$OD) δ 0.50, d, J=6.3 Hz, 3H, 0.55, d, J=6.3 Hz, 3H, 0.90, d, J=4.8 Hz, 3H, 0.94, d, J=4.8 Hz, 3H, 0.95, m, 2H, 1.14, m, 2H, 1.23, m, 2H, 1.67, m, 10H, 2.83, m, 2H, 3.18, m, 2H, 3.96, m, 1H, 4.14, m, 2H, 4.36, m, 1H, 4.48, m, 3H, 5.12, s, 2H, 7.05, d, J=3.7 Hz, 1H, 7.08, d, J=3.5 Hz, 1H, 7.17, dist t, 2H, 7.30, m, 5H, 7.38, s, 1H, 7.45, d, J=9.0 Hz, 1H, 7.54, d, J=9.0 Hz, 1H, 7.88, d, J=8.5 Hz, 1H, 7.91, d, J=8.5 Hz, 1H, 7.99, d, J=8.7 Hz, 1H, 8.02, d, J=8.5 Hz, 1H. MS (ES +ve) m/z 935.7 (5%) [M+H]$^+$; 468.7 (100) [M+2H]$^{2+}$.

Synthesis of Compound 7

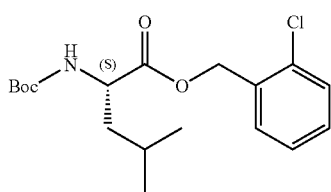

7(i)

To BOC-(L)-leu-OH (250 mg, 1.08 mmol) and potassium carbonate (1.00 g, 7.24 mmol) in acetone (25 ml) was added 2-chlorobenzyl bromide (0.16 ml, 1.23 mmol). The resulting solution was heated at reflux overnight before being cooled, filtered and evaporated to dryness. The resultant residue was subjected to flash column chromatography over silica, eluting with 5% ethyl acetate/hexane to first remove 2-chlorobenzyl bromide, then with DCM to yield the product 7(i) as a white solid (353 mg, 92%).

$^1$H NMR (500 MHz, CDCl$_3$) δ 0.92, d, J=6.4 Hz, 3H, 0.93, d, J=6.4 Hz, 3H, 1.43, s, 9H, 1.56, m, 1H, 1.68, m, 2H, 4.40, m, 1H, 5.16, d, J=8.4 Hz, NH; 5.22, ABq, J=13.1 Hz, 1H, 5.27, ABq, J=13.1 Hz, 1H, 7.25, m, 2H, 7.35, m, 1H, 7.42, m, 1H. MS (ES +ve) m/z 356.1 (100%) [M+H]$^+$; 256.0 (70) [M+H-BOC]$^+$.

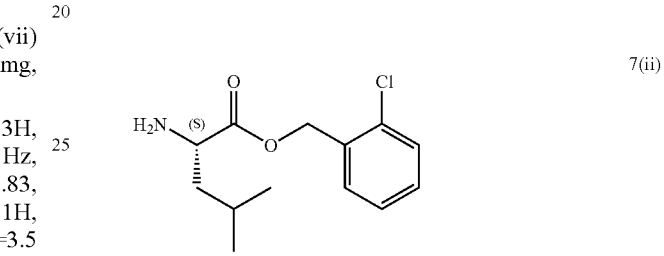

7(ii)

To 7(i) (350 mg, 0.984 mmol) in DCM (2 ml) was added TFA (2 ml) and the resulting solution stirred at room temperature for 3 hrs. The solution was then diluted with DCM (5 ml) and washed with sat. sodium bicarbonate solution until the washings were basic. The organic layer was then dried (MgSO$_4$), filtered and evaporated to dryness to yield the desired product 7(ii) as a white solid (236 mg, 94%).

$^1$H NMR (500 MHz, CDCl$_3$) δ 0.86, d, J=6.8 Hz, 3H, 0.88, d, J=6.8 Hz, 3H, 1.45, m, 1H, 1.57, m, 1H, 1.74, m, 1H, 2.64, s, NH$_2$; 3.54, m, 1H, 5.20, s, 2H, 7.22, m, 2H, 7.35, m, 2H. MS (ES +ve) m/z 256.1 (100%) [M+H]$^+$.

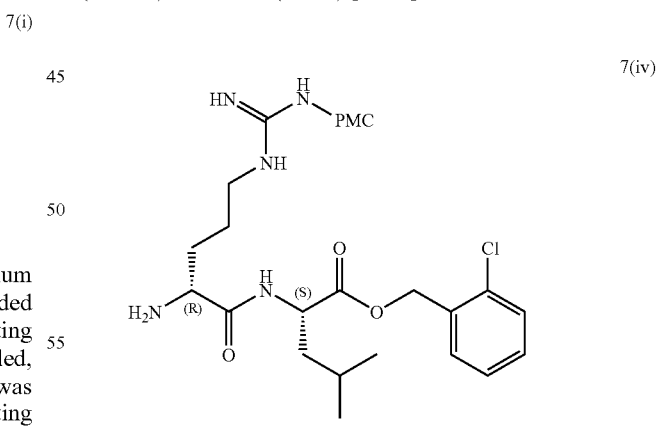

7(iv)

This compound was prepared in two steps. The first step via Protocol 1, using 7(ii) (230 mg, 0.900 mmol) and Fmoc-(D)-arg(Pmc)-OH (563 mg, 0.850 mmol) to yield the Fmoc protected precursor 7(iii) as a white foamy solid (662 mg, MS (ES +ve) m/z 900 (100%) [M+H]$^+$). The desired product was then prepared via Protocol 2, using the precursor 7(iii) (200 mg, 0.22 mmol) to afford the product 7(iv) as a white solid (135 mg, 66% two steps).

¹H NMR (500 MHz, CDCl₃) δ 0.81, d, J=5.9 Hz, 3H, 0.83, d, J=5.9 Hz, 3H, 1.21, s, 6H, 1.51, m, 5H, 1.71, m, 3H, 2.01, s, 3H, 2.01, m, 1H, 2.47, s, 3H, 2.49, s, 3H, 2.53, m, 2H, 3.08, m, 2H, 3.33, m, 1H, 4.46, m, 1H, 5.10, ABq, J=12.9 Hz, 1H, 5.15, ABq, J=12.9 Hz, 1H, 6.34, br s, NH; 7.16, m, 2H, 7.30, m, 2H, 7.75, d, J=7.8 Hz, NH. MS (ES +ve) m/z 678.0 (100%) [M+H]⁺.

¹H NMR (300 MHz, CD₃OD) δ 0.51, d, J=6.4 Hz, 3H, 0.56, d, J=6.4 Hz, 3H, 0.90, d, J=5.7 Hz, 3H, 0.95, d, J=5.7 Hz, 3H, 1.15, m, 2H, 1.25, m, 3H, 1.67, m, 11H, 2.82, m, 2H, 3.16, m, 2H, 3.97, m, 1H, 4.15, m, 2H, 4.34, m, 1H, 4.48, m, 3H, 5.21, ABq, J=12.8 Hz, 1H, 5.28, ABq, J=12.8 Hz, 1H, 7.05, d, J=4.5 Hz, 1H, 7.08, d, J=4.5 Hz, 1H, 7.20, m, 2H, 7.32, m, 4H, 7.44, m, 3H, 7.54, d, J=9.0 Hz, 1H, 7.89, d, J=8.1 Hz, 1H, 7.91, d, J=7.7 Hz, 1H, 8.01, d, J=9.0 Hz, 1H, 8.02, d, J=9.0 Hz, 1H. MS (ES +ve) m/z 935.7 (5%) [M+H]⁺; 468.7 (100) [M+2H]²⁺.

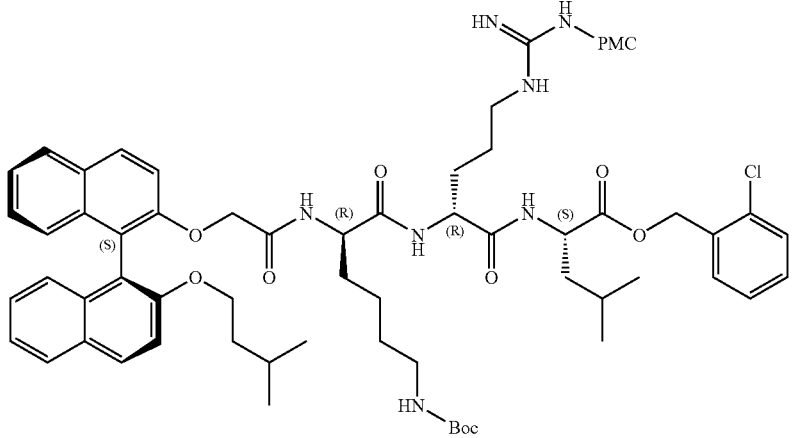

7(v)

This compound was prepared via Protocol 1, using 6(vi) (111 mg, 0.169 mmol) and 7(iv) (130 mg, 0.179 mmol) to yield 7(v) as a white solid (172 mg, 78%).

¹H NMR (500 MHz, CDCl₃) δ 0.38, d, J=6.2 Hz, 3H, 0.43, d, J=6.6 Hz, 3H, 0.70, m, 2H, 0.81, d, J=5.5 Hz, 3H, 0.82, d, J=5.5 Hz, 3H, 0.89, m, 1H, 1.12, m, 6H, 1.19, s, 6H, 1.29, m, 2H, 1.33, s, 9H, 1.58, m, 4H, 1.68, m, 2H, 1.71, m, 1H, 2.00, s, 3H, 2.46, s, 3H, 2.48, s, 3H, 2.50, m, 2H, 2.81, m, 2H, 3.07, m, 2H, 3.78, m, 1H, 3.96, m, 2H, 4.33, m, 2H, 4.46, m, 3H, 4.73, m, NH; 5.11, ABq, J=12.7 Hz, 1H, 5.19, ABq, J=12.7 Hz, 1H, 6.12, d, J=7.3 Hz, NH; 6.23, br s, NH; 7.26, m, 11H, 7.36, d, J=10.0 Hz, 1H, 7.75, d, J=8.0 Hz, 1H, 7.77, d, J=8.3 Hz, 1H, 7.84, d, J=9.0 Hz, 1H, 7.85, d, J=9.0 Hz, 1H. MS (ES +ve) m/z 1301.9 (100%) [M+H]⁺; 601.7 (60) [M+2H-BOC]²⁺.

Synthesis of Compound 8

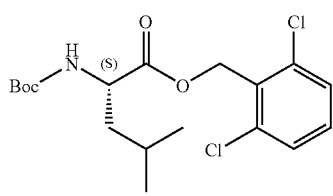

8(i)

Compound 7

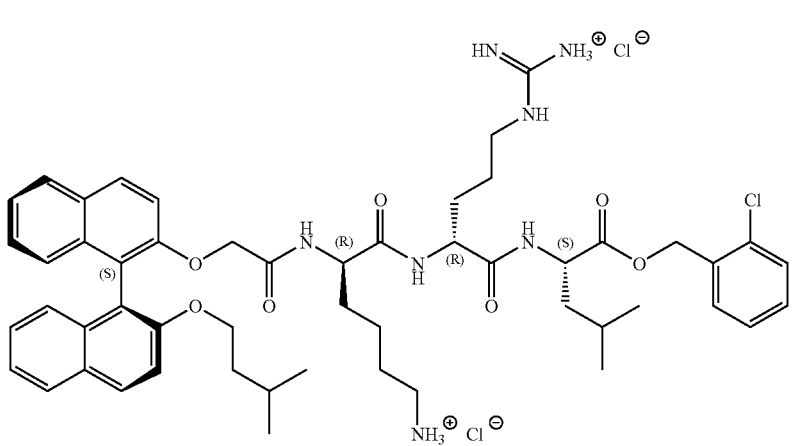

This compound was prepared via Protocol 3, using 7(v) (160 mg, 0.123 mmol) to yield 7 as an off white solid (109 mg, 88%).

To BOC-(L)-leu-OH (250 mg, 1.08 mmol) and potassium carbonate (100 mg, 7.24 mmol) in acetone (25 ml) was added 2,6-dichlorobenzyl bromide (266 mg, 1.50 mmol). The resulting solution was heated at reflux overnight before being cooled, filtered and evaporated to dryness. The resultant residue was subjected to flash column chromatography over silica, eluting with 5% ethyl acetate/hexane to first remove 2,6-dichlorobenzyl bromide, then with DCM to yield the product 8(i) as a white solid (383 mg, 91%).

$^1$H NMR (500 MHz, CDCl$_3$) δ 0.85, d, J=7.8 Hz, 6H, 1.37, s, 9H, 1.46, m, 1H, 1.58, m, 1H, 1.68, m, 1H, 4.40, m, 1H, 5.99, d, J=7.8 Hz, NH; 5.35, s, 2H, 7.18, dist t, 1H, 7.27, d, J=8.3 Hz, 2H. MS (ES +ve) m/z 333.2 (100%) [M+H-C$_4$H$_8$]$^+$; 289.9 (50) [M+H-BOC]$^+$.

m, 1H, 3.76, s, NH$_2$; 5.35, ABq, J=11.8 Hz, 1H, 5.38, ABq, J=11.8 Hz, 1H, 7.19, dist t, 1H, 7.29, d, J=7.9 Hz, 2H. MS (ES +ve) m/z 290 (100%) [M+H]$^+$.

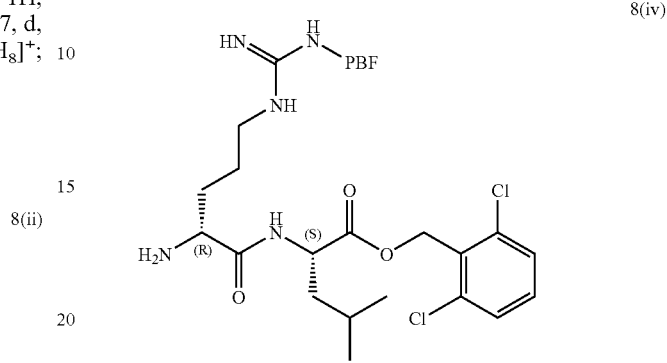

8(iv)

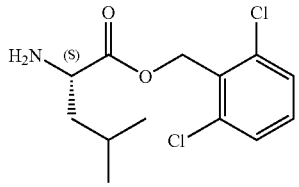

8(ii)

To 8(i) (380 mg, 0.974 mmol) in DCM (2 ml) was added TFA (2 ml) and the resulting solution stirred at room temperature for 1 hr. The solution was then diluted with ethyl acetate (20 ml) and washed with sat. sodium bicarbonate solution added until the washings were basic. The organic layer was then separated and the aqueous layer extracted once more with ethyl acetate (10 ml). The combined organic layers were dried (MgSO$_4$), filtered and evaporated to dryness to yield the desired product 8(ii) as a white solid (275 mg, 97%).

$^1$H NMR (500 MHz, CDCl$_3$) δ 0.84, d, J=7.0 Hz, 3H, 0.86, d, J=8.0 Hz, 3H, 1.48, m, 1H, 1.57, m, 1H, 1.73, m, 1H, 3.58,

This compound was prepared in two steps. The first step via Protocol 1, using 8(ii) (120 mg, 0.41 mmol) and Fmoc-(D)-arg(Pbf)-OH (260 mg, 0.40 mmol) to yield the Fmoc protected precursor 8(iii) as a white foamy solid (MS (ES +ve) m/z 900 (100%) [M+H]$^+$). This was then deprotected via Protocol 2 to afford the desired compound 8(iv) as a white solid (178 mg, 64% two steps).

$^1$H NMR (300 MHz, CDCl$_3$) δ 0.81, d, J=5.9 Hz, 3H, 0.83, d, J=5.9 Hz, 3H, 1.21, s, 6H, 1.51, m, 5H, 1.71, m, 3H, 2.01, s, 3H, 2.02, m, 1H, 2.47, s, 3H, 2.49, s, 3H, 2.53, m, 2H, 3.08, m, 2H, 3.33, m, 1H, 4.46, m, 1H, 5.10, ABq, J=12.9 Hz, 1H, 5.15, ABq, J=12.9 Hz, 1H, 6.34, br s, NH; 7.16, m, 2H, 7.30, m, 2H, 7.75, d, J=7.8 Hz, NH. MS (ES +ve) m/z 678 (100%) [M+H]$^+$.

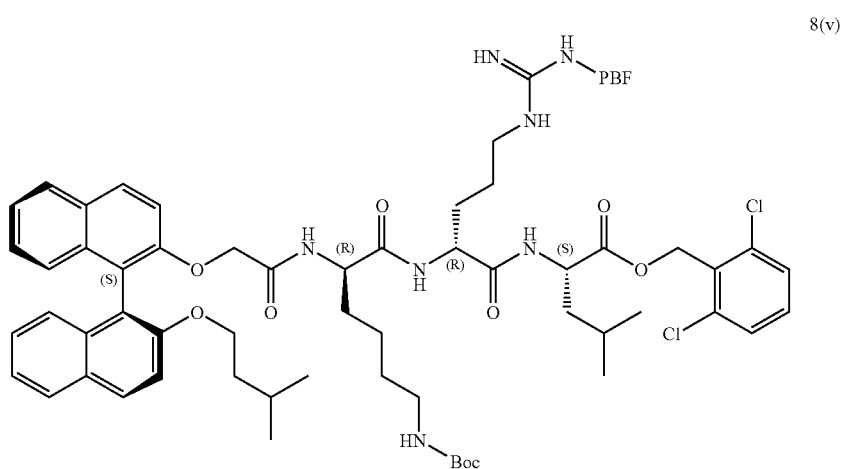

8(v)

This compound was prepared via Protocol 1, using 6(vi) (160 mg, 0.25 mmol) and 8(iv) (175 mg, 0.25 mmol) to yield 8(v) as a white solid (231 mg, 69%).

$^1$H NMR (300 MHz, CDCl$_3$) δ 0.46, d, J=6.2 Hz, 3H, 0.52, d, J=6.5 Hz, 3H, 0.79, m, 2H, 0.86, d, J=6.7 Hz, 3H, 0.88, d, J=6.7 Hz, 3H, 0.94, m, 1H, 1.19, m, 6H, 1.41, s, 6H, 1.43, s, 9H, 1.64, m, 5H, 1.83, m, 2H, 2.07, s, 3H, 2.51, s, 3H, 2.58, s, 3H, 2.92, s, 2H, 3.08, m, 2H, 3.16, m, 2H, 3.88, m, 1H, 4.05, m, 2H, 4.48, m, 5H, 4.86, m, NH; 5.37, ABq, J=11.9 Hz, 1H, 5.44, ABq, J=11.9 Hz, 1H, 6.20, d, J=7.0 Hz, NH; 6.32, br s, NH; 7.25, m, 10H, 7.47, d, J=9.1 Hz, 1H, 7.85, d, J=7.9 Hz, 2H, 7.95, d, J=9.4 Hz, 1H, 7.98, d, J=9.7 Hz, 1H. MS (ES +ve) m/z 1322.3 (60%) [M+H]$^+$; 612.8 (100) [M+2H-BOC]$^{2+}$.

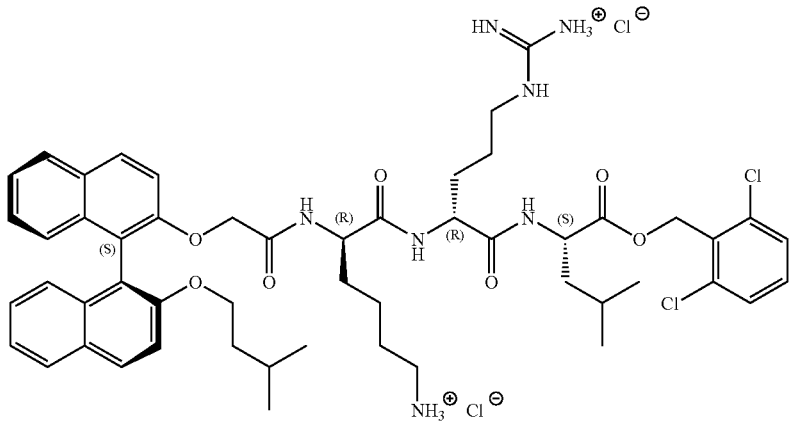

Compound 8

This compound was prepared via Protocol 3, using 8(v) (185 mg, 0.138 mmol) to yield 8 as a white solid (78 mg, 98%).

$^1$H NMR (300 MHz, CD$_3$OD) δ 0.50, d, J=6.3 Hz, 3H, 0.56, d, J=6.4 Hz, 3H, 0.87, d, J=5.2 Hz, 3H, 0.92, d, J=5.2 Hz, 3H, 0.99, m, 2H, 1.23, m, 4H, 1.66, m, 10H, 2.86, m, 2H, 3.19, m, 2H, 3.96, m, 1H, 4.16, m, 2H, 4.49, m, 4H, 5.38, ABq, J=11.7 Hz, 1H, 5.44, ABq, J=11.7 Hz, 1H, 7.10, m, 2H, 7.17, m, 2H, 7.32, m, 3H, 7.39, m, 2H, 7.46, d, J=9.0 Hz, 1H, 7.57, d, J=9.0 Hz, 1H, 7.87, d, J=8.1 Hz, 1H, 7.93, d, J=8.1 Hz, 1H, 7.99, d, J=9.0 Hz, 1H, 8.04, d, J=9.0 Hz, 1H. MS (ES +ve) m/z 969.8 (10%) [M+H]$^+$; 485.7 (100) [M+2H]$^{2+}$.

Synthesis of Compound 9

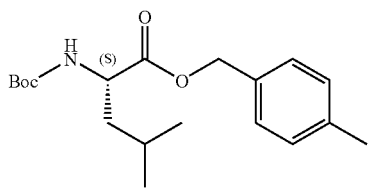

9(i)

To BOC-(L)-Leu-OH (250 mg, 1.08 mmol) and potassium carbonate (747 mg, 5.40 mmol) in acetone (50 mL) was added 4-methylbenzyl bromide (300 mg, 1.62 mmol). The resulting solution was heated at reflux overnight before being cooled, filtered and evaporated to dryness. The resultant residue was subjected to flash column chromatography over silica, eluting with 1:4 hexane/DCM to first remove 4-chlorobenzyl bromide, then with DCM to yield the product 9(i) as a colourless oil (340 mg, 94%).

$^1$H NMR (300 MHz, CDCl$_3$) δ 0.91, d, J=6.5 Hz, 3H, 0.92, d, J=6.2 Hz, 3H, 1.43, s, 9H, 1.49, m, 2H, 1.66, m, 1H, 2.35, s, 3H, 4.35, m, 1H, 4.95, d, J=9.2 Hz, NH; 5.08, ABq, J=12.3 Hz, 1H, 5.14, ABq, J=12.3 Hz, 1H; 7.16, ABq, J=7.9 Hz, 2H, 7.24, ABq, J=7.9 Hz, 2H. MS (ES +ve) m/z 353.3 (100%) [M+H$_2$O]$^+$; 336.3 (90) [M+H]$^+$.

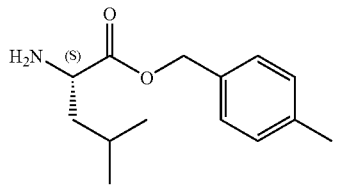

9(ii)

To 9(i) (340 mg, 1.01 mmol) in DCM (2 mL) was added TFA (2 mL) and the resulting solution stirred at room temperature for 3 hrs. The solution was then diluted with DCM (5 mL) and washed with sat. sodium bicarbonate solution until the washings were basic. The organic layer was then dried (MgSO$_4$), filtered and evaporated to dryness to yield the desired product 9(ii) as a white solid (215 mg, 90%).

$^1$H NMR (300 MHz, CDCl$_3$) δ 0.90, d, J=6.5 Hz, 3H, 0.92, d, J=6.7 Hz, 3H, 1.43, m, 1H, 1.55, m, 1H/NH$_2$; 1.76, m, 1H, 2.35, s, 3H, 3.49, m, 1H, 5.10, s, 2H, 7.18, ABq, J=7.9 Hz, 2H, 7.25, ABq, J=7.9 Hz, 2H. MS (ES +ve) m/z 236.0 (100%) [M+H]$^+$.

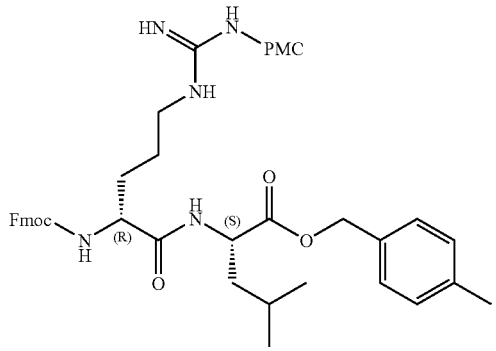

9(iii)

This compound was prepared via Protocol 1 using 9(ii) (215 mg, 0.914 mmol) and Fmoc-(D)-arg(Pmc)-OH (606 mg, 0.914 mmol) to yield the desired product 9(iii) as an off white solid (780 mg, 97%).

$^1$H NMR (500 MHz, CDCl$_3$) δ 0.78, m, 6H, 1.28, s, 6H, 1.61, m, 8H, 1.91, m, 1H, 2.01, s, 3H, 2.26, s, 3H, 2.50, m, 2H, 2.54, s, 3H, 2.57, s, 3H, 3.23, m, 2H, 4.03, m, 1H, 4.25, m, 3H, 4.52, m, 1H, 4.97, ABq, J=12.2 Hz, 1H, 5.03, ABq, J=12.2 Hz, 1H, 6.42, br s, NH; 7.06, ABq, J=7.7, Hz, 2H, 7.13, ABq, J=7.7, Hz, 2H, 7.17, m, 2H, 7.31, dd, J$_1$=7.5 Hz, J$_2$=7.5 Hz, 2H, 7.51, m, 2H, 7.68, d, J=7.5 Hz, 2H. MS (ES +ve) m/z 658.1 (100%) [M+H-Fmoc]$^+$.

9(iv)

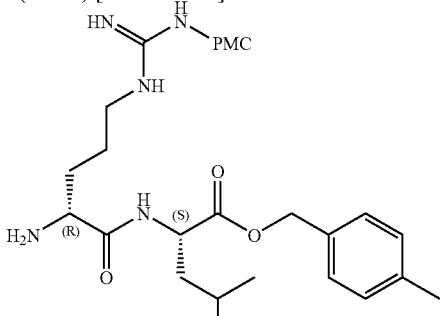

This compound was prepared via Protocol 2, using 9(iii) (650 mg, 0.739 mmol) to yield the desired product 9(iv) as a colourless oil (409 mg, 84%).

$^1$H NMR (500 MHz, CDCl$_3$) δ 0.86, d, J=5.9 Hz, 3H, 0.88, d, J=5.4 Hz, 3H, 1.28, s, 6H, 1.58, m, 5H/NH$_2$; 1.77, m, 3H, 2.00, m, 1H, 2.09, s, 3H, 2.31, s, 3H, 2.54, s, 3H, 2.56, s, 3H, 2.59, m, 2H, 3.15, m, 2H, 3.40, m, 1H, 4.49, m, 1H, 5.01, ABq, J=12.2 Hz, 1H, 5.08, ABq, J=12.2 Hz, 1H, 6.42, br s, NH; 7.11, ABq, J=8.0, Hz, 2H, 7.18, ABq, J=8.0, Hz, 2H, 7.81, d, J=7.8 Hz, NH. MS (ES +ve) m/z 658.1 (100%) [M+H]$^+$.

9(v)

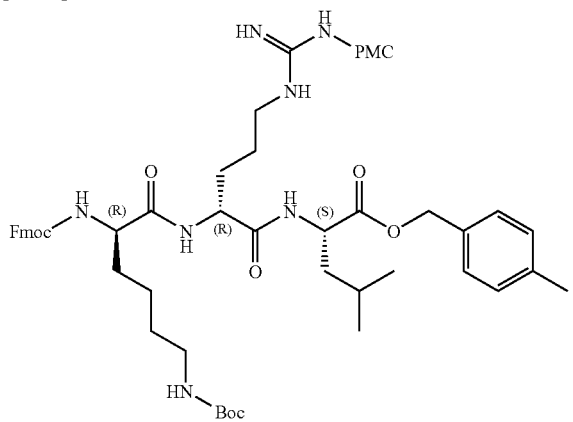

This compound was prepared via Protocol 1, using 9(iv) (377 mg, 0.573 mmol) and Fmoc-(D)-lys(BOC)-OH (268 mg, 0.573 mmol) to yield the desired product 9(v) as an off white solid (575 mg, 91%).

$^1$H NMR (500 MHz, CDCl$_3$) δ 0.82, m, 6H, 1.19, s, 6H, 1.39, s, 9H, 1.58, m, 13H, 2.02, s, 3H, 2.28, s, 3H, 2.49, m, 2H, 2.53, s, 3H, 2.55, s, 3H, 3.02, m, 2H, 3.19, m, 2H, 3.93, m, 1H, 4.19, m, 2H, 4.25, m, 1H, 4.53, m, 2H, 4.98, m, 2H, 6.23, m, NH; 6.50, br s, NH; 7.07, m, 2H, 7.11, m, 2H, 7.22, m, 2H, 7.33, m, 2H, 7.53, m, 2H, 7.68, m, 2H. MS (ES +ve) m/z 1108.3 (100%) [M+H]$^+$.

9(vi)

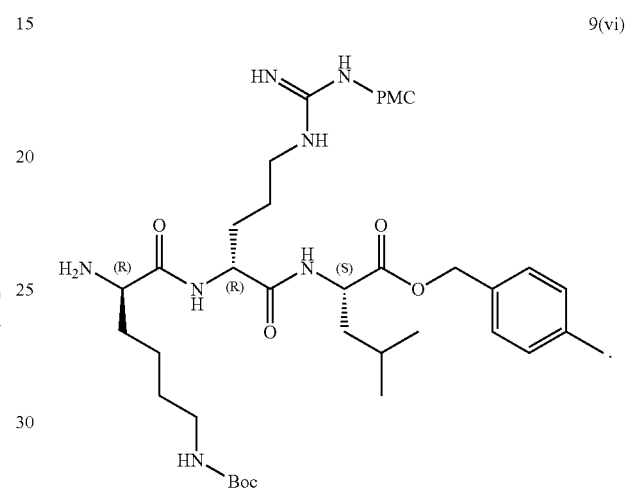

This compound was prepared via Protocol 2, using 9(v) (290 mg, 0.262 mmol) to yield the desired product 9(vi) as an off white solid (162 mg, 70%).

$^1$H NMR (500 MHz, CDCl$_3$) δ 0.85, d, J=6.3 Hz, 3H, 0.87, d, J=6.3 Hz, 3H, 1.29, s, 6H, 1.40, s, 9H, 1.58, m, 10H/NH$_2$; 1.78, dist t, 2H, 1.89, m, 1H, 2.09, s, 3H, 2.32, s, 3H, 2.54, s, 3H, 2.56, s, 3H, 2.61, m, 2H, 3.05, m, 2H, 3.22, m, 2H, 3.36, m, 1H, 4.54, m, 2H, 4.95, m, NH; 5.01, ABq, J=12.2 Hz, 1H, 5.07, ABq, J=12.2 Hz, 1H, 6.42, br s, NH; 7.12, ABq, J=7.8 Hz, 2H, 7.18, ABq, J=7.8 Hz, 2H, 7.60, d, J=7.3 Hz, NH; 8.00, d, J=6.4 Hz, NH. MS (ES +ve) m/z 886.3 (100%) [M+H]$^+$.

9(vii)

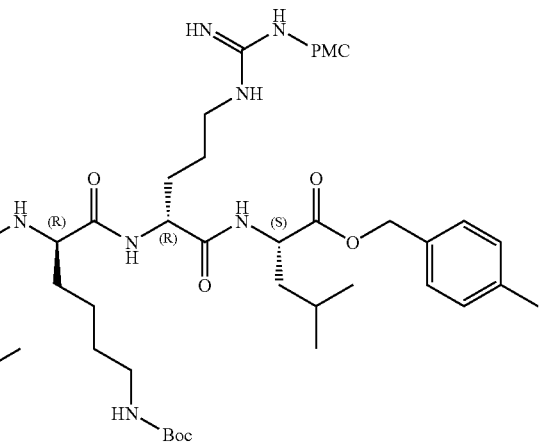

This compound was prepared via Protocol 1, using 1(ii) (75 mg, 0.181 mmol) and 9(vi) (160 mg, 0.181 mmol) to yield the desired product 9(vii) as a white solid (193 mg, 83%).

$^1$H NMR (500 MHz, CDCl$_3$) δ 0.47, d, J=6.5 Hz, 3H, 0.53, d, J=6.5 Hz, 3H, 0.78, m, 1H, 0.87, d, J=5.8 Hz, 3H, 0.89, d, J=5.8 Hz, 3H, 0.91, m, 1H, 1.22, m, 8H, 1.28, s, 6H, 1.42, s, 9H, 1.62, m, 3H, 1.76, dist t, 2H, 1.82, m, 1H, 2.09, s, 3H, 2.33, s, 3H, 2.55, s, 3H, 2.57, s, 3H, 2.59, m, 2H, 2.91, m, 2H, 3.16, m, 2H, 3.88, m, 1H, 4.05, m, 2H, 4.49, m, 4H, 4.84, m, NH; 5.04, ABq, J=12.2 Hz, 1H, 5.13, ABq, J=12.2 Hz, 1H, 6.19, d, J=6.4 Hz, NH; 6.27, s, NH; 7.22, m, 11H, 7.46, d, J=9.1 Hz, 1H, 7.85, dist t, 2H, 7.94, dist t, 2H. MS (ES +ve) m/z 1282 (100%) [M+H]$^+$.

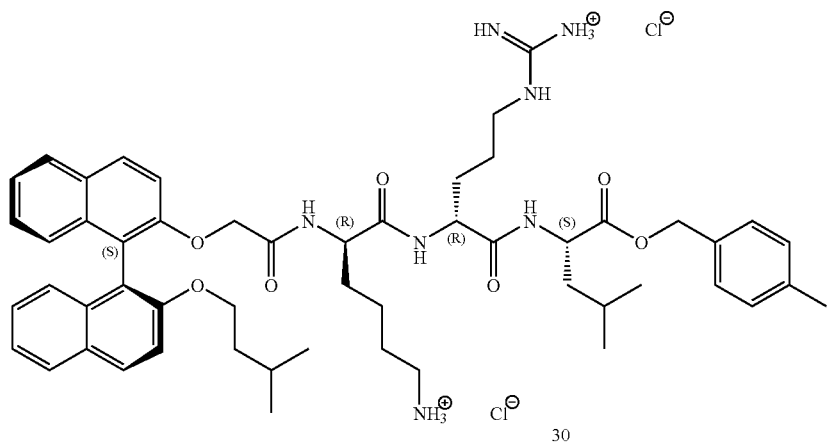

Compound 9

This compound was prepared via Protocol 3, using 9(vii) (107 mg, 0.083 mmol) to yield the product 9 as a white solid (28 mg, 34%).

$^1$H NMR (300 MHz, CD$_3$OD) δ 0.38, δ, J=6.2 Hz, 3H, 0.43, d, J=6.2 Hz, 3H, 0.85, m, 8H, 1.07, m, 2H, 1.18, m, 2H, 1.59, m, 9H, 2.25, s, 3H, 2.74, m, 2H, 3.09, m, 2H, 3.90, m, 1H, 4.06, m, 2H, 4.34, m, 3H, 4.40, ABq, J=14.7 Hz, 1H, 4.51, ABq, J=14.7 Hz, 1H, 4.99, ABq, J=12.1 Hz, 1H, 5.05, ABq, J=12.1 Hz, 1H, 6.99, d, J=8.5 Hz, 1H, 7.01, d, J=8.5 Hz, 1H, 7.09, d, J=7.8 Hz, 1H, 7.15, m, 4H, 7.27, m, 3H, 7.41, d, J=9.0 Hz, 1H, 7.49, dd, J$_1$=9.1 Hz, J$_2$=11.6 Hz, 1H, 7.84, m, 2H, 7.95, m, 2H. MS (ES +ve) m/z 916 (5%) [M+H]$^+$; 812 (10) [M+H-pMeBz]$^+$; 459 (95) [M+2H]$^{2+}$; 407 (100) [M+2H-pMeBz]$^{2+}$.

Synthesis of Compound 10

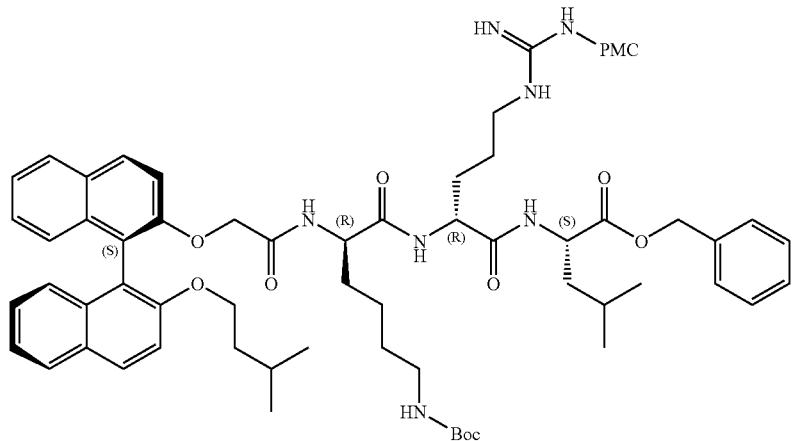

10(i)

This compound was prepared via Protocol 1, using (R)-1(ii) (67 mg, 0.162 mmol) and 1(viii) (140 mg, 0.161 mmol) to yield the desired product 10(i) as a white solid (108 mg, 53%).

$^1$H NMR (300 MHz, CDCl$_3$) δ 0.51, d, J=6.3 Hz, 3H, 0.56, d, J=6.3 Hz, 3H, 0.84, d, J=5.4 Hz, 3H, 0.86, m, 3H, 0.88, d, J=5.4 Hz, 3H, 1.21, m, 6H, 1.25, s, 6H, 1.29, m, 2H, 1.43, s, 9H, 1.64, m, 4H, 1.76, m, 2H, 1.84, m, 1H, 2.09, s, 3H, 2.52, s, 3H, 2.54, s, 3H, 2.58, m, 2H, 2.94, m, 2H, 3.11, m, 2H, 3.89, m, 1H, 3.99, m, 2H, 4.35, m, 1H, 4.37, ABq, J=14.7 Hz, 1H, 4.90, m, 1H, 4.58, ABq, J=14.7 Hz, 1H, 4.90, m, NH; 5.04, ABq, J=12.3 Hz, 1H, 5.13, ABq, J=12.3 Hz, 1H, 6.10, br s NH; 6.19, br s, NH; 7.45, m, 12H, 7.44, d, J=9.3 Hz, 1H, 7.82, d, J=8.3 Hz, 1H, 7.84, d, J=8.3 Hz, 1H, 7.89, d, J=8.8 Hz, 1H, 7.94, d, J=8.8 Hz, 1H. MS (ES +ve) m/z 1268 (50%) [M+H]$^+$; 585 (100) [M+2H-BOC]$^{2+}$.

To a solution of 1,1'-biphen-2,2'-diol (0.21 g, 1.15 mmol) in dry acetone (25 ml) was added potassium carbonate (1.62 g, 12.0 mmol). To the resulting suspension a solution of 1-bromo-3-methylbutane (0.18 ml, 1.50 mmol) in dry acetone (10 ml) was added portionwise over 90 minutes. The reaction mixture was then heated at reflux for 18 hours. The cooled mixture was filtered and the solid residue was washed with acetone (2×20 ml). The combined filtrate and washes were concentrated in vacuo to yield the product 11(i) as a colourless oil (292 mg, 99%).

$^1$H NMR (300 MHz, CDCl$_3$) δ 0.95, d, J=6.2 Hz, 6H, 1.71, m, 3H, 4.13, t, J=6.4 Hz, 2H, 7.25, m, 8H. MS (EI) m/z 256 (30%) [M]$^+$; 186 (100) [M-(CH$_2$CH$_2$CH(CH$_3$)$_2$)]$^+$.

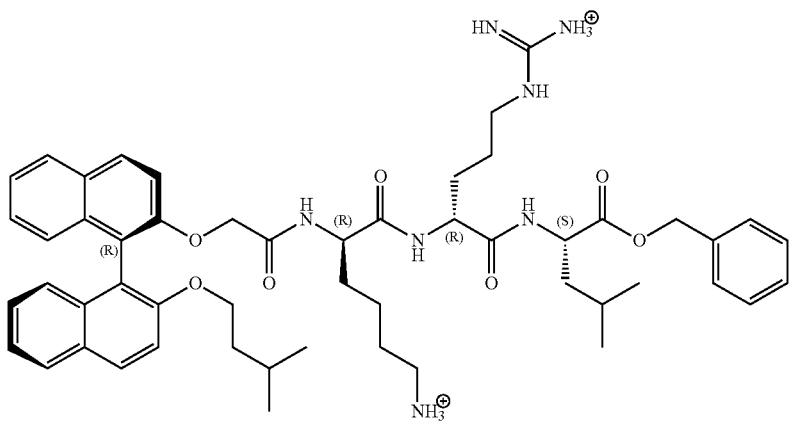

Compound 10

This compound was prepared via Protocol 3, using 10(i) (105 mg, 0.083 mmol) to yield an impure product. Protocol 3 was repeated on 80 mg of this product to yield 10 as an off white solid (58 mg, 82%).

$^1$H NMR (300 MHz, CD$_3$OD) δ 0.41, d, J=6.6 Hz, 3H, 0.46, d, J=6.6 Hz, 3H, 0.78, d, J=5.7 Hz, 3H, 0.83, d, J=5.7 Hz, 3H, 1.06, m, 6H, 1.38, m, 1H, 1.53, m, 8H, 1.72, m, 1H, 2.78, m, 2H, 3.05, m, 2H, 3.84, m, 1H, 3.97, m, 1H, 4.02, m, 1H, 4.25, m, 1H, 4.35, m, 2H, 4.51, ABq, J=15.0 Hz, 1H, 5.00, ABq, J=12.3 Hz, 1H, 5.05, ABq, J=12.3 Hz, 1H, 6.96, d, J=8.7 Hz, 1H, 7.05, d, J=8.4 Hz, 1H, 7.13, m, 2H, 7.24, m, 7H, 7.38, d, J=9.0 Hz, 1H; 7.45, d, J=9.0 Hz, 1H, 7.80, d, J=8.1 Hz, 1H, 7.84, d, J=7.8 Hz, 1H, 7.91, d, J=9.0 Hz, 1H, 7.96, d, J=8.7 Hz, 1H. MS (ES +ve) m/z 902 (10%) [M+H]$^+$; 452.0 (100) [M+H]$^{2+}$.

Synthesis of Compound 11

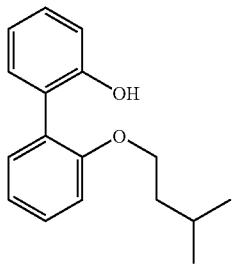

11(i)

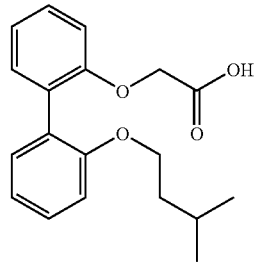

11(ii)

To a solution of 11(i) (0.29 g, 1.13 mmol) in methanol (20 ml) was added potassium carbonate (1.83 g, 13.2 mmol) and bromoacetic acid (0.56 g, 4.03 mmol) and the resulting suspension was heated at reflux for 16 hours. The cooled reaction mixture was concentrated in vacuo and the residue was dissolved in distilled water (100 ml) then washed with ether (3×20 ml). The aqueous solution was acidified (10% HCl) and extracted with DCM (3×20 ml). The combined organic layers were dried (MgSO$_4$) and concentrated in vacuo to yield the title compound 11(ii) as a thick colourless oil (111 mg, 30%).

$^1$H NMR (300 MHz, CDCl$_3$) δ 0.77, d, J=4.4 Hz, 6H, 1.45, m, 3H, 3.99, t, J=6.5 Hz, 2H, 4.62, s, 2H, 6.87, dd, J=8.2, 0.9 Hz, 1H, 7.08, m, 3H, 7.31, m, 4H. MS (ES +ve) m/z 353 (12%) [M+K]$^+$; 337 (39) [M+Na]$^+$; 332 (96) [M+NH$_4$]$^+$; 315 (100) [M+H]$^+$; 245 (38).

11(iii)

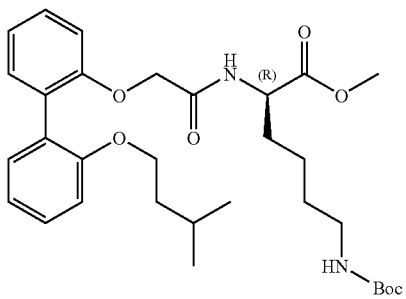

This compound was prepared via Protocol 1, using (R)-Lysine(Boc)-methyl ester (0.10 g, 0.38 mmol) and 11(ii) (0.11 g, 0.34 mmol) in anhydrous acetonitrile (10 ml) with EDCI (0.09 g, 0.45 mmol) and HObt (0.08 g, 0.58 mmol). Purification with 1-2% methanol:DCM gave product 11(iii) as a pale yellow oil (179 mg, 93%).

$^1$H NMR (300 MHz, CDCl$_3$) δ 0.76, dd, J=6.4 Hz, 6H, 1.08, m, 2H, 1.43, m, 12H, 1.67, m, 2H, 3.00, m, 3H, 3.66, s, 3H, 3.90, m, 3H, 4.44, m, 4H, 6.74, br d, J=8.5 Hz, 1H, 8.86, d, J=7.9 Hz, 1H, 7.03, m, 3H, 7.27, m, 4H. MS (ES +ve) m/z 579 (11%) [M+Na]$^+$; 557 (100) [M+H]$^+$; 457 (29) [M-Boc+H]$^+$; 233 (88).

11(vi)

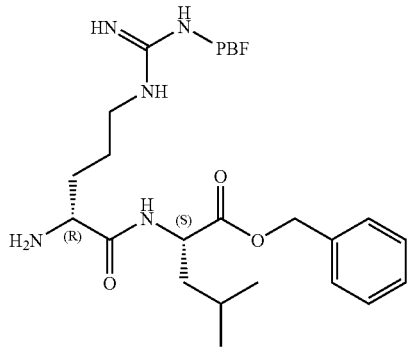

This compound was prepared in two steps. The first step via Protocol 1, using 1(iv) (1.12 g, 5.06 mmol) and Fmoc-(D)-arg(Pbf)-OH (3.06 mg, 4.72 mmol) to yield the Fmoc protected precursor 11(v) as a white foamy solid (MS (ES +ve) m/z 852 (100%) [M+H]$^+$). This was then deprotected via Protocol 2 to afford the desired compound 11(vi) as a yellow oil (1.54 g, 52% two steps).

MS (ES +ve) m/z 630 (100%) [M+H]$^+$

11(iv)

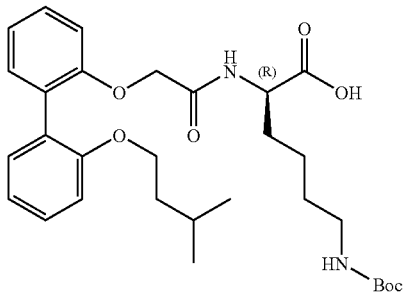

To a solution of 11(iii) (0.18 g, 0.32 mmol) in THF:water (4:1) (15 ml) was added lithium hydroxide (0.11 g, 2.60 mmol) and the resulting solution was stirred at 20° C. for 16 hours. The reaction mixture was diluted with water (5 ml), acidified with 10% HCl and extracted with DCM (4×10 ml). The combined organic layers were dried (MgSO$_4$) and concentrated in vacuo to give the product 11(iv) as a pale yellow oil (108 mg, 62%).

$^1$H NMR (500 MHz, CDCl$_3$) δ 0.77, dd, J=6.3, 4.4 Hz, 6H, 1.13, m, 2H, 1.44, m, 14H, 1.75, br s, 1H, 3.12, m, 2H, 3.94, m, 2H, 4.49, ABq, J=14.6 Hz, 2H, 4.64, m, 1H, 6.87, m, 2H, 6.99, m, 2H, 7.05, t, J=7.8 Hz, 1H, 7.26, m, 4H. MS (ES +ve) m/z 543, (100%) [M+H]$^+$; 487 (46) [M+H-56]$^+$; 443 (46) [M+H-Boc]$^+$.

11(vii)

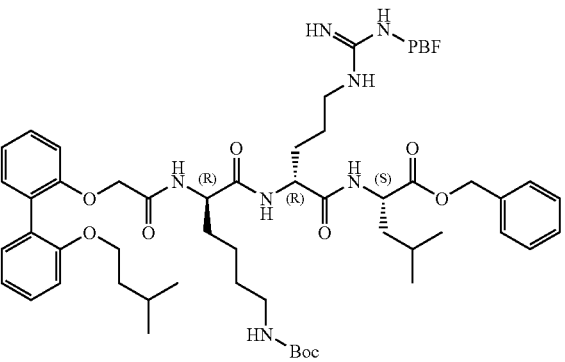

This compound was prepared via Protocol 1, using 11(iv) (70 mg, 0.13 mmol) and 11(vi) (77 mg, 0.12 mmol) in anhydrous acetonitrile with EDCI (40 mg, 0.21 mmol) and HObt (39 mg, 0.29 mmol). Purification with 1-2% methanol:DCM gave product 11(vii) as a clear colourless oil (103 mg, 71%).

$^1$H NMR (300 MHz, CDCl$_3$) δ 0.77, dd, J=6.4, 1.8 Hz, 6H, 0.88, dd, J=7.3, 7.3 Hz, 6H, 1.08, m, 2H, 1.43, m, 23H, 1.63, m, 5H, 1.83, m, 1H, 2.05, s, 3H, 2.47, s, 3H, 2.54, s, 3H, 2.91, s, 2H, 3.00, m, 2H, 3.17, m, 2H, 3.93, m, 2H, 4.46, m, 5H, 4.85, m, 1H, 5.14, ABq, J=12.3 Hz, 2H, 6.15, br s, 2H, 6.79, m, 2H, 7.01, m, 3H, 7.28, m, 10H, 7.61, br d, 1H. MS (ES +ve) m/z 1153 (100%) [M+H]$^+$; 527 (68); 288 (98).

Compound 11

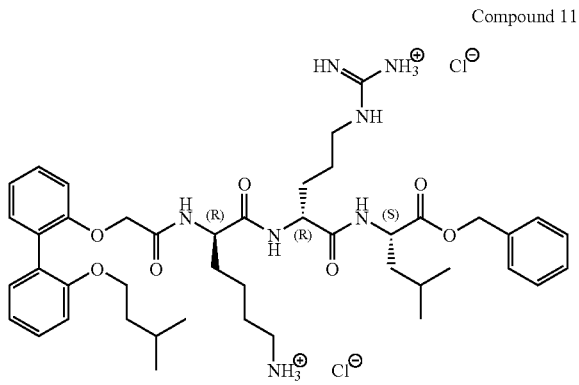

This compound was prepared via Protocol 3, using 11(vii) (95 mg, 82 µmol) and TFA:TIPS:H₂O (95:2.5:2.5) (2 ml). Precipitation from methanol using ether (3 times) gave the product 11 as off-white crystals (67 mg, 93%).

¹H NMR (300 MHz, CD₃OD) δ 0.78, dd, J=6.4, 1.2 Hz, 6H, 0.91, dd, J=14.4, 5.6 Hz, 6H, 1.25, m, 2H, 1.55, m, 14H, 2.89, m, 2H, 3.16, m, 2H, 3.96, m, 2H, 4.44, m, 5H, 5.14, ABq, J=10.7 Hz, 2H, 7.02, m, 4H, 7.23, m, 2H, 7.35, m, 7H. MS (ES +ve) m/z 802 (4%) [M+H]⁺; 401 (100) [M+H]²⁺.

Synthesis of Compound 12

12(i)

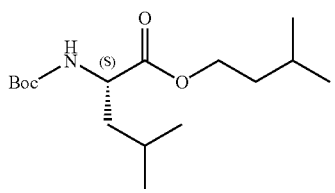

To BOC(L)-Leu-OH (300 mg, 1.30 mmol) and potassium carbonate (0.4 g, 2.90 mmol) in acetone (25 ml) was added 4-bromo-1-methylbutane (0.2 ml, 1.60 mmol). The resulting solution was heated at reflux overnight before being cooled, filtered and evaporated to dryness. The resultant residue was subjected to flash column chromatography over silica, eluting with DCM to yield the product 12(i) as a colourless oil (172 mg, 44%).

¹H NMR (300 MHz, CDCl₃) δ 0.94, m, 12H, 1.44, s, 9H, 1.55, m, 4H, 1.70, m, 2H, 4.14, dt, J=6.8 Hz, J₂=2.0 Hz, 2H. 4.29, m, 1H, 5.04, d, J=8.3 Hz, NH. MS (ES +ve) m/z 302.1 (100%) [M+H]⁺; 246.1 (70) [M+H-iBu]⁺; 202.1 (70) [M+H-BOC]⁺.

12(ii)

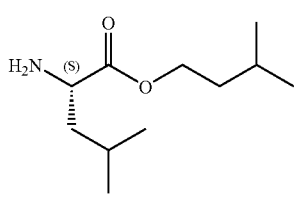

To 12(i) (170 mg, 0.592 mmol) in DCM (2 ml) was added TFA (2 ml) and the resulting solution stirred at room temperature for 1 hr. The solution was then diluted with ethyl acetate (10 ml) and washed with sat. sodium bicarbonate solution until the washings were basic. The organic layer was then dried (MgSO₄), filtered and evaporated to dryness to yield the desired product 12(ii) as a white solid (93 mg, 78%).

¹H NMR (300 MHz, CDCl₃) δ 0.93, m, 12H, 1.43, m, 1H, 1.55, m, 3H/NH₂; 1.73, m, 2H, 3.45, dd, J₁=8.2 Hz, J₂=5.9 Hz, 1H, 4.14, t, J=6.9 Hz, 2H. MS (ES +ve) m/z 202.0 (100%) [M+H]⁺.

12(iii)

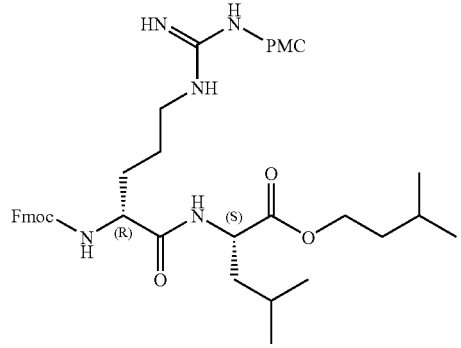

This compound was prepared via Protocol 1 using 12(ii) (90 mg, 0.481 mmol) and Fmoc-(D)-arg(Pmc)-OH (160 mg, 0.241 mmol) to yield the desired product 12(iii) as an off white solid (198 mg, 97%).

¹H NMR (300 MHz, CDCl₃) δ 0.84, m, 12H, 1.21, s, 3H, 1.22, s, 3H, 1.47, m, 2H, 1.60, m, 9H, 1.90, m, 1H, 2.05, s, 3H, 2.51, m, 2H, 2.55, s, 3H, 2.58, s, 3H, 3.24, m, 2H, 4.05, m, 3H, 4.24, m, 3H, 4.47, m, 1H, 6.26, br s, NH; 6.35, d, J=8.0 Hz, NH; 6.40, br s, NH; 7.18, t, J=7.4 Hz, 2H, 7.32, t, J=7.5 Hz, 2H, 7.37, d, J=7.7 Hz, NH; 7.51, d, J=7.4 Hz, 2H, 7.69, d, J=7.5 Hz, 2H. MS (ES +ve) m/z 846.0 (100%) [M+H]⁺.

12(iv)

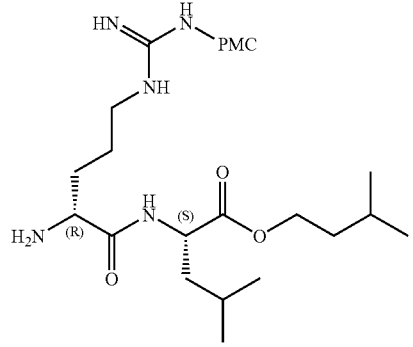

This compound was prepared via Protocol 2, using 12(iii) (150 mg, 0.177 mmol) to yield the desired product 12(iv) as a colourless oil (101 mg, 91%).

¹H NMR (300 MHz, CDCl₃) δ 0.92, m, 12H, 1.30, s, 6H, 1.52, m, 3H, 1.62, m, 4H/NH₂; 1.80, m, 5H, 2.10, s, 3H; 2.55, s, 3H, 2.57, s, 3H, 2.62, t, J=6.7 Hz, 2H, 3.19, m, 2H, 3.40, m, 1H, 4.11, m, 2H, 4.46, m, H, 6.31, br s, NH; 6.38, br s, NH; 7.76, d, J=8.0 Hz, NH. MS (ES +ve) m/z 624.0 (100%) [M+H]⁺.

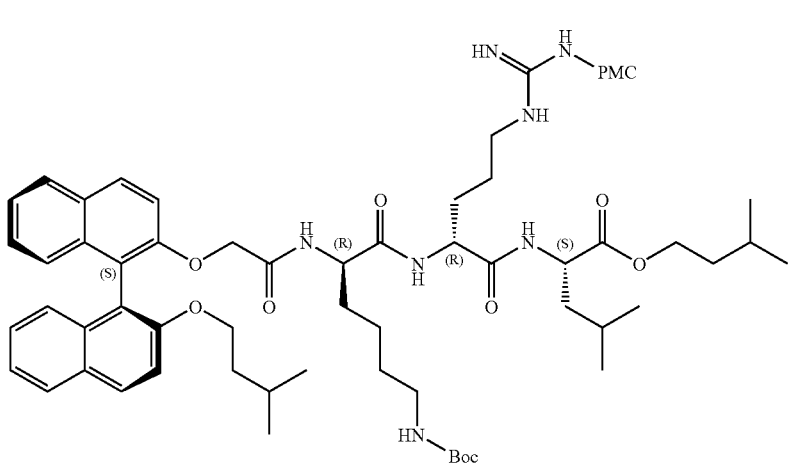

12(v)

This compound was prepared via Protocol 1, using 6(vi) (75 mg, 0.117 mmol) and 12(iv) (86 mg, 0.138 mmol) to yield 12(v) as a light brown solid (122 mg, 84%).

$^1$H NMR (300 MHz, CDCl$_3$) δ 0.47, d, J=6.6 Hz, 3H, 0.52, d, J=6.6 Hz, 3H, 0.76, m, 2H, 0.91, m, 12H, 1.18, m, 6H, 1.27, s, 6H, 1.41, s, 9H, 1.53, m, 5H, 1.63, m, 5H, 1.77, m, 3H, 2.09, s, 3H, 2.55, s, 3H, 2.57, s, 3H, 2.60, m, 2H, 2.92, m, 2H, 3.19, m, 2H, 3.89, m, 1H, 4.11, m, 4H, 4.43, m, 4H, 4.84, m, NH; 6.19, d, J=7.7 Hz, NH; 6.28, br s, NH; 7.26, m, 7H, 7.46, d, J=9.2 Hz, 1H, 7.84, d, J=8.9 Hz, 1H, 7.86, d, J=8.8 Hz, 1H, 7.93, d, J=9.3 Hz, 1H, 7.96, d, J=9.5 Hz, 1H. MS (ES +ve) m/z 1247.9 (40%) [M+H]$^+$; 574.7 (100) [M+2H-BOC]$^{2+}$.

Synthesis of Compound 13

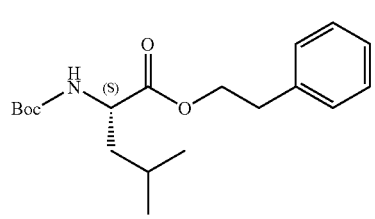

13(i)

Compound 12

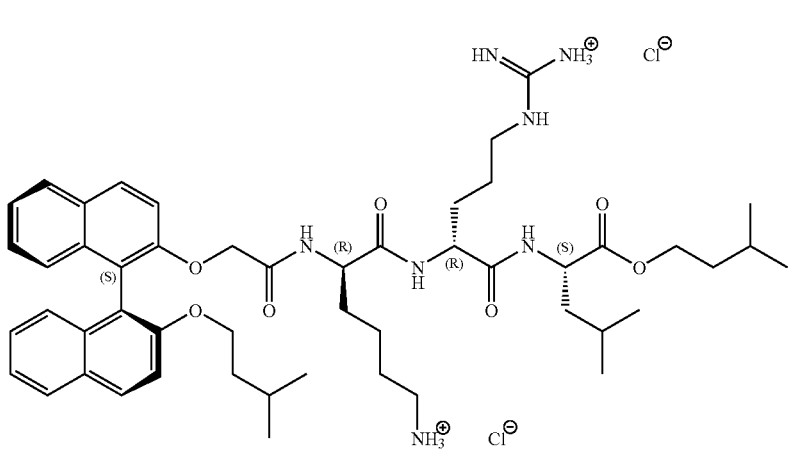

This compound was prepared via Protocol 3, using 12(v) (120 mg, 0.096 mmol) to yield 12 as an off white solid (84 mg, 92%).

$^1$H NMR (300 MHz, CD$_3$OD) δ 0.52, d, J=6.6 Hz, 3H, 0.57, d, J=6.6 Hz, 3H, 0.91, m, 14H, 1.14, m, 2H, 1.26, m, 2H, 1.54, m, 5H, 1.65, m, 7H, 1.84, m, 1H, 2.82, m, 2H, 3.18, m, 2H, 3.95, m, 1H, 4.14, m, 4H, 4.36, m, 2H, 4.46, ABq, J=14.6 Hz, 1H, 4.58, ABq, J=14.6 Hz, 1H, 7.07, dist t, 2H, 7.21, dist t, 2H, 7.34, dist t, 2H, 7.47, d, J=9.3 Hz, 1H, 7.56, d, J=9.3 Hz, 1H, 7.91, dist t, 2H, 8.03, dist t, 2H. MS (ES +ve) m/z 882.0 (5%) [M+H]$^+$; 441.6 (100) [M+2H]$^{2+}$.

To BOC-(L)-Leu-OH (200 mg, 0.865 mmol) and potassium carbonate (400 mg, 2.89 mmol) in acetone (40 ml) was added (2-bromoethyl)benzene (0.14 ml, 1 mmol). The resulting solution was heated at reflux overnight before being cooled, filtered and evaporated to dryness. The resultant residue was subjected to flash column chromatography over silica, eluting with 5% ethyl acetate/hexane to first remove (2-bromoethyl)benzene, then with DCM to yield the product 13(i) as a colourless oil (235 mg, 81%).

$^1$H NMR (500 MHz, CDCl$_3$) δ 0.86, d, J=6.6 Hz, 3H, 0.88, d, J=6.6 Hz, 3H, 1.42, s, 9H, 1.47, m, 1H, 2.92, t, J=7.0 Hz, 2H, 4.31, m, 3H, 5.04, d, J=8.3 Hz, NH; 7.19, m, 3H, 7.26, m, 2H. MS (ES +ve) m/z 374.2 (80%) [M+K]⁺; 358.3 (100) [M+Na]⁺; 336.3 (10) [M+H]⁺; 236.2 (50) [M+H-BOC]⁺.

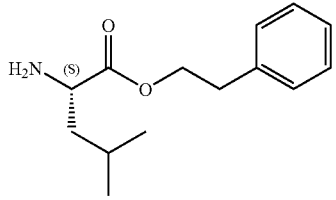

13(ii)

To 13(i) (230 mg, 0.686 mmol) dissolved in DCM (2 ml) was added TFA (2 ml) and the resulting solution stirred at room temperature for 2 hrs. Ethyl acetate (15 ml) was then added and the solution washed with sat. sodium bicarbonate solution until the washing were basic. The organic layer was then dried (MgSO₄) and evaporated to dryness to yield the desired product 13(ii) as a yellow oil (140 mg, 87%).

$^1$H NMR (500 MHz, CDCl₃) δ 0.87, d, J=5.7 Hz, 3H, 0.89, d, J=5.7 Hz, 3H, 1.35, m, 1H, 1.48, m, 1H, 1.69, m, 1H, 1.89, m, NH₂; 2.94, t, J=7.0 Hz, 2H, 3.42, dd, J=8.3 Hz, J₂=5.9 Hz, 1H, 4.33, m, 2H, 7.21, m, 3H, 7.28, m, 2H. MS (ES +ve) m/z 236.2 (100%) [M+H]⁺.

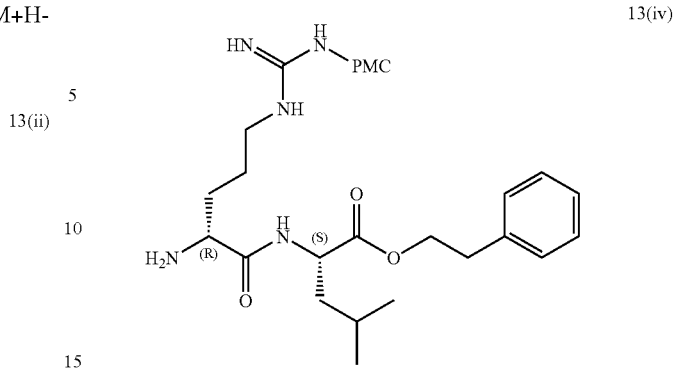

13(iv)

This compound was prepared in two steps. The first via Protocol 1, using 13(ii) (92 mg, 0.391 mmol) and Fmoc-(D)-arg(Pmc)-OH (265 mg, 0.400 mmol) to yield the Fmoc protected precursor 13(iii) as a colourless oil (308 mg, 90% MS (ES +ve) m/z 880.2 (100%) [M+H]⁺). The desired product was then prepared via Protocol 2, using 13(iii) (280 mg, 0.318 mmol) to afford the product 13(iv) as a colourless oil (123 mg, 59%).

$^1$H NMR (300 MHz, CDCl₃) δ 0.85, d, J=5.7 Hz, 3H, 0.86, d, J=5.9 Hz, 3H, 1.29, s, 6H, 1.53, m, 4H/NH₂; 1.78, m, 5H, 2.09, s, 3H, 2.54, s, 3H, 2.56, s, 3H, 2.60, m, 2H, 2.91, t, J=7.0 Hz, 2H, 3.17, m, 2H, 3.37, m, 1H, 4.29, m, 2H, 4.43, m, 1H, 6.33, br s, NH; 6.38, br s, NH; 7.22, m, 5H, 7.73, d, J=8.0 Hz, NH. MS (ES +ve) m/z 658.0 (100%) [M+H]⁺; 554.1 (60) [M+H-EtPh]⁺.

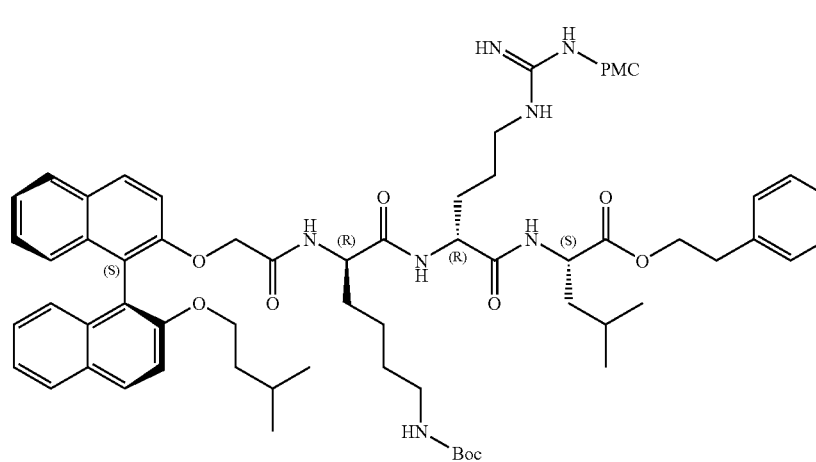

13(v)

This compound was prepared via Protocol 1, using 6(vi) (107 mg, 0.166 mmol) and 13(iv) (107 mg, 0.167 mmol) to yield 13(v) as a white solid (118 mg, 55%).

$^1$H NMR (300 MHz, CDCl₃) δ 0.46, d, J=6.3 Hz, 3H, 0.51, d, J=6.3 Hz, 3H, 0.77, m, 2H, 0.89, m, 6H; 1.19, m, 3H, 1.27, s, 6H, 1.41, s, 9H, 1.54, m, 5H, 1.76, m, 4H, 2.09, s, 3H, 2.54, s, 3H, 2.56, s, 3H, 2.61, m, 2H, 2.91, m, 2H, 2.93, t, J=7.1 Hz; 3.15, m, 2H, 3.87, m, 1H, 4.04, m, 2H, 4.42, m, 4H, 4.82, m, NH; 6.18, d, J=7.1 Hz, NH; 6.28, br s, NH; 7.21, m, 12H, 7.43, d, J=9.1 Hz, 1H, 7.83, d, J=7.8 Hz, 1H, 7.85, d, J=7.8 Hz, 1H, 7.92, d, J=9.0 Hz, 1H, 7.93, d, J=8.9 Hz, 1H. MS (ES +ve) m/z 1282.0 (80%) [M+H]⁺; 591.7 (100) [M+2H-BOC]²⁺.

Compound 13

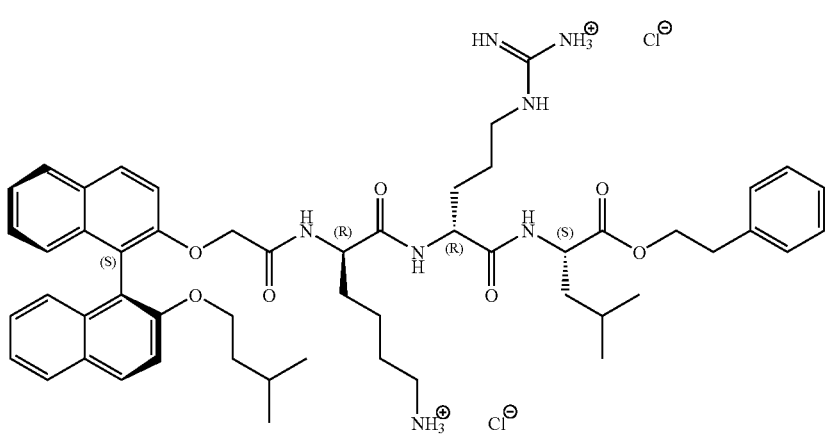

This compound was prepared via Protocol 3, using 13(v) (110 mg, 0.086 mmol) to yield 13 as a white solid (80 mg, 96%).

¹H NMR (300 MHz, CD₃OD) δ 0.50, d, J=6.2 Hz, 3H, 0.55, d, J=6.2 Hz, 3H, 0.85, d, J=6.1 Hz, 3H, 0.89, d, J=6.1 Hz, 3H, 0.96, m, 2H, 1.16, m, 5H, 1.57, m, 10H, 1.81, m, 1H, 2.80, m, 2H, 2.93, t, J=6.7 Hz, 2H, 3.16, m, 2H, 3.94, m, 1H, 4.14, m, 2H, 4.34, m, 2H, 5.45, ABq, J=14.8 Hz, 1H, 5.56, ABq, J=14.8 Hz, 1H, 7.04, d, J=4.3 Hz, 1H, 7.07, d, J=4.3 Hz, 1H, 7.22, m, 9H, 7.45, d, J=9.0 Hz, 1H, 7.53, d, J=9.0 Hz, 1H, 7.88, d, J=7.6 Hz, 1H, 7.91, d, J=7.3 Hz, 1H, 7.99, d, J=9.0 Hz, 1H, 8.00, d, J=9.0 Hz, 1H. MS (ES +ve) m/z 915.9 (5%) [M+H]⁺; 458.9 (100) [M+2H]²⁺.

Synthesis of Compound 14

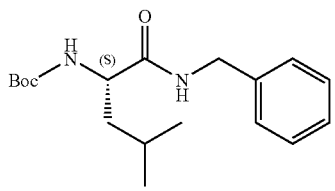

14(i)

This compound was prepared via Protocol 1, using BOC-(L)-leu-OH (200 mg, 0.865 mmol) and benzylamine (0.1 ml, 0.916 mmol) to yield the desired product 14(i) as an off white solid (239 mg, 86%).

¹H NMR (500 MHz, CDCl₃) δ 0.86, d, J=6.8 Hz, 3H, 0.88, d, J=6.8 Hz, 3H, 1.34, s, 9H, 1.53, m, 2H, 1.64, m, 1H, 4.30, m, 3H, 5.57, d, J=7.7 Hz, NH; 7.17, m, 5H, 7.50, m, NH. MS (ES +ve) m/z 359.2 (100%) [M+K]⁺; 343.3 (20) [M+Na]⁺; 321.3 (20) [M+H]⁺; 222.3 (40) [M+H-BOC]⁺.

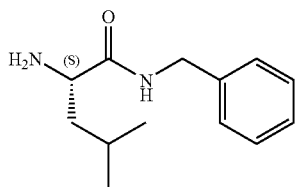

14(ii)

To 14(i) (230 mg, 0.719 mmol) dissolved in DCM (2 ml) was added TFA (2 ml) and the resulting solution stirred at room temperature for 2 hrs. Ethyl acetate (15 ml) was then added and the solution washed with sat. sodium bicarbonate solution until the washing were basic. The organic layer was then dried (MgSO₄) and evaporated to dryness to yield the desired product 14(ii) as a colourless oil (65 mg, 41%).

¹H NMR (300 MHz, CDCl₃) δ 0.93, d, J=5.6 Hz, 3H, 0.96, d, J=5.6 Hz, 3H, 1.37, m, 1H, 1.68, br s, NH₂; 1.73, m, 2H, 3.43, m, 1H, 4.42, d, J=5.8 Hz, 2H, 7.27, m, 2H, 7.32, m, 3H, 7.69, m, NH. MS (ES +ve) m/z 221.2 (100%) [M+H]⁺.

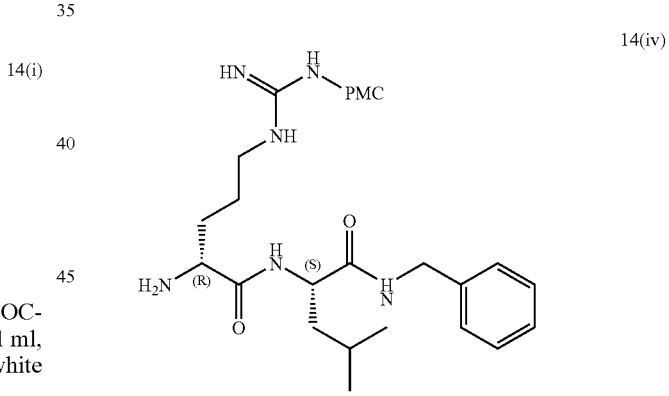

14(iv)

This compound was prepared in two steps. The first step via Protocol 1, using 14(ii) (60 mg, 0.272 mmol) and Fmoc-(D)-arg(Pmc)-OH (176 mg, 0.272 mmol) to yield the Fmoc protected precursor 14(iii) as a white foamy solid (156 mg, 67%. MS (ES +ve) m/z 851.2 (100%) [M+H]⁺). The desired product was then prepared via Protocol 2, using 14(iii) (156 mg, 0.183 mmol) to afford the product 14(iv) as a white solid (85 mg, 74%).

¹H NMR (300 MHz, CDCl₃) δ 0.83, m, 6H, 1.44, s, 9H, 1.62, m, 6H/NH₂; 1.80, m, 1H, 2.05, s, 3H, 2.43, s, 3H, 2.51, s, 3H, 2.90, s, 2H, 3.15, m, 2H, 3.62, m, 1H, 4.25, m, 2H, 4.45, m, 1H, 6.54, br s, NH; 7.14, m, 5H, 7.72, dd, J₁=7.8 Hz, J₂=16.0 Hz, NH; 8.25, m, NH. MS (ES +ve) m/z 629.0 (100%) [M+H]⁺.

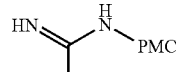

14(v)

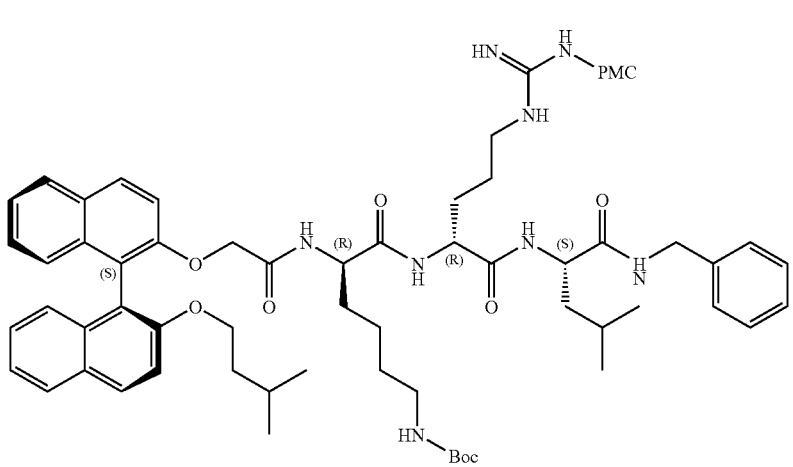

This compound was prepared via Protocol 1, using 6(vi) (82 mg, 0.127 mmol) and 14(iv)(80 mg, 0.127 mmol) to yield 14(v) as a white solid (63 mg, 41%).

$^1$H NMR (300 MHz, CDCl$_3$) δ 0.44, d, J=6.5 Hz, 3H, 0.49, d, J=6.5 Hz, 3H, 0.79, d, J=6.3 Hz, 3H, 0.83, d, J=6.3 Hz, 3H, 0.85, m, 2H, 1.11, m, 4H, 1.26, m, 4H, 1.40, s, 6H, 1.43, s, 9H, 1.69, m, 5H, 1.95, m, 1H, 2.04, s, 3H, 2.46, s, 3H, 2.52, s, 3H, 2.90, s, 2H, 2.93, m, 2H, 3.19, m, 2H, 3.80, m, 1H, 4.13, m, 2H, 4.30, m, 5H, 4.49, m, 1H, 5.05, m, NH; 5.04, ABq, J=12.2 Hz, 1H, 5.11, ABq, J=12.2 Hz, 1H, 6.19, d, J=6.8 Hz, NH; 6.15, br s, NH; 6.46, br s, NH; 7.10, m, 6H, 7.31, m, 5H, 7.71, m, 3H, 7.84, dist d, 1H, 7.90, d, J=9.2 Hz, 2H. MS (ES +ve) m/z 1252.9 (80%) [M+H]$^+$; 577.4 (100) [M+2H-BOC]$^{2+}$.

Synthesis of Compound 15

15(i)

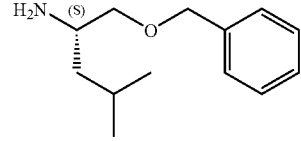

To a stirring suspension of NaH (60% dispersion, 73 mg, 1.86 mmol) in dry THF (10 ml) was added dropwise (L)-leucinol (0.2 ml, 1.55 mmol). The solution was then heated at reflux overnight before being cooled and water (1 ml) added.

Compound 14

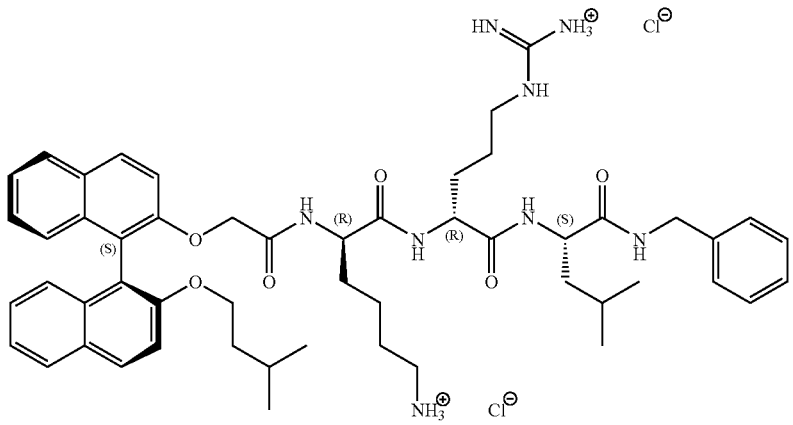

This compound was prepared via Protocol 3, using 14(v) (63 mg, 0.050 mmol) to yield 14 as a white solid (40 mg, 82%).

$^1$H NMR (500 MHz, CD$_3$OD) δ 0.48, d, J=6.5 Hz, 3H, 0.53, d, J=6.5 Hz, 3H, 0.90, m, 8H, 1.17, m, 5H, 1.36, m, 1H, 1.53, m, 3H, 1.68, m, 6H, 1.81, m, 1H, 2.77, m, 2H, 3.19, m, 2H, 3.87, m, 1H, 4.00, m, 1H, 4.10, m, 1H, 4.21, m, 1H, 4.37, m, 3H, 4.44, ABq, J=15.0 Hz, 1H, 4.52, ABq, J=15.0 Hz, 1H, 7.06, dist t, 2H, 7.25, m, 7H, 7.34, m, 2H, 7.46, d, J=9.5 Hz, 2H, 7.90, d, J=9.0 Hz, 2H, 7.99, d, J=8.8 Hz, 1H, 8.02, d, J=8.7 Hz, 1H. MS (ES +ve) m/z 901.0 (5%) [M+H]$^+$; 451.1 (100) [M+2H]$^{2+}$.

After evaporation to near dryness the residue was taken up in DCM (20 ml) and extracted with 1M HCl (3×20 ml). The combined acid extracts were then basified with 2M KOH and back extracted with DCM (5×15 ml). The combined organic extracts were then dried (MgSO$_4$), filtered and evaporated to dryness to yield the desired product 15(i) as a white solid (172 mg, 54%) of sufficient purity to use in the next step.

$^1$H NMR (300 MHz, CDCl$_3$) δ 0.87, d, J=5.4 Hz, 3H, 0.89, d, J=5.4 Hz, 3H, 1.23, m, 1H, 1.41, m, 1H, 1.56, m, 1H, 2.42, br s, NH$_2$; 2.74, m, 1H, 3.31, dABq, J=10.7 Hz, J$_2$=6.2 Hz, 1H, 3.55, dABq, J=10.7 Hz, J$_2$=3.9 Hz, 1H, 3.76, ABq, J=12.9 Hz, 1H, 3.82, ABq, J=12.9, Hz, 1H, 7.32, m, 5H. MS (ES +ve) m/z 208 (100%) [M+H]$^+$,

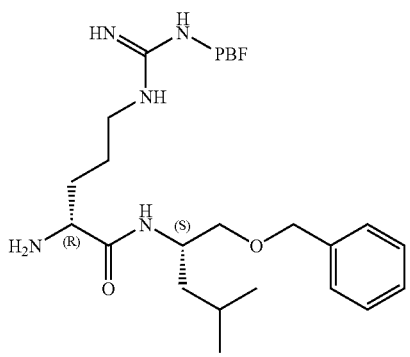

15(iii)

This compound was prepared in two steps. The initial coupling reaction via Protocol 1, using 15(i) (140 mg, 0.675 mmol) and Fmoc-(D)-arg(Pbf)-OH (438 mg, 0.675 mmol) to yield the Fmoc protected precursor 15(ii) as an off white foamy solid (MS (ES +ve) m/z 837.9 (25% [M+H]⁺; 419.8 (100) [M+2H]²⁺). This compound was then deprotected via Protocol 2, 15(ii) (200 mg, 0.238 mmol) to afford a colourless oil 15(iii) (27 mg, 18% two steps).

¹H NMR (300 MHz, CDCl₃) δ 0.88, d, J=6.5 Hz, 3H, 0.89, d, J=6.5 Hz, 3H, 1.25, m, 2H, 1.44, s, 6H, 1.56, m, 3H, 1.70, m, 2H, 2.02, br s, NH₂; 2.08, s, 3H, 2.50, s, 3H, 2.57, s, 3H, 2.93, s, 2H, 3.15, m, 2H, 3.40, m, 2H, 3.63, m, 1H, 4.13, m, 1H, 4.45, ABq, J=12.1 Hz, 1H, 4.50, ABq, J=12.1 Hz, 1H, 6.34, br s, NH; 7.29, m, 5H, 7.39, d, J=9.0 Hz, NH. MS (ES +ve) m/z 616.3 (100%) [M+H]⁺.

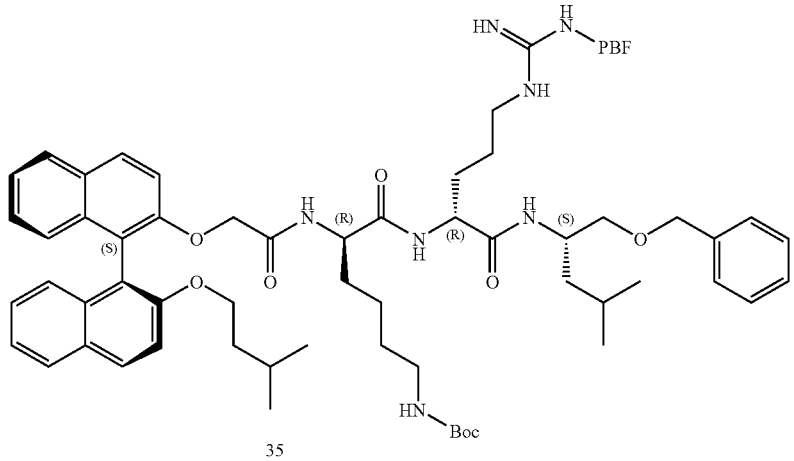

15(iv)

This compound was prepared via Protocol 1, using 6(vi) (58 mg, 0.090 mmol) and 15(iii) (53 mg, 0.086 mmol) to yield 15(iv) as a white solid (53 mg, 50%).

¹H NMR (500 MHz, CDCl₃) δ 0.49, d, J=6.5 Hz, 3H, 0.53, d, J=6.6 Hz, 3H, 0.79, m, 2H, 0.88, d, J=6.6 Hz, 3H, 0.90, d, J=6.7 Hz, 3H, 0.95, m, 2H, 1.21, m, 6H, 1.42, s, 6H, 1.44, s, 9H, 1.56, m, 5H, 1.83, m, 1H, 2.07, s, 3H, 2.49, s, 3H, 2.56, s, 3H, 2.91, s, 2H, 2.93, m, 2H, 3.17, m, 2H, 3.41, dABq, J=9.6 Hz, J₂=5.2 Hz, 1H, 3.45, dABq, J₁=9.6 Hz, J₂=4.6 Hz, 1H, 3.89, m, 1H, 4.01, m, 2H, 4.17, m, 1H, 4.46, m, 5H, 4.76, m, NH; 6.13, d, J=6.8 Hz, NH; 6.17, br s, NH; 6.66, d, J=8.4 Hz, NH; 7.14, m, 2H, 7.24, m, 4H, 7.30, m, 6H, 7.42, d, J=9.0 Hz, 1H; 7.84, d, J=8.4 Hz, 1H, 7.86, d, J=8.4 Hz, 1H, 7.92, d, J=8.8 Hz, 1H, 7.93, d, J=8.8 Hz, 1H. MS (ES +ve) m/z 1240 (100%) [M+H]⁺; 832.4 (100) [M+H-BOC-pbf-ibu]⁺.

Compound 15

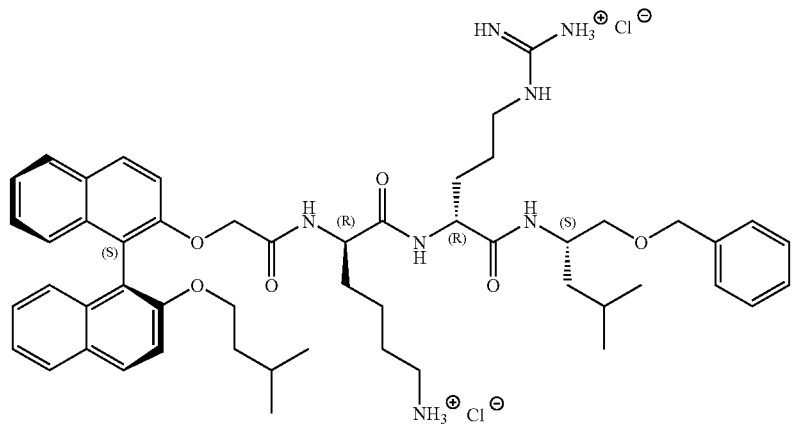

This compound was prepared via Protocol 3, using 15(iv) (50 mg, 0.040 mmol) to yield 15 as a white solid (32 mg, 83%).

$^1$H NMR (500 MHz, CDCl$_3$) δ 0.51, d, J=6.6 Hz, 3H, 0.56, d, J=6.6 Hz, 3H, 0.90, d, J=6.7 Hz, 3H, 0.92, m, 2H, 0.93, d, J=6.7 Hz, 3H, 1.24, m, 4H, 1.64, m, 9H, 1.84, m, 1H, 2.75, m, 2H, 3.17, m, 2H, 3.43, d, J=7.4 Hz, 2H, 3.92, m, 1H, 4.12, m, 2H, 4.29, m, 1H, 4.49, m, 4H, 7.06, dist t, 2H, 7.21, m, 2H, 7.34, m, 7H, 7.47, d, J=9.1 Hz, 1H, 7.54, d, J=9.1 Hz, 1H, 7.91, d, J=8.8 Hz, 1H, 7.92, d, J=8.8 Hz, 1H, 8.02, d, J=9.3 Hz, 2H. MS (ES +ve) m/z 888.3 (10%) [M+H]$^+$; 444.9 (100) [M+2H]$^{2+}$.

Synthesis of Compound 16 & Compound 17

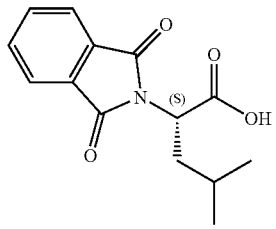

16(i)

To a suspension of L-leucine (1.17 g, 8.92 mmol) and phthalic anhydride (1.26 g, 8.51 mmol) in toluene (25 ml) was added triethylamine (0.11 ml, 0.79 mmol). The flask was fitted with a Dean-Stark water separator and a condenser and heated at vigorous reflux for 3 hours. The cooled solution was concentrated in vacuo, suspended in 2.5% HCl (50 ml) and extracted with ethyl acetate (3×25 ml). The combined organic layers were extracted with sat. aqueous sodium bicarbonate (3×25 ml), acidified with 10% HCl and back-extracted with ethyl acetate (3×25 ml). The organic layers were dried (MgSO$_4$) and concentrated in vacuo to give the product 16(i) as a white solid (2.12 g, 95%).

$^1$H NMR (500 MHz, CDCl$_3$) δ 0.87, dd, J=10.7, 6.6 Hz, 6H, 1.44, m, 1H, 1.89, m, 1H, 2.30, m, 1H, 4.93, dd. J=11.3, 4.4 Hz, 1H, 7.67, dd, J=5.3, 2.8 Hz, 2H, 7.79, dd, J=5.3, 2.8 Hz, 2H, 11.23, br s, 1H. MS (ES −ve) m/z 260 (100%) [M−H]$^+$; 216 (46) [M−COOH]$^+$.

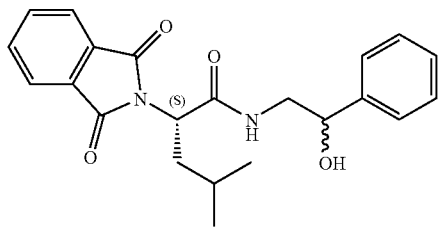

16(ii)

To a solution of 16(i) (0.70, 2.69 mmol) in THF (15 ml) under a N$_2$ atmosphere at 0° C. was added dicyclohexylcarboddimide (0.76 g, 3.69 mmol). The resultant solution was stirred at 0° C. for 1 hour. To this was added 2-amino-1-phenylethanol (0.45 g, 3.28 mmol) and the solution was stirred at 0° C. for 30 minutes then at room temperature (~15° C.) for a further 16 hours. The reaction mixture was filtered to remove the byproduct DCU, then concentrated in vacuo. The crude residue was subjected to flash silica column chromatography and elution with 50% ethyl acetate:petroleum spirit gave the title compound 16(ii) as a pale yellow oil (783 mg, 76%).

$^1$H NMR (500 MHz, CDCl$_3$) δ 0.90, d, J=6.8 Hz, 6H, 1.43, m, 1H, 1.83, m, 1H, 2.30, m, 1H, 3.28, m, 1H, 3.66, m, 1H, 4.82, m, 1H, 4.87, m, 1H, 6.73, br s, 1H, 7.26, m, 5H, 7.73, m, 2H, 7.83, m, 2H. MS (ES +ve) m/z 381.0 (100%) [M+H]$^+$; 363.0 (39); 225 (45).

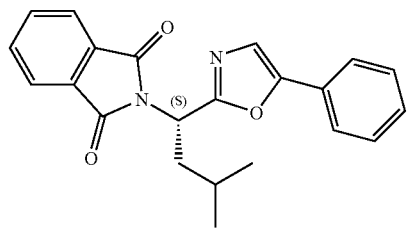

16(iii)

To a solution of chromium trioxide (0.45 g, 4.5 mmol) in water (10 ml) was slowly added concentrated H$_2$SO$_4$ (10 ml, 95%). The cooled solution was then added portionwise to a solution of 16(ii) (0.72 g, 1.9 mmol) in acetone (7.5 ml) (CAUTION: exothermic reaction). The resulting solution was stirred at room temperature for 16 hours. The reaction mixture was rendered basic by addition of sat. aqueous sodium carbonate and the alkaline solution was extracted with DCM (3×25 ml), brine was added to facilitate complete separation. The organic layers were combined, dried (MgSO$_4$) and concentrated in vacuo. The crude residue was subjected to flash silica column chromatography, eluting with 20% ethyl acetate:petroleum spirit to yield the title compound 16(iii) as a pale yellow oil (231 mg, 34%).

$^1$H NMR (500 MHz, CDCl$_3$) δ 1.02, dd, J=18.0, 6.6 Hz, 6H, 1.66, m, 1H, 2.25, m, 1H, 2.60, m, 1H, 5.64, dd, J=10.9, 5.0 Hz, 1H, 7.27, m, 1H, 7.28, t, J=7.8 Hz, 1H, 7.36, t, J=7.9 Hz, 2H, 7.56, d, J=7.4 Hz, 2H, 7.74, dd, J=5.3, 2.9 Hz, 2H, 7.87, dd, J=5.3, 2.9 Hz, 2H. MS (ES +ve) m/z 361.0 (100%) [M+H]$^+$.

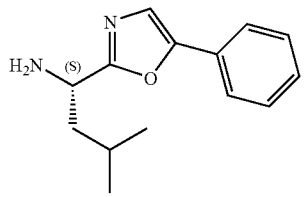

16(iv)

To a solution of 16(iii) (0.19 g, 0.53 mmol) in ethanol (10 ml) was added ethylenediamine (0.14 ml, 2.25 mmol) and the resulting solution was heated at reflux for 5 hours. The cooled reaction mixture was diluted with ethyl acetate (50 ml) then extracted with 1M HCl (3×25 ml). The combined aqueous extracts were rendered alkaline with addition of 1 M NaOH then extracted with DCM (3×25 ml). The combined organic extracts were dried (MgSO$_4$) and concentrated in vacuo to give the product 16(iv) as pale yellow crystals (100 mg, 82%).

$^1$H NMR (500 MHz, CDCl$_3$) δ 0.96, dd, J=6.2, 9.0 Hz, 6H, 1.73, m, 5H, 4.13, t, J=7.2 Hz, 1H, 7.24, s, 1H, 7.31, t, J=7.7, Hz, 1H, 7.42, t, J=7.8 Hz, 2H, 7.62, d, J=7.8 Hz, 2H. MS (ES +ve) m/z 231 (100%) [M+H]$^+$.

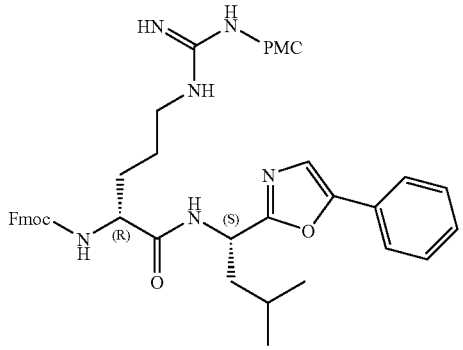

16(v)

This compound was prepared via Protocol 1, using 16(iv) (0.10 g, 0.43 mmol) and (R)-Fmoc-arginine(PMC)—OH (0.28 g, 0.42 mmol) in anhydrous acetonitrile (5 ml) with EDCI (0.11 g, 0.57 mmol) and HObt (0.07 g, 0.52 mmol). Purification with 2% methanol:DCM gave the product 16(v) as a thick off-white oil (292 mg, 79%).

$^1$H NMR (500 MHz, CDCl$_3$) δ 0.88, m, 6H, 1.23, d, J=3.2 Hz, 6H, 1.66, m, 6H, 1.77, m, 2H, 2.03, m, 4H, 2.53, m, 8H, 3.23, m, 2H, 4.02, br s, 1H, 4.23, m, 4H, 5.24, m, 2H, 6.37, m, 4H, 7.10, s, 1H, 7.26, m, 6H, 7.69, m, 3H, 7.67, m, 2H. MS (ES +ve) m/z 874.9 (48%) [M+H]$^+$; 438 (74); 143 (100).

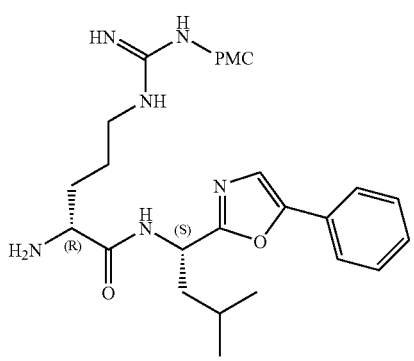

16(vi)

This compound was prepared via Protocol 2, using 16(v) (0.26 g, 0.30 mmol) and piperidine (0.1 ml, 1.01 mmol) in anhydrous acetonitrile (8 ml). Purification with 2-10% methanol:DCM gave the product 16(vi) as a pale yellow solid (189 mg, 98%).

$^1$H NMR (500 MHz, CDCl$_3$) δ; 0.94, dd, J=12.3, 6.6 Hz, 6H, 1.28, s, 6H, 1.61, m, 4H, 1.79, m, 5H, 2.07, s, 3H, 2.13, br s, 2H, 2.52, s, 3H, 2.54, s, 3H, 2.58, m, 2H, 3.17, m, 2H, 3.48, m, 1H, 5.23, ABquart, J=6.6 Hz, 1H, 6.42, br s, 3H, 7.18, s, 1H, 7.27, m, 1H, 7.35, t, J=7.6 Hz, 2H, 7.55, d, J=7.3 Hz, 2H, 8.08, br d, 1H. MS (ES +ve) m/z; 653 (100%) [M+H]$^+$; 327 (41) [M+H]$^{2+}$.

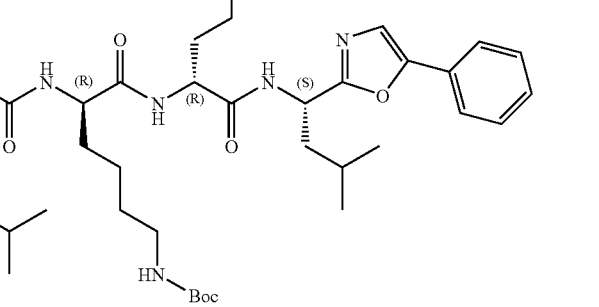

16(vii)

This compound was prepared via Protocol 1, 16(vi) (0.19 g, 0.29 mmol) and 6(vi) (0.19 g, 0.29 mmol) in anhydrous acetonitrile (7 ml) with EDCI (0.08 g, 0.42 mmol) and HObt (0.06 g, 0.41 mmol). Purification with 2% methanol:DCM gave product 16(vii) as an off-white solid (343 mg, 92%).

$^1$H NMR (300 MHz, CDCl$_3$) δ 0.48, dd, J=16.1, 6.4 Hz, 6H, 0.88, m, 2H, 0.95, m, 7H, 1.17, m, 6H, 1.27, m, 7H, 1.41, s, 9H, 1.74, m, 8H, 2.06, s, 3H, 2.52, m, 8H, 2.81, m, 3H, 3.18, m, 1H, 3.85, m, 1H, 4.03, m, 2H, 4.41, m, 3H, 4.79, m, 1H, 5.25, m, 1H, 6.15, m, 1H, 6.29, br s, 2H, 7.32, m, 17H, 7.90, m, 4H. MS (ES +ve) m/z 1278 (47%) [M+H]$^+$; 1277 (56) [M]$^+$; 639 (100) [M+H]$^+$.

Compound 16 & Compound 17

These compounds were prepared via Protocol 3, 16(vii) (0.34 g, 0.27 mmol) and TFA (2 ml, 27.0 mmol) in DCM (2 ml). Precipitation from methanol using ether (3 times) gave a mixture of two compounds that were separated by preparative reverse-phase HPLC to give 16 as a white solid (73 mg, 25%) and 17 as an off-white solid (62 mg, 21%).

Compound 16

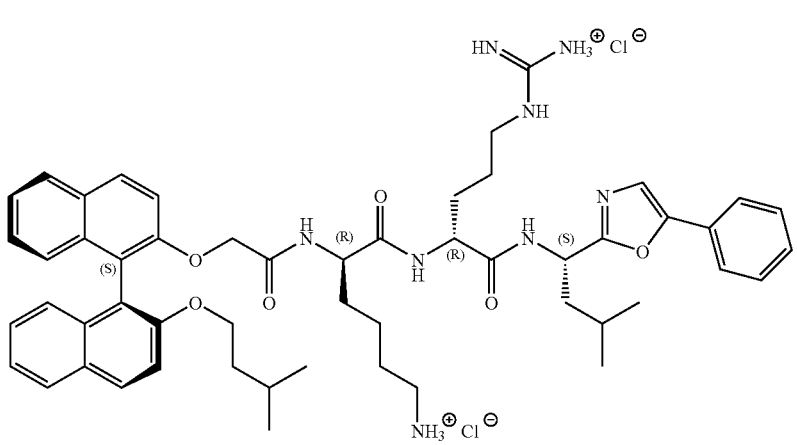

¹H NMR (300 MHz, CD₃OD) δ 0.50, dd, J=16.9, 6.6 Hz, 6H, 0.98, m, 9H, 1.21, m, 5H, 1.38, m, 4H, 1.69, m, 4H, 1.88, m, 2H, 2.73, m, 2H, 3.19, m, 1H, 3.96, m, 1H, 4.10, m, 2H, 4.45, ABquart, J=14.6 Hz, 2H, 5.22, m, 1H, 7.05, t, J=6.6 Hz, 2H, 7.21, m, 2H, 7.43, m, 8H, 7.71, m, 2H, 8.00, m, 4H. MS (ES +ve) m/z 911 (16%) [M+H]⁺; 456 (100) [M+H]²⁺.

organic layers combined, dried (MgSO₄) and concentrated in vacuo to give the product 18(i) as colourless prisms (490 mg, 86%).

¹H NMR (300 MHz, CDCl₃) δ 2.01, br s, 3H, 2.59, m, 1H, 2.73, d, J=6.4 Hz, 2H, 2.78, m, 1H, 3.72, m, 1H, 7.22, m, 5H. MS (ES +ve) m/z 152 (100%) [M+H]⁺; 134 (21); 117 (12).

Compound 17

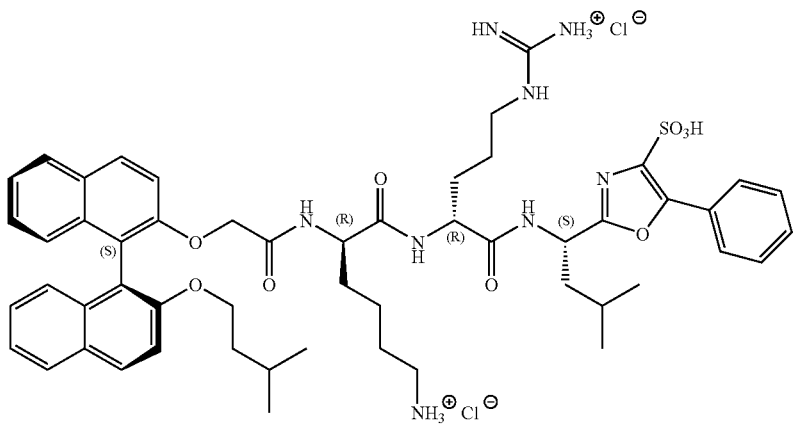

¹H NMR (300 MHz, CD₃OD) δ 0.50, dd, J=12.4, 12.4 Hz, 6H, 0.96, m, 6H, 1.24, m, 20H, 2.10, m, 2H, 3.15, m, 1H, 3.98, m, 1H, 4.15, m, 2H, 4.46, m, 2H, 5.06, m, 1H, 7.09, m, 3H, 7.40, m, 4H, 7.66, m, 4H, 7.92, m, 4H, 8.33, m, 2H. MS (ES +ve) m/z 992 (38%) [M+H]⁺; 496 (100) [M+H]²⁺.

Synthesis of Compound 18

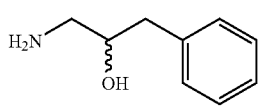

18(i)

A suspension of (2,3-epoxypropyl)benzene (0.5 ml, 3.80 mmol) in concentrated ammonia solution (10 ml, 28%) was placed in a Teflon tube with a 100 bar pressure cap, then heated in a microwave reactor at 110° C. for 30 minutes. After cooling the mixture was extracted with DCM (3×15 ml), the

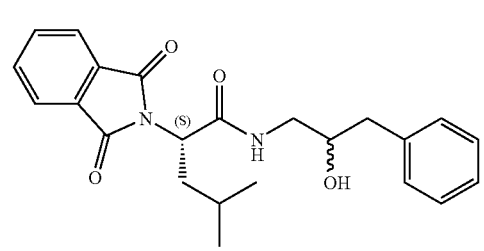

18(ii)

This compound was prepared via Protocol 1, using 18(i) (0.84, 3.23 mmol) and 16(i) in acetonitrile (10 ml), with EDCI (0.75 g, 3.94 mmol) and HObt (0.53 g, 3.97 mmol). Purification with 50% ethyl acetate:petroleum spirit gave the product 18(ii) as a colourless oil (1.02 g, 80%).

¹H NMR (300 MHz, CDCl₃) δ 0.88, dd, J=6.4, 2.1 Hz, 6H, 1.43, m, 1H, 1.81, m, 1H, 2.30, m, 1H, 2.67, m, 2H, 3.01, br s, 1H, 3.07, m, 1H, 3.44, m, 1H, 3.86, m, 1H, 4.84, dd, J=11.4, 4.7 Hz, 1H; 6.74, br s, 1H, 7.20, m, 5H, 7.69, m, 2H, 7.80, m, 2H. MS (ES +ve) 1n1z 433 (20%) [M+K]⁺; 417 (51) [M+Na]⁺; 395 (100) [M+H]⁺.

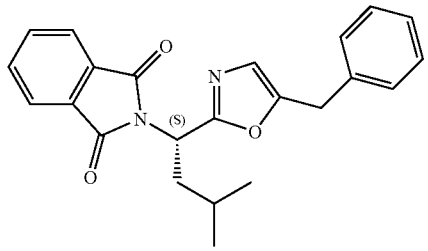

18(iii)

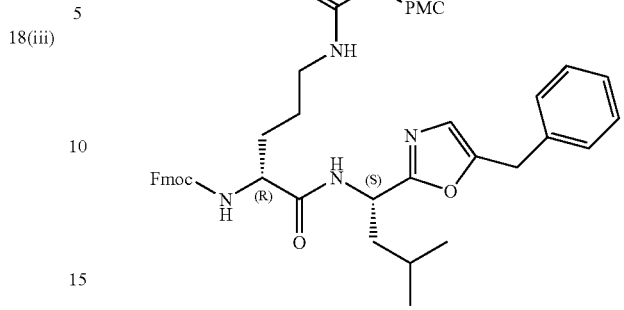

18(v)

To a solution of chromium trioxide (0.51 g, 5.1 mmol) in water (10 ml) was slowly added concentrated $H_2SO_4$ (10 ml, 95%). The cooled solution was then added portionwise to a solution of 18(ii) (0.82 g, 2.1 mmol) in acetone (7.5 ml) (CAUTION: exothermic reaction). The resulting solution was stirred at room temperature for 16 hours. The reaction mixture was rendered basic by addition of sat. aqueous sodium carbonate and the alkaline solution was extracted with DCM (3×25 ml), brine was added to facilitate complete separation. The organic layers were combined, dried ($MgSO_4$) and concentrated in vacuo. The crude residue was subjected to flash silica column chromatography, elution with 25% ethyl acetate:petroleum spirit gave the product 18(iii) as a dark yellow oil (200 mg, 25%).

¹H NMR (300 MHz, $CDCl_3$) δ 0.98, dd, J=9.1, 6.4 Hz, 6H, 1.60, m, 1H, 2.14, m, 1H, 2.51, m, 1H, 3.92, s, 2H, 5.52, dd, J=5.0, 11.1 Hz, 1H, 6.65, s, 1H, 7.22, m, 5H, 7.72, dd, J=5.3, 3.2 Hz, 2H, 7.85, dd, J=5.6, 2.9 Hz, 2H. MS (ES +ve) m/z 375 (100%) [M+H]⁺.

This compound was prepared via Protocol 1, using 18(iv) (88 mg, 36 μmol) and (R)-Fmoc-arginine(PMC)—OH (240 mg, 37 μmol) in anhydrous acetonitrile (6 ml) with EDCI (95 mg, 50 μmol) and HObt (64 mg, 47 μmol). Purification with 2% methanol:DCM gave the product 18(v) as a pale yellow oil (302 mg, 94%).

¹H NMR (300 MHz, $CDCl_3$) δ 0.82, d, J=6.4 Hz, 6H, 1.24, s, 6H, 1.72, m, 9H, 2.01, s, 3H, 2.54, m, 8H, 3.23, m, 2H, 3.81, s, 2H, 4.03, m, 1H, 4.24, m, 3H, 5.14, q, J=7.3 Hz, 1H, 6.47, m, 5H, 7.21, m, 8H, 7.37, m, 2H, 7.49, d, J=7.3 Hz, 2H, 7.69, J=7.3 Hz, 2H. MS (ES +ve) m/z 888.9, (78%) [M+H]⁺; 445.3 (100) [M+H]²⁺.

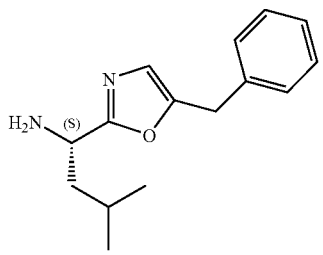

18(iv)

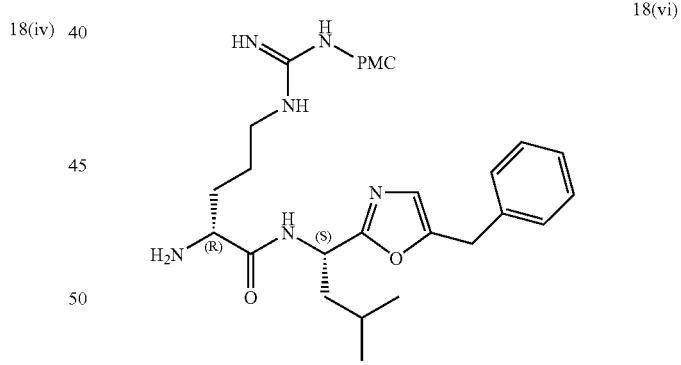

18(vi)

A solution of 18(iii) (0.20 g, 0.53 mmol) and ethylenediamine (0.20 ml, mmol) in ethanol (10 ml) was placed in a Teflon tube with a 100 bar pressure cap, then heated in a microwave reactor at 100° C. for 20 minutes The cooled reaction mixture was diluted with ethyl acetate (50 ml) then extracted with 5% HCl (4×25 ml). The combined aqueous extracts were rendered alkaline with addition of 1 M NaOH then extracted with DCM (4×25 ml). The organic extracts were dried ($MgSO_4$) and concentrated in vacuo to give the product 18(iv) as a thick colourless oil (111 mg, 81%).

¹H NMR (300 MHz, $CDCl_3$) δ 0.89, m, 6H, 1.64, m, 5H, 3.95, s, 2H, 4.0, m, 1H, 6.62, s, 1H, 7.26, m, 5H. MS (ES +ve) m/z 245 (83%) [M+H]⁺; 228 (100) [M-NH₂]⁺.

This compound was prepared via Protocol 2, using 18(v) (0.30 g, 0.34 mmol) and piperidine (0.15 ml, 1.51 mmol) in anhydrous acetonitrile (7 ml). Purification with 2-10% methanol:DCM gave the product 18(vi) as a thick pale yellow oil (222 mg, 97%).

¹H NMR (300 MHz, $CDCl_3$) δ 0.88, dd, J=6.4, 5.3 Hz, 6H, 1.28, s, 6H, 1.62, m, 9H, 2.08, s, 3H, 2.19, m, 2H, 2.53, s, 3H, 2.55, s, 3H, 2.57, m, 2H, 3.14, m, 2H, 3.42, m, 1H, 3.90, s, 2H, 5.09, q, J=7.0 Hz, 1H, 6.38, m, 3H, 6.59, s, 1H, 7.23, m, 5H, 8.00, br d, J=8.5 Hz, 1H.

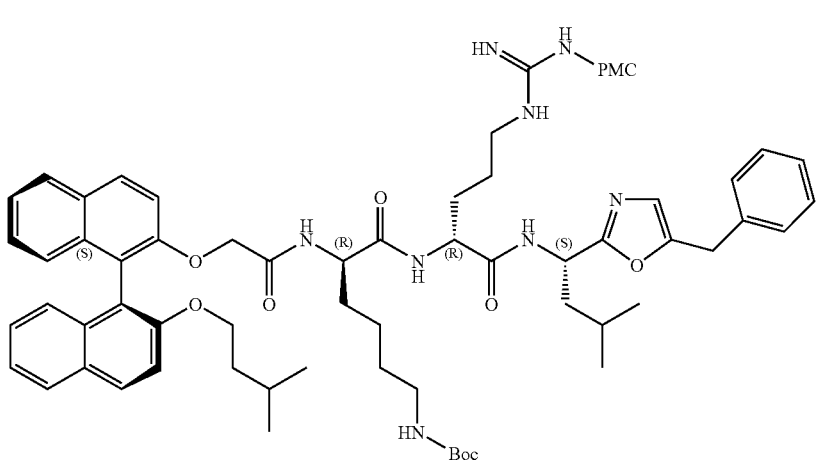

18(vii)

This compound was prepared via Protocol 1, using 18(vi) (0.11 g, 0.16 mmol) and 6(vi) (0.10 g, 0.16 mmol) in anhydrous acetonitrile (5 ml) with EDCI (0.04 g, 0.21 mmol) and HObt (0.03 g, 0.24 mmol). Purification with 2-5% methanol:DCM gave the product 18(vii) as an off-white solid (131 mg, 64%).

$^1$H NMR (300 MHz, CDCl$_3$) δ 0.46, dd, J=18.25, 6.4 Hz, 6H, 0.78, m, 2H, 0.89, m, 8H, 1.18, m, 14H, 1.42, s, 9H, 1.64, m, 8H, 2.08, s, 3H, 2.58, m, 10H, 2.79, br s, 1H, 2.91, m, 2H, 3.19, m, 1H, 3.92, m, 5H, 4.43, m, 3H, 4.79, m, 1H, 5.10, m, 1H, 6.25, m, 3H, 7.27, m, 12H, 7.91, m, 5H. MS (ES +ve) m/z 1291 (28%) [M+H]$^+$; 646 (67) [M+H]$^{2+}$; 83 (100). HRMS (ES +ve) for C$_{73}$H$_{95}$N$_8$O$_{11}$S, calculated 1291.6841, found 1291.6835.

Synthesis of Compound 19

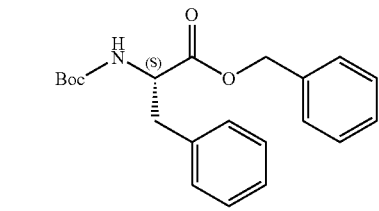

19(i)

To Boc-(L)-Phe-OH (265 mg, 1.00 mmol) and potassium carbonate (691 mg, 5.0 mmol) in acetone (30 ml) was added benzyl bromide (0.24 ml, 2.0 mmol). The resulting solution was heated at reflux overnight before being cooled, filtered and evaporated to dryness. The resultant residue was subjected to flash column chromatography over silica, eluting with 5% ethyl acetate/hexane to first remove benzyl bromide, then with DCM to yield the product 19(i) as a white solid (351 mg, 99%).

$^1$H NMR (500 MHz, CDCl$_3$) δ 1.46, s, 9H, 3.12, m, 2H, 4.68, m, 1H, 5.15, ABq, J=12.3 Hz, 1H, 5.16, m, NH; 5.19, ABq, J=12.3 Hz, 1H, 7.09, m, 2H, 7.25, m, 3H, 7.32, m, 2H, 7.36, m, 2H. MS (ES +ve) m/z 401.1 (40%) [M+HCOOH]$^+$; 378.1 (20) [M+Na]$^+$; 356.1 (25) [M+H]$^+$; 300.0 (60) [M+H-C$_4$H$_8$]$^+$; 256.0 (100) [M+H-BOC]$^+$.

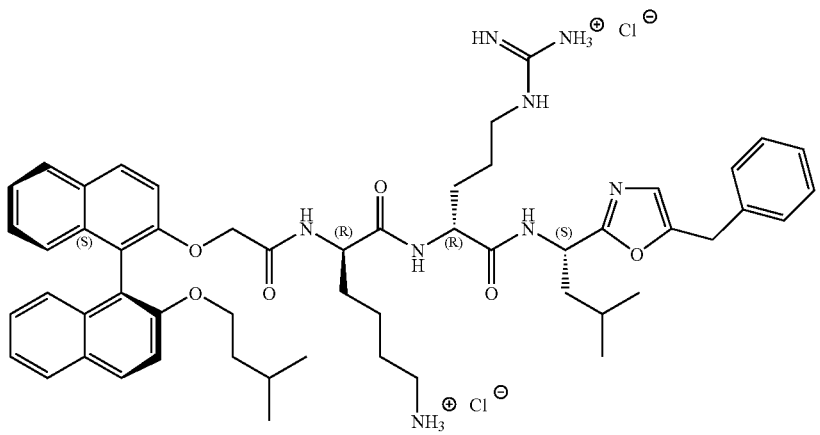

Compound 18

This compound was prepared via Protocol 3, using 18(vii) (132 mg, 0.10 mmol) and TFA:TIPS:H$_2$O (95:2.5:2.5) (2 ml). Precipitation from methanol using ether (3 times) gave the product 18 as an off-white powder (57 mg, 62%).

$^1$H NMR (300 MHz, CD$_3$OD) δ 0.52, dd, J=16.1, 6.4 Hz, 6H, 0.91, m, 8H, 1.19, m, 5H, 1.57, m, 10H, 2.78, m, 2H, 3.17, m, 2H, 3.30, m, 2H, 3.49, q, J=7.0 Hz, 2H, 4.04, m, 4H, 4.53, ABquart, J=14.1 Hz, 1H, 5.17, m, 1H, 7.08, m, 2H, 7.25, m, 9H, 7.49, dd, J=17.3, 9.0 Hz, 2H, 7.89, m, 2H, 8.01, dd, J=9.1, 2.6 Hz, 2H. MS (ES +ve) m/z 925 (4%) [M+H]$^+$; 463.5 (100) [M+H]$^{2+}$.

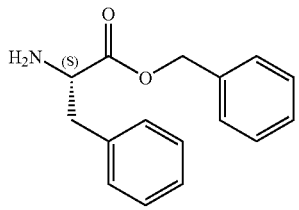

19(ii)

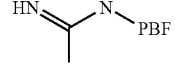

19(iv)

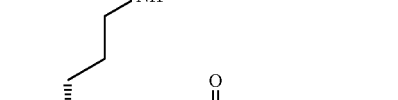

19(v)

To 19(i) (346 mg, 0.973 mmol) in DCM (2 ml) was added TFA (2 ml) and the resulting solution stirred at room temperature for 3 hrs. The solution was then diluted with DCM (5 ml) and washed with sat. sodium bicarbonate solution until the washings were basic. The organic layer was then dried (MgSO$_4$), filtered and evaporated to dryness to yield the desired product 19(ii) as a colourless oil (203 mg, 82%).

$^1$H NMR (500 MHz, CDCl$_3$) δ 1.54, s, NH$_2$; 2.78, dABq, J=13.5 Hz, J$_2$=5.5 Hz, 1H, 2.96, dABq, J=13.5 Hz, J$_2$=7.5 Hz, 1H, 3.65, m, 1H, 5.00, ABq, J=12.3 Hz, 1H, 1.56, m, NH; 5.03, ABq, J=12.3 Hz, 1H, 7.02, d, J=6.9 Hz, 2H, 7.15, m, 8H. MS (ES +ve) m/z 256.1 (100%) [M+H]$^+$.

This compound was prepared in two steps. The first step via Protocol 1, using 19(ii) (200 mg, 0.78 mmol) and Fmoc-(D)-arg(Pmc)-OH (464 mg, 0.70 mmol) to yield the Fmoc protected precursor 19(iii) as a white foamy solid (573 mg, MS (ES +ve) m/z 899.8 (100%) [M+H]$^+$). This precursor (200 mg) was then deprotected via Protocol 2 to afford the desired compound 19(iv) as a white solid (148 mg, 89% two steps).

$^1$H NMR (500 MHz, CDCl$_3$) δ 1.32, s, 6H, 1.44, m, 2H/NH$_2$; 1.66, m, 2H, 1.80, dist t, 2H, 2.12, s, 3H, 2.58, s, 3H, 2.60, s, 3H, 2.61, m, 2H, 3.12, m, 4H, 3.36, m, 1H, 4.81, m, 1H, 5.07, ABq, J=12.2 Hz, 1H, 5.15, ABq, J=12.2 Hz, 1H, 6.41, m, NH; 7.09, d, J=6.6 Hz, 2H, 7.25, m, 5H, 7.32, m, 3H, 7.88, d, J=6.8 Hz, NH. MS (ES +ve) m/z 677.9 (100%) [M+H]$^+$.

This compound was prepared via Protocol 1, using 6(vi) (122 mg, 0.190 mmol) and 19(iv) (140 mg, 0.207 mmol) to yield 19(v) as a white solid (197 mg, 71%).

$^1$H NMR (300 MHz, CDCl$_3$) δ 0.48, d, J=6.2 Hz, 3H, 0.54, d, J=6.2 Hz, 3H, 0.78, m, 2H, 0.89, m, 2H, 1.20, m, 8H, 1.43, s, 9H, 1.58, m, 1H, 1.78, dist t, 2H, 2.12, s, 3H, 2.60, s, 3H, 2.61, s, 3H, 2.62, m, 2H, 2.90, m, 3H, 3.06, m, 2H, 3.19, m, 1H, 3.88, m, 1H, 4.06, m, 2H, 4.37, m, 1H, 4.39, ABq, J=6.6 Hz, 11H, 4.52, ABq, J=6.6 Hz, 1H, 4.86, m, 1H/NH; 5.10, ABq, J=12.3 Hz, 1H, 5.18, ABq, J=12.3 Hz, 1H; 6.19, d, J=7.3 Hz, NH; 6.35, br s, NH; 7.22, m, 8H, 7.33, m, 9H, 7.45, d, J=9.1 Hz, H, 7.85, d, J=8.2 Hz, 1H, 7.88, d, J=7.9 Hz, 1H, 7.96, d, J=8.7 Hz, 2H. MS (ES +ve) m/z 1301.8 (100%) [M+H]$^+$.

Compound 19

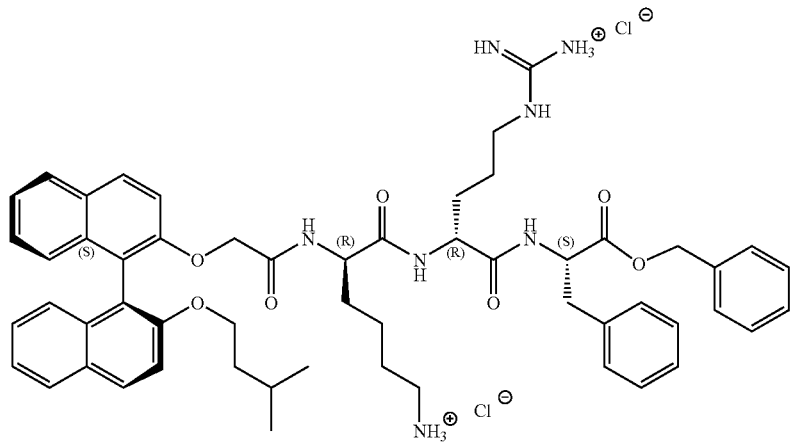

This compound was prepared via Protocol 3, using 19(v) (195 mg, 0.148 mmol) yield 19 as an off white solid (128 mg, 85%).

$^1$H NMR (300 MHz, CD$_3$OD) δ 0.46, d, J=6.6 Hz, 3H, 0.52, d, J=6.6 Hz, 3H, 0.92, m, 2H, 1.08, m, 2H, 1.20, m, 2H, 1.50, m, 5H, 2.76, m, 2H, 3.03, m, 3H, 3.15, m, 1H, 3.88, m, 1H, 4.06, m, 2H, 4.28, m, 1H, 4.46, m, 2H, 4.69, m, 1H, 5.11, s, 2H, 7.13, m, 8H, 7.27, m, 8H, 7.41, d, J=9.0 Hz, 1H, 7.51, d, J=9.1 Hz, 1H, 7.85, m, 2H, 7.98, dist t, 2H. MS (ES +ve) m/z 936 (10%) [M+H]$^+$; 468.9 (100) [M+2H]$^{2+}$.

Synthesis of Compound 20

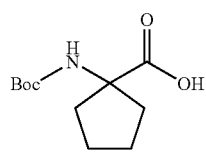

20(i)

To 1-amino-1-cyclopentane carboxylic acid (100 mg, 0.774 mmol) in dry acetonitrile (10 ml) was added tetramethylammonium hydroxide pentahydrate (190 mg, 1.04 mmol) and the mixture stirred at room temperature until the acid had dissolved. Boc anhydride (300 mg, 1.37 mmol) was then added and the resultant solution stirred for four days. The solvent was then removed and the resultant residue partitioned between water and ether. The aqueous layer was washed with an additional portion of ether and then acidified with solid citric acid to pH 3-4. The aqueous layer was then back-extracted with ethyl acetate (3×15 ml), before being combined, dried (MgSO$_4$), and evaporated to dryness to yield 20(i) as a pale yellow oil (101 mg, 57%).

$^1$H NMR (300 MHz, CDCl$_3$) δ 1.44, s, 9H, 1.78, m, 4H, 1.96, m, 2H, 2.29, m, 2H, 5.06, br s, NH; 10.19, br s, COOH.

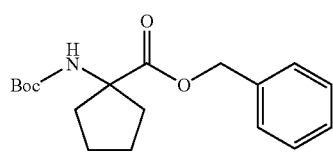

20(ii)

To 20(i) (120 mg, 0.523 mmol) and potassium carbonate (178 mg, 1.29 mmol) in acetone (25 ml) was added benzyl bromide (0.1 ml, 0.920 mmol). The resulting solution was heated at reflux overnight before being cooled, filtered and evaporated to dryness. The resultant residue was subjected to flash column chromatography over silica, eluting with 5% ethyl acetate/hexane to first remove benzyl bromide, then with DCM to yield the product 20(ii) as a colourless oil that solidified to a white solid upon standing (173 mg, 96%).

$^1$H NMR (500 MHz, CDCl$_3$) δ 1.37, s, 9H, 1.74, m, 4H, 1.91, m, 2H, 1.20, m, 2H, 5.08, br s, NH; 5.13, s, 2H, 7.30, m, 5H. MS (ES +ve) m/z 320 (50%) [M+H]$^+$; 220 (100) [M+H-BOC]$^+$.

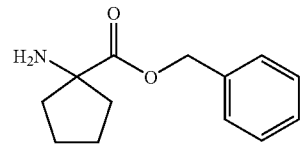

20(iii)

To 20(ii) (170 mg, 0.532 mmol) in DCM (2 ml) was added TFA (2 ml) and the resulting solution stirred at room temperature for 90 mins. The solution was then diluted with ethyl acetate (5 ml) and washed with sat. sodium bicarbonate solution until the washings were basic. The organic layer was then dried (MgSO$_4$), filtered and evaporated to dryness to yield the desired product 20(iii) as a pale yellow oil (102 mg, 87%).

$^1$H NMR (500 MHz, CDCl$_3$) δ 1.58, m, 2H, 1.67, s, NH$_2$; 1.73, m, 2H, 1.84, m, 2H, 2.08, m, 2H, 5.12, s, 2H, 7.32, m, 5H. MS (ES +ve) m/z 219.9 (100%) [M+H]$^+$.

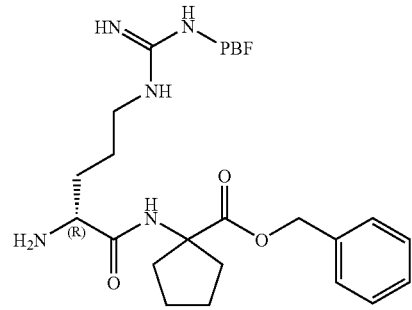

20(v)

This compound was prepared in two steps. The initial coupling via Protocol 1, using 20(iii) (100 mg, 0.456 mmol) and Fmoc-(D)-arg(Pbf)-OH (296 mg, 0.456 mmol) to yield the Fmoc protected precursor 20(iv) as a white foamy solid (MS (ES +ve) m/z 850 (100%) [M+H]⁺). This precursor was then deprotected via Protocol 2 to afford the desired compound 20(v) as a white solid (152 mg, 53% two steps).

¹H NMR (500 MHz, CDCl₃) δ 1.44, s, 6H, 1.46, m, 2H, 1.63, m, 2H, 1.76, 4H/NH₂; 1.93, m, 2H, 2.07, s, 3H, 2.24, m, 2H, 2.50, s, 3H, 2.58, s, 3H, 2.93, s, 2H, 3.20, m, 2H, 3.87, m, 1H, 5.08, s, 2H, 6.37, br s, NH; 6.42, br s, NH; 7.28, m, 5H, 7.52, s, NH; 7.75, m, NH. MS (ES +ve) m/z 628 (100%) [M+H]⁺.

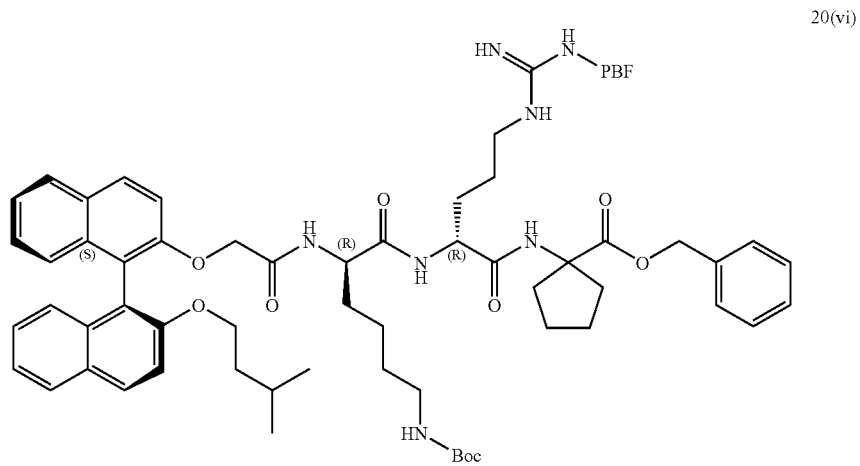

20(vi)

This compound was prepared via Protocol 1, using 6(vi) (100 mg, 0.155 mmol) and 20(v) (141 mg, 0.224 mmol) to yield 20(vi) as a white solid (123 mg, 63%).

¹H NMR (500 MHz, CDCl₃) δ 0.47, d, J=6.4 Hz, 3H, 0.52, d, J=6.4 Hz, 3H, 0.78, m, 2H, 0.94, m, 1H, 1.23, m, 7H, 1.42, s, 9H, 1.43, s, 3H, 1.44, s, 3H, 1.70, m, 4H, 1.96, m, 2H, 2.07, s, 3H, 2.11, m, 1H, 2.25, m, 1H, 2.50, s, 3H, 2.57, s, 3H, 2.91, s, 2H, 2.93, m, 2H, 3.07, m, 2H, 3.87, m, 1H, 4.00, m, 2H, 4.37, m, 2H, 4.59, m, 1H, 4.79, m, NH; 5.07, s, 2H, 6.15, d, J=6.9 Hz, NH; 6.25, br s, NH; 7.11, d, J=8.5 Hz, 1H, 7.15, d, J=8.5 Hz, 1H, 7.26, m, 10H, 7.43, d, J=9.1 Hz, 1H, 7.84, d, J=8.4 Hz, 1H, 7.85, d, J=8.4 Hz, 1H, 7.93, d, J=6.9 Hz, 1H, 7.94, d, J=9.0 Hz, 1H. MS (ES +ve) m/z 1252 (100%) [M+H]⁺.

This compound was prepared via Protocol 3, using 20(vi) (110 mg, 0.088 mmol) to yield 20 as an off white solid (83 mg, 97%).

¹H NMR (500 MHz, CD₃OD) δ 0.51, d, J=6.5 Hz, 3H, 0.57, d, J=6.5 Hz, 3H, 0.95, m, 2H, 1.14, m, 2H, 1.24, m, 2H, 1.42, m, 1H, 1.57, m, SH; 1.77, m, 4H, 1.98, m, 2H, 2.12, m, 1H, 2.30, m, 1H, 2.79, m, 2H, 3.08, m, 2H, 3.95, m, 1H, 4.14, m, 2H, 4.27, m, 1H, 4.45, ABq, J=14.7 Hz, 1H, 4.55, ABq, J=14.7 Hz, 1H, 5.07, ABq, J=12.3 Hz, 1H, 5.12, ABq, J=12.3 Hz, 1H, 7.06, t, J=9.3 Hz, 2H, 7.20, m, 2H, 7.34, m, 7H, 7.47, d, J=8.9 Hz, 1H, 7.55, d, J=9.0 Hz, 1H, 7.89, d, J=8.3 Hz, 1H, 7.92, d, J=8.3 Hz, 1H, 8.01, d, J=8.9 Hz, 1H, 8.02, d, J=8.9 Hz, 1H. MS (ES +ve) m/z 900 (5%) [M+H]⁺; 450.7 (100) [M+2H]²⁺.

Compound 20

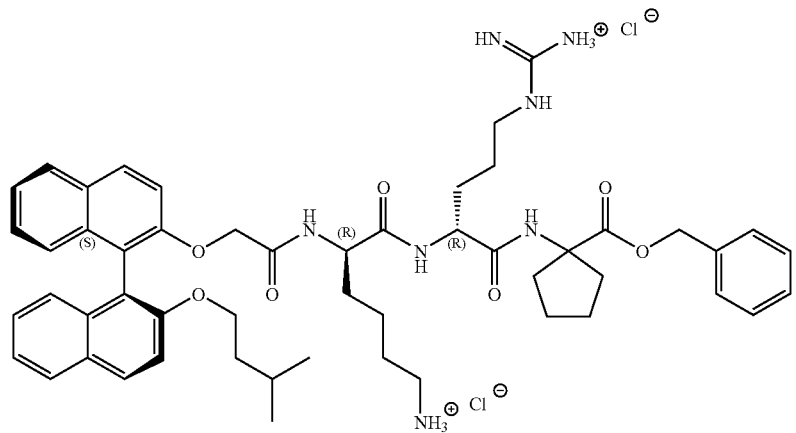

Synthesis of Compound 21

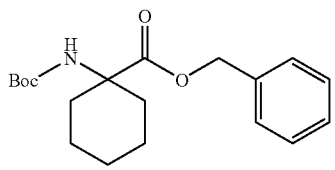

21(i)

To Boc-1-amino-1-cyclohexane carboxylic acid (168 mg, 0.69 mmol) and potassium carbonate (691 mg, 5.00 mmol) in acetone (30 ml) was added benzyl bromide (0.17 ml, 1.40 mmol). The resulting solution was heated at reflux overnight before being cooled, filtered and evaporated to dryness. The resultant residue was subjected to flash column chromatography over silica, eluting with 5% ethyl acetate/hexane to first remove benzyl bromide, then with DCM to yield the product 21(i) as a colourless oil (226 mg, 98%).

$^1$H NMR (500 MHz, CDCl$_3$) δ 1.28, m, 1H, 1.38, s, 9H, 1.42, m, 2H, 1.58, m, 3H, 1.82, m, 2H, 1.98, m, 2H, 4.86, s, NH; 5.12, s, 2H, 7.32, m, 5H. MS (ES +ve) m/z 379 (70%) [M+HCOOH]$^+$; 356.1 (20) [M+Na]$^+$; 334.1 (40) [M+H]$^+$; 278.1 (100) [M+H-C$_4$H$_8$]$^+$; 234.0 (95) [M+H-BOC]$^+$.

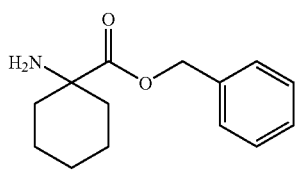

21(ii)

To 21(i) (218 mg, 0.654 mmol) in DCM (2 ml) was added TFA (2 ml) and the resulting solution stirred at room temperature for 3 hrs. The solution was then diluted with DCM (5 ml) and washed with sat. sodium bicarbonate solution until the washings were basic. The organic layer was then dried (MgSO$_4$), filtered and evaporated to dryness to yield the desired product 21(ii) as a pale yellow oil (121 mg, 79%).

$^1$H NMR (500 MHz, CDCl$_3$) δ 1.39, m, 6H, 1.56, m, 2H, 1.72, s, NH$_2$; 1.87, m, 2H, 5.06, s, 2H, 7.26, m, 5H. MS (ES +ve) m/z 234.0 (100%) [M+H]$^+$.

21(iv)

This compound was prepared in two steps. The first step via Protocol 1, using 21(ii) (115 mg, 0.49 mmol) and Fmoc-(D)-arg(Pmc)-OH (318 mg, 0.48 mmol) to yield the Fmoc protected precursor 21(iii) as a white foamy solid (402 mg, MS (ES +ve) m/z 877.9 (100%) [M+H]$^+$). This precursor 21(iii) (200 mg) was then deprotected via Protocol 2 to afford the desired compound 21(iv) as a white solid (141 mg, 87% two steps).

$^1$H NMR (500 MHz, CDCl$_3$) δ 1.30, s, 6H, 1.58, m, 10H/NH$_2$; 1.79, dist t, 2H, 1.90, m, 2H, 2.10, s, 3H, 2.57, s, 3H, 2.58, s, 3H, 2.62, m, 2H, 3.14, m, 4H, 3.44, m, 1H, 5.06, ABq, J=12.6 Hz, 1H, 5.09, ABq, J=12.6 Hz, 1H, 6.41, m, NH; 7.29, m, 5H, 7.80, s, NH. MS (ES +ve) m/z 656.3 (100%) [M+H]$^+$.

21(v)

This compound was prepared via Protocol 1, using 6(vi) (122 mg, 0.190 mmol) and 21(iv) (140 mg, 0.213 mmol) to yield 21(v) as a white solid (163 mg, 67%).

$^1$H NMR (300 MHz, CDCl$_3$) δ 0.49, d, J=6.4 Hz, 3H, 0.54, d, J=6.4 Hz, 3H, 0.78, m, 2H, 0.92, m, 2H, 1.20, m, 6H, 1.29, s, 6H, 1.44, s, 9H, 1.53, m, 2H, 1.77, m, 3H, 1.89, m, 1H, 2.09, s, 3H, 2.55, s, 3H, 2.57, s, 3H, 2.59, m, 2H, 2.89, m, 2H, 3.09, m, 2H, 3.89, m, 1H, 4.04, m, 2H, 4.36, ABq, J=14.6 Hz, 1H, 4.42, m, 1H, 4.54, ABq, J=14.6 Hz, 1H, 4.80, m, NH; 5.06, s, 2H, 6.14, br s NH; 6.36, br s, NH; 7.26, m, 12H, 7.44, d, J=9.1

Hz, 1H, 7.84, d, J=8.9 Hz, 1H, 7.86, d, J=7.9 Hz, 1H, 7.92, d, J=8.8 Hz, 1H, 7.95, d, J=7.6 Hz, 1H. MS (ES +ve) m/z 1280.3 (100%) [M+H]⁺.

¹H NMR (300 MHz, CDCl₃) δ 4.48, m, 2H, 5.00, m, 2H, 5.51, m, 1H, 7.13, dist d, J=8.3 Hz, 1H, 7.28, m, 7H, 7.83, m, 3H, 7.92, d, J=9.1 Hz, 1H.

Compound 21

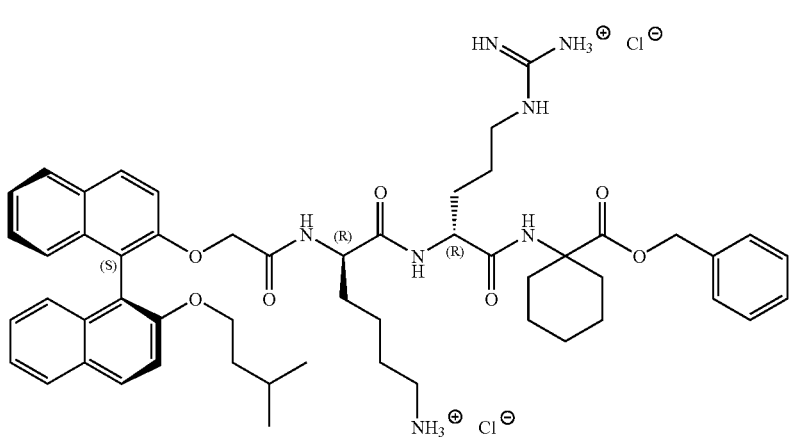

This compound was prepared via Protocol 3, using 21(v) (106 mg, 0.083 mmol) to yield 21 as an off white solid (35 mg, 43%).

¹H NMR (300 MHz, CD₃OD) δ 0.50, d, J=6.4 Hz, 3H, 0.56, d, J=6.4 Hz, 3H, 0.94, m, 2H, 1.18, m, 3H, 1.57, m, 13H, 1.94, m, 5H, 2.78, m, 2H, 3.08, m, 2H, 3.93, m, 1H, 4.12, m, 2H, 4.30, m, 1H, 4.42, ABq, J=14.6 Hz, 1H, 4.54, ABq, J=14.6 Hz, 1H, 5.02, ABq, J=12.3 Hz, 1H, 5.09, ABq, J=12.3 Hz, 1H, 7.06, dist t, 2H, 7.20, dist t, 2H, 7.32, m, 7H, 7.44, d, J=8.8 Hz, 1H, 7.53, d, J=9.1 Hz, 1H, 7.90, dist t, 2H, 8.00, d, J=9.1 Hz, 1H, 8.01, d, J=9.1 Hz, 1H, 8.09, s, NH. MS (ES +ve) m/z 915.0 (10%) [M+H]⁺; 457.9 (100) [M+2H]²⁺.

Synthesis of Compound 22

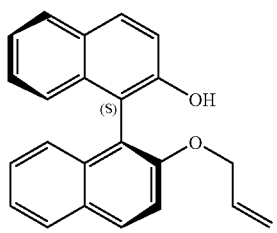

22(i)

To a solution of 1,1'-binaphth-2,2'-diol (4.89 g, 17.1 mmol) in dry acetone (40 ml) was added anhydrous potassium carbonate (3 g) under an N₂ atmosphere. After stirring for an hour a solution of allyl bromide (1.55 ml, 17.9 mmol) in acetone (20 ml) was added dropwise over a 2 hr period. The mixture was then heated at reflux overnight before being cooled and filtered. The solid residue was then washed twice more with acetone (10 ml) before the combined organic extracts were evaporated to dryness to yield a honey coloured oil. Subsequent flash column chromatography with 1:3 DCM/Hexane as the eluant affords the desired product 22(i) as a yellow solid (1.905 g, 53%). R_f=0.06 (1:1 hexane/DCM). The disubstituted product (4%) and starting material (7%) were also recovered.

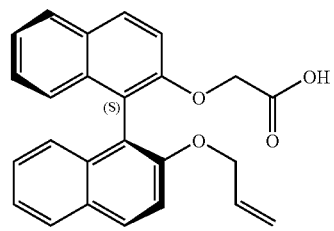

22(ii)

To 22(i) (1.91 g, 5.84 mmol) in dry MeOH (50 ml) was added potassium carbonate (8.1 g, 58.6 mmol) and bromoacetic acid (4.05 g, 29.3 mmol). The colour of the solution changed from yellow to almost clear upon addition of the bromoacetic acid. The solution was then heated at reflux for three hours over which time a white ppte had fallen out of solution. The reaction mixture was then evaporated to dryness and the residue dissolved in water (50 ml). This was then washed with three 30 ml portions of ether before the aqueous layer was acidified with 3M HCl. This acidified solution was then extracted with three 30 ml portions of DCM to yield a yellow solution. This yellow solution was then dried over MgSO₄ before being evaporated to dryness to yield the product 22(ii) as a yellow foamy solid (1.87 g, 83%).

¹H NMR (300 MHz, CDCl₃) δ 4.48, m, 2H, 4.55, ABq, J=16.7 Hz, 1H, 4.67, ABq, J=16.7 Hz, 1H, 4.95, m, 2H, 5.65, m, 1H, 7.13, app t, 2H, 7.24, m, 2H, 7.34, m, 3H, 7.42, d, J=9.1 Hz, 1H, 7.87, d, J=8.2 Hz, 1H, 7.87, d, J=8.2 Hz, 1H, 7.96, d, J=8.8 Hz, 1H, 7.97, d, J=8.8 Hz, 1H. MS (ES +ve) m/z 385.0 (90%) [M+H]⁺; 402.0 (100) [M+NH₄]⁺.

22(iii)

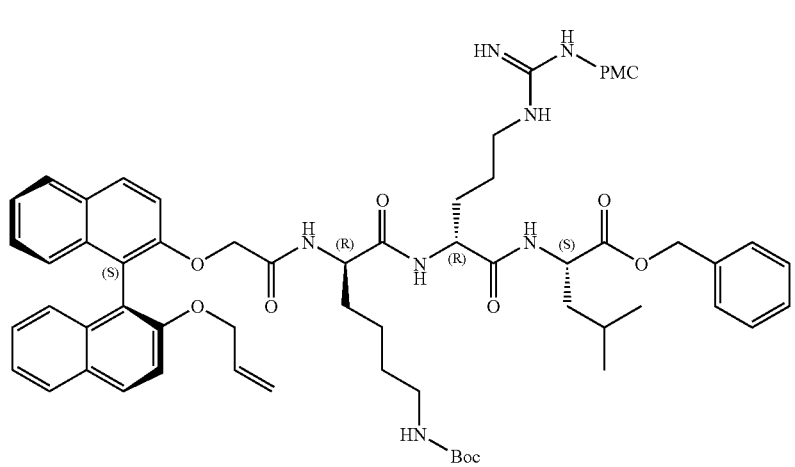

This compound was prepared via Protocol 1, using 22(ii) (46 mg, 0.12 mmol) and 1(viii) (110 mg, 0.12 mmol) to yield the desired product 22(iii) as a white solid (124 mg, 84%). $R_f$=0.16 (5% MeOH/DCM).

$^1$H NMR (300 MHz, CDCl$_3$) δ 0.78, m, 2H, 0.87, d, J=5.6 Hz, 3H, 0.89, d, J=5.6 Hz, 3H, 0.97, m, 1H, 1.20, m, 4H, 1.27, s, 6H, 1.39, m, 2H, 1.41, s, 9H, 1.63, m, 3H, 1.75, m, 3H, 2.08, s, 3H, 2.53, s, 3H, 2.56, s, 3H, 2.57, m, 2H, 2.88, m, 2H, 3.13, m, 2H, 4.09, m, 1H, 4.47, m, 6H, 4.79, m, NH; 4.86, m, 2H, 5.08, ABq, J=12.3 Hz, 1H, 5.16, ABq, J=12.3 Hz, 1H, 5.63, m, 1H, 6.24, m, NH; 7.10, dist d, 1H, 7.16, dist d, 1H, 7.32, m, 10H, 7.42, d, J=9.3 Hz, 1H, 7.85, dist t, 2H, 7.92, d, J=8.8 Hz, 2H. MS (ES +ve) m/z 1260 (100%) [M+Na]$^+$; 1238 (80) [M+H]$^+$.

Compound 22

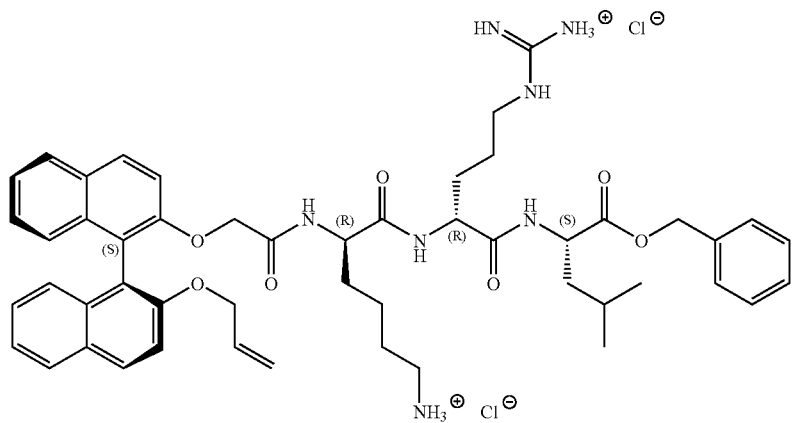

This compound was prepared via Protocol 3, using 22(iii) (94 mg, 0.076 mmol) to yield the desired product 22 as a white solid (62 mg, 86%).

$^1$H NMR (300 MHz, CD$_3$OD) δ 0.88, d, J=5.6 Hz, 3H, 0.93, d, J=5.6 Hz, 3H, 0.97, m, 2H, 1.15, m, 1H, 1.66, m, 10H, 2.79, m, 2H, 3.14, m, 2H, 4.14, m, 1H, 4.35, m, 1H, 4.46, m, 2H, 4.56, m, 3H, 4.93, m, 2H, 5.11, ABq, J=12.3 Hz, 1H, 5.17, ABq, J=12.3 Hz, 1H, 5.71, m, 1H, 7.05, m, 2H, 7.20, dist t, 2H, 7.33, m, 7H, 7.46, d, J=9.1 Hz, 1H, 7.53, d, J=9.1 Hz, 1H, 7.90, dist t, 2H, 8.01, d, J=9.1 Hz, 2H. MS (ES +ve) m/z 437 (100%) [M+2H]$^{2+}$.

Synthesis of Compound 23

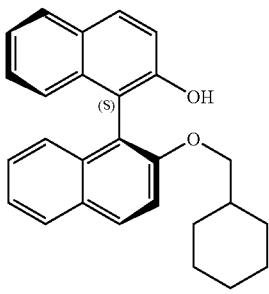

Bromomethylcyclohexane (240 µl, 1.75 mmol) was added to a mixture of 1,1'-binaphth-2,2'-diol (500 mg, 1.75 mmol), potassium carbonate (1.00 g, 7.27 mmol) and acetone (10 ml). The mixture was stirred at reflux for 3 days, and then cooled and concentrated in vacuo. The crude product was purified by flash chromatography with 1-10% ethyl acetate-petrol as eluent to give the product 23(i) as a viscous oil (400 mg, 60%).

$^1$H NMR (500 MHz, CDCl$_3$) δ 1.51, m, 10H; 2.44, m, 1H, 3.92, m, 2H, 7.06, d, J=8.5 Hz, 1H, 7.26, m, 8H, 7.44, d, J=9.2 Hz, 1H, 7.84, d, J=8.1 Hz, 1H, 7.89, dd, J=6.2, 6.2 Hz, 2H, 8.02, d, J=9.2 Hz, 1H.

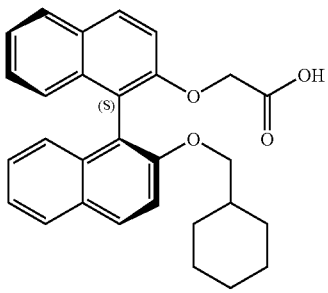

To 23(i) (400 mg, 1.05 mmol) in methanol (10 ml) was added potassium carbonate (1.50 g, 10.9 mmol) and bromoacetic acid (900 mg, 6.48 mmol) and the mixture stirred at reflux for 2 days. The reaction mixture was cooled down, methanol removed in vacuo, and the crude residue redissolved in water and acidified with 1M HCl. Extraction with ether, drying (Na$_2$SO$_4$) and concentration gave the crude product that was purified by flash chromatography. Elution with chloroform gave unreacted 23(i) (25%). Further elution with 2% methanol-chloroform gave 23(ii) as a viscous oil (240 mg, 51.9%).

$^1$H NMR (500 MHz, CDCl$_3$) δ 0.51, m, 2H, 0.83, m, 3H, 1.17, br t, 2H, 1.36, m, 4H, 3.71, m, 1H, 3.79, m; 4.49, ABq, J=16.6, 1H, 4.61, ABq, J=16.6 Hz, 1H, 7.18, m, 4H, 7.30, m, 3H, 7.40, d, J=9.3 Hz, 1H, 7.82, d, J=7.8 Hz, 1H, 7.83, d, J=7.8 Hz, 1H, 7.91, d, J=9.3 Hz, 1H, 7.92, d, J=9.3 Hz, 1H, 9.25, br s, 1H.

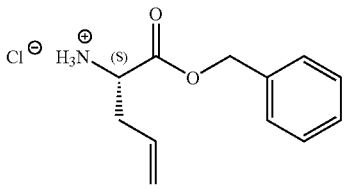

To a solution of (S)-allylglycine (225 mg, 1.96 mmol) in benzyl alcohol (5 mL) was added thionyl chloride (2 mL) and the resulting mixture was allowed to stir for 16 h before addition of diethyl ether (30 mL) and extraction with water (3×30 mL). The aqueous layer was concentrated, diluted with 2M sodium bicarbonate (20 mL), and extracted with DCM (3×30 mL). The combined organic fractions were dried and acidified with 1M HCl/diethyl ether (2 mL) and evaporated. The crude product dissolved in a minimal volume of MeOH and precipitated with diethyl ether to yield the title compound 23(iii) as a white solid (322 mg, 1.34 mmol, 68%) Mp 186-191° C.

$^1$H NMR (300 MHz, D$_2$O) δ 2.55, m, 2H, 4.08, t, J=5.4 Hz, 1H, 5.11, m, 4H, 5.51, m, 1H, 7.28, m, 5H. MS (CI +ve) m/z 205 (25%) [M+H]$^+$.

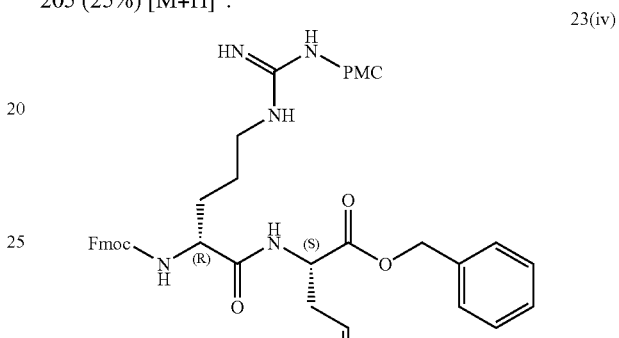

This compound was prepared via Protocol 1, using 23(iii) (155 mg, 0.65 mmol) and (R)-Fmoc-Arg(PMC)—OH (431 mg, 0.65 mmol) to afford 23(iv) (280 mg, 0.33 mmol, 51%) as a white solid. Mp 78-74° C.

$^1$H NMR (300 MHz CDCl$_3$) δ 1.22, s, 6H, 1.58, m, 2H, 1.69, t, J=6.3 Hz; 1.85, m, 2H, 2.05, s, 3H, 2.52, m, 4H, 2.54, s, 3H, 2.57, s, 3H, 3.20, m, 2H, 4.05, t, J=7.2 Hz, 1H, 4.24, m, 3H, 4.58, m, 1H, 4.99, m, 4H, 5.61, m, 1H, 5.68, m, 1H, 6.33, m, 3H, 7.28, m, 9H, 7.51, d, J=7.5 Hz, 2H, 7.69, d, J=7.5 Hz, 2H. MS (ES +ve) m/z 850 (100%) [M+H]$^+$.

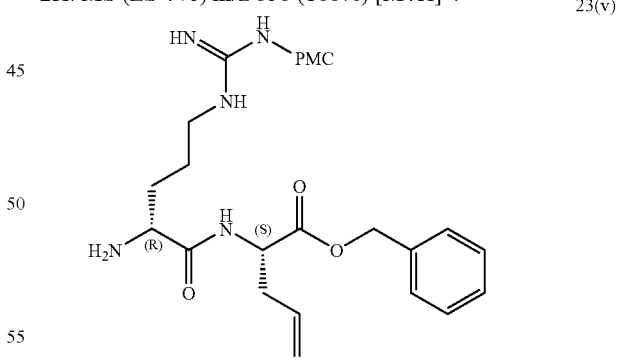

This compound was prepared via Protocol 2, using 23(iv) (278 mg, 0.33 mmol) to yield 32(v) as a cream semi-solid (144 mg, 0.23 mmole, 70%). Mp 66-68° C.

$^1$H NMR (300 MHz, CDCl$_3$) δ 1.29, s, 6H, 1.54, m, 2H, 1.68, m, 4H, 1.78, t, J=7.2 Hz, 2H, 2.09, s, 3H, 2.55, s, 3H, 2.56, s, 3H, 2.61, t, J=6.9 Hz, 2H, 3.09, m, 2H, 3.16, m, 2H, 3.40, m, 1H, 4.56, m, 1H, 5.14, m, 4H, 5.63, s, 1H, 6.33, m, 2H, 7.32, m, 5H, 7.60, d, J=7.8 Hz, 1H, 7.85, d, J=7.8 Hz, 1H. MS (ES +ve) m/z 628 (100%) [M+H]$^+$.

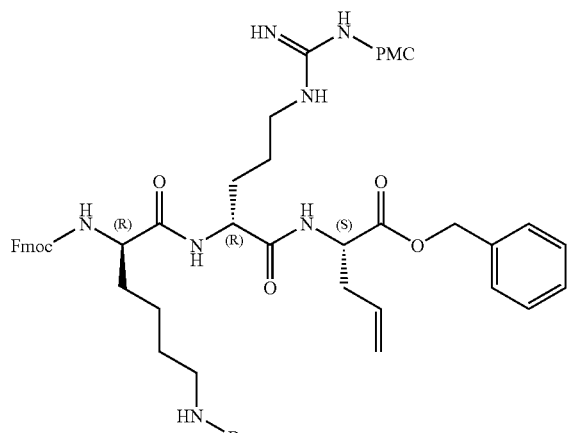

23(vi)

This compound was prepared via Protocol 1, using 23(v) (200 mg, 0.32 mmol) and (R)-Fmoc-Lys(Boc)-OH (151 mg, 0.32 mmol) to afford 23(vi) as a white solid (202 mg, 0.19 mmol, 59%). Mp 116° C.

$^1$H NMR (300 MHz, CDCl$_3$) δ 1.41, s, 6H, 1.59, m, 2H, 1.67, m, 4H, 1.74, m, 2H, 1.95, m, 4H, 2.03, s, 3H, 2.50, m, 4H, 2.52, s, 3H, 2.55, s, 3H, 3.05, m, 2H, 3.18, m, 2H, 3.98, m, 1H, 4.20, m, 2H, 4.29, m, 1H, 4.51, m, 1H, 4.59, m, 1H, 5.03, m, 4H, 5.64, m, 1H, 6.25, m, 3H, 7.29, m, 11H, 7.45, m, 1H, 7.55, d, J=7.8 Hz, 2H, 7.72, d, J=7.8 Hz, 2H. MS (ES +ve) m/z 1078 (10%) [M+H]$^+$; 288 (100)'

23(vii)

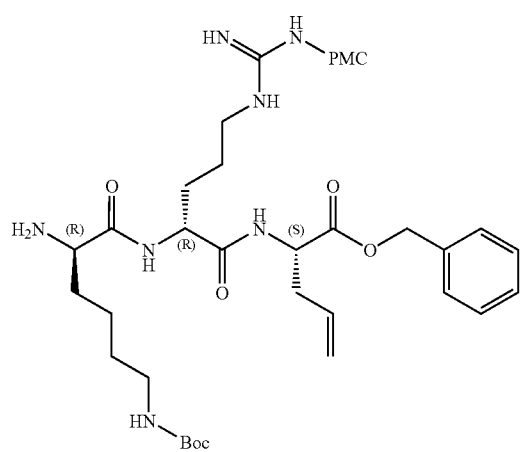

This compound was prepared via Protocol 2, using 23(vi) (202 mg, 0.19 mmol) to yield 23(vii) as a cream oil (157 mg, 0.18 mmole, 93%).

$^1$H NMR (300 MHz, CDCl$_3$) δ 1.31, s, 6H, 1.42, s, 9H, 1.58, m, 4H, 1.72, m, 4H, 1.80, t, J=6.3 Hz; 1.89, m, 2H, 2.10, s, 3H, 2.15, m, 2H, 2.47, m, 2H, 2.56, s, 3H, 2.58, s, 3H, 2.62, m, 2H, 3.05, m, 2H, 3.22, m, 2H, 3.36, m, 1H, 4.61, m, 2H, 5.09, m, 4H, 5.63, m, 1H, 6.44, m, 3H; 7.32, m, 5H, 7.58, d, J=7.2 Hz, 1H, 8.00, d, J=7.2 Hz, 1H. MS (ES +ve) m/z 856 (100%) [M+H]$^+$.

23(viii)

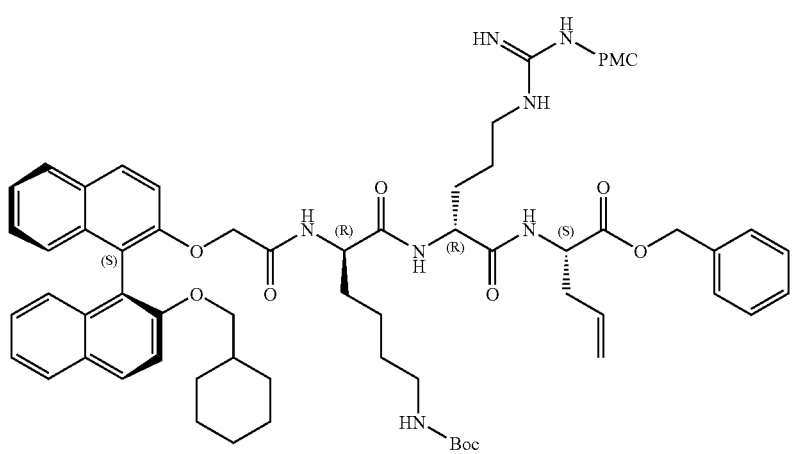

This compound was prepared via Protocol 1, from acid 23(ii) with the 23(vii) (80 mg, 94 μmol). Purification by radial chromatography (1-2% methanol-chloroform) gave the product 23(viii) (94 mg, 79%).

$^1$H NMR (500 MHz, CDCl$_3$) δ 0.48, m, 2H, 0.85, m, 6H, 1.28, s, 6H, 1.41, s, 9H, 1.32, m, 12H, 1.76, br t, 3H, 2.09, s, 3H, 2.55, s, 3H, 2.57, s, 3H, 2.56, m, 4H, 2.91, br s, 2H, 3.09, m, 2H, 3.67, m, 1H, 3.81, m, 1H, 4.12, m, 1H, 4.43, ABq, J=14.4 Hz, 1H, 4.51, ABq, J=14.4 Hz, 1H, 4.41, m, 1H, 4.60, m, 1H, 4.84, b s, 1H, 5.06, m, 2H, 5.09, ABq, 1H, J=12.5; 5.18, ABq, 1H, J=12.5; 5.68, m, 1H, 6.19, br d, J=7.0 Hz, 1H, 6.26, br s, 2H, 7.25, m, 7H, 7.43, 1H, d, J=9.0 Hz; 7.85, m, 2H, 7.95, d, J=9.0 Hz, 2H. MS (ES +ve) m/z 1278 (100%) [M+H]$^+$.

Compound 23

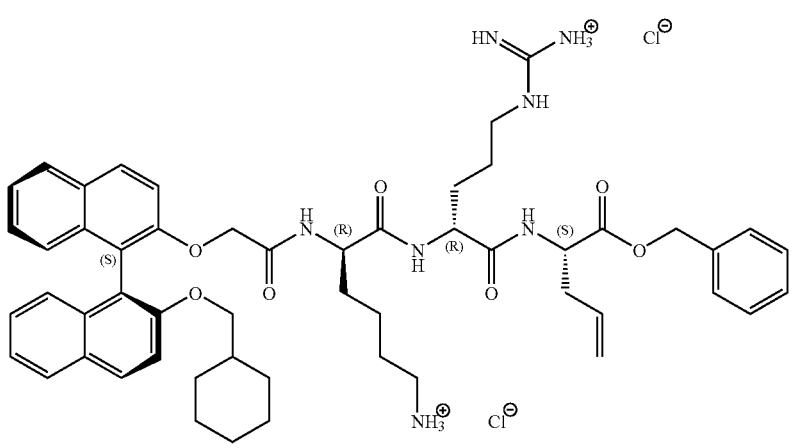

This compound was prepared via Protocol 3, using 23(viii) (80 mg, 62.6 μmol). Standard work-up gave the product 23 as a cream crystalline solid (40 mg, 65%).

$^1$H NMR (500 MHz, DMSO-d$_6$) δ 0.57, m, 2H, 0.90, m, 3H, 1.33, m, 11H, 2.39, br s, 3H, 2.49, br s, 3H, 2.65, m, 2H, 2.40, m, 4H, 3.76, m, 1H, 3.87, m, 1H, 4.20, m, 3H, 4.51, br s, 2H, 5.05, m, 4H, 5.70, m, 1H, 6.92, d, J=8.5 Hz, 1H, 7.00, d, J=8.0 Hz, 1H, 7.27, m, 10H, 7.54, m, 1H, 7.91, m, 2H, 8.02, m, 2H. MS (ES +ve) m/z 912 (45%) [M+H]$^+$; 457 (100) [M+2H]$^{2+}$.

Synthesis of Compound 24

24(i)

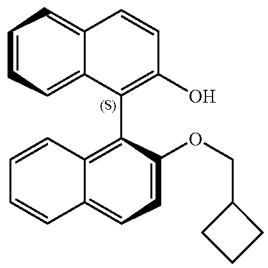

Bromomethylcyclobutane (200 μl, 1.75 mmol) was added to a mixture of 1,1'-binaphth-2,2'-diol (500 mg, 1.75 mmol), potassium carbonate (1.00 g, 7.27 mmol) and acetone (10 ml). The mixture was stirred at reflux for 18 h, and then cooled down and concentrated in vacuo. The crude product was purified by flash chromatography with 1-4% ethyl acetate-petrol as eluent to give the product 24(i) as a viscous oil (300 mg, 49%).

$^1$H NMR (500 MHz, CDCl$_3$) δ 1.52, m, 6H, 2.43, m, 1H, 3.92, m, 2H, 4.95, s, 1H, 7.06, d, J=8.3 Hz, 1H, 7.28, m, 6H, 7.43, d, J=8.8 Hz, 1H, 7.84, d, J=7.8 Hz, 1H, 7.88, d, J=9.3 Hz, 1H, 7.89, d, 1H, J=8.3 Hz; 8.00, d, J=9.3 Hz, 1H.

24(ii)

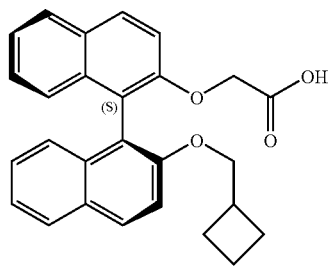

To 24(i) (300 mg, 0.85 mmol) in methanol (10 ml) was added potassium carbonate (1.00 g, 7.27 mmol) and bromoacetic acid (560 mg, 4.03 mmol) and the mixture stirred at reflux for 2 days. The reaction mixture was cooled down, methanol removed in vacuo, and the crude residue redissolved in water and acidified with 1M HCl. Extraction with ether, drying (Na$_2$SO$_4$) and concentration gave the crude product that was purified by flash chromatography. Elution with 10% methanol:DCM gave the product 24(ii) as a viscous oil (200 mg, 57%).

$^1$H NMR (500 MHz, CDCl$_3$) δ 1.43, m, 6H, 2.33, m, 1H, 3.80, m, 1H, 3.99, m, 1H, 4.52, ABq, 1H, J=16.5 Hz; 4.69, ABq, 1H, J=16.5 Hz; 7.15, d, J=8.5 Hz, 2H, 7.29, m, 5H, 7.43, d, J=8.8 Hz, 1H, 7.87, d, J=7.0 Hz, 2H, 7.94, d, J=8.5 Hz, 1H, 7.96, d, J=8.8 Hz, 1H.

24(iii)

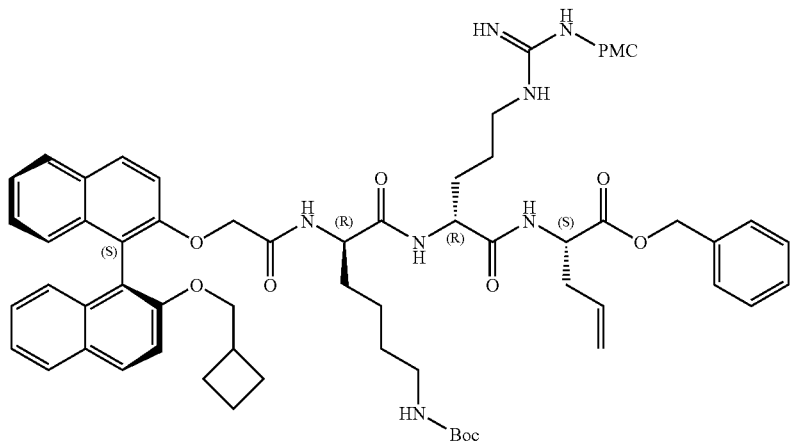

This compound was prepared via Protocol 1, using 24(ii) and 23(viii) (110 mg, 117 µmol). Purification by radial chromatography (1-3% methanol-DCM) gave the product 24(iii) (80 mg, 55%).

$^1$H NMR (500 MHz, CDCl$_3$) δ 0.79, m, 2H, 0.94, m, 1H, 1.28, s, 6H, 1.41, s, 9H, 1.38, m, 12H, 1.76, br t, 3H, 2.09, s, 3H, 2.29, m, 1H, 2.55, s, 3H, 2.57, s, 3H, 2.54, m, 4H, 2.90, m, 2H, 3.08, m, 2H, 3.80, m, 1H, 3.97, m, 1H, 4.09, br s, 1H, 4.41, ABq, J=14.5 Hz, 1H, 4.51, ABq, J=14.5 Hz, 1H, 4.42, m, 1H, 4.59, m, 1H, 4.84, br s, 1H, 5.06, m, 2H, 5.12, ABq, J=12.5 Hz, 1H, 5.18, ABq, J=12.5 Hz, 1H, 5.66, m, 1H, 6.22, m, 3H, 7.25, m, 7H, 7.43, d, J=8.8 Hz, 1H, 7.84, d, J=8.3 Hz, 1H, 7.86, d, J=8.8 Hz, 1H, 7.93, d, J=9.3 Hz, 1H, 7.94, d, J=8.8 Hz, 1H. MS (ES +ve) m/z 1250 (100%) [M+H]$^+$.

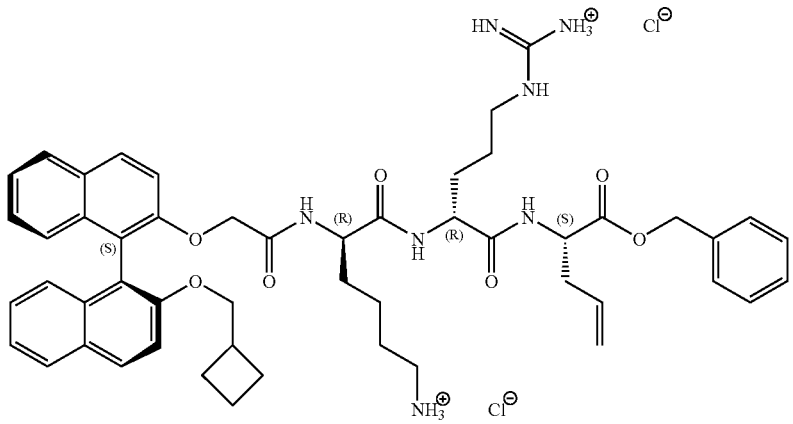

Compound 24

This compound was prepared via Protocol 3, using 24(iii) (70 mg, 55.98 µmol). Standard work-up gave the product 24 as a cream crystalline solid (35 mg, 65%).

$^1$H NMR (300 MHz, DMSO-d$_6$) δ 0.97, br s, 1H, 1.15, br s, 1H, 1.45, m, 10H, 2.10, s, 1H, 2.45, m, 5H, 2.66, br s, 1H, 3.07, br s, 3H, 3.99, m, 3H, 4.34, m, 4H, 5.09, m, 4H, 5.73, br s, 1H, 6.03, m, 3H, 7.29, m, 8H, 7.57, m, 2H, 8.01, m, 4H, 8.19, br s, 1H, 8.41, br s, 2H. MS (ES +ve) m/z 884 (95%) [M+H]$^+$; 443 (100) [M+2H]$^{2+}$.

Synthesis of Compound 25

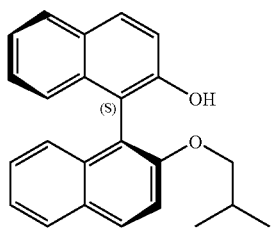

25(i)

1-Bromo-2-methylpropane (190 µl, 1.75 mmol) was added to a mixture of 1,1'-binaphth-2,2'-diol (500 mg, 1.75 mmol), potassium carbonate (1.00 g, 7.27 mmol) and acetone (10 ml). The mixture was stirred at reflux for 42 h, and then cooled down and concentrated in vacuo. The crude product was purified by flash chromatography with 1-4% ethyl acetate-petrol as eluent to give the product 25(i) as a viscous oil (280 mg, 47%). Further elution with 10% ethyl acetate-petrol gave unreacted diol (200 mg, 40%).

$^1$H NMR (300 MHz, CDCl$_3$) δ 0.63, d, J=6.6 Hz, 3H, 0.66, d, J=6.6 Hz, 3H, 1.77, m, 1H, 3.75, m, 2H, 4.98, br s, 1H, 7.09, d, J=8.4 Hz; 7.30, m, 6H, 7.44, d, J=9.3 Hz, 1H, 7.87, d, J=8.1 Hz, 1H, 7.91, d, J=8.4 Hz, 2H, 8.01, d, J=9.0 Hz, 1H.

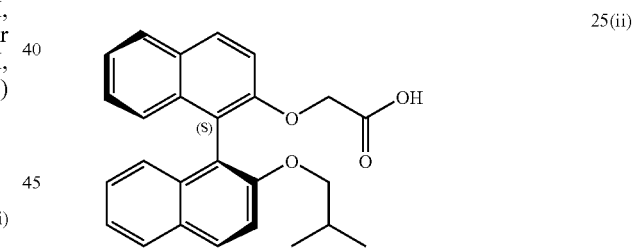

25(ii)

To 25(i) (280 mg, 0.82 mmol) in methanol (10 ml) was added potassium carbonate (500 mg, 3.63 mmol) and bromoacetic acid (454 mg, 3.27 mmol) and the mixture stirred at reflux for 4 days. The reaction mixture was cooled down, methanol removed in vacuo, and the crude residue redissolved in water and acidified with 1M HCl. Extraction with ether, drying (Na$_2$SO$_4$) and concentration gave the crude product which was purified by flash chromatography. Elution with 4% ethyl acetate:petrol gave unreacted 25(i) (150 mg, 54%). Further elution with 10% methanol:DCM gave the product 25(ii) (100 mg, 31%).

$^1$H NMR (500 M, CDCl$_3$) δ 0.44, d, J=6.5 Hz, 3H, 0.51, d, J=7.0 Hz, 3H, 1.68, m, 1H, 3.63, ABq, J=7.0, 9.5 Hz, 1H, 3.83, ABq, J=6.5, 9.5 Hz, 1H, 4.56, ABq, J=17 Hz, 1H, 4.71, ABq, J=16 Hz, 1H, 7.14, d, J=8.0 Hz; 7.25, m, 2H, 7.35, m, 4H, 7.45, d, J=9.5 Hz, 1H, 7.89, d, J=8.5 Hz, 2H, 7.99, d, J=8.5 Hz, 2H.

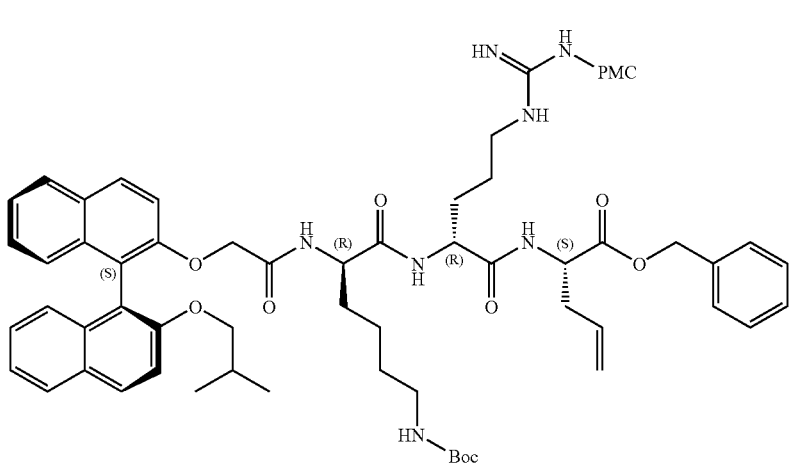

25(iii)

This compound was prepared via Protocol 1, using 25(ii) with 23(viii). Purification by radial chromatography (1-4% methanol:DCM) gave the product 25(iii) (90 mg, 70%).

$^1$H NMR (500 MHz, CDCl$_3$) δ 0.43, d, J=7.0 Hz, 3H, 0.49, d, J=6.0 Hz, 3H, 0.77, m, 2H, 0.93, m, 1H, 1.28, s, 6H, 1.41, s, 9H, 1.45, m, 7H, 1.76, br t, 3H, 2.08, b s, 2H, 2.54, s, 3H, 2.56, s, 3H, 2.56, m, 4H, 2.95, m, 2H, 3.13, m, 1H, 3.60, m, 1H, 3.81, m, 1H, 4.07, br s, 1H, 4.40, ABq, J=14.5 Hz, 1H, 4.50, ABq, J=14.5 Hz, 1H, 4.40, m, 1H, 4.57, m, 1H, 4.83, b s, 1H, 5.03, m, 2H, 5.09, ABq, J=12.5 Hz; 5.18, ABq, J=12.5 Hz; 5.63, m, 1; 6.20, m, 3H, 7.26, m, 7H, 7.43, d, J=9.5 Hz, 1H, 7.85, m, 2H, 7.94, d, J=9.0 Hz, 2H. MS (ES +ve) 1260 (35%) [M+Na]$^+$; 1238 (15) [M+H]$^+$.

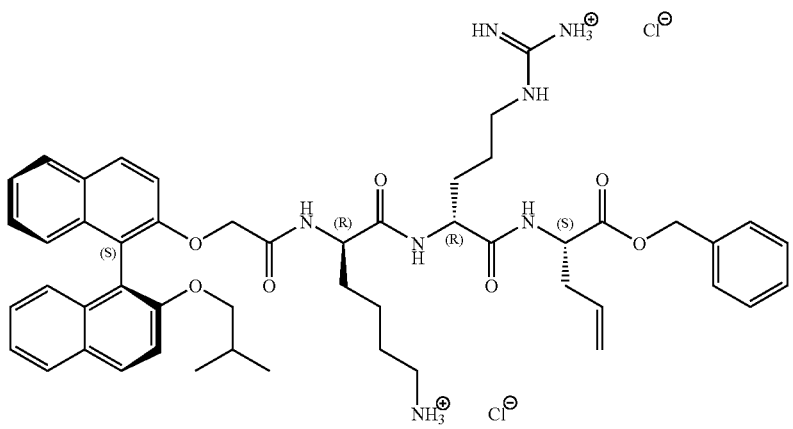

Compound 25

This compound was prepared via Protocol 3, using 25(iii) (70 mg, 56.5 μmol) to give the product 25 as a cream crystalline solid (30 mg, 56%).

$^1$H NMR (500 MHz, CD$_3$OD) δ 0.52, d, J=6.2 Hz, 3H, 0.57, d, J=6.6 Hz, 3H, 0.87, m, 2H, 0.96, br s, 1H, 1.13, m, 1H, 1.62, m, 4H, 1.28, m, 2H, 2.57, m, 2H, 2.79, br s, 2H, 3.15, br s, 2H, 3.70, m, 1H, 3.91, m, 1H, 4.14, b s, 1H, 4.48, m, 4H, 4.89, br s, 1H, 5.11, m, 2H, 5.15, ABq, 1H, J=12.5 Hz; 5.19, ABq, 1H, J=12.5 Hz; 5.74, m, 1H, 7.09, m, 2H, 7.22, m, 2H, 7.37, m, 7H, 7.47, d, J=8.5 Hz, 1H, 7.54, d, J=8.5 Hz, 1H, 7.91, d, J=7.7 Hz, 2H, 8.03, d, J=8.5 Hz, 2H. MS (ES +ve) 872 (25%) [M+H]$^+$; 437 (100) [M+2H]$^{2+}$.

Synthesis of Compound 26

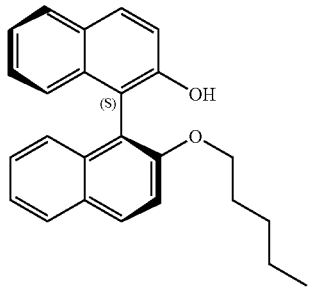

26(i)

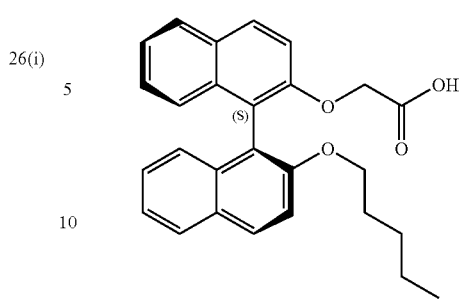

26(ii)

Bromopentane (216 µl, 1.75 mmol) was added to a mixture of 1,1'-binaphth-2,2'-diol (500 mg, 1.75 mmol), potassium carbonate (1.00 g, 7.27 mmol) and acetone (10 ml). The mixture was stirred at reflux for 18 h, and then cooled and concentrated in vacuo. The crude product was purified by flash chromatography with 1-4% ethyl acetate:petrol as eluent to give the product 26(i) as a viscous oil (380 mg, 61%).

$^1$H NMR (500 MHz, CDCl$_3$) δ 0.66, t, J=7 Hz, 3H, 0.96, m, 2H, 1.03, m, 2H, 1.43, m, 2H, 3.95, m, 2H, 4.94, s, 1H, 7.05, d, J=8.5 Hz, 1H, 7.28, m, 6H, 7.42, d, J=9.0 Hz, 1H, 7.83, d, J=8.5 Hz; 7.87, d, J=9.0 Hz, 2H, 7.98, d, J=9.0 Hz, 1H.

To 26(i) (280 mg, 0.82 mmol) in methanol (10 ml) was added potassium carbonate (500 mg, 3.63 mmol) and bromoacetic acid (454 mg, 3.27 mmol) and the mixture stirred at reflux for 4 days. The reaction mixture was cooled down, methanol removed in vacuo, and the crude residue redissolved in water and acidified with 1M HCl. Extraction with ether, drying (Na$_2$SO$_4$) and concentration gave the crude product that was purified by flash chromatography. Elution with 4% ethyl acetate:petrol gave unreacted 26(i) (150 mg, 54%). Further elution with 10% methanol:DCM gave the desired compound 26(ii) as a viscous oil (100 mg, 31%).

$^1$H NMR (500 MHz, CDCl$_3$) δ 0.53, t, J=7.5 Hz, 3H, 0.79, m, 4H, 1.35, m, 2H, 3.88, m, 1H, 4.05, m, 1H, 4.55, ABq, J=16.5 Hz, 1H, 4.74, ABq, J=16.5 Hz, 1H, 7.14, dd, J=8.5, 2.5 Hz, 1H, 7.25, dd, J=5.5, 5.5 Hz, 1H, 7.33, d, J=9.5 Hz, 1H, 7.36, m, 3H, 7.46, d, J=7.46 Hz, 1H, 7.89, d, J=8.0 Hz, 1H, 7.98, d, J=8.5 Hz, 1H.

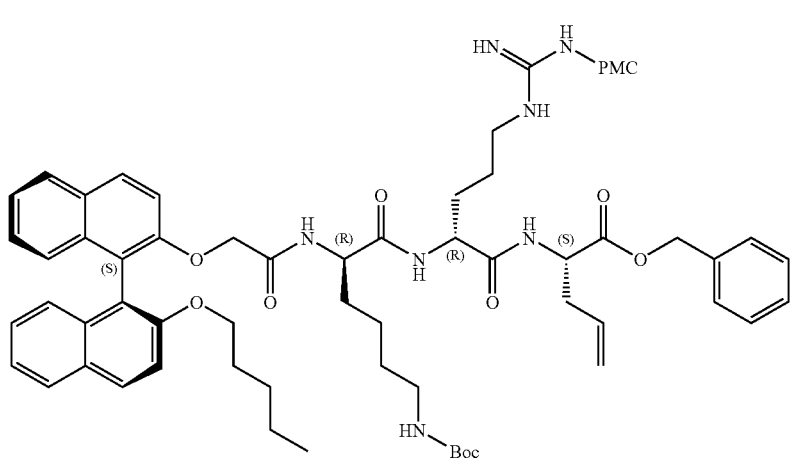

26(iii)

This compound was prepared via Protocol 1, using 26(ii) with 23(viii) (80 mg, 94 µmol). Purification by radial chromatography (1-4% methanol:DCM) gave the desired product 26(iii) (110 mg, 95%).

$^1$H NMR (500 MHz, CDCl$_3$) δ 0.54, d, J=7.2 Hz, 3H, 0.83, m, 7H, 1.27, s, 6H, 1.41, s, 9H, 1.33, m, 8H, 1.76, br t, 3H, 2.08, br s, 3H, 2.54, s, 3H, 2.56, s, 3H, 2.53, m, 4H, 2.90, m, 2H, 3.06, m, 4H, 3.85, m, 1H, 4.00, m, 1H, 4.08, br s, 1H, 4.40, ABq, J=14.5 Hz, 1H, 4.52, ABq, J=14.5 Hz, 1H, 4.54, m, 2H, 4.85, br s, 1H, 5.05, m, 2H, 5.15, ABq, J=12.0 Hz, 1H, 5.17, ABq, J=12.0 Hz, 1H, 5.65, m, 1H, 6.23, m, 3H, 7.11, d, J=8.3 Hz, 1H, 7.15, d, J=8.3 Hz, 1H, 7.26, m, 10H, 7.44, d, J=9.05 Hz; 7.85, m, 2H, 7.93, m, 2H. MS (ES +ve) m/z 1252 (100%) [M+H]$^+$.

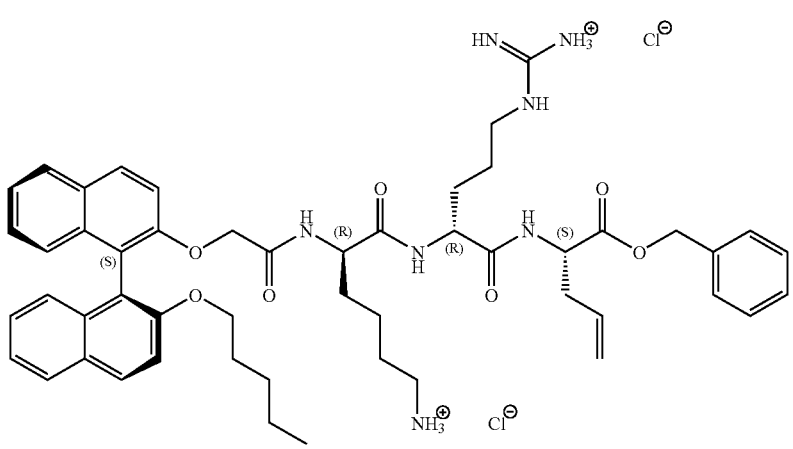

Compound 26

This compound was prepared via Protocol 3, using 26(iii) (90 mg, 71.9 µmol). Standard work-up gave the product 26 as a white crystalline solid (45 mg, 65%).

MS (ES +ve) m/z 886 (70%) [M+H]$^+$; 444 (100) [M+2H]$^{2+}$.

Synthesis of Compound 27

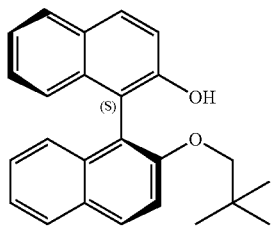

27(i)

1-Bromo-2,2-dimethylpropane (220 µl, 1.75 mmol) was added to a mixture of 1,1'-binaphth-2,2'-diol (500 mg, 1.75 mmol), potassium carbonate (1.00 g, 7.27 mmol) and dimethylformamide (10 ml). The mixture was stirred at 80° C. for 7 days, and then cooled down and acidified with diluted hydrochloric acid. The mixture was diluted with water and extracted with ether. The crude product was purified by flash chromatography with 1-4% ethyl acetate:petrol as eluent to give the product 27(i) as a viscous oil (80 mg, 13%).

$^1$H NMR (500 MHz, CDCl$_3$) δ 0.57, s, 9H, 3.57, m, 2H, 4.94, s, 1H, 7.05, d, 1H, J=8.5 Hz; 7.17, m, 1H, 7.26, m, 2H, 7.35, m, 4H, 7.81, d, J=8 Hz, 1H, 7.85, d, J=9 Hz, 2H, 7.95, d, J=9.5 Hz, 1H.

27(ii)

To 27(i) (80 mg, 0.22 mmol) in methanol (10 ml) was added potassium carbonate (1.00 g, 7.27 mmol) and bromoacetic acid (560 mg, 4.03 mmol) and the mixture stirred at reflux for 18 h. The reaction mixture was cooled down, methanol removed in vacuo, and the crude residue redissolved in water and acidified with 1M HCl. Extraction with ether, drying (Na$_2$SO$_4$) and concentration gave the crude product that was purified by flash chromatography. Elution with 10% methanol:DCM gave the acid 27(ii) as a viscous oil (85 mg, 92%).

$^1$H NMR (500 MHz, CDCl$_3$) δ 0.50, s, 9H, 3.51, ABq, J=8.0 Hz, 1H, 3.66, ABq, J=8.0 Hz, 1H, 4.52, s, 2H, 7.20, m, 4H, 7.32, m, 3H, 7.38, d, J=9.0 Hz, 1H, 7.85, d, J=8.5 Hz, 2H, 7.93, m, 2H.

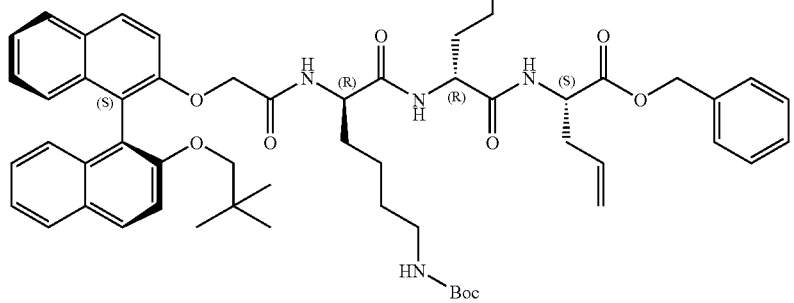

27(iii)

This compound was prepared via Protocol 1, using 27(ii) and 23(viii) (82 mg, 96 μmol). Purification by radial chromatography (1-3% methanol:DCM) gave the product 27(iii) (73 mg, 61%).

$^{1}$H NMR (300 MHz, CDCl$_3$) δ 0.47, s, 9H, 0.80, m, 2H, 0.91, m, 1H, 1.28, s, 6H, 1.41, s, 9H, 1.40, m, 6H, 1.77, br t, 3H, 2.08, s, 3H, 2.54, 4H, 3.11, m, 4H, 3.48, ABq, J=8.1 Hz, 1H, 3.72, ABq, J=8.4 Hz, 1H, 4.08, br s, 1H, 4.49, m, 4H, 4.84, br s, 1H, 5.03, m, 2H, 5.09, ABq, J=12.3 Hz, 1H, 5.18, ABq, J=12.3 Hz, 1H, 5.66, m, 1H, 6.13, d, J=7.2 Hz, 1H, 6.30, br s, 2H, 7.27, m, 7H, 7.42, d, J=9.0 Hz, 1H, 7.85, m, 2H, 7.94, d, J=8.7 Hz, 2H. MS (ES +ve) m/z 1252 (20%) [M+H]$^+$.

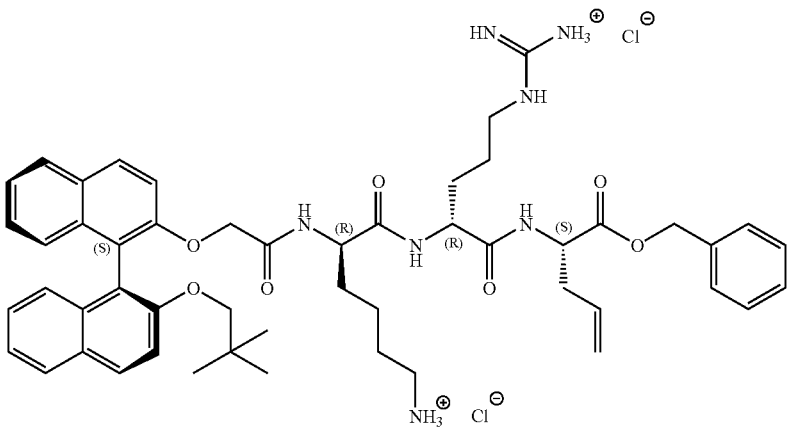

Compound 27

This compound was prepared via Protocol 3, using 27(iii) (60 mg, 47.9 μmol). Standard work-up gave the product 27 as a cream crystalline solid (30 mg, 65%).

$^{1}$H NMR (300 MHz, CD$_3$OD) δ 0.52, br s, 9H, 1.05, m, 3H, 1.66, m, 6H, 2.52, m, 2H, 2.79, br s, 2H, 3.34, br s, 2H, 3.55, ABq, J=8.1 Hz, 1H, 3.79, ABq, J=8.1 Hz, 1H, 4.14, br s, 1H, 4.42, m, 4H, 4.86, br s, 1H, 5.11, m, 4H, 5.73, m, 1H, 7.31, 13H, 7.90, d, J=8.1 Hz, 2H, 8.02, d, J=8.4 Hz, 2H. MS (ES +ve) m/z 887 (20%) [M+H]$^+$; 444 (100) [M+2H]$^{2+}$.

Synthesis of Compound 28

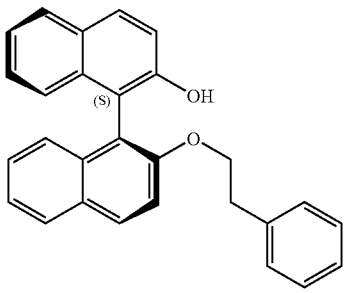

28(i)

2-Bromoethylbenzene (240 μl, 1.75 mmol) was added to a mixture of 1,1'-binaphth-2,2'-diol (500 mg, 1.75 mmol), potassium carbonate (1.00 g, 7.27 mmol) and acetone (10 ml). The mixture was stirred at reflux for 18 h, and then cooled down and filtered. The crude product was purified by flash chromatography with 1-4% ethyl acetate:petrol as eluent to give the product 28(i) as viscous oil (250 mg, 37%)

$^{1}$H NMR (300 MHz, CDCl$_3$) δ 2.69, m, 2H, 4.12, m, 2H, 4.90, s, 1H, 6.76, m, 2H, 7.02, m, 4H, 7.26, m, 7H, 7.89, m, 4H.

28(ii)

To 28(i) (250 mg, 0.64 mmol) in methanol (10 ml) was added potassium carbonate (1.00 g, 7.27 mmol) and bromoacetic acid (560 mg, 4.03 mmol) and the mixture stirred at reflux for 18 h. The reaction mixture was cooled down, methanol removed in vacuo, and the crude residue redissolved in water and acidified with 1M HCl. Extraction with ether, drying (Na$_2$SO$_4$) and concentration gave the crude product that was purified by flash chromatography. Elution with 10% methanol-DCM gave the acid 28(ii) as a viscous oil (257 mg, 89%).

$^{1}$H NMR (500 MHz, CDCl$_3$) δ 2.62, m, 2H, 4.06, m, 2H, 4.15, m, 2H, 6.67, d, J=7.5 Hz, 2H, 6.98, m, 3H, 7.15, m, 3H, 7.27, m, 2H, 7.34, m, 3H, 7.80, d, J=8.5 Hz, 1H, 7.89, m, 3H, 10.30, br s, 1H.

28(iii)

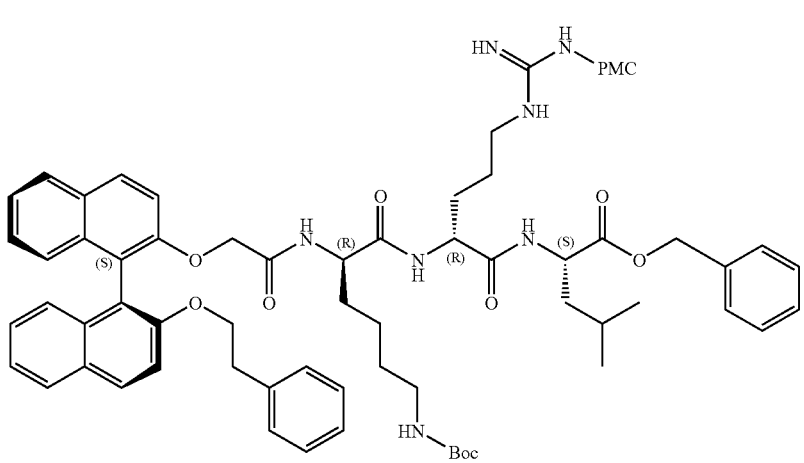

This compound was prepared via Protocol 1, using 28(ii) and 1(viii) (100 mg, 115 µmol). Purification by radial chromatography (1-3% methanol:DCM) gave the product 28(iii) (83 mg, 56%).

$^1$H NMR (300 M, CDCl$_3$) δ 0.75, m, 2H, 0.89, m, 6H, 1.26, s, 6H, 1.40, s, 9H, 1.60, m, 6H, 1.76, br t, 3H, 2.08, s, 3H, 2.62, m, 4H, 3.00, m, 4H, 4.05, m, 2H, 4.31, m, 4H, 4.54, m, 1H, 4.80, m, 1H, 5.09, ABq, J=12.6 Hz, 1H, 5.17, ABq, J=12.6 Hz, 1H, 6.10, br d, J=7.2 Hz, 1H, 6.31, br s, 2H, 6.59, d, J=6.9 Hz, 2H, 6.99, m, 1H, 7.22, m, 9H, 7.82, d, J=8.1 Hz, 1H, 7.90, m, 2H. MS (ES +ve) m/z 1302 (100%) [M]$^+$.

Compound 28

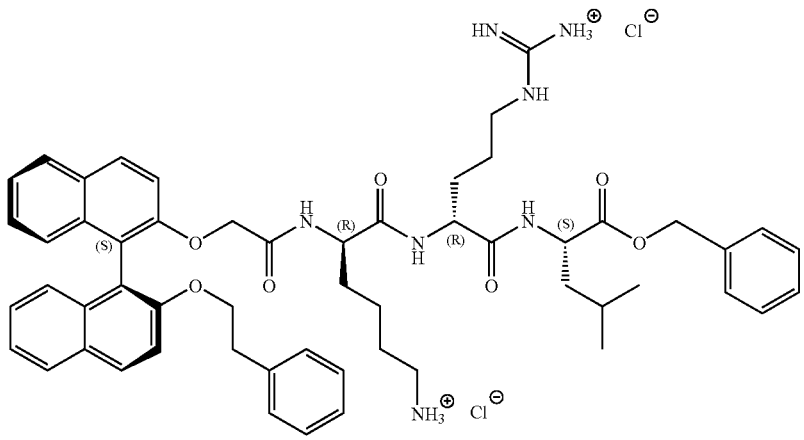

his compound was prepared via Protocol 3, using 28(iii) (80 mg, 61.4 µmol). Standard work-up gave the product 28 as a cream crystalline solid (40 mg, 65%).

$^1$H NMR (300 MHz, DMSO-d$_6$) δ 0.47, m, 6H, 1.12, m, 3H, 1.47, m, 4H, 2.07, s, 1H, 2.41, m, 1H, 2.49, br s, 3H, 2.66, m, 1H, 2.66, m, 1H, 3.04, m, 1H, 3.55, m, 8H, 4.26, m, 4H, 5.03, m, 2H, 5.74, m, 1H, 6.94, br d, J=8.4 Hz, 1H, 7.02, br d, J=8.4 Hz, 1H, 7.30, m, 15H, 7.51, m, 1H, 7.92, m, 2H, 8.02, m, 2H. MS (ES +ve) m/z 936 (100%) [M]$^+$.

Synthesis of Compound 29

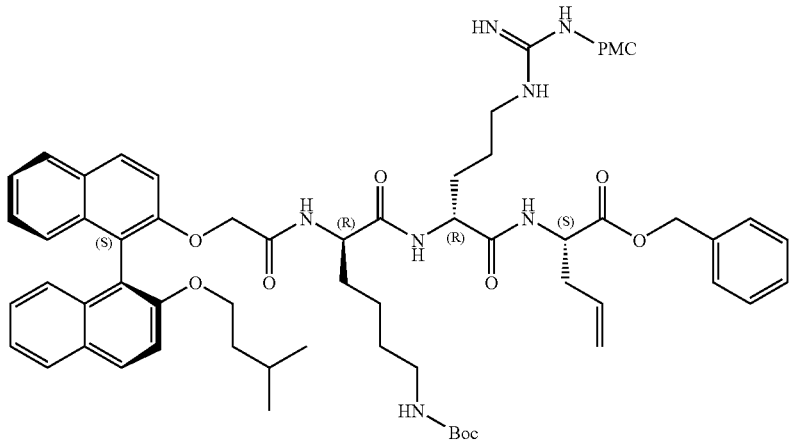

29(i)

This compound was prepared via Protocol 1, using 23(vii) (121 mg, 0.14 mmol) and 1(ii) (58 mg, 0.14 mmol) to afford 29(i) as a white solid (114 mg, 65%) Mp 90-94° C.

$^1$H NMR (300 MHz, CDCl$_3$) δ 0.46, d, J=6.3 Hz, 3H, 0.52, d, J=6.3 Hz, 3H, 0.79, m, 4H, 0.92, m, 2H, 1.12, m, 2H, 1.26, s, 6H, 1.41, s, 9H, 1.52, m, 4H, 1.76, t, J=5.7 Hz, 1H, 2.09, s, 3H, 2.49, m, 2H, 2.55, s, 3H, 2.56, s, 3H, 2.64, m, 2H, 2.92, m, 2H, 3.14, m, 2H, 3.95, m, 2H, 4.80, m, 5H, 5.05, m, 2H, 5.13, ABq, J=12.3 Hz, 2H, 5.65, m, 1H, 6.18, d, J=6.9 Hz, 1H, 6.29, br s, 2H, 6.47, m, 1H, 7.30, m, 13H, 7.90, m, 4H. MS (ES +ve) m/z 1274 (100%) [M+NH$_4$]$^+$.

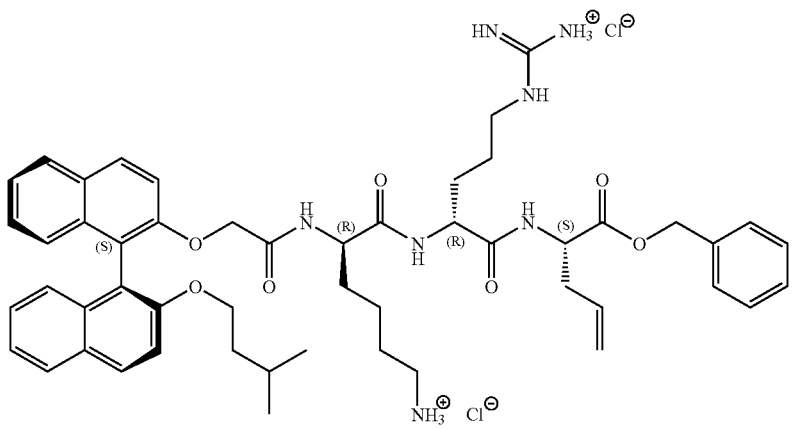

Compound 29

This compound was prepared via Protocol 3, using 29(i) (114 mg, 0.091 mmol) to yield 29 as a highly hydroscopic cream solid (48 mg, 55%).

$^1$H NMR (500 MHz, CD$_3$OD) δ 0.47, d, J=6.3 Hz, 3H, 0.53, d, J=6.3 Hz, 3H, 0.96, m, 2H, 1.17, m, 2H, 1.24, m, 2H, 1.55, m, 4H, 1.71, m, 2H, 1.79, m, 2H, 2.55, m, 2H, 2.79, m, 2H, 3.14, m, 2H, 3.95, m, 1H, 4.14, m, 2H, 4.35, m, 1H, 4.49, m, 3H, 5.11, m, 4H, 5.74, m, 1H, 5.32, m, 13H, 7.96, m, 4H. MS (ES +ve) m/z 886 (5%) [M]$^{2+}$; 444 (100%).

General Synthetic Scheme for Reverse-Peptide Compounds (Example - Compound 30)
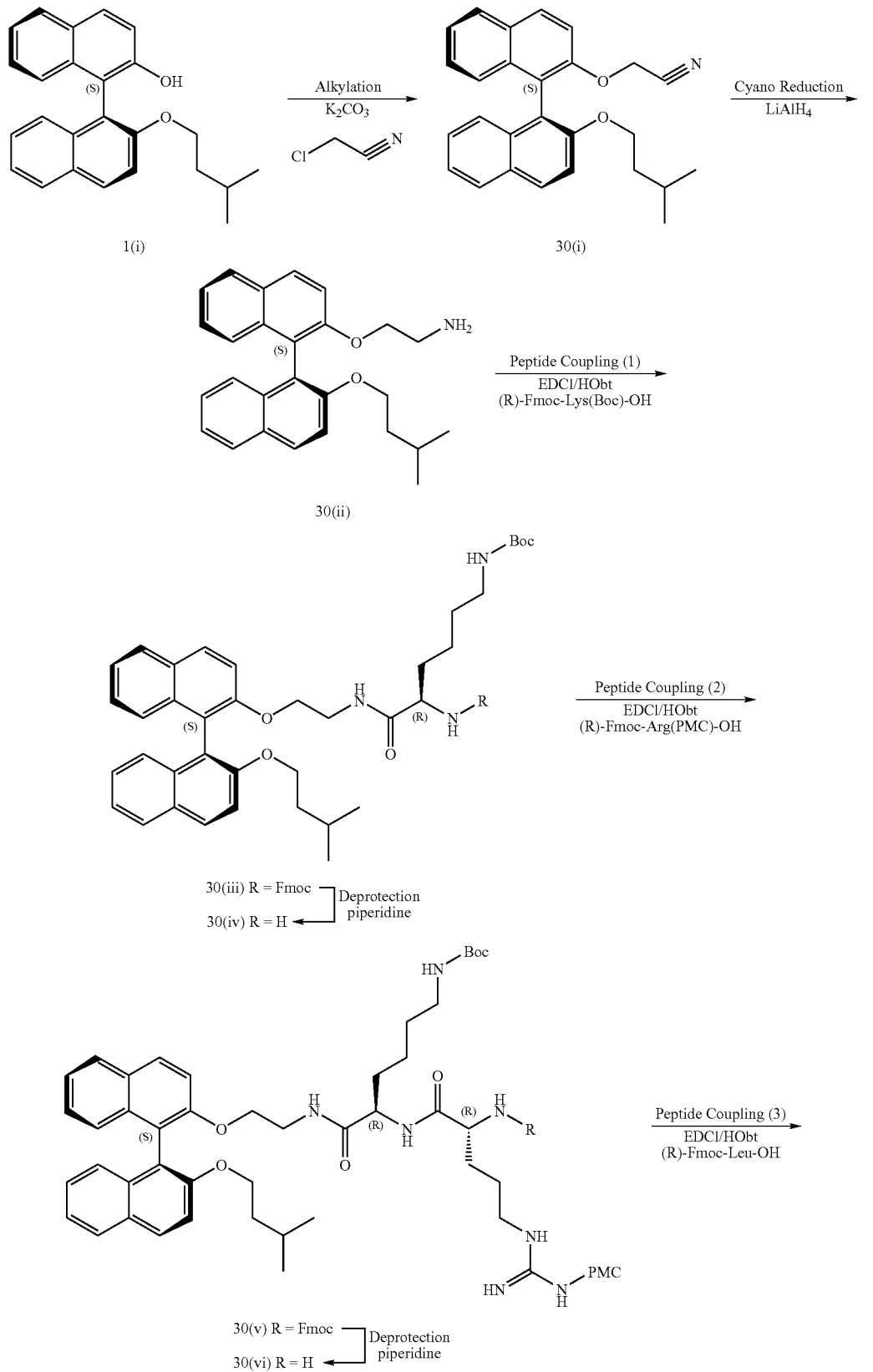

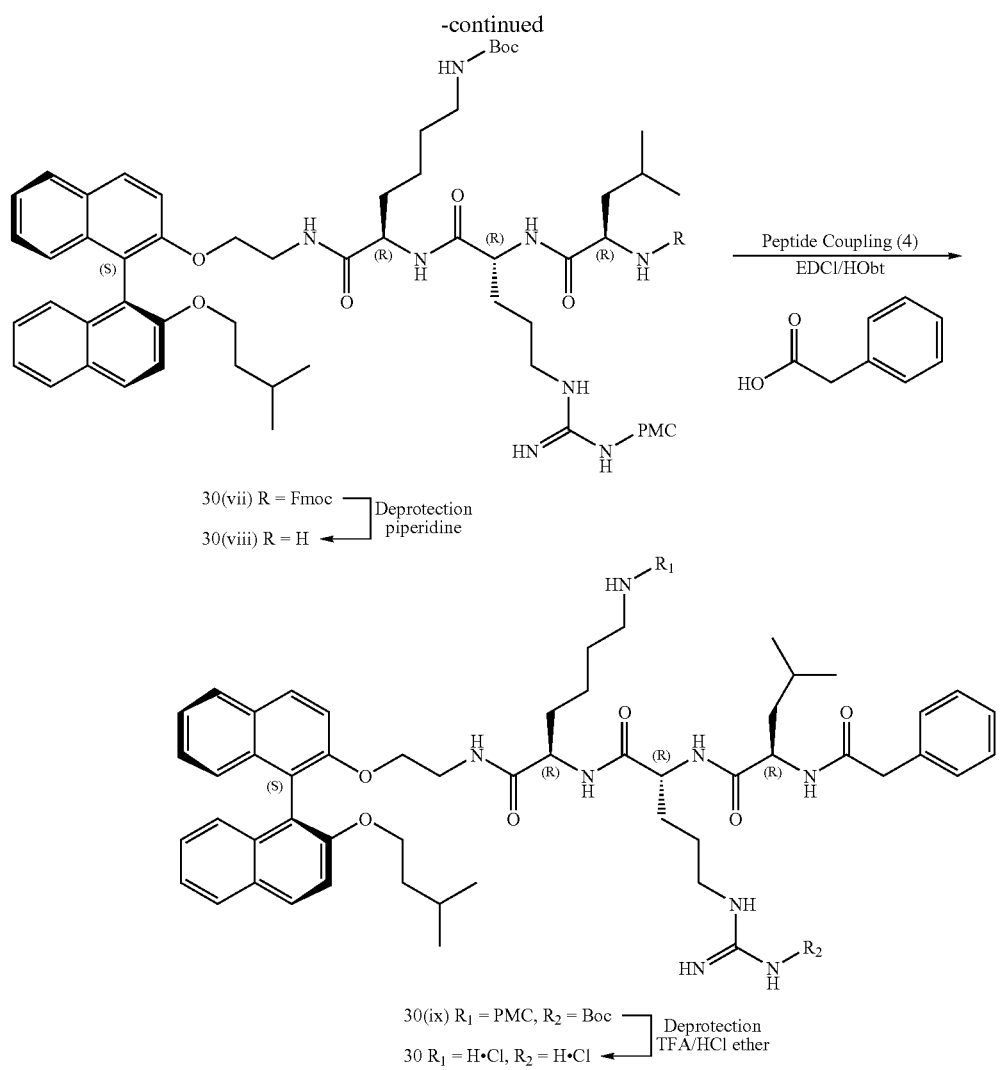

30(vii) R = Fmoc
30(viii) R = H
Deprotection piperidine

30(ix) R₁ = PMC, R₂ = Boc
30 R₁ = H·Cl, R₂ = H·Cl
Deprotection TFA/HCl ether

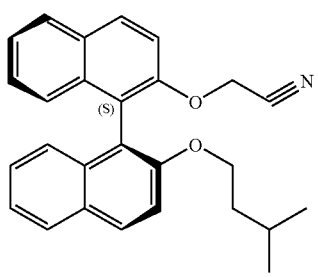

30(i)

To 1(i) (10.0 g, 28 mmol) in dry acetone (200 ml) was added potassium carbonate (20.0 g, 145 mmol), chloroacetonitrile (3.0 ml, 47 mmol) and potassium iodide (2.50 g, 15 mmol). The resultant solution was heated at reflux for 18 hrs and then cooled down and filtered. Acetone was removed and the residue redissolved in ethyl acetate and water, and neutralized with 1M HCl. Organic extract was separated and water phase extracted with more ethyl acetate. Organic extracts were combined, dried (MgSO₄) and concentrated. Purification by column chromatography with 1-20% ethyl acetate/petrol gave the product 30(i) as a colourless viscous oil (10.0 g, 90%).

$^1$H NMR (300 MHz, CDCl₃) δ 0.54, d, J=6.0 Hz, 3H, 0.60, d, J=5.7 Hz, 3H, 1.25, m, 2H, 3.89, m, 1H, 4.05, m, 1H, 7.22, m, 6H, 7.38, d, J=9.0 Hz, 1H, 7.40, d, J=9.3 Hz, 1H, 7.80, d, J=7.5 Hz, 7.81, d, J=8.1 Hz, 1H, 7.90, d, J=9.0 Hz, 1H, 7.91, d, J=9.3 Hz, 1H.

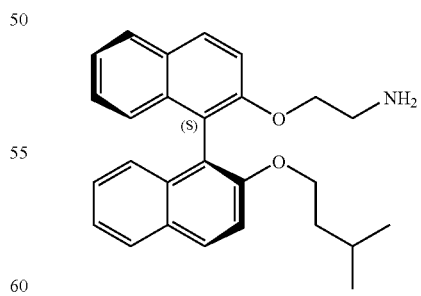

30(ii)

A solution of 30(i) (10.00 g, 25 mmol) in dry ether (50 ml) was added dropwise to a suspension of lithium aluminium hydride (3.00 g, 79 mmol) in ether (30 ml) during 2 hrs with ice bath cooling, and then stirred for 18 hrs at room temperature. Ether (100 ml) was added to the reaction mixture and then a potassium hydroxide solution in water (20%) was added until a white precipitate separated on the bottom of the flask. Ether solution was filtered to give the crude product that was purified by column chromatography to give the product 30(ii) (8.05 g, 80%).

$^1$H NMR (300 MHz, CDCl$_3$) δ 0.55, d, J=6.3 Hz, 3H, 0.60, d, J=6.3 Hz, 3H, 0.87 m, 1H, 1.22, m, 4H, 2.64, br s, 2H, 3.95, m, 4H, 7.20, m, 4H, 7.31, m, 2H, 7.38, d, J=8.7 Hz, 1H, 7.41, d, J=8.7 Hz, 1H, 7.84, d, J=8.1 Hz, 2H, 7.91, d, J=8.7 Hz, 2H.

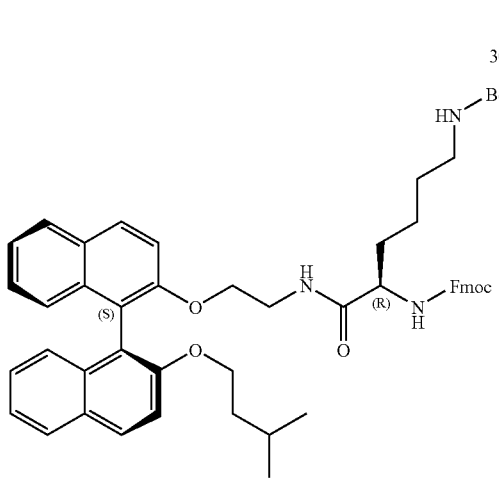

30(iii)

This compound was prepared via Protocol 1, using 30(ii) (260 mg, 0.65 mmol) and (R)-Fmoc-Lys(Boc)-OH (305 mg, 0.65 mmol) to yield the desired product 30(iii) as an off white solid (310 mg, 56%).

$^1$H NMR (300 MHz, CDCl$_3$) δ 0.41, d, J=6.0 Hz, 3H, 0.53, d, J=6.5 Hz, 3H, 1.27, m, 11H, 1.44, s, 9H, 2.85, m, 2H, 3.35, m, 2H, 3.81, m, 2H, 4.03, m, 2H, 4.12, m, 1H, 4.21, m, 1H, 4.38, m, 2H, 4.53, m, 1H, 5.38, br d, 1H, 5.78, br s, 1H, 7.09, d, J=8.5 Hz, 1H, 7.25, m, 10H, 7.49, d, J=9.0 Hz, 1H, 7.58, d, J=7.0 Hz, 2H, 7.73, d, J=7.5 Hz, 2H, 7.85, d, J=8.0 Hz, 1H, 7.90, d, J=7.5 Hz, 1H, 7.94, d, J=9.0 Hz, 1H, 8.00, d, J=9.0 Hz, 1H. MS (ES +ve) m/z 849 (100%) [M+Na]$^+$.

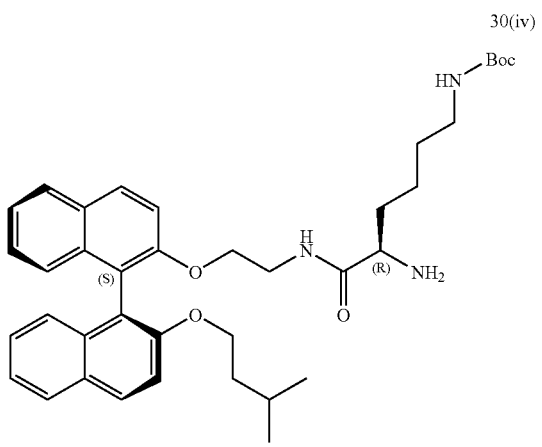

30(iv)

This compound was prepared via Protocol 2, using 30(iii) (310 mg, 0.365 mmol) to yield the desired product 30(iv) as an off white solid (172 mg, 75%).

$^1$H NMR (300 MHz, CDCl$_3$) δ 0.58, 3H, dd, J=6.3, 1.5 Hz; 0.65, 3H, dd, J=6.6, 1.5 Hz; 1.51, m, 11H, 1.51, s, 9H, 2.93, m, 1H, 3.17, m, 3H, 3.30, m, 1H, 3.45, m, 1H, 3.92, m, 1H, 4.12, m, 3H, 4.79, br s, 1H, 6.73, m, 1H, 7.15, m, 1H, 7.25, m, 3H, 7.36, m, 2H, 7.48, m, 2H, 7.91, m, 2H, 7.99, m, 2H. MS (ES +ve) m/z 628 (100%).

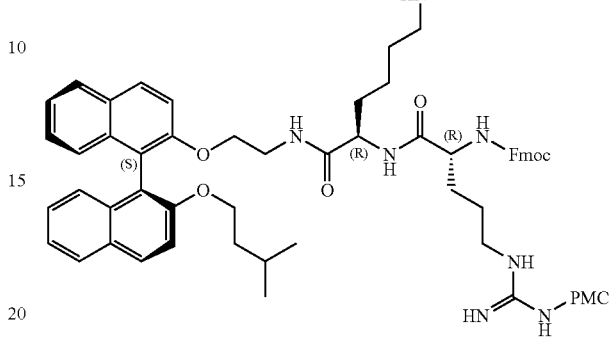

30(v)

This compound was prepared via Protocol 1, using 30(iv) (172 mg, 0.274 mmol) and (R)-Fmoc-Arg(Pmc)-OH (182 mg, 0.274 mmol) to yield the desired product 30(v) as an off white solid (165 mg, 47%).

$^1$H NMR (300 MHz, CDCl$_3$) δ 0.41, d, J=6.6 Hz, 3H, 0.52, d, J=6.3 Hz, 3H, 1.25, s, 6H, 1.37, s, 9H, 1.30, m, 13H, 1.71, br t, 3H, 1.83, br s, 1H, 2.07, s, 3H, 2.55, s, 3H, 2.59, s, 3H, 2.84, m, 3H, 3.19, m, 4H, 3.81, m, 1H, 4.02, m, 3H, 4.12, m, 1H, 4.31, m, 3H, 4.84, br s, 1H, NH; 6.22, m, 5H, NH; 7.21, m, 10H, 7.48, m, 4H, 7.70, d, J=7.5 Hz, 2H, 7.89, m, 4H. MS (ES +ve) m/z 1272 (5%) [M+H]$^+$.

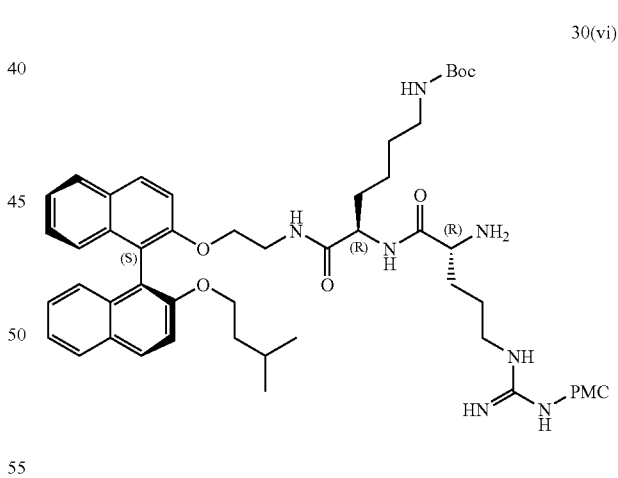

30(vi)

This compound was prepared via Protocol 2, using 30(v) (165 mg, 0.130 mmol) to yield the desired product 30(vi) as an off white solid (100 mg, 73%).

$^1$H NMR (300 MHz, CDCl$_3$) δ 0.41, d, J=6.6 Hz, 3H, 0.53, d, J=6.3 Hz, 3H, 1.28, s, 6H, 1.41, s, 9H, 1.36, m, 14H, 1.77, br t, 3H, 2.10, s, 3H, 2.56, s, 3H, 2.58, s, 3H, 2.92, m, 2H, 3.20, m, 3H, 3.37, m, 2H, 3.81, m, 1H, 4.08, m, 4H, 4.84, br s, 1H, NH; 6.22, m, 5H, NH; 7.23, m, 6H, 7.38, d, J=9.0 Hz, 1H, 7.49, d, J=9.0 Hz, 1H, 7.96, m, 4H.

30(vii)

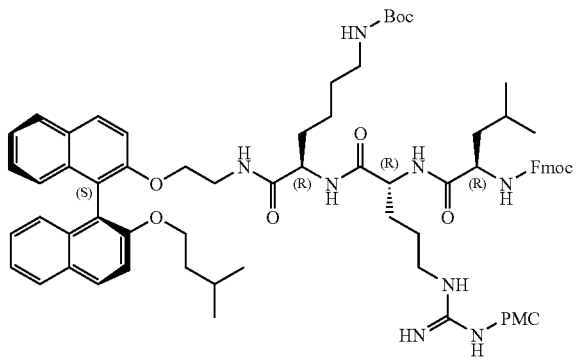

This compound was prepared via Protocol 1, using 30(vi) (100 mg, 95 μmol) and (R)-Fmoc-Leu-OH (34 mg, 95 μmol) to yield the desired product 30(vii) as an off white solid (120 mg, 91%).

$^1$H NMR (300 MHz, CDCl$_3$) 0.41, br d, J=6.0 Hz, 3H, 0.51, br d, J=6.3 Hz, 3H, 0.88, br d, J=5.7 Hz, 3H, 0.90, br d, J=5.7 Hz, 3H, 1.24, s, 6H, 1.39, s, 9H, 1.56, m, 23H, 2.06, s, 3H, 2.51, s, 3H, 2.54, s, 3H, 2.71, s, 1H, 2.88, m, 2H, 3.11, m, 3H, 3.31, m, 1H, 3.77, m, 1H, 3.98, m, 2H, 4.11, m, 1H, 4.27, m, 2H, 4.54, br s, 1H, NH; 4.92, br s, 1H, NH; 6.35, m, 5H, NH; 7.26, m, 10H, 7.55, m, 4H, 7.70, d, J=7.2 Hz, 2H, 7.89, m, 4H. MS (ES +ve) m/z 1385 (15%) [M]$^+$.

30(viii)

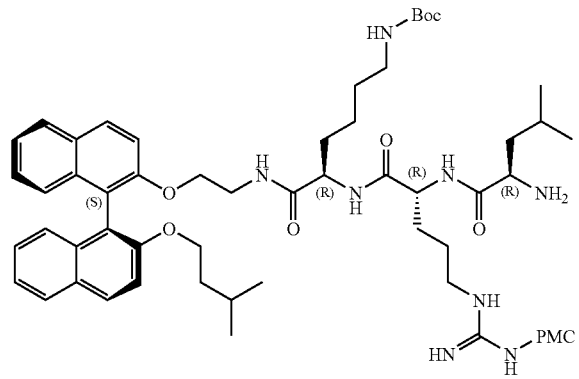

This compound was prepared via Protocol 2, using 30(vii) (120 mg, 87 μmol) to yield the desired product 30(viii) as an off white solid (80 mg, 79%).

MS (ES +ve) m/z 1163 (80%) [M]$^+$.

30(ix)

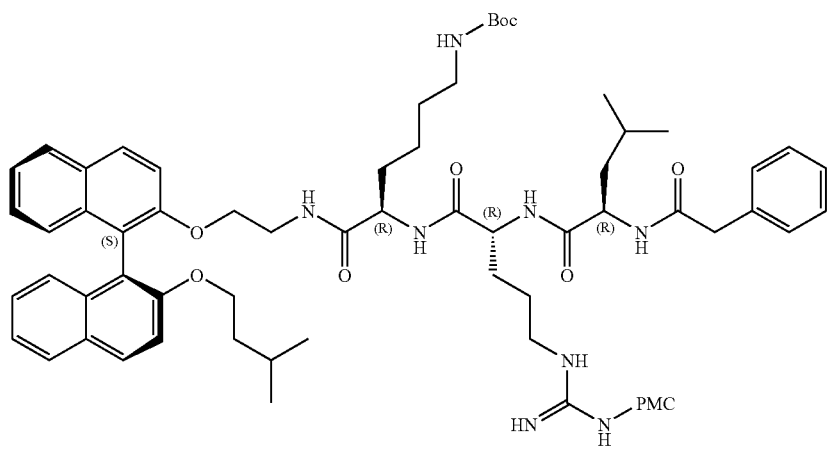

This compound was prepared via Protocol 1, using 30(viii) (50 mg, 43 μmol) and phenylacetic acid (6 mg, 43 μmol) to yield the desired product 30(ix) as a cream solid (50 mg, 91%).

$^1$H NMR (300 MHz, CDCl$_3$) δ 0.43, d, J=6.0 Hz, 3H, 0.53, d, J=6.3 Hz, 3H, 0.80, br d, 3H, 0.83, br d, 3H, 1.28, s, 6H, 1.26, m, 14H, 1.41, s, 9H, 1.77, br t, 3H, 2.09, s, 3H, 2.53, s, 3H, 2.55, s, 3H, 2.90, m, 3H, 3.13, m, 2H, 3.29, m, 1H, 3.50, m, 2H, 3.62, s, 2H, 3.81, m, 1H, 3.99, m, 4H, 4.46, m, 2H, 4.86, br s, 1H, 6.25, m, 5H, 7.24, m, 11H, 7.89, m, 6H. MS (ES +ve) m/z 1303 (75%) [M+Na]$^+$.

Compound 30
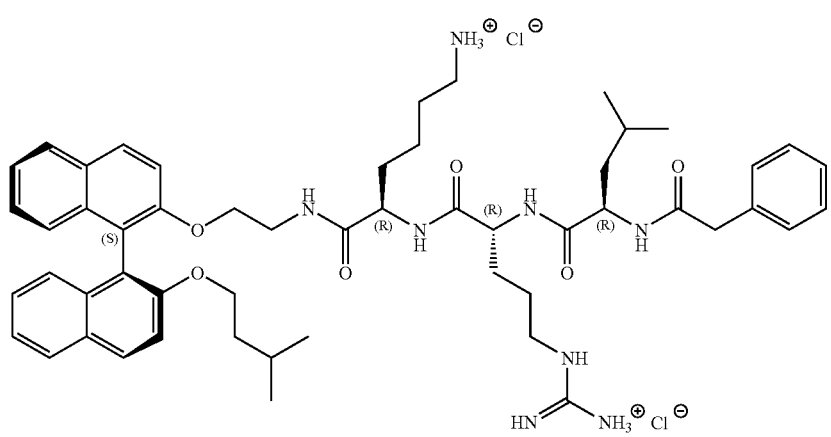
This compound was prepared via Protocol 3, using 30(ix) (50 mg, 39 µmol) to yield the desired product 30 as a cream solid (20 mg, 56%).
$^1$H NMR (300 MHz, CDCl$_3$) δ 0.48, d, J=6.3 Hz, 3H, 0.57, d, J=6.6 Hz, 3H, 0.88, br d, 3H, 0.95, br d, 3H, 1.19, m, 6H, 1.58, m, 7H, 2.82, br s, 2H, 3.27, m, 7H, 3.65, m, 2H, 3.87, m, 1H, 4.07, m, 4H, 4.27, m, 2H, 4.54, br s, 1H, NH; 4.92, br s, 1H, NH; 6.35, m, 5H, NH; 7.22, m, 10H, 7.55, m, 4H, 7.70, d, J=7.2 Hz, 2H, 7.89, m, 4H. MS (ES +ve) m/z 915 (5%) [M]$^+$, 458 (100) [M+2H]$^{2+}$.
General Synthetic Scheme (Example - Compound 31)
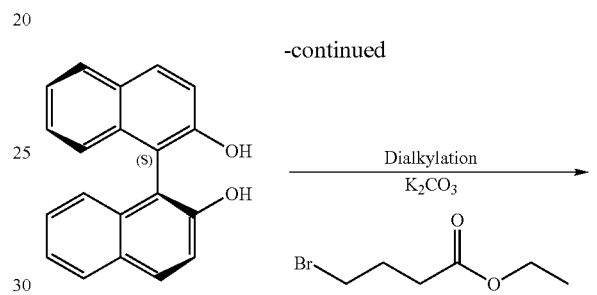
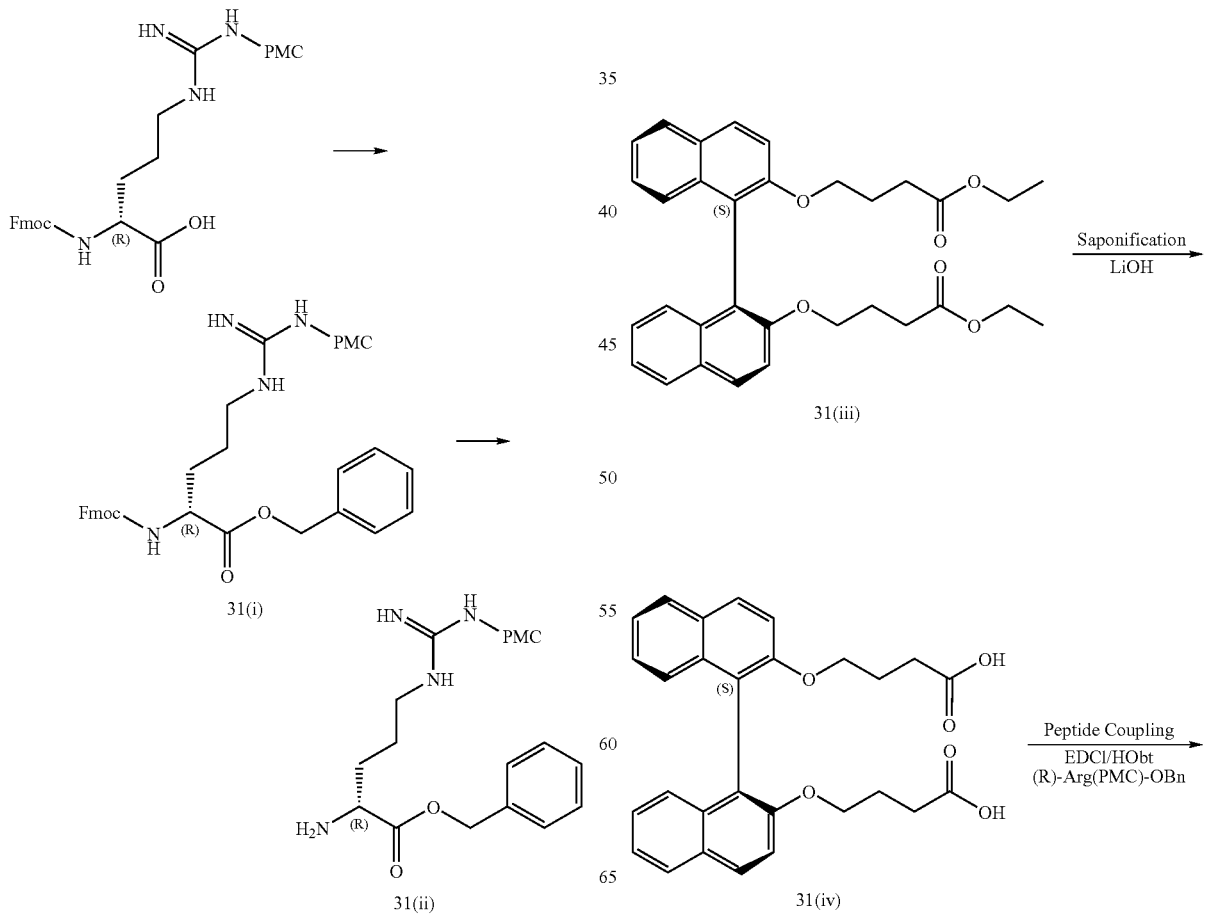

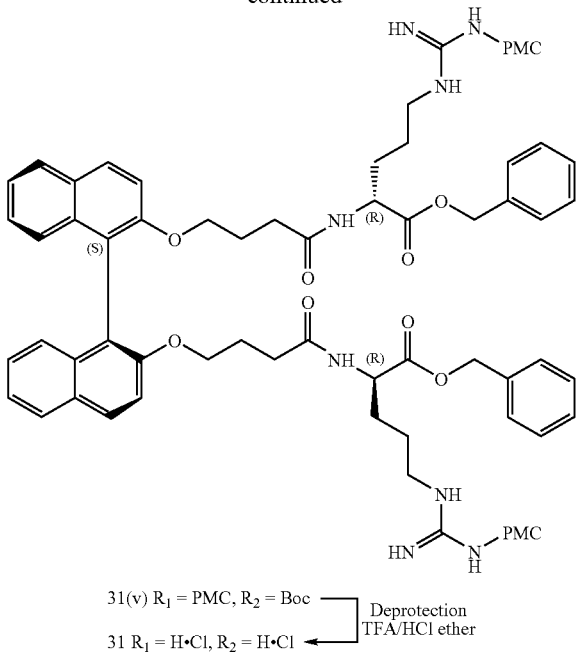

31(v) R₁ = PMC, R₂ = Boc  
31 R₁ = H•Cl, R₂ = H•Cl ⟵ Deprotection TFA/HCl ether

Synthesis of Compound 31

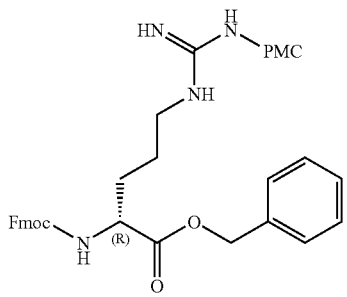
31(i)

To Fmoc-(D)-Arg(Pmc)-OH (400 mg, 604 mmol) suspended in DCM was added SOCl₂ (2 ml) at 0° C. After stirring for an hour the solvent was removed and the resultant residue resuspended in DCM and BzOH (0.1 ml) added. The solution was then stirred overnight at 40° C. before being evaporated to dryness. The crude residue was then subjected to flash column chromatography over silica using 2% MeOH/DCM as the eluant to afford the desired product 31(i) as a white solid (341 mg, 75%).

¹H NMR (300 MHz, CDCl₃) δ 1.29, s, 6H, 1.51, m, 2H, 1.74, m, 4H, 2.11, s, 3H, 2.58, m, 8H, 3.13, m, 2H, 4.14, m, 1H, 4.34, m, 3H, 5.11, s, 2H, 5.98, d, J=9.2 Hz, NH; 6.16, br s, NH; 6.29, br s, NH; 7.30, m, 9H, 7.58, d, J=7.5 Hz, 2H, 7.75, d, J=7.2 Hz, 2H.

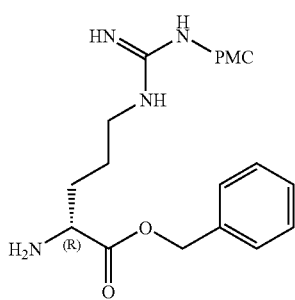
31(ii)

This compound was prepared via Protocol 2, using 31(i) (341 mg, 0.463 mmol) to yield the desired product 31(ii) as a white solid (159 mg, 65%).

¹H NMR (300 MHz, CDCl₃) δ 1.27, s, 6H, 1.51, m, 2H, 1.78, m, 4H, 2.07, s, 3H, 2.52, m, 8H, 3.11, m, 2H, 3.41, m, 1H, 5.07, s, 2H, 6.38, s, NH; 7.30, m, 5H.

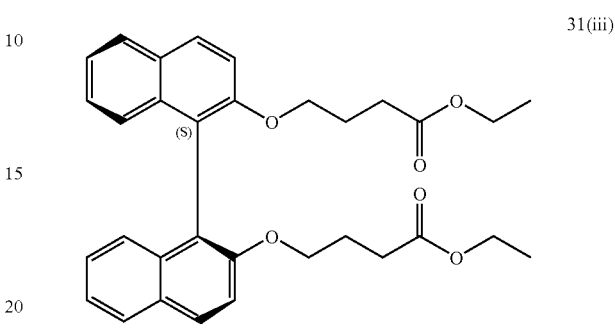
31(iii)

To a suspension of (S)-1,1'-binaphth-2,2'-diol (1 g, 3.5 mmol) and anhydrous potassium carbonate (2.4 g, 5 equiv) dissolved in acetone (25 ml), was added ethyl bromobutyrate (1.15 ml, 2.3 equivalents) under an N₂ atmosphere. The mixture was then heated at reflux for 24 hrs before being evaporated to dryness and the residue partitioned between ethyl acetate and water. The organic layer was then washed twice with water before being dried and evaporated to dryness to yield an oil 31(iii) which was used in the next step without further purification.

¹H NMR (300 MHz, CDCl₃) δ 1.17, t, J=7.2 Hz, 6H, 1.70, m, 4H, 1.85, m, 4H, 3.98, m, 8H, 7.17, m, 4H, 7.30, m, 2H, 7.39, d, J=8.8 Hz, 2H, 7.84, d, J=8.0 Hz, 2H, 7.92, d, J=8.8 Hz, 2H. MS (EI) m/z 514 (90%) [M]⁺; 400 (80); 115 (100).

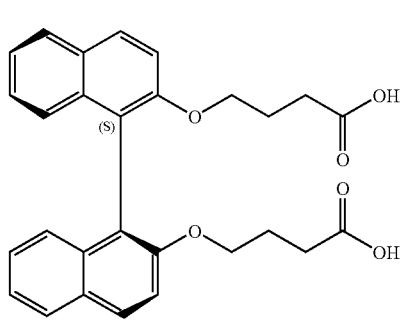
31(iv)

To 31(iii) (598 mg, 1.52 mmol) dissolved in THF (30 ml), was added a solution of LiOH (250 mg, 10.5 mmol) in water (20 ml), After stirring at RT for 4 hrs, diethyl ether was added and the layers separated. The aqueous layer was then acidified with 1M HCl before being extracted with diethyl ether (3×20 ml). The combined organic extracts were then dried (MgSO₄) and evaporated to dryness to yield the product 31(iv) as a white foamy solid (342 mg, 64%).

¹H NMR (300 MHz, CDCl₃) δ 1.65, m, 4H, 1.82, m, 4H, 3.93, m, 2H, 3.98, m, 2H, 7.15, m, 4H, 7.27, m, 2H, 7.35, d, J=9.1 Hz, 2H, 7.81, d, J=8.2 Hz, 2H, 7.90, d, J=8.8 Hz, 2H, 11.84, br s, 1H. MS (EI) m/z 458 (50%) [M]⁺; 372 (25) [M-CH₂CH₂CH₂COOH]⁺; 286 (100) [M-2× CH₂CH₂CH₂COOH]⁺.

31(v)

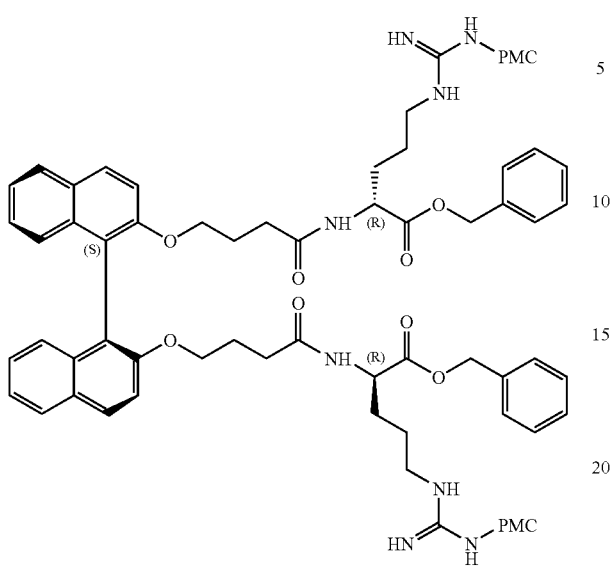

This compound was prepared via protocol 1, using 31(ii) (159 mg, 0.30 mmol) and 31(iv)(68.7 mg, 0.15 mmol) to yield 31(v) as a white solid (124 mg, 59%).

$^1$H NMR (300 MHz, CDCl$_3$) δ 1.25, s, 12H, 1.34, m, 8H, 1.70, m, 12H, 2.06, s, 6H, 2.51, m, 16H, 3.05, m, 4H, 3.75, m, 2H, 3.96, m, 2H, 4.34, m, 2H, 5.04, s, 4H, 6.11, br s, NH; 6.22, br s, NH; 6.42, d, J=7.2 Hz; NH; 7.06, d, J=8.5 Hz, 2H, 7.15, dist t, 2H, 7.25, m, 12H, 7.32, d, J=9.1 Hz; 2H, 7.79, d, J=8.2 Hz, 2H, 7.85, d, J=8.0 Hz, 2H. MS (ES +ve) m/z 742.7 (100%) [M+H]$^{2+}$.

Compound 31

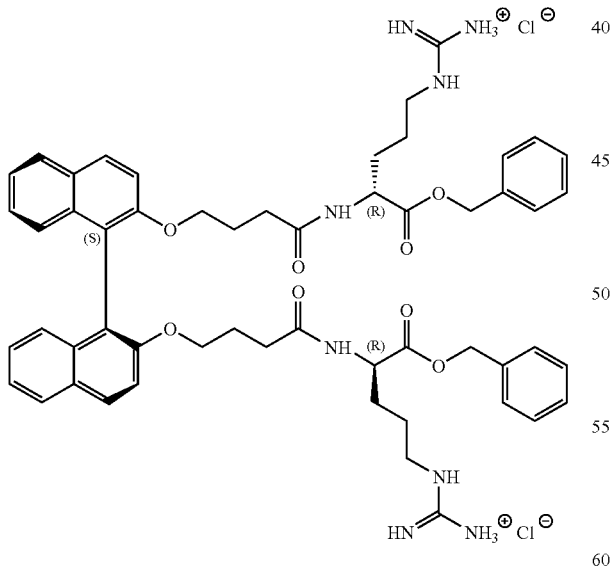

This compound was prepared via Protocol 3, using 31(v) (124 mg, 0.089 mmol) to yield 31 as a white solid (65.9 mg, 73%).

$^1$H NMR (300 MHz, CD$_3$OD) δ 1.58, m, 4H, 1.70, m, 6H, 1.85, m, 2H, 1.95, m, 4H, 3.12, m, 4H, 3.98, m, 4H, 4.38, m, 2H, 5.08, s, 4H, 7.06, m, 2H, 7.15, m, 2H, 7.25, m, 12H, 7.42, m, 2H, 7.83, m, 2H, 7.95, m, 2H. MS (ES +ve) m/z 951.2 (10%) [M+H]$^+$; 476.8 (100) [M+H]$^{2+}$.

Synthesis of Compound 32

32(i)

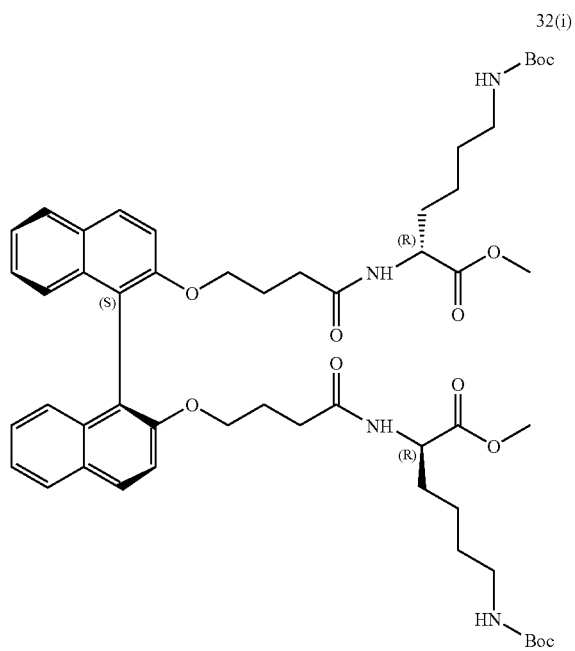

This compound was prepared via protocol 1, using 31(iv) (50 mg, 0.11 mmol) and (D)-lys(BOC)-OMe (68 mg, 0.23 mmol) to yield the desired product 32(i) as an off white solid (90 mg, 87%). R$_f$=0.44 (5% MeOH/DCM).

$^1$H NMR (300 MHz, CDCl$_3$) δ 1.18, m, 4H, 1.40, m, 4H, 1.43, s, 18H, 1.69, m, 12H, 3.01, m, 4H, 3.73, s, 6H, 3.87, m, 2H, 4.15, m, 2H, 4.47, m, 2H, 4.53, m, NH; 5.62, d, J=8.2 Hz, NH; 7.19, m, 2H, 7.22, m, 2H, 7.35, m, 2H, 7.45, d, J=9.1 Hz, 2H, 7.91, d, J=8.2 Hz, 2H, 7.99, d, J=8.8 Hz, 2H. MS (ES +ve) m/z 981.5 (30%) [M+K]$^+$; 968.6 (100) [M+Na]$^+$; 943.6 (10) [M+H]$^+$.

Compound 32

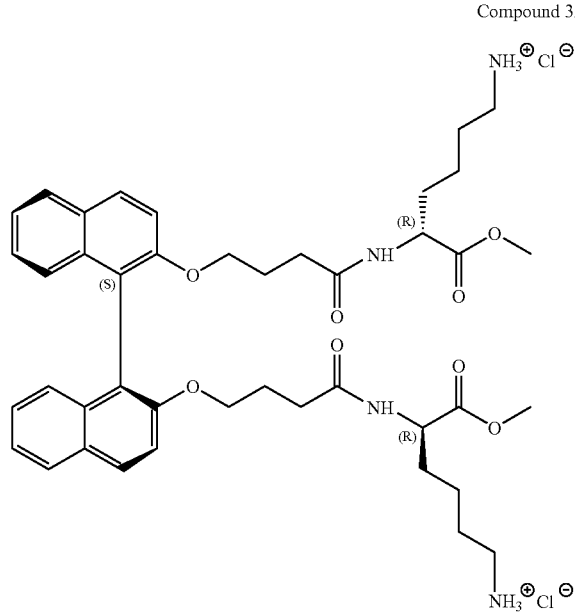

This compound was prepared via Protocol 3, using 32(i) (88 mg, 0.093 mmol) to yield the desired product 32 as an off white solid (50 mg, 76%).

¹H NMR (300 MHz, CD₃OD) δ 1.39, m, 4H, 1.67, m, 12H, 1.96, m, 4H, 2.89, m, 4H, 3.35, s, 6H, 4.02, m, 4H, 4.30, m, 2H, 7.02, dist d; J=8.0 Hz, 2H, 7.17, m, 2H, 7.29, m, 2H, 7.52, m, 2H, 7.87, m, 2H, 7.98, m, 2H. MS (ES +ve) m/z 743.3 (10%) [M+H]⁺; 372.6 (100) [M+2H]²⁺.

Synthesis of Compound 33

33(i)

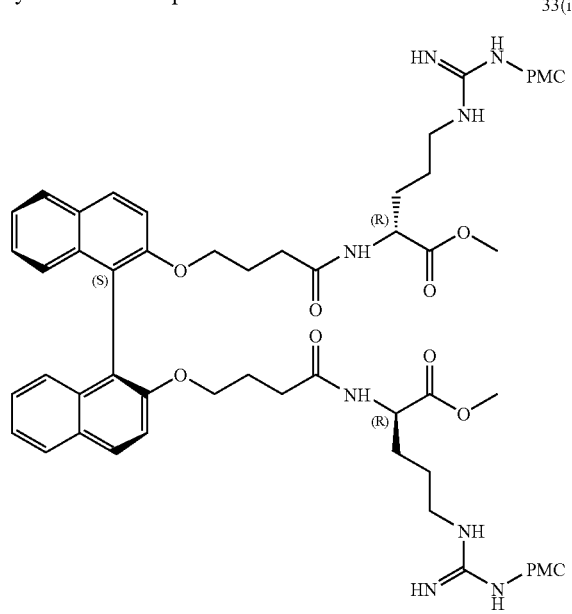

This compound was prepared via Protocol 1, using (D)-arg (Pmc)-OMe (40 mg, 0.088 mmol) and 31(iv) (20 mg, 0.044 mmol) to yield 33(i) as a white solid (18 mg, 31%).

¹H NMR (300 MHz, CDCl₃) δ 1.28, s, 12H, 1.43, m, 4H, 1.77, m, 12H, 1.86, m, 4H, 2.09, s, 6H, 2.52, s, 6H, 2.55, s, 6H, 2.59, m, 2H, 3.12, m, 4H, 3.65, s, 6H, 3.84, m, 2H, 4.01, m, 2H, 4.37, m, 2H, 6.20, br s, NH; 6.42, m, NH; 7.02, dist d, NH; 7.09, d, J=8.3 Hz, 2H, 7.19, dist t, 2H, 7.30, dist t, 2H, 7.39, d, J=9.1 Hz, 2H, 7.85, m, 2H, 7.92, d, J=9.1 Hz, 2H, 7.97, d, NH; 7.99, d, NH.

Compound 33

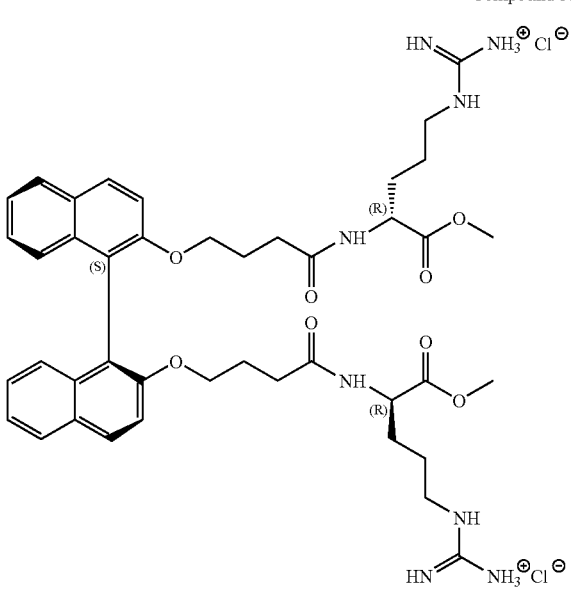

This compound was prepared via Protocol 3, using 33(i) (20 mg, 0.015 mmol) to yield 33 as a white solid (9 mg, 64%).

¹H NMR (300 MHz, CD₃OD) δ 1.34, m, 10H, 1.61, m, 6H, 2.93, m, 4H, 3.46, s, 6H, 3.62, m, 2H, 3.75, m, 2H, 4.05, m, 2H, 6.53, m, 2H, 6.74, m, 4H, 7.16, d, J=8.8 Hz, 2H, 7.42, d, J=7.7 Hz, 2H, 7.57, d, J=8.3 Hz, 2H. MS (ES +ve) m/z: 401 (100%) [M+2H]²⁺.

Synthesis of Compound 34

34(i)

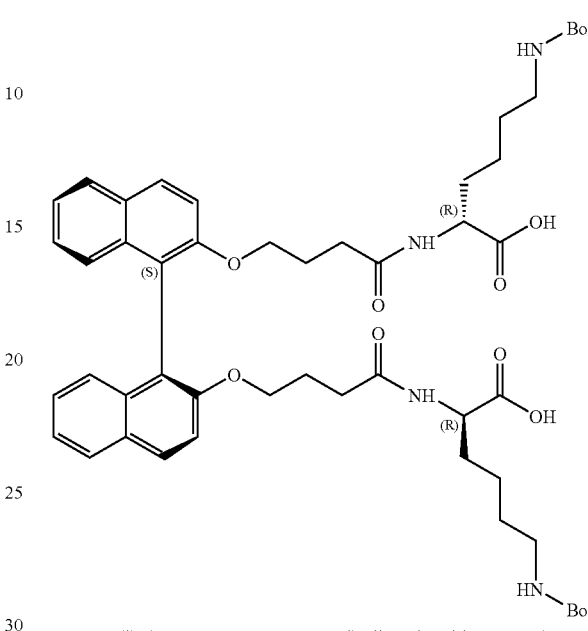

To 32(i) (200 mg, 0.212 mmol) dissolved in THF (20 ml), was added a solution of LiOH (75 mg, 3.14 mmol) in water (10 ml). After stirring at RT for 90 minutes, ethyl acetate was added and the layers separated. The aqueous layer was then acidified with a dilute potassium bisulphate solution. This was then extracted with DCM (3×20 ml) and the combined organic extracts then dried and evaporated to dryness to yield the product 34(i) as a white foamy solid (178 mg, 92%).

¹H NMR (300 MHz, CDCl₃) δ 1.24, m, 4H, 1.40, s, 18H, 1.44, m, 4H, 1.76, m, 12H, 3.00, m, 4H, 3.77, m, 2H, 4.09, m, 2H, 4.46, m, 2H, 4.85, m, NH; 6.29, m, NH; 7.16, m, 2H, 7.21, m, 2H, 7.28, m, 2H, 7.30, d, J=9.0 Hz, 2H, 7.84, d, J=7.8 Hz, 2H, 7.87, d, J=8.7 Hz, 2H. MS (ES +ve) m/z 937.2 (15%) [M+Na]⁺; 915.2 (15) [M+H]⁺. MS (ES −ve) m/z 913.1 (100%) [M−H]⁻.

Compound 34

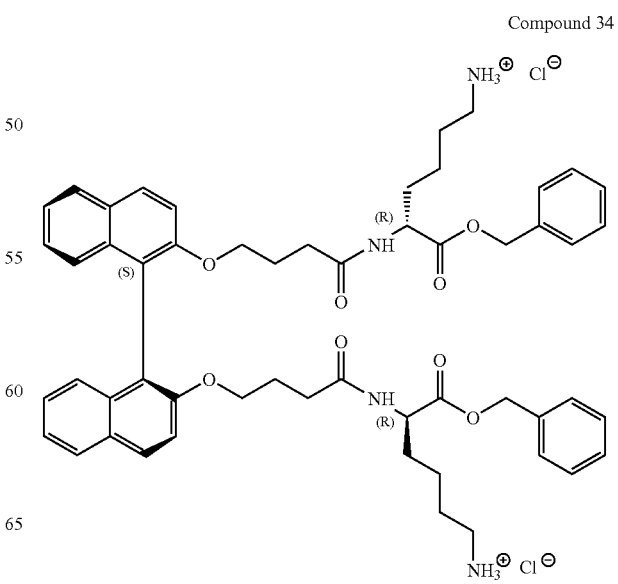

This compound was prepared via Protocol 4, using 34(i) (120 mg, 0.131 mmol), triphenyl phosphine (73 mg, 0.278 mmol), DIAD (0.055 ml, 0.275 mmol) and BzOH (0.05 ml, 0.275 mmol). The BOC-protected intermediate 34(ii) eluted at the same time as a reaction by product, and so this material was then deprotected via protocol 3 to yield the desired product 34 as a pale yellow hydrochloride salt (101 mg, 80%).

$^1$H NMR (300 MHz, CDCl$_3$) δ 1.32, m, 4H, 1.68, m, 10H, 1.79, m, 2H, 1.93, m, 4H, 2.82, m, 4H, 3.97, m, 4H, 4.33, m, 2H, 5.11, ABq, J=12.3 Hz, 4H, 7.01, dist d, J=8.5 Hz, 2H, 7.14, app t, 2H, 7.31, m, 14H, 7.48, m, 2H, 7.62, m, 2H, 7.85, d, J=7.9 Hz, 2H, 7.94, d, J=8.8 Hz, 2H. MS (ES +ve) m/z 895.5 (10%) [M+H]$^+$; 825.4 (40) [M-lys]$^+$; 448.7 (100) [M+2H]$^{2+}$.

Synthesis of Compound 35

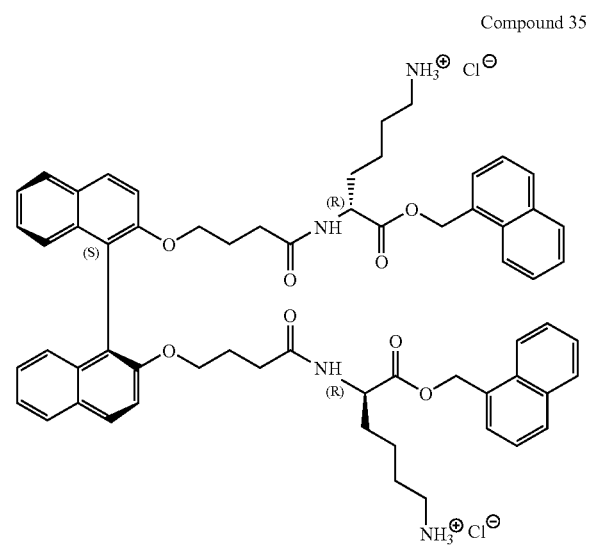

Compound 35

This compound was prepared via Protocol 4, using 34(i) (60 mg, 0.066 mmol), triphenylphosphine (73 mg, 278 mmol), DIAD (0.055 ml, 0.275 mmol) and 1-naphthalene methanol (45 mg, 0.0.28 mmol). The BOC-protected intermediate 35(i) eluted at the same time as a reaction by product, and so this material was then deprotected via Protocol 3 to yield the desired product 35 as a pale yellow hydrochloride salt (58 mg, 83%).

$^1$H NMR (500 MHz, CDCl$_3$) δ 1.10, m, 4H, 1.40, m, 4H, 1.51, m, 4H, 1.63, m, 4H, 1.76, m, 4H, 2.58, m, 4H, 3.73, m, 2H, 3.80, m, 2H, 4.19, m, 2H, 6.90, dist t, 2H, 7.00, t, J=7.1 Hz, 2H, 7.13, dist t, 2H, 7.30, m, 4H, 7.37, m, 6H, 7.38, m, 8H, 7.84, d, J=8.0 Hz; 2H. MS (ES +ve) m/z 995.5 (10%) [M+H]$^+$; 825.4 (40) [M-lys]$^+$; 448.7 (100) [M+2H]$^{2+}$.

Synthesis of Compound 36

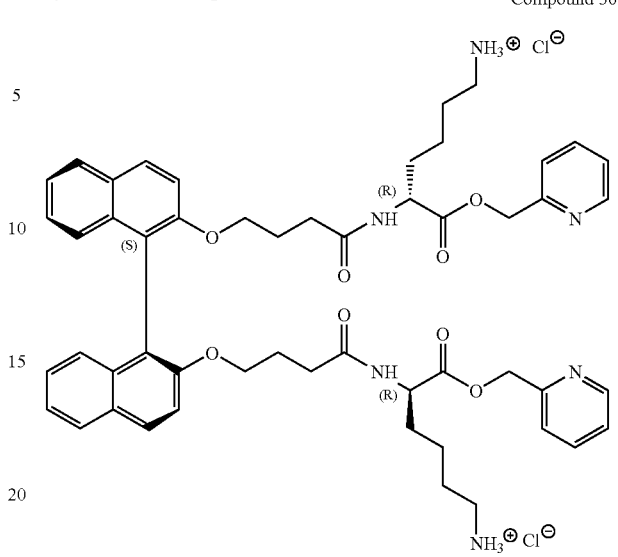

Compound 36

The crude PMC protected precursor 36(i) was prepared via Protocol 1 using 34(i) (120 mg, 0.131 mmol) and 2-pyridyl carbinol (0.026 ml) to yield an impure light brown solid. This was then deprotected via protocol 3 to yield 36 as an off white solid (68 mg, 54%).

$^1$H NMR (300 MHz, CD$_3$OD) δ 1.41, m, 4H, 1.65, m, 8H, 1.95, m, 4H, 2.87, m, 4H, 3.97, m 4H, 4.31, m, 2H, 5.41, ABq, J=14.4 Hz, 2H, 5.52, ABq, J=14.4 Hz, 2H, 6.96, dist d, 2H, 7.14, dist t, 2H, 7.26, dist t, 2H, 7.46, dist d, 2H, 7.83, d, J=7.9 Hz, 2H, 7.92, m, 4H, 8.00, dist d, 2H, 8.47, dist t 2H, 8.76, br d, 2H. MS (ES +ve) m/z 449.4 (100%) [M+2H]$^{2+}$.

Synthesis of Compound 37

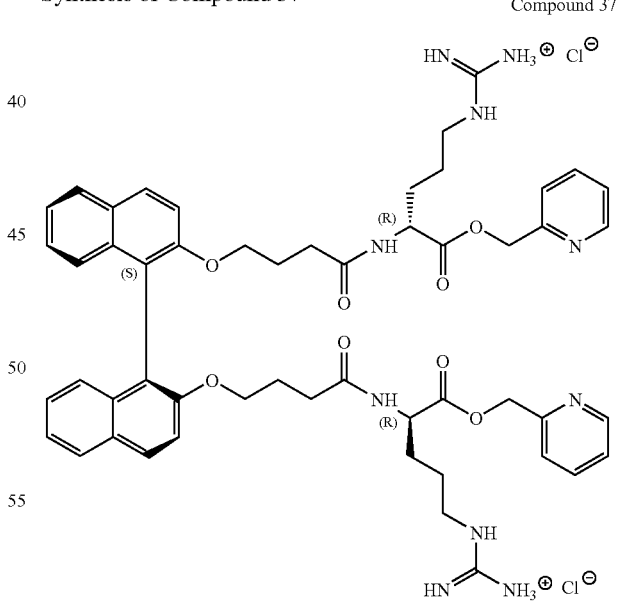

Compound 37

To 33(i) (200 mg, 0.2 mmol) dissolved in THF (20 ml), was added a solution of LiOH (75 mg, 3.1 mmol) in water (10 ml). After stirring at RT for 90 minutes, ethyl acetate was added and the layers separated. The aqueous layer was then acidified with a dilute potassium bisulphate solution. This was then extracted with DCM (3×20 ml) and the combined organic extracts then dried and evaporated to dryness to yield the product 37(i) as a white foamy solid (145 mg, 88%). The protected precursor was prepared via Protocol 1 using 37(i) (60 mg, 0.046 mmol) and 2-pyridyl carbinol (0.02 ml) to yield 37(ii) as an impure light brown solid (MS (ES +ve) m/z 1485.5 (10%) [M+H]$^+$; 743.3 (20) [M+H]$^{2+}$). This was then deprotected via Protocol 3 to yield 37 as an off white solid (28 mg, 64%).

$^1$H NMR (300 MHz, CD$_3$OD) δ 1.69, m, 10H, 2.00, m, 6H, 3.20, m, 4H, 4.00, m, 4H, 4.39, m, 2H, 5.44, ABq, J=14.9 Hz, 2H, 5.53, ABq, J=14.9 Hz, 2H, 6.99, m, 2H, 7.16, m, 2H, 7.28, m, 2H, 7.50, m, 2H, 7.94, m, 8H, 8.47, m, 2H, 8.78, m, 2H. MS (ES +ve) m/z 477.5 (100%) [M+2H]$^{2+}$.

Synthesis of Compound 38

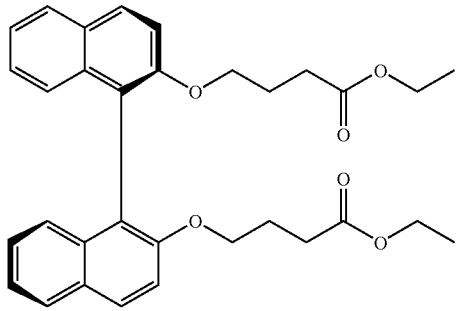

38(i)

To a suspension of (R)-1,1'-binapth-2,2'-ol (1 g, 3.5 mmol) and anhydrous potassium carbonate (2.4 g, 5 equiv) dissolved in acetone (25 ml), was added ethyl bromobutyrate (1.15 ml, 2.3 equivalents) under an N$_2$ atmosphere. The mixture was then heated at reflux for 4 days before being evaporated to dryness and the residue partitioned between ethyl acetate and water. The organic layer was then washed twice with water before being dried and evaporated to dryness. The crude residue was subjected to flash column chromatography to yield the desired compound 38(i) (1.05 g, 68%).

$^1$H NMR (300 MHz, CDCl$_3$) δ 1.15, t, J=7.2 Hz, 6H, 1.70, m, 4H, 1.86, m, 4H, 3.98, m, 8H, 7.16, m, 4H, 7.27, m, 2H, 7.38, d, J=9.1 Hz, 2H, 7.82, d, J=8.2 Hz, 2H, 7.90, d, J=9.1 Hz, 2H.

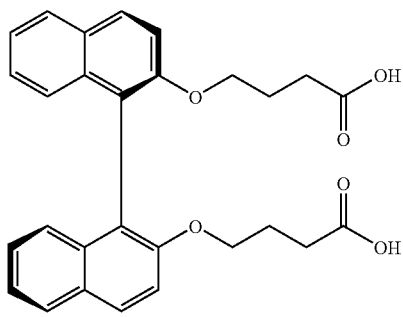

38(ii)

To 38(i) (1.0 g, 1.94 mmol) dissolved in THF (30 ml), was added a solution of LiOH (300 mg, 12.5 mmol) in water (20 ml), After stirring at RT overnight, diethyl ether was added and the layers separated. The aqueous layer was then acidified with a dilute HCl solution. This was then extracted with diethyl ether (3×20 ml), the combined organic extracts were then dried and evaporated to dryness to yield 38(ii) as a white foamy solid (646 mg, 89%).

$^1$H NMR (300 MHz, CDCl$_3$) δ 1.71, m, 4H, 1.90, m, 4H, 3.91, m, 2H, 3.99, m, 2H, 7.11, dist d, J=8.3 Hz, 2H, 7.18, m, 2H, 7.27, m, 2H, 7.37, d, J=8.8 Hz, 2H, 7.83, d, J=8.0 Hz, 2H, 7.90, d, J=8.8 Hz, 2H, 9.34, bs s, COOH.

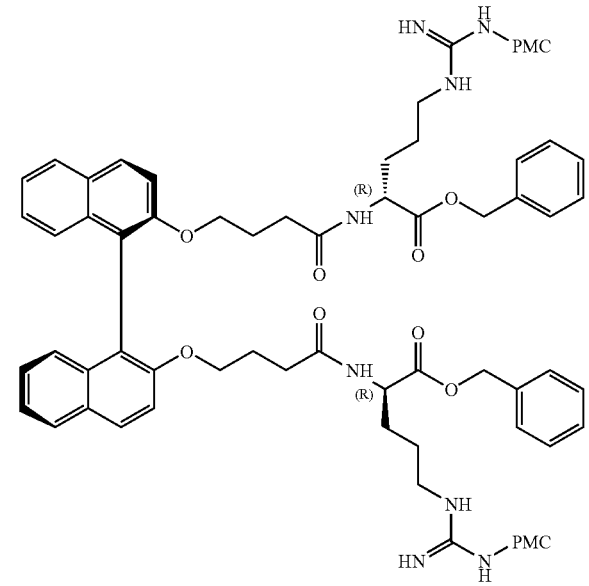

38(iii)

This compound was prepared via Protocol 1, using 31(ii) (125 mg, 0.236 mmol) and 38(ii) (45 mg, 0.098 mmol) to yield 38(iii) as a white solid (123 mg, 86%).

$^1$H NMR (300 MHz, CDCl$_3$) δ 1.25, s, 12H, 1.34, m, 4H, 1.70, m, 16H, 2.06, s, 6H, 2.51, m, 16H, 3.04, m, 4H, 3.79, m, 2H, 3.96, m, 2H, 4.37, m, 2H, 5.04, s, 4H, 6.05, br s, NH; 6.21, br s, NH; 7.06, d, J=8.5 Hz, 2H, 7.15, dist t, 2H, 7.25, m, 12H, 7.32, d, J=9.1 Hz; 2H, 7.79, d, J=7.9 Hz, 2H, 7.87, d, J=9.1 Hz, 2H. MS (ES +ve) m/z 1483.4 (10%) [M+H]$^+$; 742.4 (20) [M+H]$^{2+}$.

Compound 38

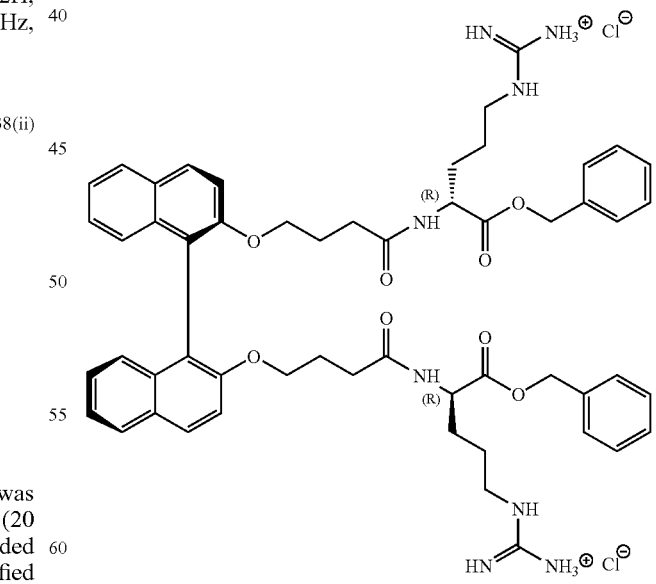

This compound was prepared via Protocol 3, using 38(iii) (120 mg, 0.081 mmol) to yield 38 as a white solid (71 mg, 86%).

$^1$H NMR (300 MHz, CD$_3$OD) δ 1.56, m, 4H, 1.67, m, 6H, 1.83, m, 2H, 1.93, m, 4H, 3.12, m, 4H, 3.93, m, 2H, 4.02, m, 2H, 4.34, m, 2H, 5.07, ABq, J=12.3 Hz, 2H, 5.12, ABq, J=12.3 Hz, 2H, 7.00, m, 2H, 7.12, m, 2H, 7.27, m, 12H, 7.46, m, 2H, 7.83, d, J=7.9 Hz, 2H, 7.93, d, J=9.1 Hz, 2H. MS (ES +ve) m/z 476.5 (100%) [M+H]$^{2+}$.

Synthesis of Compound 39

39(i)

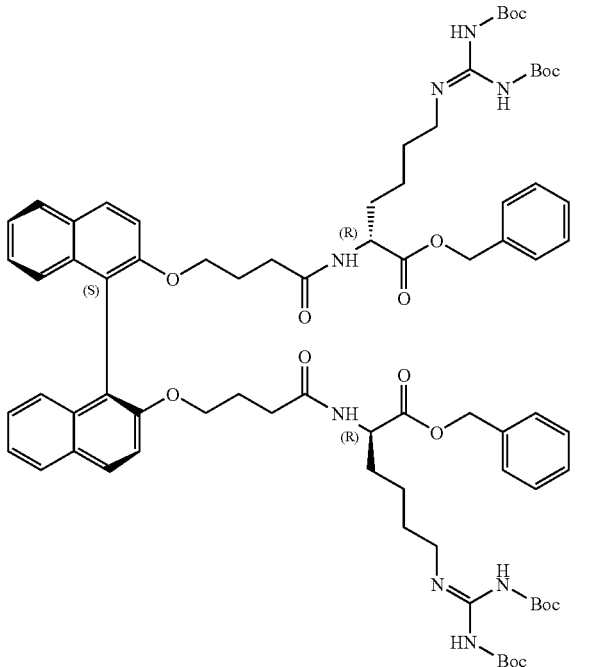

To 34 (20 mg, 0.021 mmol) in DCM (2 ml) was added triethylamine (0.09 ml) and N,N'-bis(tert-butoxycarbonyl)-N"-triflyl guanadine (25 mg, 0.062 mmol) under N$_2$. The solution was allowed to stir overnight before being evaporated to dryness. The resultant residue was then subjected to flash column chromatography (over silica), using 2% MeOH/DCM as the eluant to yield the desired compound 39(i) as a pale yellow oil (23 mg, 79%).

$^1$H NMR (300 MHz, CDCl$_3$) δ 1.18, m, 4H, 1.48, m, 40H, 1.59, m, 4H, 1.70, m, 8H, 3.27, m, 4H, 3.82, m, 2H, 4.09, m, 2H, 4.45, m, 2H, 5.15, ABq, J=12.3 Hz, 4H, 5.54, d, J=8.2 Hz, NH; 7.16, dist d, J=8.2 Hz, 2H, 7.24, m, 2H, 7.31, m, 11H; 7.49, m, 1H, 7.62, m, 2H, 7.87, d, J=7.9 Hz, 2H, 7.94, d, J=9.1 Hz, 2H, 8.28, m, NH. MS (ES +ve) m/z 1401.7 (40%) [M+Na]$^+$; 1379 (100) [M+H]$^+$.

Compound 39

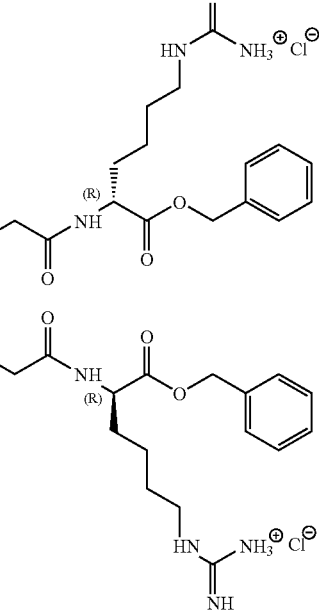

This compound was prepared via Protocol 3, using 39(i) (20 mg, 0.014 mmol) to yield the desired product 39 as a light brown solid (15 mg, 86%).

$^1$H NMR (300 MHz, CDCl$_3$) δ 1.18, m, 4H, 1.48, m, 40H, 1.59, m, 4H, 1.70, m, 8H, 3.27, m, 4H, 3.82, m, 2H, 4.09, m, 2H, 4.45, m, 2H, 5.15, ABq, J=12.3 Hz, 4H, 5.54, d, J=8.2 Hz, NH; 7.16, dist d, J=8.2 Hz, 2H, 7.24, m, 2H, 7.31, m, 11H, 7.49, m, 1H, 7.62, m, 2H, 7.87, d, J=7.9 Hz, 2H, 7.94, d, J=9.1 Hz, 2H, 8.28, m, NH. MS (ES +ve) m/z 490.5 (60%) [M+2H]$^{2+}$; 452.4 (100) [M+H-Ph]$^{2+}$; 414.5 (80) [M+2H-2Ph]$^{2+}$.

Synthesis of Compound 40

40(i)

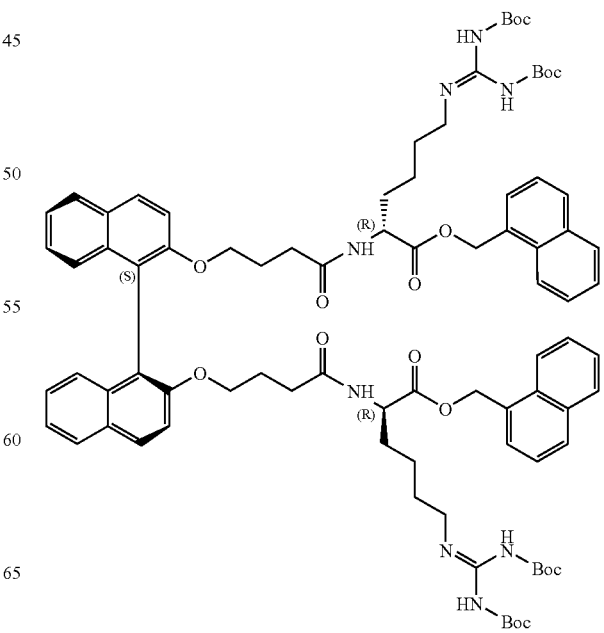

To 35 (47 mg, 0.044 mmol) in DCM (2 ml) was added triethylamine (0.19 ml) and N,N'-bis(tert-butoxycarbonyl)-N''-triflylguanadine (53 mg, 0.13 mmol) under N2. The solution was allowed to stir overnight before being evaporated to dryness. The resultant residue was then subjected to flash column chromatography (over silica), eluting with 2% MeOH/DCM to yield the desired compound 40(i) as an off white solid (40 mg, 61%).

$^1$H NMR (300 MHz, CDCl$_3$) δ 1.01, m, 2H, 1.32, m, 2H, 1.48, m, 44H, 1.54, m, 4H, 1.70, m, 8H, 3.14, m, 4H, 3.73, m, 2H, 4.00, m, 2H, 4.42, m, 2H, 5.51, d, J=7.9 Hz, NH; 5.61, ABq, J=12.3 Hz, 4H, 7.12, dist d, J=7.9 Hz, 2H, 7.26, m, 6H, 7.53, m, 8H, 7.80, m, 4H, 7.88, m, 4H, 7.97, dist d, J=7.9 Hz, 2H, 8.24, m, NH. MS (ES +ve) m/z 1501.8 (10%) [M+Na]$^+$; 1479.7 (10) [M+H]$^+$; 740.5 (20) [M+2H]$^{2+}$.

Compound 40

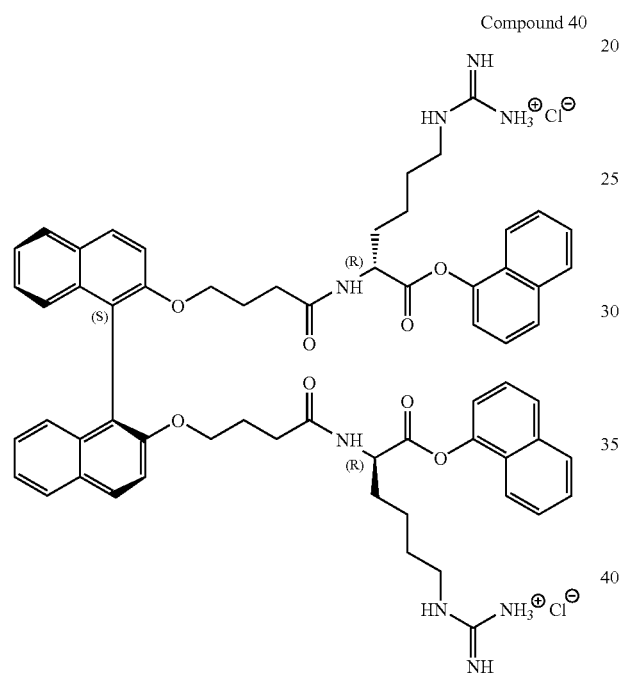

This compound was prepared via Protocol 3, using 40(i) (38 mg, 0.026 mmol) to yield the desired product 40 as a light brown solid (18 mg, 61%).

$^1$H NMR (300 MHz, CDCl$_3$) δ 1.32, m, 6H, 1.62, m, 10H; 1.92, m, 4H, 2.95, m, 2H, 3.10, m, 2H, 3.97, m, 4H, 4.30, m, 2H, 5.57, m, 4H, 7.02, m, 2H, 7.17, m, 2H, 7.229, m, 2H, 7.50, m, 10H, 7.88, m, 10H. MS (ES +ve) m/z 540.4 (20%) [M+2H]$^{2+}$; 477.3 (95) [M+H-nap]$^{2+}$; 414.4 (100) [M+H-2nap]$^{2+}$.

Compounds of Formula III

General Synthetic Scheme (Example - Compound 41)

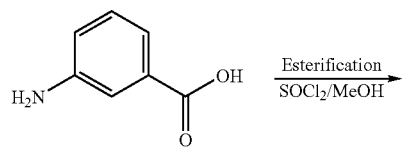

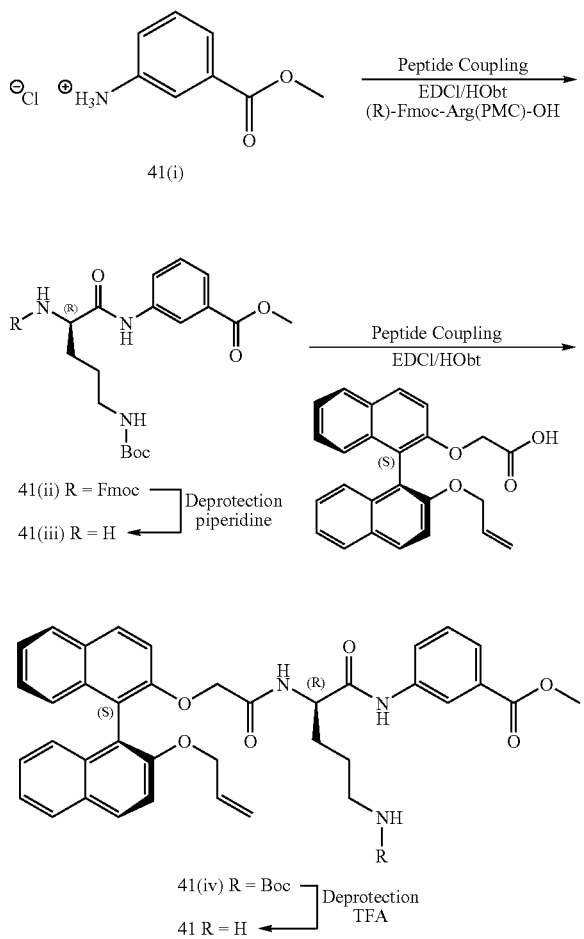

Synthesis of Compound 41

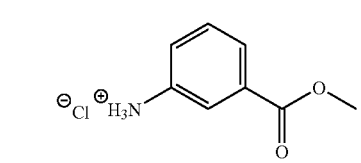

To a suspension of 3-aminobenzoic acid (1.03 g mg, 7.52 mmol) in MeOH (80 ml) at 0° C. was added dropwise thionyl chloride (5 ml). The resulting solution was allowed to stir for 16 h before the solvent was removed by evaporation and the product precipitated with diethyl ether. The diethyl ether was removed by evaporation to yield the title compound 41(i) as a white solid (1.38 g, 98%). Mp 176-178° C.

$^1$H NMR (300 MHz, D$_2$O) δ 3.66, s, 3H, 7.37, m, 1H, 7.42, m, 1H, 7.71, m, 1H, 7.75, dt, J=1.8, 3.3, 7.2 Hz, 1H. MS (CI) m/z 152 (100%) [M]$^+$.

41(ii)

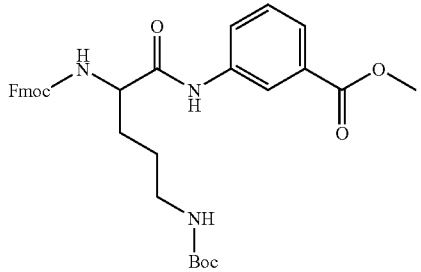

This compound was prepared via Protocol 1, from 41(i) (220 mg, 2.27 mmol) and (R)-Fmoc-Lys(Boc)-OH (578 mg, 1.27 mmol) to afford 41(ii) as a white solid (277 mg, 36%). Mp 96-98° C.

$^1$H NMR (300 MHz, CDCl$_3$) δ 1.42, s, 9H, 1.60, m, 2H, 1.78, m, 2H, 3.08, m, 2H, 3.86, s, 3H, 4.17, t, J=6.9 Hz, 1H, 4.36, d, J=6.9 Hz, 2H, 4.63, m, 1H, 6.03, d, J=8.1 Hz, 2H, 7.26, m, 2H, 7.36, m, 2H, 7.56, d, J=7.2, Hz, 2H, 7.72, d, J=7.8 Hz, 2H, 7.77, m, 1H, 7.88, d, J=8.1 Hz, 1H, 8.17, s, 1H, 9.15, s, 1H. MS (ES +ve) m/z 610 (100%) [M+Na]$^+$; 588 (70) [M+H]$^+$.

41(iii)

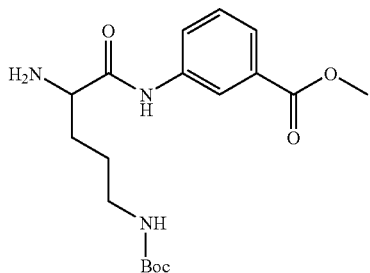

This compound was prepared via Protocol 2, from 41(ii) (555 mg, 0.95 mmol) to yield 41(iii) as a colourless viscous oil (285 mg, 82%).

$^1$H NMR (300 MHz, CDCl$_3$) δ 1.43, s, 9H, 1.65, m, 4H, 2.08, m, 2H, 3.19, m, 2H, 3.69, m, 1H, 3.91, s, 3H, 5.11, m, 1H, 7.36, m, 1H, 7.51, t, J=7.8 Hz, 1H, 7.84, t, J=1.8 Hz, 1H, 8.04, m, 1H. MS (ES +ve) m/z 264 (100%) [M-Boc+H]$^+$.

41(iv)

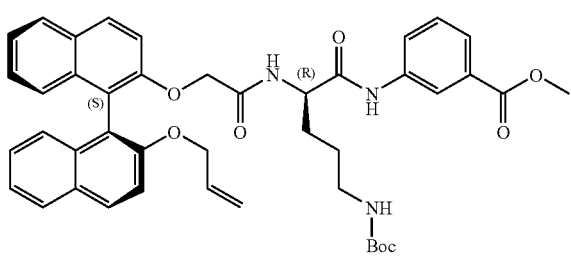

This compound was prepared via Protocol 1, from 22(ii) (288 mg, 0.75 mmol) and 41(iii) (275 mg, 0.75 mmol) to afford 41(iv) as a white foam (434 mg, 79%). Mp 70° C.

$^1$H NMR (300 MHz, CDCl$_3$) δ 1.04, m, 2H, 1.44, s, 9H, 1.62, m, 2H, 2.96, m, 2H, 3.87, s, 3H, 4.55, m, 5H, 4.94, m, 2H, 5.69, m, 1H, 6.45, d, J=8.1 Hz, 1H, 7.85, m, 8H, 7.91, m, 7H, 9.08, s, 1H. MS (ES +ve) m/z 732 (50%) [M+H]$^+$; 351 (100).

Compound 41

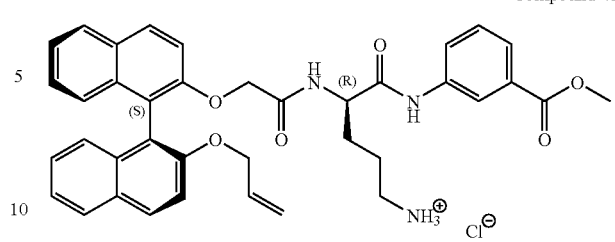

This compound was prepared via Protocol 3, from 41(iv) (56 mg, 0.077 mmol) to yield 41 as a highly hydroscopic cream solid (38 mg, 74%).

$^1$H NMR (300 MHz, CD$_3$OD) δ 1.30, m, 2H, 1.67, m, 2H, 2.76, m, 2H, 3.93, s, 3H, 4.59, m, 5H, 4.90, m, 2H, 5.71, m, 1H, 7.06, m, 2H, 7.34, m, 8H, 7.75, m, 2H, 7.92, m, 2H, 8.02, m, 2H. MS (ES +ve) m/z 632 (100%) [M]$^+$.

Synthesis of Compound 42

42(i)

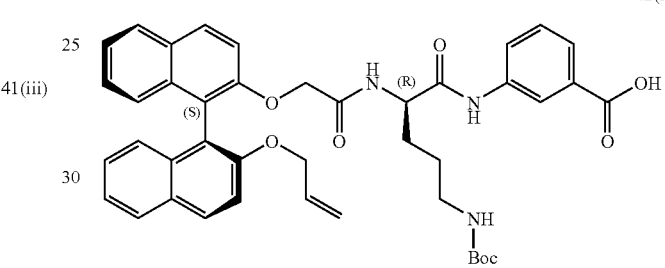

To a solution of 41(iv) (370 mg, 0.51 mmol) in THF/water, 3:1 (8 ml) was added lithium hydroxide monohydrate (43 mg, 0.51 mmol) and the resulting suspension was allowed to stir for 16 h. The reaction mixture was diluted with water (30 ml) and the THF was removed by evaporation before the remaining aqueous layer was washed with diethyl ether (40 ml) to remove unreacted starting material. The aqueous phase was acidified with dilute potassium bisulfate and the resulting precipitate was extracted with DCM (3×40 ml). The combined DCM fractions were dried and evaporated to yield the title compound 42(i) as a white solid (350 mg, 96%). Mp 86-90° C.

$^1$H NMR (300 MHz, CDCl$_3$) δ 1.15, m, 2H, 1.49, s, 9H, 1.65, m, 2H, 3.03, m, 2H, 4.59, m, 5H, 5.01, m, 2H, 5.71, m, 1H, 6.63, d, J=9.0 Hz, 1H, 7.34, m, 8H, 7.97, m, 7H, 9.26, s, 1H, 9.70, br s, 1H. MS (ES +ve) m/z 740 (100%) [M+Na]$^+$; 718 (20) [M+H]$^+$.

42(ii)

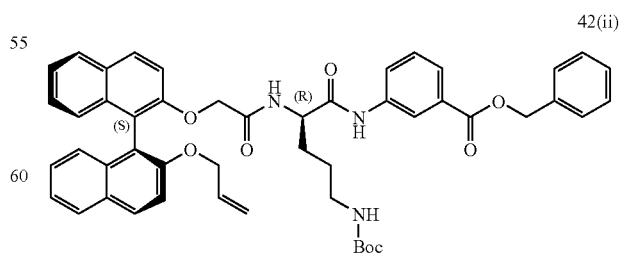

To a solution of 42(i) (40 mg, 0.056 mmol) in acetone (2 ml) was added K$_2$CO$_3$ (17 mg, 0.12 mmol) and benzyl bromide (21 mg, 0.12 mmol). The resulting suspension was allowed to stir for 16 h before concentration and purification by flash column chromatography (5% MeOH/DCM) to yield the title compound 42(ii) as a white solid (36 mg, 80%). Mp 145-152° C.

¹H NMR (300 MHz, CDCl₃) δ 1.05, m, 2H, 1.42, s, 9H, 1.52, m, 2H, 3.00, m, 2H, 4.50, m, 5H, 4.87, m, 2H, 5.30, s, 2H, 5.68, m, 1H, 6.27, d, J=8.4 Hz, 1H, 7.30, m, 11H; 7.90, m, 7H, 8.63, s, 1H. MS (ES +ve) m/z 808 (30%) [M+H]⁺; 414 (100%).

This compound was prepared via Protocol 3, from 43(i) (73 mg, 0.089 mmol) to yield 43 as a hydroscopic white solid (67 mg, 99%).

¹H NMR (500 MHz, CD₃OD) δ 1.15, m, 2H, 1.62, m, 2H, 3.23, m, 2H, 3.90, m, 1H, 4.46, m, 6H, 4.90, m, 2H, 5.63, m, 1H, 7.50, m, 20H. MS (ES +ve) m/z 723 (20%) [M]⁺; 360 (100%).

Synthesis of Compound 44

Compound 42

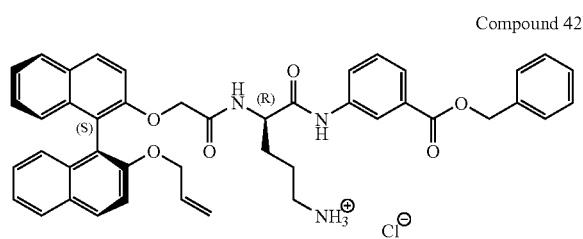

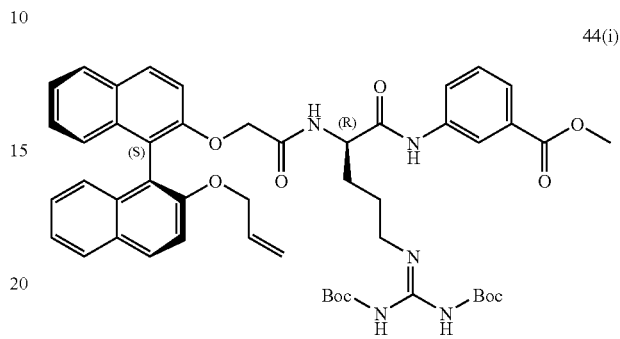

44(i)

This compound was prepared via Protocol 3, from 42(ii) (35 mg, 0.043 mmol) to yield 42 as a highly hydroscopic cream solid (30 mg, 93%).

¹H NMR (500 MHz, CD₃OD) δ 1.22, m, 2H, 1.59, m, 2H, 2.68, m, 2H, 4.46, m, 5H, 4.79, m, 2H, 5.27, s, 2H, 5.58, m, 1H, 7.28, m, 11H; 7.80, m, 7H, 8.25, s, 1H. MS (ES +ve) m/z 750 (35%) [M+K]⁺; 360 (100%).

Synthesis of Compound 43

To a solution of 41 (32 mg, 0.048 mmol) in DCM (3 ml) was added N1-tert-butoxycarboxamido(trifluoromethylsulfonylimino)methyl propanamide (28 mg, 0.072 mmol), triethylamine (7.3 mg, 0.072 mmol). The resulting solution was allowed to stir for 16 h under a nitrogen atmosphere. The solvent was evaporated and the crude product was purified by 43(i)

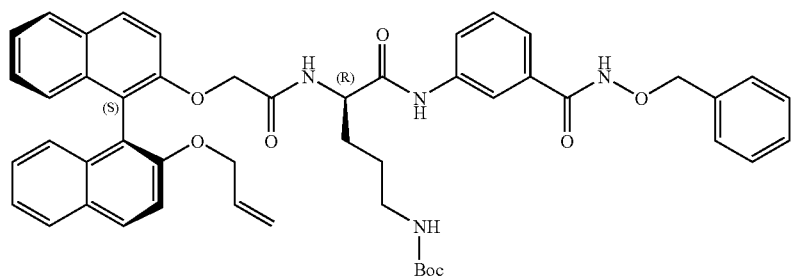

This compound was prepared via Protocol 1, from 42(i) (91 mg, 0.127 mmol) and O-benzylhydroxylamine (20 mg, 1.27 mmol) to afford 43(i) as a white solid (82 mg, 78%). Mp 141-144° C.

¹H NMR (300 MHz, CDCl₃) δ 1.06, m, 2H, 1.43, s, 9H, 1.54, m, 2H, 2.93, m, 2H, 4.30, m, 1H, 4.54, m, 4H, 4.66, t, J=5.1 Hz, 1H, 4.95, m, 4H, 5.66, m, 1H, 6.41, d, J=7.5 Hz, 1H, 7.31, m, 10H, 7.88, m, 2H, 7.97, m, 2H, 9.14, s, 1H. MS (ES +ve) m/z 823 (100%) [M+H]⁺.

flash column chromatography (15:1, DCM/MeOH) to yield the title compound 44(i) as a white solid (41 mg, 98%). Mp 74-76° C.

¹H NMR (300 MHz, CDCl₃) δ 1.14, m, 2H, 1.46, s, 9H, 1.51, s, 9H, 1.65, m, 2H, 3.26, m, 2H, 3.91, s, 3H, 4.34, m, 1H, 4.48, m, 2H, 4.57, d, J=3.3 Hz, 2H, 4.67, m, 2H, 5.59, m, 1H, 6.34, d, J=8.4 Hz, 1H, 7.26, m, 8H, 7.77, m, 7H, 8.27, br s, 1H, 8.55, s, 1H. MS (ES +ve) m/z 896 (100%) [M+Na]⁺; 875 (95%) [M+H]⁺.

Compound 43

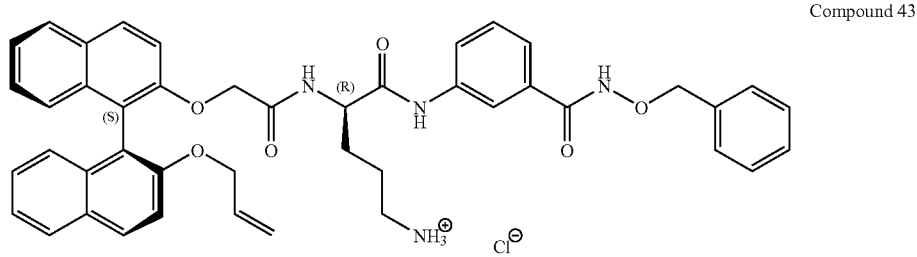

Compound 44

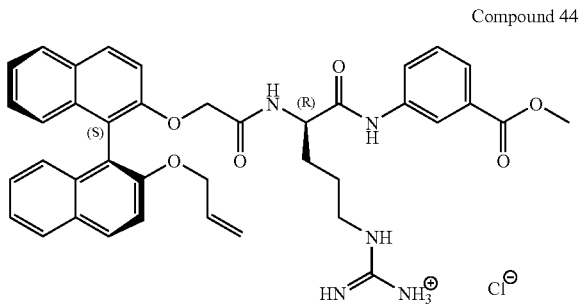

This compound was prepared via Protocol 3, from 44(i) (49 mg, 0.056 mmol) to yield 44 as a cream solid (32 mg, 0.045 mmol, 80%). Mp 124-126° C.

$^1$H NMR (300 MHz, CD$_3$OD) δ 1.17, m, 2H, 1.63, m, 2H, 3.01, m, 2H, 3.92, s, 3H, 4.52, m, 5H, 4.97, m, 2H, 5.73, m, 1H, 7.07, m, 2H; 7.32, m, 9H, 7.90, m, 4H, 8.28, s, 1H. MS (ES +ve) m/z 698 (25%) [M+Na]$^+$; 413 (100%).

Synthesis of Compound 45

45(i)

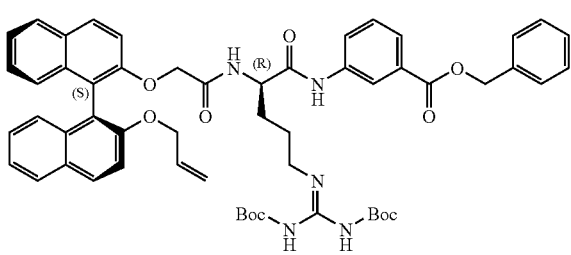

To a solution of 42 (20 mg, 0.027 mmol) in DCM (2 ml) was added N1-tert-butoxycarboxamido(trifluoromethylsulfonylimino)methyl propanamide (16 mg, 0.041 mmol), and triethylamine (4 mg, 0.041 mmol). The resulting solution was allowed to stir for 16 h under N$_2$. The solvent was evaporated and the crude product was purified by flash column chromatography (15:1, DCM/MeOH) to yield the title compound 45(i) as a white solid (15 mg, 58%). Mp 122-126° C.

$^1$H NMR (300 MHz, CDCl$_3$) δ 1.15, m, 2H, 1.46, s, 9H, 1.50, s, 9H, 1.63, m, 2H, 3.25, m, 2H, 4.32, m, 1H, 4.45, m, 2H, 4.56, m, 2H, 4.85, m, 2H, 5.37, s, 2H, 5.56, m, 1H, 6.31, d, J=8.1 Hz, 1H, 7.32, m, 8H, 7.85, m, 7H, 8.26, br s, 1H, 8.41, s, 1H. MS (ES +ve) m/z 950 (100%) [M+H]$^+$.

Compound 45

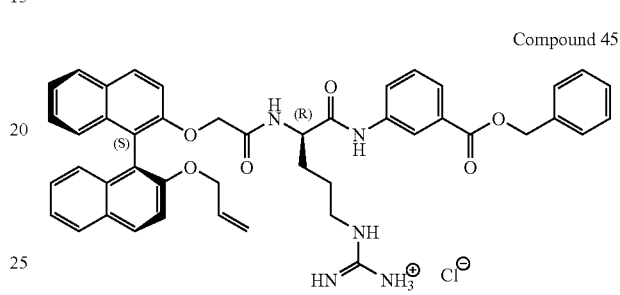

This compound was prepared via Protocol 3, from 45(i) (15 mg, 0.016 mmol) to yield 45 as a highly hydroscopic cream solid (6 mg, 48%).

$^1$H NMR (500 MHz, CD$_3$OD) δ 1.08, m, 2H, 1.54, m, 2H, 2.92, m, 2H, 4.28, dd, J=5.0, 7.0 Hz, 1H, 4.47, m, 4H, 4.80, m, 2H, 5.27, s, 2H, 5.59, m, 1H, 7.25, m, 13H, 7.79, m, 7H, 8.22, s, 1H. MS (ES +ve) m/z 750 (100%) [M]$^+$.

Synthesis of Compound 46

46(i)

To a solution of 43 (51 mg, 0.067 mmol) in DCM (3 ml) was added N1-tert-butoxycarboxamido(trifluoromethylsulfonylimino)methyl propanamide (39 mg, 0.10 mmol), and triethylamine (0.1 ml). The resulting solution was allowed to stir for 16 hr under N$_2$. The solvent was evaporated and the crude product was purified by flash column chromatography (15:1, DCM/MeOH) to yield the title compound 46(i) as a white solid (58 mg, 90%). Mp 112° C.

$^1$H NMR (300 MHz, CDCl$_3$) δ 1.10, m, 2H, 1.44, s, 9H, 1.50, s, 9H, 1.65, m, 2H, 3.23, m, 2H, 4.25, m, 1H, 4.51, m, 4H, 4.89, m, 2H, 5.00, s, 2H, 5.63, m, 1H, 6.34, d, J=7.5 Hz, 1H, 7.31, m, 16H, 7.90, m, 4H, 8.25, br s, 1H, 9.05, s, 1H. MS (ES +ve) m/z 987 (100%) [M+Na]$^+$; 965 (90%) [M+H]$^+$.

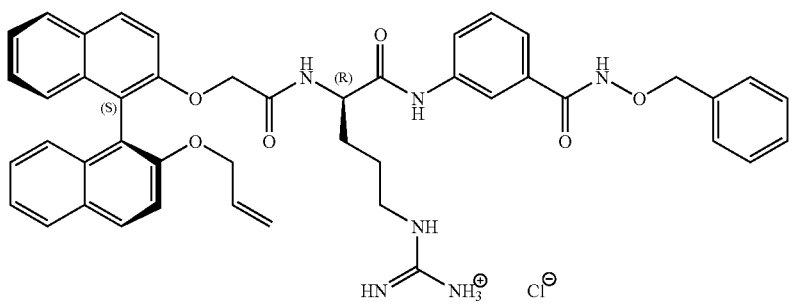

Compound 46

This compound was prepared via Protocol 3, from 46(i) (16 mg, 0.017 mmol) to yield 46 as a cream solid (7 mg, 51%). Mp 142-C.

$^1$H NMR (300 MHz, CD$_3$OD) δ 1.20, m, 2H, 1.66, m, 2H, 3.04, m, 2H, 3.97, m, 1H, 4.49, m, 6H, 4.96, m, 2H, 5.60, m, 1H, 7.33, m, 16H, 7.95, m, 4H. MS (ES +ve) m/z 765 (20%) [M]$^+$; 102 (100).

Synthesis of Compound 47

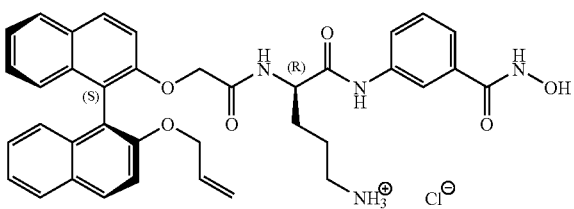

Compound 47

To a solution of 43(i) (28 mg, 0.034 mmol) in THF (3 ml) was added palladium on activated carbon (15 mg). The resulting mixture was flushed with hydrogen gas and allowed to stir for 16 h. The mixture was filtered through celite and evaporated to dryness. This intermediate product was then subjected to the Protocol 3 to yield the title compound 47 as a white solid (16 mg, 70%). Mp 116° C.

$^1$H NMR (500 MHz, CD$_3$OD) δ 0.76, m, 3H, 1.35, m, 4H, 1.67, m, 2H, 3.66, m, 2H, 3.88, m, 2H, 4.08, m, 1H, 4.56, m, 2H, 7.30, m, 9H, 7.89, m, 5H. MS (ES +ve) m/z 636 (50%) [M]$^+$; 623 (100).

Synthesis of Compound 48

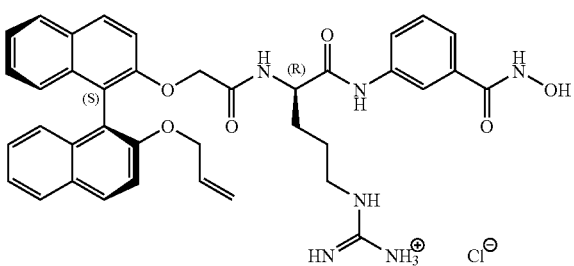

Compound 48

To a solution of 46(i) (39 mg, 0.040 mmol) in THF (3 ml) was added palladium on activated carbon. The resulting mixture was flushed with hydrogen gas and allowed to stir for 16 h. The mixture was filtered through celite and evaporated to dryness. This intermediate product was then subjected to Protocol 3 to yield the title compound 48 as a white solid (24 mg, 84%). Mp 158-160° C.

$^1$H NMR (300 MHz, CD$_3$OD) δ 0.51, t, J=7.2 Hz, 3H, 1.17, m, 2H, 1.40, m, 2H, 1.62, m, 2H, 3.03, m, 2H, 3.92, m, 2H, 4.09, m, 1H, 4.45, ABq, J=14.1 Hz, 2H, 7.24, m, 9H, 7.95, m, 5H, 9.96, br s, 1H. MS (ES +ve) m/z 677 (100%) [M]$^+$.

Activity

Antibacterial Assay Method for *Staphylococcus aureus* (ATCC 6538P) and *Enterococcus faecium*

Bacterial Strains:

*Staphylococcus aureus* (ATCC 6538P)

*Enterococcus faecium*

VRE strains: #243 *E. faecium* van B ST17 #449 *E. faecium* van B ST17

820 *E. faecium* van A ST17 #987 *E. faecium* van B ST39

The *S. aureus* assay is performed in the PC2 lab and the *E. faecium* assay is performed in the PC3 lab.

Compound Preparation:

Compounds are accurately weighed out (between approx. 1-2 mg) and dissolved in either 10% methanol/water (v/v) or 100% DMSO to a final stock concentration of 5 mg/ml.

Compounds are then diluted 1/10 in H$_2$O to a test conc of 500 ug/ml ready for immediate use, or storage at −20° C.

Starter Culture:

Grow up an o/n starter culture of *Staphylococcus aureus* and each VRE strain by diluting previous culture (stored at 4° C.) 1/1000 into ~50 mls Luria Broth (LB) for *S. aureus* or Enterococossel Broth (EB) for the VRE strains.

Incubate o/n at 37° C.+shaking.

A glycerol stock (0.6 mls bacterial culture, 0.3 mls glycerol) of each strain is kept at −80° C. if needed.

Assay Set Up:

In a 96well round bottom plate add 50 ul LB/well for the *S. aureus* plate and add 50 ul EB/well for the VRE plates.

Add 50 ul of compound dilution (500 ug/ml test conc) to each of three top row wells (ie: tested in triplicate) and dilute 1 in 2 from the top row to the bottom row.

After the compound dilution, add to each well 50 ul of a 1/1000 dilution of the appropriate overnight bacterial culture, either *S. aureus* or the different VRE strains.

Plates are incubated at 37° C. on a slowly rotating plate incubator.

test concentrations are (in ug/ml) 125, 62.5, 31.25, 15.6, 7.8, 3.9, 1.9, 0.98 final DMSO concentration in the first row of wells of the assay is 2.5%

Vancomycin is included in the assay (in triplicate) at a starting test concentration of 5 ug/ml for *S. aureus* and 125 ug/ml for the VRE strains Reading Results of Assay:

After incubation for 24 hrs the plates are removed and read. Inhibition of bacterial growth is indicated by lack of bacterial pellet or a clear well. In the VRE plates bacterial growth is indicated by black coloured media (EB) as well as a bacterial pellet.

Untreated control wells are included in the assay to check they all contain bacterial pellets. Uninoculated untreated control wells are included to check they all contain clear medium.

The plates are analysed for MIC and the results tabulated. Antibacterial Assay Results for *Staphylococcus Aureus* (ATCC 6538P) and *Enterococcus faecium*

Activity for Compounds was determined in the assays described. The minimum inhibitory concentration (μg/ml) was determined to be in a given range if at least two of three values fell within that range.

MIC of the compound in the range of less than 0.98 (μg/ml) is designated in the table by ++++

MIC of the compound in the range of greater than or equal to 0.99 (μg/ml) and less than or equal to 15.6 (μg/ml) is designated in the table by +++

MIC of the compound in the range of greater than or equal to 15.7 (μg/ml) and less than or equal 62.5 (μg/ml) is designated in the table by ++

MIC of the compound in the range of greater than or equal to 62.6 (μg/ml) is designated in the table by +

| Compound | Sa | 243 | 449 | 820 | 987 |
|---|---|---|---|---|---|
| Van | +++ | ++++ | ++ | + | ++++ |
| 1 | +++ | ++ | ++ | +++ | ++ |
| 2 | +++ | ++ | ++ | ++ | ++ |
| 3 | +++ | ++ | ++ | ++ | ++ |
| 4 | +++ | ++ | ++ | ++ | ++ |
| 5 | +++ | ++ | ++ | ++ | ++ |
| 6 | +++ | ++ | ++ | ++ | ++ |
| 7 | +++ | ++ | ++ | ++ | ++ |
| 8 | ++ | + | + | + | + |
| 9 | +++ | + | ++ | ++ | ++ |
| 10 | +++ | ++ | ++ | ++ | ++ |
| 11 | +++ | ++ | ++ | ++ | ++ |
| 12 | +++ | ++ | +++ | ++ | ++ |
| 13 | +++ | ++ | ++ | ++ | ++ |
| 14 | +++ | ++ | ++ | ++ | + |
| 15 | +++ | ++ | ++ | ++ | ++ |
| 16 | +++ | + | + | + | + |
| 17 | ++++ | ++ | ++ | ++ | ++ |
| 18 | +++ | ++ | ++ | ++ | ++ |
| 19 | +++ | ++ | ++ | ++ | ++ |
| 20 | +++ | ++ | ++ | ++ | ++ |
| 21 | +++ | ++ | ++ | ++ | ++ |
| 22 | +++ | ++ | ++ | ++ | ++ |
| 23 | +++ | ++ | ++ | ++ | ++ |
| 24 | +++ | ++ | ++ | ++ | ++ |
| 25 | +++ | ++ | ++ | ++ | ++ |
| 26 | +++ | ++ | ++ | ++ | ++ |
| 27 | +++ | ++ | ++ | ++ | + |
| 28 | +++ | ++ | ++ | ++ | ++ |
| 29 | +++ | ++ | +++ | +++ | ++ |
| 30 | +++ | + | + | + | + |
| 31 | +++ | ++ | ++ | ++ | ++ |
| 32 | + | + | + | + | + |
| 33 | +++ | | + | + | |
| 34 | +++ | + | ++ | ++ | + |
| 35 | +++ | + | + | ++ | + |
| 36 | + | + | + | + | + |
| 37 | +++ | + | + | + | + |
| 38 | +++ | ++ | ++ | ++ | ++ |
| 39 | +++ | + | ++ | ++ | + |
| 40 | +++ | + | + | ++ | + |
| 41 | +++ | + | + | + | + |
| 42 | ++ | + | + | + | + |
| 43 | +++ | + | + | ++ | + |
| 44 | +++ | + | + | ++ | + |
| 45 | +++ | ++ | ++ | ++ | ++ |
| 46 | +++ | + | + | + | + |
| 47 | +++ | + | + | + | + |

Antibacterial Assay Methods for *Staphylococcus aureus* Mu50 (ATCC 700699), Methicillin-Resistant *Staphylococcus aureus* (ATCC 43300), Multi-Drug-Resistant *Staphylococcus epidermidis* (ATCC 700562) Compounds The compounds were stored at room temperature in the dark prior to use. Each compound was solubilized in DMSO to a final concentration of 40 mg/mL. The stock material was diluted to a concentration equivalent to two times the final in-well high test concentration (100 μg/mL for all experimental compounds) in Mueller Hinton II broth. Precipitation was observed in the wells at 100 and 50 μg/mL with all eight compounds. Vancomycin and oxacillin were obtained from Sigma Aldrich Chemical Company and were used as positive and/or negative control compounds in the reported assays at high test concentrations of 100, 25 and 100 μg/mL respectively.

Bacterial Strains

The bacterial strains employed in these assays were obtained from the American Type Culture Collection (ATCC). All of the bacterial strains were propagated as recommended by the ATCC. Each strain was stored as a frozen glycerol stock at −80° C. and a 10 μL loop of the frozen stocks was used to inoculate each culture for these assays. The strains with their classification and properties are listed in the table below.

| Bacteria Strain | ATCC # | Classification | Properties |
|---|---|---|---|
| *Staphylococcus aureus* | 700699 | Gram Positive | Mu50, Reduced Vancomycin Susceptibility |
| *Staphylococcus aureus* | 43300 | Gram Positive | Methicillin-Resistant |
| *Staphylococcus epidermidis* | 700562 | Gram Positive | Multi-Drug-Resistant |

MIC Determination

The susceptibility of the above microorganisms to the test compounds was evaluated by determining the MIC of each compound using micro-broth dilution analysis according to the methods recommended by the NCCLS. All microbial strains were obtained from American Type Culture Collections (ATCC) and cultured according to the suppliers recommendations. Evaluation of the susceptibility of each organism against the test compounds included a positive control antibiotics Vancomycin and Oxacillin. For each organism, a standardized inoculum was prepared by direct suspension of freshly plated colonies in Mueller Hinton II broth to an optical density 625 nm ($OD_{625}$) of 0.1 (equivalent to a 0.5 McFarland standard). The suspended inoculum was diluted to a concentration of approximately $1 \times 10^6$ colony forming units per milliliter (CFU/mL) and 100 μL placed into triplicate wells of a 96-well plate containing 100 μL of test compound serially diluted 2-fold in Mueller Hinton II broth. One hundred microliters of the inoculum was also added to triplicate wells containing 100 μL of two-fold serial dilutions of a positive control antibiotic and to wells containing 100 μL of media only. This dilution scheme yielded final concentrations for each microbial organism estimated to be $5 \times 10^5$ CFU/mL (verified by colony quantification on appropriate agar plates, data is not presented). Test compound concentrations ranged from a high-test of 1:2 (100 μg/mL)) to a low test of 1:2048 (0.1 μg/mL) using a two-fold dilution scheme. The plates were incubated for 24 hours at 37° C., and the microbial growth at each concentration of compound was determined by measuring the optical density at 625 nm on a Molecular Devices SpectraMax Plus-384 plate reader. The MIC for each compound was determined as the lowest compound dilution that completely inhibited microbial growth.

Antibacterial Assay Results for *Staphylococcus aureus* Mu50 (ATCC 700699), Methicillin-Resistant *Staphylococcus aureus* (ATCC 43300), Multi-Drug-Resistant *Staphylococcus epidermidis* (ATCC 700562)

Microsoft Excel 2003 was used to analyze and graph the data, and the MIC (minimal inhibitory concentration) was determined from the resulting data. The MIC is defined as the lowest concentration of compound that completely inhibited bacterial.

Activity for Compounds was determined in the assays described. The minimum inhibitory concentration (μg/ml) was determined to be in a given range if at least two of three values fell within that range.

MIC of the compound in the range of less than 0.98 (μg/ml) is designated in the table by ++++

MIC of the compound in the range of greater than or equal to 0.99 (μg/ml) and less than or equal to 15.6 (μg/ml) is designated in the table by +++

MIC of the compound in the range of greater than or equal to 15.7 (μg/ml) and less than or equal 62.5 (μg/ml) is designated in the table by ++

MIC of the compound in the range of greater than or equal to 62.6 (μg/ml) is designated in the table by +

| Compound | *Staphylococcus aureus* Mu50 (ATCC 700699) | Methicillin-Resistant *Staphylococcus aureus* (ATCC 43300) | Multi-Drug-Resistant *Staphylococcus epidermidis* (ATCC 700562) |
|---|---|---|---|
| 1 | +++ | +++ | +++ |
| 12 | +++ | +++ | +++ |
| 15 | +++ | +++ | +++ |
| 16 | +++ | +++ | +++ |
| 17 | +++ | +++ | +++ |
| 21 | +++ | +++ | +++ |
| 30 | +++ | +++ | +++ |
| 31 | ++ | +++ | +++ |

Example 2

Preparation and Biological Activity of Further Compounds According to the Present Invention General Notes Melting point determinations were carried out on a Gallenkamp melting point apparatus. Chemical ionization (CI) and electron impact (EI) mass spectra were obtained on a Shimadzu QP-5000 mass spectrometer by a direct insertion technique with an electron beam energy of 70 eV. Electrospray (ES) mass spectra were obtained on a VG Autospec spectrometer. High-resolution mass spectra (HRMS) were determined on a micromass QTof2 spectrometer using polyethylene glycol or polypropylene glycol as the internal standard. The m/z values are stated with their peak intensity as a percentage in parentheses. Optical rotations were measured using a Jasco polarimeter with a 10 mm path length. Proton and carbon nuclear magnetic resonance (NMR) spectra were obtained as specified on a Varian Mercury 300 MHz or Varian Inova 500 MHz spectrometer. Spectra were recorded in the specified deuterated solvent, and referenced to the residual non-deuterated solvent signal. Chemical shifts (δ) in ppm were measured relative to the internal standard. Where samples exhibited (E) and (Z) isomers the chemical shifts are separated by (/). In general, the two forms could not be separated by flash chromatography. Multiplet (m) signals are reported from the centre of the peak. Proton and carbon assignments were determined through the interpretation of two dimensional spectra (COSY, gHSQC and gHMBC). Analytical thin layer chromatography (TLC) was carried out on Merck silica gel 60 $F_{254}$ pre-coated aluminium plates with a thickness of 0.2 mm. All column chromatography was performed under 'flash' conditions on Merck silica gel 60 (230-400 mesh). Chromatography solvent mixtures were measured by volume. Organic solvent extracts were dried with anhydrous magnesium sulfate, and the solvent removed under reduced pressure with a Buchi rotary evaporator. Solvents were purified and dried based upon standard techniques.[120] All compounds were judged to be of greater than 95% purity based upon $^1$H NMR and TLC analysis. Starting materials and reagents were purchased from Sigma-Aldrich Pty Ltd or Auspep Pty Ltd and were used as received. The Grubbs' first generation catalyst used was specifically benzylidene bis(tricyclohexylphosphene)dichlororuthenium.

Proton and carbon NMR spectra for all compounds were assigned using the numbering systems illustrated below. Cyclic peptoids were named using the IUPAC "superatom" convention, in which the aromatic ring is considered equivalent to, and sequentially numbered like all other atoms in the macrocycle.[121]

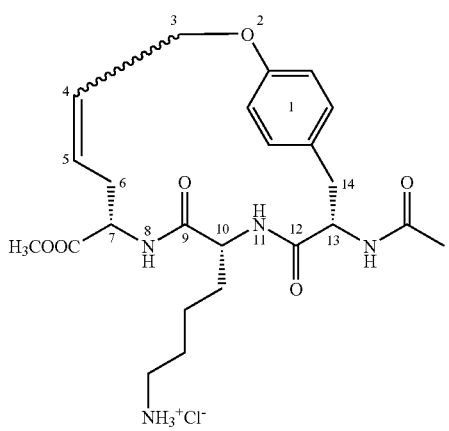

-continued

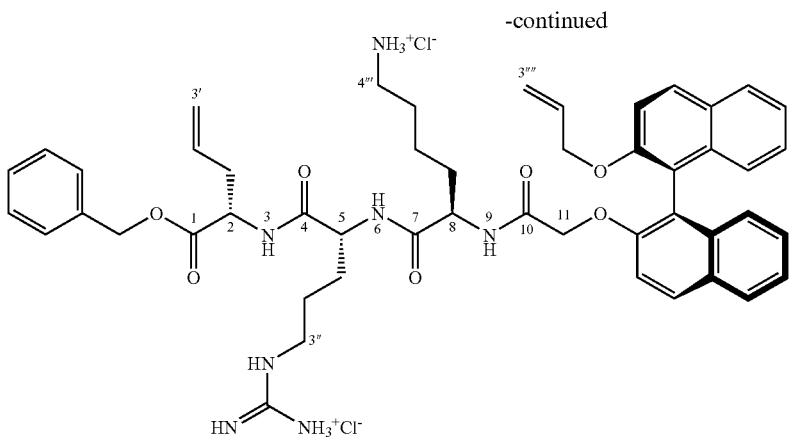
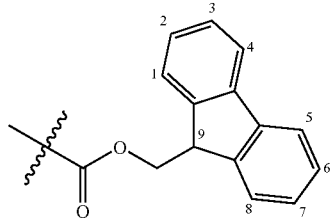

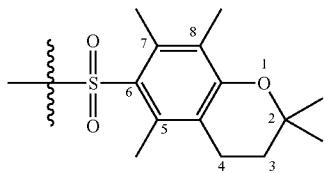

General Synthetic Procedures

N-Boc and Pmc Deprotection (Procedure A)

The N-Boc or Pmc protected amine was stirred for 3 h in 1:1 DCM/TFA (10 mL) solution at RT. The solvent was removed under reduced pressure, and the residue was resuspended in a minimal volume of methanol. The solution was then treated with an excess of 1M HCl/ether solution and the solvent evaporated. The crude product was purified by precipitation from DCM and/or MeOH by addition of diethyl ether.

Peptide Coupling (Procedure B)

To a solution of the acid (1 equiv.) in DMF or $CH_3CN$ (10 mL) at room temperature was added HOBt (1.1 equiv.), EDCI (1 equiv.) and the amine (1.2 equiv.). If the amine was a hydrochloride salt, DIPEA (1 equiv.) was also added. The mixture was allowed to stir for 16 h before dilution with EtOAc (30 mL) and washing with water (30 mL) and brine (30 mL). The organic fraction was dried ($MgSO_4$) and further purified by column chromatography if required.

N-Fmoc Deprotection (Procedure C)

The Fmoc protected amine was stirred in 1% piperidine/acetonitrile (10 mL) for 3 h at RT. The solvent was removed under reduced pressure and the crude product was purified by flash column chromatography (15:1, DCM/MeOH) to yield the free amine.

Macrocyclization by Olefin Metathesis (Procedure D)

To a solution of the precursor tripeptide (1 equiv.) in DCM (to 0.004 M) was added Grubbs' first generation catalyst (15 mol %) and the resulting solution was heated at reflux for 48 h before the solvent was removed by evaporation and the product isolated by flash column chromatography (15:1, DCM/MeOH) to yield the corresponding macrocycle.

EXPERIMENTAL

Ethyl(2S)-2-acetamido-3-(4-allyloxyphenyl)propanoate (15)

To a solution of ethyl(2S)-2-acetamido-3-(4-hydroxyphenyl) propanoate monohydrate 13 (2.69 g, 9.98 mmol) and anhydrous $K_2CO_3$ (2.75 g, 20.0 mmol) in DMF (15 mL) was added allyl bromide (2.42 g, 19.96 mmol). The resulting mixture was allowed to stir for 16 h under nitrogen before the reaction was quenched with water (30 mL) and extracted with ethyl acetate (3×50 mL). The combined organic fractions were washed with water (5×50 mL), dried and the solvent was evaporated to yield the title compound (2.91 g, 9.98 mmol, 100%) as a white solid, which had spectral data in agreement with that reported.[122] $[\alpha]_D^{25}$ +23.1 (c. 0.1, EtOH). Mp 69-70° C. (lit. 69.5° C.)[122] $^1$H NMR ($CDCl_3$, 300 MHz): δ 7.02 (d, J=8.4 Hz, 2H, ArH2' and ArH6'); 6.83 (d, J=8.8 Hz, 2H, ArH3' and ArH5'); 6.14 (d, J=8.0 Hz, 1H, NH); 6.06 (m, 1H, H2");

5.31 (m, 2H, H3"); 4.81 (dd, J=13.5, 6.0 Hz, 1H, H2); 4.50 (d, J=5.1 Hz, 2H, H1"); 4.16 (dd, J=13.9, 6.7 Hz, 2H, OCH$_2$CH$_3$); 3.04 (m, 2H, H3); 1.98 (s, 3H, NCOCH$_3$); 1.25 (t, J=7.2 Hz, 3H, OCH$_2$CH$_3$). Mass Spectrum (CI, +ve) m/z 292 (100%) [MH$^+$]. HRMS calcd for C$_{16}$H$_{22}$NO$_4$ 292.1549, found 292.1559.

(2S)-2-Acetamido-3-(4-allyloxyphenyl)propanoic acid (16)

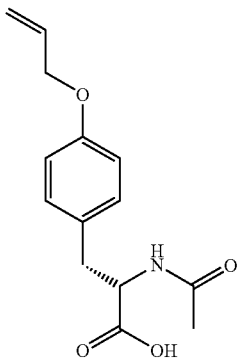

To a solution of 15 (2.90 g, 9.98 mmol) in THF/water, (3:1, 80 mL) was added lithium hydroxide monohydrate (838 mg, 20.0 mmol) and the resulting suspension was allowed to stir for 16 h. The reaction mixture was diluted with water (30 mL) and the THF was removed by evaporation. The aqueous layer was extracted with DCM (40 mL) to remove unreacted starting material. The aqueous phase was acidified with 10% HCl and the resulting precipitate was extracted with DCM (3×40 mL). The combined organic fractions were dried and evaporated to yield the title compound (2.62 g, 9.98 mmol, 100%) as white needles, which had spectral data in agreement with that reported.[122] Mp 170-172° C. (lit. 200° C.)[122] $^1$H NMR (D$_6$ acetone, 300 MHz): δ 7.09 (s, 1H, NH); 7.04 (d, J=8.4 Hz, 2H, ArH2' and ArH6'); 6.73 (d, J=8.4 Hz, 2H, ArH3' and ArH5'); 5.94 (m, 1H, H2"); 5.27 (dd J=1.3, 17.3 Hz, 1H, H3$_a$"); 5.10 (dd J=1.3, 10.5 Hz, 1H, H3b"); 4.52 (m, 1H, H2); 4.41 (d J=5.5 Hz, 2H, H1"); 2.98 (dd, J=5.7, 14.1 Hz, 2H, H3$_a$); 2.79 (dd, J=8.1, 14.1 Hz, 2H, H3b); 1.75 (s, 3H, NCOCH$_3$). Mass Spectrum (CI, +ve) m/z 264 (100%) [MH$^+$]. HRMS calcd for C$_{14}$H$_{18}$NO$_4$ 264.1236, found 264.1246.

Methyl(2S)-2-amino-4-pentenoate hydrochloride (18)

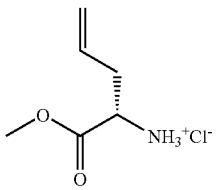

To a suspension of (2S)-2-amino-4-pentenoic acid 17 (200 mg, 1.74 mmol) in MeOH (6 mL) at 0° C. was added dropwise thionyl chloride (1 mL). The resulting solution was allowed to stir for 16 h before the solvent was removed by evaporation and the product crystallized with ether. The ether was removed by evaporation to yield the title compound (287 mg, 1.74 mmol, 100%) as a white solid, which had spectral data in agreement with that reported.[82] Mp 172-174° C. (lit. 174-176° C.)[82] $^1$H NMR (CDCl$_3$, 300 MHz): δ 8.74 (bs, 3H, NH$_3^+$); 5.88 (m, 1H, H4); 5.32 (d, J=16.8 Hz, 1H, H15$_a$); 5.25 (d, J=10.2 Hz, 1H, H5$_b$); 4.29 (t, J=5.1 Hz, 1H, H2); 3.81 (s, 3H, OCH$_3$); 2.86 (t, J=5.7 Hz, 2H, H3). Mass Spectrum (ES, +ve) m/z 130 (100%) [M+]. HRMS calcd for C$_6$H$_{12}$NO$_2$ 130.0868, found 130.0876.

Methyl(2S,5R)-2-allyl-3-aza-9-(tert-butoxycarboxamido)-5-(9H-9-fluorenylmethyloxycarboxamido)-4-oxononanoate (19)

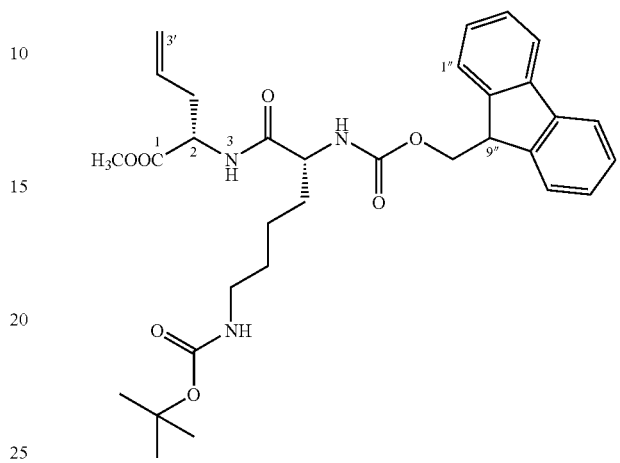

The title compound was synthesised using the general peptide coupling procedure (Procedure B), from 18 (186 mg, 1.62 mmol) and (2R)-6-tert-butoxycarboxamido-2-(9H-9-fluorenylmethyloxy carboxamido)hexanoic acid (633 mg, 1.35 mmol) to afford 19 (733 mg, 1.27 mmol, 94%) as a cream solid. Mp 117-120° C. $^1$H NMR (CDCl$_3$, 300 MHz): δ 7.76 (d, J=7.6 Hz, 2H, ArH1" and ArH8"); 7.59 (d, J=7.6 Hz, 2H, ArH4" and ArH5"); 7.39 (t, J=7.6 Hz, 2H, ArH3" and ArH6"); 7.31 (dd, J=9.0, 7.2, 1.2 Hz, 2H, ArH2" and ArH7"); 6.75 (d, J=7.2 Hz, 1H, NH); 5.65 (m, 1H, H2'); 5.07 (m, 2H, H3'); 4.65 (m, 2H, H2 and NH); 4.38 (d, J=6.7 Hz, 2H, OCH$_2$—H9"); 4.21 (m, 2H, H15 and H9"); 3.71 (s, 3H, OCH$_3$); 3.10 (d, J=6.3 Hz, 2H, H9); 2.52 (m, 2H, H1'); 1.85 (m, 2H, H8); 1.66 (m, 2H, H7); 1.39 (m 2H, H7); 1.43 (s, 9H, C(CH$_3$)$_3$). Mass Spectrum (ES, +ve) m/z 579.9 (80%) [M], 479.9 (100%) [MH$^+$ (less Boc)]. HRMS calcd for C$_{32}$H$_{42}$N$_3$O$_7$ 580.3023, found 580.3041.

Methyl(2S,5R)-2-allyl-5-amino-3-aza-9-(tert-butoxycarboxamido)-4-oxononanoate (20)

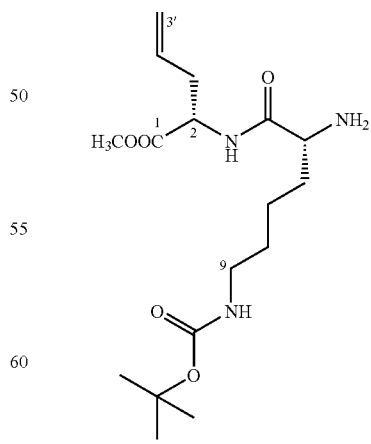

The title compound was synthesized using the general N-Fmoc deprotection procedure (Procedure C), from 19 (715 mg, 1.23 mmol) to yield 20 (436 mg, 1.22 mmole, 99%) as a cream oil, and is in agreement with the literature.[78] $^1$H NMR (CDCl$_3$, 300 MHz): δ 7.75 (d, J=8.0 Hz, 1H, NH); 5.70 (m, 1H, H2'); 5.13 (m, 2H, H3'); 4.80 (bs, 1H, NH); 4.64 (m, 1H, H2); 3.74 (s, 3H, OCH$_3$); 3.38 (dd, J=4.6, 7.6 Hz, 1H, H5); 3.12 (d, J=6.3 Hz, 2H, H9); 2.57 (m, 2H, H1'); 1.61 (m, 8H, H6, H7, H8 and NH$_2$); 1.44 (s, 9H, C(CH$_3$)$_3$). Mass Spectrum (ES, +ve) m/z 358.5 (70%) [MH$^+$], 258.4 (100%) [MH$^+$ (less Boc)]. HRMS calcd for C$_{17}$H$_{32}$N$_3$O$_5$ 358.2342, found 358.2334.

Methyl(2S,5R,8S)-2-allyl-8-(4-allyloxybenzyl)-3,6,9-triaza-5-(4-[tert-butoxycarboxamido]butyl)-4,7,10-trioxoundecanoate (21)

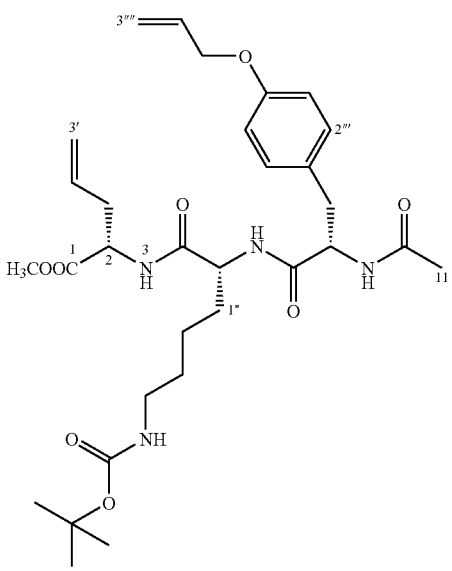

The title compound was synthesised using the general peptide coupling procedure (Procedure B), from 20 (440 mg, 1.20 mmol) and 16 (270 mg, 1.03 mmol) to afford 21 (424 mg, 0.70 mmol, 69%) as a white solid. Mp 149-150° C. $^1$H NMR (CDCl$_3$, 300 MHz): δ 7.20 (d, J=8.0 Hz, 1H, NH); 7.11 (d, J=8.4 Hz, 2H, ArH2''' and ArH6'''); 6.84 (d, J=8.4 Hz, 2H, ArH3''' and ArH5'''); 6.67 (d, J=8.0 Hz, 1H, NH); 6.48 (d, J=7.2 Hz, 1H, NH); 6.04 (m, 1H, H2''''); 5.67 (m, 1H, H2'); 5.41 (dd, J=1.3, 17.3 Hz, 1H, H3$_a$''''); 5.28 (dd, J=1.3, 10.5 Hz, 1H, H3$_b$''''); 5.10 (m, 2H, H3'); 4.75 (t, J=5.9 Hz, 1H, H2); 4.60 (m, 1H, H8); 4.50 (d, J=5.5 Hz, 2H, H1''''); 4.42 (dd, J=7.6, 13.1 Hz, 1H, H5); 3.71 (s, 3H, OCH$_3$); 2.97 (m, 4H, H4'' and ArCH$_2$); 2.52 (m, 2H, H1'); 1.97 (s, 3H, H11); 1.44 (s, 9H, C(CH$_3$)$_3$); 1.34 (m, 6H, H1'', H2'' and H3''). Mass Spectrum (ES, +ve) m/z 603.4 (40%) [MH$^+$], 503.4 (100%) [MH$^+$ (less Boc)]. HRMS calcd for C$_{31}$H$_{47}$N$_4$O$_8$ 603.3394, found 603.3389.

(7S,10R,13S,4E/Z)-13-Acetamido-8,11-diaza-10-(4-[tert-butoxycarboxamido]butyl)-7-methoxycarbonyl-2-oxa-9,12-dioxo-1(1,4)phenylenacyclotetradecaphane-4-ene (22)

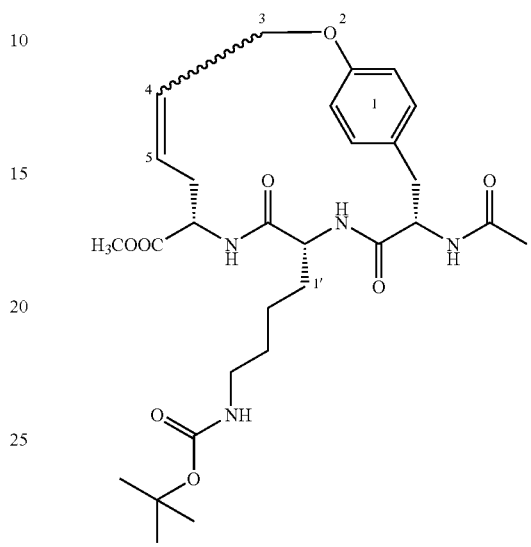

The title compound was prepared using the general procedure for olefin metathesis (Procedure D), from 21 (277 mg, 0.46 mmol) to yield 22 (199 mg, 0.35 mmol, 75%) as a brown solid. Mp 178-180° C. $^1$H NMR (CDCl$_3$, 300 MHz): δ 8.08 (m, 2H, NH); 7.07 (m, 2H, ArH); 6.71 (m, 2H, ArH); 5.63 (m, 2H, H4 and H5); 4.48 (m, 4H, H7, H13 and H3); 4.13 (m, 2H, NH and H10); 3.60 (m, 3H, OCH$_3$); 2.79 (bs, 4H, H4' and H14); 2.38 (m, 2H, H6); 1.80 (m, 3H, NCOCH$_3$); 1.10 (m, 6H, H1', H2' and H3'); 1.26 (s, 9H, C(CH$_3$)$_3$). Mass Spectrum (ES, +ve) m/z 575.3 (20%) [MH$^+$], 475.3 (100%) [MH$^+$ (less Boc)]. HRMS calcd for C$_{29}$H$_{43}$N$_4$O$_8$ 575.3081, found 575.3091.

(7S,10R,13S,4E/Z)-13-Acetamido-10-(4-aminobutyl)-8,11-diaza-7-methoxycarbonyl-2-oxa-9,12-dioxo-1(1,4)phenylenacyclotetradecaphane-4-ene hydrochloride (12)

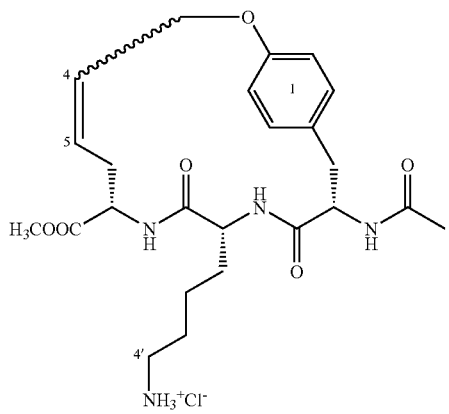

The title compound was synthesized using the general N-Boc deprotection procedure (Procedure A), from 22 (49 mg, 0.084 mmol) to yield 12 (17 mg, 0.033 mmol, 49%) as a highly hydroscopic yellow solid. $^1$H NMR (CD$_3$OD, 300 MHz): δ 7.10 (m, 3H, ArH and NH); 6.85 (bs, 1H, NH); 6.71 (d, J=7.5 Hz, 2H, ArH); 5.75 (m, 2H, H4 and H5); 4.39 (m, 5H, H3, H7, H$_{10}$ and H13); 3.68 (s, 3H, OCH$_3$); 2.85 (m, 4H, H6 and H4'); 2.52 (m, 2H, H14); 1.93 (s, 3H, NCOCH$_3$); 1.50 (m, 6H, H1', H2' and H3'). $^{13}$C NMR (CD$_3$OD, 75 MHz): δ 173.5, C9; 173.1, 7-CO; 173.0, 13-NCO; 172.6, C12; 157.7, 1-ArC1; 132.4, 1-ArCH2 and 1-ArCH6; 131.1, C4; 129.6, C5; 129.3, 1-ArC4; 116.8, 1-ArCH3 and 1-ArCH5; 70.0, C3; 57.9, C13; 54.9, C10; 53.5, C4'; 53.0, OCH$_3$; 40.7, C7; 38.2, C14; 32.1, C1'; 31.7, C6; 28.0, C3'; 23.5, NCOCH$_3$; 22.6, C2'. Mass Spectrum (ES, +ve) m/z 475.3 (100%) [M$^+$]. HRMS calcd for C$_{24}$H$_{35}$N$_4$O$_6$ 475.2557, found 475.2534.

Methyl(2S,5S)-2-allyl-3-aza-9-(tert-butoxycarboxamido)-5-(9H-9-fluorenylmethyloxycarboxamido)-4-oxononanoate (23)

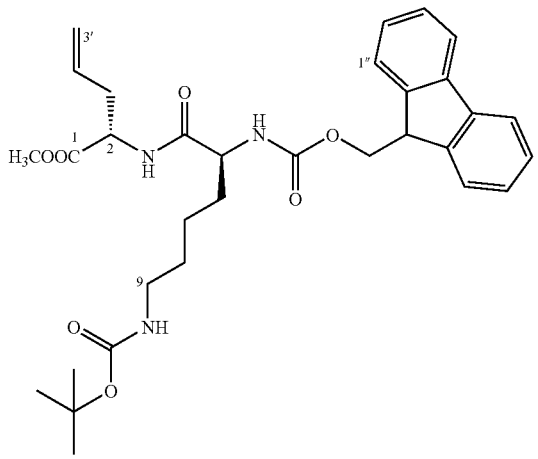

To a solution of 18 (430 mg, 2.61 mmol) and (2S)-6-tert-butoxycarboxamido-2-(9H-9-fluorenylmethyloxy)carboxamido hexanoic acid (1.22 g, 2.61 mmol) in DCM (10 mL) was added EDCI (500 mg, 2.61 mmol) and a catalytic quantity of DMAP. The resulting mixture was allowed to stir at RT for 16 h. The reaction was diluted with DCM (25 mL), then the organic layer was washed with brine (2×25 mL) and water (2×25 mL) and dried, before being concentrated. The crude product was purified by flash column chromatography (25:1 DCM/MeOH) to afford the title compound (1.31 g, 2.27 mmol, 87%) as a cream coloured solid. Mp 123-126° C. $^1$H NMR (CDCl$_3$, 300 MHz): δ 7.76 (d, J=7.6 Hz, 2H, ArH1" and ArH8"); 7.59 (d, J=7.6 Hz, 2H, ArH4" and ArH5"); 7.40 (t, J=7.6 Hz, 2H, ArH3" and ArH6"); 7.31 (ddd, J=9.0, 7.2, 1.2 Hz, 2H, ArH2" and ArH7"); 6.46 (bs, 1H, NH); 5.64 (m, 1H, H2'); 5.44 (s, 1H, NH); 5.10 (m, 2H, H3'); 4.65 (m, 1H, H2); 4.39 (d, J=7.2 Hz, 2H, OCH$_2$—H9"); 4.22 (m, 1H, H5); 4.17 (bs, 1H, H9"); 3.74 (s, 3H, OCH$_3$); 3.11 (m, 2H, H9); 2.55 (m, 2H, H1'); 1.85 (m, 2H, H7); 1.65 (m, 2H, H6); 1.50 (m 2H, H8); 1.44 (s, 9H, C(CH$_3$)$_3$). Mass Spectrum (ES, +ve) m/z 580.5 (10%) [MH$^+$], 130.5 (100%) [MH$^+$ (less allylgly)]. HRMS calcd for C$_{32}$H$_{42}$N$_3$O$_7$ 580.3023, found 580.3025.

Methyl(2S,5S)-2-allyl-5-amino-3-aza-9-(tert-butoxycarboxamido)-4-oxononanoate (24)

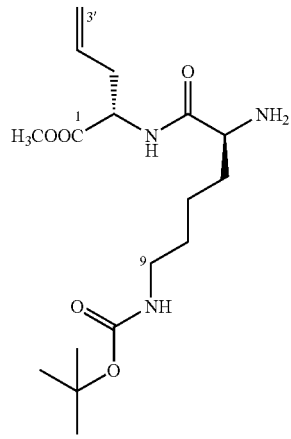

The title compound was synthesized using the general N-Fmoc deprotection procedure (Procedure C), from 23 (1.27 g, 2.19 mmol) to yield 24 (778 mg, 2.18 mmole, 100%) as a cream oil. $^1$H NMR (CDCl$_3$, 300 MHz): δ 7.81 (d, J=8.0 Hz, 1H, NH); 5.69 (m, 1H, H2'); 5.11 (m, 2H, H3'); 4.76 (bs, 1H, NH); 4.67 (m, 1H, H2); 3.75 (s, 3H, OCH$_3$); 3.39 (dd, J=4.6, 7.6 Hz, 1H, H5); 3.12 (d, J=6.3 Hz, 2H, H9); 2.54 (m, 2H, H1'); 1.52 (m, 8H, H6, H7, H8 and NH$_2$); 1.44 (s, 9H, C(CH$_3$)$_3$). $^{13}$C NMR (CDCl$_3$, 75 MHz): δ 174.8, C4; 172.1, C1; 156.0, NCO$_2$; 132.2, C2'; 118.9, C3'; 78.9, C(CH$_3$)$_3$; 54.8, C5; 52.2, C2; 51.1, OCH$_3$; 40.0, C9; 36.4, C1'; 34.4, C6; 29.7, C8; 28.3, C(CH$_3$)$_3$; 22.6, C7. Mass Spectrum (ES, +ve) m/z 358.5 (85%) [MH$^+$], 258.4 (100%) [MH$^+$ (less Boc)]. HRMS calcd for C$_{17}$H$_{32}$N$_3$O$_5$ 358.2342, found 358.2339.

Methyl(2S,5S,8S)-2-allyl-8-(4-allyloxybenzyl)-3,6,9-triaza-5-(4-[tert-butoxycarboxamido]butyl)-4,7,10-trioxoundecanoate (25)

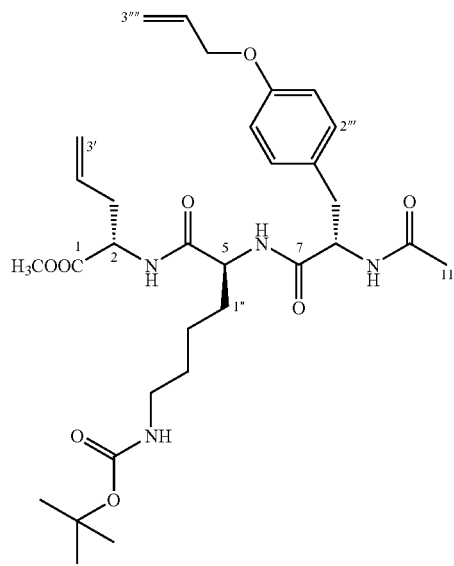

To a solution of 24 (782 mg, 2.19 mmol) and 16 (576 mg, 2.19 mmol) in DCM (10 mL) was added EDCI (420 mg, 2.19 mmol) and a catalytic quantity of DMAP. The resulting mixture was allowed to stir at RT for 16 h. The reaction was diluted with DCM (25 mL) and the organic layer was washed with brine (2×25 mL) and water (2×25 mL) and dried, before being concentrated by evaporation. The crude product was purified by flash column chromatography (25:1 DCM/MeOH) to afford the title compound (664 mg, 1.10 mmol, 50%) as a 1:1 mixture of 2 epimers, as a white solid. Mp 112-114° C. ¹H NMR (CDCl₃, 300 MHz): δ 7.09 (m, 2H, ArH2''' and ArH6'''); 6.91 (d, J=8 Hz, 1H, NH); 6.82 (m, 2H, ArH3''' and ArH5'''); 6.69 (d, J=8.0 Hz, 1H, NH); 6.55 (bs, 1H, NH); 6.03 (m, 1H, H1''''); 5.68 (m, 1H, H2'); 5.25 (m, 4H, H3' and H3''''); 4.96 (bs, 1H, H2); 4.86 (bs, 1H, H8); 4.67 (m, 2H, H2''''); 4.48 (dd, J=3.0, 8.4 Hz, 1H, H5); 3.74/3.71 (s, 3H, OCH₃); 3.04 (m, 4H, H4'' and ArCH₂); 2.51 (m, 2H, H1'); 1.98/1.96 (s, 3H, H11); 1.79 (s, 2H, H2''); 1.60 (s, 2H, H1''); 1.43 (s, 9H, C(CH₃)₃); 1.28 (s, 2H, H3''). Mass Spectrum (ES, +ve) m/z 603.4 (35%) [MH⁺], 503.4 (100%) [MH⁺ (less Boc)]. HRMS calcd for C₃₁H₄₇N₄O₈ 603.3394, found 603.3397.

(7S,10S,13S,4E/Z)-13-Acetamido-8,11-diaza-10-(4-[tert-butoxycarboxamido]butyl)-7-methoxycarbonyl-2-oxa-9,12-dioxo-1(1,4)phenylenacyclotetradecaphane-4-ene (26)

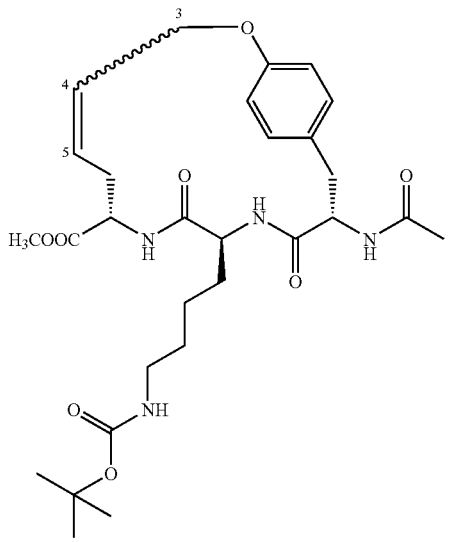

The title compound was prepared using the general procedure for olefin metathesis (Procedure D) using 25 (311 mg, 0.52 mmol) to yield 26 as a mixture of epimers and E/Z isomers (228 mg, 0.40 mmol, 76%) as a brown solid. Mp 196-201° C. ¹H NMR (CDCl₃, 300 MH⁺): δ 7.54 (m, 2H, NH); 7.34 (bs, 1H, NH); 7.06 (m, 2H, ArH); 6.81/6.73 (d, J=8.0 Hz, 2H, ArH); 5.66 (d, J=16.4 Hz, 1H, H4-trans); 5.55 (m, 1H, H5); 4.90 (m, 2H, H7 and H13); 4.64 (m, 3H, H2 and H10); 3.80/3.77 (s, 3H, OCH₃); 3.10 (m, 4H, H6 and H4'); 2.70 (m, 2H, H14); 2.10 (s, 3H, NCOCH₃); 1.51 (m, 6H, H1', H2' and H3'); 1.44/1.40 (s, 9H, C(CH₃)₃). Mass Spectrum (ES, +ve) m/z 575.3 (25%) [MH⁺], 475.3 (40%) [MH⁺ (less Boc)]. HRMS calcd for C₂₉H₁₃N₄O₈ 575.3081, found 575.3092.

(7S,10S,13S,4E/Z)-13-Acetamido-10-(4-aminobutyl)-8,11-diaza-7-methoxycarbonyl-2-oxa-9,12-dioxo-1(1,4)phenylenacyclotetradecaphane-4-ene hydrochloride (27)

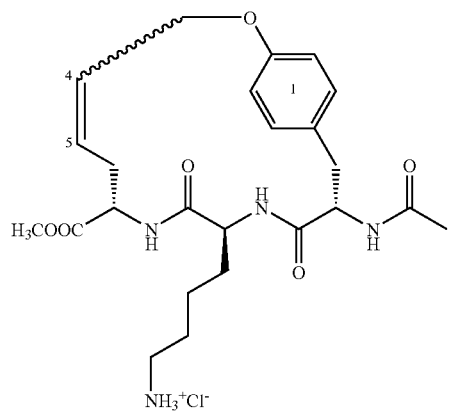

The title compound was synthesized using the general N-Boc deprotection procedure (Procedure A) using 26 (220 mg, 0.380 mmol) to yield 27 as a mixture of epimers and E/Z isomers (152 mg, 0.300 mmol, 79%) as a highly hydroscopic yellow solid. ¹H NMR (CD₃OD, 300 MHz): δ 8.19 (d, J=8.4 Hz, 1H, NH); 6.98/6.92 (d, J=8.0 Hz, 2H, ArH); 6.74/6.64 (d, J=8.0 Hz, 2H, ArH); 5.57 (d, J=16.0 Hz, 2H, H4-trans); 5.39 (m, 1H, H5); 4.53 (m, 4H, H7, H13 and H2); 4.21 (m, 1H, H10); 3.93 (bs, 1H, NH); 3.63/3.60 (s, 3H, OCH₃); 2.76 (m, 6H, H6, H4' and H14); 1.99/1.89 (s, 3H, NCOCH₃); 1.64 (m, 2H, H2'); 1.51 (bs, 2H, H3'); 1.22 (m, 2H, H1'). ¹³C NMR (CD₃OD, 75 MHz): δ 174.5, C9; 173.3, 7-CO; 173.1, 13-NCO; 172.5, C12; 157.7, 1-ArC1; 131.4, 1-ArCH2 and 1-ArCH6; 131.1, C4; 129.5, C5; 129.1, 1-ArC4; 116.4, 1-ArCH3 and 1-ArCH5; 66.9, C3; 57.7, C13; 53.9, C10; 53.1, C4'; 53.0, OCH₃; 40.5, C7; 38.1, C14; 32.0, C1'; 31.8, C6; 28.0, C3'; 23.5, NCOCH₃; 22.5, C2'. Mass Spectrum (ES, +ve) m/z 475.4 (100%) [M⁺]. HRMS calcd for C₂₄H₃₅N₄O₆ 475.2557, found 475.2581.

Methyl(2S,5R)-2-allyl-3-aza-5-(9H-9-fluorenylmethyloxycarboxamido)-8-[(2,2,5,7,8-pentamethyl-3,4-dihydro-2H-6-chromenylsulfonyl)guanidino]-4-oxooctanoate (28)

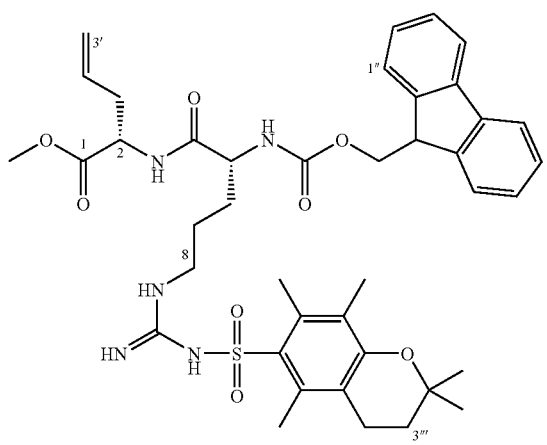

The title compound was synthesised using the general peptide coupling procedure (Procedure B), from 18 (287 mg, 1.74 mmol) and (2R)-2-(9H-9-fluorenylmethyloxycarboxamido)-8-[(2,2,5,7,8-pentamethyl-3,4-dihydro-2H-6-chromenylsulfonyl)guanidino]pentanoic acid (961 mg, 1.45 mmol) to afford 28 (1.01 g, 1.31 mmol, 90%) as a brown solid. Mp 96-100° C. $^1$H NMR (CDCl$_3$, 300 MHz): δ 7.70 (d, J=7.5 Hz, 2H, ArH1" and ArH8"); 7.52 (d, J=7.2 Hz, 2H, ArH4" and ArH5"); 7.35 (bs, 1H, NH); 7.33 (dd, J=7.2, 7.2 Hz, 2H, ArH3" and ArH6"); 7.20 (t, J=7.2 Hz, 2H, ArH2" and ArH7"); 6.35 (s, 2H, NH); 6.26 (bs, 2H, NH); 5.62 (m, 1H, H2'); 5.03 (d, J=18.0 Hz, 1H, H3$_a$'); 4.98 (d, J=10.2 Hz, 1H, H3$_b$'); 4.53 (dd, J=7.2, 12.9 Hz, 1H, H2); 4.27 (d, J=6.6 Hz, 2H, OCH$_2$—H9"); 4.10 (m, 2H, H5 and H9"); 3.63 (s, 3H, OCH$_3$); 3.23 (m, 2H, H8); 2.57 (s, 3H, 7'''-CH$_3$); 2.54 (s, 3H, 5'''-CH$_3$); 2.49 (m, 4H, H1' and H4'''); 2.06 (s, 3H, 8'''-CH$_3$); 1.88 (m, 2H, H7); 1.71 (t, J=6.6 Hz, 2H, H3); 1.61 (m, 2H, H6); 1.24 (s, 6H, 2×2'''-CH$_3$). Mass Spectrum (ES, +ve) m/z 774 (100%) [MH$^+$]. HRMS calcd for C$_{41}$H$_{52}$N$_5$O$_8$S 774.3537, found 774.3559.

Methyl(2S,5R)-2-allyl-5-amino-3-aza-8-[(2,2,5,7,8-pentamethyl-3,4-dihydro-2H-6-chromenylsulfonyl) guanidino]-4-oxooctanoate (29)

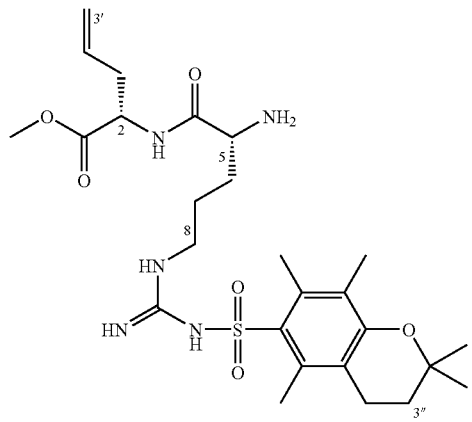

The title compound was synthesized using the general N-Fmoc deprotection procedure (Procedure C), from 28 (717 mg, 0.93 mmol) to yield 29 (407 mg, 0.74 mmol, 80%) as a cream oil, and is in agreement with the literature.[80] $^1$H NMR (CDCl$_3$, 300 MHz): δ 7.87 (d, J=8.1 Hz, 1H, NH); 6.36 (bs, 3H, NH); 5.68 (m, 1H, H2'); 5.10 (m, 2H, H3'); 4.52 (dd, J=6.9, 12.9 Hz, 1H, H2); 3.71 (s, 3H, OCH$_3$); 3.42 (m 1H, H5); 3.19 (dd, J=6.9, 11.1 Hz, 2H, H8); 2.62 (t, J=6.9 Hz, 2H, H4"); 2.56 (s, 3H, 7"-CH$_3$); 2.54 (s, 3H, 5"-CH$_3$); 2.49 (m, 2H, H1'); 2.10 (s, 3H, 8"-CH$_3$); 1.80 (t, J=6.9 Hz, 2H, H2"); 1.74 (m, 2H, H7); 1.58 (m, 2H, H6); 1.30 (s, 6H, 2×2"-CH$_3$). Mass Spectrum (ES, +ve) m/z 552 (100%) [MH$^+$]. HRMS calcd for C$_{26}$H$_{42}$N$_5$O$_6$S 552.2856, found 552.2839.

Methyl(2S,5R,8S)-2-allyl-8-(4-allyloxybenzyl)-3,6,9-triaza-5-([{2,2,5,7,8-pentamethyl-3,4-dihydro-2H-6-chromenylsulfonyl}guanidino]propyl)-4,7,10-trioxoundecanoate (30)

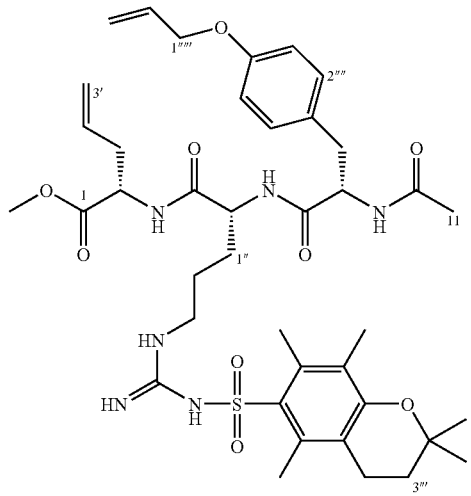

The title compound was synthesised using the general peptide coupling procedure (Procedure B) using 29 (387 mg, 0.70 mmol) and 16 (153 mg, 0.58 mmol) to afford 30 (336 mg, 0.42 mmol, 73%) as a light brown solid. Mp 172-176° C. $^1$H NMR (CDCl$_3$, 500 MHz): δ 7.75 (d, J=7.5 Hz, 1H, NH); 7.11 (d, J=8.7 Hz, 2H, ArH2'''' and ArH6''''); 6.78 (d, J=8.4 Hz, 2H, ArH3'''' and ArH5''''); 6.36 (bs, 2H, NH); 6.18 (bs, 1H, NH); 5.98 (m, 1H, H2'''''); 5.69 (m, 1H, H2'); 5.36 (dd, J=1.5, 17.4 Hz, 1H, H3$_a$'''''); 5.24 (dd, J=1.5, 10.5 Hz, 1H, H3$_b$'''''); 5.08 (d, J=15.6 Hz, 1H, H3$_a$'); 5.04 (d, J=8.4 Hz, 1H, H3$_b$'); 4.48 (m, 2H, H12 and H5); 4.42 (d, J=4.8 Hz, 1H, H1''''); 4.29 (m, 1H, H8); 3.69 (s, 3H, OCH$_3$); 3.05 (m, 2H, H3"); 2.99 (m, 2H, ArCH$_2$); 2.63 (t, J=6.9 Hz, 2H, H14'''); 2.59 (s, 3H, 7'''-CH$_3$); 2.57 (s, 3H, 5'''-CH$_3$); 2.54 (m, 2H, H11'); 2.09 (s, 3H, 8'''-CH$_3$); 1.93 (s, 3H, H11); 1.80 (t, J=6.6 Hz, 2H, H3'''); 1.51 (m, 4H, H1" and H2"); 1.30 (s, 6H, 2×2'''-CH$_3$). Mass Spectrum (ES, +ve) m/z 797 (100%) [MH$^+$]. HRMS calcd for C$_{40}$H$_{57}$N$_6$O$_9$S 797.3908, found 797.3913.

(7S,10R,13S,4E/Z)-13-Acetamido-8,11-diaza-10-(3 [{2,2,5,7,8-pentamethyl-3,4-dihydro-2H-6-chromenylsulfonyl}guanidino]propyl)-7-methoxycarbonyl-2-oxa-9,12-dioxo-1(1,4) phenylenacyclotetradecaphane-4-ene (31)

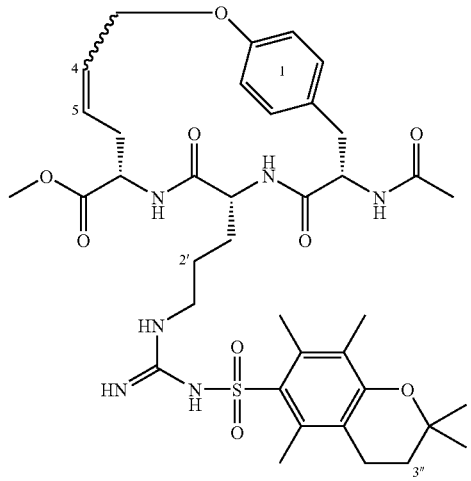

The title compound was prepared using the general procedure for olefin metathesis (Procedure D), from 30 (104 mg, 0.13 mmol) to yield 31 (103 mg, 0.13 mmol, 100%) as a grey solid. Mp 172-175° C. $^1$H NMR (CDCl$_3$, 300 MHz): δ 7.04 (m, 2H, ArH); 6.72 (m, 2H, ArH); 6.37 (bs, 1H, NH); 5.45 (m, H4 and H5); 4.79 (m, 2H, H3); 4.57 (m, 3H, H7, H10 and H13); 3.63 (s, 3H, OCH$_3$); 2.97 (m, 4H, H3' and H6); 2.54 (m, 10H, H14, 7"-CH$_3$, 5"-CH$_3$ and H4"'); 2.06 (s, 3H, 8"'-CH$_3$); 1.90 (s, 3H, NCOCH$_3$); 1.76 (m, 2H, H1'); 1.48 (m, 2H, H3"'); 1.27 (s, 6H, 2×2"-CH$_3$). Mass Spectrum (ES, −ve) m/z 767 (100%) [MH$^+$]. HRMS calcd for C$_{38}$H$_{53}$N$_6$O$_9$S 769.3595, found 769.3558.

(7S,10R,13S,4E/Z)-13-Acetamido-8,11-diaza-10-(3-[guanidino]propyl)-7-methoxycarbonyl-2-oxa-9,12-dioxo-1(1,4)phenylenacyclotetradecaphane-4-ene (32)

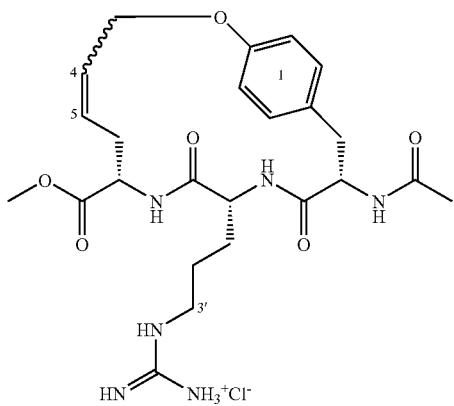

The title compound was synthesized using the general N-Boc deprotection procedure (Procedure A), from 31 (60 mg, 0.078 mmol) to yield 32 (38 mg, 0.071 mmol, 91%) as a white solid. Mp 218-224° C. $^1$H NMR (CD$_3$OD, 300 MHz): δ 7.10 (m, 2H, ArH); 6.79 (m, 2H, ArH); 5.70 (m, 1H, H5); 5.51 (m, 1H, H4); 4.44 (m, 5H, H3, H7, H10 and H13); 3.69 (m, 3H, OCH$_3$); 3.10 (m, 2H, H3'); 2.94 (m, 2H, H14); 2.49 (m, 2H, H6); 1.94 (s, 3H, NCOCH$_3$); 1.71 (m, 2H, H1'); 1.33 (m, 2H, H2'). $^{13}$C NMR (CD$_3$OD, 75 MHz): δ 173.6, COOCH$_3$; 173.5, C11; 173.1, C9; 172.4, NCOCH$_3$; 158.4, CN$_3$; 157.4, 1-ArC4; 131.5, C4; 129.5, C5; 129.1, 1-ArCH2 and 1-ArCH6; 129.0, 1-ArC1; 116.5, 1-ArCH3 and 1-ArCH5; 66.9, C3; 57.5, C7; 56.2, C10; 54.3, C10; 53.6, C3'; 52.5, OCH$_3$; 42.1, C6; 38.7, C14; 35.3, NCOCH$_3$; 26.6, C1'; 22.7, C2'. Mass Spectrum (ES, +ve) m/z 503 (100%) [M$^+$]. HRMS calcd for C$_{24}$H$_{35}$N$_6$O$_6$ 503.2618, found 503.2626.

Methyl(2S,5S)-2-allyl-3-aza-5-(9H-9-fluorenylmethyloxycarboxamido)-8-[(2,2,5,7,8-pentamethyl-3,4-dihydro-2H-6-chromenylsulfonyl)guanidino]-4-oxooctanoate (33)

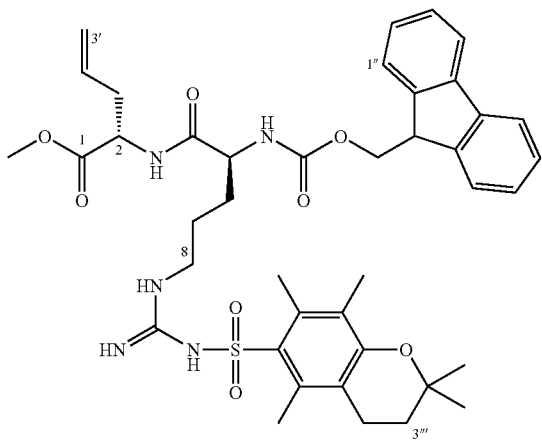

The title compound was synthesised using the general peptide coupling procedure (Procedure B), from 18 (287 mg, 1.74 mmol) and (2S)-2-(9H-9-fluorenylmethyloxycarboxamido)-8-[(2,2,5,7,8-pentamethyl-3,4-dihydro-2H-6-chromenylsulfonyl)guanidino]pentanoic acid (961 mg, 1.45 mmol) to afford 33 (936 mg, 1.21 mmol, 83%) as a brown solid. Mp 90-94° C. $^1$H NMR (CDCl$_3$, 300 MHz): δ 7.71 (d, J=7.5 Hz, 2H, ArH1" and ArH8"); 7.54 (d, J=7.0 Hz, 2H, ArH4" and ArH5"); 7.39 (bs, 1H, NH) 7.34 (t, J=7.5 Hz, 2H, ArH3" and ArH6"); 7.22 (t, J=7.5 Hz, 2H, ArH2" and ArH7"); 6.34 (bs, 1H, NH); 6.12 (d, J=7.5 Hz 1H, NH); 5.65 (m, 1H, H2'); 5.03 (d, J=17.0 Hz, 1H, H3$_a$'); 4.98 (d, J=10.0 Hz, 1H, H3$_b$'); 4.54 (m, 1H, H2); 4.36 (m, 1H, H5); 4.29 (d, J=7.2 Hz, 2H, OCH$_2$—H9"); 4.11 (m, 1H, H9"); 3.65 (s, 3H, OCH$_3$); 3.25 (m, 2H, H8); 2.58 (s, 3H, 7"'-CH$_3$); 2.55 (s, 3H, 5"'-CH$_3$); 2.48 (m, 4H, H1' and H4"'); 2.07 (s, 3H, 8"'-CH$_3$); 1.93 (m, 2H, H6); 1.73 (t, J=6.5 Hz, 2H, H3"'); 1.60 (m, 2H, H7); 1.26 (s, 6H, 2×2"'-CH$_3$). Mass Spectrum (ES, +ve) m/z 774 (20%) [MH$^+$], 130 (100%) [allylGly]. HRMS calcd for C$_{41}$H$_{52}$N$_5$O$_8$S 774.3537, found 774.3517.

Methyl(2S,5S)-2-allyl-5-amino-3-aza-8-[(2,2,5,7,8-pentamethyl-3,4-dihydro-2H-6-chromenylsulfonyl)guanidino]-4-oxooctanoate (34)

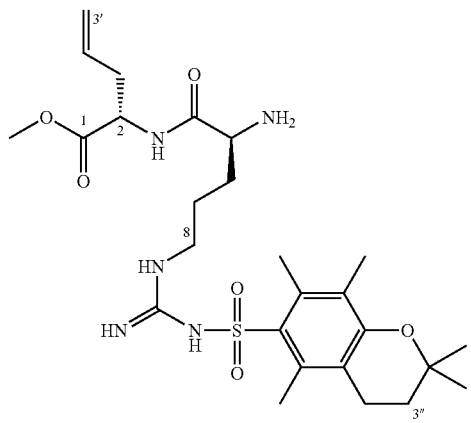

The title compound was synthesized using the general N-Fmoc deprotection procedure (Procedure C), from 33 (749 mg, 0.97 mmol) to yield 34 (259 mg, 0.47 mmol, 48%) as a cream oil, which had spectral data in agreement with that reported.[80] $^1$H NMR (CDCl$_3$, 300 MHz): δ 7.86 (d, J=8.1 Hz, 1H, NH); 6.33 (bs, 3H, NH); 5.66 (m, 1H, H2'); 5.09 (m, 2H, H3'); 4.54 (m, 1H, H2); 3.73 (s, 3H, OCH$_3$); 3.43 (m, 1H, H5); 3.20 (m, 2H, H8); 2.63 (t, J=6.9 Hz, 2H, H4"'); 2.57 (s, 3H, 7"-CH$_3$); 2.55 (s, 3H, 5"-CH$_3$); 2.50 (m, 2H, H1'); 2.10 (s, 3H, 8"-CH$_3$); 1.80 (m, 4H, H7 and H3"'); 1.60 (m, 2H, H6); 1.30 (s, 6H, 2×2"-CH$_3$). Mass Spectrum (ES, +ve) m/z 552 (100%) [MH$^+$]. HRMS calcd for C$_{26}$H$_{42}$N$_5$O$_6$S 552.2856, found 552.2856.

Methyl(2S,5S,8S)-2-allyl-8-(4-allyloxybenzyl)-3,6,9-triaza-5-([{2,2,5,7,8-pentamethyl-3,4-dihydro-2H-6-chromenylsulfonyl}guanidino]propyl)-4,7,10-trioxoundecanoate (35)

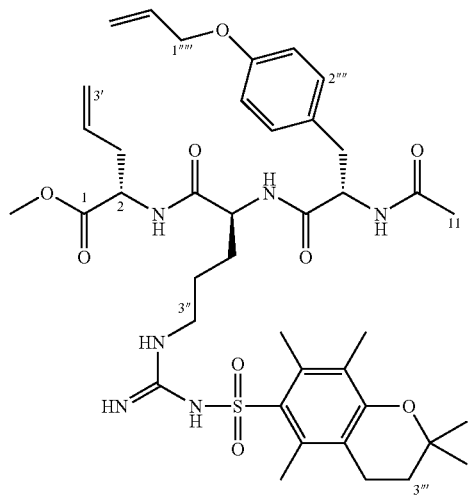

The title compound was synthesized using the general peptide coupling procedure (Procedure B), from 34 (236 mg, 0.43 mmol) and 16 (95 mg, 0.36 mmol) to afford 35 (207 mg, 0.25 mmol, 72%) as a light brown solid. Mp 99-104° C. $^1$H NMR (CDCl$_3$, 500 MHz): δ 7.77 (d, J=7.8 Hz, 1H, NH); 7.69 (bs, 1H, NH); 7.14 (d, J=7.5 Hz, 1H, NH); 7.04 (d, J=8.4 Hz, 2H, ArH2'''' and ArH6''''); 6.74 (d, J=8.4 Hz, 2H, ArH3'''' and ArH5''''); 6.41 (bs, 2H, NH); 6.01 (m, 1H, H2'''''); 5.70 (m, 1H, H2'); 5.37 (dd, J=1.5, 17.4 Hz, 1H, H3$_a$'''''); 5.25 (dd, J=1.5, 10.5 Hz, $^1$H, H3$_b$'''''); 5.07 (d, J=15.3 Hz, 1H, H3$_a$'); 5.03 (d, J=9.3 Hz, 1H, H3$_b$'); 4.74 (m, 1H, H2); 4.64 (bs, 1H, H5); 4.56 (dd, J=6.9, 13.5 Hz, 2H, H8); 4.44 (d, J=5.4 Hz, 2H, H1'''''); 3.68 (s, 3H, OCH$_3$); 3.17 (d, J=4.5 Hz, 2H, H3''); 2.95 (m, 2H, ArCH$_2$); 2.59 (t, J=6.3 Hz, 2H, H4'''); 2.55 (s, 3H, 7'''-CH$_3$); 2.53 (s, 3H, 5'''-CH$_3$); 2.50 (m, 2H, H1'); 2.08 (s, 3H, 8'''-CH$_3$); 1.88 (s, 3H, H11); 1.78 (t, J=6.3 Hz, 2H, H13'''); 1.72 (m, 2H, H7); 1.55 (m, 2H, H6); 1.29 (s, 6H, 2×2'''-CH$_3$). Mass Spectrum (ES, +ve) m/z 797 (100%) [MH$^+$]. HRMS calcd for C$_{40}$H$_{57}$N$_6$O$_9$S 797.3908, found 797.3890.

(7S,10S,13S,4E/Z)-13-Acetamido-8,11-diaza-10-(3-[{2,2,5,7,8-pentamethyl-3,4-dihydro-2H-6-chromenylsulfonyl}guanidino]propyl)-7-methoxycarbonyl-2-oxa-9,12-dioxo-1(1,4)phenylenacyclotetradecaphane-4-ene (36)

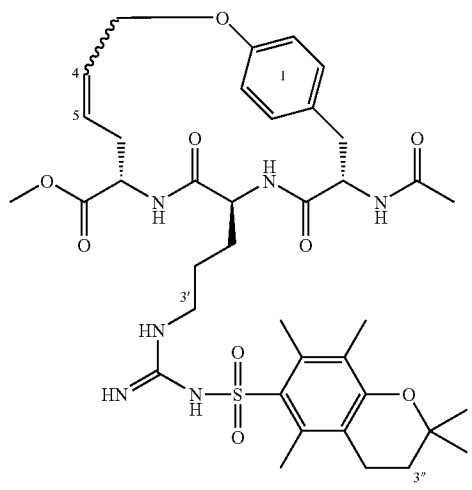

The title compound was prepared using the general procedure for olefin metathesis (Procedure D), from 35 (127 mg, 0.16 mmol) to yield 36 (117 mg, 0.15 mmol, 95%) as a grey solid. Mp 224-228° C. $^1$H NMR (CDCl$_3$, 300 MHz): δ 6.97 (m, 2H, ArH); 6.71 (m, 2H, ArH); 6.41 (bs, 1H, NH); 5.50 (m, H4 and H5); 4.57 (bs, 5H, H3, H7, H10 and H13); 3.67 (s, 3H, OCH$_3$); 3.16 (m, 2H, H3'); 2.56 (m, 10H, H14, 7''-CH$_3$, 5''-CH$_3$ and H4''); 2.08 (s, 3H, 8''-CH$_3$); 1.78 (s, 3H, NCOCH$_3$); 1.52 (m, 2H, H1'); 1.35 (m, 2H, H3''); 1.30 (s, 6H, 2×2''-CH$_3$). Mass Spectrum (ES, +ve) m/z 769 (100%) [MH$^+$]. HRMS calcd for C$_{38}$H$_{53}$N$_6$O$_9$S 769.3595, found 769.3574.

(7S,10S,13S,4E/Z)-13-Acetamido-8,11-diaza-10-(3-[guanidino]propyl)-7-methoxycarbonyl-2-oxa-9,12-dioxo-1(1,4)phenylenacyclotetradecaphane-4-ene hydrochloride (37)

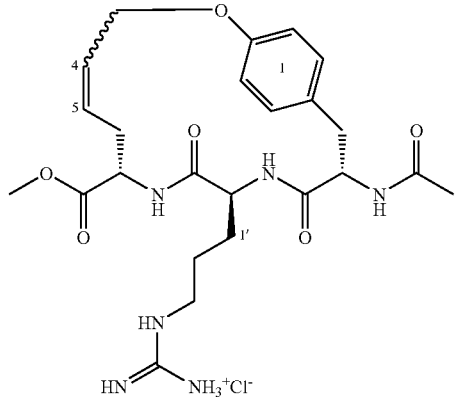

The title compound was synthesized using the general N-Boc deprotection procedure (Procedure A), from 36 (91 mg, 0.12 mmol) to yield 37 as a white solid (38 mg, 0.071, 59%). Mp 218-220° C. $^1$H NMR (CD$_3$OD, 300 MHz): δ 7.05 (m, 2H, ArH); 6.74 (m, 2H, ArH); 5.80 (m, 1H, H5); 5.55 (m, 1H, H4); 4.51 (m, 5H, H3, H7, H10 and H13); 3.68 (m, 3H, OCH$_3$); 3.18 (m, 2H, H3'); 2.84 (m, 2H, H14); 2.49 (m, 2H, H6); 1.99 (s, 3H, NCOCH$_3$); 1.76 (m, 2H, H1'); 1.64 (m, 2H, H2'). $^{13}$C NMR (CD$_3$OD, 75 MHz): δ 173.5, COOCH$_3$; 173.3, C11; 173.2, C9; 172.2, NCOCH$_3$; 158.9, CN$_3$; 157.8, 1-ArC4; 131.5, C4; 129.9, C5; 129.1, 1-ArCH2 and 1-ArCH6; 129.0, 1-ArC1; 116.2, 1-ArCH3 and 1-ArCH5; 66.8, C3; 57.6, C7; 56.0, C10; 54.1, C10; 53.6, C3'; 52.9, OCH$_3$; 42.0, C6; 38.0, C14; 35.3, NCOCH$_3$; 26.2, C1'; 22.6, C2'. Mass Spectrum (ES, +ve) m/z 503 (100%) [M$^+$]. HRMS calcd for C$_{24}$H$_{35}$N$_6$O$_6$ 503.2618, found 503.2603.

Methyl(2R)-2-amino-4-pentenoate hydrochloride (38)

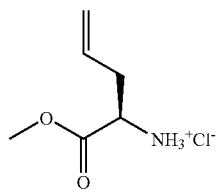

To a suspension of (2R)-2-amino-4-pentenoic acid (200 mg, 1.74 mmol) in methanol (6 mL) at 0° C. was added dropwise thionyl chloride (1 mL). The resulting solution was allowed to stir for 16 h before the solvent was removed by evaporation and the product crystallized with diethyl ether. The diethyl ether was removed by evaporation to yield the title compound (287 mg, 1.74 mmol, 100%) as a white solid which had spectral data in agreement with that reported.[123] Mp 135-140° C. $^1$H NMR (CDCl$_3$, 300 MHz): δ 8.70 (bs, 3H, NH$_3^+$); 5.89 (m, 1H, H4); 5.32 (d, J=17.3 Hz, 1H, H5$_a$); 5.24 (d, J=10.1 Hz, 1H, H5$_b$); 4.31 (m, 1H, H2); 3.81 (s, 3H, OCH$_3$); 2.87 (t, J=6.3 Hz, 2H, H3). Mass Spectrum (ES, +ve) m/z 130 (100%) [M$^+$]. HRMS calcd for C$_6$H$_{12}$NO$_2$ 130.0868, found 130.0870.

Methyl(2R,5R)-2-allyl-3-aza-5-(9H-9-fluorenylmethyloxycarboxamido)-8-[(2,2,5,7,8-pentamethyl-3,4-dihydro-2H-6-chromenylsulfonyl)guanidino]-4-oxooctanoate (39)

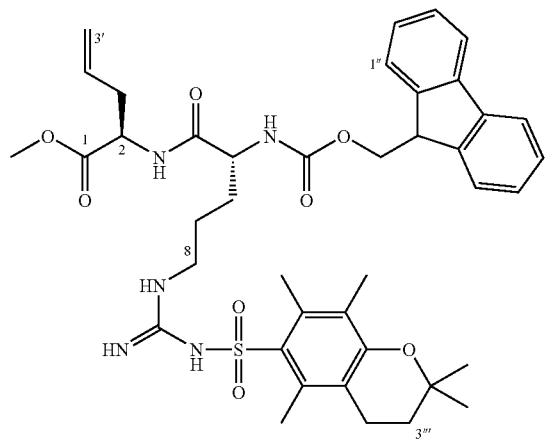

The title compound was synthesised using the general peptide coupling procedure (Procedure B), from 38 (287 mg, 1.74 mmol) and (2R)-2-(9H-9-fluorenylmethyloxycarboxamido)-8-[(2,2,5,7,8-pentamethyl-3,4-dihydro-2H-6-chromenylsulfonyl)guanidino]pentanoic acid (961 mg, 1.45 mmol) to afford 39 (1.01 g, 1.31 mmol, 90%) as a brown solid. Mp 96-98° C. $^1$H NMR (CDCl$_3$, 500 MHz): δ 7.70 (d, J=7.5 Hz, 2H, ArH1" and ArH8"); 7.53 (d, J=5.0 Hz, 2H, ArH4" and ArH5"); 7.40 (d, J=4.5 Hz, 1H, NH); 7.34 (t, J=7.5 Hz, 2H, ArH3" and ArH6"); 7.22 (t, J=7.5 Hz, 2H, ArH2" and ArH7"); 6.34 (s, 2H, NH); 6.12 (bs, 2H, NH); 5.64 (m, 1H, H2'); 5.03 (d, J=17.0 Hz, 1H, H3$_a$'); 4.98 (d, J=10.0 Hz, 1H, H3$_b$'); 4.53 (m, 1H, H2); 4.36 (dd, J=8.5, 12.5 Hz, 1H, H5); 4.29 (d, J=7.0 Hz, 2H, 9"-CH$_2$); 4.10 (m, 1H, H9"); 3.65 (s, 3H, OCH$_3$); 3.28 (m, 2H, H8); 3.22 (bs, 1H, NH); 2.58 (s, 3H, 7'''-CH$_3$); 2.55 (s, 3H, 5'''-CH$_3$); 2.47 (m, 4H, H1' and H14'''); 2.07 (s, 3H, 8'''-CH$_3$); 1.91 (m, 2H, H7); 1.73 (t, J=6.5 Hz, 2H, H3); 1.60 (m, 2H, H6); 1.25 (s, 6H, 2×2'''-CH$_3$). Mass Spectrum (ES, +ve) m/z 774 (100%) [MH$^+$]. HRMS calcd for C$_{41}$H$_{52}$N$_5$O$_8$S 774.3537, found 774.3524.

Methyl(2R,5R)-2-allyl-5-amino-3-aza-8-[(2,2,5,7,8-pentamethyl-3,4-dihydro-2E-6-chromenylsulfonyl)guanidino]-4-oxooctanoate (40)

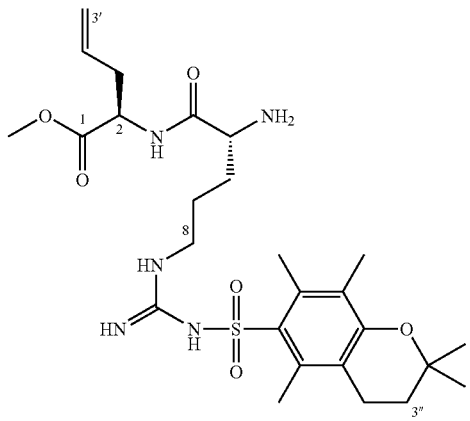

The title compound was synthesized using the general N-Fmoc deprotection procedure (Procedure C), from 39 (693 mg, 0.900 mmol) to yield 40 (387 mg, 0.0700 mmole, 78%) as a cream oil. $^1$H NMR (CDCl$_3$, 300 MHz): δ 7.87 (d, J=7.5 Hz, 1H, NH); 6.35 (bs, 3H, NH); 5.67 (m, 1H, H2'); 5.09 (d, J=16.2 Hz, 1H, H3$_a$'); 5.09 (d, J=12.0 Hz, 1H, H3$_b$'); 4.54 (m, 1H, H2); 3.72 (s, 3H, OCH$_3$); 3.42 (m 1H, H5); 3.19 (d, J=5.4 Hz, 2H, H8); 2.56 (s, 3H, 7"-CH$_3$); 2.54 (s, 3H, 5"-CH$_3$); 2.51 (m, 2H, H11'); 2.10 (s, 3H, 8"-CH$_3$); 2.05 (bs, 2H, H7); 1.80 (t, J=6.3 Hz, 2H, H2"); 1.57 (m, 2H, H6); 1.30 (s, 6H, 2×2"-CH$_3$). Mass Spectrum (ES, +ve) m/z 552.1 (40%) [MH$^+$], 243.0 (100%) [MH$^+$ less allylGly]. HRMS calcd for C$_{26}$H$_{42}$N$_5$O$_6$S 552.2856, found 552.2829.

Methyl(2R,5R,8S)-2-allyl-8-(4-allyloxybenzyl)-3,6,9-triaza-5-([{2,2,5,7,8-pentamethyl-3,4-dihydro-2H-6-chromenylsulfonyl}guanidino]propyl)-4,7,10-trioxoundecanoate (41)

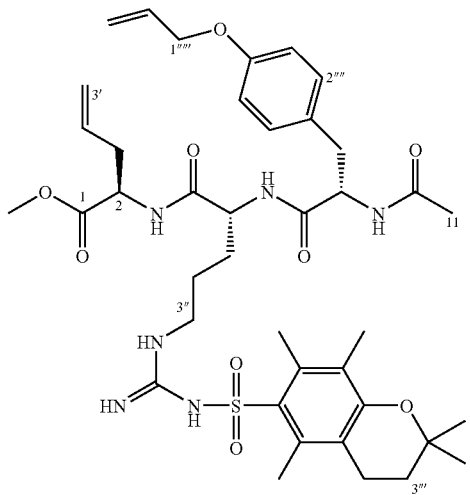

The title compound was synthesised using the general peptide coupling procedure (Procedure B) using 40 (387 mg, 0.700 mmol) and 16 (153 mg, 0.580 mmol) to afford 41 (297 mg, 0.37 mmol, 64%) as a light brown solid. Mp 217-220° C. $^1$H NMR (CDCl$_3$, 500 MHz): δ 7.22 (bs, 1H, NH); 7.10 (d, J=8.0 Hz, 2H, ArH2"" and ArH6""); 6.88 (bs, 1H, NH); 6.82 (d, J=8.5 Hz, 2H, ArH3"" and ArH5""); 6.31 (d, J=7.0 Hz, 1H, NH); 6.17 (bs, 1H, NH); 6.01 (m, 1H, H2''''); 5.69 (m, 1H, H2'); 5.38 (d, J=17.0 Hz, 1H, H3$_a$''''); 5.26 (d, J=10 Hz, 1H, H3$_b$''''); 5.11 (d, J=17.0 Hz, 1H, H3$_a$'); 5.08 (d, J=10.5 Hz, 1H, H3$_b$'); 4.56 (m, 1H, H2); 4.99 (m, 3H, H5 and H1''''); 4.43 (d, J=7.5 Hz, 1H, H8); 3.71 (s, 3H, OCH$_3$); 3.15 (bs, 2H, H3''); 3.00 (m, 2H, ArCH$_2$); 2.63 (t, J=6.5 Hz, 2H, H4'''); 2.59 (s, 3H, 7'''-CH$_3$); 2.57 (s, 3H, 5'''-CH$_3$); 2.51 (m, 2H, H1'); 2.11 (s, 3H, 8'''-CH$_3$); 1.97 (s, 3H, H11); 1.80 (t, J=6.5 Hz, 2H, H3'''); 1.58 (s, 6H, 2×2'''-CH$_3$); 1.30 (s, 4H, H1'' and H2''). Mass Spectrum (ES, +ve) m/z 797.4 (100%) [M]. HRMS calcd for C$_{40}$H$_{57}$N$_6$O$_9$S 797.3908, found 797.3915.

(7R,10R,13S,4E/Z)-13-Acetamido-8,11-diaza-10-(3-imino[{2,2,5,7,8-pentamethyl-3,4-dihydro-2H-6-chromenylsulfonyl}guanidino]propyl)-7-methoxycarbonyl-2-oxa-9,12-dioxo-1(1,4)phenylenacyclotetradecaphane-4-ene (42)

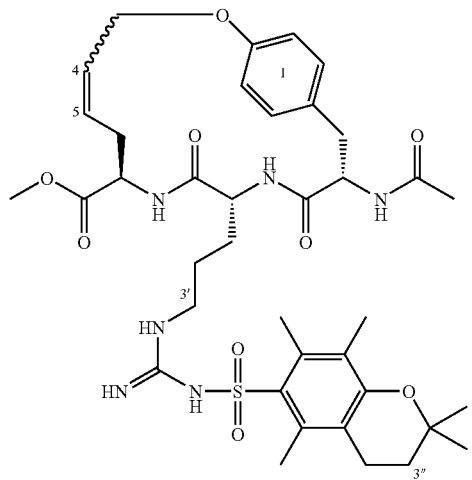

The title compound was prepared using the general procedure for olefin metathesis (Procedure D), from 41 (170 mg, 0.210 mmol) to yield 42 (160 mg, 0.210 mmol, 99%) as a grey solid. Mp 205-207° C. $^1$H NMR (CD$_3$OD, 300 MHz): δ 8.05 (m, 2H, NH); 7.02 (m, 2H, ArH); 6.72 (m, 2H, ArH); 6.48 (bs, 1H, NH); 5.75 (m, 2H, NH); 5.42 (m, H4 and H5); 4.62 (bs, 2H, H3); 4.30 (m, 3H, H7, H10 and H13); 3.66 (s, 3H, OCH$_3$); 2.90 (m, 4H, H3' and H14); 2.60 (m, 6H, 5''-CH$_3$ and 7''-CH$_3$); 2.55 (m, 2H, H4''); 2.00 (s, 3H, 8''-CH$_3$); 1.75 (s, 3H, NCOCH$_3$); 1.55 (m, 2H, H1'); 1.34 (bs, 2H, H3''); 1.27 (s, 6H, 2×2''-CH$_3$). Mass Spectrum (ES, -ve) m/z 769.5 (85%) [M$^+$]. HRMS calcd for C$_{38}$H$_{53}$N$_6$O$_9$S 769.3595, found 769.3631.

(7R,10R,13S,4E/Z)-13-Acetamido-8,11-diaza-10-(3-[guanidino]propyl)-7-methoxycarbonyl-2-oxa-9,12-dioxo-1(1,4)phenylenacyclotetradecaphane-4-ene hydrochloride (43)

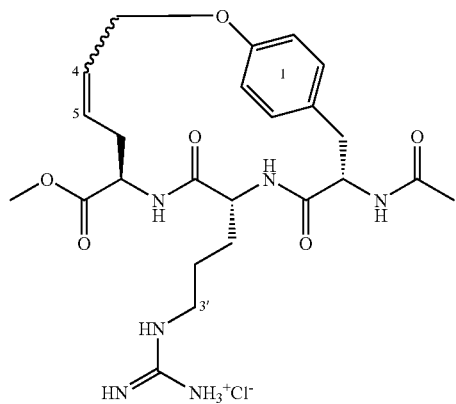

The title compound was synthesized using the general N-Boc deprotection procedure (Procedure A), from 42 (108 mg, 0.140 mmol) to yield 43 (25 mg, 0.049 mmol, 35%) as a white solid. Mp 170-176° C. $^1$H NMR (CD$_3$OD, 300 MHz): δ 7.08 (m, 2H, ArH); 6.76 (m, 2H, ArH); 5.90 (m, 1H, H5); 5.54 (m, 1H, H4); 4.45 (m, 5H, H3, H7, H10 and H13); 3.69 (m, 3H, OCH$_3$); 3.07 (m, 2H, H3'); 2.92 (m, 2H, H14); 2.49 (m, 2H, H6); 1.94 (s, 3H, NCOCH$_3$); 1.65 (m, 2H, H1'); 1.33 (m, 2H, H2'). $^{13}$C NMR (CD$_3$OD, 75 MHz): δ 173.8, COOCH$_3$; 173.5, C11; 173.2, C9; 172.6, NCOCH$_3$; 158.4, $\overline{C}$N$_3$; 157.2, 1-ArC4; 131.4, C4; 130.6, C5; $\overline{1}$29.7, 1-ArCH2 and 1-ArCH6; 129.3, 1-ArC1; 115.9, 1-ArCH3 and 1-ArCH5; 67.3, C3; 57.2, C7; 54.0, C10; 53.7, C13; 53.2, C3'; 52.9, OCH$_3$; 42.0, C6; 37.9, C14; 35.2, NCOCH$_3$; 26.1, C1'; 22.6, C2'. Mass Spectrum (ES, +ve) m/z $\overline{503}$ (35%) [M$^+$]. HRMS calcd for C$_{24}$H$_{35}$N$_6$O$_6$ 503.2618, found 503.2644.

Methyl(2R,5S)-2-allyl-3-aza-5-(9H-9-fluorenylmethyloxycarboxamido)-8-[(2,2,5,7,8-pentamethyl-3,4-dihydro-2H-6-chromenylsulfonyl)guanidino]-4-oxooctanoate (44)

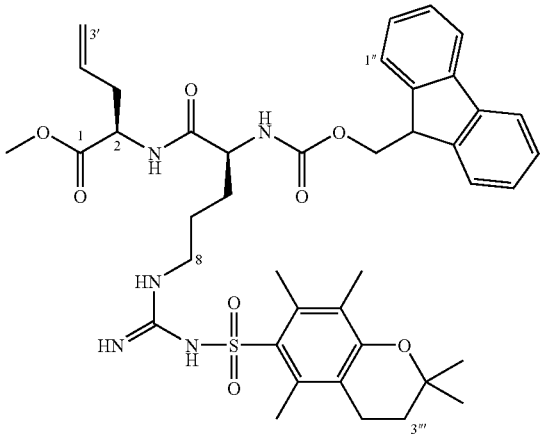

The title compound was synthesized using the general peptide coupling procedure (Procedure B), from 38 (287 mg, 1.74 mmol) and (2S)-2-(9H-9-fluorenylmethyloxycarboxamido)-8-[(2,2,5,7,8-pentamethyl-3,4-dihydro-2H-6-chromenylsulfonyl)guanidino]pentanoic acid (961 mg, 1.45 mmol) to afford 44 (1.00 g, 1.29 mmol, 89%) as a brown foam. Mp 90-92° C. $^1$H NMR (CDCl$_3$, 300 MHz): δ 7.70 (d, J=7.6 Hz, 2H, ArH1'' and ArH8''); 7.51 (d, J=7.6 Hz, 2H, ArH4'' and ArH5''); 7.33 (t, J=7.2 Hz, 2H, ArH3'' and ArH6''); 7.20 (t, J=7.2 Hz, 2H, ArH2'' and ArH7''); 6.42 (d, J=7.6 Hz, 1H, NH); 6.34 (s, 1H, NH); 6.20 (bs, 1H, NH); 5.61 (m, 1H, H2'); 5.02 (d, J=18.1 Hz, 1H, H3$_a$'); 4.97 (d, J=10.5 Hz, 1H, H3$_b$'); 4.53 (dd, J=7.6, 13.1 Hz, 1H, H2); 4.26 (d, J=7.2 Hz, 3H, H5 and 9''-CH$_2$); 4.06 (t, J=7.2 Hz, 1H, H9''); 3.63 (s, 3H, OCH$_3$); 3.23 (bs, 2H, H8); 2.57 (s, 3H, 7'''-CH$_3$); 2.54 (s, 3H, 5'''-CH$_3$); 2.47 (m, 4H, H1' and H14'''); 2.07 (s, 3H, 8'''-CH$_3$); 1.88 (m, 2H, H6); 1.70 (t, J=6.7 Hz, 2H, H3'''); 1.60 (m, 2H, H7); 1.23 (s, 6H, 2×2'''-CH$_3$). Mass Spectrum (ES, +ve) m/z 774 (12%) [MH$^+$], 130 (100%) [allylGly]. HRMS calcd for C$_{41}$H$_{52}$N$_5$O$_8$S 774.3537, found 774.3536.

Methyl(2R,5S)-2-allyl-5-amino-3-aza-8-[(2,2,5,7,8-pentamethyl-3,4-dihydro-2H-6-chromenylsulfonyl)guanidino]-4-oxooctanoate (45)

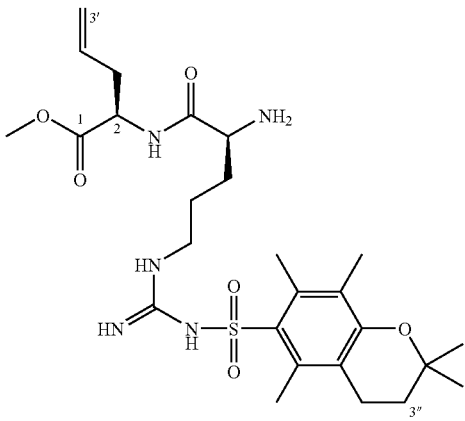

The title compound was synthesized using the general N-Fmoc deprotection procedure (Procedure C), from 44 (788 mg, 1.01 mmol) to yield 45 (552 mg, 1.00 mmole, 99%) as a cream oil. $^1$H NMR (CDCl$_3$, 300 MHz): δ 7.86 (d, J=7.5 Hz, 1H, NH); 6.33 (bs, 3H, NH); 5.69 (m, 1H, H2'); 5.12 (d, J=16.8 Hz, 1H, H3$_a$'); 5.11 (d, J=10.8 Hz, 1H, H3$_b$'); 4.53 (dd, J=7.2, 12.9 Hz, 1H, H2); 3.71 (s, 3H, OCH$_3$); 3.41 (d, J=7.2 Hz, 1H, H5); 3.19 (m, 2H, H8); 2.57 (m, 2H, H1'); 2.57 (s, 3H, 7"-CH$_3$); 2.55 (s, 3H, 5"-CH$_3$); 2.10 (s, 3H, 8"-CH$_3$); 1.80 (m, 4H, H7 and H3"); 1.58 (m, 2H, H6); 1.30 (s, 6H, 2×2"-CH$_3$). Mass Spectrum (ES, +ve) m/z 552.1 (50%) [MH$^+$], 162.7 (100%). HRMS calcd for C$_{26}$H$_{42}$N$_5$O$_6$S 552.2856, found 552.2834.

Methyl(2R,5S,8S)-2-allyl-8-(4-allyloxybenzyl)-3,6,9-triaza-5-([{2,2,5,7,8-pentamethyl-3,4-dihydro-2H-6-chromenylsulfonyl}guanidino]propyl)-4,7,10-trioxoundecanoate (46)

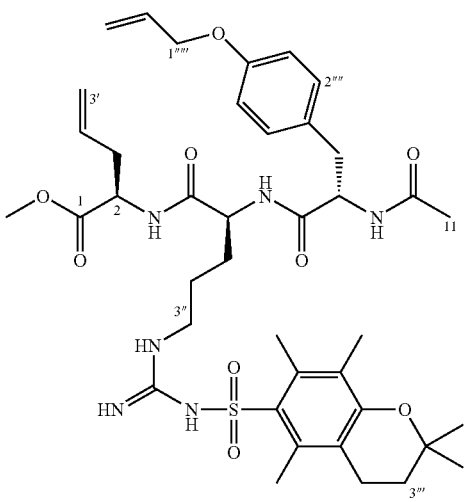

The title compound was synthesised using the general peptide coupling procedure (Procedure B), from 45 (513 mg, 0.930 mmol) and 16 (204 mg, 0.78 mmol) to afford 46 (496 mg, 0.622 mmol, 80%) as a light brown solid. Mp 98-102° C. $^1$H NMR (CDCl$_3$, 500 MHz): δ 7.71 (d, J=7.0 Hz, 1H, NH); 7.40 (d, J=7.0 Hz, 1H, NH); 7.06 (d, J=8.5 Hz, 2H, ArH2"" and ArH6""); 6.99 (bs, 1H, NH); 6.76 (d, J=9.0 Hz, 2H, ArH3"" and ArH5""); 6.38 (bs, 2H, NH); 6.20 (bs, 1H, NH); 6.02 (m, 1H, H2""'); 5.69 (m, 1H, H2'); 5.38 (dd, J=1.5, 17.0 Hz, 1H, H3$_a$""'); 5.25 (dd, J=1.0, 11.0 Hz, 1H, H3$_b$""'); 5.09 (d, J=17.5 Hz, 1H, H3$_a$'); 5.06 (d, J=10.5 Hz, 1H, H3$_b$'); 4.66 (m, 1H, H2); 4.55 (m, 2H, H5 and H8); 4.45 (d, J=5.5 Hz, 2H, H1""'); 3.67 (s, 3H, OCH$_3$); 3.20 (d, J=4.5 Hz, 2H, H3'); 2.97 (m, 2H, ArCH$_2$); 2.61 (t, J=6.0 Hz, 2H, H4'''); 2.57 (s, 3H, 7'''-CH$_3$); 2.55 (s, 3H, 5'''-CH$_3$); 2.53 (m, 2H, H1'); 2.09 (s, 3H, 8'''-CH$_3$); 1.88 (s, 3H, H11); 1.79 (t, J=7.0 Hz, 2H, H3'''); 1.74 (m, 2H, H7); 1.57 (m, 2H, H6); 1.30 (s, 6H, 2×2'''-CH$_3$). Mass Spectrum (ES, +ve) m/z 819 (100%) [MNa$^+$]. HRMS calcd for C$_{40}$H$_{57}$N$_6$O$_9$S 797.3908, found 797.3873.

(7R,10S,13S,4E/Z)-13-Acetamido-8,11-diaza-10-(3-imino[{2,2,5,7,8-pentamethyl-3,4-dihydro-2H-6-chromenylsulfonyl}guanidino]propyl)-7-methoxycarbonyl-2-oxa-9,12-dioxo-1(1,4)phenylenacyclotetradecaphane-4-ene (47)

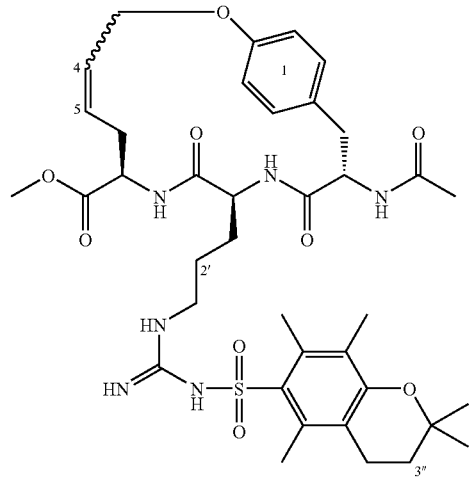

The title compound was prepared using the general procedure for olefin metathesis (Procedure D), from 46 (262 mg, 0.330 mmol) to yield 47 (217 mg, 0.280 mmol, 86%) as a grey solid. Mp 174-176° C. $^1$H NMR (DMSO, 500 MHz): δ 8.10 (m, 2H, NH); 7.06 (m, 2H, ArH); 6.73 (m, 2H, ArH); 6.44 (bs, 1H, NH); 5.70 (m, 2H, NH); 5.40 (m, H4 and H5); 4.62 (bs, 2H, H3); 4.28 (m, 3H, H7, H10 and H13); 3.55 (s, 3H, OCH$_3$); 3.00 (m, 2H, H3'); 2.80 (m, 2H, H14); 2.44 (m, 6H, 5"-CH$_3$ and 7"'-CH$_3$); 2.55 (m, 2H, H4"); 2.00 (s, 3H, 8"-CH$_3$); 1.73 (s, 3H, NCOCH$_3$); 1.51 (m, 2H, H1'); 1.35 (bs, 2H, H3"); 1.23 (s, 6H, 2×2"-CH$_3$). Mass Spectrum (ES, +ve) m/z 767 (65%) [MH$^+$]. HRMS calcd for C$_{38}$H$_{53}$N$_6$O$_9$S 769.3595, found 769.3630.

(7R,10S,13S,4E/Z)-13-Acetamido-8,11-diaza-10-(3-[guanidino]propyl)-7-methoxycarbonyl-2-oxa-9,12-dioxo-1(1,4)phenylenacyclotetradecaphane-4-ene hydrochloride (48)

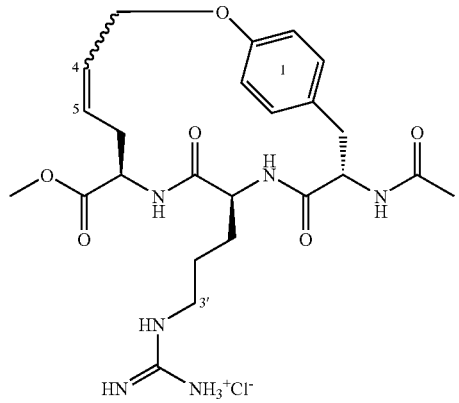

The title compound was synthesized using the general N-Boc deprotection procedure (Procedure A), from 47 (129 mg, 0.16 mmol) to yield 48 as a white solid (71 mg, 0.14 mmol, 86%). Mp 134-138° C. $^1$H NMR (CD$_3$OD, 300 MHz): δ 7.10 (m, 2H, ArH); 6.78 (m, 2H, ArH); 5.85 (m, 1H, H5); 5.46 (m, 1H, H4); 4.43 (m, 5H, H3, H7, H10 and H13); 3.69 (m, 3H, OCH$_3$); 3.30 (m, 2H, H3'); 2.95 (m, 2H, H14); 2.53 (m, 2H, H6); 1.94 (s, 3H, NCOCH$_3$); 1.80 (m, 2H, H1'); 1.62 (m, 2H, H2'). $^{13}$C NMR (CD$_3$OD, 75 MHz): δ 174.0, COOCH$_3$; 173.6, C11; 173.3, C9; 173.0, NCOCH$_3$; 158.4, $\overline{C}$N$_3$; 157.2, 1-ArC4; 131.3, C4; 130.6, C5; $\overline{12}$9.7, 1-ArCH2 and 1-ArCH6; 129.5, 1-ArC1; 115.8, 1-ArCH3 and 1-ArCH5; 67.7, C3; 57.8, C7; 54.9, C10; 54.0, C10; 53.2, C3'; 52.9, OCH$_3$; 42.0, C6; 37.7, C14; 33.2, NCOCH$_3$; 26.5, C1'; 22.3, C2'. Mass Spectrum (ES, +ve) m/z 503.$\overline{4}$ (100%) [M$^+$]. HRMS calcd for C$_{24}$H$_{35}$N$_6$O$_6$ 503.2618, found 503.2666.

Methyl(2R)-2-amino-(4-hydroxyphenyl)-2-propanoate hydrochloride (50)

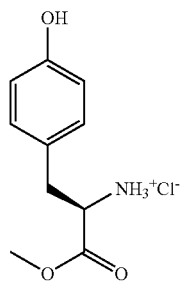

To a solution of (2R)-2-amino-3-(4-hydroxyphenyl)propanoic acid 49 (1.07 g, 5.9 mmol) in anhydrous MeOH (10 mL) at 0° C. was added dropwise thionyl chloride (2 mL). The resulting mixture was allowed to stir for 16 h before the solvent was removed by evaporation to yield the title compound (1.36 g, 5.9 mmol, 100%) as a white solid, which had spectral data in agreement with that reported.[124] [α]$_D^{23}$ -27.7 (c. 0.1, EtOH). (lit. [α]$_D^{24}$ -27.1 (c. 2.0, MeOH)[124] Mp 176° C. (lit. 134-136° C.)[124] $^1$H NMR (CD$_3$OD, 300 MHz): δ 7.05 (d, J=8.4 Hz, 2H, ArH2' and ArH6'); 6.82 (d, J=8.4 Hz, 2H, ArH3' and ArH5'); 4.13 (t, J=6.9 Hz, 1H, H2), 3.83 (s, 3H, OCH$_3$); 3.22 (dd, J=6.0, 14.4 Hz, 1H, 3H$_a$); 3.12 (dd, J=6.9, 14.7 Hz, 1H, $^3$H$_b$). Mass Spectrum (CI, +ve) m/z 196 (100%) [M]. HRMS calcd for C$_{10}$H$_{14}$NO$_3$ 196.0974, found 196.0985.

Methyl(2R)-2-acetamido-3-(4-hydroxyphenyl)propanoate (51)

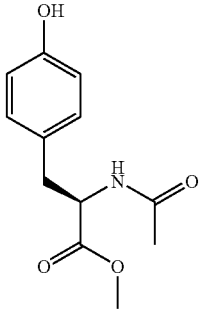

A solution of the HCl salt 50 (1.09 g, 6.02 mmol) in water (3 mL) was cooled to 0° C. before the addition of 5M sodium acetate solution (35 mL) and a small amount of ice. Acetic anhydride (10 mL) was added and the resulting precipitate was collected by vacuum filtration and dried to yield the title compound (1.09 g, 4.58 mmol, 76%) as a white solid, which had spectral data in agreement with that reported.[124] [α]$_D^{25}$ -27.2 (c. 0.1, EtOH) (lit. [α]$_D^{25}$ -26.6 (c. 0.1, MeOH)[124] Mp 132-133° C. (lit. 134-135.5° C.)[124] $^1$H NMR (CDCl$_3$, 300 MHz): δ 6.94 (d, J=8.4 Hz, 2H, ArH2' and ArH6'); 6.75 (d, J=8.4 Hz, 2H, ArH3' and ArH5'); 4.77 (m, 1H, H2); 3.71 (s, 3H, OCH$_3$); 3.04 (dd, J=5.7, 14.1 Hz, 1H, 3H1$_a$); 2.95 (dd, J=6.6, 14.1 Hz, 1H, 3H$_b$); 1.96 (s, 3H, NCOCH$_1$). Mass Spectrum (CI, +ve) m/z 238 (100%) [MH$^+$]. HRMS calcd for C$_{12}$H$_{16}$N$_1$O$_4$ 238.107933, found 238.108226.

Methyl(2R)-2-acetamido-3-(4-allyloxyphenyl)propanoate (52)

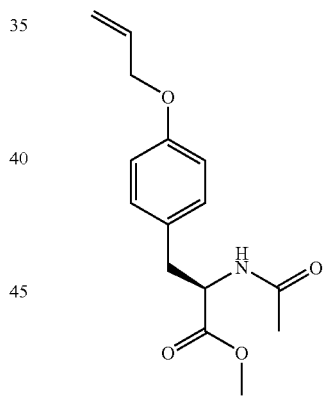

To a solution of 51 (989 mg, 4.17 mmol), and anhydrous K$_2$CO$_3$ (1.15 g, 8.34 mmol) in DMF (10 mL) was added allyl bromide (1.01 g, 8.34 mmol) and the resulting mixture was allowed to stir for 16 h under a nitrogen atmosphere. The reaction was quenched with water (30 mL), extracted with ethyl acetate (3×30 mL), and the combined organics were washed with water (5×20 mL) before drying. The solvent was evaporated to yield the title compound (985 mg, 3.56 mmol, 85%) as a pale yellow solid. [α]$_D^{25}$ -24.2 (c. 0.1, EtOH). Mp 90° C. $^1$H NMR (CDCl$_3$, 300 MHz): δ 6.97 (d, J=8.7 Hz, 2H, ArH2' and ArH6'); 6.80 (d, J=8.7 Hz, 2H, ArH3' and ArH5'); 6.09 (d, J=7.8 Hz, 1H, NH); 6.01 (m, 1H, H2"); 5.37 (dd, J=1.8, 17.4 Hz, 1H, H3$_a$"); 5.25 (dd, J=1.8, 10.5 Hz, 1H, H3$_b$"); 4.80 (m, 1H, H2); 4.47 (d, J=5.5 Hz, 2H, H1"); 3.68 (s, 3H, OCH$_3$); 3.04 (m, 2H, H3); 1.99 (s, 3H, NCOCH$_3$). Mass Spectrum (CI, +ve) m/z 278 (100%) [MH$^+$]. HRMS (EI) calcd for C$_{15}$H$_{19}$NO$_4$ 277.131408, found 277.130309.

183

(2R)-2-Acetamido-3-(4-Allyloxyphenyl)propanoic acid (53)

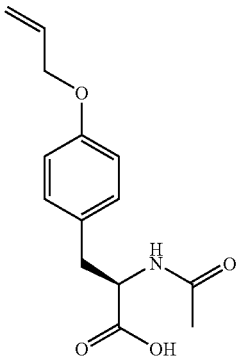

To a solution of 52 (900 mg, 3.25 mmol) in THF/water, 3:1 (10 mL) was added lithium hydroxide monohydrate (273 mg, 6.5 mmol), and the resulting suspension was allowed to stir for 16 h. The reaction mixture was diluted with water (30 mL) and the THF was removed ii vacuo.

The aqueous layer was extracted with diethyl ether (40 mL) to remove unreacted starting material. The aqueous phase was acidified with 10% HCl and the resulting precipitate was extracted with DCM (3×40 mL). The combined DCM fractions were dried and evaporated to yield the title compound (750 mg, 2.85 mmol, 88%) as a white solid. [α]$D^{23}$ −23.2 (c. 0.1, EtOH). Mp 75° C. $^1$H NMR (D$_6$ acetone, 300 MHz): δ 7.27 (d, J=7.8 Hz, 1H, NH); 7.17 (d, J=8.7 Hz, 2H, ArH2' and ArH6'); 6.86 (d, J=8.7 Hz, 2H, ArH3' and ArH5'); 6.06 (m, 1H, H2"); 5.40 (dd J=1.5 Hz, 17.5 Hz, 1H, H3$_a$"); 5.23 (dd, J=1.5, 10.5 Hz, 1H, H3$_b$"); 4.67 (dd, J=5.1, 8.1, 10.5 Hz 1H, H2); 4.53 (d, J=5.1 Hz, 2H, H1"); 3.11 (dd, J=5.4, 14.1 Hz, 1H, 3H$_a$); 2.93 (dd, J=8.1, 14.1, 1H, 3H$_b$); 1.89 (s, 3H, NCOCH$_3$). Mass Spectrum (CI, +ve) m/z 264 (100%) [MH$^+$]. HRMS calcd for C$_{14}$H$_{18}$NO$_4$ 264.123583, found 264.123770.

Methyl(2S,5S,8R)-2-allyl-8-(4-allyloxybenzyl)-3,6,9-triaza-5-([{2,2,5,7,8-pentamethyl-3,4-dihydro-2H-6-chromenylsulfonyl}guanidino]propyl)-4,7,10-trioxoundecanoate (54)

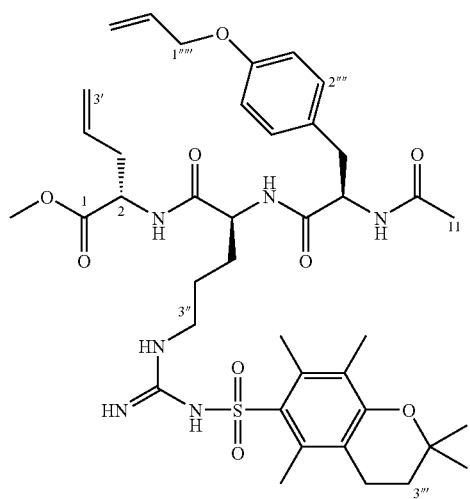

184

The title compound was synthesised using the general peptide coupling procedure (Procedure B), from 34 (654 mg, 1.19 mmol) and 53 (260 mg, 0.99 mmol) to afford 54 (683 mg, 0.86 mmol, 87%) as a light brown solid. Mp 200-204° C. $^1$H NMR (CDCl$_3$, 300 MHz): δ 7.10 (d, J=8.4 Hz, 2H, ArH2"" and ArH6""); 6.90 (d, J=4.8 Hz, 1H, NH); 6.57 (d, J=8.4 Hz, 2H, ArH3"" and ArH5""); 6.34 (d, J=7.5 Hz, 1H, NH); 6.19 (bs, 2H, NH); 6.00 (m, 1H, H2""'); 5.70 (m, 1H, H2'); 5.37 (dd, J=1.8, 17.1 Hz, 1H, H3$_a$""'); 5.26 (dd, J=1.8, 10.5 Hz, 1H, H3$_b$""'); 5.11 (d, J=12.0 Hz, 1H, H3$_a$'); 5.03 (d, J=10.0 Hz, 1H, H3$_b$'); 4.49 (m, 5H, H2, H5, H8 and H1""'); 3.70 (s, 3H, OCH$_3$); 3.16 (m, 2H, H3"); 2.99 (m, 2H, ArCH$_2$); 2.63 (t, J=6.3 Hz, 2H, H4'''); 2.59 (s, 3H, 7'''-CH$_3$); 2.57 (s, 3H, 5'''-CH$_3$); 2.54 (m, 2H, H1'); 2.11 (s, 3H, 8'''-CH$_3$); 1.96 (s, 3H, H11); 1.80 (t, J=6.3 Hz, 2H, H3'''); 1.72 (m, 2H, H7); 1.58 (m, 2H, H6); 1.30 (s, 6H, 2×2'''-CH$_3$). Mass Spectrum (ES, +ve) m/z 797 (40%) [MH$^+$], 106 (100%). HRMS calcd for C$_{40}$H$_{57}$N$_6$O$_9$S 797.3908, found 797.3926.

(7S,10S,13R,4E/Z)-13-Acetamido-8,11-diaza-10-(3-[{2,2,5,7,8-pentamethyl-3,4-dihydro-2H-6-chromenylsulfonyl}guanidino]propyl)-7-methoxycarbonyl-2-oxa-9,12-dioxo-1(1,4)phenylenacyclotetradecaphane-4-ene (55)

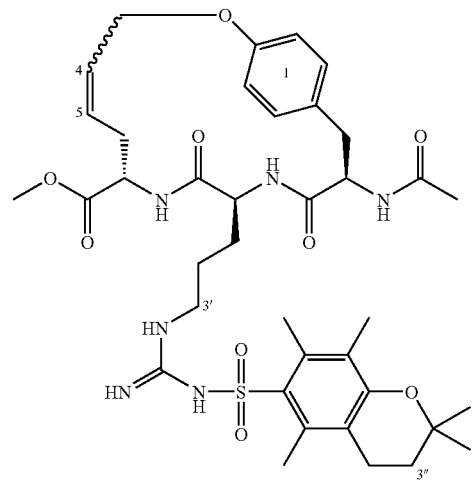

The title compound was prepared using the general procedure for olefin metathesis (Procedure D), from 54 (366 mg, 0.46 mmol) to yield 55 (307 mg, 0.40 mmol, 87%) as a grey solid. Mp 186-190° C. $^1$H NMR (DMSO 500 MHz): δ 8.17 (m, 3H, NM; 7.02 (m, 2H, ArH); 6.75 (m, 2H, ArH); 6.41 (bs, 1H, NH); 5.75 (m, 1H H5); 5.45 (m, 1H, H4); 4.42 (m, 5H, H3, H7, H10 and H13); 3.69 (s, 3H, OCH$_3$); 3.06 (m, 2H, H3'); 2.62 (m, 2H, H4"); 2.56 (m, 8H, H14, 7"-CH$_3$, and 5"-CH$_3$); 2.08 (s, 3H, 8"-CH$_3$); 1.85 (s, 3H, NCOCH$_3$); 1.60 (m, 2H, H1'); 1.40 (m, 2H, H3"); 1.26 (s, 6H, 2×$\overline{2}$"-CH$_3$). Mass Spectrum (ES, +ve) m/z 769 (40%) [MH$^+$], 106 (100%). HRMS calcd for C38H$_{53}$N$_6$O$_9$S 769.3595, found 769.3600.

(7S,10S,13R,4E/Z)-13-Acetamido-8,11-diaza-10-(3-[amino{imino}methylamino]propyl)-7-methoxycarbonyl-2-oxa-9,12-dioxo-1(1,4)phenylenacyclotetradecaphane-4-ene (56)

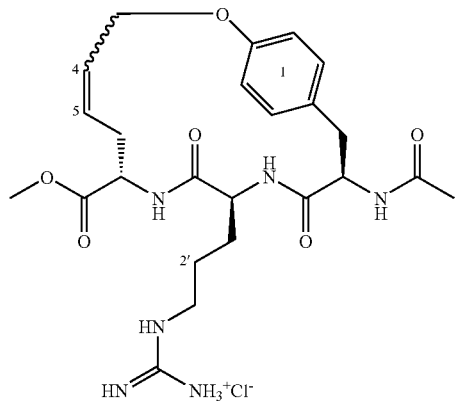

The title compound was synthesized using the general N-Boc deprotection procedure (Procedure A), from 55 (128 mg, 0.17 mmol) to yield 56 as a highly hydroscopic solid (29 mg, 0.058 mmol, 34%). $^1$H NMR (CD$_3$OD, 300 MHz): δ 8.19 (m, 3H, NH); 7.63 (bs, 1H, NH); 7.05 (m, 2H, ArH); 6.67 (m, 2H, ArH); 5.78 (m, 1H, H5); 5.25 (m, 1H, H4); 4.43 (m, 5H, H3, H7, H10 and H13); 3.58 (m, 3H, OCH$_3$); 3.06 (m, 2H, H3'); 2.85 (m, 2H, H14); 2.51 (m, 2H, H6); 1.77 (s, 3H, NCOCH$_3$); 1.65 (m, 2H, H11'); 1.37 (m, 2H, H2'). $^{13}$C NMR (CD$_3$OD, 75 MHz): δ 171.3, COOCH$_3$; 171.6, C11; 171.3, C9; 169.4, NCOCH$_3$; 156.8, $\overline{C}\overline{N}_3$; 155.8, 1-ArC4; 130.2, C4; 128.8, C5; $\overline{1}\overline{2}8.2$, 1-ArCH2 and 1-ArCH6; 127.9, 1-ArC1; 114.9, 1-ArCH3 and 1-ArCH5; 67.1, C3; 55.2, C7; 54.7, C10; 52.9, C10; 51.8, C3'; 51.6, OCH$_3$; 42.0, C6; 36.9, C14; 33.9, NCOCH$_3$; 29.0, C1'; 22.4, C2'. Mass Spectrum (ES, +ve) m/z 503 ($\overline{30}$%) [M$^+$], 102 (100%). HRMS calcd for C$_{24}$H$_{35}$N$_6$O$_6$ 503.2618, found 503.2638.

Methyl(2S)-(4-hydroxyphenyl)-2-tert-butoxycarboxamido propanoate (58)

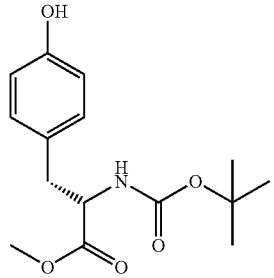

To a solution of (2S)-2-amino-3-(4-hydroxyphenyl)propanoic acid 57 (5.23 g, 28.9 mmol) in anhydrous MeOH (20 mL) at 0° C. was added dropwise thionyl chloride (2 mL). The resulting mixture was allowed to stir for 40 h before the solvent was removed by evaporation and the resulting hydrochloride salt was dissolved in DMF (15 mL). To this solution was added di-tert-butyl-dicarbonate (9.44 g, 43.3 mmol) and the reaction mixture was allowed to reach RT whilst stirring. After 16 h the reaction was quenched with water (30 mL) and extracted with EtOAc (3×30 mL). The combined organic fractions were washed with water (5×20 mL), dried and evaporated. The crude product was purified by flash column chromatography (25:1, DCM/MeOH) to yield the title compound (1.32 g, 4.48 mmol, 16%) as a yellow oil, which had spectral data in agreement with that reported.[125] $^1$H NMR (CDCl$_3$, 300 MHz): δ 6.95 (d, J=8.4 Hz, 2H, ArH2' and ArH6'); 6.73 (d, J=8.4 Hz, 2H, ArH3' and ArH5'); 6.51 (bs, OH); 5.05 (d, J=8.4 Hz, 1H, NH); 4.53 (m, 1H, H2), 3.71 (s, 3H, OCH$_3$); 2.99 (m, 2H, H3); 1.42 (s, 9H, C(CH$_3$)$_3$). Mass Spectrum (CI, +ve) m/z 196 (100%) [MH$^+$ (less Boc)]. HRMS calcd for C$_{16}$H$_{22}$NO$_5$ 296.1498, found 296.1503.

Methyl(2S)-3-(4-allyloxyphenyl)-2-tert-butoxycarboxamidopropanoate (59)

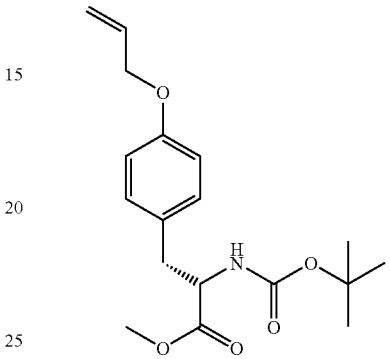

To a solution of 58 (1.30 g, 4.39 mmol) in DMF (15 mL) under N$_2$ atmosphere was added K$_2$CO$_3$ (1.21 g, 8.79 mmol) and the resulting suspension was allowed to stir for 20 min before the addition of allyl bromide (0.76 mL, 8.79 mmol). The reaction mixture was allowed to stir for 16 h before quenching with water (40 mL) and extracting with EtOAc (3×40 mL). The combined organic fractions were washed with water (4×40 mL), dried and evaporated to yield the title compound (1.21 g, 3.35 mmol, 76%) as a clear solid, which had spectral data in agreement with that reported.[126] Mp 142-144° C. (lit. 145° C.)[126] $^1$H NMR (CDCl$_3$, 300 MHz): δ 7.03 (d, J=8.8 Hz, 2H, ArH2' and ArH6'); 6.84 (d, J=8.4 Hz, 2H, ArH3' and ArH5'); 6.04 (m, 1H, H2"); 5.34 (m, 2H, H3"); 4.97 (d, J=8.0 Hz, 1H, NH); 4.50 (m, 3H, H1" and H2); 3.70 (s, 3H, OCH$_3$); 3.02 (m, 2H, H3); 1.42 (s, 9H, C(CH$_3$)$_3$). Mass Spectrum (CI, +ve) m/z 320 (100%) [MH$^+$]. HRMS calcd for C$_{17}$H$_{24}$N$_2$O$_4$ 320.1736, found 320.1714.

Methyl(2S)-2-(4-allyloxyphenyl)-2-aminopropanoate hydrochloride (60)

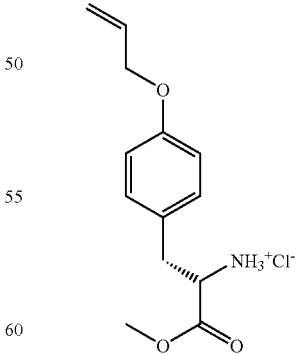

To a solution of 59 (1.10 g, 3.28 mmol) in DCM (5 mL) was added TFA (5 mL) dropwise. After stirring for 16 h the solvent was removed by evaporation and the resulting trifluoroacetate salt was resuspended in methanol (2 mL) and treated with 1M HCl/diethyl ether (2 mL). The solution was stirred for 5 min before the solvent was evaporated to yield the crude hydrochloride salt. The crude product was purified by precipitation (DCM/diethyl ether) to give the title compound (889 mg, 3.28 mmol, 100%) as a white solid. Mp 216-220° C. $^1$H NMR (CD$_3$OD, 300 MHz): δ 7.16 (d, J=8.4 Hz, 2H, ArH2' and ArH6'); 6.93 (d, J=8.8 Hz, 2H, ArH3' and ArH5'); 6.05 (m, 1H, H2''); 5.38 (dd, J=17.3, 1.7 Hz, 1H, H3$_a$''); 5.24 (dd, J=11.8, 1.3 Hz, 1H, H3$_b$''); 4.54 (m, 2H, H1''); 4.26 (m, 1H, H2); 3.81 (s, 3H, OCH$_3$); 3.14 (m, 2H, H3). $^{13}$C NMR (CD$_3$OD, 75 MHz): δ 170.3, C1; 159.6, ArC4'; 139.6, C2''; 131.4, ArCH2' and ArCH6'; 127.0, ArC1; 117.4, C3''; 116.2, ArCH3' and ArCH5'; 69.7, C1''; 55.3, C2; 53.6, OCH$_3$; 36.6, C3. Mass Spectrum (CI, +ve) m/z 236 (90%) [M$^+$]. HRMS calcd for C$_{13}$H$_{15}$NO$_3$ 236.1287, found 236.1276.

Methyl(2S,5R)-2-(4-allyloxybenzyl)-3-aza-9-(tert-butoxycarboxamido)-5-(9H-9-fluorenylmethylcarboxamido)-4-oxononanoate (61)

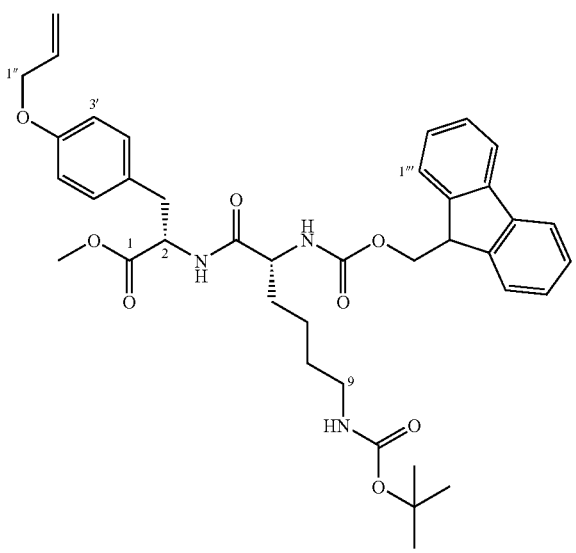

The title compound was synthesized using the general peptide coupling procedure (Procedure B), from 60 (200 mg, 0.74 mmol) and (2R)-6-tert-butoxycarboxamido-2-[(9H-9-fluorenylmethyloxy)carboxamido]hexanoic acid (291 mg, 0.62 mmol) to afford 61 (317 mg, 0.47 mmol, 75%) as a pale yellow solid. Mp 114-116° C. $^1$H NMR (CDCl$_3$, 300 MHz): δ 7.74 (d, J=7.6 Hz, 2H, ArH1''' and ArH8'''); 7.57 (d, J=6.3 Hz, 2H, ArH4''' and ArH5'''); 7.38 (t, J=7.2 Hz, 2H, ArH3''' and ArH6'''); 7.28 (t, J=7.6 Hz, 2H, ArH2''' and ArH7'''); 6.99 (d, J=7.6 Hz, 2H, ArH2' and ArH6'); 6.82 (d, J=7.2 Hz, 1H, NH); 6.76 (d, J=8.0 Hz, 2H, ArH3' and ArH5'); 5.97 (m, 1H, H2''); 5.67 (d, J=7.2 Hz, 1H, NH); 5.34 (d, J=16.8 Hz, 1H, H3$_a$''); 5.23 (d, J=10.5 Hz, 1H, H3$_b$''); 4.81 (d, J=5.8 Hz, 1H, H2); 4.70 (t, J=5.9 Hz, 1H, H5); 4.36 (m, 3H, OCH$_2$ and OCH$_2$—H9'''); 4.19 (m, 2H, H1''); 3.68 (s, 3H, OCH$_3$); 3.05 (m, 4H, H9 and ArCH$_2$); 1.73 (m, 2H, H6); 1.56 (m, 2H, H7); 1.42 (s, 9HC(CH$_3$)$_3$); 1.24 (m, 2H, H8). Mass Spectrum (ES, +ve) m/z 708.4 (100%) [MNa$^+$]. HRMS calcd for C$_{39}$H$_{48}$N$_3$O$_8$ 686.3439, found 686.3441.

Methyl(2S,5R)-2-(4-allyloxybenzyl)-5-amino-3-aza-9-(tert-butoxycarboxamido)-4-oxononanoate (62)

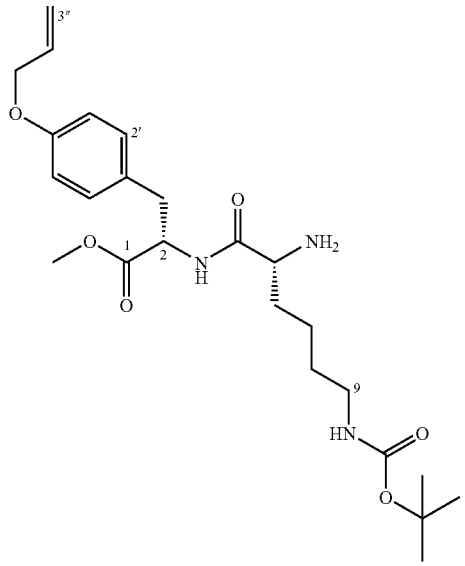

The title compound was synthesized using the general N-Fmoc deprotection procedure (Procedure C), from 61 (198 mg, 0.290 mmol) to yield 62 (131 mg, 0.280 mmole, 97%) as a cream oil. $^1$H NMR (CDCl$_3$, 300 MHz): δ 7.63 (d, J=8.4 Hz, 1H, NH); 7.04 (d, J=8.4 Hz, 2H, ArH2' and ArH6'); 6.83 (d, J=8.4 Hz, 2H, ArH3' and ArH5'); 6.05 (m, 1H, H2''); 5.40 (dd, J=1.7, 17.3 Hz, 1H, H3$_a$''); 5.28 (dd, J=1.7, 11.8 Hz, 1H, H3$_b$''); 4.78 (m, 1H, NH); 4.50 (m, 2H, H1''); 3.71 (s, 3H, OCH$_3$); 3.32 (dd, J=4.2, 7.6 Hz, 1H, H5); 2.61 (m, 4H, ArCH$_2$ and H8); 1.52 (m, 6H, H6, H7 and H8); 1.43 (s, 9H, C(CH$_3$)$_3$). Mass Spectrum (ES, +ve) m/z 464.3 (100%) [MH$^+$]. HRMS calcd for C$_{24}$H$_{38}$N$_3$O$_6$ 464.2761, found 464.2749.

Methyl(2S,5R,8S)-2,8-di(4-allyloxybenzyl)-3,6,9-triaza-5-(4-[tert-butoxycarboxamido]butyl)-4,7,10-trioxoundecanoate (63)

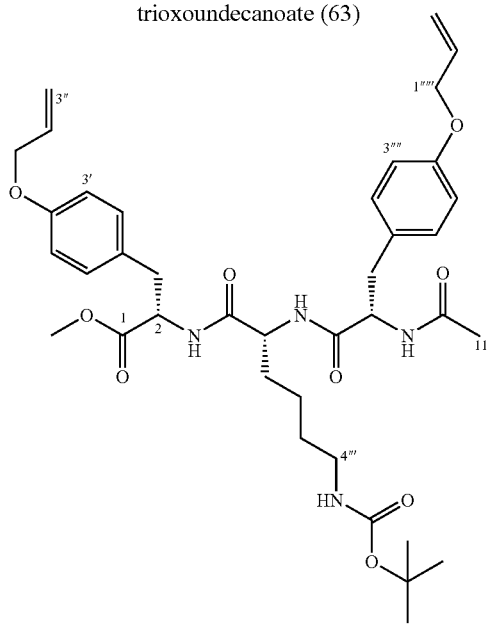

The title compound was synthesized using the general peptide coupling procedure (Procedure B), from 62 (220 mg, 0.600 mmol) and 16 (132 mg, 0.500 mmol) to yield 63 (130 mg, 0.180 mmol, 37%) as a white solid. Mp 185-186° C. $^1$H NMR (CDCl$_3$, 300 MHz): δ 7.36 (d, J=7.6 Hz, 2H, NH); 7.08 (d, J=8.4 Hz, 2H, ArH2' and ArH6'); 7.02 (d, J=8.4 Hz, 2H, ArH2'''' and ArH6''''); 6.82 (d, J=8.4 Hz, 4H, ArH3', ArH5', ArH3'''' and ArH5''''); 6.63 (d, J=7.2 Hz, 1H, NH); 6.02 (m, 2H, H2'' and H2'''''); 5.34 (m, 4H, H3'' and H3'''''); 4.78 (m, 2H, H2 and H8); 4.60 (m, 1H, H5); 4.47 (m, 4H, H1'' and H1'''''); 3.67 (s, 3H, OCH$_3$); 2.97 (m, 6H, Ar'—CH$_2$, Ar''''—CH$_2$ and H14'''); 1.93 (s, 3H, H111); 1.43 (s, 9H, C(CH$_3$)$_3$); 1.19 (m, 6H, H1''', H2''' and H3'''). Mass Spectrum (ES, +ve) m/z 709.3 (100%) [MH$^+$]. HRMS calcd for C$_{38}$H$_{52}$N$_4$O$_9$ 709.3813, found 709.3793.

(10S,13R,16S,4E/Z)-16-Acetamido-11,14-diaza-13-([tert-butoxycarboxamido]butyl)-10-methoxycarbonyl-2,7-dioxa-12,15-dioxo-1(1,4),8(4,1)-diphenylenecycloheptadecaphane-4-ene (64)

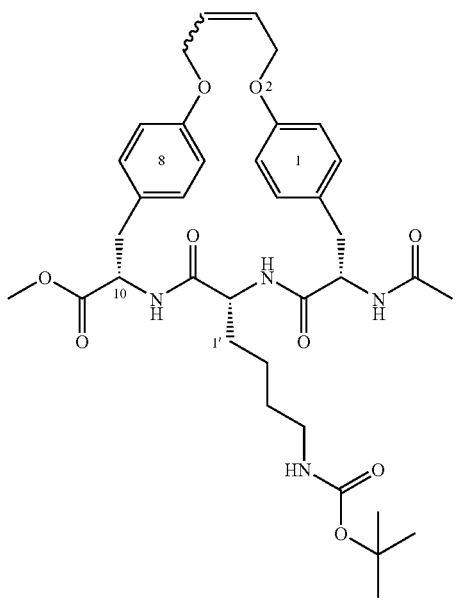

The title compound was prepared using the general procedure for olefin metathesis (Procedure D), from 63 (56 mg, 0.079 mmol) to yield 64 (22 mg, 0.032 mmol, 41%) as a brown solid. Mp 190-194° C. $^1$H NMR (CDCl$_3$, 300 MHz): δ 6.96 (m, 8H, ArH); 5.93 (m, 2H, H4 and H5); 4.18 (m, 1H, H10); 4.83 (m, 1H, H16); 4.56 (m, 4H, H3 and H6); 4.13 (m, 1H, H13); 3.74 (s, 3H, OCH$_3$); 3.28 (m, 2H, H4'); 2.84 (m, 4H, H9 and H17); 1.97 (s, 3H, NCOCH$_3$); 1.25 (s, 9H, C(CH$_3$)$_3$); 1.40 (m, 6H, H1', H2' and H3'). Mass Spectrum (ES, –ve) m/z 725.4 (100%) [MH$^+$+formate], 681 (85%) [MH$^+$]. HRMS calcd for C$_{36}$H$_{49}$N$_4$O$_9$ 681.3500, found 681.3521.

(10S,13R,16S,4E/Z)-16-Acetamido-13-(4-aminobutyl)-11,14-diaza-10-methoxycarbonyl-2,7-dioxa-12,15-dioxo-1(1,4),8(4,1)-diphenylenecycloheptadecaphane-4-ene (65)

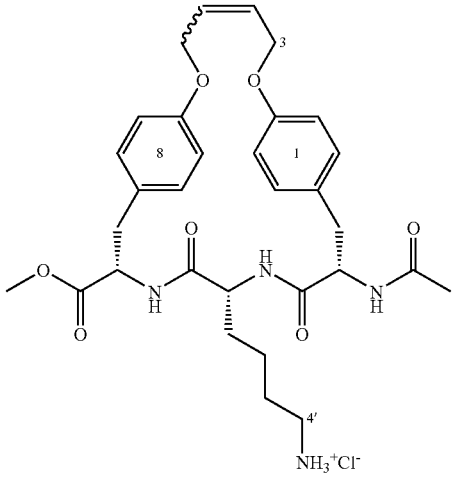

The title compound was synthesized using the general N-Boc deprotection procedure (Procedure A), from 64 (22 mg, 0.038 mmol) to yield 65 (20 mg, 0.034 mg, 89%) as a yellow solid. Mp>260° C. $^1$H NMR (CD$_3$OD, 300 MHz): δ 8.06 (m, 3H, NH); 7.07 (m, 4H, ArH); 6.78 (m, 4H, ArH); 5.95 (m, 2H, H4 and H5); 4.66 (bs, 4H, H3 and H6); 4.56 (m, 1H, H10); 4.40 (m, 1H, H16); 4.11 (m, 1H, H13); 3.75 (m, 3H, OCH$_3$); 2.90 (m, 6H, H9, H17 and H4'); 1.92 (s, 3H, NCOCH$_3$); 1.45 (m, 4H, H1' and H2'); 0.90 (m, 2H, H3'). $^{13}$C NMR (CD$_3$OD, 75 MHz): δ 171.1, C12; 170.3, NCOCH$_3$; 169.9, 10-CO; 169.4, C15; 157.3, 1-ArC1; 157.13, 8-ArC1; 130.9, 8-ArC4; 130.5, 8-ArCH2 and 8-ArCH6; 130.1, 1-ArCH2 and 1-ArCH6; 128.8, C4; 128.4, C5; 126.3, 1-ArCH4; 115.5, 8-ArCH3 and 8-ArCH5; 114.4, 1-ArCH3 and 1-ArCH5; 68.6, C3; 67.9, C6; 54.8, C16; 52.6, C13; 52.4, OCH$_3$; 52.2, C10; 39.5, C4'; 38.0, C9'; 35.8, C17; 34.9, C1'; 32.0, C3'; 26.5, 16-NCOCH$_3$; 23.3, C2'. Mass Spectrum (ES, –ve) m/z 581.6 (100%) [M$^+$]. HRMS calcd for C$_{31}$H$_{41}$N$_3$O$_7$ 581.2975, found 581.2980.

Methyl(2S,5S)-2-(4-allyloxybenzyl)-3-aza-9-(tert-butoxycarboxamido)-5-(9H-9-fluorenylmethylcarboxamido)-4-oxononanoate (66)

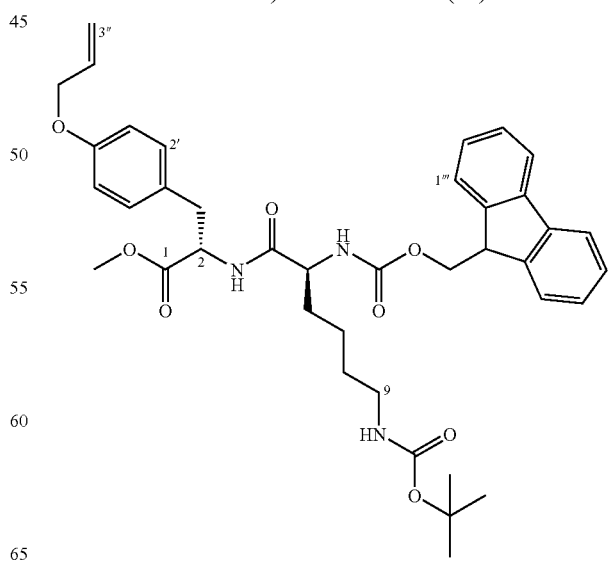

The title compound was synthesized using the general peptide coupling procedure (Procedure B), from 60 (200 mg, 0.74 mmol) and (2S)-6-tert-butoxycarboxamido-2-[(9H-9-fluorenylmethyloxy)carboxamido]hexanoic acid (291 mg, 0.62 mmol) to afford 66 (328 mg, 0.48 mmol, 77%) as a pale yellow solid. Mp 52-54° C. $^1$H NMR (CDCl$_3$, 300 MHz): δ 7.75 (d, J=7.5 Hz, 2H, ArH1''' and ArH8'''); 7.59 (d, J=6.9 Hz, 2H, ArH4''' and ArH5'''); 7.39 (t, J=7.5 Hz, 2H, ArH3''' and ArH6'''); 7.30 (dd, J=1.2, 7.5 Hz, 2H, ArH2''' and ArH7'''); 6.98 (d, J=8.4 Hz, 2H, ArH2' and ArH6'); 6.77 (d, J=8.7 Hz, 2H, ArH3' and ArH5'); 6.58 (d, J=7.2 Hz, 1H, NH); 5.98 (m, 1H, H2''); 5.56 (d, J=6.9 Hz, 1H, NH); 5.35 (dd, J=1.5, 17.1 Hz, 1H, H3$_a$''); 5.24 (dd, J=1.5, 10.8 Hz, 1H, H3$_b$''); 4.81 (dd, J=6.0, 13.8 Hz, 1H, H2); 4.70 (t, J=5.1 Hz, 1H, H5); 4.40 (m, 4H, H1'' and OCH$_2$—H9'''); 4.20 (d, J=7.2 Hz, 2H, H1''); 3.70 (s, 3H, OCH$_3$); 3.04 (m, 4H, H9 and ArCH$_2$); 1.80 (m, 2H, H6); 1.64 (m, 2H, H7); 1.43 (s, 9HC(CH$_3$)$_3$); 1.35 (m, 2H, H8). Mass Spectrum (ES, +ve) m/z 686.4 (10%), 708.4 (100%) [MNa$^+$]. HRMS calcd for C$_{39}$H$_{48}$N$_3$O$_8$ 686.3441, found 686.3454.

Methyl(2S,5R)-2-(4-allyloxybenzyl)-3-aza-5-(9H-9-fluorenylmethylcarboxamido)-4-oxo-8-[(2,2,5,7,8-pentamethyl-3,4-dihydro-2H-6-chromenylsulfonyl)guanidino]nonanoate (67)

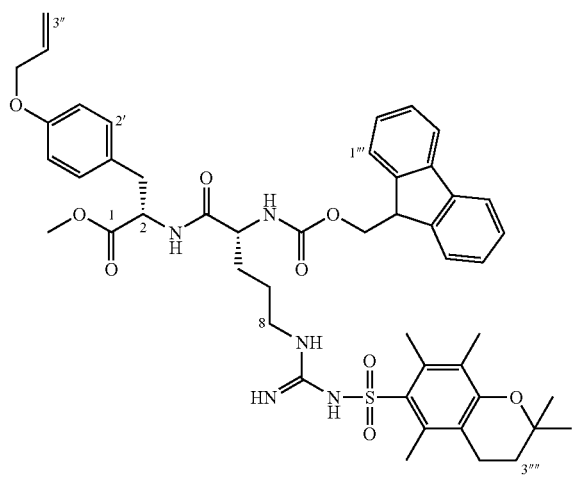

The title compound was synthesized using the general peptide coupling procedure (Procedure B), from 60 (200 mg, 0.74 mmol) and (2R)-2-(9H-9-fluorenylmethyloxycarboxamido)-8-[(2,2,5,7,8-pentamethyl-3,4-dihydro-2H-6-chromenylsulfonyl)guanidino]pentanoic acid (411 mg, 0.62 mmol) to afford 67 (386 mg, 0.44 mmol, 71%) as a pale yellow solid. Mp 86° C. $^1$H NMR (CDCl$_3$, 300 MHz): δ 7.70 (d, J=7.5 Hz, 2H, ArH1''' and ArH8'''); 7.52 (d, J=8.7 Hz, 2H, ArH4''' and ArH5'''); 7.33 (dd, J=7.8, 7.8 Hz, 2H, ArH3''' and ArH6'''); 7.19 (m, 2H, ArH2''' and ArH7'''); 6.90 (d, J=8.1 Hz, 2H, ArH2' and ArH6'); 6.68 (d, J=8.1 Hz, 2H, ArH3' and ArH5'); 6.32 (bs, 2H, NH); 6.15 (d, J=8.1 Hz, 1H, NH); 5.91 (m, 1H, H2''); 5.29 (d, J=17.4, 1H, H3$_a$''); 5.18 (d, J=10.5 Hz, 1H, H3$_b$''); 4.71 (dd, J=7.8, 13.5 Hz, 1H, H2); 4.26 (m, 5H, H1'', OCH$_2$—H9''' and H5); 4.06 (m, 1H, H9'''); 3.62 (s, 3H, OCH$_3$); 3.17 (m, 2H, H8); 2.98 (m, 2H, ArCH$_2$); 2.58 (s, 3H, 7''''-CH$_3$); 2.56 (m, 2H, H4''''); 2.55 (s, 3H, 5''''-CH$_3$); 2.06 (s, 3H, 8''''-CH$_3$); 1.71 (t, J=6.6 Hz, 2H, H3''''); 1.60 (m, 2H, H6); 1.48 (m, 2H, H7); 1.24 (s, 6H, 2×2''''-CH$_3$). Mass Spectrum (ES, +ve) m/z 880 (100%), [MH$^+$]. HRMS calcd for C$_{48}$H$_{58}$N$_5$O$_9$S 880.3955, found 880.3944.

Methyl(2S,5S)-2-(4-allyloxybenzyl)-3-aza-5-(9H-9-fluorenylmethylcarboxamido)-4-oxo-8-[(2,2,5,7,8-pentamethyl-3,4-dihydro-2H-6-chromenylsulfonyl)guanidino]nonanoate (67)

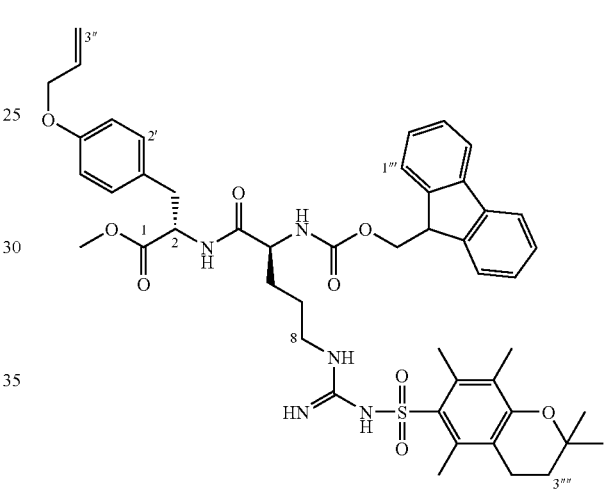

The title compound was synthesized using the general peptide coupling procedure (Procedure B), from 60 (200 mg, 0.74 mmol) and (2S)-2-(9H-9-fluorenylmethyloxycarboxamido)-8-[(2,2,5,7,8-pentamethyl-3,4-dihydro-2H-6-chromenylsulfonyl)guanidino]pentanoic acid (411 mg, 0.62 mmol) to afford 67 (460 mg, 0.52 mmol, 84%) as a pale yellow solid. Mp 88-90° C. $^1$H NMR (CDCl$_3$, 300 MHz): δ 7.70 (d, J=7.8 Hz, 2H, ArH1''' and ArH8'''); 7.53 (d, J=6.6 Hz, 2H, ArH4''' and ArH5'''); 7.33 (m, 2H, ArH3''' and ArH6'''); 7.18 (m, 2H, ArH2''' and ArH7'''); 6.98 (d, J=8.1 Hz, 2H, ArH2' and ArH6'); 6.70 (d, J=8.1 Hz, 2H, ArH3' and ArH5'); 6.34 (bs, 2H, NH); 6.13 (bs, 1H, NH); 5.93 (m, 1H, H2''); 5.30 (dd, J=1.5, 17.1, 1H, H3$_a$''); 5.19 (d, J=1.5, 10.5 Hz, 1H, H3$_b$''); 4.68 (m, 1H, H2); 4.30 (m, 5H, H1'', OCH$_2$—H9''' and H5); 4.08 (m, 1H, H9'''); 3.60 (s, 3H, OCH$_3$); 3.21 (m, 2H, H8); 2.97 (m, 2H, ArCH$_2$); 2.58 (s, 3H, 7''''-CH$_3$); 2.56 (m, 2H, H4''''); 2.54 (s, 3H, 5''''-CH$_3$); 2.07 (s, 3H, 8''''-CH$_3$); 1.84 (m, 2H, H6); 1.72 (t, J=6.9 Hz, 2H, H3''''); 1.55 (m, 2H, H7); 1.25 (s, 6H, 2×2''''-CH$_3$). Mass Spectrum (ES, +ve) m/z 880 (30%), 902 (100%) [MNa$^+$]. HRMS calcd for C$_{48}$H$_{58}$N$_5$O$_9$S 880.3955, found 880.3943.

Methyl(2S,5R)-2-allyl-3-aza-5-(9H-9-fluorenylmethyloxycarboxamido)-8-(guanidino)-4-oxooctanoate hydrochloride (69)

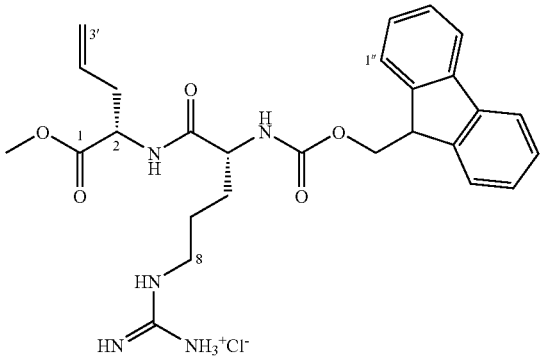

The title compound was synthesized using the general N-Boc deprotection procedure (Procedure A), from 28 (81 mg, 0.105 mmol) giving 69 as a highly hydroscopic solid (43 mg, 0.079 mmol, 75%). Mp 203-208° C. $^1$H NMR (CD$_3$OD, 300 MHz): δ 7.88 (m, 2H, ArH1" and ArH8"); 7.62 (m, 2H, ArH4" and ArH5"); 7.36 (m, 4H, ArH3" and ArH6" and ArH2" and ArH7"); 5.72 (m, 1H, H2'); 5.06 (m, 2H, H3); 4.46 (dd, J=5.4, 8.4 Hz, 1H, H2); 4.39 (d, J=6.3 Hz, 2H, OCH$_2$—H9"); 4.31 (m, 1H, H5); 4.19 (m, 1H, H9"); 3.68 (s, 3H, OCH$_3$); 3.17 (bs, 2H, H8); 2.51 (m, Hz, 2H, H1'); 1.79 (m, 2H, H7); 1.64 (m, 2H, H6). $^{13}$C NMR (CD$_3$OD, 75 MHz): δ 174.1, C4; 172.9, C1; 158.4, 5-NCO$_2$; 146.3, ArC8a" and ArC9a"; 142.4, ArC4a and ArC4b; 134.1, C2'; 129.1, ArCH3" and ArCH6"; 128.0, ArCH2" and ArCH7"; 126.6, ArCH4" and ArCH5"; 120.8, ArCH1" and ArCH8"; 118.9, C3'; 67.9, CH$_2$—C9"; 55.8, C9"; 53.4, C2; 52.8, OCH$_3$; 51.1, C5; 42.0, C8; 36.8, C1'; 30.5, H7; 26.3, H6. Mass Spectrum (ES, +ve) m/z 508 (100%) [M$^+$]. HRMS calcd for C$_{27}$H$_{34}$N$_5$O$_5$ 508.2526, found 508.2570.

Methyl(2S,5S)-2-allyl-3-aza-5-(9H-9-fluorenylmethyloxycarboxamido)-8-(guanidino)-4-oxooctanoate hydrochloride (70)

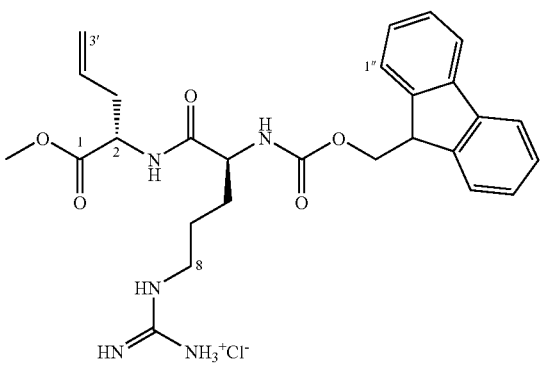

The title compound was synthesized using the general N-Boc deprotection procedure (Procedure A) using 33 (81 mg, 0.105 mmol) giving 70 (27 mg, 0.05 mmol, 47%) as a highly hydroscopic solid. Mp 176-182° C. $^1$H NMR (CD$_3$OD, 500 MHz): δ 7.79 (d, J=7.5 Hz, 2H, ArH1" and ArH8"); 7.62 (m, 2H, ArH4" and ArH5"); 7.34 (m, 4H, ArH3" and ArH6" and ArH2" and ArH7"); 5.77 (m, 1H, H2'); 5.10 (m, 2H, H3'); 4.46 (dd, J=6.0, 8.1 Hz, 1H, H2); 4.34 (d, J=7.2 Hz, 2H, OCH$_2$—H9"); 4.32 (m, 1H, H5); 4.19 (m, 1H, H9"); 3.69 (s, 3H, OCH$_3$); 3.20 (m, 2H, H8); 2.52 (m, 2H, H1'); 1.83 (m, 2H, H7); 1.68 (m, 2H, H6). $^{13}$C NMR (CD$_3$OD, 75 MHz): δ 174.4, C4; 173.2, C1; 158.4, CN$_3$; 158.3, 5-NCO$_2$; 144.2, ArC8a" and ArC9a"; 142.4, ArC4a" and ArC4b"; 134.1, C2'; 129.1, ArCH3" and ArCH6"; 128.7, ArCH2" and ArCH7"; 126.7, ArCH4" and ArCH5"; 120.9, ArCH1" and ArCH8"; 119.0, C3'; 67.9, CH$_2$—C9"; 55.6, C9"; 53.5, C2; 52.8, OCH$_3$; 48.1, C5; $\overline{42}$.0, C8; 36.6, C1'; 30.3, H7; 26.2, H6. Mass Spectrum (ES, +ve) m/z 508 (100%) [M$^+$]. HRMS calcd for C$_{37}$H$_{34}$N$_5$O$_5$ 508.2560, found 508.2574.

Methyl(2R,5R)-2-allyl-3-aza-5-(9H-9-fluorenylmethyloxycarboxamido)-8-(guanidino)-4-oxooctanoate hydrochloride (71)

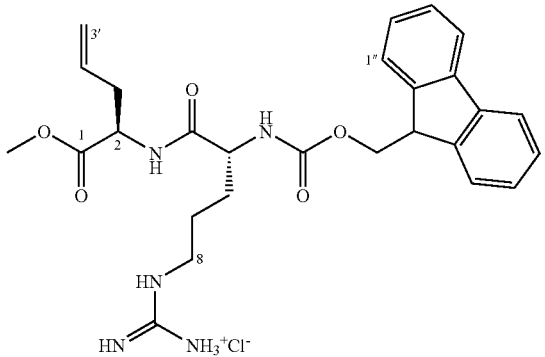

The title compound was synthesized using the general N-Boc deprotection procedure (Procedure A), from 39 (80 mg, 0.10 mmol) to yield 71 as a highly hydroscopic white solid (45 mg, 0.083 mmol, 80%). $^1$H NMR (CD$_3$OD, 500 MHz): δ 7.61 (d, J=7.5 Hz, 2H, ArH1" and ArH8"); 7.47 (d, J=8.5 Hz, 2H, ArH4" and ArH5"); 7.20 (t, J=7.5 Hz, 2H, ArH3" and ArH6"); 7.12 (t, J=7.5 Hz, 2H, ArH2" and ArH7"); 5.58 (m, 1H, H2'); 4.93 (d, J=17.0 Hz, 1H, H3$_a$'); 4.87 (d, J=10.0 Hz, 1H, H3$_b$'); 4.28 (dd, J=6.0, 8.0 Hz, 1H, H2); 4.20 (d, J=7.0 Hz, 2H, OCH$_2$—H9"); 4.03 (t, J=7.0 Hz, 1H, H5); 3.99 (t, J=7.0 Hz, 1H, $\overline{H9}$"); 3.51 (s, 3H, OCH$_3$); 3.01 (bs, 2H, H8); 2.34 (m, 2H, H1'); 1.64 (bs, 2H, H7); 1.47 (bs, 2H, H6). $^{13}$C NMR (CD$_3$OD, 75 MHz): δ 174.1, C4; 173.1, C1; 158.4, CN$_3$; 158.2, 5-NCO$_2$; 145.1, ArC8a" and ArC9a"; 142.4, ArC4a and ArC4b; 133.9, C2'; 128.6, ArCH3" and ArCH6"; 128.0, ArCH2" and ArCH7"; 126.0, ArCH4" and ArCH5"; 120.8, ArCH1" and ArCH8"; 118.8, C3'; 67.9, CH$_2$—C9"; 55.6, C9"; 53.6, C2; 52.7, OCH$_3$; 49.3, C5; 42.$\overline{1}$, C8; 36.7, C1'; 30.4, C7; 26.2, C6. Mass Spectrum (ES, +ve) m/z 508 (45%) [M$^+$]. HRMS calcd for C$_{27}$H$_{34}$N$_5$O$_5$ 508.2560, found 508.2592.

Methyl(2R,5S)-2-allyl-3-aza-5-(9H-9-fluorenylmethyloxycarboxamido)-8-(guanidino)-4-oxooctanoate hydrochloride (72)

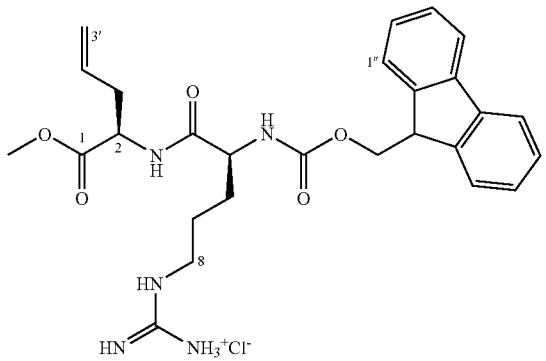

The title compound was synthesized using the general N-Boc deprotection procedure (Procedure A) using 44 (94 mg, 0.12 mmol) to yield 72 as a highly hydroscopic white solid (33 mg, 0.061 mmol, 51%). $^1$H NMR (CD$_3$OD, 300 MHz): δ 7.79 (d, J=7.5 Hz, 2H, ArH1" and ArH8"); 7.65 (m, 2H, ArH4" and ArH5"); 7.39 (t, J=7.2 Hz, 2H, ArH3" and ArH6"); 7.30 (t, J=7.2 Hz, 2H, ArH2" and ArH7"); 5.72 (m, 1H, H2'); 5.09 (d, J=16.5 Hz, 1H, H3$_a$'); 5.04 (d, J=9.6 Hz, 1H, H3$_b$'); 4.46 (dd, J=5.7, 8.4 Hz, 1H, H2); 4.40 (d, J=6.3 Hz, 2H, OCH$_2$—H9"); 4.22 (t, J=6.6 Hz, 1H, H5); 4.16 (m, 1H, H9"); 3.69 (s, 3H, OCH$_3$); 3.17 (t, J=6.6 Hz, 2H, H8); 2.51 (m, 2H, H1'); 1.80 (m, 2H, H7); 1.62 (m, 2H, H6). $^{13}$C NMR (CD$_3$OD, 75 MHz): δ 174.0, C4; 172.9, C1; 158.4, CN$_3$; 158.2, 5-NCO$_2$; 145.1, ArC8a" and ArC9a"; 142.4, ArC4a" and ArC4b"; 134.1, C2'; 128.7, ArCH3" and ArCH6"; 128.0, ArCH2" and ArCH7"; 126.0, ArCH4" and ArCH5"; 120.8, ArCH1" and ArCH8"; 118.9, C3'; 67.9, CH$_2$—C9"; 55.8, C9"; 53.4, C2; 52.8, OCH$_3$; 49.3, C5; 42.0, C8; 36.8, C1'; 30.5, C7; 26.3, C6. Mass Spectrum (ES, +ve) m/z 508 (25%) [M$^+$], 179 (100%) [Sodium allylglycinamide]. HRMS calcd for C$_{27}$H$_{34}$N$_5$O$_5$ 508.2560, found 508.2555.

Methyl(2S,5R)-2-(4-allyloxybenzyl)-9-amino-3-aza-5-(9H-9-fluorenylmethyloxycarboxamido)-4-oxononanoate hydrochloride (73)

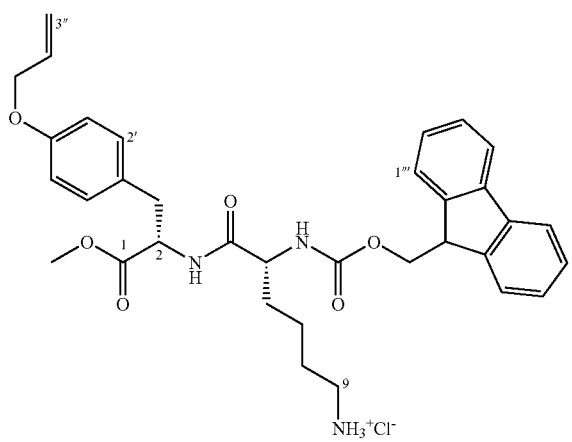

The title compound was synthesized using the general N-Boc deprotection procedure (Procedure A), from 61 (132 mg, 0.19 mmol) to yield 73 (92 mg, 0.15 mmol, 79%) as a white solid. Mp 162-170° C. $^1$H NMR (CD$_3$OD, 300 MHz): δ 8.02 (d, J=8.0 Hz, 1H, NH); 7.79 (d, J=7.6 Hz, 2H, ArH1'" and ArH8'"); 7.64 (t, J=8.4 Hz, 2H, ArH4'" and ArH5'"); 7.38 (t, J=7.2 Hz, 2H, ArH3'" and ArH6'"); 7.29 (m, 2H, ArH2'" and ArH7'"); 7.04 (d, J=8.4 Hz, 2H, ArH2' and ArH6'); 6.73 (d, J=8.4 Hz, 2H, ArH3' and ArH5'); 5.94 (m, 1H, H2"); 5.28 (d, J=17.3 Hz, 1H, H3$_a$"); 5.16 (d, J=10.5 Hz, 1H, H3b"); 4.62 (dt, J=5.0, 8.8 Hz, 1H, H5); 4.33 (m, 4H, H1' and OCH$_2$—H9'"); 4.19 (t, J=6.7 Hz, 1H, H9'"); 4.07 (dd, J=5.1, 8.0 Hz, 1H, H2); 3.70 (s, 3H, OCH$_3$); 3.11 (m, 2H, H9); 2.90 (m, 2H, ArCH$_2$); 1.60 (m, 4H, H6 and H7); 1.33 (m, 2H, H8). $^{13}$C NMR (CD$_3$OD, 75 MHz): δ 174.2, C4; 173.2, C1; 158.1, NCO$_2$; 145.1, ArC4'; 145.0, ArC8a'" and ArC9a'"; 142.4, ArC4a'" and ArC4b'"; 134.7, C2"; 131.1, ArCH2' and ArCH6'; 129.8, ArCH3'" and ArCH6'"; 128.7, ArCH2'" and ArCH7'"; 128.7, ArCH1'" and ArCH8'"; 128.1, ArCH4'" and ArCH5'"; 120.8, ArC1'; 117.3, C3'; 115.6, ArCH3' and ArCH5'; 69.6, CH$_2$—C9'"; 68.0, C1"; 56.1, C5; 55.2, C2; 55.1, OCH$_3$; 52.8, C9'"; 40.5, C9; 37.3, ArCH$_2$; 32.6, C6; 28.1, C8; 23.6, C7. Mass Spectrum (ES, +ve) m/z 586.3 (100%) [M$^+$]. HRMS calcd for C$_{34}$H$_{40}$N$_3$O$_6$ 586.2917, found 586.2935.

Methyl(2S,5S)-2-(4-allyloxybenzyl)-9-amino-3-aza-5-(9H-9-fluorenylmethyloxycarboxamido)-4-oxononanoate hydrochloride (74)

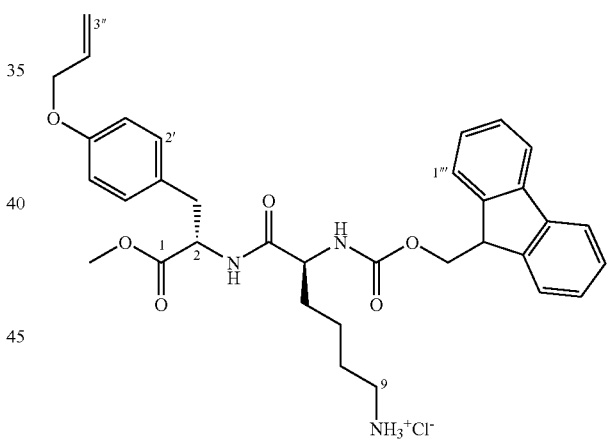

The title compound was synthesized using the general N-Boc deprotection procedure (Procedure A), from 66 (73 mg, 0.106 mmol) to yield 74 (48 mg, 0.07 mmol, 68%) as a white solid. Mp 160-168° C. $^1$H NMR (CD$_3$OD, 300 MHz): δ 7.79 (d, J=7.2 Hz, 2H, ArH1'" and ArH8'"); 7.65 (d, J=7.2 Hz, 2H, ArH4'" and ArH5'"); 7.39 (t, J=7.2 Hz, 2H, ArH3'" and ArH6'"); 7.29 (t, J=7.2 Hz, 2H, ArH2'" and ArH7'"); 7.07 (d, J=8.4 Hz, 2H, ArH2' and ArH6'); 6.77 (d, J=8.4 Hz, 2H, ArH3' and ArH5'); 5.96 (m, 1H, H2"); 5.29 (dd, J=1.2, 18.3 Hz, 1H, H3$_a$"); 5.16 (dd, J=1.2, 10.5 Hz, 1H, H3b"); 4.63 (m, 1H, H5); 4.37 (m, 4H, H1' and OCH$_2$—H9'"); 4.20 (m, 1H, H9'"); 4.09 (m, 1H, H2); 3.67 (s, 3H, OCH$_3$); 3.00 (m, 2H, H9); 2.90 (m, 2H, ArCH$_2$); 1.65 (m, 4H, H6 and H7); 1.39 (m, 2H, H8). $^{13}$C NMR (CD$_3$OD, 125 MHz): δ 174.4, C4; 173.3, C1; 158.1, NCO$_2$; 145.2, ArC4'; 145.0, ArC8a'" and ArC9a'"; 142.4, ArC4a'" and ArC4b'"; 134.7, C2"; 131.2, ArCH2' and ArCH6'; 129.8, ArCH3'" and ArCH6'"; 128.8, ArCH2'" and ArCH7'''; 128.1, ArCH1''' and ArCH8'''; 126.2, ArCH4''' and ArCH5'''; 120.9, ArC1'; 117.4, C3'; 115.6, ArCH3' and ArCH5'; 69.6, CH₂—C9'''; 68.0, C1''; 55.9, C5; 55.2, C2; 55.1, OCH₃; 52.8, C9'''; 40.4, C9; 37.3, ArCH₂; 32.4, C6; 27.9, C8; 23.6, C7. Mass Spectrum (ES, +ve) m/z 586.7 (100%) [M⁺]. HRMS calcd for C₃₄H₄₀N₃O₆ 586.2917, found 586.2925.

Methyl(2S,5R)-2-(4-allyloxybenzyl)-3-aza-5-(9H-9-fluorenylmethylcarboxamido)-8-guanidino-4-ox-ononanoate hydrochloride (75)

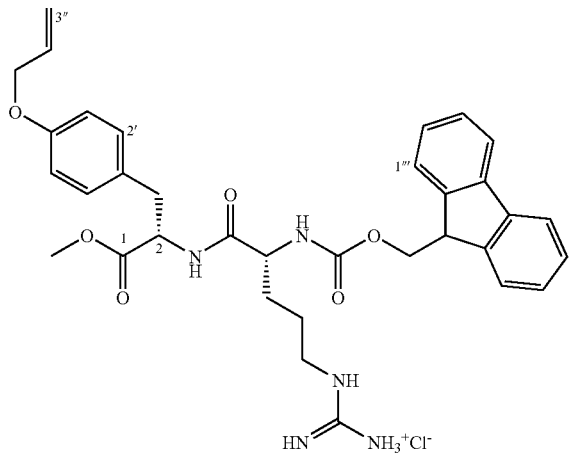

The title compound was synthesized using the general N-Boc deprotection procedure (Procedure A), from 67 (62 mg, 0.068 mmol) to yield 75 (35 mg, 0.054 mmol, 79%) as a white solid. Mp 158-162° C. ¹H NMR (CD₃OD, 300 MHz): δ 7.78 (d, J=7.5 Hz, 2H, ArH1''' and ArH8'''); 7.64 (d, J=8.1 Hz, 2H, ArH4''' and ArH5'''); 7.38 (t, J=6.9 Hz, 2H, ArH3''' and ArH6'''); 7.37 (m, 2H, ArH2''' and ArH7'''); 7.04 (d, J=8.4 Hz, 2H, ArH2' and ArH6'); 6.72 (d, J=8.4 Hz, 2H, ArH3' and ArH5'); 5.92 (m, 1H, H2''); 5.28 (d, J=17.1, 1H, H3ₐ''); 5.16 (d, J=10.8 Hz, 1H, H3b''); 4.61 (dd, J=5.1, 9.0 Hz, 1H, H2); 4.32 (m, 4H, H1'' and OCH₂—H9'''); 4.18 (m, 1H, H5); 4.09 (m, 1H, H9'''); 3.69 (s, 3H, OCH₃); 3.09 (m, 2H, H8); 2.91 (m, 2H, ArCH₂); 1.62 (m, 2H, H6); 1.51 (m, 2H, H7). ¹³C NMR (CD₃OD, 75 MHz): δ 172.0, C4; 171.8, C1 156.8, CN₃; 156.6, ArC4'; 155.9, NCO₂; 143.8, ArC8a''' and ArC9a'''; 140.8, ArC4a''' and ArC4b'''; 135.5, C2''; 130.1, ArC1'; 129.6, ArCH4''' and ArCH5'''; 127.7, ArCH2''' and ArCH7'''; 127.2, ArCH1''' and ArCH8'''; 125.4, ArCH3''' and ArCH6'''; 120.2, ArCH2' and ArCH6'; 117.3, C3''; 114.3, ArCH3' and ArCH5'; 68.0, C1''; 65.8, CH₂—C9'''; 59.3, C9'''; 54.0, C5; 52.0, OCH₃; 46.7, C2; 40.3, C8; 36.1, ArCH₂; 29.1, C6; 24.9, C7. Mass Spectrum (ES, +ve) m/z 614.6 (100%) [M⁺]. HRMS calcd for C₃₄H₄₀N₅O₆ 614.2979, found 614.3007.

Methyl(2S,5S)-2-(4-allyloxybenzyl)-3-aza-5-(9H-9-fluorenylmethylcarboxamido)-8-guanidino-4-ox-ononanoate hydrochloride (76)

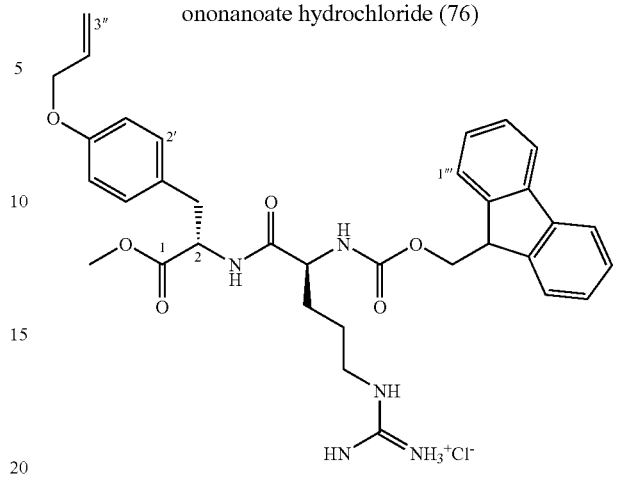

The title compound was synthesized using the general N-Boc deprotection procedure (Procedure A), from 68 (93 mg, 0.10 mmol) to yield 76 (54 mg, 0.083 mmol, 83%) as a white solid. Mp 170-175° C. ¹H NMR (CD₃OD, 300 MHz): δ 7.90 (d, J=7.2 Hz, 2H, ArH1''' and ArH8'''); 7.75 (m, 2H, ArH4''' and ArH5'''); 7.38 (m, 4H, ArH3''', ArH6''', ArH2''' and ArH7'''); 7.14 (d, J=8.1 Hz, 2H, ArH2' and ArH6'); 6.82 (d, J=8.1 Hz, 2H, ArH3' and ArH5'); 5.98 (m, 1H, H2''); 5.34 (d, J=17.1, 1H, H3ₐ''); 5.21 (d, J=10.8 Hz, 1H, H3b''); 4.46 (m, 2H, H2 and H5); 4.26 (m, 4H, H1'' and OCH₂—H9'''); 4.08 (m, 1H, H9'''); 3.59 (s, 3H, OCH₃); 3.12 (m, 2H, H8); 2.94 (m, 2H, ArCH₂); 1.69 (m, 2H, H6); 1.52 (m, 2H, H7). ¹³C NMR (CD₃OD, 75 MHz): δ 171.9, C4; 171.8, C1 157.0, CN₃; 156.6, ArC4'; 155.9, NCO₂; 143.9, ArC8a''' and ArC9a'''; 140.7, ArC4a''' and ArC4b'''; 133.8, C2''; 130.1, ArC1'; 129.0, ArCH4''' and ArCH5'''; 127.7, ArCH2''' and ArCH7'''; 127.1, ArCH1''' and ArCH8'''; 125.4, ArCH3''' and ArCH6'''; 120.1, ArCH2' and ArCH6'; 117.3, C3''; 114.4, ArCH3' and ArCH5'; 68.1, C1''; 65.7, CH₂—C9'''; 59.3, C9'''; 53.9, C5; 51.8, OCH₃; 46.7, C2; 40.3, C8; 35.7, ArCH₂; 29.0, C6; 25.1, C7. Mass Spectrum (ES, +ve) m/z 614.8 (100%) [M⁺]. HRMS calcd for C₃₄H₄₀N₅O₆ 614.2979, found 614.2972.

Methyl(2S,5R,8S)-2-allyl-8-(4-allyloxyphenyl)-5-(4-aminobutyl)-3,6,9-triaza-4,7,10-trioxoundecanoate hydrochloride (77)

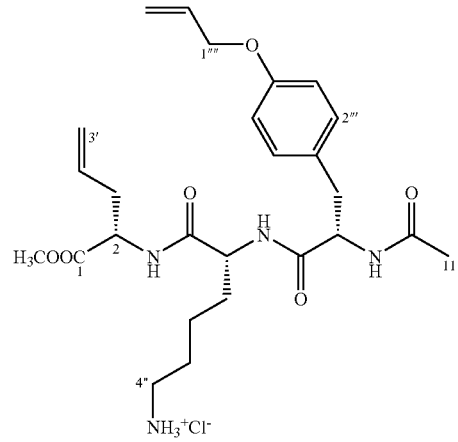

The title compound was synthesized using the general N-Boc deprotection procedure (Procedure A), from 21 (64 mg, 0.11 mmol) to yield 77 (22 mg, 0.041 mmol, 37%) as a cream highly hydroscopic solid. ¹H NMR (CD₃OD, 500

MHz): δ 7.15 (d, J=8.0 Hz, 2H, ArH2''' and ArH6'''); 6.87 (d, J=8.0 Hz, 2H, ArH3''' and ArH5'''); 6.05 (m, 1H, H2''''); 5.73 (m, 1H, H2'); 5.39 (d, J=17.0 Hz, 1H, H3''''); 5.24 (d, J=10.5 Hz, 1H, H3''''); 5.08 (d, J=17.0 Hz, 1H, H3'); 5.04 (d, J=10.0 Hz, 1H, H3'); 4.52 (d, J=5.5 Hz, 2H, H1''''); 4.44 (m, 2H, H2 and H5); 4.15 (d, J=6.5 Hz, 1H, H8); 3.69 (s, 3H, OCH$_3$); 2.92 (m, 2H, H11'); 2.83 (bs, 2H, H4''); 2.54 (m, 2H, ArCH$_2$); 1.93 (s, 3H, H11); 1.74 (bs, 2H, H1''); 1.50 (bs, 2H, H2''); 1.00 (bs, 2H, H3''). $^{13}$C NMR (CD$_3$OD, 75 MHz): δ 174.3, C7; 173.7, C1; 173.2, C4; 173.1, C10; 158.8, ArC4'''; 134.8, C2'; 134.5, C2''''; 131.3, ArCH2''' and ArCH6'''; 129.9, ArC1'''; 118.4, C3'; 117.5, C3''''; 115.8, ArCH3''' and ArCH5'''; 69.8, C1''''; 57.6, C5; 54.2, OCH$_3$; 53.8, C8; 52.7, C2; 40.3, C4'; 37.4, ArCH$_2$; 36.4, C1'; 31.7, C1''; 28.0, C3''; 23.5, C11; 22.4, C2''. Mass Spectrum (ES, +ve) m/z 503.7 (100%) [M$^+$]. HRMS calcd for C$_{26}$H$_{39}$N$_4$O$_6$ 503.2870, found 503.2881.

Methyl(2S,5S,8S)-8-acetamido-2-allyl-9-(4-allyloxyphenyl)-5-(4-aminobutyl)-3,6-diaza-4,7-dioxononanoate hydrochloride (78)

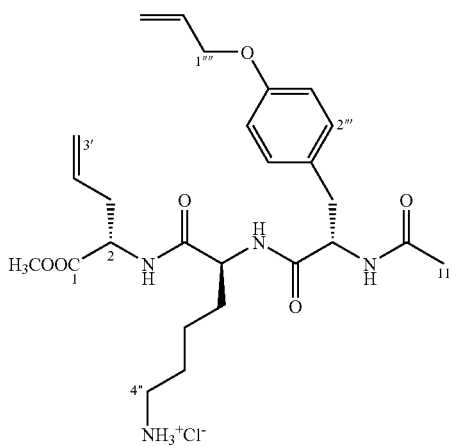

The title compound was synthesized using the general procedure (Procedure A), by deprotection of 25 (104 mg, 0.170 mmol) to yield 78 as a 1:1 mixture of epimers (55 mg, 0.10 mmol, 60%) as a highly hydroscopic yellow solid. Mp 150-154° C. $^1$H NMR (CD$_3$OD, 300 MHz): δ 7.14 (d, J=8.0 Hz, 2H, ArH2''' and ArH6'''); 6.84 (t, J=8.0 Hz, 2H, ArH3''' and ArH5'''); 6.03 (m, 1H, H2''''); 5.76 (m, 1H, H2'); 5.37 (d, J=17.3 Hz, 1H, H3$_a$''''); 5.22 (d, J=9.7 Hz, 1H, H3$_b$''''); 5.10 (m, 2H, H3'); 4.53 (m, 5H, H2, H5, H8 and H1''''); 3.69/3.67 (s, 3H, OCH$_3$); 2.87 (m, 4H, H1' and H4''); 2.54 (m, 2H, ArCH$_2$); 1.93/1.91 (s, 3H, H11); 1.50 (s, 6H, H1'', H2'' and H3''). $^{13}$C NMR (CD$_3$OD, 75 MHz): δ 173.7/173.6, C7; 173.4, C1; 173.1, C4; 173.0/172.9, C10; 158.7, ArCH4'''; 134.8, C2'; 134.3/134.0, C2''''; 131.2/131.1, ArCH2''' and ArCH6'''; 130.2/130.1, ArC1'''; 118.8/118.5, C3'; 117.4/117.3, C3''''; 115.7/115.6, ArCH3''' and ArCH5'''; 69.8/69.7, C1''''; 57.2, C5; 54.0, OCH$_3$; 53.8/53.7, C8; 52.8/52.7, C2; 40.6/40.5, C4'; 37.8/37.7, ArCH$_2$; 36.6/36.5, C1'; 31.9, C1''; 28.0, C3''; 23.4, C11; 22.5, C2''. Mass Spectrum (ES, +ve) m/z 503.3 (100%) [M$^+$]. HRMS calcd for C$_{26}$H$_{39}$N$_4$O$_6$ 503.2870, found 503.2894.

Methyl(2R,5R,8S)-2-allyl-8-(4-allyloxybenzyl)-3,6,9-triaza-5-(3-[guanidino)-4,7,10-oxoundecanoate hydrochloride (79)

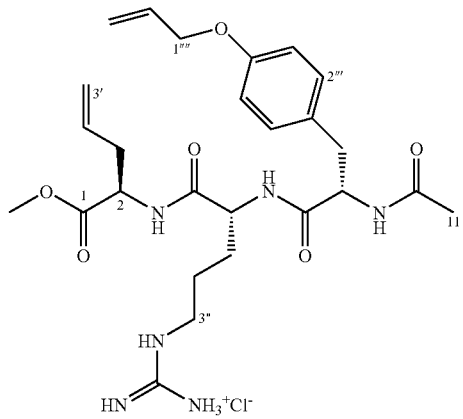

The title compound was synthesized using the general N-Boc deprotection procedure (Procedure A), from 41 (48 mg, 0.60 mmol) to yield 79 as a highly hydroscopic solid (32 mg, 0.060 mmol, 100%). $^1$H NMR (CD$_3$OD, 300 MHz): δ 7.15 (d, J=8.4 Hz, 2H, ArH2''' and ArH6'''); 6.86 (d, J=8.7 Hz, 2H, ArH3''' and ArC5'''); 6.04 (m, 1H, H2''''); 5.77 (m, 1H, H2'); 5.38 (dd, J=1.5, 17.4 Hz, 1H, H3$_a$''''); 5.23 (dd, J=1.2, 10.5 Hz, 1H, H3$_b$''''); 5.09 (dd, J=1.2, 16.8 Hz, 1H, H3$_a$'); 5.06 (d, J=10.6 Hz, 1H, H3$_b$'); 4.50 (m, 4H, H2'''' and H2); 4.39 (dd, J=5.7, 8.1 Hz, 1H, H5); 4.26 (dd, J=4.5, 8.7 Hz, 1H, H8); 3.68 (s, 3H, OCH$_3$); 3.07 (t, J=7.2 Hz, 2H, H3''); 2.94 (m, 2H, ArCH$_2$); 2.54 (m, 2H, H1'); 1.95 (s, 3H, H11); 1.62 (m, 2H, H1''); 1.32 (m, 2H, H2''). $^{13}$C NMR (CD$_3$OD, 75 MHz): δ 173.7, C4; 173.6, C11; 173.4, C1; 172.9, C7; 158.8, ArC4'''; 158.4, CN$_3$; 134.8, C2''''; 134.3, C2'; 131.2, ArC1'''; 130.0, ArCH2''' and ArCH6'''; 118.6, C3'; 117.4, C3''''; 115.7, ArCH3''' and ArCH5'''; 69.8, C1''''; 57.2, C2; 53.8, C5; 53.8, C8; 52.8, OCH$_3$; 50.1, C3''; 37.7, ArCH$_2$; 36.5, C1'; 29.7, C2''; 22.9, C11; 22.3, C1'''. Mass Spectrum (ES, +ve) m/z 531.5 (80%) [M$^+$]. HRMS calcd for C$_{26}$H$_{39}$N$_6$O$_6$ 531.2931, found 531.2936.

Methyl(2R,5S,8S)-2-allyl-8-(4-allyloxybenzyl)-3,6,9-triaza-5-(3-[guanidino)-4,7,10-oxoundecanoate hydrochloride (80)

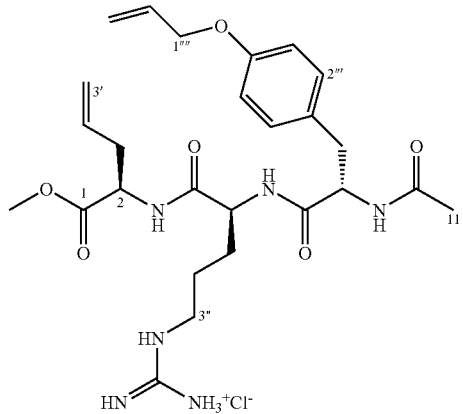

The title compound was synthesized using the general N-Boc deprotection procedure (Procedure A), from 46 (87 mg, 0.11 mmol) to yield 80 as a highly hydroscopic solid (35 mg, 0.062 mmol, 56%). $^1$H NMR (CD$_3$OD, 300 MHz): δ 7.16 (d, J=8.5 Hz, 2H, ArH2''' and ArH6'''); 6.83 (d, J=8.0 Hz, 2H, ArH3''' and ArH5'''); 6.04 (m, 1H, H2''''); 5.74 (m, 1H, H2'); 5.38 (dd, J=1.5, 17.5 Hz, 1H, H3$_a$''''); 5.23 (dd, J=1.0, 10.5

Hz, 1H, H3$_b$''''); 5.12 (d, J=17.0 Hz, 1H, H3$_a$'); 5.08 (d, J=10.5 Hz, 1H, H3$_b$'); 4.50 (d, J=5.0 Hz, 2H, H1''''); 4.43 (m, H2, H5 and H8); 3.71 (s, 3H, OCH$_3$); 2.97 (t, J=7.5 Hz, 2H, H3''); 2.94 (m, 2H, ArCH$_2$); 2.52 (m, 2H, H1'); 1.93 (s, 3H, CH$_3$, H11); 1.78 (m, 2H, H1''); 1.61 (m, 2H, H2''). $^{13}$C NMR (CD$_3$OD, 75 MHz): δ 173.9, C4; 173.4, C11; 173.1, C1; 172.9, C7; 158.8, ArC4'''; 158.4, CN$_3$; 134.8, C2''''; 134.1, C2'; 131.1, ArC1'''; 130.2, ArCH2''' and ArCH6'''; 118.9, C3'; 117.2, C3''''; 115.6, ArCH3''' and ArCH5'''; 69.7, C1''''; 56.9, C2; 53.8, C5; 53.6, C8; 52.8, OCH$_3$; 50.1, C3''; 37.7, ArCH$_2$; 36.9, C1'; 26.1, C2''; 22.5, C11; 20.7, C1''. Mass Spectrum (ES, +ve) m/z 531.1 (85%) [M$^+$]. HRMS calcd for C$_{26}$H$_{39}$N$_6$O$_6$ 531.2931, found 531.2952.

Methyl(2S,5S,8S)-2-allyl-8-(4-allyloxybenzyl)-3,6,9-triaza-5-(3-[guanidino]propyl)-4,7,10-oxoundecanoate hydrochloride (81)

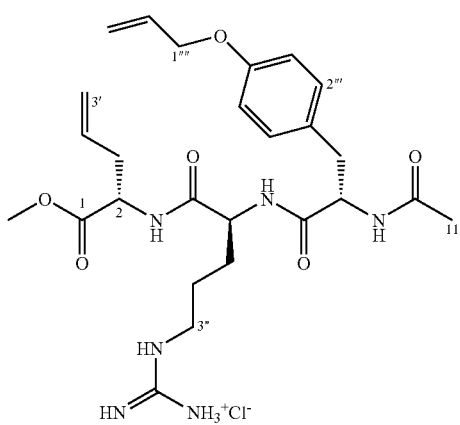

The title compound was synthesized using the general N-Boc deprotection procedure (Procedure A), from 36 (63 mg, 0.079 mmol) to yield 81 as a highly hydroscopic solid (38 mg, 0.036 mmol, 85%). $^1$H NMR (CD$_3$OD, 300 MHz): δ 7.13 (d, J=8.7 Hz, 2H, ArH2''' and ArH6'''); 6.82 (d, J=8.7 Hz, 2H, ArH3''' and ArH5'''); 6.03 (m, 1H, H2''''); 5.77 (m, 1H, H2'); 5.36 (dd, J=1.5, 17.4 Hz, 1H, H3$_a$''''); 5.22 (dd, J=1.5, 10.5 Hz, 1H, H3$_b$''''); 5.13 (d, J=18.3 Hz, 1H, H3$_a$'); 5.08 (d, J=9.6 Hz, 1H, H3$_b$'); 4.49 (m, 3H, H1'''' and H5); 4.40 (m, 2H, H2 and H8); 3.69 (s, 3H, OCH$_3$); 3.18 (m, 2H, H3''); 3.02 (dd, J=5.7, 13.8 Hz, 1H, ArCH); 2.82 (dd, J=9.0, 14.1 Hz, 1H, ArCHH; 2.51 (m, 2H, H1'); 1.92 (s, 3H, H11); 1.83 (m, 2H, H1''); 1.64 (m, 2H, H2''). $^{13}$C NMR (CD$_3$OD, 75 MHz): δ 173.9, C4; 173.5, C11; 173.4, C1; 173.2, C7; 158.8, ArC4'''; 158.4, CN$_3$; 134.9, C2''''; 134.2, C2'; 131.2, ArC1'''; 130.3, ArCH2''' and ArCH6'''; 117.4, C3'; 116.2, C3''''; 115.6, ArCH3''' and ArCH5'''; 69.7, C1''''; 56.6, C2; 53.8, C5; 53.6, C8; 52.8, OCH$_3$; 50.1, C3''; 36.6, ArCH$_2$; 36.5, C1'; 30.3, C2''; 23.0, C11; 22.5, C1''. Mass Spectrum (ES, +ve) m/z 531.1 (100%) [M$^+$]. HRMS calcd for C$_{26}$H$_{39}$N$_6$O$_6$ 531.2931, found 531.2916.

Methyl(2S,5R,8S)-2-allyl-8-(4-allyloxybenzyl)-3,6,9-triaza-5-(3-[guanidino]propyl)-4,7,10-oxoundecanoate hydrochloride (82)

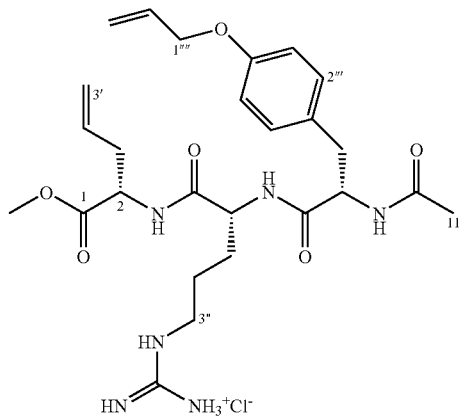

The title compound was synthesized using the general N-Boc deprotection procedure (Procedure A), from 30 (70 mg, 0.088 mmol) to yield 82 as a highly hydroscopic solid (37 mg, 0.065 mmol, 74%). $^1$H NMR (CD$_3$OD, 300 MHz): δ 7.12 (d, J=7.5 Hz, 2H, ArH2''' and ArH6'''); 6.83 (d, J=7.5 Hz, 2H, ArH3''' and ArC5'''); 6.01 (m, 1H, H2''''); 5.69 (m, 1H, H2'); 5.35 (d, J=17.4 Hz, 1H, H3$_a$''''); 5.19 (d, J=9.9 Hz, 1H, H3$_b$''''); 5.09 (m, 2H, H3'); 4.47 (m, 2H, H2''''); 4.40 (m, 2H, H2 and H5); 4.16 (m, 1H, H8); 3.65 (s, 3H, OCH$_3$); 3.31 (m, 2H, H3''); 2.95 (m, 2H, ArCH$_2$); 2.50 (m, 2H, H1'); 1.92 (s, 3H, H11); 1.74 (m, 2H, H1''); 1.23 (m, 2H, H2''). $^{13}$C NMR (CD$_3$OD, 75 MHz): δ 174.0, C4; 173.4, Cl$_1$; 172.9, C1; 169.0, C7; 158.8, ArC4'''; 158.2, CN$_3$; 134.7, C2''''; 134.3, C2'; 131.2, ArC1'''; 129.8, ArCH2''' and ArCH6'''; 118.4, C3'; 117.4, C3''''; 115.7, ArCH3''' and ArCH5'''; 69.8, C1''''; 57.7, C2; 54.0, C5; 53.7, C8; 52.8, OCH$_3$; 50.1, C3''; 37.5, ArCH$_2$; 36.4, C1'; 29.5, C2''; 24.0, C11; 22.3, C1''. Mass Spectrum (ES, +ve) m/z 531 (100%) [M$^+$]. HRMS calcd for C$_{26}$H$_{39}$N$_6$O$_6$ 531.2931, found 531.2939.

Methyl(2S,5R,8S)-2,8-di(4-allyloxybenzyl)-5-(4-aminobutyl)-3,6,9-triaza-4,7,10-trioxoundecanoate hydrochloride (83)

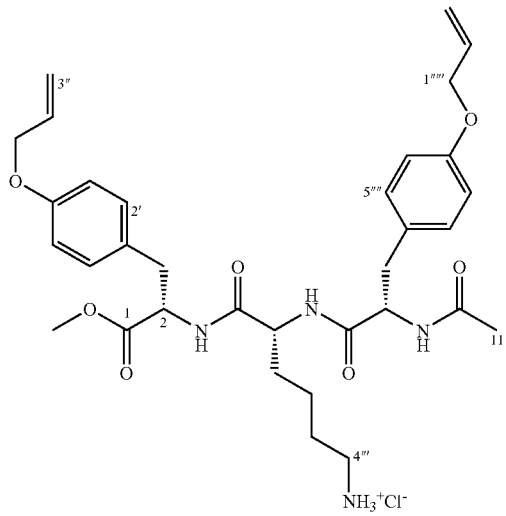

The title compound was synthesized using the general N-Boc deprotection procedure (Procedure A), from 63 (33 mg, 0.051 mmol) to yield 83 (18 mg, 0.028 mmol, 55%) as a yellow solid. Mp 186-190° C. $^1$H NMR (CD$_3$OD, 500 MHz): δ 7.50 (bs, 1H, NH); 7.41 (m, 4H, ArH); 7.17 (m, 4H, ArH); 6.38 (m, 2H, H2″ and H12″″); 5.64 (m, 4H, H3″ and H3″″); 4.83 (m, 6H, H2, H8, H1″ and H1″″); 4.51 (m, 1H, H5); 3.70 (s, 3H, OCH$_3$); 3.28 (m, 6H, H4‴, Ar′—CH$_2$ and Ar″″—CH$_2$); 2.27 (s, 3H, H111); 1.87 (m, 4H, H1″ and H3″); 1.33 (m, 2H, H2″). $^{13}$C NMR (CD$_3$OD, 125 MHz): δ 173.9, C7; 173.7, C4; 173.1, C1; 172.0, C10; 158.5, ArC4″″ and ArC4′; 134.7, C2″ and C2″″; 131.3, ArCH2′ and ArCH6′; 131.1, ArCH2″″ and ArCH6″″; 130.0, ArC1″″; 129.8, ArC1′; 117.8, C3″; 117.5, C3″″; 115.8, ArCH3′ and ArCH5′; 115.6, ArCH3″″ and ArCH5″″; 70.0, C1″; 69.8, C1″″; 57.2, C2; 55.2, C5; 53.8, OCH$_3$; 52.4, C8; 40.7, C4‴; 37.4, Ar′—CH$_2$; 37.1, Ar″″—CH$_2$; 31.7, C1‴; 27.9, C3‴; 23.2, C11; 22.2, C2‴. Mass Spectrum (ES, +ve) m/z 609.7 (100%) [M$^+$]. HRMS calcd for C$_{33}$H$_{45}$N$_4$O$_7$ 609.3288, found 609.3301.

Methyl(2S,5R,8S)-2-allyl-8-(4-allyloxybenzyl)-3,6,9-triaza-5-(4-[{N,N-di-tert-butoxycarbonyl}guanidino]butyl)-4,7,10-trioxoundecanoate (84)

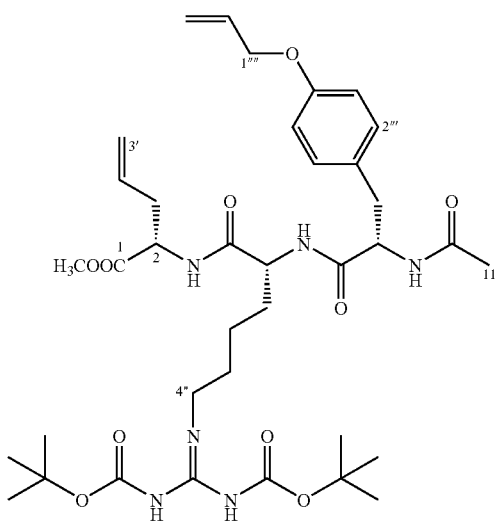

To a solution of 21 (56 mg, 0.093 mmol) in DCM (2 mL) was added TFA (2 mL) and the resulting mixture was allowed to stir for 3 h. The solvent was concentrated and the intermediate trifluoroacetate salt was precipitated by addition of diethyl ether and collected as a solid by vacuum filtration. To this solid was added N-tert-butoxycarboxamido(trifluoromethylsulfonylimino)methyl propanamide (65 mg, 0.17 mmol), triethylamine (0.2 mL) and DCM (2 mL). The resulting solution was allowed to stir for 16 h under N$_2$. The solvent was evaporated and the crude product was purified by flash column chromatography (15:1, DCM/MeOH) to yield the title compound as a 1:1 mixture of epimers (70 mg, 0.093 mmole, 100%) as an orange/yellow solid. Mp 112-114° C. $^1$H NMR (CDCl$_3$, 300 MHz): δ 8.31 (bs, 1H, NH); 7.20 (d, J=8.0 Hz, 1H, NH); 7.08 (m, 2H, ArH2‴ and ArH6‴); 6.94 (d, J=7.6 Hz, 1H, NH); 6.84 (m, 2H, ArH3‴ and ArH5‴); 6.72 (d, J=7.2 Hz, 1H, NH); 6.60 (d, J=7.6 Hz, 1H, NH); 6.02 (m, 1H, H2″″); 5.65 (m, 1H, H2′); 5.38 (d, J=17.3 Hz, 1H, H3$_a$″″); 5.26 (d, J=10.5 Hz, 1H, H3$_b$″″); 5.11 (m, 2H, H3′); 4.52 (m, 5H, H2, H5, H8 and H2″″); 3.74/3.70 (s, 3H, OCH$_3$); 3.32 (d, J=6.7 Hz, 2H, H4″); 2.95 (m, 2H, ArCH$_2$); 2.50 (m, 2H, H1′); 1.97./1.96 (s, 3H, H$_{11}$); 1.37 (m, 6H, H1″, H2″ and H3″); 1.49 (s, 18H, 2×C(CH$_3$)$_3$). Mass Spectrum (ES, +ve) m/z 745.4 (100%) [MH$^+$]. HRMS calcd for C$_{37}$H$_{57}$N$_6$O$_{10}$ 745.4136, found 745.4138.

Methyl(2S,5S,8S)-2-allyl-8-(4-allyloxybenzyl)-3,6,9-triaza-5-(4-[{N,N-di-tert-butoxycarbonyl}guanidino]butyl)-4,7,10-trioxoundecanoate (85)

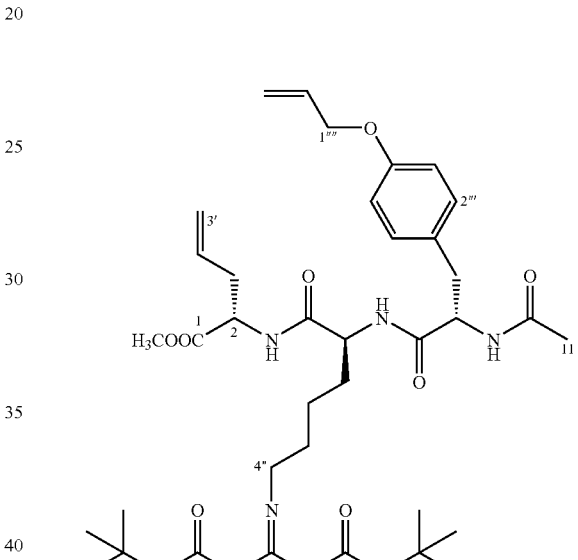

To a solution of 25 (41 mg, 0.081 mmol) in DCM (2 mL) was added N-tert-butoxycarboxamido (trifluoromethylsulfonylimino)methyl propanamide (35 mg, 0.089 mmol), triethylamine (0.1 mL). The resulting solution was allowed to stir for 16 h under N$_2$. The solvent was evaporated and the crude product was purified by flash column chromatography (15:1, DCM/MeOH) to yield the title compound as a 1:1 mixture of epimers (45 mg, 0.060 mmole, 74%) as an orange/yellow solid. Mp 114-118° C. $^1$H NMR (CDCl$_3$, 300 MHz): δ 8.26 (bs, 1H, NH); 7.08 (t, J=8.4 Hz, 2H, ArH2‴ and ArH6‴); 6.97 (m, 1H, NH); 6.83 (t, J=8.4 Hz, 2H, ArH3‴ and ArH5‴); 6.73 (d, J=8.0 Hz, 1H, NH); 6.57 (t, J=9.3 Hz, 1H, NH); 6.03 (m, 1H, H2″″); 5.66 (m, 1H, H2′); 5.39 (d, J=17.3 Hz, 1H, H3$_a$″″); 5.26 (d, J=10.1 Hz, 1H, H3$_b$″″); 5.10 (m, 2H, H3′); 4.51 (m, 5H, H2, H5, H8 and H1″″); 3.74/3.71 (s, 3H, OCH$_3$); 3.33 (bs, 2H, H4″); 2.96 (m, 2H, H1′); 2.52 (m, 2H, ArCH$_2$); 1.97 (s, 3H, H$_{11}$); 1.47 (m, 6H, H1″, H2″ and H3″); 1.49 (s, 18H, C(CH$_3$)$_3$). Mass Spectrum (ES, +ve) m/z 745.2 (100%) [MH$^+$]. HRMS calcd for C$_{37}$H$_{57}$N$_6$O$_{10}$ 745.4136, found 745.4105.

(7S,10S,13S,4E/Z)-13-Acetamido-8,11-diaza-10-(4-[{N,N-di-tert-butoxycarbonyl}guanidino]butyl)-7-methoxycarbonyl-2-oxa-9,12-dioxo-1(1,4)phenylenacyclotetradecaphane-4-ene (86)

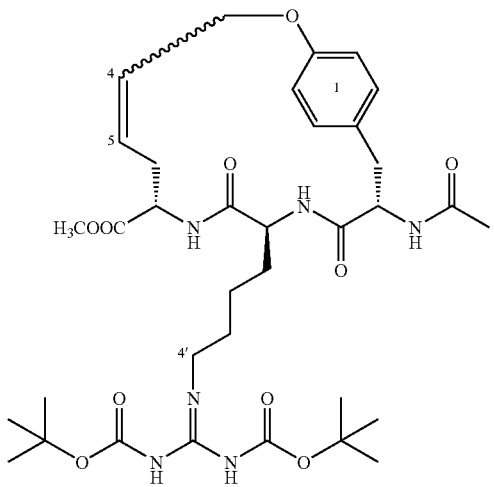

To a solution of 26 (75 mg, 0.15 mmol) in DCM (2 mL) was added N-tert-butoxycarboxamido(trifluoromethylsulfonylimino)methyl propanamide (115 mg, 0.29 mmol), triethylamine (0.1 mL) and DCM (2 mL). The resulting solution was allowed to stir for 16 h under $N_2$. The solvent was evaporated and the crude product was purified by flash column chromatography (15:1, DCM/MeOH) to yield 86 as a 1:1 mixture of epimers (96 mg, 0.13 mmole, 87%) as an orange/yellow solid. Mp 104-102° C. $^1$H NMR (CDCl$_3$, 300 MHz): δ 8.26 (m, 1H, NH); 6.89 (m, 4H, ArH); 5.63 (m, 2H, H4 and H5); 4.65 (m, 5H, H2, H7, H10 and H13); 3.79/3.78 (s, 3H, OCH$_3$); 3.30 (m, 2H, H4'); 2.92 (m, 2H, H6); 2.67 (m, 2H, H14); 2.09/2.07 (s, 3H, NCOCH$_3$); 1.55 (m, 6H, H1', H2' and H3'); 1.49/1.48 (s, 18H, C(CH$_3$)$_3$). Mass Spectrum (ES, +ve) m/z 717.4 (100%) [MH$^+$]. HRMS calcd for C$_{35}$H$_{53}$N$_6$O$_{10}$ 717.3823, found 717.3806.

Methyl(2S,5R,8S)-2-allyl-9-(4-allyloxybenzyl)-5-(4-[guanidino]butyl)-3,6,9-triaza-4,7,10-trioxoundecanoate hydrochloride (87)

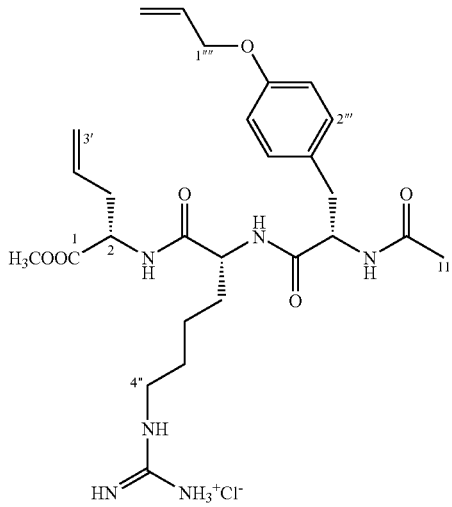

The title compound was synthesized using the general N-Boc deprotection procedure (Procedure A), from 84 (71 mg, 0.095 mmol) to yield 87 (43 mg, 0.074 mmol, 78%) as a yellow hydroscopic solid. $^1$H NMR (CD$_3$OD, 300 MHz): δ 8.20 (m, 2H, NH×2); 7.15 (d, J=8.4 Hz, 2H, ArH2''' and ArH6'''); 6.87 (d, J=8.4 Hz, 2H, ArH3''' and ArH5'''); 6.03 (m, 1H, H2''''); 5.73 (m, 1H, H2'); 5.39 (d, J=17.3 Hz, 1H, H3$_a$''''); 5.24 (d, J=10.5 Hz, 1H, H3$_b$''''); 5.12 (d, J=6.0 Hz, 1H, H3$_a$'); 5.05 (d, J=9.9 Hz, 1H, H3$_b$'); 4.45 (m, 4H, H2, H5 and H11''''); 4.17 (dd, J=4.0, 8.7 Hz, 1H, H8); 3.72 (s, 3H, OCH$_3$); 2.99 (m, 4H, H1' and H4''); 2.53 (m, 2H, ArCH$_2$); 1.94 (s, 3H, H11); 1.59 (m, 4H, H2'' and H3''); 1.00 (m, 2H, H1''). $^{13}$C NMR (CD$_3$OD, 75 MHz): δ 174.3, C4; 174.0, C11; 173.3, C1; 173.2, C7; 159.0, ArC4'''; 158.5, CN$_3$; 134.9, C2''''; 134.5, C2'; 131.4, ArC1'''; 130.4, ArCH2''' and ArCH6'''; 118.6, C3'; 117.5, C3''''; 115.9, ArCH3''' and ArCH5'''; 69.8, C1''''; 57.5, C2; 54.3, C5; 53.8, C8; 52.7, OCH$_3$; 42.1, C4''; 37.5, ArCH$_2$; 36.4, C1'; 31.9, C2''; 29.2, C3''; 23.6, C11; 22.4, C1''. Mass Spectrum (ES, +ve) m/z 545.4 (100%) [M$^+$]. HRMS calcd for C$_{27}$H$_{41}$N$_6$O$_6$ 545.3088, found 545.3073.

Methyl(2S,5S,8S)-2-allyl-9-(4-allyloxyphenyl)-5-(4-[guanidino]butyl)-3,6,9-triaza-4,7,10-trioxoundecanoate hydrochloride (88)

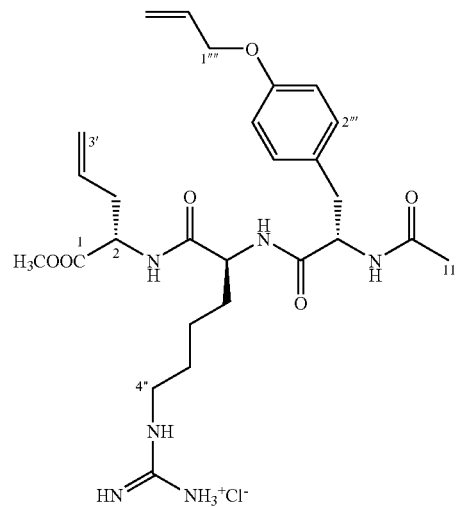

The title compound was synthesized using the general N-Boc deprotection procedure (Procedure A), from 85 (40 mg, 0.054 mmol) to yield 88 (11 mg, 0.019 mmol, 35%) as a highly hydroscopic yellow solid. $^1$H NMR (CD$_3$OD, 300 MHz): δ 7.10 (bs, 2H, ArH2''' and ArH6'''); 6.79 (bs, 2H, ArH3''' and ArH5'''); 6.00 (m, 1H, H2''''); 5.72 (m, 1H, H2'); 5.16 (m, 4H, H3'''' and H3'); 4.40 (m, 5H, H2, H5, H8 and H1''''); 3.65 (s, 3H, OCH$_3$); 3.00 (m, 4H, H1' and H4''); 2.49 (bs, 2H, ArCH$_2$); 1.87 (s, 3H, H11); 1.36 (m, 6H, H1'', H2'' and H3''). $^{13}$C NMR (CD$_3$OD, 75 MHz): δ 174.2, C4; 174.1, C11; 173.6, C1; 173.2, C7; 159.4, ArC4'''; 158.4, CN$_3$; 134.6, C2''''; 134.2, C2'; 131.2, ArC1'''; 130.3, ArCH2''' and ArCH6'''; 119.6, C3'; 118.2, C3''''; 116.3, ArCH3''' and ArCH5'''; 70.0, C1''''; 57.4, C2; 54.4, C5; 53.9, C8; 52.4, OCH$_3$; 42.2, C4''; 37.6, ArCH$_2$; 36.6, C1'; 32.5, C2''; 29.5, C3''; 23.6, C11; 22.8, C1''. Mass Spectrum (ES, +ve) m/z 545.3 (100%) [M$^+$]. HRMS calcd for C$_{27}$H$_{41}$N$_6$O$_6$ 545.3088, found 545.3066.

(7S,10S,13S,4E/Z)-13-Acetamido-10-(4-[guanidino]butyl)-8,11-diaza-7-methoxycarbonyl-2-oxa-9,12-dioxo-1(1,4)phenylenacyclotetradecaphane-4-ene hydrochloride (89)

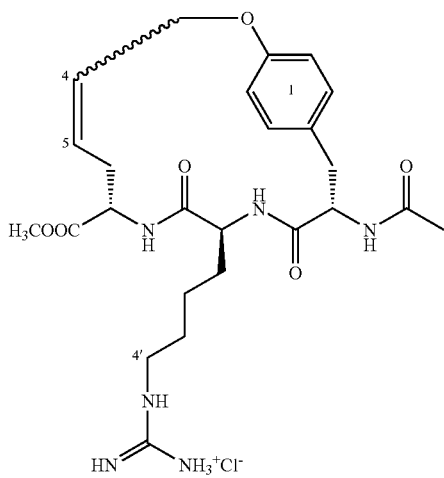

The title compound was synthesized using the general N-Boc deprotection procedure (Procedure A), from 86 (86 mg, 0.12 mmol) to yield 89 (50 mg, 0.097 mmol, 81%) as a highly hydroscopic yellow solid. $^1$H NMR (CD$_3$OD, 500 MHz): δ 10.34 (bs, 1H, NH); 0.42 (m, 2H, ArH); 7.08 (m, 2H, ArH); 5.97 (m, 2H, H4 and H5); 4.80 (m, 5H, H2, H7, H10 and H13); 3.65 (s, 3H, OCH$_3$); 3.32 (m, 2H, H4'); 3.09 (m, 2H, H6); 2.42 (m, 2H, H14); 2.10 (s, 3H, NCOCH$_3$); 2.04 (m, 2H, H3'); 1.86 (m, 2H, H1'); 1.50 (m, 2H, H2'). $^{13}$C NMR (CD$_3$OD, 125 MHz): δ 173.3/173.2, C9; 172.7/173.6, 7-CO; 172.5, 13-NCO; 169.4, C12; 158.5/158.4, 1-ArC1; 131.4/131.3, 1-ArCH2 and 1-ArCH6; 131.0, C4; 129.3, C5; 129.0, 1-ArC4; 116.5, 1-ArCH3 and 1-ArCH5; 67.0, C3; 58.2, C7; 57.5, C13; 57.4, C10; 53.9, OCH$_3$; 42.1, C4'; 33.9, C14; 29.0, C6; 23.5, C3'; 22.7, C1'; 22.5, NCOCH$_3$; 22.5, C2'. Mass Spectrum (ES, +ve) m/z 517.4 (100%) [M$^+$]. HRMS calcd for C$_{25}$H$_{37}$N$_6$O$_6$ 517.2775, found 517.2765.

(S)-2-Amino-3-(4-iodophenyl)propanoic acid (92)

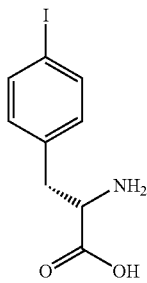

To a solution (S)-2-amino-3-phenylpropanoic acid 91 (4.01 g, 24.3 mmol) in acetic acid (22 mL) was added sulfuric acid (2.9 mL, 5.14 mmol), iodine (2.47 g, 4.7 mmol) and sodium iodate (1.02 g, 5.14 mmol). The mixture was heated to 70° C. and allowed to stir at this temperature for 16 h before an additional portion of sodium iodate (1.02 g, 5.14 mmol) was added. The reaction was left for a further 2 h before being concentrated, dissolved in methanol (20 mL) and treated with NaOH (60 mL). The mixture was left to precipitate out of the basic solution overnight and the resulting solid was filtered by vacuum filtration to yield the title compound (7.07 g, 24.3 mmol, 100%) as a pink solid, which had spectral data in agreement with that reported.[93] $[α]_D^{21}$ −10.6 (c. 0.3, HCl). Mp 258-260° C. (lit. 261-262° C.)[93] $^1$H NMR (CD$_3$OD, 300 MHz): δ 7.71 (d, J=8.4 Hz, 2H, ArH2' and ArH6'); 7.10 (d, J=8.4 Hz, 2H, ArH3' and ArH5'); 4.26 (dd, J=6.3, 7.2 Hz, H2); 3.26 (dd, J=5.4, 14.1 Hz, 1H, H3$_a$); 3.04 (dd, J=7.2, 14.4 Hz, 1H, H3$_b$). Mass Spectrum (CI, +ve) m/z 279 (100%), 292 (70%) [M$^+$]. HRMS calcd for C$_9$H$_{11}$NO$_2$ 291.9834 found 291.9568.

Methyl(2S)-2-amino-3-(4-iodophenyl)propanoate hydrochloride (93)

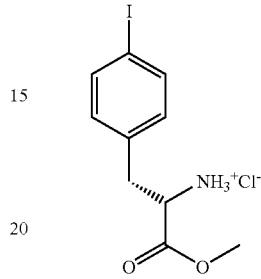

To a solution of 92 (2.00 g, 6.87 mmol) in MeOH (10 mL) at 0° C. was added thionyl chloride (2 mL) and the resulting solution was allowed to stir for 16 h whilst equilibrating to RT. The reaction was evaporated to dryness in vacuo to yield the title compound (2.25 g, 6.80 mmol, 99%) as a white solid, which had spectral data in agreement with that reported.[93] $[α]_D^{21}$ −9.3 (c. 0.15, HCl). Mp 195-198° C. (lit. 199.5-200.5° C.)[93] $^1$H NMR (CD$_3$OD, 300 MHz): δ 7.72 (d, J=8.4 Hz, 2H, ArH2' and ArH6'); 7.06 (d, J=8.4 Hz, 2H, ArH3' and ArH5'); 4.33 (dd, J=6.3, 6.9 Hz, 1H, H2); 3.80 (s, 3H, OCH$_3$); 3.23 (dd, J=6.6, 14.4 Hz, 1H, H3$_a$); 3.15 (dd, J=7.2, 14.4 Hz, 1H, H3$_b$). Mass Spectrum (ES, +ve) m/z 306 (100%) [M$^+$]. HRMS calcd for C$_{10}$H$_{13}$INO$_2$ 305.9986 found 305.9980.

Methyl(2S)-2-acetamido-3-(4-iodophenyl)propanoate (94)

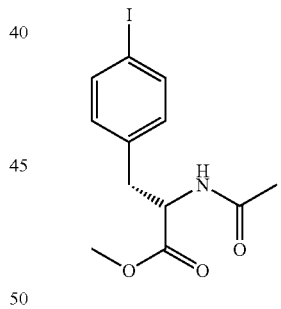

To a solution of 93 (2.25 g, 6.80 mmol) in 10% HCl (10 mL) at 0° C. was added 4M sodium acetate (115 mL) and the resulting reaction was allowed to stir whilst equilibrating to 0° C. Acetic anhydride (50 mL) was added and the reaction allowed to proceed with vigorous stirring. After 1 h the product was collected by vacuum filtration, dissolved in ethyl acetate (30 mL) and washed with 2M sodium bicarbonate (2×30 mL). The organic layer was dried and evaporated to yield the title compound (1.31 g, 3.79 mmol, 56%) as a white solid. Mp 118-120° C. $[α]_D^{27}$ +93.8 (c. 0.1, CHCl$_3$). $^1$H NMR (CDCl$_3$, 300 MHz): δ 7.61 (d, J=8.4 Hz, 2H, ArH2' and ArH6'); 6.84 (d, J=8.1 Hz, 2H, ArH3' and ArH5'); 5.92 (d, J=7.2 Hz, 1H, NH); 4.87 (m, 1H, H2); 3.73 (s, 3H, OCH$_3$); 3.11 (dd, J=6.0, 13.8, Hz, 1H, H3$_a$); 3.03 (dd, J=5.4, 13.8 Hz, 1H, H3$_b$); 1.99 (s, 3H, NCOCH$_3$). Mass Spectrum (CI, +ve) m/z 348 (100%) [MH$^+$]. HRMS calcd for C$_{12}$H$_{15}$NO$_3$I 348.0097, found 348.0104.

Methyl(2S)-2-acetamido-3-(4-trimethylstannylphenyl)propanoate (95)

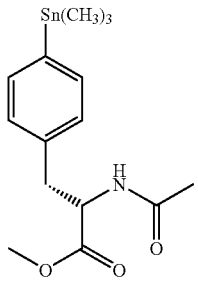

A solution of 94 (590 mg, 1.7 mmol), hexamethyldistannane (781 mg, 2.38 mmol), palladium acetate (20 mg, 0.085 mmol), and triphenylphosphine (45 mg, 0.17 mmol) in toluene (7 mL) was flushed with nitrogen for 15 minutes and then heated at 100° C. for 30 min under $N_2$. The brown mixture was filtered through a short pad of silica, diluted with diethyl ether (40 mL) and washed twice with water. The organic layer was dried and evaporated to yield the title compound (497 mg, 1.29 mmol, 76%) as a clear oil. $[\alpha]_D^{27}$ +13.7 (c. 0.3, $CHCl_3$). $^1H$ NMR ($CDCl_3$, 300 MHz): δ 7.41 (d, J=7.5 Hz, 2H, ArH2' and ArH6'); 7.07 (d, J=7.8 Hz, 2H, ArH3' and ArH5'); 6.25 (d, J=7.8 Hz, 1H, NH); 4.87 (m, 1H H2); 3.72 (s, 3H, $OCH_3$); 3.12 (dd, J=5.7, 14.1 Hz, 1H, $H3_a$); 3.04 (dd, J=6.0, 13.9 Hz, 1H, $H3_b$); 1.98 (s, 3H, $NCOCH_3$); 0.27 (t, J=27.6 Hz, 9H, $Sn(CH_3)_3$). Mass Spectrum (CI, +ve) m/z 386 (50%) [MH$^+$], 382 (10%) [MH$^+$] (Sn 112), δ (100%). HRMS calcd for $C_{15}H_{24}NO_3Sn$ (Sn 112) 382.075357 found 382.075603.

Methyl(2S)-2-acetamido-3-(4-[9-anthracenyl]phenyl)-propanoate (96)

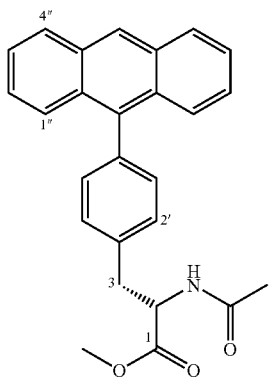

A solution of 95 (192 mg, 0.50 mmol), 9-bromoanthracene (141 mg, 0.55 mmol), palladium acetate (6 mg, 0.025 mmol), and tri-o-tolylphosphine (15 mg, 0.05 mmol) in DMF (2 mL) was flushed with $N_2$ for 15 min then heated to 70° C. and allowed to stir for 16 h. The reaction was diluted with diethyl ether (20 mL) and washed with water (5×20 mL), dried and evaporated. The crude product was purified by flash column chromatography (15% EtOAc/hexane then 5% MeOH/DCM) to yield the title compound (133 mg, 0.33 mmol, 67%) as an orange oil. $[\alpha]_D^{27}$ +66.9 (c. 0.1, $CHCl_3$). $^1H$ NMR ($CDCl_3$, 300 MHz): δ 8.48 (s, 1H, ArH10"); 8.03 (dd, J=0.9, 8.7 Hz, 2H, ArH3" and ArH6"); 7.63 (dd, J=0.6, 9.0 Hz, 2H, ArH8" and ArH1"); 7.45 (m, 2H, ArH4" and ArH5"); 7.36 (m, 6H, ArH2" and ArH7", 4×ArH'); 5.40 (d, J=7.8 Hz, 1H, NH); 5.04 (m, 1H, H2); 3.79 (s, 3H, $OCH_3$); 3.32 (dd, J=5.7, 13.8 Hz, 1H, $H3_a$); 3.25 (dd, J=6.3, 13.8 Hz, 1H, $H3_b$); 2.08 (s, 3H, $COCH_3$). Mass Spectrum (CI, +ve) m/z 398 (100%) [MH$^+$]. HRMS calcd for $C_{26}H_{23}NO_3$ 397.1678, found 397.1675.

Methyl(2S)-2-acetamido-3-(4-[9-phenanthrenyl]phenyl)propanoate (98)

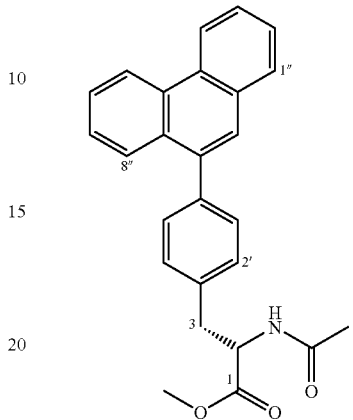

A solution of 95 (259 mg, 0.67 mmol), 9-bromophenanthrene (190 mg, 0.74 mmol), palladium acetate (8 mg, 0.034 mmol), and tri-o-tolylphosphine (20 mg, 0.067 mmol) in DMF (2 mL) was flushed with $N_2$ for 15 min then heated to 70° C. and allowed to stir for 16 h. The reaction was diluted with diethyl ether (20 mL) and washed with water (5×20 mL), dried and evaporated. The crude product was purified by flash column chromatography (15% EtOAc/hexane then 5% MeOH/DCM) to yield the title compound (157 mg, 0.40 mmol, 59%) as a clear oil. $[\alpha]_D^{27}$ +94.6 (c. 0.1, $CHCl_3$). $^1H$ NMR ($CDCl_3$, 300 MHz): δ 8.77 (d, J=9.0 Hz, 1H, ArH4"); 8.71 (d, J=8.1 Hz, 1H, ArH3"); 7.89 (m, 2H, ArH1" and ArH10"); 7.61 (m, 5H, ArH7", ArH6", ArH5", ArH2" and ArH1"); 7.48 (d, J=8.4 Hz, 2H, ArH2' and ArH6'); 7.26 (d, J=8.1 Hz, 2H, ArH3' and ArH5'); 6.25 (d, J=7.5 Hz, 1H, NH); 5.00 (m, 1H, H2); 3.79 (s, 3H, $OCH_3$); 3.30 (dd, J=5.7, 13.8 Hz, 1H, $H3_a$); 3.20 (dd, J=6.0, 13.8 Hz, 1H, $H3_b$); 2.05 (s, 3H, $COCH_3$). Mass Spectrum (CI, +ve) m/z 398 (100%) [MH$^+$]. HRMS (EI) calcd for $C_{26}H_{23}NO_3$ 397.1678, found 397.1680.

(2S)-2-Acetamido-3-(4-[9-anthracenyl]phenyl) propanoic acid (97)

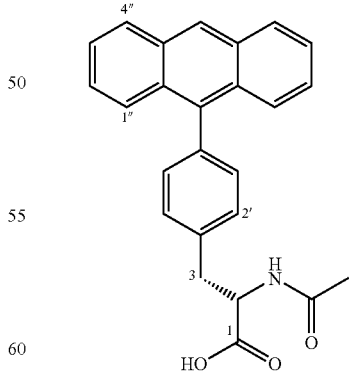

To a solution of 96 (80 mg, 0.02 mmol) in THF/water, 2:1 (3 mL) was added lithium hydroxide monohydrate (17 mg, 0.40 mmol) and the resulting suspension was allowed to stir for 16 h. The reaction mixture was diluted with water (30 mL) and the THF was removed by evaporation. The aqueous layer was washed with DCM (40 mL) to remove unreacted starting material. The aqueous phase was acidified with 10% HCl and the resulting precipitate was extracted with DCM (3×40 mL). The combined organics were dried and evaporated to yield the title compound (69 mg, 0.18 mmol, 90%) as a white solid. Mp 76° C. $[\alpha]_D^{20}$ +29.7 (c. 0.1, EtOH). $^1$H NMR (CDCl$_3$, 300 MHz): δ 8.47 (s, 1H, ArH10"); 8.02 (d, J=8.4 Hz, 2H, ArH3" and ArH6"); 7.59 (d, J=8.7 Hz, 2H, ArH8" and ArH1"); 7.45 (m, 2H, ArH4" and ArH5"); 7.35 (m, 6H, ArH2" and ArH7", 4×ArH'); 6.27 (d, J=6.6 Hz, 1H, NH); 5.00 (m, 1H, H2); 3.39 (dd, J=4.8, 12.9 Hz, 1H, H3$_a$); 3.26 (dd, J=6.3, 14.4 Hz, 1H, H3$_b$); 2.07 (s, 3H, COCH$_3$). Mass Spectrum (ES, +ve) m/z 383 (70%) [MH$^+$]. HRMS calcd for C$_{25}$H$_{22}$NO$_3$ 384.1600, found 384.1610.

(2S)-2-Acetamido-3-(4-[9-phenanthrenyl]phenyl) propanoic acid (99)

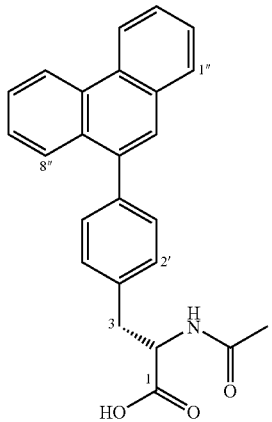

To a solution of 98 (124 mg, 0.31 mmol) in THF/water, 2:1 (9 mL) was added lithium hydroxide monohydrate (26 mg, 0.62 mmol) and the resulting suspension was allowed to stir for 16 h. The reaction mixture was diluted with water (30 mL) and the THF was removed by evaporation. The aqueous layer was washed with DCM (40 mL) to remove unreacted starting material. The aqueous phase was acidified with 10% HCl and the resulting precipitate was extracted with DCM (3×40 mL). The combined organics were dried and evaporated to yield the title compound (65 mg, 0.17 mmol, 55%) as a white solid. Mp 128-132° C. $[\alpha]_D^{20}$ +36.8 (c. 0.1, EtOH). $^1$H NMR (CD$_3$OD, 300 MHz): δ 8.71 (d, J=8.1 Hz, 1H, ArH4"); 8.66 (d, J=8.4 Hz, 1H, ArH3"); 7.79 (s, 1H, ArH1"); 7.76 (s, 1H, ArH10"); 7.51 (m, 5H, ArH7", ArH6", ArH5", ArH2" and ArH1"); 7.32 (m, 2H, Ar'H); 4.76 (dd, J=5.1, 9.0 Hz, 1H, H2); 3.29 (dd, J=4.8, 13.5 Hz, 1H, H3$_a$); 3.03 (dd, J=8.7, 13.5 Hz, 1H, H3$_b$); 1.95 (s, 3H, COCH$_3$). Mass Spectrum (ES, +ve) m/z 384 (50%) [MH$^+$]. HRMS calcd for C$_{25}$H$_{22}$NO$_3$ 384.1600, found 384.1628.

(2'-Allyloxy-[1,1']-(S)-binaphthalen-2-yloxy)-acetic acid (101)

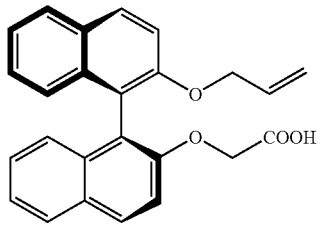

To a solution of 1,1'-(S)-binapthol (1.00 g, 3.50 mmol) and K$_2$CO$_3$ (600 mg, 4.35 mmol) in acetone (12 mL) was added dropwise, allyl bromide (0.26 mL, 3.68 mmol). The resulting mixture was heated at reflux with stirring for 16 h before being filtered, concentrated and dissolved in anhydrous MeOH (40 mL). To this solution was added K$_2$CO$_3$ (2.4 g, 17.4 mmol) and bromoacetic acid (1.21 g, 8.75 mmol). This mixture was heated at reflux for a further 3 h before evaporation to dryness and dissolution in water (50 mL). The aqueous layer was then washed with diethyl ether (3×30 mL) before acidification with 3M HCl. The acidified solution was extracted with DCM, dried before being evaporated to dryness to yield the title compound (825 mg, 2.15 mmol, 61%) as a viscous yellow oil. $^1$H NMR (CDCl$_3$, 300 MHz): δ 7.96 (m, 2H, ArH); 7.86 (m, 2H, ArH); 7.26 (m, 8H, ArH); 5.66 (m, 1H, H2"); 4.94 (m, 2H, H3"); 4.61 (AB$_q$, J=16.8 Hz, 2H, CH$_2$—COOH); 4.48 (m, 2H, H1"). Mass Spectrum (CI, +ve) m/z 339 (40%) [—COOH], 385 (100%) [MH$^+$]. HRMS calcd for C$_{25}$H$_{21}$O$_4$ 385.143984, found 385.142526.

(2'-Benzyloxy-[1,1']-(S)-binaphthalen-2-yloxy)-acetic acid (102)

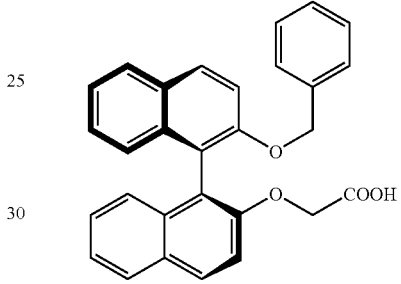

To a solution of 1,1'-(S)-binapthol (500 mg, 1.75 mmol) and K$_2$CO$_3$ (300 mg, 2.18 mmol) in acetone (6 mL) was added dropwise, benzyl bromide (0.21 mL, 1.75 mmol). The resulting mixture was heated at reflux with stirring for 16 h before being filtered, concentrated and dissolved in anhydrous MeOH (5 mL). To this solution was added K$_2$CO$_3$ (2.4 g, 17.4 mmol) and bromoacetic acid (740 g, 5.25 mmol). This mixture was heated at reflux for a further 3 h before evaporation to dryness and dissolution in water (50 mL). The aqueous layer was then washed with diethyl ether (3×30 mL) before acidification with 3M HCl. The acidified solution was extracted with DCM, dried before being evaporated to dryness to yield the title compound (218 mg, 0.50 mmol, 29%) as a viscous yellow oil. $^1$H NMR (CDCl$_3$, 300 MHz): δ 10.30 (bs, 1H, COOH); 7.85 (m, 4H, ArH); 7.16 (m, 13H, ArH); 4.99 (AB$_q$, J=12.6 Hz, 2H, CH$_2$—COOH); 4.48 (AB$_q$, J=17.1 Hz, 2H, H1"). Mass Spectrum (CI, +ve) m/z 435 (100%) [MH$^+$]. HRMS calcd for C$_{29}$H$_{23}$O$_4$ 435.159634, found 435.158151.

(2'-Methyloxy-[1,1']-(S)-binaphthalen-2-yloxy)-acetic acid (103)

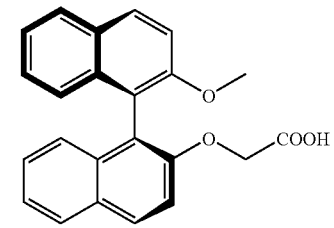

To a solution of 1,1'-(S)-binapthol (500 mg, 1.75 mmol) and K$_2$CO$_3$ (300 mg, 2.18 mmol) in acetone (6 mL) was added dropwise, methyl iodide (0.11 mL, 1.75 mmol). The resulting mixture was heated at reflux with stirring for 16 h before being filtered, concentrated and dissolved in anhydrous MeOH (5 mL). To this solution was added $K_2CO_3$ (2.4 g, 17.4 mmol) and bromoacetic acid (740 g, 5.25 mmol). This mixture was heated at reflux for a further 3 h before evaporation to dryness and dissolution in water (50 mL). The aqueous layer was then washed with diethyl ether (3×30 mL) before acidification with 3M HCl. The acidified solution was extracted with DCM, and dried before being evaporated to dryness to yield the title compound (236 mg, 0.66 mmol, 38%) as a viscous yellow oil. $^1$H NMR (CDCl$_3$, 300 MHz): δ 10.22, COOH; 7.84 (m, 4H, ArH); 7.22 (m, 8H, ArH); 4.49 (AB$_q$, J=16.8 Hz, 2H, CH$_2$—COOH); 3.65 (s, 3H, OCH$_3$). Mass Spectrum (CI, +ve) m/z 359 (100%) [MH$^+$]. HRMS (EI) calcd for $C_{23}H_{18}O_4$ 358.120509, found 358.120418.

(2'-(3-Phenylallyloxy)-[1,1']-(S)-binaphthalen-2-yloxy)-acetic acid (104)

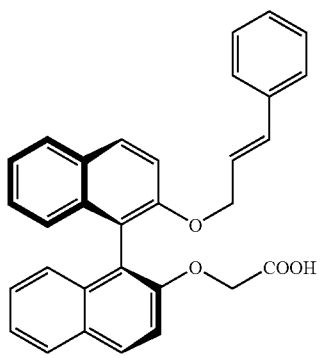

To a solution of 1,1'-(S)-binapthol (500 mg, 1.75 mmol) and $K_2CO_3$ (300 mg, 2.18 mmol) in acetone (6 mL) was added dropwise, cinnamyl bromide (362 mg, 1.84 mmol). The resulting mixture was heated at reflux with stirring for 16 h before being filtered, concentrated and dissolved in anhydrous MeOH (5 mL). To this solution was added $K_2CO_3$ (2.4 g, 17.4 mmol) and bromoacetic acid (740 g, 5.25 mmol). This mixture was heated at reflux for a further 3 h before evaporation to dryness and dissolution in water (50 mL). The aqueous layer was then washed with diethyl ether (3×30 mL) before acidification with 3M HCl. The acidified solution was extracted with DCM, dried, then evaporated to dryness to yield the title compound (544 mg, 1.18 mmol, 67%) as a viscous yellow oil. $^1$H NMR (CDCl$_3$, 300 MHz): δ 10.20, COOH; 7.84 (m, 4H, ArH); 7.29 (m, 4H, ArH); 7.09 (m, 8H, ArH); 6.12 (d, J=15.9 Hz, 1H, H3"); 5.90 (dt, J=5.7, 15.9 Hz, 1H, H2"); 5.58 (m, 2H, H1"); 4.49 (AB$_q$, J=16.8 Hz, 2H, CH$_2$—COOH). Mass Spectrum (CI, +ve) m/z 117 (100%), 461 (50%) [MH$^+$]. HRMS calcd for $C_{31}H_{24}O_4$ 460.167460, found 460.167568.

[2'-(3-Methylbutoxy-[1,1']-(S)-binaphthalen-2-yloxy]-acetic acid (105)

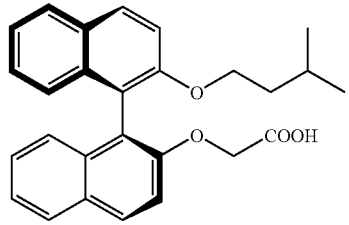

To a solution of 1,1'-(S)-binapthol (500 mg, 1.75 mmol) and $K_2CO_3$ (300 mg, 2.18 mmol) in acetone (6 mL) was added dropwise, 1-bromo-3-methylbutane (0.22 mL, 1.75 mmol). The resulting mixture heated at reflux with stirring for 16 h before being filtered, concentrated and dissolved in anhydrous MeOH (5 mL). To this solution was added $K_2CO_3$ (2.4 g, 17.4 mmol) and bromoacetic acid (740 g, 5.25 mmol). This mixture was heated at reflux for a further 3 h before evaporation to dryness and dissolution in water (50 mL). The aqueous layer was then washed with diethyl ether (3×30 mL) before acidification with 3M HCl. The acidified solution was extracted with DCM, dried before being evaporated to dryness to yield the title compound (604 mg, 1.46 mmol, 83%) as a viscous yellow oil. $^1$H NMR (CDCl$_3$, 300 MHz): δ 9.93, COOH; 7.95 (m, 4H, ArH); 7.40 (m, 8H, ArH); 4.65 (m, 2H, CH$_2$—COOH); 4.09 (m, 2H, H1"); 1.38 (m, 2H, H2"); 1.26 (m, 1H, H3"); 0.71 (d, J=6.3 Hz, 3H, H4a"); 0.61 (d, J=6.3 Hz, 3H, H4b"). Mass Spectrum (CI, +ve) m/z 415 (100%) [MH$^+$]. HRMS calcd for $C_{27}H_{27}O_4$ 415.1090, found 415.1913.

(2'-(3-Phenylpropyloxy)-[1,1']-(S)-binaphthalen-2-yloxy)-acetic acid (107)

To a solution 104 (213 mg, 0.46 mmol) in THF (15 mL) was added palladium on activated carbon (5 mol %). The resulting mixture was allowed to stir for 16 h under a hydrogen atmosphere (balloon) before being filtered and evaporated to dryness to yield the title compound (188 mg, 0.4 mmol, 87%) as a viscous yellow oil. $^1$H NMR (CDCl$_3$, 300 MHz): δ 7.97 (m, 4H, ArH); 7.24 (m, 11H, ArH); 6.68 (m, 2H, ArH); 4.65 (AB$_q$, J=16.8 Hz, 2H, CH$_2$—COOH); 3.96 (m, 2H, H1"); 2.09 (m, 2H, H3"); 1.69 (m, 2H, H2"). Mass Spectrum (CI, +ve) m/z 463 (100%) [MH$^+$]. HRMS calcd for $C_{31}H_{27}O_4$ 463.1909, found 463.1915.

Benzyl(2S)-2-amino-4-pentenoate hydrochloride (108)

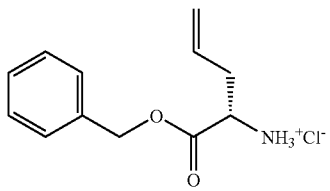

To a solution of (2S)-2-amino-4-pentenoic acid 17 (225 mg, 1.96 mmol) in benzyl alcohol (5 mL) was added thionyl chloride (2 mL) and the resulting mixture was allowed to stir for 16 h before addition of diethyl ether (30 mL) and extraction with water (3×30 mL). The aqueous layer was concentrated, diluted with 2M sodium bicarbonate (20 mL), and extracted with DCM (3×30 mL). The combined organic fractions were dried and acidified with 1M HCl/diethyl ether (2 mL) and evaporated. The crude product dissolved in a minimal volume of MeOH and precipitated with diethyl ether to yield the title compound (322 mg, 1.34 mmol, 68%) as a white solid. $[\alpha]_D^{20}$ −40.6 (c. 0.1, H$_2$O). Mp 186-191° C. $^1$H NMR (D$_2$O, 300 MHz): δ 7.28 (m, 5H, ArH); 5.51 (m, 1H, H4); 5.11 (m, 4H, H5 and ArCH$_2$); 4.08 (t, J=5.4 Hz, 1H, H2); 2.55 (m, 2H, H3). Mass Spectrum (CI, +ve) m/z 205 (25%) [MH$^+$]. HRMS calcd for C$_{12}$H$_{16}$NO$_2$ 206.1181, found 206.1169.

Benzyl(2S,5R)-2-allyl-3-aza-5-(9H-9-fluorenylmethyloxycarboxamido)-4-oxo-8-[(2,2,5,7,8-pentamethyl-3,4-dihydro-2H-6-chromenylsulfonyl)guanidino]octanoate (109)

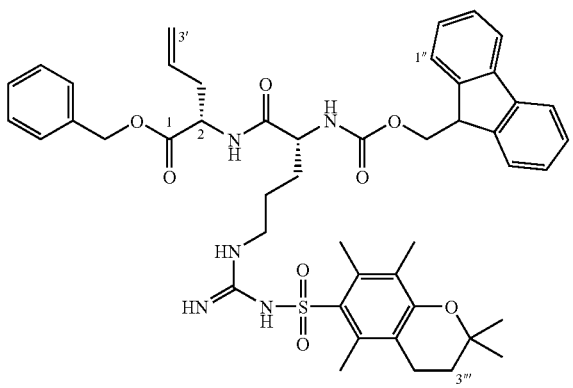

The title compound was synthesised using the general peptide coupling procedure (Procedure B), from 108 (155 mg, 0.65 mmol) and (2R)-2-(9H-9-fluorenylmethyloxycarboxamido)-8-[(2,2,5,7,8-pentamethyl-3,4-dihydro-2H-6-chromenylsulfonyl)guanidine]pentanoic acid (431 mg, 0.65 mmol) to afford 109 (280 mg, 0.33 mmol, 51%) as a white solid. Mp 78-74° C. $^1$H NMR (CDCl$_3$, 300 MHz): δ 7.69 (d, J=7.5 Hz, 2H, ArH1" and ArH8"); 7.51 (d, J=7.5 Hz, 2H, ArH4" and ArH5"); 7.28 (m, 9H, ArH); 6.33 (m, 3H, NH); 5.68 (m, 1H, H2'); 5.61 (m, 1H, NH); 4.99 (m, 4H, ArCH$_2$ and H3'); 4.58 (m, 1H, H2); 4.24 (m, 3H, OCH$_2$—H9" and H5); 4.05 (t, J=7.2 Hz, 1H, H9"); 3.20 (m, 2H, H8); 2.57 (s, 3H, 7'''-CH$_3$); 2.54 (s, 3H, 5'''-CH$_3$); 2.52 (m, 4H, H3''' and H1'); 2.05 (s, 3H, 8'''-CH$_3$); 1.85 (m, 2H, H6); 1.69 (t, J=6.3 Hz, H4'''); 1.58 (m, 2H, H7); 1.22 (s, 6H, 2×2'''-CH$_3$). Mass Spectrum (ES, +ve) m/z 850 (100%) [MH$^+$]. HRMS calcd for C$_{47}$H$_{56}$N$_5$O$_8$S 850.3850, found 850.3855.

Benzyl(2S,5R)-2-allyl-5-amino-3-aza-8-[(2,2,5,7,8-pentamethyl-3,4-dihydro-2H-6-chromenylsulfonamido)guanidino]-4-oxooctanoate (110)

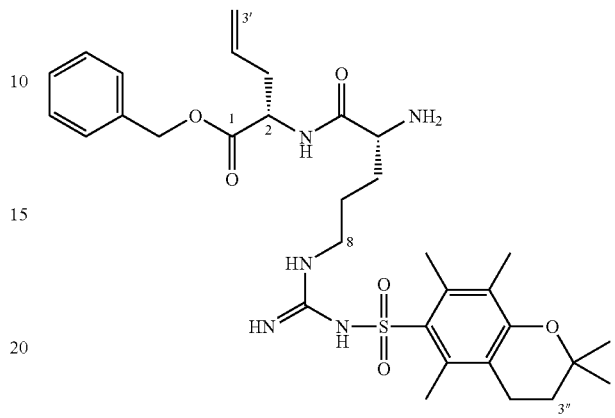

The title compound was synthesized using the general N-Fmoc deprotection procedure (Procedure C), from 109 (278 mg, 0.33 mmol) to yield 110 (144 mg, 0.23 mmole, 70%) as a cream semi-solid. Mp 66-68° C. $^1$H NMR (CDCl$_3$, 300 MHz): δ 7.85 (d, J=7.8 Hz, 1H, NH); 7.60 (d, J=7.8 Hz, 1H, NH); 7.32 (m, 5H, ArH); 6.33 (m, 2H, NH$_2$); 5.63 (s, 1H, H2'); 5.14 (m, 4H, ArCH$_2$ and H3'); 4.56 (m, 1H, H2); 3.40 (m, 1H, H5); 3.16 (m, 2H, H8); 3.09 (m, 2H, H11'); 2.61 (t, J=6.9 Hz, 2H, H4"); 2.56 (s, 3H, 7"-CH$_3$); 2.55 (s, 3H, 5"-CH$_3$); 2.09 (s, 3H, 8"-CH$_3$); 1.78 (t, J=7.2 Hz, 2H, H3"); 1.68 (m, 4H, H6 and NH$_2$); 1.54 (m, 2H, H7); 1.29 (s, 6H, 2×2"-CH$_3$). Mass Spectrum (ES, +ve) m/z 628 (100%) [MH$^+$]. HRMS calcd for C$_{32}$H$_{46}$N$_5$O$_6$S 628.3169, found 628.3157.

Benzyl(2S,5R,8R)-2-allyl-3,6-diaza-12-(tert-butoxycarboxamido)-8-(9H-9-fluorenylmethyloxycarboxamido)-5-([{2,2,5,7,8-pentamethyl-3,4-dihydro-2H-6-chromenylsulfonamido}guanidino]propyl)-4,7-dioxododecanoate (111)

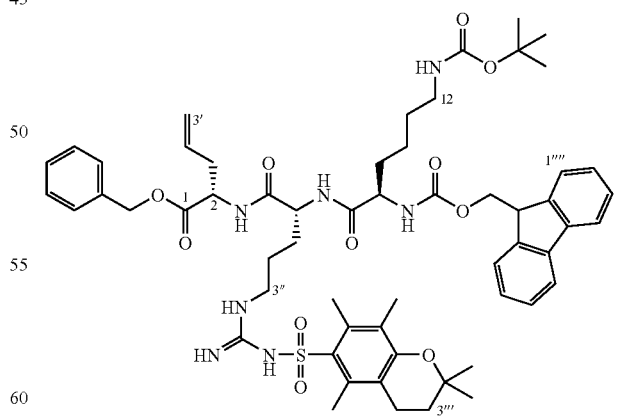

The title compound was synthesised using the general peptide coupling procedure (Procedure B), from 110 (200 mg, 0.32 mmol) and (2R)-6-tert-butoxycarboxamido-2-(9H-9-fluorenylmethyloxycarboxamido)hexanoic acid (151 mg, 0.32 mmol) to afford 111 (202 mg, 0.19 mmol, 59%) as a white solid. Mp 116° C. $^1$H NMR (CDCl$_3$, 300 MHz): δ 7.72 (d, J=7.8 Hz, 2H, ArH1'''' and ArH8''''); 7.55 (d, J=7.8 Hz, 2H, ArH4'''' and ArH5''''); 7.45 (m, 1H, NH); 7.29 (m, 1H, ArH); 6.25 (m, 3H, NH); 5.64 (m, 1H, H2'); 5.03 (m, 4H, ArCH$_2$, H3'); 4.59 (m, 1H, H2); 4.51 (m, 1H, H5); 4.29 (m, 1H, H8); 4.20 (m, 2H, OCH$_2$—H9''''); 3.98 (m, 1H, H19''''); 3.18 (m, 2H, H3''); 3.05 (m, 2H, H12); 2.55 (s, 3H, 7'''-CH$_3$); 2.52 (s, 3H, 5'''-CH$_3$); 2.50 (m, 4H, H4''' and H1'); 2.03 (s, 3H, 8'''-CH$_3$); 1.95 (m, 4H, H1'' and H9); 1.74 (m, 2H, H13'''); 1.67 (m, 4H, H2'' and H10); 1.59 (m, 2H, H11); 1.41 (s, 6H, 2×2'''-CH$_3$). Mass Spectrum (ES, +ve) m/z 1078 (10%) [MH$^+$]; 288 (100%). HRMS calcd for C$_{58}$H$_{76}$N$_7$O$_{11}$S 1078.5324, found 1078.5333.

Benzyl(2S,5R,8R)-2-allyl-8-amino-3,6-diaza-12-(tert-butoxycarboxamido)-5-([{2,2,5,7,8-pentamethyl-3,4-dihydro-2H-6-chromenylsulfonamido}guanidino]propyl)-4,7-dioxododecanoate (112)

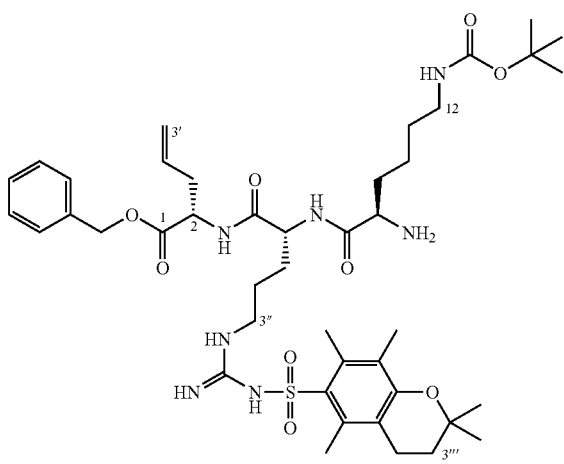

The title compound was synthesized using the general N-Fmoc deprotection procedure (Procedure C), from 111 (202 mg, 0.19 mmol) to yield 112 (157 mg, 0.18 mmole, 93%) as a cream oil. $^1$H NMR (CDCl$_3$, 300 MHz): δ 8.00 (d, J=7.2 Hz, 1H, NH); 7.58 (d, J=7.2 Hz, 1H, NH); 7.32 (m, 5H, ArH); 6.44 (m, 3H, NH); 5.63 (m, 1H, H2'); 5.09 (m, 4H, ArCH$_2$ and H3'); 4.61 (m, 2H, H2 and H5); 3.36 (m, 1H, H8); 3.22 (m, 2H, H3''); 3.05 (m, 2H, H12); 2.62 (m, 2H, H4'''); 2.58 (s, 3H, 7'''-CH$_3$); 2.56 (s, 3H, 5'''-CH$_3$); 2.47 (m, 2H, H1'); 2.15 (m, 2H, H1''); 2.10 (s, 3H, 8'''-CH$_3$); 1.89 (m, 2H, H9); 1.80 (t, J=6.3 Hz, H13'''); 1.72 (m, 4H, H2'' and H10); 1.58 (m, 4H, H$_{11}$ and NH$_2$); 1.42 (s, 9H, C(CH$_3$)$_3$); 1.31 (s, 6H, 2×2'''-CH$_3$). Mass Spectrum (ES, +ve) m/z 856 (100%) [MH$^+$]. HRMS calcd for C$_{43}$H$_{66}$N$_7$O$_9$S 856.4643, found 856.4655.

Methyl(2S,5R)-2-(4-allyloxybenzyl)-5-amino-3-aza-8-[(2,2,5,7,8-pentamethyl-3,4-dihydro-2H-6-chromenylsulfonyl)guanidino]-4-oxononanoate (113)

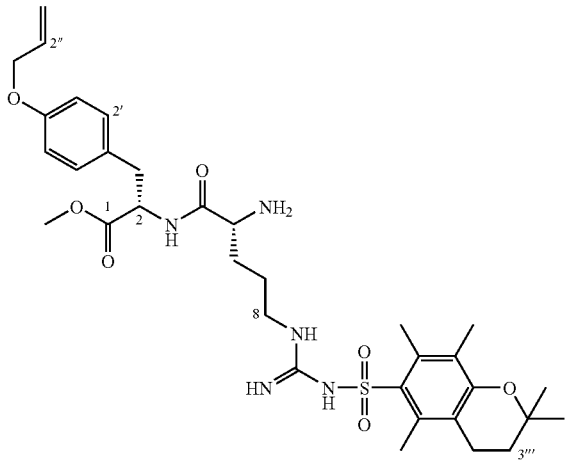

The title compound was synthesized using the general N-Fmoc deprotection procedure (Procedure C), from 67 (295 mg, 0.32 mmol) to yield 113 (145 mg, 0.21 mmol, 66%) as a cream oil. $^1$H NMR (CDCl$_3$, 300 MHz): δ 7.83 (d, J=7.5 Hz, 1H, NH); 7.04 (d, J=8.4 Hz, 2H, ArH2' and ArH6'); 6.81 (d, J=8.4 Hz, 2H, ArH3' and ArH5'); 6.37 (bs, 2H, NH); 6.01 (m, 1H, H2''); 5.30 (m, 2H, H3''); 4.68 (dd, J=7.5, 13.2 Hz, 1H, H2); 4.47 (m, 2H, H1''); 4.22 (m, 1H, H5); 3.67 (s, 3H, OCH$_3$); 3.07 (m, 4H, H8 and ArCH$_2$); 2.61 (t, J=6.6 Hz, 2H, H14'''); 2.56 (s, 3H, 7'''-CH$_3$); 2.54 (s, 3H, 5'''-CH$_3$); 2.10 (s, 3H, 8'''-CH$_3$); 1.87 (m, 2H, NH$_2$); 1.79 (m, 2H, H13'''); 1.68 (m, 2H, H6); 1.50 (m, 2H, H7); 1.29 (s, 6H, 2×2'''-CH$_3$). Mass Spectrum (ES, +ve) m/z 658 (100%) [MH$^+$]. HRMS calcd for C$_{33}$H$_{48}$N$_5$O$_2$S 658.3274 found 658.3282.

Methyl(2S,5S,8S)-2-allyl-8-(4-[9-anthrecenyl]benzyl)-3,6,9-triaza-5-(4-[tert-butoxycarboxamido]butyl)-4,7,10-trioxoundecanoate (114)

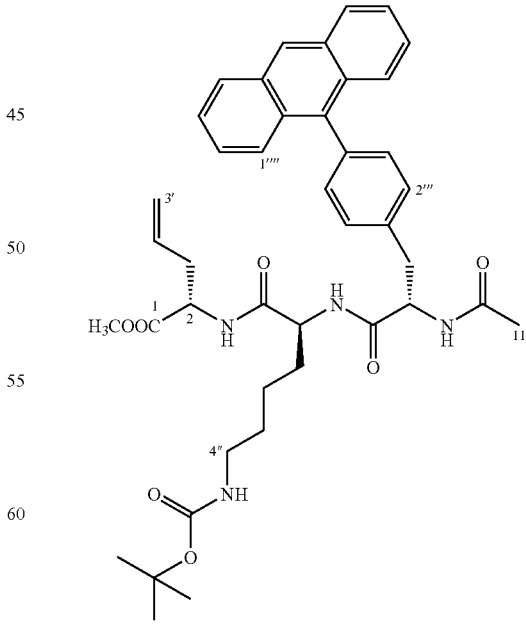

The title compound was synthesised using the general peptide coupling procedure (Procedure B), from 24 (35 mg, 0.098 mmol) and 97 (20 mg, 0.052 mmol) to afford the title compound (22 mg, 0.030 mmol, 59%) as a cream solid. Mp 128° C. ¹H NMR (CDCl₃, 300 MHz): δ 8.49 (s, 1H, ArH10''''); 8.04 (d, J=8.7 Hz, 2H, ArH2''' and ArH6'''); 7.64 (d, J=8.4 Hz, 2H, ArH3''' and ArH5'''); 7.38 (m, 8H, ArH''''); 6.72 (d, J=7.2 Hz, 1H, NH); 6.48 (d, J=7.2 Hz, 1H, NH); 6.37 (bs, 1H, NH); 5.59 (m, 1H, H2'); 5.06 (m, 2H, H3'); 4.82 (m, 1H, H8); 4.60 (dd, J=6.9, 14.1 Hz, 1H, H2); 4.45 (m, 1H, H5); 3.73 (s, 3H, OCH₃); 3.24 (m, 2H, ArCH₂); 3.08 (m, 2H, H4''); 2.47 (m, 2H, H1'); 2.07 (s, 3H, H11); 1.93 (m, 2H, H1''); 1.68 (m, 2H, H3'''); 1.50 (m, 2H, H2''); 1.44 (s, 9H, C(CH₃)₃). Mass Spectrum (ES, +ve) m/z 745 (50%) [MNa⁺], 723 (20%) [MH⁺], 623 (100%) [M less Boc]. HRMS calcd for C₄A₄₉N₄O₇ 745.3601, found 745.3590.

Methyl(2S,5S,8S)-2-allyl-3,6,9-triaza-5-(4-[tert-butoxycarboxamido]butyl)-4,7,10-trioxo-8-(4-[9-phenanthrenyl]benzyl)undecanoate (115)

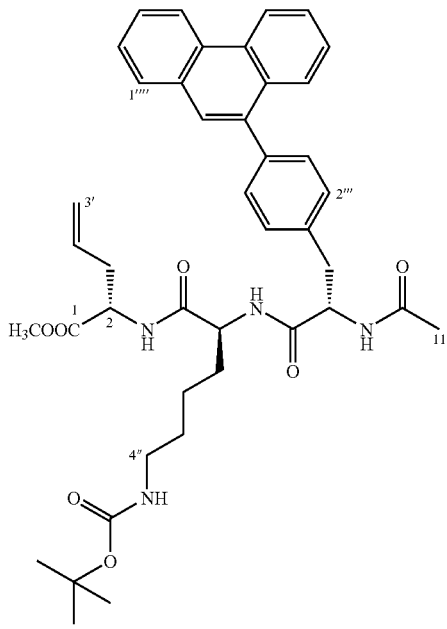

The title compound was synthesised using the general peptide coupling procedure (Procedure B), from 24 (28 mg, 0.078 mmol) and 99 (15 mg, 0.039 mmol) to afford 115 (14 mg, 0.019 mmol, 50%) as a cream solid. Mp 132-134° C. ¹H NMR (CDCl₃, 300 MHz): δ 8.76 (d, J=8.1 Hz, 1H, ArH4''''); 8.71 (d, J=8.4 Hz, 1H, ArH3''''); 7.88 (m, 2H, ArH1'''' and ArH10''''); 7.60 (m, 5H, ArH7'''', ArH6'''', ArH5'''', ArH2'''' and ArH1''''); 7.45 (d, J=7.8 Hz, 2H, ArH2''' and ArH6'''); 7.33 (d, J=7.8 Hz, 2H, ArH3''' and ArH5'''); 7.10 (d, J=8.4 Hz, 1H, NH); 6.94 (d, J=8.7 Hz, 1H, NH); 6.74 (d, J=8.1 Hz, 1H, NH); 5.61 (m, 1H, H2'); 5.06 (m, 2H, H3'); 4.90 (m, 1H, H8); 4.57 (m, 2H, H2 and H5); 3.72 (s, 3H, OCH₃); 3.20 (m, 2H, ArCH₂); 3.08 (m, 2H, H4''); 2.47 (m, 2H, H1'); 2.04 (s, 3H, H11); 1.92 (m, 2H, H1''); 1.68 (m, 2H, H3'''); 1.48 (m, 2H, H2''); 1.42 (s, 9H, C(CH₃)₃). Mass Spectrum (ES, +ve) m/z 745 (60%) [MNa⁺], 723 (20%) [MH⁺], 623 (100%) [M less Boc]. HRMS calcd for C₄₂H₅₁N₄O₇ 723.3758, found 723.3767.

Methyl(2S,5R)-2-allyloxybenzyl-8-(2-[2'-allyloxy-{1,1'}-(S)-binaphthalen-2-yloxy])-3,6-diaza-5-([{2,2,5,7,8-pentamethyl-3,4-dihydro-2H-6-chromenylsulfonyl}guanidino]propyl)-4,7-dioxooctanoate (116)

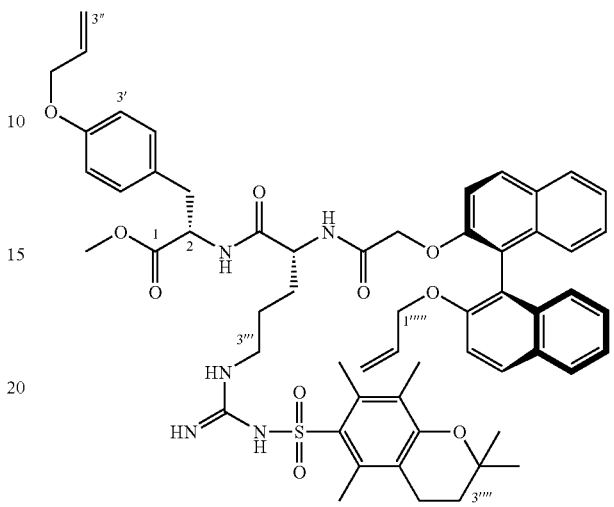

The title compound was synthesised using the general peptide coupling procedure (Procedure B), from 113 (81 mg, 0.11 mmol) and 101 (49 mg, 0.13 mmol) to afford 116 (70 mg, 0.065 mmol, 59%) as a white solid. Mp 110° C. ¹H NMR (CDCl₃, 300 MHz): δ 7.88 (m, 4H, ArH); 7.75 (d, J=8.4 Hz, 1H, NH); 7.22, (m, 8H, ArH); 6.99 (d, J=8.7 Hz, 2H, ArH2' and ArH6'); 6.79 (d, J=8.7 Hz, 2H, ArH3' and ArH5'); 6.31 (d, J=8.1 Hz, 1H, NH); 6.15 (bs, 2H, NH); 5.98 (m, 1H, H2''); 5.77 (bs, 1H, NM; 5.63 (m, 1H, H2''''); 5.35 (dd, J=1.5, 18.9 Hz, 1H, H3ₐ''); 5.23 (dd, J=1.5, 10.5 Hz, 1H, H3b''); 4.88 (m, 2H, H3''''); 4.64 (m, 1H, H2); 4.40 (m, 6H, H1'', H1'''' and H8); 4.13 (m, 1H, H5); 3.61 (s, 3H, OCH₃); 2.91 (m, 4H, ArCH₂ and H3'''); 2.60 (s, 3H, 7''''-CH₃); 2.78 (s, 3H, 5''''-CH₃); 2.54 (m, 2H, H4''''); 2.10 (s, 3H, 8''''-CH₃); 1.75 (t, J=6.6 Hz, 2H, H3''''); 1.36 (m, 2H, H2''); 1.26 (s, 6H, 2×2''''-CH₃); 0.84 (m, 2H, H1'''). Mass Spectrum (ES, +ve) 7m/z 1024 (100%) [MH⁺]. HRMS calcd for C₅₈H₆₆N₅O₁₀S 1024.4530, found 1024.4513.

Methyl(2S,5R)-2-allyloxybenzyl-3,6-diaza-5-([{2,2,5,7,8-pentamethyl-3,4-dihydro-2H-6-chromenylsulfonyl}guanidino]propyl)-4,7-dioxo-8-(2-[2'-{3-phenyl-allyloxy}-{1,1'}-(S)-binaphthalen-2-yloxy])octanoate (117)

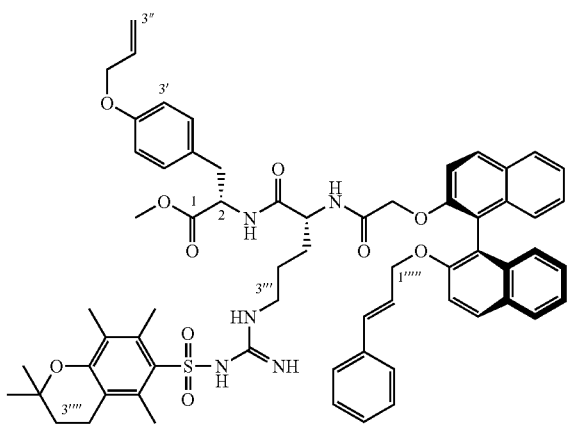

The title compound was synthesised using the general peptide coupling procedure (Procedure B), from 113 (64 mg, 0.09 mmol) and 104 (42 mg, 0.09 mmol) to afford 117 (61 mg, 0.055 mmol, 62%) as a cream solid. Mp 100° C. $^1$H NMR (CDCl$_3$, 300 MHz): δ 7.90 (m, 4H, ArH); 7.76 (d, J=8.1 Hz, 1H, NH); 7.46 (d, J=9.0 Hz, 1H, NH); 7.17, (m, 13H, ArH); 6.99 (d, J=8.4 Hz, 2H, ArH2' and ArH6'); 6.79 (d, J=8.4 Hz, 2H, ArH3' and ArH5'); 6.39 (d, J=8.1 Hz, 1H, NH); 6.13 (m, 2H, H2'''' and H3''''); 5.98 (m, 1H, H2''); 5.30 (m, 2H, H3''); 4.64 (m, 1H, H2); 4.39 (m, 6H, H1'', H1'''' and H8); 4.15 (m, 1H, H5); 3.60 (s, 3H, OCH$_3$); 2.95 (m, 4H, ArCH$_2$ and H13'''); 2.60 (s, 3H, 7''''-CH$_3$); 2.58 (s, 3H, 5''''-CH$_3$); 2.52 (m, 2H, H4''''); 2.10 (s, 3H, 8''''-CH$_3$); 1.74 (t, J=6.7 Hz, 2H, H3'''); 1.36 (m, 2H, H12'''); 1.25 (s, 6H, 2×2''''-CH$_3$); 0.85 (m, 2H, H1'''). Mass Spectrum (ES, +ve) m/z 1100 (100%) [MH$^+$]. HRMS calcd for C$_{64}$H$_{70}$N$_5$O$_{10}$S 1100.4843, found 1100.4833.

Methyl(2S,5S,8S)-2-allyl-5-(4-aminobutyl)-8-(4-[9-anthrecenyl]benzyl)-3,6,9-triaza-5-butylamino-4,7,10-trioxoundecanoate hydrochloride (118)

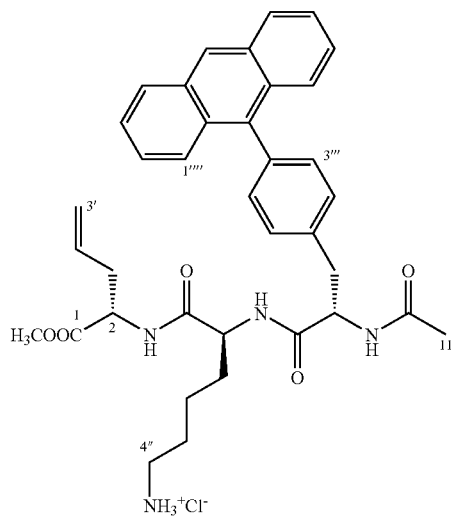

The title compound was synthesized using the general N-Boc deprotection procedure (Procedure A), from 114 (20 mg, 0.028 mmol) to yield 118 (13 mg, 0.017 mmol, 61%) as a light yellow solid. Mp 194-202° C. $^1$H NMR (CD$_3$OD, 300 MHz): δ 8.53 (s, 1H, ArH10''''); 8.26 (m, 3H, exchanging NH's); 8.06 (d, J=8.1 Hz, 2H, ArH2''' and ArH6'''); 7.64 (d, J=9.0 Hz, 2H, ArH3''' and ArH5'''); 7.38 (m, 8H, ArH''''); 5.68 (m, 1H, H2'); 5.02 (m, 2H, H3'); 4.67 (m, 1H, H8); 4.45 (m, 2H, H2 and H5); 3.69 (s, 3H, OCH$_3$); 2.93 (m, 4H, H4'' and ArCH$_2$); 2.44 (m, 2H, H1'); 2.00 (s, 3H, H11); 1.69 (m, 4H, H1'' and H3''); 1.50 (m, 2H, H2''). $^{13}$C NMR (CD$_3$OD, 75 MHz): δ 174.4, C7; 173.7, C1; 173.6, C4; 173.5, C10; 138.7, ArC4'''; 137.8, ArC1''''; 137.7, ArC9''''; 134.1, C2'; 132.9, ArCH2''' and ArCH6'''; 132.4, ArC4a'''' and ArC10a''''; 131.5, ArC8a'''' and ArC9a''''; 130.4, ArCH4'''' and ArCH5''''; 130.1, ArCH3''' and ArCH5'''; 129.5, ArCH10''''; 127.7, ArCH8'''' and ArCH1''''; 126.5, ArCH2'''' and ArCH7''''; 126.2, ArCH3'''' and ArCH6''''; 118.8, C3'; 56.7, C5; 53.8, OCH$_3$; 53.6, C8; 52.7, C2; 40.5, C4''; 38.6, ArCH$_2$; 36.6, C1'; 32.8, C1''; 28.1, C3''; 23.4, C11; 22.4, C2''. Mass Spectrum (ES, +ve) m/z 623 (100%) [M$^+$]. HRMS calcd for C$_{37}$H$_{43}$N$_4$O$_5$ 623.3233, found 623.3215.

Methyl(2S,5S,8S)-2-allyl-5-(4-aminobutyl)-3,6,9-triaza-5-butylamino-4,7,10-trioxo-8-(4-[9-[phenanthrenyl]benzyl)undecanoate hydrochloride (119)

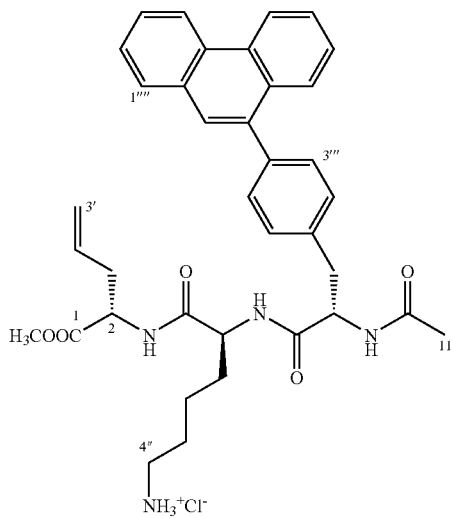

The title compound was synthesized using the general N-Boc deprotection procedure (Procedure A), from 115 (24 mg, 0.033 mmol) to yield 119 (15 mg, 0.023 mmol, 69%) as a light yellow solid. Mp 198° C. $^1$H NMR (CD$_3$OD, 300 MHz): δ 8.84 (d, J=7.8 Hz, 1H, ArH4''''); 8.78 (d, J=8.1 Hz, 1H, ArH5''''); 8.30 (d, J=7.2 Hz, 1H, exchanging NH); 8.15 (d, J=8.1 Hz, 1H, exchanging NH); 7.90 (m, 2H, ArH1'''' and ArH10''''); 7.60 (m, 5H, ArH7'''', ArH6'''', ArH15'''', ArH2'''' and ArH1''''); 7.45 (d, J=8.4 Hz, 2H, ArH2''' and ArH6'''); 7.40 (d, J=8.7 Hz, 2H, ArH3''' and ArH5'''); 5.68 (m, 1H, H2'); 4.98 (m, 2H, H3'); 4.61 (m, 1H, H8); 4.40 (m, 2H, H2 and H5); 3.67 (s, 3H, OCH$_3$); 2.93 (t, J=7.5 Hz, 2H, H4''); 2.40 (m, 2H, H1'); 1.99 (s, 3H, H111); 1.83 (m, 4H, H1'' and ArCH$_2$); 1.69 (m, 2H, H3''); 1.49 (m, 2H, H2''). $^{13}$C NMR (CD$_3$OD, 75 MHz): δ 173.7, C7; 173.6, C1; 173.5, C4; 173.4, C10; 140.7, ArC4'''; 139.8, ArC1''''; 137.5, ArC9''''; 134.0, C2'; 133.0, ArC8a''''; 132.3, ArC4b''''; 132.0, ArC4a''''; 131.3, ArCH2''' and ArCH6'''; 131.2, ArC10a''''; 130.3, ArCH3''' and ArCH5'''; 129.7, ArCH1''''; 128.5, ArCH7''''; 128.0, ArCH6''''; 127.9, ArCH1''''; 127.8, ArCH5''''; 127.7, ArCH10''''; 127.6, ArCH2''''; 124.2, ArC4''''; 124.1, ArCH3''''; 118.8, C3'; 56.7, C5; 53.7, OCH$_3$; 53.6, C8; 52.7, C2; 40.5, C4''; 38.5, ArCH$_2$; 36.5, C1'; 32.8, C1''; 28.0, C3''; 23.3, C11; 22.4, C2''. Mass Spectrum (ES, +ve) m/z 623 (100%) [M$^+$]. HRMS calcd for C$_{37}$H$_{43}$N$_4$O$_5$ 623.3233, found 623.3262.

223

Methyl(2S,5R)-2-allyloxybenzyl-8-(2-[2'-allyloxy-{1,1'}-(S)-binaphthalen-2-yloxy])-3,6-diaza-5-(3-[guanidino]-4,7-dioxooctanoate hydrochloride (120)

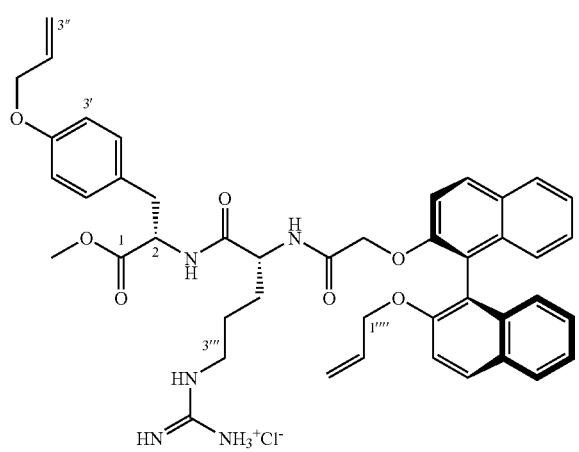

The title compound was synthesized using the general N-Boc deprotection procedure (Procedure A) using 116 (70 mg, 0.068 mmol) to yield 120 (31 mg, 0.039 mmol, 58%) as a cream solid. Mp 104-110° C. $^1$H NMR (CD$_3$OD, 500 MHz): δ 7.62 (m, 4H, ArH); 6.95, (m, 8H, ArH); 6.82 (d, J=7.0 Hz, 2H, ArH2' and ArH6'); 6.58 (d, J=7.0 Hz, 2H, ArH3' and ArH5'; 5.74 (m, 1H, H2''); 5.40 (m, 1H, H12''''); 5.09 (d, J=17.0 Hz, 1H, H3$_a$''); 4.93 (d, J=10.0 Hz, 1H, H3b''); 4.62 (m, 2H, H3''''); 4.37 (m, 1H, H2); 4.18 (m, 6H, H1'', H1'''' and H8); 3.98 (m, 1H, H5); 3.36 (s, 3H, OCH$_3$); 2.75 (m, 4H, ArCH$_2$ and H13'''); 1.40 (m, 2H, H1'''); 0.68 (m, 2H, H2''''). $^{13}$C NMR (CD$_3$OD, 125 MHz): δ 173.1, C1; 172.3, C7; 170.5, C4; 158.8, CN$_3$; 158.2, ArC; 155.1, ArC; 153.8, ArC; 134.9, ArC4'; 134.8, ArC; 134.7, C2''; 134.7, C2''''; 131.3, ArCH; 131.2, ArCH; 130.8, ArCH; 130.7, ArCH; 130.5, ArCH2' and ArCH6'; 130.0, ArCH; 129.1, ArCH; 129.1, ArC; 129.1, ArC; 127.5, ArCH; 127.4, ArC; 126.4, ArC1'; 125.7, ArCH; 125.2, ArCH; 124.8, ArC; 121.6, ArCH; 120.1, ArCH; 117.5, C3''; 117.0, C3''''; 116.1, ArC; 115.6, ArCH3' and ArCH5'; 70.7, C8; 69.6, C1''; 69.2, C1''''; 55.0, C2; 52.8, OCH$_3$; 52.6, C5; 41.6, C3'''; 37.4, ArCH$_2$; 30.4, C1'''; 25.6, C2'''. Mass Spectrum (ES, +ve) m/z 758 (100%) [M$^+$]. HRMS calcd for C$_{44}$A$_{49}$N$_5$O$_7$ 759.3632, found 759.3555.

224

Methyl(2S,5R)-2-allyloxybenzyl-3,6-diaza-8-(2-[2'-hydroxy-{1,1'}-(S)-binaphthalen-2-yloxy])-5-(3-[guanidino]propyl)-4,7-dioxooctanoate (121)

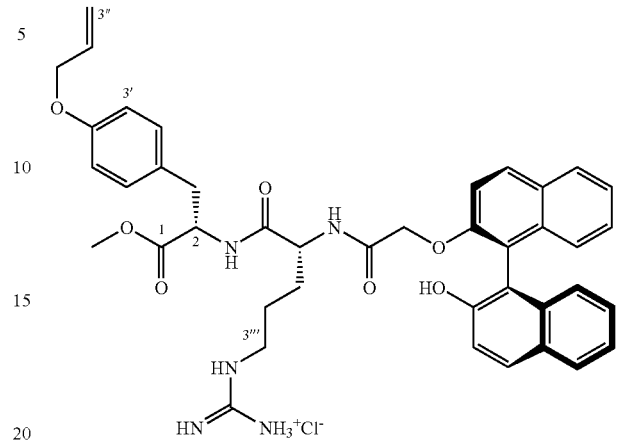

The title compound was synthesized using the general N-Boc deprotection procedure (Procedure A) using 117 (58 mg, 0.053 mmol) to yield 121 (28 mg, 0.037 mmol, 70%) as a cream solid. Mp 132° C. $^1$H NMR (CD$_3$OD, 500 MHz): δ 7.91 (m, 4H, ArH); 7.20, (m, 8H, ArH); 7.06 (d, J=8.4 Hz, 2H, ArH2' and ArH6'); 6.83 (d, J=8.4 Hz, 2H, ArH3' and ArH5'); 6.01 (m, 1H, H2''); 5.29 (m, 2H, H3''); 4.62 (m, 2H, H8); 4.55 (dd, J=4.5, 9.6 Hz, 1H, H2); 4.46 (m, 2H, H1''); 4.22 (dd, J=5.4, 8.7 Hz, 1H, H5); 3.67 (s, 3H, OCH$_3$); 3.00 (m, 4H, ArCH$_2$ and H3'''); 1.58 (m, 2H, H1'''); 1.06 (m, 2H, H12'''). $^{13}$C NMR (CD$_3$OD, 125 MHz): δ 173.2, C1; 172.7, C7; 171.0, C4; 159.5, CN$_3$; 159.1, ArC; 158.4, ArC; 153.7, ArC4'; 135.4, ArC; 135.3, ArC; 134.9, C2''; 132.5, ArCH; 131.5, ArCH; 131.4, ArCH; 131.2, ArCH; 130.6, ArCH2' and ArCH6'; 130.3, ArCH; 130.1, ArCH; 129.2, ArCH; 128.2, ArCH; 127.7, ArCH; 127.4, ArCH; 126.4, ArC1'; 125.3, ArC; 124.1, ArC; 121.1, ArC; 119.6, ArC; 117.5, C3''; 116.7, ArCH; 115.9, ArCH; 115.8, ArCH3' and ArCH5'; 69.7, C8; 69.0, C1''; 55.2, C2; 53.1, OCH$_3$; 52.8, C5; 42.0, C3'''; 37.4, ArCH$_2$; 30.1, C1'''; 25.5, C2'''. Mass Spectrum (ES, +ve) m/z 718 (100%) [M$^+$]. HRMS calcd for C$_{41}$H$_{44}$N$_5$O$_7$ 718.3241, found 718.3209.

Benzyl(2S,5R,8R)-2-allyl-1-(2-[2'-allyloxy-{1,1'}-(S)-binaphthalen-2-yloxy])-3,6,9-triaza-8-(tert-butoxycarboxamidobutyl)-5-(3-[{2,2,5,7,8-pentamethyl-3,4-dihydro-2H-6-chromenylsulfonyl}guanidino]propyl)-4,7,10-trioxoundecanoate (122)

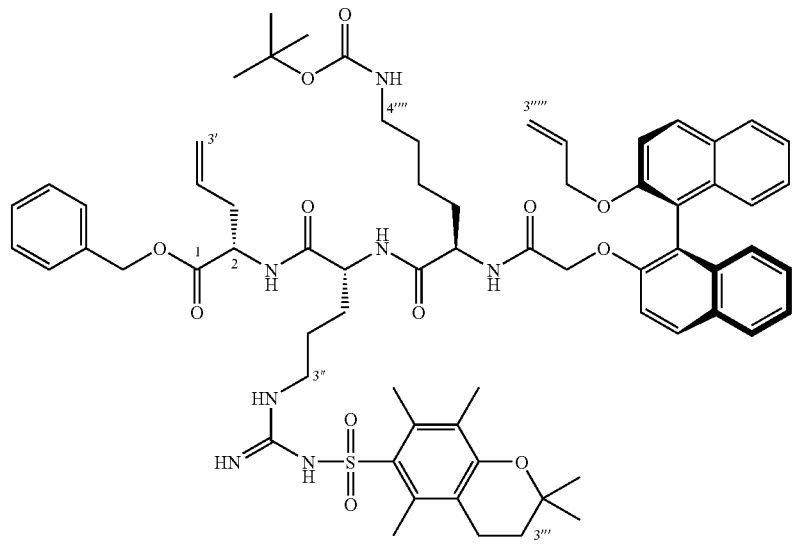

The title compound was synthesised using the general peptide coupling procedure (Procedure B), from 112 (63 mg, 0.073 mmol) and 101 (28 mg, 0.073 mmol) to afford 122 (71 mg, 0.058 mmol, 79%) as a white solid. Mp 72-74° C. $^1$H NMR (CDCl$_3$, 300 MHz): δ 7.93 (m, 2H, ArH); 7.85 (m, 2H, ArH); 7.27 (m, 13H, ArH); 6.20 (m, 2H, NH); 5.63 (m, 2H, H2' and H2'''''); 5.13 (AB$_q$, J=12.3 Hz, 2H, PhCH$_2$O); 4.94 (m, 6H, H11, H3' and H3'''''); 4.50 (m, 4H, H1'''', H2 and H5); 4.06 (m, 1H, H8); 3.08 (m, 2H, H3"); 2.89 (m, 2H, H4''''); 2.57 (m, 2H, H4'''); 2.55 (s, 3H, 7'''-CH$_3$); 2.53 (s, 3H, 5'''-CH$_3$); 2.49 (m, 2H, H1'); 2.08 (s, 3H, 8'''-CH$_3$); 1.75 (t, J=6.3 Hz, H3'''); 1.52 (m, 2H, H1"); 1.40 (s, 9H, C(CH$_3$)$_3$); 1.34 (m, 2H, H1''''); 1.27 (s, 6H, 2×2'''-CH$_3$); 1.21 (m, 2H, H3''''); 0.95 (m, 2H, H2"); 0.77 (m, 2H, H2''''). Mass Spectrum (ES, +ve) m/z 1222 (10%) [M], 1172 (100%). HRMS calcd for C$_{68}$H$_{84}$N$_7$O$_{12}$S 1222.5899, found 1222.5889.

Benzyl(2S,5R,8R,11S)-2-allyl-11-(4-allyloxybenzyl)-3,6,9,12-tetraaza-8-(4-[tert-butoxycarboxamido]butyl)-5-([{2,2,5,7,8-pentamethyl-3,4-dihydro-2H-6-chromenylsulfonamido}guanidino]propyl)-4,7,10,13-tetraoxotetradecanoate (123)

The title compound was synthesised using the general peptide coupling procedure (Procedure B), from 112 (60 mg, 0.069 mmol) and 16 (18 mg, 0.068 mmol) to afford the 123 (65 mg, 0.058 mmol, 85%) as a white solid. Mp 94-102° C. $^1$H NMR (CDCl$_3$, 300 MHz): δ 7.76 (bs, 1H, NH); 7.54 (bs, 1H, NH); 7.41 (bs, 1H, NH); 7.31 (m, 5H, ArH); 7.09 (d, J=8.7 Hz, 2H, ArH2'''' and ArH6''''); 6.77 (d, J=8.4 Hz, 2H, ArH3'''' and ArH5''''); 6.39 (bs, 3H, 3×NH's); 6.02 (m, 1H, H2'''''); 5.70 (m, 1H, H2'); 5.39 (dd, J=1.5, 17.1 Hz, 1H, H3$_a$'''''); 5.26 (dd, J=1.2, 10.5 Hz, 1H, H3$_b$'''''); 5.06 (m, 2H, H3'); 5.05 (m, 2H, PhCH$_2$O); 4.65 (dd, J=6.9, 13.5 Hz, 1H, H11); 4.57 (dd, J=8.1, 13.5 Hz, 1H, H2); 4.50 (m, 1H, H5); 4.45 (d, J=5.4 Hz, 2H, H1'''''); 4.41 (m, 1H, H8); 4.14 (bs, 1H, NH); 3.15 (m, 2H, H3"); 2.92 (m, 4H, H4'''' and 11-CH$_2$); 2.58 (m, 4H, H1' and H4'''); 2.53 (s, 3H, 7'''-CH$_3$); 2.52 (s, 3H, 5'''-CH$_3$); 2.08 (s, 3H, H14); 1.94 (m, 4H, H1" and H1''''); 1.84 (s, 3H, 8'''-CH$_3$); 1.78 (m, 2H, H3'''); 1.69 (m, 4H, H2" and H2''''); 1.55 (m, 2H, H3''''); 1.40 (s, 9H, C(CH$_3$)$_3$); 1.30 (s, 6H, 2×2'''-CH$_3$). Mass Spectrum (ES, +ve) m/z 1101 (30%) [MH$^+$]; 288 (100%). HRMS calcd for C$_{57}$H$_{81}$N$_8$O$_{12}$S 1101.5695, found 1101.5731.

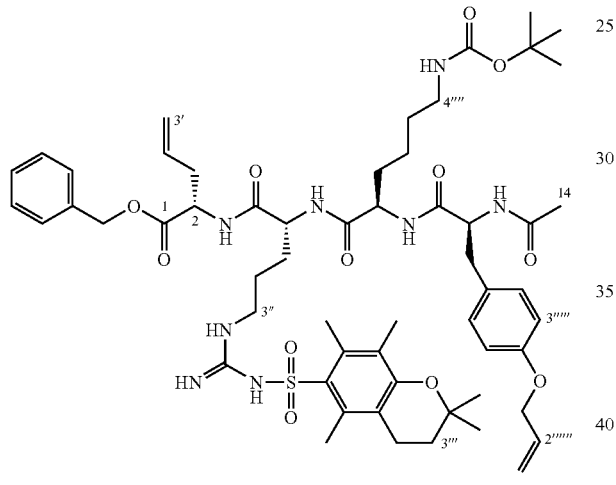

Benzyl(2S,5R,8R)-2-allyl-3,6,9-triaza-11-(2-[2'-benzyloxy-{1,1'}-(S)-binaphthalen-2-yloxy])-8-(tert-butoxycarboxamidobutyl)-5-(3-[{2,2,5,7,8-pentamethyl-3,4-dihydro-2H-6-chromenylsulfonyl}guanidino]propyl)-4,7,10-trioxoundecanoate (124)

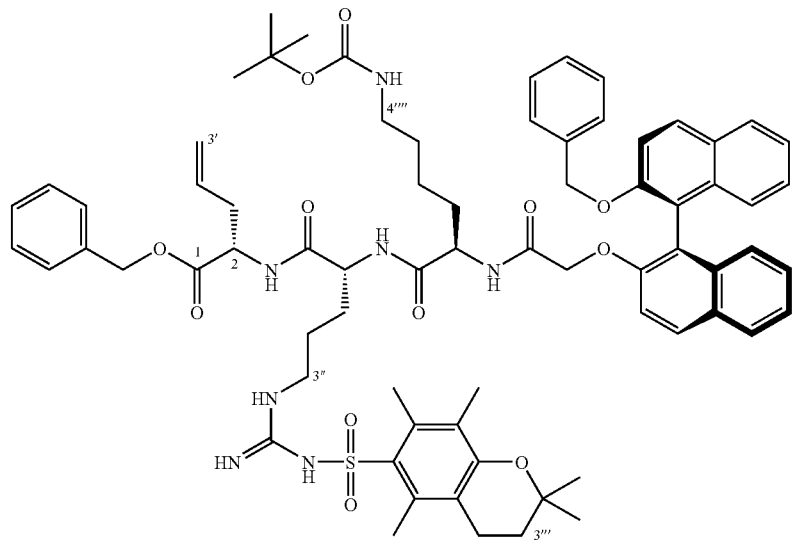

The title compound was synthesised using the general peptide coupling procedure (Procedure B), from 112 (58 mg, 0.067 mmol) and 102 (29 mg, 0.067 mmol) to afford 124 (61 mg, 0.048 mmol, 71%) as a white solid. Mp 114-119° C. $^1$H NMR (CDCl$_3$, 300 MHz): δ 7.90 (m, 4H, ArH); 7.26 (m, 18H, ArH); 6.80 (d, J=6.9 Hz, 1H, NH); 6.23 (m, 3H, NH); 5.65 (m, 1H, H2'); 5.07 (m, 6H, H11, PhCH$_2$O-ester and H3'); 4.81 (m, 1H, H2); 4.60 (m, 1H, H5); 4.40 (m, 2H, H11); 4.08 (m, 1H, H8); 3.01 (m, 2H, H3''); 2.89 (m, 2H, H4''''); 2.59 (m, 2H, H4'''); 2.57 (s, 3H, 7'''-CH$_3$); 2.54 (s, 3H, 5'''-CH$_3$); 2.50 (m, 2H, H1'); 2.08 (s, 3H, 8'''-CH$_3$); 1.75 (t, J=6.6 Hz, H3'''); 1.52 (m, 2H, H1''); 1.41 (s, 9H, C(CH$_3$)$_3$); 1.35 (m, 2H, H1'''' and H3''''); 1.27 (s, 6H, 2×2'''-CH$_3$); 1.15 (m, 4H, H2'' and H2''''). Mass Spectrum (ES, +ve) m/z 1272 (100%) [MH$^+$]. HRMS calcd for C$_{72}$H$_{86}$N$_7$O$_{12}$S 1272.6055, found 1272.6061.

Benzyl(2S,5R,8R)-2-allyl-3,6,9-triaza-8-(tert-butoxycarboxamidobutyl)-11-(2-[2'-methoxy-{1,1'}-(S)-binaphthalen-2-yloxy])-5-(3-[{2,2,5,7,8-pentamethyl-3,4-dihydro-2H-6-chromenylsulfonyl}guanidino]propyl)-4,7,10-trioxoundecanoate (125)

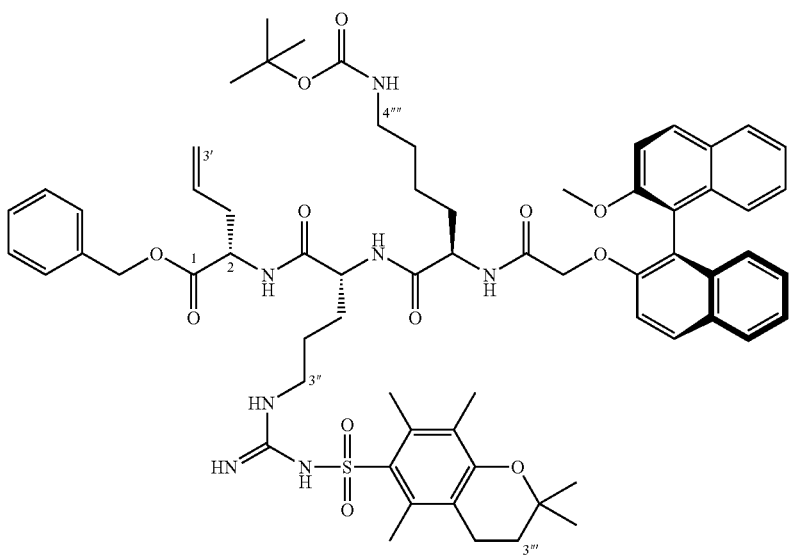

The title compound was synthesised using the general peptide coupling procedure (Procedure B), from 112 (55 mg, 0.064 mmol) and 103 (23 mg, 0.064 mmol) to afford 125 (51 mg, 0.042 mmol, 66%) as a white solid. Mp 104° C. $^1$H NMR (CDCl$_3$, 300 MHz): δ 7.91 (m, 4H, ArH); 7.30 (m, 13H, ArH); 6.23 (m, 3H, NH); 5.63 (m, 1H, H2'); 5.10 (m, 4H, PhCH$_2$O and H3'); 4.80 (m, 1H, H2); 4.58 (m, 2H, H111); 4.41 (m, 1H, H5); 4.11 (m, 1H, H8); 3.71 (s, 3H, OCH$_3$); 3.09 (m, 2H, H3''); 2.89 (m, 2H, H4''''); 2.56 (m, 2H, H4'''); 2.54 (s, 3H, 7'''-CH$_3$); 2.51 (s, 3H, 5'''-CH$_3$); 2.48 (m, 2H, H1'); 2.07 (s, 3H, 8'''-CH$_3$); 1.86 (m, 2H, H1''); 1.75 (t, J=5.7 Hz, H3'''); 1.56 (m, 2H, H1''''); 1.41 (s, 9H, C(CH$_3$)$_3$); 1.34 (m, 4H, H1'''' and H3''''); 1.27 (s, 6H, 2×2'''-CH$_3$); 1.54 (m, 4H, H2'' and H2''''). Mass Spectrum (ES, +ve) m/z 1196 (30%) [MH$^+$], 346 (100%). HRMS calcd for C$_{66}$H$_{82}$N$_7$O$_{12}$S 1196.5742, found 1196.5757.

Benzyl(2S,5R,8R)-2-allyl-3,6,9-triaza-8-(tert-butoxycarboxamidobutyl)-5-(3-[{2,2,5,7,8-pentamethyl-3,4-dihydro-2H-6-chromenylsulfonyl}guanidino]propyl)-11-(2-[2'-{3-phenylallyloxy}-[1,1']-(S)-binaphthalen-2-yloxy])-4,7,10-trioxoundecanoate (126)

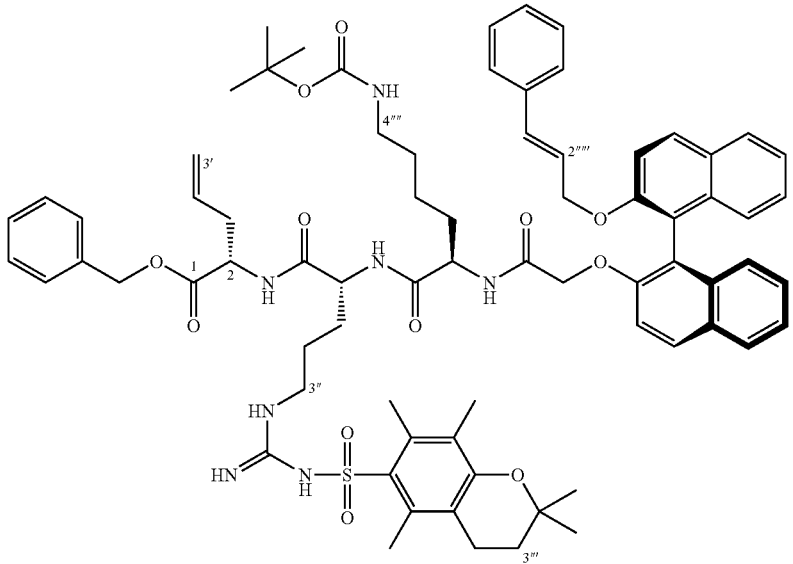

The title compound was synthesised using the general peptide coupling procedure (Procedure B), from 112 (63 mg, 0.073 mmol) and 104 (34 mg, 0.073 mmol) to afford 126 (64 mg, 0.049 mmol, 67%) as a white solid. Mp 110-112° C. $^1$H NMR (CDCl$_3$, 300 MHz): δ 7.91 (m, 4H, ArH); 7.28 (m, 18H, ArH); 6.22 (m, 3H, NH); 6.11 (d, J=16.2 Hz, 1H, H3''''); 5.91 (dt, J=5.1, 16.2 Hz, 1H, H2''''); 5.64 (m, 1H, H2'); 5.10 (m, 6H, PhCH$_2$O, H1'''' and H3'); 4.81 (m, 1H, H2); 4.67 (m, 2H, H11); 4.59 (dd, J=7.5, 12.9 Hz, 1H, H5); 4.09 (m, 1H, H8); 3.05 (m, 2H, H3''); 2.88 (m, 2H, H4''''); 2.56 (m, 2H, H4'''); 2.56 (s, 3H, 7'''-CH$_3$); 2.53 (s, 3H, 5'''-CH$_3$); 2.49 (m, 2H, H1'); 2.08 (s, 3H, 8'''-CH$_3$); 1.74 (m, 2H, H3''); 1.55 (m, 4H, H1'' and H1''''); 1.41 (s, 9H, C(CH$_3$)$_3$); 1.32 (m, 2H, H3''''); 1.26 (s, 6H, 2×2'''-CH$_3$); 1.15 (m, 4H, H2'' and H2''''). Mass Spectrum (ES, +ve) m/z 1298 (5%) [MH$^+$], 1172 (100%). HRMS calcd for C$_{74}$H$_{88}$N$_7$O$_{12}$S 1298.6212, found 1298.6185.

Benzyl(2S,5R,8R)-2-allyl-3,6,9-triaza-8-(tert-butoxycarboxamidobutyl)-5-(3-[{2,2,5,7,8-pentamethyl-3,4-dihydro-2H-6-chromenylsulfonyl}guanidino]propyl)-11-(2-[2'-{3-phenylpropyloxy}-[1,1']-(S)-binaphthalen-2-yloxy])-4,7,10-trioxoundecanoate (127)

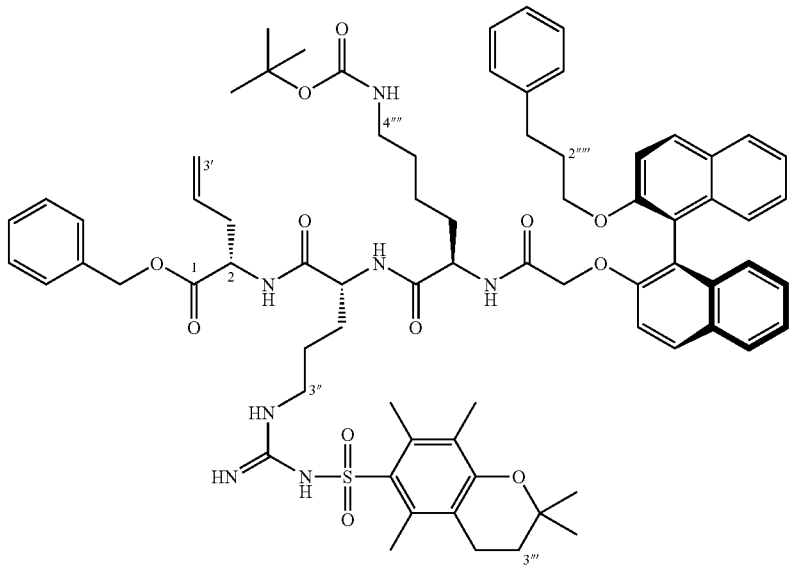

The title compound was synthesised using the general peptide coupling procedure (Procedure B), from 112 (124 mg, 0.14 mmol) and 107 (68 mg, 0.14 mmol) to afford 127 (146 mg, 0.11 mmol, 80%) as a white solid. Mp 92-98° C. $^1$H NMR (CDCl$_3$, 300 MHz): δ 7.90 (m, 4H, ArH); 7.23 (m, 18H, ArH); 6.68 (d, J=9.0 Hz, 1H, NH); 6.27 (bs, 1H, NH); 6.21 (d, J=7.2 Hz, 1H, NH); 5.65 (m, 1H, H2'); 5.12 (AB$_q$, J=12.3 Hz, 2H, PhCH$_2$O); 5.03 (m, 2H, H3'); 4.55 (m, 2H, H5 and H2); 4.40 (AB$_q^-$, J=14.4 Hz, 2H, H111); 4.07 (m, 1H, H8); 3.85 (m, 2H, H1''''); 3.08 (m, 2H, H3''); 2.90 (m, 4H, H4'''' and H3'''''); 2.58 (m, 2H, H4'''); 2.55 (s, 3H, 7'''-CH$_3$); 2.53 (s, 3H, 5'''-CH$_3$); 2.47 (m, 2H, H1'); 2.08 (s, 3H, 8'''-CH$_3$); 1.99 (m, 2H, H1'); 1.74 (t, J=6.6 Hz, 2H, H13'''); 1.62 (m, 2H, H2'''''); 1.40 (s, 9H, C(CH$_3$)$_3$); 1.23 (s, 6H, 2×2'''-CH$_3$); 1.14 (m, 2H, H3''''); 0.95 (m, 2H, H2''); 0.77 (m, 2H, H2''''). Mass Spectrum (ES, +ve) m/z 1321 (100%) [MH$^+$]. HRMS calcd for C$_{74}$H$_{90}$N$_7$O$_{12}$S 1300.6368, found 1300.6356.

Benzyl(2S,5R,8R)-2-allyl-3,6,9-triaza-8-(tert-butoxycarboxamidobutyl-11-(2-[2'-(3-methylbutoxy)-{1,1'}-(S)-binaphthalen-2-yloxy])-5-(3-[{2,2,5,7,8-pentamethyl-3,4-dihydro-2H-6-chromenylsulfonyl}guanidino]propyl)-4,7,10-trioxoundecanoate (128)

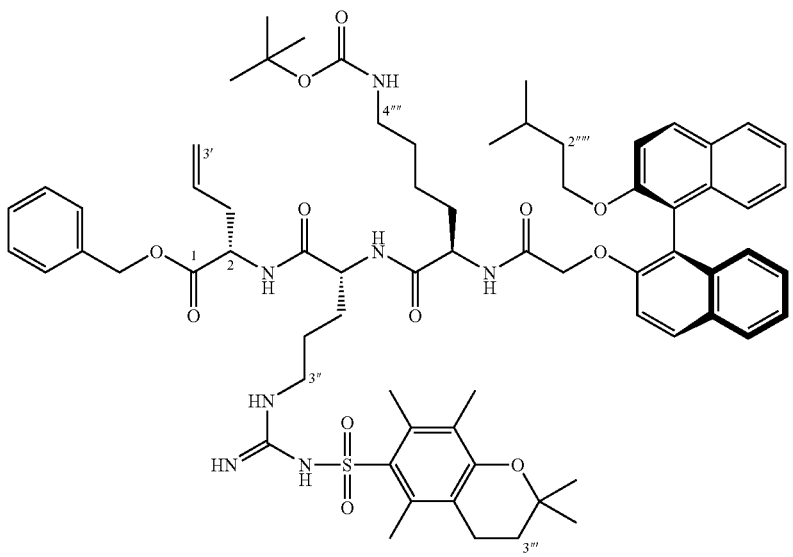

The title compound was synthesised using the general peptide coupling procedure (Procedure B), from 112 (121 mg, 0.14 mmol) and 105 (58 mg, 0.14 mmol) to afford 128 (114 mg, 0.091 mmol, 65%) as a white solid. Mp 90-94° C. $^1$H NMR (CDCl$_3$, 300 MHz): δ 7.90 (m, 4H, ArH); 7.30 (m, 13H, ArH); 6.47 (m, 1H, NH); 6.29 (bs, 2H, NH); 6.18 (d, J=6.9 Hz, 1H, NH); 5.65 (m, 1H, H2'); 5.13 (AB$_q$, J=12.3 Hz, 2H, PhCH$_2$O); 5.05 (m, 2H, H3'); 4.80 (m, 5H, H2, H5, H8 and H11); 3.95 (m, 2H, H1''''); 3.14 (m, 2H, H3''); 2.92 (m, 2H, H4''''); 2.64 (m, 2H, H4'''); 2.56 (s, 3H, 7'''-CH$_3$); 2.55 (s, 3H, 5'''-CH$_3$); 2.49 (m, 2H, H1'); 2.09 (s, 3H, 8'''-CH$_3$); 1.76 (t, J=5.7 Hz, H3'''); 1.52 (m, 4H, H1'' and H1''''); 1.41 (s, 9H, C(CH$_3$)$_3$); 1.26 (s, 6H, 2×2'''-CH$_3$); 1.12 (m, 2H, H3''''); 0.92 (m, 2H, H2''''); 0.79 (m, 4H, H3'''' and H2''); 0.52 (d, J=6.3 Hz, 3H, H4$_a$'''''); 0.46 (d, J=6.3 Hz, 3H, H4$_b$'''''). Mass Spectrum (ES, +ve) m/z 1274 (100%) [MNH$_4^+$]. HRMS calcd for C$_{70}$H$_{90}$N$_7$O$_{12}$S 1252.6368, found 1252.6388.

Benzyl(2S,5R,8R,11S)-2-allyl-11-(4[9-anthracenyl]
benzyl)-3,6,9,12-tetraaza-8-(4-[tert-butoxycarboxa-
mido]butyl)-5-([2,2,5,7,8-pentamethyl-3,4-dihydo-
2H-6-chromenylsulfonyl}guanidino]propyl)-4,7,10,
13-tetraoxotetradecanoate (129)

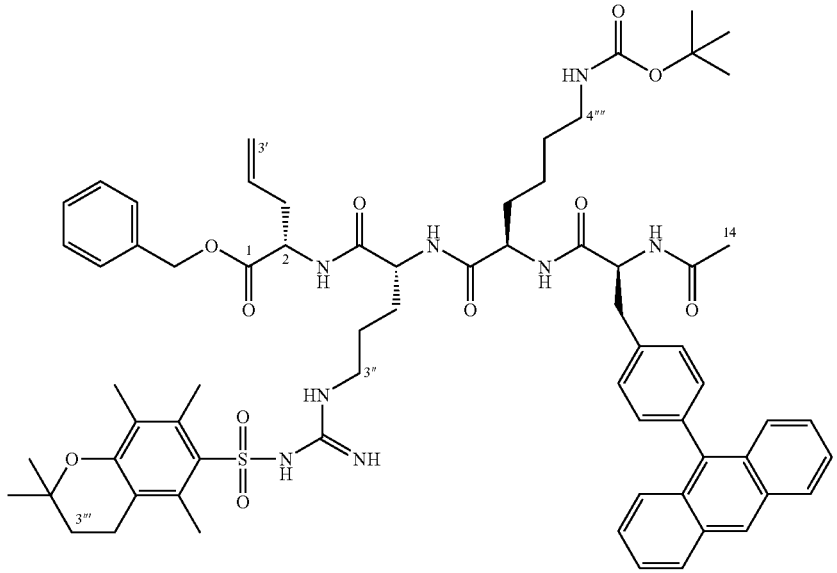

The title compound was synthesised using the general peptide coupling procedure (Procedure B), from 112 (40 mg, 0.045 mmol) and 97 (17 mg, 0.045 mmol) to afford 129 (20 mg, 0.016 mmol, 36%) as a white solid. Mp 108-110° C. $^1$H NMR (CDCl$_3$ 300 MHz): δ 8.48 (s, 1H, ArH10''''); 8.03 (m, 2H, ArH); 7.58 (m, 2H, ArH); 7.44 (m, 2H, ArH); 7.30 (m, 11H, ArH); 6.82 (bs, 1H, NH); 6.36 (bs, 2H, n 2×NH's); 5.77 (m, 1H, H2'); 5.12 (m, 4H, H3' and PhCH$_2$O); 4.85 (m, 1H, H11); 4.59 (m, 1H, H2); 4.44 (m, 1H, H5); 4.31 (m, 1H, H8); 3.19 (m, 2H, 11-CH$_2$); 2.95 (m, 4H, H4'''' and H3''); 2.56 (s, 3H, 7'''-CH$_3$); 2.54 (s, 3H, 5'''-CH$_3$); 2.52 (m, 4H, H4''' and H1'); 2.06 (s, 3H, 8'''-CH$_3$); 1.97 (m, 2H, H3'''); 1.94 (s, 3H, H14); 1.74 (m, 4H, H1'' and H1''''); 1.71 (m, 2H, H13'''); 1.62 (m, 2H, H2''); 1.38 (m, 2H, H2''''); 1.36 (s, 9H, C(CH$_3$)$_3$); 1.23 (s, 6H, 2×2'''-CH$_3$). Mass Spectrum (ES, +ve) m/z 1221 (10%) [MH$^+$]; 282 (100%). HRMS calcd for C$_{68}$H$_{85}$N$_8$O$_{11}$S 1221.6059, found 1221.6089.

Benzyl(2S,5R,8R,11S)-2-allyl-3,6,9,12-tetraaza-8-
(4-[tert-butoxycarboxamido]butyl)-5-([{2,2,5,7,8-
pentamethyl-3,4-dihydro-2H-6-
chromenylsulfonyl}guanidino]propyl)-4,7,10,13-
tetraoxo-11-(4-[9-phenanthrenyl]benzyl)
tetradecanoate (130)

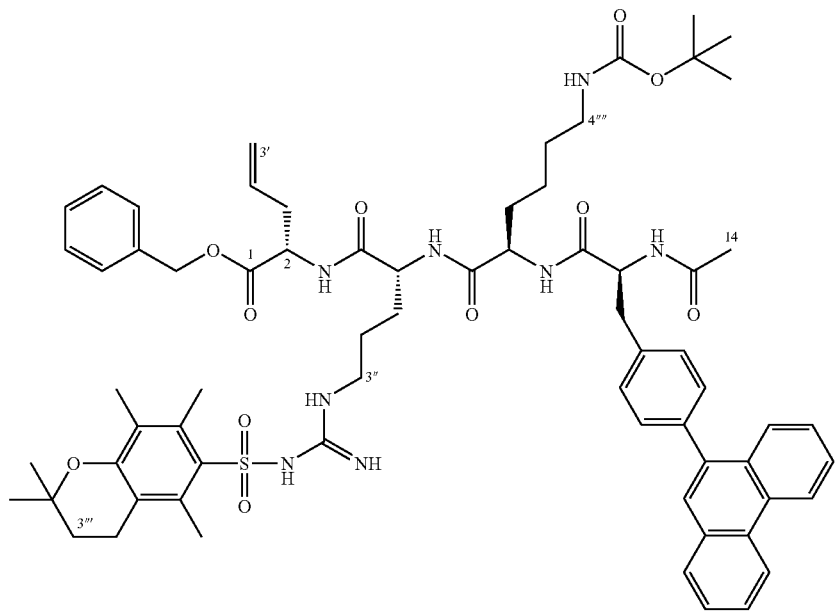

The title compound was synthesised using the general peptide coupling procedure (Procedure B), from 112 (38 mg, 0.044 mmol) and 99 (16 mg, 0.042 mmol) to afford 130 (41 mg, 0.034 mmol, 80%) as a white solid. Mp 108° C. $^1$H NMR (CDCl$_3$, 300 MHz): δ 8.72 (m, 2H, ArH); 7.58 (m, 16H, ArH); 6.40 (bs, 2H, NH); 5.71 (m, 1H, H2'); 5.13 (m, 2H, PhCH__2); 5.03 (m, 2H, H3'); 4.83 (m, 1H, H11); 4.60 (m, 1H, H2); 4.59 (m, 1H, H5); 4.29 (m, H, H8); 3.12 (m, 2H, 11-CH$_2$); 2.94 (m, 4H, H4'''' and H3''); 2.56 (s, 3H, 7'''-CH$_3$); 2.54 (s, 3H, 5'''-CH$_3$); 2.53 (m, 4H, H4''' and H1'); 2.07 (s, 3H, 8'''-CH$_3$); 1.91 (s, 3H, H14); 1.82 (m, 4H, H1'' and H1''''); 1.72 (t, J=6.6 Hz, 2H, H3'''); 1.62 (m, 4H, H2'' and H3''''); 1.39 (m, 2H, H2''''); 1.34 (s, 9H, C(CH$_3$)$_3$); 1.23 (s, 6H, 2×2'''-CH$_3$). Mass Spectrum (ES, +ve) m/z 1221 (100%) [MH$^+$]. HRMS calcd for C$_{68}$H$_{85}$N$_8$O$_{11}$S 1221.6059, found 1221.6045.

Benzyl(2S,5R,8R)-3,6,9-triaza-8-(tert-butoxycarboxamidobutyl)-5-(3-[{2,2,5,7,8-pentamethyl-3,4-dihydro-2H-6-chromenylsulfonyl}guanidino]propyl)-4,7,10-trioxo-2-propyl-1-(2-[2'-3-(propyloxy)-{1,1'}-(S)-binaphthalen-2-yloxy])undecanoate (131)

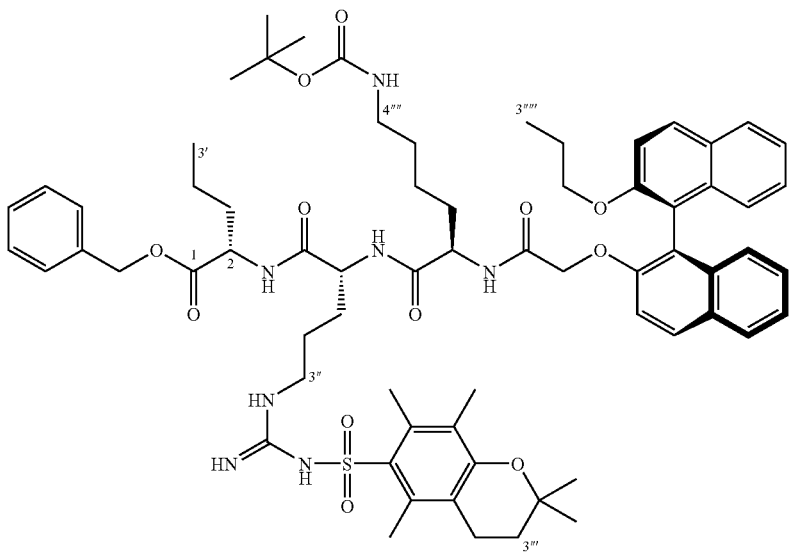

To a solution of 122 (170 mg, 0.145 mmol) in THF (5 mL) was added palladium on activated carbon. The reaction vessel was degassed under vacuum and regassed with hydrogen before being allowed to stir for 13 h. The solution was filtered, evaporated to dryness and dissolved in acetone (5 mL). To this solution was added K$_2$CO$_3$ (39 mg, 0.28 mmol) and benzyl bromide (24 mg, 0.14 mmol). After a further 13 h the reaction was concentrated by vacuum and the product isolated by flash column chromatography (5% MeOH/DCM) to yield 131 (127 mg, 0.10 mmol, 71%) as a white solid. Mp 118-123° C. $^1$H NMR (CDCl$_3$, 300 MHz): δ 7.90 (m, 4H, ArH); 7.30 (m, 13H, ArH); 6.26 (bs, 2H, NH); 6.20 (d, J=7.2 Hz, 1H, NH); 5.13 (AB$_q$, J=12.6 Hz, 2H, PhCH$_2$); 4.50 (m, 2H, H2 and H5) 4.43 (m, 2H, H11); 3.99 (m, 1H, H8); 3.69 (m, 2H, H1''''); 3.13 (m, 2H, H3''); 2.91 (m, 2H, H4''''); 2.60 (m, 2H, H4'''); 2.56 (s, 3H, 7'''-CH$_3$); 2.54 (s, 3H, 5'''-CH$_3$); 2.08 (s, 3H, 8'''-CH$_3$); 1.90 (m, 2H, H1'); 1.88 (m, 2H, H12''''); 1.76 (m, 2H, H13'''); 1.58 (m, 2H, H2''''); 1.41 (s, 9H, C(CH$_3$)$_3$); 1.38 (m, 4H, H1'' and H1''''); 1.34 (m, 2H, H2'); 1.27 (s, 6H, 2×2'''-CH$_3$); 1.20 (m, 2H, H2''); 0.87 (t, J=6.9 Hz, 3H, H3''''); 0.43 (t, J=7.2 Hz, 3H, H3'). Mass Spectrum (ES, +ve) 7m/z 1226 (100%) [MH$^+$]. HRMS calcd for C$_{68}$H$_{88}$N$_7$O$_{12}$S 1226.6212, found 1226.6240.

Benzyl(2S,5R,8R)-2-allyl-11-(2-[2'-allyloxy-{1,1'}-(S)-binaphthalen-2-yloxy])-3,6,9-triaza-8-(butylamino)-5-(3-guanidinopropyl)-4,7,10-trioxoundecanoate dihydrochloride (132)

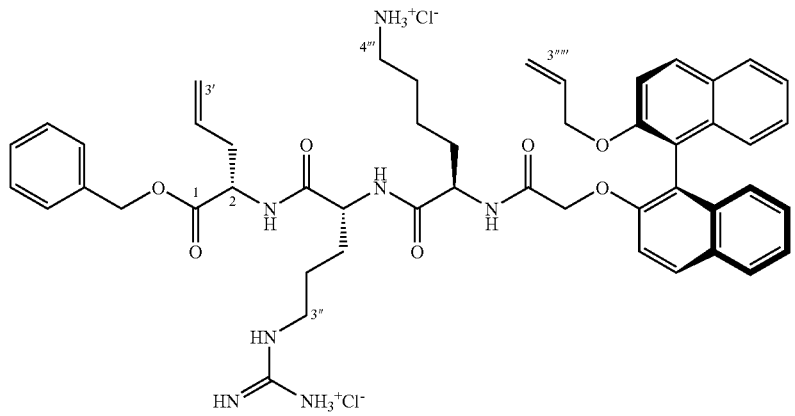

The title compound was synthesized using the general N-Boc deprotection procedure (Procedure A), from 122 (65 mg, 0.055 mmol) to yield 132 (29 mg, 0.034 mmol, 62%) as a highly hydroscopic cream solid. $^1$H NMR (CD$_3$OD, 300 MHz): δ 8.04 (d, J=6.0 Hz, 1H, ArH); 8.01 (d, J=6.0 Hz, 1H, ArH); 7.93 (s, 1H, ArH); 7.90 (s, 1H, ArH); 7.55 (d, J=9.3 Hz, 1H, ArH); 7.48 (d, J=9.3 Hz, 1H, ArH); 7.35 (m, 7H, ArH); 7.23 (m, 2H, ArH); 7.07 (m, 1H, ArH); 7.05 (m, 1H, ArH); 5.73 (m, 2H, H-2' and H2''''); 5.16 (AB$_q$, J=3.6 Hz, 2H, PhCH$_2$O); 5.01 (m, 4H, H3' and H3''''); 4.55 (m, 6H, H2, H5, H11 and H1''''); 4.13 (m, 1H, H8); 3.13 (m, 2H, H3''); 2.77 (m, 2H, H14'''); 2.54 (ddd, J=5.4, 14.4, 24.3 Hz, 2H, H1'); 1.77 (m, 2H, H1'''); 1.62 (m, 2H, H1'''); 1.52 (m, 2H, H3'''); 1.44 (m, 2H, H2''); 0.95 (m, 2H, H2''''). $^{13}$C NMR (CD$_3$OD, 75 MHz): δ 173.8, C4; 173.2, C2; 172.5, C7; 170.9, C10; 158.5, CN$_3$; 155.4, ArC; 154.1, ArC; 137.1, ArC; 135.1, C2'; 135.1, C2''''; 135.0, ArC; 134.2, ArC; 131.4, ArCH; 131.0, ArCH; 130.8, ArCH; 130.8, ArCH; 129.6, ArC; 129.4, ArC; 129.3, ArCH; 129.3, ArCH; 129.2, ArCH; 127.6, ArCH; 127.6, ArCH; 126.4, ArCH; 126.0, ArCH; 125.3, ArCH; 124.9, ArCH; 21.6, ArCH; 120.5, ArC; 119.1, ArC; 117.0, C3'; 116.9, C3''''; 116.0, ArCH; 70.9, C11; 69.2, C1''''; 68.1, ArCH$_2$; 53.9, C5; 53.7, C2; 53.6, C8; 41.9, C3''; 40.4, C4'''; 36.7, C1'; 32.2, C1''; 30.3, C1'''; 27.8, C2''; 26.2, C2'''; 23.2, C3'''. Mass Spectrum (ES, +ve) 7m/z 856 (100%) [M$^{2+}$]. HRMS calcd for C$_{49}$H$_{58}$N$_7$O$_7$ 856.4398, found 856.4367.

Benzyl(2S,5R,8R,11S)-2-allyl-11-(4-allyloxybenzyl)-8-(4-aminobutyl)-3,6,9,12-tetraaza-5-(3-[guanidino]propyl)-4,7,10,13-tetraoxotetradecanoate hydrochloride (133)

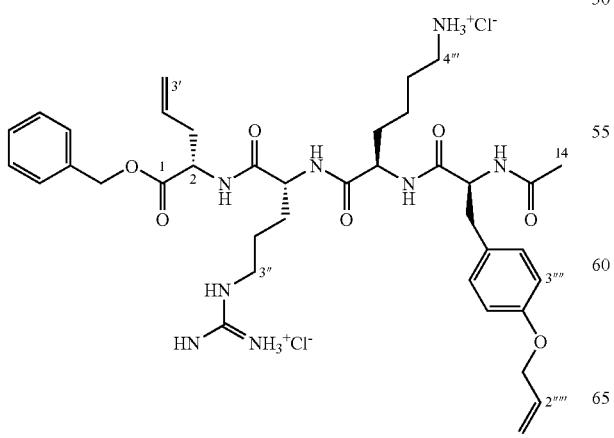

The title compound was synthesized using the general N-Boc deprotection procedure (Procedure A), from 123 (65 mg, 0.059 mmol) to yield 133 (39 mg, 0.048 mmol, 82%) as a cream solid. Mp 108° C. $^1$H NMR (CDCl$_3$, 300 MHz): δ 7.35 (m, 5H, ArH); 7.16 (d, J=8.7 Hz, 2H, ArH2''' and ArH6'''); 6.87 (d, J=8.7 Hz, 2H, ArH3''' and ArH5'''); 6.02 (m, 1H, H12'''); 5.78 (m, 1H, H2'); 5.39 (dd, J=1.8, 17.1 Hz, 1H, H3$_a$''''); 5.24 (dd, J=1.8, 10.5 Hz, 1H, H3$_b$''''); 5.10 (m, 4H, H3' and PhCH$_2$O); 4.52 (m, 2H, H1''''); 4.39 (m, 2H, H13 and H2); 4.24 (dd, J=4.8, 9.0 Hz, 1H, H5); 3.98 (dd, J=3.9, 9.9 Hz, 1H, H8); 3.16 (m, 2H, H3''); 2.94 (m, 2H, 11-CH$_2$); 2.84 (m, 2H, H4'''); 2.55 (m, 2H, H1'); 1.94 (s, 3H, H14); 1.87 (m, 2H, H1'''); 1.73 (m, 2H, H1''''); 1.54 (m, 4H, H2'' and H2'''); 1.03 (m, 2H, H3'''). $^{13}$C NMR (CDCl$_3$, 75 MHz): δ 175.4, C1; 174.4, C4; 174.2, C7; 172.5, C10; 159.0, C13; 158.5, NCO; 137.2, ArC4''''; 134.9, C2''''; 134.3, C2'; 131.5, ArC; 130.0, ArCH2''' and ArCH6'''; 129.6, ArCH; 129.4, ArCH; 129.4, ArCH; 128.5, ArC1''; 119.0, C3'; 117.6, C3''''; 115.9, ArCH3''' and ArCH5'''; 69.8, C1''''; 67.9, CH$_2$-ester); 57.8, C11; 55.3, C5; 54.8, C8; 54.0, C2; 41.9, C3''; 40.3, C4'''; 37.4, 11-CH$_2$; 36.5, C1'; 31.2, C1'''; 29.5, C2''; 28.0, C2'''; 26.5, C14; 23.8, C3'''; 22.5, C1''. Mass Spectrum (ES, +ve) m/z 735 2 [M$^{2+}$] (70%), 368 (100%). HRMS calcd for C$_{38}$H$_{55}$N$_8$O$_7$ 735.4194, found 735.4200.

Benzyl(2S,5R,8R)-2-allyl-3,6,9-triaza-11-(2-[2'-benzyloxy-{1,1'}-(S)-binaphthalen-2-yloxy])-8-(butylamino)-5-(3-guanidinopropyl)-4,7,10-trioxoundecanoate dihydrochloride (134)

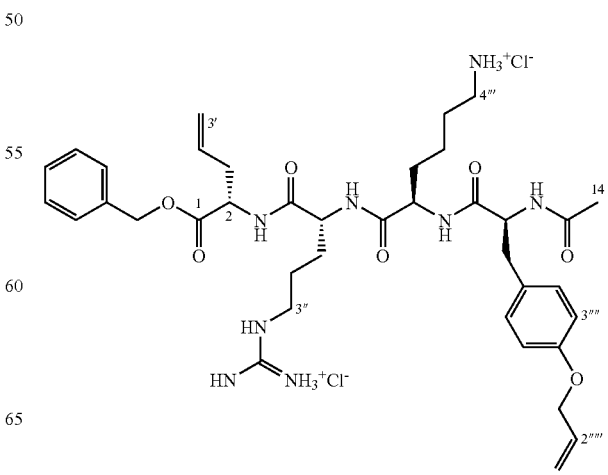

The title compound was synthesized using the general N-Boc deprotection procedure (Procedure A), from 124 (50 mg, 0.039 mmol) to yield 134 (29 mg, 0.030 mmol, 76%) as a cream solid. Mp 116-118° C. $^1$H NMR (CD$_3$OD, 300 MHz): δ 7.70 (m, 4H, ArH); 6.91 (m, 18H, ArH); 5.54 (m, 1H, H2'); 4.89 (m, 6H, PhCH$_2$O, H1'''' and H3'); 4.49 (m, 1H, H2); 4.30 (m, 1H, H5); 4.23 (m, 2H, H11); 4.05 (m, 1H, H8); 3.21 (m, 2H, H3''); 2.95 (m, 2H, H4'''); 2.50 (m, 2H, H1'); 1.62 (m, 2H, H1''); 1.43 (m, 4H, H1''' and H3'''); 1.15 (m, 2H, H2''); 0.89 (m, 2H, H2'''). $^{13}$C NMR (CD$_3$OD, 75 MHz): δ 173.6, C4; 173.4, C2; 172.4, C7; 171.1, C10; 158.2, CN$_3$; 154.3, ArC; 154.1, ArC; 153.4, ArC; 142.1, ArC; 141.8, ArC; 140.8, ArC; 136.8, ArCH; 135.9, ArCH; 135.2, C2'; 132.6, ArC; 131.1, ArCH; 130.6, ArCH; 130.1, ArCH; 129.7, ArC; 129.6, ArC; 129.5, ArCH; 129.3, ArCH; 129.2, ArCH; 129.1, ArCH; 128.8, ArCH; 127.4, ArCH; 126.9, ArCH; 126.7, ArCH; 126.3, ArCH; 125.5, ArCH; 125.1, ArCH; 120.6, ArCH; 120.2, ArCH; 119.2, ArC; 116.6, C3'; 68.7, C11; 68.7, C1''''; 68.0, ArCH$_2$; 54.0, C5; 53.9, C2; 53.6, C8; 41.8, C3''; 40.4, C4'''; 36.5, C1'; 31.9, C1''; 30.0, C1'''; 27.6, C2''; 26.1, C2'''; 23.2, C3'''. Mass Spectrum (ES, +ve) m/z 906 (100%) [M$^{2+}$]. HRMS calcd for C$_{53}$H$_{60}$N$_7$O$_7$ 906.4554, found 906.4544.

Benzyl(2S,5R,8R)-2-allyl-3,6,9-triaza-8-(butylamino)-5-(3-guanidinopropyl)-11-(2-[2'-methyloxy-{1,1'}-(S)-binaphthalen-2-yloxy])-4,7,10-trioxoundecanoate dihydrochloride (135)

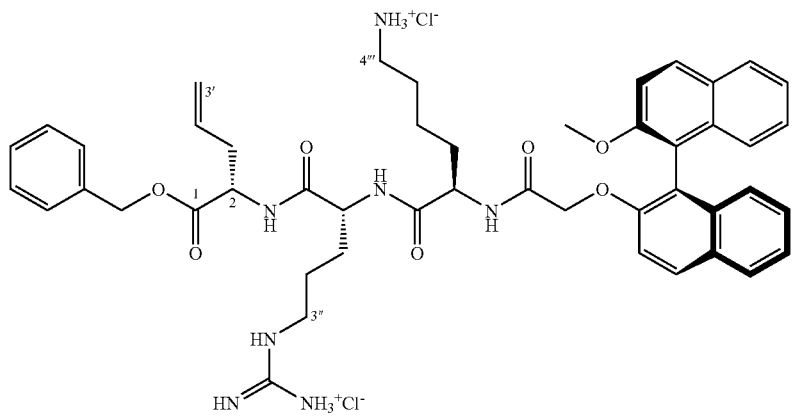

The title compound was synthesized using the general N-Boc deprotection procedure (Procedure A), from 125 (45 mg, 0.037 mmol) to yield 135 (24 mg, 0.027 mmol, 72%) as a highly hydroscopic cream solid. $^1$H NMR (CD$_3$OD, 300 MHz): δ 7.76 (m, 4H, ArH); 7.03 (m, 13H, ArH); 5.56 (m, 1H, H2'); 4.94 (m, 4H, PhCH$_2$O and H3'); 4.31 (m, 4H, H2, H5 and H11); 4.03 (m, 1H, H8); 3.56 (s, 3H, OCH$_3$); 2.98 (m, 2H, H3''); 2.64 (m, 2H, H4'''); 2.36 (m, 2H, H1'); 1.42 (m, 4H, H1'' and H1'''); 0.99 (m, 2H, H2''); 0.78 (m, 2H, H2''''). $^{13}$C NMR (CD$_3$OD, 75 MHz): δ 173.7, C4; 173.1, C2; 172.4, C7; 170.8, C10; 158.4, CN$_3$; 156.2, ArC; 153.8, ArC; 136.9, ArC; 135.0, ArC; 134.8, C2'; 134.1, ArCH; 131.2, ArC; 131.0, ArCH; 130.9, ArCH; 130.5, ArC; 129.5, ArCH; 129.3, ArCH; 129.2, ArCH; 129.2, ArC; 129.1, ArCH; 127.6, ArC; 127.5, ArCH; 126.1, ArCH; 125.7, ArCH; 125.2, ArCH; 124.7, ArCH; 121.4, ArC; 119.5, ArCH; 119.2, C3'; 116.0, ArCH; 115.3, ArCH; 69.1, C11; 68.0, ArCH$_2$; 57.2, OCH$_3$; 54.0, C5; 53.6, C2; 53.6, C8; 41.9, C3''; 40.5, C4'''; 36.6, C1'; 32.2, C1''; 30.1, C1'''; 27.7, C2''; 26.2, C2'''; 23.1, C3'''. Mass Spectrum (ES, +ve) m/z 830 (100%) [M$^{2+}$]. HRMS calcd for C$_{47}$H$_{56}$N$_7$O$_7$ 830.4241, found 830.4219.

Benzyl(2S,5R,8R)-2-allyl-3,6,9-triaza-8-(buty-lamino)-5-(3-guanidinopropyl)-11-(2-[2'-hydroxy-{1,1'}-(S)-binaphthalen-2-yloxy])-4,7,10-trioxoun-decanoate dihydrochloride (136)

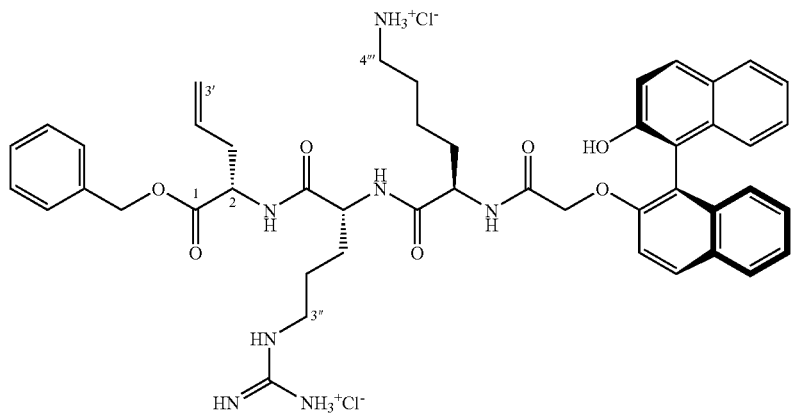

The title compound was synthesized using the general N-Boc deprotection procedure (Procedure A), from 126 (50 mg, 0.038 mmol) to yield 136 (35 mg, 0.036 mmol, 96%) as a highly hydroscopic cream solid. $^1$H NMR (CD$_3$OD, 300 MHz): δ 7.62 (m, 4H, ArH); 6.90 (m, 13H, ArH); 5.44 (m, 1H, H2'); 4.82 (m, 4H, PhC$\underline{H}_2$° and H3'); 4.40 (m, 1H, H5); 4.31 (m, 2H, H11); 4.21 (m, 1H, H2); 3.96 (m, 1H, H8); 2.86 (m, 2H, H3"); 2.54 (m, 2H, H4'''); 2.26 (m, 2H, H1'); 1.54 (m, 2H, H1"); 1.34 (m, 4H, H3''' and H1'''); 1.05 (m, 2H, H2"); 0.79 (m, 2H, H2''''). $^{13}$C NMR (CD$_3$OD, 75 MHz): δ 173.6, C4; 173.4, C2; 172.4, C7; 171.1, C10; 158.2, CN$_3$; 154.0, ArC; 153.3, ArC; 136.7, ArC; 135.2, ArC; 135.0, C2'; 133.9, ArCH; 131.0, ArCH; 130.8, ArC; 130.6, ArCH; 130.0, ArCH; 129.4, ArCH; 129.2, ArCH; 129.1, ArCH; 128.1, ArC; 127.8, ArCH; 127.5, ArC; 127.3, ArC; 126.2, ArCH; 125.5, ArCH; 125.1, ArCH; 124.1, ArCH; 120.5, ArC; 119.5, ArCH; 119.2, C3'; 116.5, ArCH; 115.5, ArCH; 68.6, C11; 67.9, ArCH$_2$; 54.0, C5; 53.9, C2; 53.5, C8; 41.7, C3"; 40.3, C4'''; 36.4, C1'; 32.0, C1"; 30.0, C1'''; 27.6, C2"; 26.0, C2'''; 23.2, C3''''. Mass Spectrum (ES, +ve) m/z 888 (5%) [M$^{2+}$], 831 (100%). HRMS calcd for C$_{46}$H$_{54}$N$_7$O$_7$ 816.4085, found 816.4086.

Benzyl(2S,5R,8R)-2-allyl-3,6,9-triaza-8-(buty-lamino)-5-(3-guanidinopropyl)-4,7,10-trioxo-11-(2-[2'-(3-phenylpropyloxy)-{1,1'}-(S)-binaphthalen-2-yloxy])-undecanoate dihydrochloride (137)

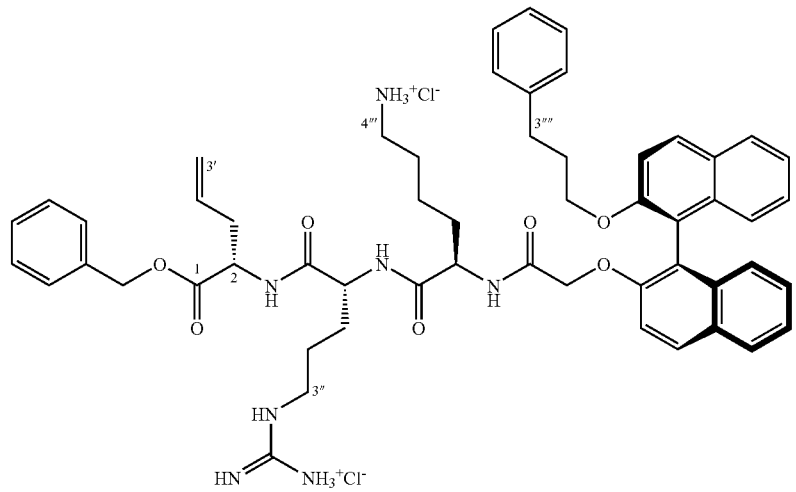

The title compound was synthesized using the general N-Boc deprotection procedure (Procedure A), from 127 (146 mg, 0.11 mmol) to yield 137 (91 mg, 0.090 mmol, 82%) as a highly hydroscopic cream solid. $^1$H NMR (CD$_3$OD, 500 MHz): δ 7.95 (m, 4H, ArH); 7.15 (m, 18H, ArH); 5.73 (m, 1H, H2'); 5.10 (m, 4H, H3' and PhCH$_2$O); 4.47 (m, 1H, H5); 4.35 (m, 2H, H11); 4.17 (m, 1H, H2); 4.08 (m, 1H, H8); 3.86 (m, 2H, H1''''); 3.13 (m, 2H, H3"); 2.80 (m, 2H, H2''''); 2.52 (m, 2H, H4'''); 2.10 (m, 2H, H1'); 1.61 (m, 4H, H3'''' and H1"); 1.49 (m, 4H, H3' and H1'''); 1.12 (m, 2H, H2"); 0.96 (m, 2H, H2''''). $^{13}$C NMR (CD$_3$OD, 125 MHz): δ 173.8, C4; 173.1, C2; 172.4, C7; 170.7, C10; 158.5, CN$_3$; 155.6, ArC; 154.0, ArC; 142.7, ArC; 137.0, C2'; 135.2, ArCH; 135.0, ArCH; 134.4, ArC; 134.1, ArCH; 131.3, ArC; 130.9, ArC; 130.6, ArCH; 129.6, ArCH; 129.3, ArCH; 129.3, ArCH; 129.2, ArCH; 129.2, ArCH; 129.0, ArCH; 127.9, ArC; 127.6, ArCH; 126.5, ArCH; 126.4, ArC; 125.9, ArC; 125.3, ArCH; 124.8, ArCH; 121.7, ArCH; 120.9, ArCH; 120.3, ArC; 119.1, C3'; 116.7, ArCH; 116.0, ArCH; 69.3, C11; 69.2, ArCH$_2$; 68.0, C1''''; 54.1, C5; 53.6, C2; 53.5, C8; 41.9, C3''; 40.3, C4'''; 36.6, C1'; 32.5, C1''; 32.2, C1'''; 32.1, C3''''; 30.1, C2''''; 27.7, C2''; 26.2, C2'''; 23.1, C3'''. Mass Spectrum (ES, +ve) m/z 934 (5%) [M$^{2+}$], 468 (100%). HRMS calcd for C$_{55}$H$_{64}$N$_7$O$_7$ 934.4867, found 934.4844.

Benzyl(2S,5R,8R)-2-allyl-3,6,9-triaza-8-(butylamino)-5-(3-guanidinopropyl)-11-(2-[2'-(3-methylbutoxy)-{1,1'}-(S)-binaphthalen-2-yloxy])-4,7,10-trioxoundecanoate dihydrochloride (138)

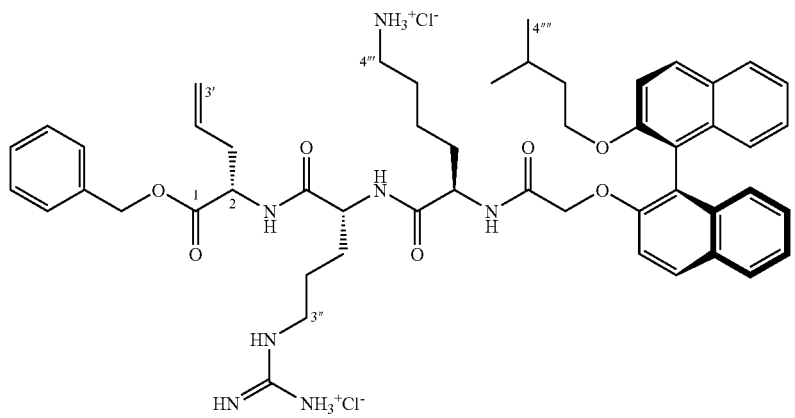

The title compound was synthesized using the general N-Boc deprotection procedure (Procedure A), from 128 (114 mg, 0.091 mmol) to yield 138 (48 mg, 0.050 mmol, 55%) as a highly hydroscopic cream solid. $^1$H NMR (CD$_3$OD, 500 MHz): δ 7.968 (m, 4H, ArH); 5.32 (m, 13H, ArH); 5.74 (m, 1H, 1H2'); 5.11 (m, 4H, PhCH$_2$O and H3'); 4.49 (m, 3H, H5 and H11); 4.35 (m, 1H, H2); 4.14 (m, 2H, H1''''); 3.95 (m, 1H, H8); 3.14 (m, 2H, H3''); 2.79 (m, 2H, H4''); 2.55 (m, 2H, H1'); 1.79 (m, 2H, H1''); 1.71 (m, 2H, H3'''); 1.55 (m, 4H, H2'''' and H1'''); 1.24 (m, 2H, H3''''); 1.17 (m, 2H, H2''); 0.96 (m, 2H, H12'''); 0.53 (d, J=6.3 Hz, 3H, H4$_a$''''); 0.47 (d, J=6.3 Hz, 3H, H4$_b$''''). $^{13}$C NMR (CD$_3$OD, 125 MHz): δ 173.9, C4; 173.2, C2; 172.5, C7; 170.9, C10; 158.5, CN$_3$; 155.9, ArC; 154.0, ArC; 137.1, C2'; 135.2, ArC; 135.0, ArC; 134.3, ArCH; 134.2, ArCH; 131.4, ArC; 129.6, ArCH; 129.6, ArCH; 129.4, ArCH; 129.3, ArC; 129.1, ArCH; 128.2, ArC; 128.0, ArC; 127.6, ArCH; 127.5, ArCH; 126.4, ArCH; 126.0, ArCH; 125.2, ArC; 124.8, ArCH; 121.8, ArCH; 120.5, ArCH; 119.1, C3'; 117.0, ArCH; 116.0, ArCH; 69.0, ArCH$_2$; 68.0, C11; 65.2, C1''''; 54.2, C5; 53.7, C2; 53.6, C8; 41.9, C3''; 40.4, C4'''; 39.3, C2''''; 36.7, C1'; 32.2, C1''; 30.1, C2''; 27.7, C2'''; 26.2, C3''''; 25.6, C3'''; 22.8, C4$_a$'''', 22.6, C4$_b$''''. Mass Spectrum (ES, +ve) m/z 886 (5%) [M$^{2+}$], 444 (100%). HRMS calcd for C$_{51}$H$_{64}$N$_7$O$_7$ 886.4867, found 886.4869.

Benzyl(2S,5R,8R,11S)-2-allyl-8-(4-aminobutyl)-11-
(4-[9-anthracenyl]benzyl)-3,6,9,12-tetraaza-5-(3-
guanidinopropyl)-4,7,10,13-tetraoxotetradecanoate
(139)

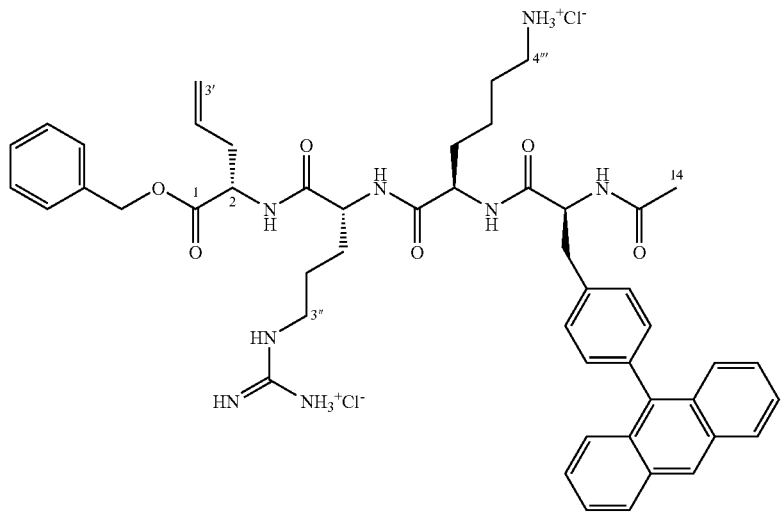

The title compound was synthesized using the general N-Boc deprotection procedure (Procedure A), from 129 (20 mg, 0.016 mmol) to yield 139 (13 mg, 0.014 mmol, 88%) as a white solid. Mp 218-220° C. $^1$H NMR (CD$_3$OD, 300 MHz): δ 7.68 (m, 17H, ArH); 5.77 (m, 1H, H2'); 5.15 (m, 4H, H3' and PhCH$_2$O); 4.82 (m, 1H, H11); 4.42 (m, 1H, H2); 4.25 (m, 1H, H5); 4.07 (m, 1H, H8); 3.18 (m, 2H, 11-CH$_2$); 2.88 (m, 4H, H4'''' and H3''); 2.55 (m, 2H, H1'); 1.95 (s, 3H, H14); 1.85 (m, 2H, H1''); 1.65 (m, 2H, H1'''); 1.53 (m, 2H, H2''); 0.94 (m, 2H, H2'''). $^{13}$C NMR (CD$_3$OD, 75 MHz): δ 175.2, C13; 174.4, C1; 174.2, C4; 174.1, C10; 172.5, C7; 158.6, CN$_3$; 140.0, ArC; 139.9, ArC; 138.1, ArC; 137.4, ArC; 133.2, ArC; 134.3, C2'; 131.5, ArC; 131.3, ArCH; 130.1, ArCH; 129.2, ArC; 128.1, ArC; 127.9, ArCH; 127.6, ArCH; 127.5, ArCH; 126.6, ArCH; 125.9, ArCH; 125.8, ArCH; 125.6, ArCH; 124.2, ArCH; 119.1, C3'; 68.1, CH$_2$-ester; 57.9, C11; 55.3, C8; 54.7, C5; 54.2, C2; 42.1, C3''; 40.3, C4'''; 38.1, 11-CH$_2$; 36.7, C1'; 31.4, C1''; 29.4, C1'''; 27.3, C14; 26.5, C2''; 23.6, C3'''; 22.5, C2'''. (Mass Spectrum (ES, +ve) m/z 855 (50%) [M$^{2+}$]; 428 (100%). HRMS calcd for C$_{49}$H$_{59}$N$_8$O$_6$ 855.4558, found 855.4539.

Benzyl(2S,5R,8R,11S)-2-allyl-8-(4-aminobutyl)-3,6,
9,12-tetraaza-5-(3-guanidinopropyl)-4,7,10,13-tet-
raoxo-11-(4-[9-phenanthrenyl]benzyl)tetradecanoate
(140)

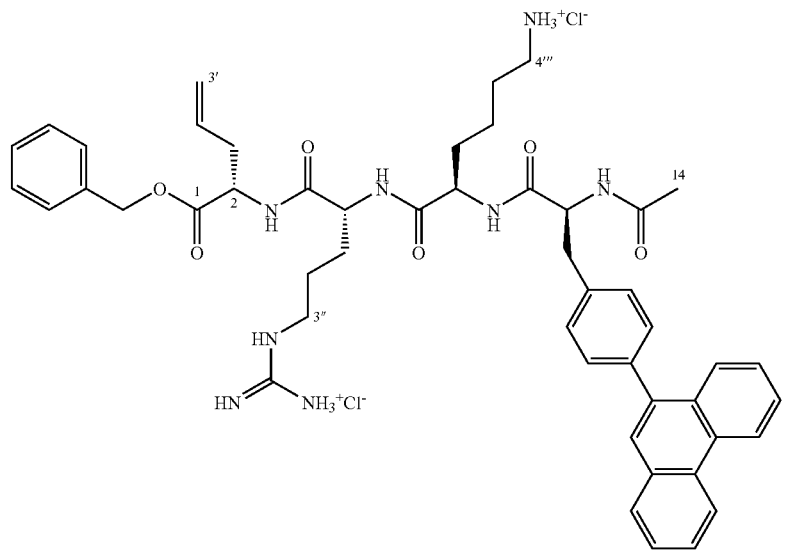

The title compound was synthesized using the general N-Boc deprotection procedure (Procedure A), from 130 (42 mg, 0.034 mmol) to yield 140 (25 mg, 0.027 mmol, 79%) as a white solid. Mp 215-220° C. $^1$H NMR (CD$_3$OD, 300 MHz): δ 8.82 (m, 2H, ArH); 7.60 (m, 16H, ArH); 5.81 (m, 1H, H2'); 5.15 (m, 4H, PhCH$_2$O and H3'); 4.58 (m, 1H, H11); 4.43 (m, 1H, H2); 4.35 (dd, J=4.8, 9.0 Hz, 1H, H5); 4.17 (dd, J=4.8, 9.6 Hz, 1H, H8); 3.17 (m, 4H, H4'''' and H3''); 2.72 (m, 2H, 11-ArCH$_2$); 2.59 (m, 1H, H1'); 1.96 (s, 3H, H14); 1.80 (m, 4H, H1'' and H1'''); 1.65 (m, 2H, H3'''); 1.51 (m, 2H, H2''); 1.22 (m, 2H, H2'''). $^{13}$C NMR (CD$_3$OD, 75 MHz): δ 175.2, C13; 174.4, C1; 174.2, C4; 174.1, C10; 172.5, C7; 158.6, CN$_3$; 140.7, ArC; 139.6, ArC; 137.4, ArC; 137.2, ArC; 134.3, C2'; 132.9, ArC; 132.1, ArC; 131.3, ArCH; 130.5, ArCH; 129.7, ArC; 129.6, ArC; 129.4, ArCH; 129.4, ArCH; 128.5, ArCH; 128.1, ArCH; 127.9, ArCH; 127.8, ArCH; 127.6, ArCH; 124.2, ArCH; 123.7, ArCH; 12.4, ArCH; 122.1, ArCH; 121.8, ArCH; 119.0, C3'; 68.0, CH$_2$-ester; 57.7, C11; 55.2, C8; 54.7, C5; 54.0, C2; 42.0, C3''; 40.1, C4'''; 38.1, 11-CH$_2$; 36.6, C1'; 31.3, C1''; 29.6, C1'''; 27.8, C14; 26.4, C2''; 23.8, C3'''; 22.6, C2'''. Mass Spectrum (ES, +ve) m/z 855 (30%) [M$^{2+}$], 428 (100%). HRMS calcd for C$_{49}$H$_{59}$N$_9$O$_6$ 855.4558, found 855.4528.

Benzyl(2S,5R,8R)-3,6,9-triaza-8-(4-aminobutyl)-5-(3-guanidinopropyl)-4,7,10-trioxo-2-propyl-11-(2-[2'-3-(propyloxy)-{1,1'}-(S)-binaphthalen-2-yloxy]) undecanoate (141)

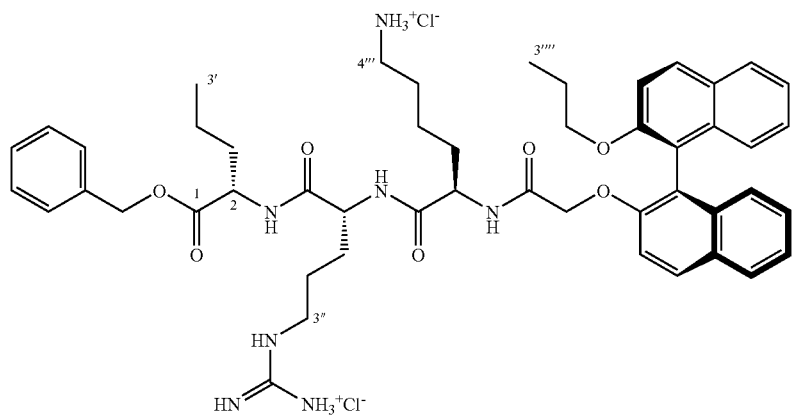

The title compound was synthesized using the general N-Boc deprotection procedure (Procedure A), from 131 (115 mg, 0.094 mmol) to yield 141 (75 mg, 0.080 mmol, 85%) as a highly hydroscopic white solid. $^1$H NMR (CD$_3$OD, 500 MHz) δ 7.95 (m, 4H, ArH); 7.30 (m, 13H, ArH); 5.11 (m, 2H, PhCH$_2$O); 4.58 (m, 2H, H111); 4.39 (m, 1H, H5); 4.15 (m, 1H, H2); 4.89 (m, 1H, H8); 3.68 (m, 2H, H1''''); 3.17 (m, 2H, H3''); 2.55 (m, 2H, H4'''); 2.07 (m, 4H, H11' and H2''''); 1.38 (m, 6H, H1'', H3''' and H11'''); 1.34 (m, 2H, H2'); 1.13 (m, 2H, H12'''); 1.08 (m, 2H, H2''); 0.89 (m, 3H, H3''''); 0.50 (m, 3H, H3'). $^{13}$C NMR (CD$_3$OD, 125 MHz) δ 173.9, C4; 173.3, C2; 173.1, C7; 170.8, C10; 158.4, CN$_3$; 155.8, ArC; 153.9, ArC; 142.6, ArC; 137.1, ArC; 135.1, ArCH; 135.1, ArCH; 131.3, ArC; 130.9, ArC; 130.6, ArC; 129.6, ArCH; 129.3, ArCH; 129.3, ArCH; 129.1, ArC; 128.2, ArC; 127.6, ArCH; 127.4, ArCH; 126.3, ArCH; 125.9, ArCH; 125.2, ArCH; 124.8, ArCH; 11.7, ArCH; 120.4, ArCH; 116.8, ArCH; 116.0, ArCH; 72.1, C1''''; 69.2, C11; 67.9, ArCH$_2$; 54.1, C5; 53.7, C2; 53.6, C8; 41.9, C3''; 40.4, C4'''; 34.3, C1'; 32.2, C1''; 30.1, C1'''; 27.7, C2''; 26.2, C2''''; 23.7, C2'''; 23.1, C3'''; 20.0, C2'; 13.9, C3'; 10.8, C3''''. Mass Spectrum (ES, +ve) m/z 860 (30%) [M$^{2+}$], 431 (100%). HRMS calcd for C$_{49}$H$_{62}$N$_7$O$_7$ 860.4711, found 860.4730.

Methyl 3-amino-benzoate hydrochloride (143)

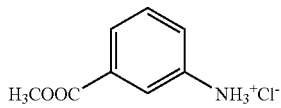

To a suspension of 3-aminobenzoic acid (1.03 g mg, 7.52 mmol) in MeOH (80 mL) at 0° C. was added dropwise thionyl chloride (5 mL). The resulting solution was allowed to stir for 16 h before the solvent was removed by evaporation and the product precipitated with diethyl ether. The diethyl ether was removed by evaporation to yield the title compound (1.38 g, 7.38 mmol, 98%) as a white solid. Mp 176-178° C. $^1$H NMR (D$_2$O, 300 MHz): δ 7.75 (dt, J=1.8, 3.3, 7.2 Hz, 1H, ArH); 7.71 (m, 1H, ArH); 7.42 (m, 1H, ArH); 7.37 (m, 1H, ArH); 3.66 (s, 3H, OCH$_3$). Mass Spectrum (CI) m/z 152 (100%) [M$^+$]. HRMS calcd for C$_8$H$_{10}$NO$_2$ 152.0712, found 152.0698.

Methyl(3'R)-3-(1-aza-6-tert-butoxycarboxamido-3'-[9H-9-fluororenylmethoxycarboxamido]-2-oxo-hexyl)benzoate (144)

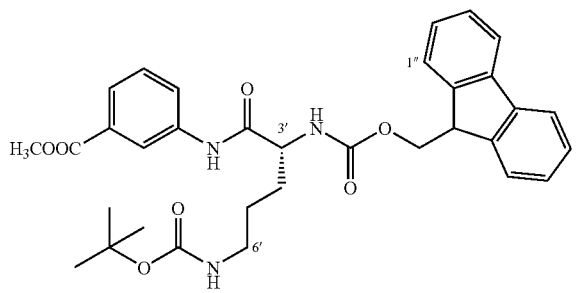

The title compound was synthesised using the general peptide coupling procedure (Procedure B), from 143 (220 mg, 2.27 mmol) and (R)-5-(tert-butoxycarboxamido)-2-(9H-9-fluorenylmethyloxycarboxamido)pentanoic acid (578 mg, 1.27 mmol) to afford 144 (277 mg, mmol, 36%) as a white solid. Mp 96-98° C. $^1$H NMR (CDCl$_3$, 300 MHz): δ 9.15 (s, 1H, ArH); 8.17 (s, 1H, NH); 7.88 (d, J=8.1 Hz, 1H, ArH); 7.77 (m, 1H, ArH1); 7.72 (d, J=7.8 Hz, 2H, ArH1" and ArH8"); 7.56 (d, J=7.2, Hz, 2H, ArH4" and ArH5"); 7.36 (m, 2H, ArH3" and ArH6"); 7.26 (m, 2H, ArH2" and ArH7"); 6.03 (d, J=8.1 Hz, 2H, NH); 4.63 (m, 1H, H3'); 4.36 (d, J=6.9 Hz, 2H, OCH$_2$—H9"); 4.17 (t, J=6.9 Hz, 1H, H9"); 3.86 (s, 3H, OCH$_3$); 3.08 (m, 2H, H6'); 1.78 (m, 2H, H4'); 1.60 (m, 2H, H5'); 1.42 (s, 9H, (CH$_3$)$_3$). Mass Spectrum (ES, +ve) m/z 610 (100%) [MNa$^+$], 588 (70%) [MH$^+$]. HRMS calcd for C$_{33}$H$_{38}$N$_3$O$_7$ 588.2710, found 588.2726.

Methyl(3R)-3-(3'-amino-1-aza-6-tert-butoxycarboxamido-2-oxohexyl)benzoate (145)

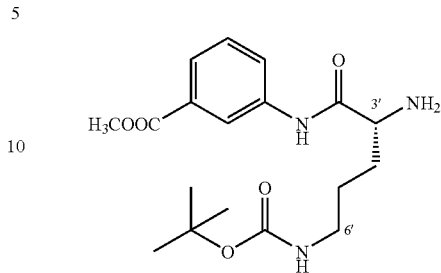

The title compound was synthesized using the general N-Fmoc deprotection procedure (Procedure C), from 144 (555 mg, 0.95 mmol) to yield 145 (285 mg, 0.78 mmole, 82%) as a colourless viscous oil. $^1$H NMR (CDCl$_3$, 300 MHz): δ 8.04 (m, 1H, ArH); 7.84 (t, J=1.8 Hz, 1H, ArH); 7.51 (t, J=7.8 Hz, 1H, ArH); 7.36 (m, 1H, ArH); 5.11 (m, 1H, NH); 3.91 (s, 3H, OCH$_3$); 3.69 (m, 1H, H3'); 3.19 (m, 2H, H6'); 2.08 (m, 2H, H4'); 1.65 (m, 4H, H5' and NH$_2$); 1.43 (s, 9H, (CH$_3$)$_3$). HRMS calcd for C$_{18}$H$_{28}$N$_3$O$_5$ 366.2029, found 366.2051.

Methyl(3R)-3-(6-(2-[2'-allyloxy-{1,1'}-(S)-binaphthalen-2-yloxy])-1,4-diaza-3-[(3-tert-butoxycarboxamido)propyl]-2,5-dioxohexyl)benzoate (146)

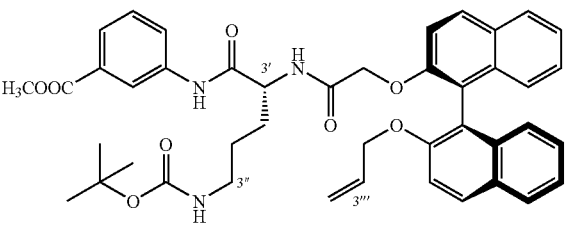

The title compound was synthesised using the general peptide coupling procedure (Procedure B), from 101 (288 mg, 0.75 mmol) and 145 (275 mg, 0.75 mmol) to afford 146 (434 mg, 0.59 mmol, 79%) as a white foam. Mp 70° C. $^1$H NMR (CDCl$_3$, 300 MHz): δ 9.08 (s, 1H, ArH); 7.91 (m, 7H, ArH); 7.85 (m, 8H, ArH); 6.45 (d, J=8.1 Hz, 1H, NH); 5.69 (m, 1H, H2'''); 4.94 (m, 2H, H3'''); 4.55 (m, 5H, H6', H1''' and H3'); 3.87 (s, 3H, OCH$_3$); 2.96 (m, 2H, H3"); 1.62 (m, 2H, H1"); 1.44 (s, 9H, (CH$_3$)$_3$); 1.04 (m, 2H, H2")". Mass Spectrum (ES, +ve) m/z 732 (50%) [MH$^+$], 351 (100%). HRMS calcd for C$_{43}$H$_{46}$N$_3$O$_8$ 732.3285, found 732.3316.

(3R)-3-(6-(2-[2'-allyloxy-{1,1'}-(S)-binaphthalen-2-yloxy])-1,4-diaza-3-[(3-tert-butoxycarboxamido)propyl]-2,5-dioxohexyl)benzoic acid (147)

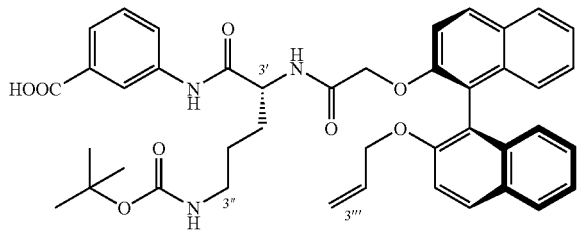

To a solution of 146 (370 mg, 0.51 mmol) in THF/water, 3:1 (8 mL) was added lithium hydroxide monohydrate (43 mg, 0.51 mmol) and the resulting suspension was allowed to stir for 16 h. The reaction mixture was diluted with water (30 mL) and the THF was removed by evaporation before the remaining aqueous layer was washed with diethyl ether (40 mL) to remove unreacted starting material. The aqueous phase was acidified with dilute potassium bisulfate and the resulting precipitate was extracted with DCM (3×40 mL). The combined DCM fractions were dried and evaporated to yield the title compound (350 mg, 0.49 mmol, 96%) as a white solid. Mp 86-90° C. $^1$H NMR (CDCl$_3$, 300 MHz): δ 9.70 (bs, 1H, COOH); 9.26 (s, 1H, ArH); 7.97 (m, 7H, ArH); 7.34 (m, 8H, ArH); 6.63 (d, J=9.0 Hz, 1H, NH); 5.71 (m, 1H, H2'''); 5.01 (m, 2H, H3'''); 4.59 (m, 5H, H6', H1''' and H3'); 3.03 (m, 2H, H3''); 1.65 (m, 2H, H1''); 1.49 (s, 9H, (CH$_3$)$_3$); 1.15 (m, 2H, H2''). Mass Spectrum (ES, +ve) m/z 740 (100%) [MNa$^+$], 718 (20%) [MH$^+$]. HRMS calcd for C$_{42}$H$_{44}$N$_3$O$_5$ 718.3128, found 718.3152.

Benzyl(3R)-3-(6-(2-[2'-allyloxy-{1,1'}-(S)-binaphthalen-2-yloxy])-1,4-diaza-3-[(3-tert-butoxycarboxamido)propyl]-2,5-dioxohexyl)benzoate (148)

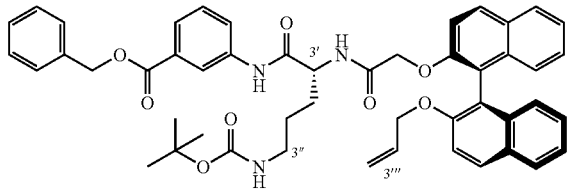

To a solution of 147 (40 mg, 0.056 mmol) in acetone (2 mL) was added K$_2$CO$_3$ (17 mg, 0.12 mmol) and benzyl bromide (21 mg, 0.12 mmol). The resulting suspension was allowed to stir for 16 h before concentration and purification by flash column chromatography (5% MeOH/DCM) to yield the title compound (36 mg, 0.045 mmol, 80%) as a white solid. Mp 145-152° C. $^1$H NMR (CDCl$_3$, 300 MHz): δ 8.63 (s, 1H, ArH); 7.90 (m, 7H, ArH); 7.30 (m, 11H, ArH); 6.27 (d, J=8.4 Hz, 1H, NH); 5.68 (m, 1H, H2'''); 5.30 (s, 2H, ArCH$_2$); 4.87 (m, 2H, H3'''); 4.50 (m, 5H, H6', H1''' and H3'); 3.00 (m, 2H, H3''); 1.52 (m, 2H, H1''); 1.42 (s, 9H, (CH$_3$)$_3$); 1.05 (m, 2H, H2''). Mass Spectrum (ES, +ve) m/z 808 (30%) [MH$^+$]; 414 (100%). HRMS calcd for C$_{49}$H$_{50}$N$_3$O$_8$ 808.3598, found 808.3634.

Allyl(3R)-3-(6-(2-[2'-allyloxy-{1,1'}-(S)-binaphthalen-2-yloxy])-1,4-diaza-3-[(3-tert-butoxycarboxamido)propyl]-2,5-dioxohexyl)benzoate (149)

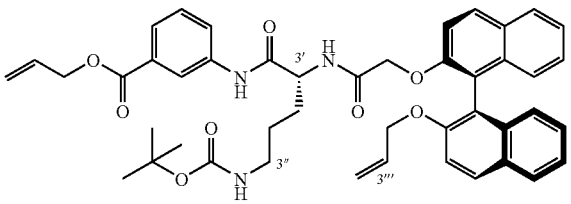

To a solution of 147 (43 mg, 0.060 mmol) in acetone (2 mL) was added K$_2$CO$_3$ (18 mg, 0.12 mmol) and allyl bromide (0.1 mL, 0.12 mmol). The resulting suspension was allowed to stir for 16 h before concentration and purification by flash column chromatography (5% MeOH/DCM) to yield the title compound (36 mg, 0.047 mmol, 79%) as a white solid. Mp 142-150° C. $^1$H NMR (CDCl$_3$, 300 MHz): δ 8.75 (s, 1H, ArH); 7.90 (m, 7H, ArH); 7.29 (m, 8H, ArH); 6.32 (d, J=8.4 Hz, 1H, NH); 6.02 (m, 1H, CH-ester); 5.65 (m, 1H, H12'''); 5.39 (dd, J=1.5, 17.4 Hz, 1H, H3$_a$-ester); 5.27 (dd, J=1.5, 10.5 Hz, 1H, H3$_b$-ester); 4.89 (m, 2H, H3'''); 4.81 (m, 2H, H1-ester); 4.55 (AB$_q$, J=14.7 Hz, 2H, H6'); 4.52 (m, 2H, H1'''); 4.23 (m, 1H, H3'); 3.00 (m, 2H, H3''); 1.91 (m, 2H, H1''); 1.44 (s, 9H, (CH$_3$)$_3$); 1.01 (m, 2H, H2''). Mass Spectrum (ES, +ve) m/z 758 (10%) [MH$^+$]; 444 (100%). HRMS calcd for C$_{45}$H$_{47}$N$_3$O$_8$Na 780.3261, found 780.3290.

(3R)-3-(6-(2-[2'-allyloxy-{1,1'}-(S)-binaphthalen-2-yloxy])-1,4-diaza-3-[(3-tert-butoxycarboxamido)propyl]-2,5-dioxohexyl)-N-benzyloxybenzamide (150)

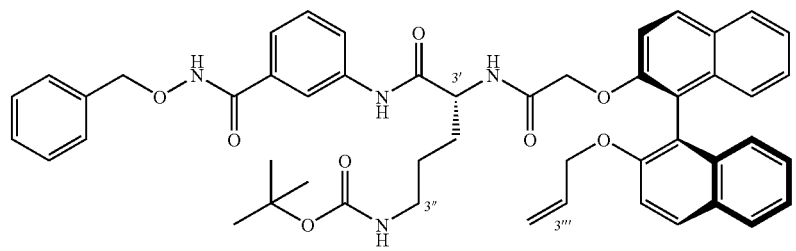

The title compound was synthesised using the general peptide coupling procedure (Procedure B), from 147 (91 mg, 0.127 mmol) and O-benzylhydroxylamine (20 mg, 1.27 mmol) to afford 150 (82 mg, 0.100 mmol, 78%) as a white solid. Mp 141-144° C. $^1$H NMR (CDCl$_3$, 300 MHz): δ 9.14 (s, 1H, ArH); 7.97 (m, 2H, ArH); 7.88 (m, 2H, ArH); 7.31 (m, 10H, ArH); 6.41 (d, J=7.5 Hz, 1H, NH); 5.66 (m, 1H, H12'''); 4.95 (m, 4H, H3''' and ArCH$_2$); 4.66 (t, J=5.1 Hz, 1H, NH); 4.54 (m, 4H, H6', H1'''); 4.30 (m, 1H, H3'); 2.93 (m, 2H, H3''); 1.54 (m, 2H, H1''); 1.43 (s, 9H, (CH$_3$)$_3$); 1.06 (m, 2H, H2''). Mass Spectrum (ES, +ve) m/z 823 (100%) [MH$^+$]. HRMS calcd for C$_{49}$H$_{51}$N$_4$O$_8$ 823.3707, found 823.3726.

Methyl(3R)-3-(6-(2-[2'-allyloxy-{1,1'}-(S)-binaphthalen-2-yloxy])-1,4-diaza-3-(3[{di-tert-butoxycarbonyl}guanidino]propyl)-2,5-dioxohexyl)benzoate (151)

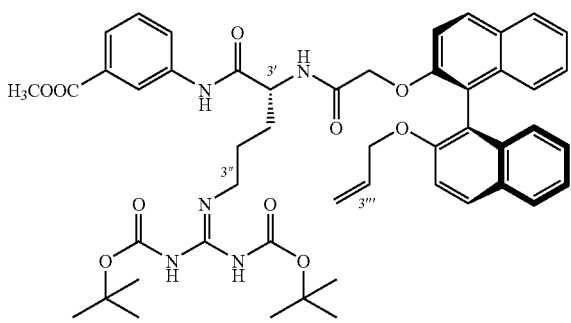

To a solution of 155 (32 mg, 0.048 mmol) in DCM (3 mL) was added N1-tert-butoxycarboxamido(trifluoromethylsulfonylimino)methyl propanamide (28 mg, 0.072 mmol), triethylamine (7.3 mg, 0.072 mmol). The resulting solution was allowed to stir for 16 h under a nitrogen atmosphere. The solvent was evaporated and the crude product was purified by flash column chromatography (15:1, DCM/MeOH) to yield the title compound (41 mg, 0.047 mmole, 98%) as a white solid. Mp 74-76° C. $^1$H NMR (CDCl$_3$, 300 MHz): δ 8.55 (s, 1H, ArH); 8.27 (bs, 1H, NH); 7.77 (m, 7H, ArH); 7.26 (m, 8H, ArH); 6.34 (d, J=8.4 Hz, 1H, NH); 5.59 (m, 1H, H2'''); 4.67 (m, 2H, H3'''); 4.57 (d, J=3.3 Hz, 2H, H1'''); 4.48 (m, 2H, C6'); 4.34 (m, 1H, H3'); 3.91 (s, 3H, OCH$_3$); 3.26 (m, 2H, H3''); 1.65 (m, 2H, H1''); 1.51 (s, 9H, (CH$_3$)$_3$); 1.46 (s, 9H, (CH$_3$)$_3$); 1.14 (m, 2H, H2''). Mass Spectrum (ES, +ve) m/z 896 (100%) [MNa$^+$], 875 (95%) [MH$^+$]. HRMS calcd for C$_{49}$H$_{56}$N$_5$O$_{10}$ 874.4027, found 874.4043.

Benzyl(3R)-3-(6-(2-[2'-allyloxy-{1,1'}-(S)-binaphthalen-2-yloxy])-1,4-diaza-3-(3[{di-tert-butoxycarbonyl}guanidino]propyl)-2,5-dioxohexyl)benzoate (152)

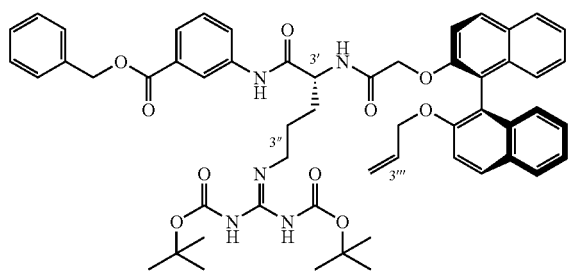

To a solution of 157 (20 mg, 0.027 mmol) in DCM (2 mL) was added N1-tert-butoxycarboxamido(trifluoromethylsulfonylimino)methyl propanamide (16 mg, 0.041 mmol), and triethylamine (4 mg, 0.041 mmol). The resulting solution was allowed to stir for 16 h under N$_2$. The solvent was evaporated and the crude product was purified by flash column chromatography (15:1, DCM/MeOH) to yield the title compound (15 mg, 0.016 mmole, 58%) as a white solid. Mp 122-126° C. $^1$H NMR (CDCl$_3$, 300 MHz): δ 8.41 (s, 1H, ArH); 8.26 (bs, 1H, NH); 7.85 (m, 7H, ArH); 7.32 (m, 8H, ArH); 6.31 (d, J=8.1 Hz, 1H, NH); 5.56 (m, 1H, H2'''); 5.37 (s, 2H, ArCH$_2$); 4.85 (m, 2H, H3'''); 4.56 (m, 2H, H1'''); 4.45 (m, 2H, H6'); 4.32 (m, 1H, H3'); 3.25 (m, 2H, H3''); 1.63 (m, 2H, H1''); 1.50 (s, 9H, (CH$_3$)$_3$); 1.46 (s, 9H, (CH$_3$)$_3$); 1.15 (m, 2H, H2''). Mass Spectrum (ES, +ve) m/z 950 (100%) [MH$^+$]. HRMS calcd for C$_{55}$H$_{60}$N$_5$O$_{10}$ 950.4340, found 950.4339.

Allyl(3R)-3-(6-(2-[2'-allyloxy-{1,1'}-(S)-binaphthalen-2-yloxy])-1,4-diaza-3-(3[{di-tert-butoxycarbonyl}guanidino]propyl)-2,5-dioxohexyl)benzoate (153)

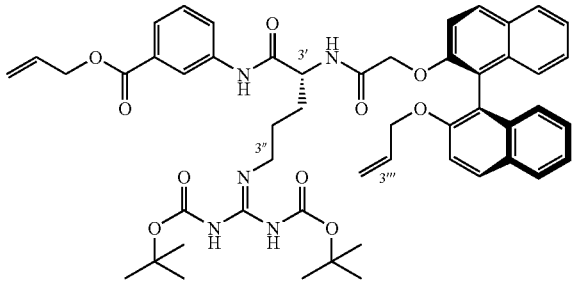

To a solution of 159 (25 mg, 0.036 mmol) in DCM (2 mL) was added N1-tert-butoxycarboxamido(trifluoromethylsulfonylimino)methyl propanamide (21 mg, 0.054 mmol), and triethylamine (0.1 mL). The resulting solution was allowed to stir for 16 h under N$_2$. The solvent was evaporated and the crude product was purified by flash column chromatography (15:1, DCM/MeOH) to yield the title compound (31 mg, 0.034 mmole, 97%) as a white solid. Mp 70° C. $^1$H NMR (CDCl$_3$, 300 MHz): δ 8.57 (s, 1H, ArH); 8.26 (bs, 1H, NH); 7.88 (m, 7H, ArH); 7.28 (m, 8H, ArH); 6.34 (d, J=8.1 Hz, 1H, NH); 6.03 (m, 1H, CH-ester); 5.58 (m, 1H, H2'''); 5.40 (dd, J=1.5, 17.1 Hz, 1H, H3$_a$-ester); 5.28 (dd, J=1.5, 10.5 Hz, 1H, H3$_b$-ester); 4.85 (m, 4H, H1-ester and H3'''); 4.50 (m, 4H, H6' and H1'''); 4.34 (m, 1H, H3'); 3.26 (m, 2H, H3''); 1.62 (m, 2H, H1''); 1.50 (s, 9H, (CH$_3$)$_3$); 1.46 (s, 9H, (CH$_3$)$_3$); 1.10 (m, 2H, H12''). Mass Spectrum (ES, +ve) m/z 900 (10%) [MH$^+$], 700 (100%). HRMS calcd for C$_{51}$H$_{58}$N$_5$O$_{10}$ 900.4184, found 900.4179.

(3R)-3-(6-(2-[2'-allyloxy-{1,1'}-(S)-binaphthalen-2-yloxy])-1,4-diaza-3-(3[{di-tert-butoxycarbonyl}guanidino]propyl)-2,5-dioxohexyl)-N-benzyloxybenzamide (154)

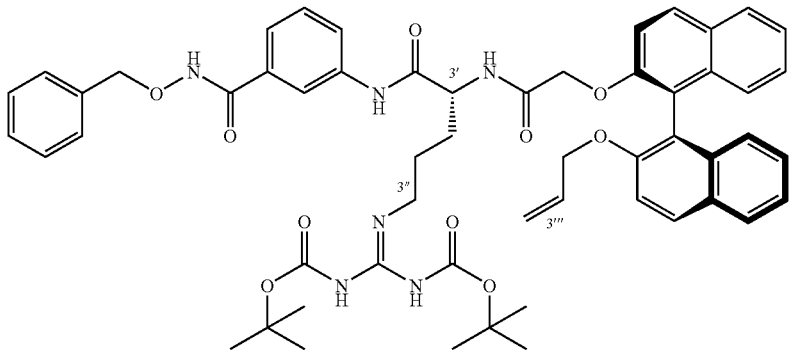

To a solution of 161 (51 mg, 0.067 mmol) in DCM (3 mL) was added N1-tert-butoxycarboxamido(trifluoromethylsulfonylimino)methyl propanamide (39 mg, 0.10 mmol), and triethylamine (0.1 mL). The resulting solution was allowed to stir for 16 hr under $N_2$. The solvent was evaporated and the crude product was purified by flash column chromatography (15:1, DCM/MeOH) to yield the title compound (58 mg, 0.060 mmole, 90%) as a white solid. Mp 112° C. $^1$H NMR (CDCl$_3$, 300 MHz): δ 9.05 (s, 1H, ArH); 8.25 (bs, 1H, NH); 7.90 (m, 4H, ArH); 7.31 (m, 16H, ArH); 6.34 (d, J=7.5 Hz, 1H, NH); 5.63 (m, 1H, H2'''); 5.00 (s, 2H, ArCH$_2$); 4.89 (m, 2H, H3'''); 4.51 (m, 4H, H6' and H1'''); 4.25 (m, 1H, H3'); 3.23 (m, 2H, H3''); 1.65 (m, 2H, H1''); 1.50 (s, 9H, (CH$_3$)$_3$); 1.44 (s, 9H, (CH$_3$)$_3$); 1.10 (m, 2H, H2''). Mass Spectrum (ES, +ve) m/z 987 (100%) [MNa$^+$], 965 (90%) [MH$^+$]. HRMS calcd for C$_{55}$H$_{61}$N$_6$O$_{10}$ 965.4449, found 965.4422.

Methyl(3R)-3-(6-(2-[2'-allyloxy-{1,1'}-(S)-binaphthalen-2-yloxy])-3-(3-aminopropyl)-1,4-diaza-2,5-dioxohexyl)benzoate hydrochloride (155)

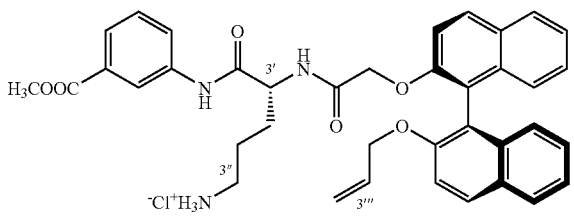

The title compound was synthesized using the general N-Boc deprotection procedure (Procedure A), from 146 (56 mg, 0.077 mmol) to yield 155 (38 mg, 0.057 mmol, 74%) as a highly hydroscopic cream solid. $^1$H NMR (CD$_3$OD, 300 MHz): δ 8.02 (m, 2H, ArH); 7.92 (m, 2H, ArH); 7.75 (m, 2H, ArH); 7.34 (m, 8H, ArH); 7.06 (m, 2H, ArH); 5.71 (m, 1H, H2'''); 4.90 (m, 2H, H3'''); 4.59 (m, 5H, H6', H1''' and H3'); 3.93 (s, 3H, OCH$_3$); 2.76 (m, 2H, H3''); 1.67 (m, 2H, H1''); 1.30 (m, 2H, H2''). $^{13}$C NMR (CD$_3$OD, 75 MHz): δ 170.9, 1-CO; 170.6, C5'; 168.1, C2'; 155.4, ArC; 154.1, ArC; 139.8, C2'''; 138.0, ArC; 135.1, ArC; 134.9, ArC; 132.1, ArCH; 131.5, ArC; 131.3, ArC; 131.0, ArCH; 130.8, ArCH; 130.2, ArCH; 129.3, ArC; 129.2, ArCH; 127.6, ArCH; 127.3, ArCH; 127.1, ArCH; 126.4, ArCH; 126.3, ArCH; 126.0, ArCH; 125.5, ArCH; 125.3, ArCH; 124.8, ArCH; 122.1, ArC; 121.8, ArC; 117.0, C3'''; 117.0, ArCH; 116.2, ArCH; 70.9, C1'''; 67.4, C6'; 53.1, H3'; 52.6, OCH$_3$; 40.1, C3''; 30.3, C2''; 24.5, C1''. Mass Spectrum (ES, +ve) m/z 632 (100%) [M$^+$]. HRMS calcd for C$_{38}$H$_{38}$N$_3$O$_6$ 632.2761, found 632.2777.

Methyl(3R)-3-(6-(2-[2'-allyloxy-{1,1'}-(S)-binaphthalen-2-yloxy])-1,4-diaza-3-(3-guanidylpropyl)-2,5-dioxohexyl)benzoate hydrochloride (156)

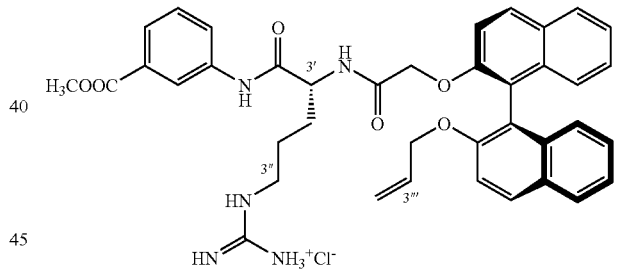

The title compound was synthesized using the general N-Boc deprotection procedure (Procedure A), from 151 (49 mg, 0.056 mmol) to yield 156 (32 mg, 0.045 mmol, 80%) as a cream solid. Mp 124-126° C. $^1$H NMR (CD$_3$OD, 300 MHz): δ 8.28 (s, 1H, ArH); 7.90 (m, 4H, ArH); 7.32 (m, 9H, ArH); 7.07 (m, 2H, ArH); 5.73 (m, 1H, H2'''); 4.97 (m, 2H, H3'''); 4.52 (m, 5H, H6', H1''' and H3'); 3.92 (s, 3H, OCH$_3$); 3.01 (m, 2H, H3''); 1.63 (m, 2H, H1''); 1.17 (m, 2H, H2''). $^{13}$C NMR (CD$_3$OD, 75 MHz): δ. 171.0, 1-CO; 170.4, C5'; 168.0, C2'; 158.4, CN$_3$; 155.4, ArC; 154.2, ArC; 140.0, C2'''; 138.8, ArC; 135.1, ArC; 135.0, ArC; 132.0, ArCH; 131.3, ArC; 131.1, ArC; 131.0, ArCH; 130.7, ArCH; 130.2, ArCH; 129.4, ArC; 129.3, ArCH; 127.7, ArCH; 127.6, ArCH; 126.4, ArCH; 126.3, ArCH; 126.1, ArCH; 126.0, ArCH; 125.9, ArCH; 125.4, ArCH; 125.4, ArCH; 122.0, ArC; 121.9, ArC; 117.2, C3'''; 117.0, ArCH; 116.4, ArCH; 70.8, C1'''; 69.4, C6'; 53.5, H3'; 52.9, OCH$_3$; 41.8, C3''; 30.6, C2''; 25.8, C1''. Mass Spectrum (ES, +ve) m/z 698 (25%) [MNa$^+$], 413 (100%). HRMS calcd for C$_{39}$H$_{40}$N$_5$O$_6$ 674.2979, found 674.2979.

Benzyl(3R)-3-(6-(2-[2'-allyloxy-{1,1'}-(S)-binaphthalen-2-yloxy])-3-(3-aminopropyl)-1,4-diaza-2,5-dioxohexyl)benzoate hydrochloride (157)

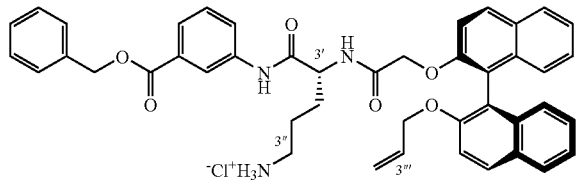

The title compound was synthesized using the general N-Boc deprotection procedure (Procedure A), from 148 (35 mg, 0.043 mmol) to yield 157 (30 mg, 0.040 mmol, 93%) as a highly hydroscopic cream solid. $^1$H NMR (CD$_3$OD, 500 M) δ 8.25 (s, 1H, ArH); 7.80 (m, 7H, ArH); 7.28 (m, 11H, ArH); 5.58 (m, 1H, H2'''); 5.27 (s, 2H, ArCH$_2$); 4.79 (m, 2H, H3'''); 4.46 (m, 5H, H6', H1''' and H3'); 2.68 (m, 2H, H3''); 1.59 (m, 2H, H1''); 1.22 (m, 2H, H2''). $^{13}$C NMR (CD$_3$OD, 125 MHz): δ. 171.2, 1-CO; 169.8, C5'; 167.2, C2'; 153.9, ArC; 152.8, ArC; 137.2, C2'''; 136.4, ArC; 133.7, ArC; 133.6, ArC; 133.1, ArCH; 131.0, ArCH; 129.2, ArC; 129.0, ArC; 128.4, ArCH; 128.2, ArCH; 128.0, ArCH; 127.0, ArCH; 126.8, ArCH; 126.6, ArCH; 126.4, ArCJH; 126.4, ArCH; 125.2, ArCH; 126.0, ArCH; 125.6, ArCH; 125.2, ArCH; 124.4, ArCH; 123.9, ArCH; 123.0, ArC; 122.8, ArC; 121.0, ArCH; 120.8, ArCH; 119.5, ArC; 117.2, ArC; 116.2, C3'''; 115.0, ArCH; 112.3, ArCH; 70.2, C1'''; 67.7, C6'; 51.2, C3'; 40.4, C3''; 32.8, C2''; 23.0, C1''. Mass Spectrum (ES, +ve) m/z 750 (35%) [MH$^+$], 360 (100%). HRMS calcd for C$_4$H$_2$N$_3$O$_6$ 708.3074, found 708.3062.

Benzyl(3R)-3-(6-(2-[2'-allyloxy-{1,1'}-(S)-binaphthalen-2-yloxy])-1,4-diaza-3-(3-guanidylpropyl)-2,5-dioxohexyl)benzoate hydrochloride (158)

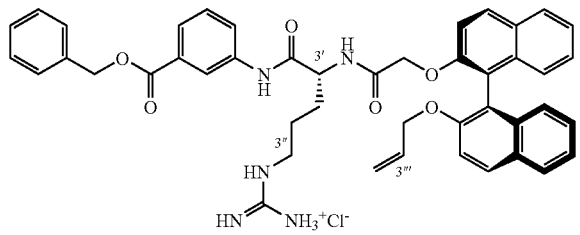

The title compound was synthesized using the general N-Boc deprotection procedure (Procedure A), from 152 (15 mg, 0.016 mmol) to yield 158 (6 mg, 0.0076 mmol, 48%) as a highly hydroscopic cream solid. $^1$H NMR (CD$_3$OD, 500 MHz): δ 8.22 (s, 1H, ArH); 7.79 (m, 7H, ArH); 7.25 (m, 13H, ArH); 5.59 (m, 1H, H2'''); 5.27 (s, 2H, ArCH$_2$); 4.80 (m, 2H, H3'''); 4.47 (m, 4H, H1''' and H6'); 4.28 (dd, J=5.0, 7.0 Hz, 1H, H3'); 2.92 (m, 2H, H3''); 1.54 (m, 2H, H1''); 1.08 (m, 2H, H2''). $^{13}$C NMR (CDCl$_3$, 125 MHz): δ 169.8, 1-CO; 168.9, C5'; 166.4, C2'; 153.4, ArC; 152.7, ArC; 137.5, C2'''; 136.2, ArC; 133.4, ArC; 133.3, ArC; 133.2, ArCH; 131.4, ArC; 131.2, ArC; 130.5, ArCH; 130.4, ArCH; 129.7, ArCH; 129.4, ArC; 128.8, ArCH; 128.5, ArCH; 128.7, ArCH; 128.4, ArCH; 126.9, ArCH; 126.8, ArCH; 126.2, ArCH; 125.9, ArCH; 125.6, ArCH; 124.8, ArCH; 124.6, ArCH; 124.5, ArCH; 121.7, ArCH; 121.2, ArC; 120.9, ArC; 119.6, ArC; 116.9, C3'''; 116.5, ArCH; 114.7, ArCH; 70.2, C1'''; 68.5, C6'; 66.9, ArCH$_2$; 52.8, C3'; 40.3, C3''; 29.8, C2''; 25.3, C1''. Mass Spectrum (ES, +ve) m/z 750 (100%) [M$^+$]. HRMS calcd for C$_{45}$H$_{44}$N$_5$O$_6$ 750.3292, found 750.3273.

Allyl(3R)-3-(6-(2-[2'-allyloxy-{1,1'}-(S)-binaphthalen-2-yloxy])-3-(3-aminopropyl)-1,4-diaza-2,5-dioxohexyl)benzoate hydrochloride (159)

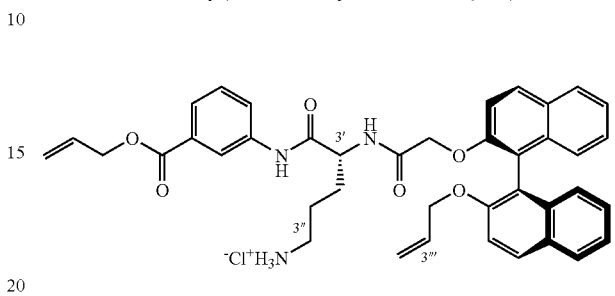

The title compound was synthesized using the general N-Boc deprotection procedure (Procedure A), from 149 (8 mg, 0.011 mmol) to yield 159 (7 mg, 0.010 mmol, 92%) as a highly hydroscopic cream solid. $^1$H NMR (CDCl$_3$, 300 MHz): δ 8.20 (s, 1H, ArH); 7.89 (m, 7H, ArH); 7.26 (m, 8H, ArH); 6.02 (m, 1H, CH-ester); 5.62 (m, 1H, H2'''); 5.34 (dd, J=1.5, 15.5 Hz, 1H, H3$_a$-ester); 5.20 (dd, J=1.5, 10.5 Hz, 1H, H3$_b$-ester); 4.83 (m, 2H, H13'''); 4.81 (m, 2H, H1-ester); 4.50 (m, 5H, H6', H3' and H1'''); 2.68 (m, 2H, H3''); 1.59 (m, 2H, H1''); 1.12 (m, 2H, H2''). $^{13}$C NMR (CDCl$_3$, 75 MHz): δ 169.5, 1-CO; 169.2, C5'; 166.0, C2'; 154.2, ArC; 152.6, ArC; 138.4, ArC; 133.9, C2-ester; 133.8, C2'''; 133.7, ArC; 132.5, ArC; 131.2, ArC; 130.9, ArCH; 130.4, ArCH; 129.9, ArC; 129.7, ArC; 129.6, ArCH; 128.9, ArCH; 128.4, ArCH; 128.2, ArCH; 126.9, ArCH; 126.0, ArCH; 125.8, ArCH; 125.4, ArCH; 125.3, ArCH; 124.6, ArCH; 124.5, ArCH; 124.0, ArCH; 120.8, ArC; 119.8, ArC; 118.5, C3-ester; 116.8, C3'''; 116.1, ArCH; 114.9, ArCH; 70.7, C1-ester; 68.7, C1'''; 66.4, C6'; 52.2, C3'; 39.3, C3''; 28.6, C2''; 26.2, C1''. Mass Spectrum (ES, +ve) m/z 698 (30%) [MH$^+$], 123 (100%). HRMS calcd for C$_{40}$H$_{40}$N$_3$O$_6$ 658.2917, found 658.2918.

Allyl(3R)-3-(6-(2-[2'-allyloxy-{1,1'}-(S)-binaphthalen-2-yloxy])-1,4-diaza-3-(3-guanidinopropyl)-2,5-dioxohexyl)benzoate hydrochloride (160)

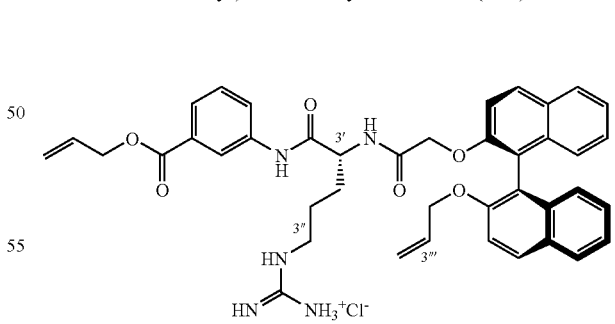

The title compound was synthesized using the general N-Boc deprotection procedure (Procedure A), from 153 (40 mg, 0.044 mmol) to yield 160 (11 mg, 0.015 mmol, 34%) as a highly hydroscopic cream solid. $^1$H NMR (CD$_3$OD, 500 MHz): δ 8.38 (s, 1H, ArH); 7.99 (t, J=7.5 Hz, 2H, ArH); 7.88 (t, J=7.5, 2H, ArH); 7.76 (t, J=8.0 Hz, 2H, ArH); 7.52 (d, J=9.0 Hz, 1H, ArH); 7.45 (d, J=9.0, 1H, ArH); 7.40 (t, J=8.0 Hz, 1H, ArH); 7.31 (dd, J=7.0, 14.5 Hz, 2H, ArH); 7.19 (t, J=7.0 Hz, 2H, ArH); 7.07 (m, 2H, ArH); 6.82 (d, J=8.0 Hz, 1H, NH); 6.04 (m, 1H, CH-ester); 5.70 (m, 1H, H2'''); 5.30 (m, 2H, H3-ester); 4.92 (m, 2H, H3'''); 4.53 (m, 6H, H6', H1-ester and H1'''); 4.43 (m, 1H, H3'); 3.04 (m, 2H, H3''); 1.68 (m, 2H, H1''); 1.20 (m, 2H, H2'). $^{13}$C NMR (CD$_3$OD, 125 MHz): δ. 171.0, 1-CO; 167.3, C2'; 158.4, CN$_3$; 155.3, ArC; 154.0, ArC; 139.9, ArC; 135.1, C2-ester; 135.0, C2'''; 134.8, ArC; 131.9, ArC; 130.9, ArCH; 130.9, ArC; 130.8, ArC; 130.1, ArCH; 129.2, ArCH; 129.1, ArCH; 127.6, ArCH; 127.5, ArCH; 126.3, ArCH; 126.2, ArC; 125.8, ArCH; 125.7, ArCH; 125.7, ArCH; 125.3, ArCH; 124.9, ArCH; 122.2, ArC; 122.1, ArCH; 121.8, ArCH; 120.4, ArC; 118.6, C3-ester; 117.1, C3'''; 117.0, ArCH; 116.1, ArCH; 72.4, C1-ester; 70.9, C1'''; 69.4, C6'; 66.7, ArCH$_2$; 53.5, C3'; 41.8, C3''; 30.4, C2''; 25.6, C1''. Mass Spectrum (ES, +ve) m/z 700 (100%) [M$^+$]. HRMS calcd for C$_{41}$H$_{42}$N$_5$O$_6$ 700.3135, found 700.3129.

(3R)-3-(6-(2-[2'-allyloxy-{1,1'}-(S)-binaphthalen-2-yloxy])-3-[(3-aminopropyl]-1,4-diaza-2,5-dioxo-hexyl)-N-benzyloxybenzamide hydrochloride (161)

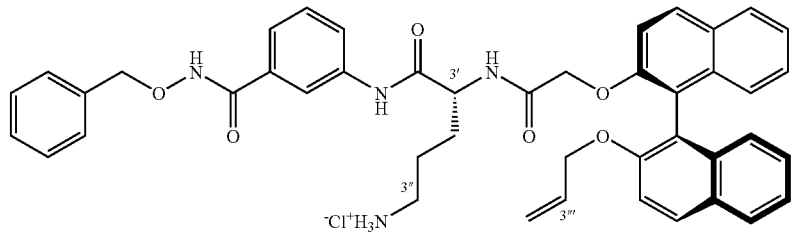

The title compound was synthesized using the general N-Boc deprotection procedure (Procedure A), from 150 (73 mg, 0.089 mmol) to yield 161 (67 mg, 0.088 mmol, 99%) as a hydroscopic white solid. $^1$H NMR (CD$_3$OD, 500 MHz): δδ 7.50 (m, 20H, ArH); 5.63 (m, 1H, H2'''); 4.90 (m, 2H, H3'''); 4.46 (m, 6H, H6', H1''' and ArCH$_2$); 3.90 (m, 1H, H3'); 3.23 (m, 2H, H3''); 1.62 (m, 2H, H1''); 1.15 (m, 2H, H2''). $^{13}$C NMR (CD$_3$OD, 75 MHz): δ 170.7, 1-CO; 170.5, C5'; 167.7, C2'; 155.4, ArC; 154.0, ArC; 139.9, C2'''; 137.3, ArC; 135.1, ArC; 134.9, ArC; 134.8, ArCH; 134.1, ArC; 131.6, ArC; 131.0, ArCH; 130.9, ArCH; 130.8, ArCH; 130.6, ArCH; 130.4, ArCH; 130.2, ArCH; 129.6, ArCH; 129.5, ArCH; 129.3, ArCH; 129.2, ArCH; 127.8, ArCH; 127.6, ArCH; 126.8, ArCH; 125.6, ArCH; 125.2, ArCH; 123.8, ArC; 121.9, ArC; 120.6, ArCH; 120.2, ArCH; 118.8, ArCH; 118.4, ArCH; 117.4, C3'''; 116.6, ArC; 79.2, C1'''; 71.0, ArCH$_2$; 69.5, C6'; 53.2, C3'; 40.0, C3''; 30.3, C2''; 24.5, C1''. Mass Spectrum (ES, +ve) m/z 723 (20%) [M$^+$], 360 (100%). HRMS calcd for C$_{44}$H$_{43}$N$_4$O$_6$ 723.3183, found 723.3137.

(3R)-3-(6-(2-[2'-allyloxy-{1,1'}-(S)-binaphthalen-2-yloxy])-1,4-diaza-3-[(3-guanidinopropyl]-2,5-(di-oxohexyl)-N-benzyloxybenzamide hydrochloride (162)

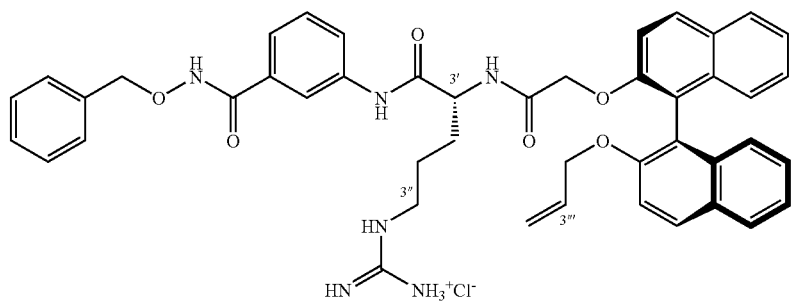

The title compound was synthesized using the general N-Boc deprotection procedure (Procedure A), from 154 (16 mg, 0.017 mmol) to yield 162 (7 mg, 0.0087 mmol, 51%) as a cream solid. Mp 142° C. $^1$H NMR (CD$_3$OD, 300 MHz): δ 7.95 (m, 4H, ArH); 7.33 (m, 16H, ArH); 5.60 (m, 1H, H2''');

4.96 (m, 2H, H3'''); 4.49 (m, 6H, H6', H1'''' and ArCH₂); 3.97 (m, 1H, H3'); 3.04 (m, 2H, H3''); 1.66 (m, 2H, H1''); 1.20 (m, 2H, H2''). ¹³C NMR (CD₃OD, 75 MHz): δ 172.6, 1-CO; 171.1, C5'; 167.7, C2'; 158.4, CN₃; 155.4, ArC; 154.0, ArC; 139.8, C2''''; 136.8, ArC; 135.1, ArC; 135.0, ArC; 134.9, ArCH; 134.0, ArC; 131.4, ArC; 130.9, ArCH; 130.9, ArCH; 130.8, ArCH; 130.4, ArCH; 130.2, ArCH; 130.0, ArCH; 129.7, ArCH; 129.5, ArCH; 129.3, ArCH; 129.2, ArCH; 127.6, ArCH; 127.5, ArCH; 126.4, ArCH; 125.9, ArCH; 124.6, ArC; 123.8, ArC; 121.9, ArC; 120.4, ArCH; 120.3, ArCH; 118.8, ArCH; 118.0, ArCH; 117.0, C3''''; 116.2, ArC; 79.2, C1''''; 71.0, ArCH₂; 69.4, C6'; 53.6, C3'; 41.8, C3''; 30.5, C2''; 25.7, C1''. Mass Spectrum (ES, +ve) m/z 765 (20%) [M⁺], 102 (100%). HRMS calcd for C₄₅H₄₅N₆O₆ 765.3401, found 765.3375.

(3R)-(3-(3-aminopropyl)-1,4-diaza-7-oxa-2,5-dioxohexyl-3-(6-(2-[2'-propyloxy-{1,1'}-(S)-binaphthalen-2-yloxy])-N-hydroxybenzamide hydrochloride (163)

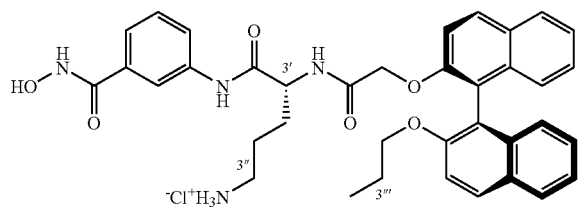

To a solution of 150 (28 mg, 0.034 mmol) in THF (3 mL) was added palladium on activated carbon (15 mg). The resulting mixture was flushed with hydrogen gas and allowed to stir for 16 h. The mixture was filtered through celite and evaporated to dryness. This intermediate product was then subjected to the general acid deprotection procedure (Procedure A) to yield the title compound (16 mg, 0.024 mmole, 70%) as a white solid. Mp 116° C. ¹H NMR (CD₃OD, 500 MHz): δ 7.89 (m, 5H, ArH); 7.30 (m, 9H, ArH); 4.56 (m, 2H, H6'); 4.08 (m, 1H, H3'); 3.88 (m, 2H, H1'''); 3.66 (m, 2H, H3''); 1.67 (m, 2H, H1''); 1.35 (m, 4H, H2'' and H2'''); 0.76 (m, 3H, H13'''). ¹³C NMR (CD₃OD, 125 MHz): δ 170.9, 1-CO; 170.7, C5'; 166.3, C2'; 155.9, ArC; 154.1, ArC; 139.7, ArC; 135.3, ArCH; 135.1, ArCH; 131.0, ArC; 130.9, ArCH; 130.7, ArCH; 130.5, ArCH; 130.4, ArC; 130.2, ArC; 130.1, ArCH; 129.5, ArCH; 129.3, ArCH; 129.1, ArCH; 127.5, ArCH; 126.9, ArCH; 126.4, ArCH; 125.9, ArCH; 125.6, ArCH; 125.3, ArC; 124.7, ArC; 124.5, ArC; 117.0, ArCH; 116.9, ArCH; 116.2, ArC; 72.1, C6'; 69.5, C1''''; 53.1, C3'; 40.0, C3''; 30.4, C2''; 24.8, C2''''; 23.7, C1''; 10.5, C3''''. Mass Spectrum (ES, +ve) m/z 636 (50%) [M⁺], 623 (100%). HRMS calcd for C₃₇H₃₉N₄O₆ 635.2870, found 635.2863.

(3R)-(1,4-diaza-3-(3-guanidinopropyl)-7-oxa-2,5-dioxohexyl-3-(6-(2-[2'-propyloxy-{1,1'}-(S)-binaphthalen-2-yloxy])-N-hydroxybenzamide hydrochloride (164)

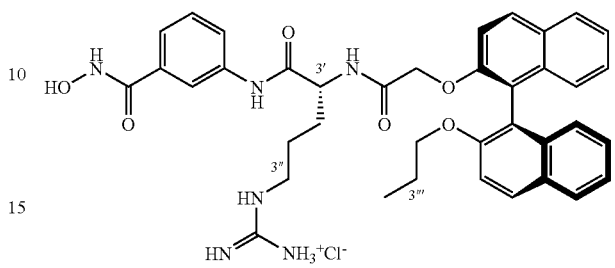

To a solution of 154 (39 mg, 0.040 mmol) in THF (3 mL) was added palladium on activated carbon. The resulting mixture was flushed with hydrogen gas and allowed to stir for 16 h. The mixture was filtered through celite and evaporated to dryness. This intermediate product was then subjected to the general acid deprotection procedure (Procedure A) to yield the title compound (24 mg, 0.034 mmole, 84%) as a white solid. Mp 158-160° C. ¹H NMR (CD₃OD, 300 MHz): δ 9.96 (bs, 1H, OH); 7.95 (m, 5H, ArH); 7.24 (m, 9H, ArH); 4.45 (AB_q, J=14.1 Hz, 2H, H6'); 4.09 (m, 1H, H3'); 3.92 (m, 2H, H1'''); 3.03 (m, 2H, H3''); 1.62 (m, 2H, H1''); 1.40 (m, 2H, H2'''); 1.17 (m, 2H, H2''); 0.51 (t, J=7.2 Hz, 3H, H3'''). ¹³C NMR (CDCl₃, 75 MHz): δ 170.9, 1-CO; 170.8, C5'; 170.8, C2'; 158.5, CN₃; 155.9, ArC; 154.0, ArC; 139.9, ArC; 135.2, ArCH; 135.1, ArCH; 131.5, ArC; 131.0, ArC; 130.9, ArCH; 130.7, ArCH; 130.2, ArC; 130.1, ArC; 129.3, ArCH; 129.1, ArCH; 127.6, ArCH; 127.5, ArCH; 126.4, ArCH; 125.9, ArCH; 125.3, ArCH; 124.7, ArCH; 124.4, ArCH; 124.2, ArCH; 123.6, ArC; 122.0, ArC; 120.3, ArC; 116.9, ArCH; 116.2, ArCH; 72.1, C6'; 69.4, C1''''; 52.5, C3'; 41.9, C3''; 30.5, C2''; 25.7, C2''''; 23.7, C1''; 10.5, C3''''. Mass Spectrum (ES, +ve) m/z 677 (100%) [M⁺]. HRMS calcd for C₃₈H₄₁N₆O₆ 677.3088, found 677.3130.

Methyl(2S)-3-(4-hydroxyphenyl)-2-methoxycarboxamidopropanoate (170)

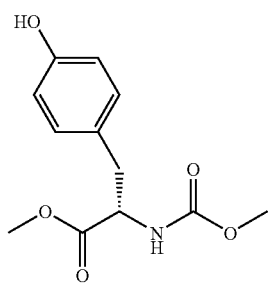

To a solution of methyl(2S)-2-amino-3-(4-hydroxyphenyl) propanoate hydrochloride (189 mg, 0.82 mmol) and sodium bicarbonate (210 mg, 2.5 mmol) in THF (3 mL) and water (3 mL) at 0° C. was added methyl chloroformate (86 mg, 0.9 mmol) and the resulting mixture was allowed to stir for 3 h. The reaction was quenched with water (30 mL) and extracted with EtOAc (30 mL) and DCM (2×30 mL). The combined organic fractions were dried and evaporated to dryness to yield the title compound (195 mg, 0.77 mmol, 94%) as a clear oil, which had spectral data in agreement with that reported.[127] $^1$H NMR (CDCl$_3$, 300 MHz): δ 6.95 (d, J=8.7 Hz, 2H, ArH2' and ArH6'); 6.73 (d, J=8.4 Hz, 2H, ArH3' and ArH5'); 5.31 (d, J=8.4 Hz, 1H, NH); 4.59 (m, 1H, H2); 3.71 (s, 3H, CH$_3$, NCOOCH$_3$); 3.65 (s, 3H, OCH$_3$); 3.01 (m, 2H, C3). Mass Spectrum (ES, +ve) m/z 254 (100%) [MH$^+$]. HRMS calcd for C$_{12}$H$_{16}$NO$_5$ 254.1029, found 254.1036.

Methyl(2S)-3-(4-allyloxyphenyl)-2-methoxycarboxamidopropanoate (171)

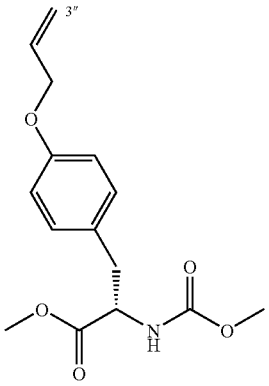

To a solution of 170 (195 mg, 0.77 mmol) in DMF (6 mL) was added K$_2$CO$_3$ (213 mg, 1.54 mmol) and the resulting mixture was allowed to stir at RT under N$_2$ for 20 min before the addition of allyl bromide (0.14 mL, 1.54 mmol). After 16 h the reaction was quenched with water (30 mL) and extracted with EtOAc (3×30 mL). The combined organic fractions were washed with water (5×30 mL) and brine (30 mL). The remaining organic fractions were dried and evaporated to dryness to yield the title compound (220 mg, 0.75 mmol, 98%) as a white solid. Mp 145-146° C. $^1$H NMR (CDCl$_3$, 300 MHz): δ 7.02 (d, J=8.7 Hz, ArH2' and ArH6'); 6.83 (d, J=8.4 Hz, ArH3' and ArH5'); 6.04 (m, 1H, H2"); 5.40 (dd, J=1.5, 17.1 Hz, 1H, H3$_a$"); 5.27 (dd, J=1.2, 10.5 Hz, 1H, H3$_b$"); 5.18 (d, J=7.5 Hz, NH); 4.60 (m, 1H, H2); 4.50 (d, J=5.1 Hz, 2H, H1"); 3.71 (s, 3H, NCOOCH$_3$); 3.66 (s, 3H, OCH$_3$); 3.03 (m, 2H, C3). Mass Spectrum (ES, +ve) m/z [MH$^+$]. HRMS calcd for C$_{15}$H$_{20}$NO$_5$ 294.1342, found 294.1346.

(2S)-3-(4-Allyloxyphenyl)-2-methoxycarboxamidopropanoic acid (172)

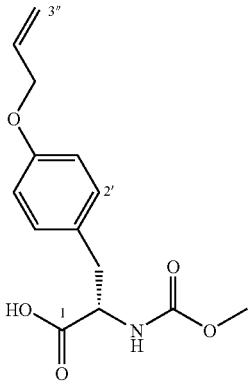

To a solution of 171 (220 mg, 0.75 mmol) in THF/water (3:1, 10 mL) was added lithium hydroxide (63 mg, 1.50 mmol) and the resulting suspension was allowed to stir for 16 h. The reaction mixture was diluted with water (30 mL) and the THF was removed by evaporation in vacuo. The aqueous layer was washed with DCM (30 mL) to remove unreacted starting material. The pH of the aqueous phase was adjusted to pH 3 with 10% HCl and the resulting precipitate was extracted with DCM (3×40 mL). The combined organic fractions were dried, and evaporated to dryness to yield the title compound (186 mg, 0.67 mmol, 89%) as a white solid. Mp 170-172° C. $^1$H NMR (CDCl$_3$, 300 MHz): δ 9.39 (bs, 1H, COOH); 7.07 (d, J=8.7 Hz, ArH2' and ArH6'); 6.84 (d, J=8.4 Hz, ArH3' and ArH5'); 6.03 (m, 1H, H2"); 5.39 (dd, J=1.2, 17.1 Hz, 1H, H3$_a$"); 5.27 (dd, J=1.2, 10.5 Hz, 1H, H3$_b$"); 4.62 (dd, J=6.0, 13.2 Hz 1H, H2); 4.50 (d, J=5.4 Hz, C1"); 3.65 (s, 3H, NCOOCH$_3$); 3.08 (m, 2H, H3). Mass Spectrum (CI, +ve) m/z 280 (50%) [MH$^+$], 220 (100%) [MH$^+$ less methoxycarbonate] HRMS calcd for C$_{14}$H$_{17}$NO$_5$ 279.1107, found 279.1114.

Methyl(2S)-2-benzyloxycarboxamido-4-pentenoate (173)

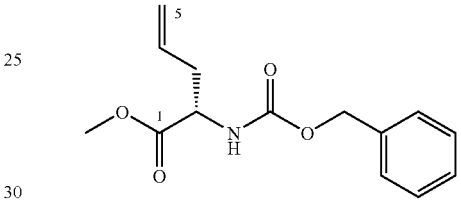

To a solution of methyl(2S)-2-amino-4-propenoate hydrochloride (422 mg, 2.56 mmol) and NaHCO$_3$ (645 mg, 7.68 mmol) in THF/water (3 mL/3 mL, 1:1) was added benzyl chloroformate (482 mg, 2.82 mmol) and the mixture was allowed to stir for 16 h. The reaction was quenched with 3% HCl (20 mL) and extracted with DCM (3×20 mL), dried and concentrated to give the title compound (676 mg, 2.56 mmol, 100%) as a clear oil, which had spectral data in agreement with that reported.[128] [α]$_D^{20}$ +9.1 (c. 0.15 in CHCl$_3$) (lit. [α]$^{20}$ +6.4 (c. 1.05 in MeOH))[128] $^1$H NMR (CDCl$_3$, 300 MHz): δ 7.33 (m, 5H, ArH); 5.69 (m, 1H, H4); 5.56 (d, J=7.8 Hz, 1H, NH); 5.12 (m, 4H, ArCH$_2$, C5); 4.47 (m, 1H, H2); 3.72 (s, 3H, OCH$_3$); 2.54 (m, 2H, H3). Mass Spectrum (CI, +ve) m/z 264 (20%) [MH$^+$], 113 (100%). HRMS calcd for C$_{14}$H$_{18}$NO$_4$ 264.12358, found 264.12421.

Methyl(2S,4E/Z)-2-benzyloxycarboxamido-6-phenyl-4-hexenoate (174)

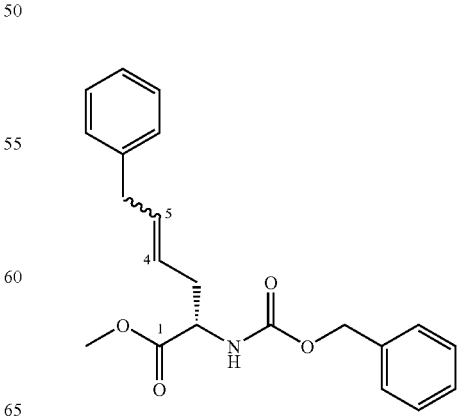

To a solution of 173 (181 mg, 0.69 mmol) in DCM (13.8 mL) was added allylbenzene (163 mg, 1.38 mmol) and Grubbs' first generation catalyst (28 mg, 0.0345 mmol). The mixture was heated at reflux for 16 h. The solvent was removed and the crude product purified by flash column chromatography (4:1, hexane/EtOAc) to yield the title compound as a 1:1 ratio mixture of E and Z isomers (103 mg, 0.29 mmol, 42%) as a brown oil. $^1$H NMR (CDCl$_3$, 300 MHz): δ 7.26 (m, 10H, ArH); 5.72 (m, 1H, H4); 5.42 (m, 2H, NH and H5); 5.13 (s, 2H, ArCH$_2$O); 5.50 (m, 1H, H2); 3.74/3.71 (s, 3H, OCH$_3$ [E & Z]); 3.39/3.34 (d, J=357.5, 6.6 Hz, 2H, H6); 2.54 (m, 2H, H3). Mass Spectrum (CI, +ve) m/z 354 (20%) [MH$^+$], 263 (100%). HRMS calcd for C$_{21}$H$_{24}$NO$_4$ 354.17053, found 354.17077.

Methyl(2S)-2-amino-6-phenylhexanoate (175)

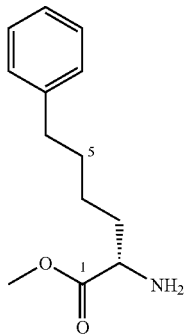

To a solution of 174 (118 mg, 0.33 mmol) in THF (30 mL) was added palladium on activated carbon (62 mg, 0.029 mmol). The flask was evacuated and twice filled with H$_2$ gas before stirring at RT for 16 h. The reaction mixture was filtered through celite and evaporated to dryness to yield the title compound (73 mg, 0.33 mmol, 100%) as a light brown oil. $^1$H NMR (CDCl$_3$, 300 MHz): δ 7.21 (m, 5H, ArH); 3.71 (m, 6H, OCH$_3$, NH$_2$ and H2); 2.60 (m, 2H, H6); 1.62 (m, 6H, H3, H4 and H5). Mass Spectrum (CI, +ve) m/z 222 (30%) [MH$^+$], 113 (100%). HRMS calcd for C$_{13}$H$_{20}$NO$_2$ 222.14940, found 222.14934.

Methyl(2S,5S)-3-aza-2-benzyl-9-(tert-butoxycarboxamido)-5-(9H-9-fluorenylmethyloxycarboxamido)-4-oxononanoate (176)

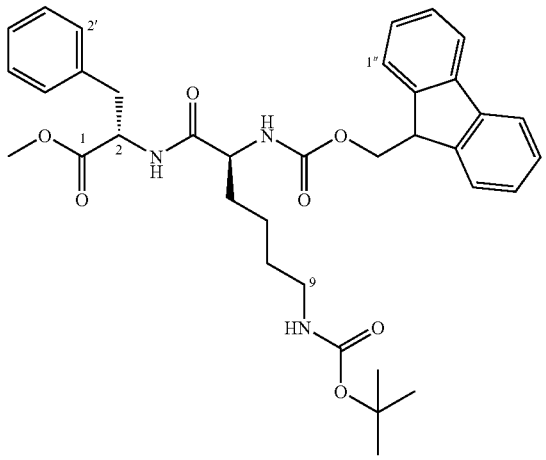

The title compound was synthesized using the general coupling procedure (Procedure B) from (1S)-2-phenyl-1-methoxycarbonylethylammonium chloride (300 mg, 1.39 mmol) and (2S)-6-tert-butoxycarboxamido-2-(9H-9-fluorenylmethyloxy)carboxamido hexanoic acid (769 mg, 1.64 mmol) to afford 176 (848 mg, 1.35 mmol, 97%) as a white solid. Mp 87-90° C. $^1$H NMR (CDCl$_3$, 300 MHz): δ 7.75 (d, J=7.2 Hz, 2H, ArH1" and ArH8"); 7.58 (d, J=7.2 Hz, 2H, ArH4" and ArH5"); 7.39 (t, J=7.2 Hz, 2H, ArH3" and ArH6"); 7.30 (t, J=6.9 Hz, 2H, ArH2" and ArH7"); 7.21 (m, 2H, ArH3' and ArH5'); 7.07 (m, 1H, ArH4'); 6.61 (d, J=7.2 Hz, 1H, NH); 5.56 (d, J=8.4 Hz, 1H, NH); 4.85 (dd, J=6.3, 14.1 Hz, 1H, H2); 5.69 (bs, 1H, NH); 4.36 (m, 2H, OCH$_2$—H9"); 4.19 (m, 2H, H5 and H9"); 3.69 (s, 3H, OCH$_3$); 3.09 (m, 2H, H2-CH$_2$); 3.04 (m, 2H, H9); 1.77 (m, 2H, H7); 1.63 (m, 2H, H6); 1.42 (s, 9H, C(CH$_3$)$_3$); 1.33 (m, 2H, H8). Mass Spectrum (ES, +ve) m/z 630 (10%) [MH$^+$], 104 (100%). HRMS calcd for C$_{36}$H$_{44}$N$_3$O$_7$ 630.3179, found 630.3189.

Methyl(2S,5S)-3-aza-9-(tert-butoxycarboxamido)-5-(9H-9-fluorenylmethyloxycarboxamido)-4-oxo-3-(4'-phenylbutyl)nonanoate (177)

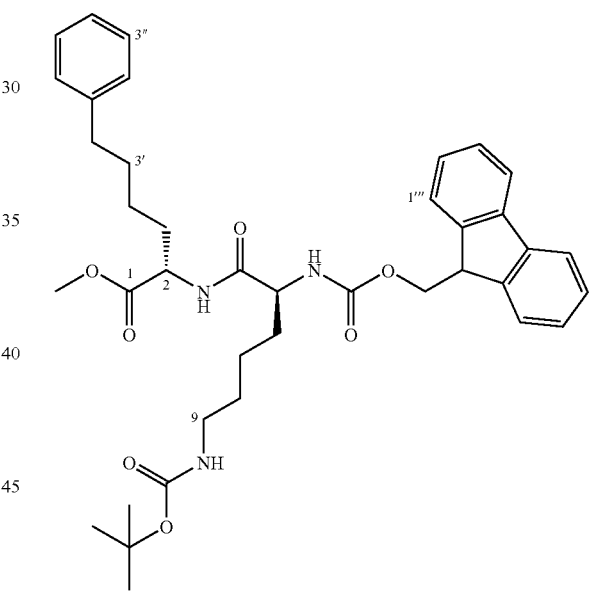

The title compound was synthesized using the general coupling procedure (Procedure B) from 175 (63 mg, 0.29 mmol) and (2S)-6-tert-butoxycarboxamido-2-(9H-9-fluorenylmethyloxy)carboxamido hexanoic acid (113 mg, 0.24 mmol) to afford 177 (138 mg, 0.21 mmol, 86%) as a clear oil. $^1$H NMR (CDCl$_3$, 300 MHz): δ 7.73 (d, J=7.2 Hz, 2H, ArH1'" and ArH8'"); 7.57 (d, J=5.4 Hz, 2H, ArH4'" and ArH5'"); 7.37 (t, J=7.8 Hz, 2H, ArH3'" and ArH6'"); 7.19 (m, 7H, ArH2'", ArH7'", ArH1", ArH2", ArH3", ArH4", ArH5" and ArH6); 6.80 (d, J=7.2 Hz, 1H, NH); 5.71 (d, J=7.8 Hz, 1H, NH); 4.78 (bs, 1H, NH); 4.55 (m, 1H, H2); 4.37 (d, J=6.9 Hz, 2H, OCH$_2$-H9'"); 4.20 (m, 2H, H5 and H19'"); 3.69 (s, 3H, OCH$_3$); 3.07 (m, 2H, H9); 2.53 (t, J=7.8 Hz, 2H, H4'); 1.84 (m, 2H, H7); 1.62 (m, 2H, H6); 1.42 (s, 9H, C(CH$_2$)$_3$); 1.36 (m, 2H, H8); 1.26 (m, 4H, H2' and H3'). Mass Spectrum (ES, +ve) m/z 673 (100%) [MH$^+$]. HRMS calcd for C$_{39}$H$_{50}$N$_3$O$_7$ 672.3649, found 672.3624.

Methyl(2S,5S)-5-amino-3-aza-2-benzyl-9-(tert-butoxycarboxamido)-4-oxononanoate (178)

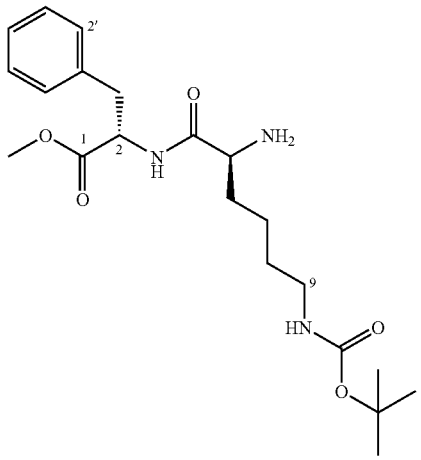

The title compound was synthesized using the general N-Fmoc deprotecting procedure (Procedure C) from 176 (836 mg, 1.33 mmol) to afford 178 (142 mg, 0.35 mmol, 26%) as a clear oil. $^1$H NMR (CDCl$_3$, 300 MHz): δ 7.66 (d, J=7.8 Hz, 1H, NH); 7.22 (m, 3H, ArH3', ArH4' and ArH5'); 7.10 (m, 2H, ArH2' and ArH6'); 4.83 (m, 1H, H2); 4.60 (bs, 1H, NH); 3.69 (s, 3H, OCH$_3$); 3.29 (dd, J=4.5, 7.5 Hz, 1H, H5); 3.08 (m, 2H, H2-CH$_2$); 3.06 (m, 2H, H9); 1.67 (m, 2H, H7); 1.46 (m, 2H, H6); 1.41 (s, 9H, C(CH$_3$)$_3$); 1.24 (m, 2H, H8). Mass Spectrum (ES, +ve) m/z 409 (100%) [MH$^+$].

Methyl(2S,5S)-2-amino-3-aza-9-(tert-butoxycarboxamido)-4-oxo-2-(4-phenylbutyl)nonanoate (179)

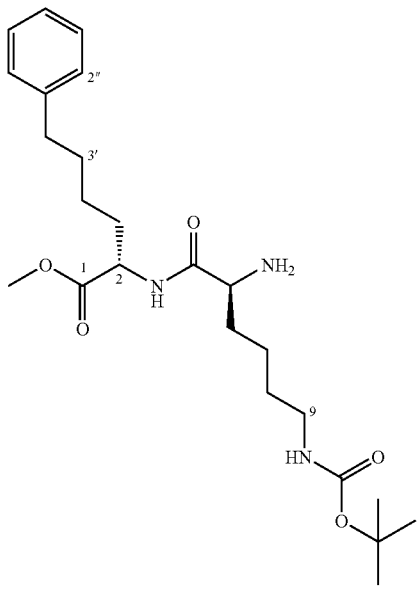

The title compound was synthesized using the general N-Fmoc deprotecting procedure (Procedure C) from 177 (138 mg, 0.21 mmol) to afford 179 (78 mg, 0.17 mmol, 81%) as a light brown oil. $^1$H NMR (CDCl$_3$, 300 MHz): δ 7.67 (d, J=8.1 Hz, 1H, NH); 7.22 (m, 5H, ArH); 4.56 (m, 2H, H2 and H5); 3.72 (s, 3H, OCH$_3$); 3.11 (m, 2H, H9); 2.60 (t, J=7.5 Hz, 2H, H4'); 1.83 (m, 2H, H7); 1.66 (m, 6H, H1', H2' and H3'); 1.44 (s, 9H, C(CH$_2$)$_3$); 1.29 (m, 2H, H8); 0.86 (m, 2H, H6). Mass Spectrum (ES, +ve) m/z 450 (100%) [MH$^+$]. HRMS calcd for C$_{24}$H$_{40}$N$_3$O$_5$ 450.2968, found 450.2950.

Methyl(2S,5S,8S)-8-(4-allyloxybenzyl)-3,6,9-triaza-2-benzyl-5-(4-[tert-butoxycarboxamido]butyl)-4,7,10-trioxoundecanoate (180)

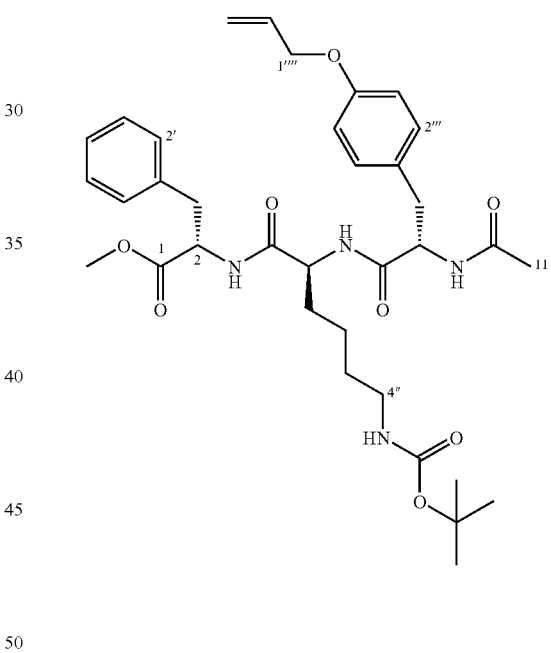

The title compound was synthesized using the general peptide coupling procedure (Procedure B) from 16 (76 mg, 0.29 mmol) and 178 (142 mg, 0.35 mmol) to afford 180 (135 mg, 0.21 mmol, 72%) as an off-white solid. Mp 122-126° C. $^1$H NMR (CDCl$_3$, 300 MHz): δ 7.24 (m, 3H, ArH3', ArH4' and ArH5'); 7.12 (m, 2H, ArH2' and ArH6'); 7.05 (d, J=8.7 Hz, 2H, ArH2''' and ArH6'''); 6.79 (d, J=8.4 Hz, 1H, ArH3''' and ArH5'''); 6.50 (d, J=6.9 Hz, 1H, NH); 6.01 (m, 1H, H2''''); 5.37 (dd, J=1.5, 17.1 Hz, 1H, H3$_a$''''); 5.25, J=1.2, 10.5 Hz, 1H, H3$_b$''''); 4.87 (bs, 1H, NH); 4.79 (m, 1H, H2); 4.68 (m, 1H, H5); 4.45 (d, J=5.1 Hz, 2H, H1''''); 4.43 (m, 1H, H8); 3.69 (s, 3H, OCH$_3$); 3.06 (m, 4H, 2-CH$_2$ and 8-CH$_2$); 2.93 (m, 2H, H4''); 1.95 (s, 3H, H11); 1.75 (m, 2H, H2''); 1.55 (m, 2H, H1''); 1.32 (s, 9H, C(CH$_3$)$_3$); 1.26 (m, 2H, H3''). Mass Spectrum (ES, +ve) m/z 653 (10%) [MH$^+$]; 104 (100%). HRMS calcd for C$_{35}$H$_{48}$N$_4$O$_8$Na 675.3370, found 675.3358.

Methyl(2S,5S,8S)-2-allyl-8-(4-allyloxybenzyl)-3,6,9-triaza-5-(4-[tert-butoxycarboxamido]butyl)-11-oxa-4,7,10-trioxododecanoate (181)

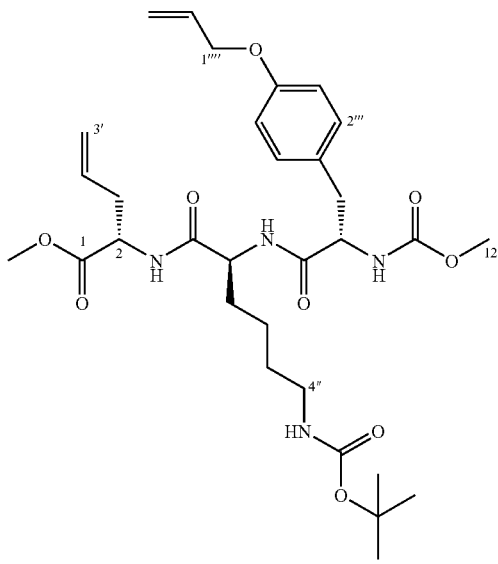

The title compound was synthesized using the general peptide coupling procedure (Procedure B) from 24 (340 mg, 0.95 mmol) and 172 (148 mg, 0.53 mmol) to afford 181 (264 mg, 0.43 mmol, 81%) as an off-white solid. Mp 90-91° C. $^1$H NMR (CDCl$_3$, 300 MHz): δ 7.08 (d, J=9.0 Hz, 2H, ArH2''' and ArH6'''); 7.00 (d, J=7.5 Hz, 1H, NH); 6.81 (d, J=8.7 Hz, 2H, ArH3''' and ArH5'''); 6.03 (m, 1H, H2''''); 5.63 (m, 1H, H2'); 5.39 (dd, J=1.5, 17.1 Hz, 1H, H3$_a$''''); 5.27 (dd, J=1.5, 10.8 Hz, 1H, H3$_b$''''); 5.12 (m, 2H, H3'); 4.93 (bs, 1H, NH); 4.61 (m, 1H, H2); 4.51 (m, 2H, H5 and H8); 4.49 (d, J=5.1 Hz, 2H, H1''''); 3.74 (s, 3H, NCOOCH$_3$); 3.62 (s, 3H, OCH$_3$); 3.00 (m, 4H, H4'' and ArCH$_2$); 2.51 (m, 2H, H1'); 1.80 (m, 2H, H2''); 1.60 (m, 2H, H1''); 1.43 (s, 9H, C(CH$_3$)$_3$); 1.28 (m, 2H, H3''). Mass Spectrum (ES, +ve) 7m/z 619 (60%) [M$^+$]; 641 (100%) [M$^+$+Na]. HRMS calcd for C$_{31}$H$_{46}$N$_4$O$_9$Na 641.3162, found 641.3184.

Methyl(2S,5S,8S)-8-(4-allyloxybenzyl)-3,6,9-triaza-5-(4-[tert-butoxycarboxamido]butyl)-4,7,10-trioxo-2-(4-phenylbutyl)undecanoate (182)

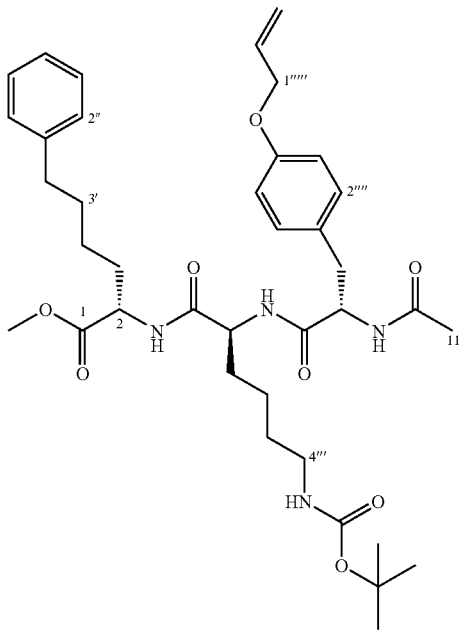

The title compound was synthesized using the general peptide coupling procedure (Procedure B) from 16 (37 mg, 0.14 mmol) and 179 (78 mg, 0.17 mmol) to afford 182 (72 mg, 0.10 mmol, 74%) as an off-white solid. Mp 112-117° C. $^1$H NMR (CDCl$_3$, 300 MHz): δ 7.20 (m, 5H, ArH); 7.09 (d, J=8.4 Hz, 2H, ArH2'''' and ArH6''''); 6.82 (d, J=8.7 Hz, 2H, ArH3'''' and ArH5''''); 6.45 (m, 2H, NH); 6.09 (m, 1H, NH); 6.02 (m, 1H, H2'''''); 5.39 (dd, J=1.5, 17.1 Hz, 1H, H3$_a$'''''); 5.27 (dd, J 1.5, 10.5 Hz, 1H, H3$_b$'''''); 4.79 (bs, 1H, NH); 4.60 (m, 1H, H2); 4.48 (m, 3H, H5 and H1'''''); 4.35 (m, 1H, H8); 3.72 (s, 3H, OCH$_3$); 3.02 (m, 4H, H4''', 8-CH$_2$); 2.60 (t, J=8.1 Hz, 2H, H4'); 1.97 (s, 3H, H11); 1.84 (m, 2H, H2'''); 1.66 (m, 6H, H1', H2' and H3'); 1.43 (s, 9H, C(CH$_3$)$_3$); 1.32 (m, 4H, H1''' and H3)'. Mass Spectrum (ES, +ve) m/z 695 (100%) [MH$^+$]. HRMS calcd for C$_{38}$H$_{55}$N$_4$O$_8$ 695.4020, found 695.4008.

Methyl(2S,5S,8S)-8-(4-allyloxybenzyl)-3,6,9-triaza-2-benzyl-5-(4[{di-tert-butoxycarbonyl}guanidino]butyl)-4,7,10-trioxoundecanoate (183)

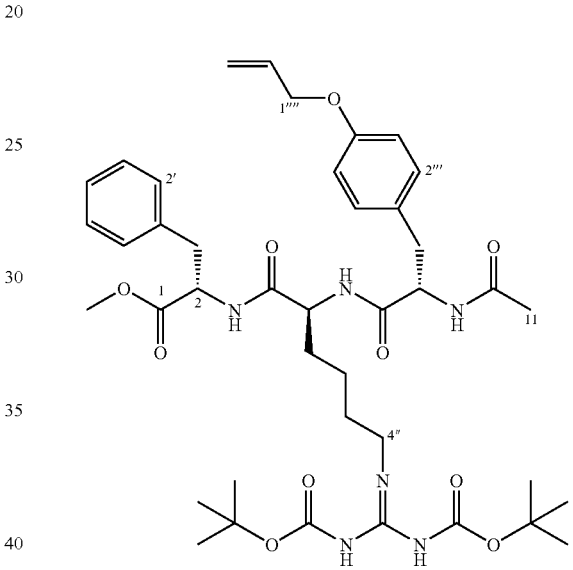

To a solution of 180 (125 mg, 1.19 mmol) in DCM (2 mL) was added TFA (2 mL) and the resulting mixture was allowed to stir for 3 h. The solvent was removed by evaporation and the oily intermediate was precipitated by the addition of diethyl ether (5 mL) which was decanted and the solid product was dried in vacuo. To the salt was added N1-tert-butoxycarboxamido(trifluoromethylsulfonylimino)methyl propanamide (82 mg, 0.21 mmol), triethylamine (0.1 mL) and DCM (3 mL). The resulting solution was allowed to stir for 16 h under N$_2$. The solvent was removed by evaporation in vacuo, and the crude product was purified by flash chromatography (20:1, DCM/MeOH) to yield the title compound (177 mg, 0.21 mmol, 100%) as an off white solid. Mp 228° C. $^1$H NMR (CDCl$_3$, 300 MHz): δ 7.26 (m, 3H, ArH3', ArH4' and ArH5'); 7.08 (m, 4H, ArH2', ArH6', ArH2''' and ArH6'''); 6.81 (d, J=8.7 Hz, 2H, ArH3''' and ArH5'''); 6.46 (t, J=8.4 Hz, 2H, NH); 6.21 (d, J=7.8 Hz, 1H, NH); 6.00 (m, 1H, H2''''); 5.37 (dd, J=1.2, 16.8 Hz, 1H, H3$_a$''''); 5.26 (dd, J=1.5, 10.8 Hz, 1H, H3$_b$''''); 4.78 (m, 1H, H2); 4.61 (m, 1H, H5); 4.47 (d, J=5.4 Hz, 2H, H1''''); 4.32 (m, 1H, H8); 3.71 (s, 3H, OCH$_3$); 3.31 (m, 2H, 2-CH$_2$); 3.08 (m, 2H, 8-CH$_2$); 2.97 (d, J=6.9 Hz, 2H, H4''); 1.98 (s, 3H, H11); 1.76 (m, 2H, H2'''); 1.52 (m, 2H, H1''); 1.48 (s, 18H, C(CH$_3$)$_3$); 1.25 (m, 2H, H3''). Mass Spectrum (ES, +ve) m/z 795 (20%) [MH$^+$]; 104 (100%). HRMS calcd for C$_{41}$H$_{59}$N$_6$O$_{10}$ 795.4293, found 795.4310.

Methyl(2S,5S,8S)-8-(4-allyloxybenzyl)-3,6,9-triaza-2-benzyl-5-(4-guanidinobutyl)-4,7,10-trioxoundecanoate hydrochloride (165)

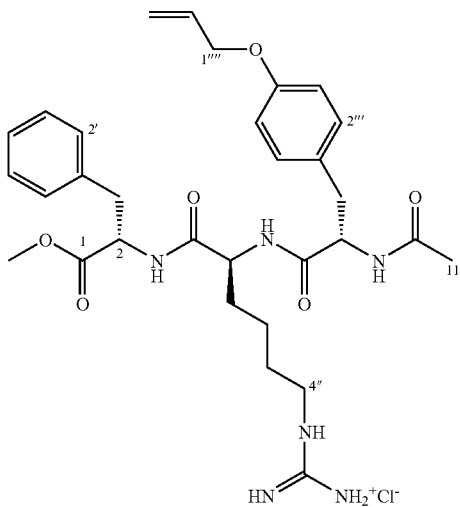

The title compound was synthesized using the general N-Boc deprotection procedure (Procedure A) from 183 (157 mg, 0.20 mmol) to yield 165 (93 mg, 0.15 mmol, 74%) as a white solid. Mp 175-179° C. $^1$H NMR (CD$_3$OD, 300 MHz): δ 7.20 (m, 5H, ArH'); 7.11 (d, J=8.1 Hz, 2H, ArH2''' and ArH6'''); 6.78 (d, J=8.4 Hz, 2H, ArH3''' and ArH5'''); 6.01 (m, 1H, H2''''); 5.35 (dd, J=1.2, 16.8 Hz, 1H, H3$_a$''''); 5.20, J=1.5, 10.8 Hz, 1H, H3$_b$''''); 4.60 (dd, J=5.7, 8.1 Hz, 1H, H2); 4.45 (m, 1H, H5); 4.47 (d, J=5.4 Hz, 2H, H1''''); 4.34 (dd, J=4.8, 8.4 Hz, 1H, H8); 3.65 (s, 3H, OCH$_3$); 3.05 (m, 4H, 2-CH$_2$ and 8-CH$_2$); 2.77 (m, 2H, H4''); 1.90 (s, 3H, H111); 1.73 (m, 2H, H2''); 1.56 (m, 2H, H1''); 1.37 (m, 2H, H3''). $^{13}$C NMR (CD$_3$OD, 75 MHz): δ 173.6, C7; 173.4, C4; 173.3, C2; 173.0, C10; 158.7, CN$_3$; 158.4, ArC4'''; 137.8, ArCH6'; 134.8, C2''''; 131.0, ArCH2''' and ArC6'''; 130.3, ArC1'''; 130.1, ArCH4'; 129.4, ArC1'; 127.8, ArCH3' and ArCH5'; 117.2, C3''''; 115.6, ArCH3''' and ArCH5'''; 69.7 C1''''; 56.6, C2; 55.2, C5; 54.0, OCH$_3$; 52.7, C8; 42.2, C4''; 38.3, 2-CH$_2$; 37.8, 8-CH$_2$; 32.6, C1''; 28.2, C3''; 23.6, C11; 22.5, C2''. Mass Spectrum (ES, +ve) m/z 596 (100%) [MH$^+$]. HRMS calcd for C$_{31}$H$_{43}$N$_6$O$_6$ 595.3244, found 595.3225.

Methyl(2S,5S,8S)-2-allyl-8-(4-allyloxybenzyl)-3,6,9-triaza-5-(4-{[di-tert-butoxycarbonyl]guanidino}butyl)-11-oxa-4,7,10-trioxododecanoate (184)

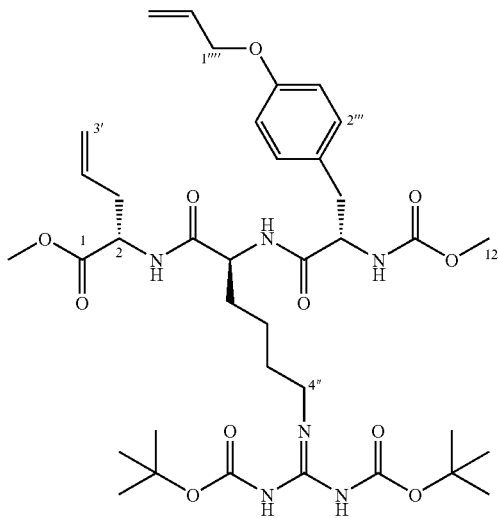

To a solution of 181 (250 mg, 0.40 mmol) in DCM (3 mL) was added TFA (3 mL) and the resulting mixture was allowed to stir for 3 h. The solvent was removed by evaporation in vacuo, and the oily intermediate was precipitated by the addition of diethyl ether (5 mL) which was decanted and the solid product was dried in vacuo. To the remaining salt was added N1-tert-butoxycarboxamido(trifluoromethylsulfonylimino)methyl propanamide (172 mg, 0.44 mmol), triethylamine (0.5 mL) and DCM (3 mL). The resulting solution was allowed to stir for 16 h under N$_2$. The solvent was removed and the crude product was purified by flash chromatography (20:1, DCM/MeOH) to yield the title compound (309 mg, 0.40 mmol, 100%) as an off white oil. $^1$H NMR (CDCl$_3$, 300 MHz): δ 8.33 (bs, 1H, NH); 7.08 (d, J=8.7 Hz, 2H, ArH2''' and ArH6'''); 6.83 (d, J=8.7 Hz, 2H, ArH3''' and ArH5'''); 6.69 (t, J=6 Hz, 2H, NH); 6.03 (m, 1H, H2''''); 5.67 (m, 1H, H2'); 5.40 (dd, J=1.2, 17.1 Hz, 1H, H3$_a$''''); 5.33 (d, J=7.8 Hz, 1H, NH); 5.27 (m, J=1.5, 10.5 Hz, 1H, H3$_b$''''); 5.12 (m, 2H, H3'); 4.57 (m, 1H, H2); 4.50 (d, J=5.1 Hz, 2H, H1''''); 4.40 (m, 2H, H5 and H8); 3.74 (s, 3H, H12); 3.62 (s, 3H, OCH$_3$); 3.35 (t, J=6.0 Hz, 2H, H4''); 2.99 (m, 2H, ArCH$_2$); 2.52 (m, 2H, H1'); 1.83 (m, 2H, H2''); 1.57 (m, 2H, H1''); 1.48 (s, 18H, C(CH$_3$)$_3$); 1.32 (m, 2H, H3''). Mass Spectrum (ES, +ve) m/z 761 (100%) [MH$^+$]. HRMS calcd for C$_{37}$H$_{57}$N$_6$O$_1$, 761.4085, found 761.4067.

Methyl(2S,5S,8S)-2-allyl-8-(4-allyloxybenzyl)-3,6,9-triaza-5-(4-{guanidino}butyl)-11-oxo-4,7,10-trioxododecanoate hydrochloride (166)

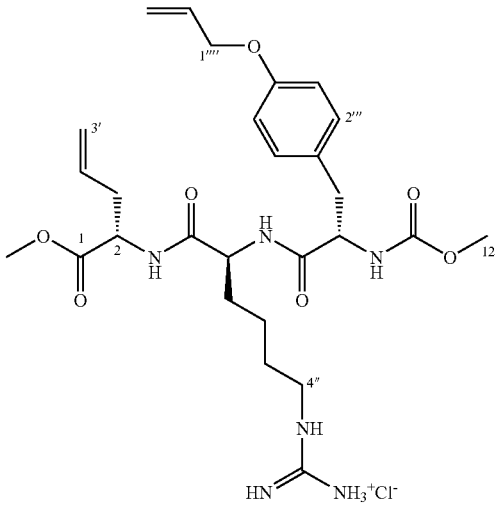

The title compound was synthesized using the general N-Boc deprotection procedure (Procedure A) from 184 (290 mg, 0.38 mmol) to yield 166 (171 mg, 0.29 mmol, 76%) as a highly hydroscopic white solid. $^1$H NMR (CD$_3$OD, 300 MHz): δ 8.24 (d, J=7.2 Hz, 1H, NH); 8.09 (d, J=7.8 Hz, 1H, NH); 7.13 (d, J=8.7 Hz, 2H, ArH2''' and ArH6''); 6.82 (d, J=8.7 Hz, 2H, ArH3''' and ArH5'''); 6.03 (m, 1H, H2''''); 5.77 (m, 1H, H2'); 5.37 (dd, J=1.8, 17.4 Hz, 1H, H3$_a$''''); 5.22 (dd, J=1.5, 10.5 Hz, 1H, H3$_b$''''); 5.11 (m, 2H, H3'); 4.50 (d, J=5.1 Hz, 2H, H1''''); 4.42 (m, 2H, H5 and H8); 4.31 (dd, J=5.4, 9.0 Hz, 1H, H2); 3.70 (s, 3H, H12); 3.58 (s, 3H, OCH$_3$); 3.17 (t, J=6.9 Hz, 2H, H4''); 2.91 (m, 2H, ArCH$_2$); 2.52 (m, 2H, H1'); 1.82 (m, 2H, H2''); 1.62 (m, 2H, H1''); 1.43 (m, 2H, H3''). $^{13}$C NMR (CD$_3$OD, 75 MHz): δ 174.0, C7; 173.6, C1; 172.9, C4; 158.5, CN$_3$; 158.2, ArC4'''; 158.2, C12; 134.7, C2'; 133.9, C2''''; 131.1, ArCH2''' and ArCH6'''; 130.3, ArC1'''; 118.9, C3'; 117.3, C3''''; 114.5, ArCH3''' and ArCH5'''; 69.6, C1''''; 57.9, C8; 54.2, C5; 53.6, C2; 52.8, OCH$_3$; 42.3, C12; 38.2, C4''; 36.6, ArCH$_2$; 32.7, C1'; 29.2, C1''; 23.6, C3''; 15.5, C2''. Mass Spectrum (ES, +ve) m/z 658 (100%) [MH$^+$ less Cl$^-$]. HRMS calcd for C$_{27}$H$_{41}$N$_6$O$_7$ 561.3037, found 561.3016.

Methyl(2S,5S,8S)-8-(4-allyloxybenzyl)-3,6,9-triaza-5-(4-[{di-tert-butoxycarbonyl}guanidino]butyl)-4,7,10-trioxo-2-(4-phenylbutyl)undecanoate (185)

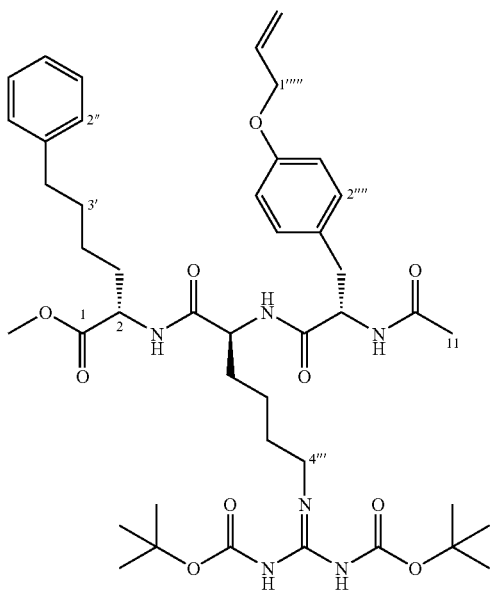

To a solution of 182 (40 mg, 0.058 mmol) in DCM (2 mL) was added TFA (2 mL) and the resulting mixture was allowed to stir for 3 h. The solvent was removed and the oily intermediate was solidified upon the addition of diethyl ether (5 mL) which was decanted and the solid product was dried in vacuo. To the remaining salt was added N1-tert-butoxycarboxamido(trifluoromethylsulfonylimino)methyl propanamide (34 mg, 0.086 mmol), triethylamine (0.1 mL) and DCM (2 mL). The resulting solution was allowed to stir for 16 h under $N_2$. The solvent was removed and the crude product was purified by flash chromatography (20:1, DCM/MeOH) to yield the title compound (46 mg, 0.054 mmol, 95%) as an off white solid. Mp 198° C. $^1$H NMR (CDCl$_3$, 300 MHz): δ 7.20 (m, 5H, ArH); 7.08 (d, J=8.4 Hz, 2H, ArH2'''' and ArH6''''); 6.81 (d, J=8.4 Hz, 2H, ArH3'''' and ArH5''''); 6.71 (d, J=7.8 Hz, 1H, NH); 6.45 (d, J=7.8 Hz, 1H, NH); 6.02 (m, 1H, H2'''''); 5.38 (dd, J=1.5, 17.4 Hz, 1H, H3$_z$'''''); 5.26 (dd, J 1.2, 10.5 Hz, 1H, H3$_b$'''''); 4.65 (m, 1H, H2); 4.47 (d, J=5.1 Hz, 2H, H1'''''); 4.40 (m, 2H, H5 and H8); 3.97 (s, 1H, NH); 3.71 (s, 3H, OCH$_3$); 3.37 (bs, 2H, H4'''); 2.98 (m, 2H, 8-CH$_2$); 2.59 (t, J=7.8 Hz, 2H, H4'); 1.96 (s, 3H, C11); 1.84 (m, 2H, H2'''); 1.63 (m, 6H, H1', H2' and H3'); 1.49 (s, 18H, C(CH$_3$)$_3$); 1.36 (m, 4H, H1''' and H3). Mass Spectrum (ES, +ve) m/z 837 (100%) [MH$^+$]. HRMS calcd for C$_{44}$H$_{65}$N$_6$O$_{10}$ 837.4762, found 837.4744.

Methyl(2S,5S,8S)-8-(4-allyloxybenzyl)-3,6,9-triaza-5-(4-guanidinobutyl)-4,7,10-trioxo-2-(4-phenylbutyl)undecanoate hydrochloride (167)

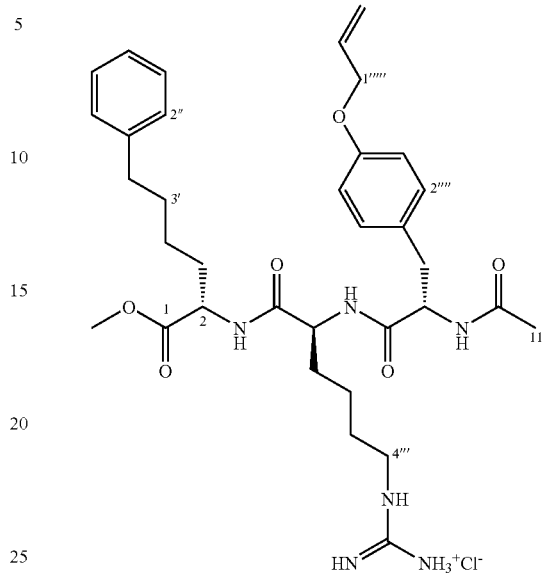

The title compound was synthesized using the general N-Boc deprotection procedure (Procedure A) from 185 (40 mg, 0.048 mmol) to yield 167 (18 mg, 0.026 mmol, 56%) as a white solid. Mp 180-188° C. $^1$H NMR (CD$_3$OD, 300 MHz) δ 8.23 (d, J=7.2 Hz, 1H, NH); 8.08 (d, J=7.2 Hz, 1H, NH); 7.15 (m, 7H, ArH); 6.81 (d, J=8.7 Hz, 2H, ArH3'''' and ArH5''''); 6.02 (m, 1H, H12'''''); 5.36 (dd, J=1.5, 17.1 Hz, 1H, H3$_a$'''''); 5.21 (dd, J=1.5, 10.5 Hz, 1H, H3$_b$'''''); 4.49 (m, 3H, H2 and H'''''); 4.36 (m, 2H, H5 and H8); 3.68 (s, 3H, OCH$_3$); 3.16 (m, 2H, H4'''); 2.92 (m, 2H, 8-CH$_2$); 2.60 (t, J=7.2 Hz, 2H, H4'); 1.91 (s, 3H, H11); 1.82 (m, 2H, H2'''); 1.61 (m, 8H, H1', H2', H3' and H1'''); 1.42 (m, 2H, H3). $^{13}$C NMR (CD$_3$OD, 75 MHz): δ 174.1, C7; 173.9, C4; 174.4, C1; 159.0, C10; 158.6, CN$_3$; 143.5, ArC4''''; 135.0, ArC1''; 131.2, C2'''''; 130.4, ArC1''''; 129.4, ArCH2'''' and ArCH6''''; 129.3, ArCH3'' and ArCH5''; 126.8, ArCH4''; 117.4, C3'''''; 115.7, ArCH3'''' and ArCH5''''; 69.7, C1'''''; 56.6, C5; 53.9, C2; 53.7, OCH$_3$; 52.7, C8; 42.3, C4'''; 37.9, 8-CH$_2$; 36.6, C4'; 32.7, C1'; 32.2, C3'; 32.1, C1'''; 29.2, C3'''; 26.4, C11; 23.6, C2'; 22.4, C2'''. Mass Spectrum (ES, +ve) m/z 638 (100%) [M$^+$]. HRMS calcd for C$_{34}$H$_{49}$N$_6$O$_{65}$ 637.3714, found 637.3745.

Di-tert-butyl N-3-butenyliminodicarboxylate (186)

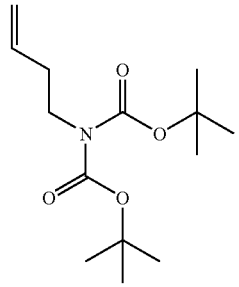

To a solution of di-tert-butyliminodicarboxylate (868 mg, 4 mmol), cesium carbonate (2.61 g, 8 mmol), and lithium 4iodide (28 mg, 0.2 mmol) in 2-butanone (20 mL) was added 4-bromobutene (812 mg, 6 mmol) and the mixture was heated at reflux for 48 h. The reaction was allowed to cool and was quenched with brine (40 mL) and extracted with diethyl ether (3×20 mL). The combined organic fractions were washed with brine (30 mL), dried, and evaporated to yield the title compound (1.01 g, 3.7 mmol, 93%) as a light brown oil. $^1$H NMR (CDCl$_3$, 300 MHz): δ 5.77 (m, 1H, H3); 5.04 (m, 2H, H4); 3.62 (dd, J=6.0, 8.7 Hz, 2H, H1); 2.30 (m, 2H, H2); 1.51 (s, 18H, 2×(CH$_3$)$_3$). Mass Spectrum (ES, +ve) m/z 310 (55%) [MH$^+$], 294 (30%) [MNa$^+$], 272 (40%) [MH$^+$]. HRMS calcd for C$_{14}$H$_{26}$NO$_4$ 272.1862, found 272.1848.

tert-Butyl N-3-butenylcarbamate (187)

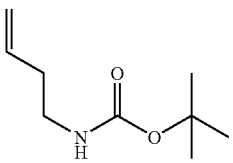

To a solution of 186 (708 mg, 2.60 mmol) in DCM (20 mL) was added trifluoroacetic acid (593 mg, 5.20 mmol) and the mixture was allowed to stir for 5 min before being quenched with 2M NaOH (25 mL) and extracted with DCM (3×20 mL). The combined organic fractions were dried, and concentrated to yield the title compound (429 mg, 2.50 mmol, 96%) as a light brown oil, which had spectral data in agreement with that reported.[104] $^1$H NMR (CDCl$_3$, 300 MHz): δ 5.75 (m, 1H, H3); 5.08 (m, 2H, H4); 4.59 (bs, 1H, NH); 3.20 (dd, J=6.3, 12.6 Hz, 2H, H1); 2.24 (dd, J=6.9, 12.6 Hz, 2H, H2); 1.44 (s, 9H, (CH$_3$)$_3$). Mass Spectrum (ES, +ve) m/z 116 (100%) [MH$^+$ less 56 (Boc rearrangement].

Methyl(2S,4E/Z)-2-(benzyloxycarboxamido)-7-(tert-butoxycarboxamido)-4-heptenoate (188)

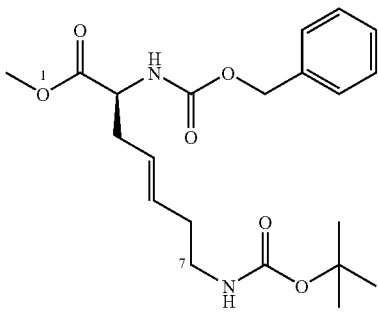

To a solution of 187 (220 mg, 1.29 mmol) in DCM (13 mL) was added 173 (169 mg, 0.64 mmol) and Grubbs' first generation catalyst (53 mg, 0.064 mmol). The mixture was heated at reflux under N$_2$ for 16 h. The solvent was removed and the crude product purified by flash column chromatography (6:1, hexane/EtOAc) to yield the title compound (180 mg, 0.44 mmol, 69%) as a brown oil as a 1:1 mixture of E and Z isomers. $[α]_D^{24}$ −34.6 (c. 0.3 in EtOH). $^1$H NMR (CDCl$_3$, 300 MHz): δ 7.35 (m, 5H, ArH); 5.43 (m, 3H, H4, H5, NH); 5.11/5.10 (s, 2H, OCH$_2$Ph[E and Z]); 4.61 (bs, 1H, NH); 4.43 (m, 1H, H2); 3.75/3, 72 (s, 3H, OCH$_3$[E and Z]); 3.11 (m, 2H, H7); 2.47 (m, 2H, H3); 2.17 (m, 2H, H6); 1.43 (s, 9H, (CH$_3$)$_3$). Mass Spectrum (ES, +ve) m/z 429 (100%) [MNa$^+$], 407 (20%) [MH$^+$]. HRMS calcd for C$_{21}$H$_{31}$N$_2$O$_6$ 407.2182, found 407.2171.

Methyl(2S)-2-amino-7-(tert-butoxycarboxamido)-4-heptanoate (189)

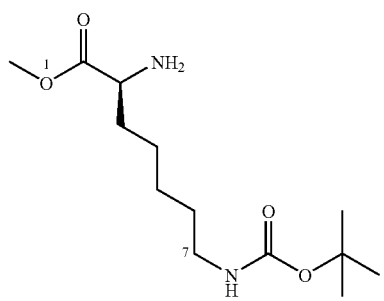

To a solution of 188 (25 mg, 0.061 mmol) in THF (4 mL) was added palladium on activated carbon (13 mg, 0.0061 mmol) The reaction vessel was evacuated, flushed with H2 and allowed to stir for 16 h. The resulting crude product was filtered through celite and evaporated to yield the title compound (15 mg, 0.055 mmol, 90%) as a clear oil. $[α]_D^{24}$ +9.6 (c. 0.1 in EtOH). $^1$H NMR (CDCl$_3$, 300 MHz): δ 4.55 (bs, 1H, NH); 3.72 (s, 3H, OCH$_3$); 3.44 (t, J=6.0 Hz, 1H, H2); 3.10 (m, 2H, H7); 1.86 (m, 4H, H3, H4); 1.44 (s, 9H, (CH$_3$)$_3$); 1.37 (m, 4H, H5, H6). Mass Spectrum (ES, +ve) m/z 275 (90%) [MH$^+$]; 219 (100%). HRMS calcd for C$_{13}$H$_{27}$N$_2$O$_4$ 275.1971, found 275.1967.

(2S)-2,7-Diaminoheptanoic acid dihydrochloride (193)

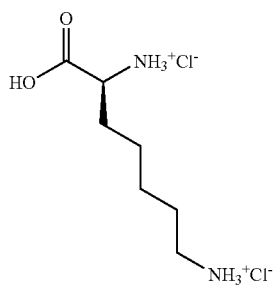

A solution of 189 (16 mg, 0.058 mmol) in 10M HCl (3 mL) was allowed to stir for 48 h. The product was isolated by evaporation and dried over P$_2$O$_5$ to yield the title compound (14 mg, 0.058 mmol, 100%) as a hydroscopic white solid, which had spectral data in agreement with that reported.[106] $[α]_D^{22}$ +10.9 (c. 0.1 in HCl) (Lit. $[α]_D^{23}$+14.4)[106] $^1$H NMR (D$_2$O, 300 MHz): δ 3.90 (t, J=6.3 Hz, 1H, H2); 2.83 (t, J=7.5 Hz, 2H, H7); 1.81 (m, 2H, H3); 1.64 (m, 2H, H5); 1.52 (m, 2H, H6); 1.30 (m, 2H, H4). Mass Spectrum (ES, +ve) m/z 161 (100%) [M$^{2+}$]. HRMS calcd for C$_7$H$_{17}$N$_2$O$_2$ 161.1290, found 161.1294.

Methyl(2S,5S)-5-(4-allyloxybenzyl)-3,6-diaza-2-(5-[tert-butoxycarboxamido]pentyl)-4,7-dioxooctanoate (190)

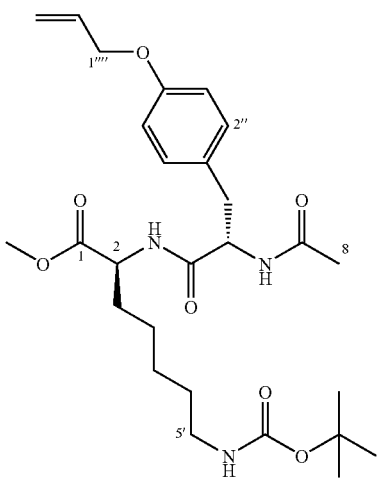

The title compound was synthesized using the general peptide coupling procedure (Procedure B) from 16 (53 mg, 0.20 mmol) and 189 (65 mg, 0.24 mmol) to afford 190 (103 mg, 0.20 mmol, 100%) as an off-white solid. Mp 96-103° C. $^1$H NMR (CDCl$_3$, 300 MHz): δ 7.11 (d, J=8.7 Hz, 2H, ArH2" and ArH6"); 6.82 (d, J=8.7 Hz, 2H, ArH3" and ArH5"); 6.50 (d, J=7.8 Hz, 1H, NH); 6.03 (m, 1H, H2'''); 5.39 (dd, J=1.8, 17.4 Hz, 1H, H3$_a$'''); 5.26 (dd, J=1.8, 9.3 Hz, 1H, H3$_b$'''); 4.66 (m, 2H, H2 and H5); 4.48 (m, 2H, H1'''); 3.69 (s, 3H, OCH$_3$); 2.98 (m, 4H, H5' and ArCH$_2$); 1.96 (s, 3H, H8); 1.75 (m, 2H, H1'); 1.64 (m, 2H, H3'); 1.43 (s, 9H, C(CH$_3$)$_3$); 1.26 (m, 4H, H2' and H4'). Mass Spectrum (ES, +ve) m/z 520 (100%) [MH$^+$]. HRMS calcd for C$_{27}$H$_{41}$N$_3$O$_7$ 542.2842, found 542.2855.

(2S,5S)-5-(4-Allyloxybenzyl)-3,6-diaza-2-(5-[tert-butoxycarboxamido]pentyl)-4,7-dioxooctanoic acid (191)

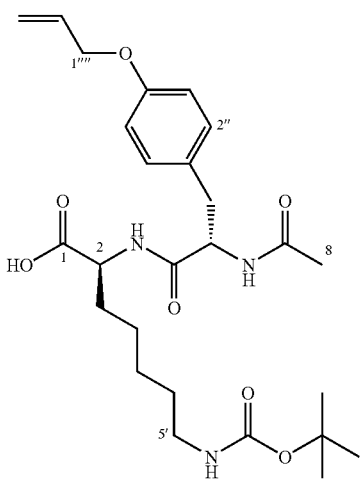

To a solution of 190 (70 mg, 0.13 mmol) in THF/water, 3:1 (8 mL) was added lithium hydroxide monohydrate (11 mg, 0.26 mmol) and the resulting suspension was allowed to stir for 16 h. The reaction mixture was diluted with water (30 mL) and the THF was removed by evaporation. The aqueous layer was extracted with DCM (40 mL) to remove unreacted starting material. The aqueous phase was acidified with 10% HCl and the resulting precipitate was extracted with DCM (3×40 mL). The combined organic fractions were dried and evaporated to yield the title compound (39 mg, 0.08 mmol, 62%) as a clear oil. $^1$H NMR (CDCl$_3$, 300 MHz): δ 7.09 (d, J=8.7 Hz, 2H, ArH2" and ArH6"); 6.82 (d, J=8.7 Hz, 2H, ArH3" and ArH5"); 6.05 (m, 1H, H12'''); 5.39 (dd, J=1.8, 17.4 Hz, 1H, H3$_a$'''); 5.25 (dd, J=1.8, 9.3 Hz, $^1$H, H3$_b$'''); 4.63 (t, J=6.9 Hz, 1H, H2); 4.47 (m, 3H, H1''' and H5); 3.05 (m, 4H, H5' and ArCH$_2$); 1.95 (s, 3H, H8); 1.84 (m, 2H, H1'); 1.69 (m, 2H, H3'); 1.44 (s, 9H, C(CH$_3$)$_3$); 1.28 (m, 4H, H2' and H4').

Methyl(2S,5S,8S)-2-allyl-8-(4-allyloxybenzyl)-3,6,9-triaza-5-(4-[tert-butoxycarboxamido]pentyl)-4,7,10-trioxoundecanoate (192)

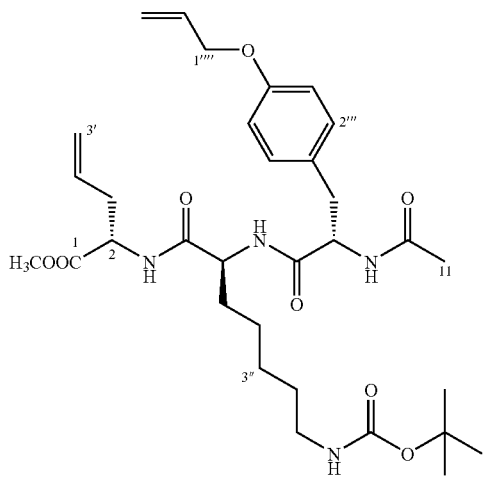

The title compound was synthesized using the general peptide coupling procedure (Procedure B) from 18 (14 mg, 0.084 mmol) and 191 (35 mg, 0.07 mmol) to afford 192 (31 mg, 0.048 mmol, 69%) as an off-white solid. Mp 130-136° C. $^1$H NMR (CDCl$_3$, 300 MHz): δ 7.07 (d, J=8.7 Hz, 2H, ArH2''' and ArH6'''); 6.80 (d, J=8.7 Hz, 2H, ArH3''' and ArH5'''); 6.59 (d, J=8.1 Hz, 1H, NH); 6.49 (d, J=7.2 Hz, 1H, NH); 6.43 (d, J=7.5 Hgz, 1H, NH); 6.02 (m, 1H, H2''''); 5.67 (m, 1H, H2'); 5.39 (dd, J=1.5, 17.4 Hz, 1H, H3$_a$''''); 5.26 (dd, 1.5, 10.5 Hz, 1H, H3$_b$''''); 5.10 (m, 2H, H3'); 4.70 (m, 1H, H2); 4.58 (m, 1H, H5); 4.48 (m, 2H, H1''''); 4.41 (m, 1H, H8); 3.73 (s, 3H, OCH$_3$); 3.04 (m, 2H, H5''); 2.98 (t, J=6.0 Hz, 2H, ArCH$_2$); 2.53 (m, 2H, H1'); 1.96 (s, 3H, H11); 1.76 (m, 2H, H1''); 1.58 (m, 2H, H3''); 1.43 (s, 9H, C(CH$_3$)$_3$); 1.28 (m, 4H, H2'' and H4''). Mass Spectrum (ES, +ve) m/z 639 (100%) [MNa$^+$], 617 (10%) [MH$^+$], 517 (95%) [MH$^+$ less Boc]. HRMS calcd for C$_{32}$H$_{49}$N$_4$O$_8$Na 639.3370, found 639.3371.

Methyl(2S,5S,8S)-2-allyl-8-(4-allyloxybenzyl)-3,6,9-triaza-5-(4-[{di-tert-butoxycarbonyl}guanidino]pentyl)-4,7,10-trioxoundecanoate (195)

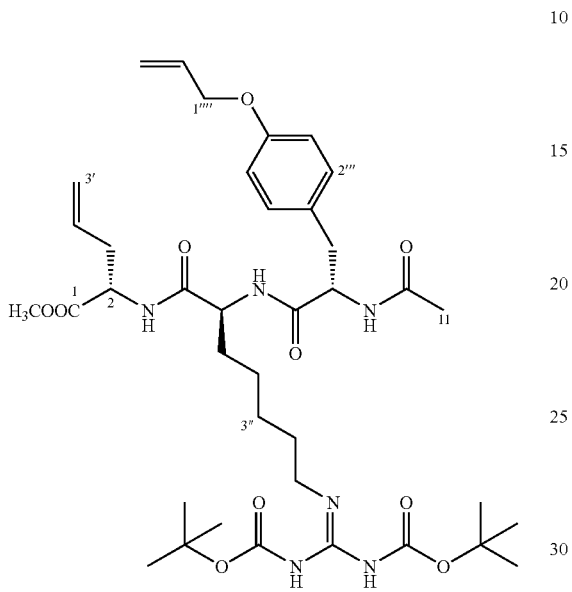

To a solution of 192 (20 mg, 0.032 mmol) in DCM (2 mL) was added TFA (2 mL) and the resulting mixture was allowed to stir for 3 h. The solvent was removed and the oily intermediate was solidified upon the addition of diethyl ether (5 mL) which was decanted and the solid product was dried in vacuo. To the remaining salt was added N1-tert-butoxycarboxamido (trifluoromethylsulfonylimino)methyl propanamide (34 mg, 0.086 mmol), triethylamine (0.1 mL) and DCM (2 mL). The resulting solution was allowed to stir for 16 h under $N_2$. The solvent was removed and the crude product was purified by flash chromatography (20:1, DCM/MeOH) to yield the title compound (23 mg, 0.030 mmol, 95%) as a clear oil. $^1H$ NMR (CDCl$_3$, 300 MHz): δ 8.31 (bs, 1H, NH); 7.08 (d, J=8.7 Hz, 2H, ArH2''' and ArH6'''); 6.82 (d, J=8.7 Hz, 2H, ArH3''' and ArH5'''); 6.72 (d, J=8.1 Hz, 1H, NH); 6.60 (d, J=7.5 Hz, 1H, NH); 6.41 (d, J=7.8 Hz, 1H, NH); 6.03 (m, 1H, H2''''); 5.65 (m, 1H, H2'); 5.40 (dd, J=1.5, 17.1 Hz, 1H, H3$_a$''''); 5.27 (dd, 1.5, 10.5 Hz, 1H, H3$_b$''''); 5.11 (m, 2H, H3'); 4.66 (m, 1H, H2); 4.57 (m, 1H, H5); 4.49 (m, 2H, H1''''); 4.38 (m, 1H, H8); 3.74 (s, 3H, OCH$_3$); 3.34 (m, 2H, H5''); 2.98 (m, 2H, ArCH$_2$); 2.52 (m, 2H, H1'); 1.97 (s, 3H, H111); 1.80 (m, 2H, H1''); 1.70 (m, 2H, H3''); 1.49 (s, 18H, C(CH$_3$)$_3$); 1.32 (m, 4H, H2'' and H4''). Mass Spectrum (ES, +ve) m/z 759 (100%) [MH$^+$]. HRMS calcd for $C_{38}H_{59}N_6O_{10}$ 759.4293, found 759.4272.

Methyl(2S,5S,8S)-2-allyl-8-(4-allyloxybenzyl)-3,6,9-triaza-5-(4-guanidinopentyl)-4,7,10-trioxoundecanoate hydrochloride (168)

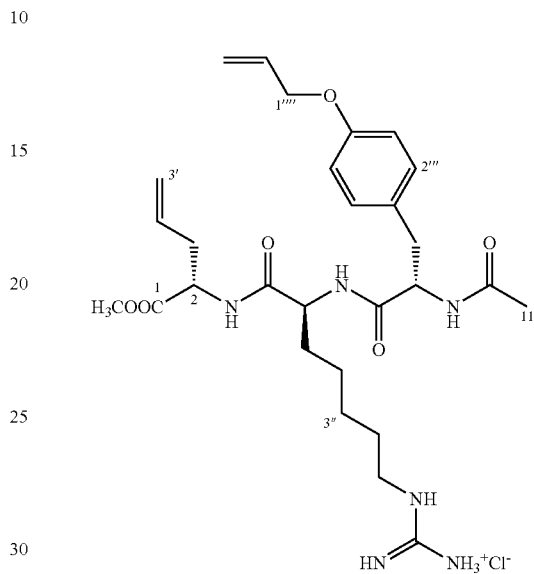

The title compound was synthesized using the general N-Boc deprotection procedure (Procedure A) from 195 (20 mg, 0.026 mmol) to yield 168 (10 mg, 0.017 mmol, 65%) as a white hydroscopic solid. $^1H$ NMR (CDCl$_3$, 300 MHz): δ 7.13 (d, J=8.4 Hz, 2H, ArH2''' and ArH6'''); 6.82 (d, J=8.4 Hz, 2H, ArH3''' and ArH5'''); 6.03 (m, 1H, H2''''); 5.76 (m, 1H, H2'); 5.37 (dd, J=1.5, 17.1 Hz, 1H, H3$_a$''''); 5.22 (dd, 1.5, 10.5 Hz, 1H, H3$_b$''''); 5.10 (m, 2H, H3'); 4.50 (m, 2H, H1''''); 4.38 (m, 3H, H2, H5 and H8); 3.69 (s, 3H, OCH$_3$); 3.15 (m, 2H, H5''); 2.92 (m, 2H, ArCH$_2$); 2.51 (m, 2H, H1'); 1.90 (s, 3H, H11); 1.78 (m, 2H, H1''); 1.58 (m, 2H, H3''); 1.38 (m, 4H, H2'' and H4''). $^{13}C$ NMR (CDCl$_3$, 75 MHz): δ 174.1, C7; 173.8, C1; 173.3, C4; 168.9, C10; 159.0, CN$_3$; 158.6, ArC4'''; 134.4, C2'; 131.4, C2''''; 131.2, ArCH2''' and ArCH6'''; 130.4, ArC1'''; 118.9, C3'; 117.4, C3''''; 115.7, ArCH3''' and ArCH5'''; 69.8, C1''''; 56.5, C5; 54.1, OCH$_3$; 53.6, C8; 52.7, C2; 42.2, C5''; 37.9, ArCH$_2$; 36.7, C1'; 33.1, C1''; 29.6, C4''; 27.1, C3''; 26.0, C11; 22.3, C2''. Mass Spectrum (ES, +ve) m/z 559 (100%) [M$^+$]. HRMS calcd for $C_{28}H_{3}N_6O_6$ 559.3244, found 559.3226.

Antibacterial Screening Methodology for Compounds of Example 2

Bacterial Strain
   All assays used the *Staphylococcus aureus* strain ATCC 6538P.
   Assays described in Chapter 5 additionally used the vancomycin-resistant enterococci and vancomycin-sensitive enterococci strains Ef243, Ef449, Ef820 and Ef487.

Culture Media
   Mueller-Hinton Broth Medium (MHB): MHB (Oxoid CM405) was prepared with final concentrations of 1 μl/mL MgCl$_2$ and 2 μg/mL CaCl$_2$. Culture medium was pre-warmed for approximately 2-3 h at 37° C. before use.

Mueller-Hinton Agar Medium (MHA): MMB containing 1.5% Agar (Merck Agar 1.01614).

Maintenance of Bacteria

From a thawed cryovial, the bacteria was streaked onto MHA and the plate incubated overnight at 37° C.

From this plate, 10 cryovials were prepared by looping several colonies into 0.5 mL of 20% glycerol solution. The cryovials were immediately stored at −140° C.

Preparation of Seed Cultures

A cryovial was removed from −140° C. storage and thawed at room temperature.

An MHA plate was streaked with a loopful of bacterial suspension and incubated overnight at 37° C. to create a parent plate (P1).

A daughter plate (D1) was streaked from the parent plate and incubated overnight at 37° C. The parent plate was stored at 4° C.

A loop of colony from the daughter plate was used to innoculate a 125 mL flask containing 20 mL of MHB containing 25 µg/mL $CaCl_2.2H_2O$ and 12.5 µg/mL $MgCl_2.6H_2O$.

The flask was shaken at 260 rpm for 18 h at 37° C. on an orbital incubator shaker.

The parent plate (P1) was reused within 9 days to generate another daughter plate (D2), which was used to inoculate a broth culture.

Parent plates were used twice (to generate D1 and D2 plates) before a new one was prepared from the previously thawed cryovial. The second parent plate (P2) was used to generate two additional daughter plates using the procedure outlined above before being discarded.

Cryovials were used twice to prepare parent plates (P1 and P2) before being discarded.

Preparation of Standardized Inocula for Assays

A 1/10 dilution of seed cultures was prepared by adding 250 µL of the cultures to 2,250 µL of MHB in a disposable cuvette.

The $OD_{650}$ was read and multiplied by a factor of 10 to calculate the optical density of the undiluted culture.

The required dilution factor for the preparation of standardized inocula was calculated by dividing the observed $OD_{650}$ by the standard $OD_{650}$ (previously determined as an $OD_{650}$ of 4.75 from optimization studies).

A 10 mL sample of standardized inocula was prepared as illustrated by the following example:

Sample Calculation:

$OD_{650}=0.492$ (1/10 dilution)

$10 \times 0.492 = 4.92$ as; $4.75/4.92=0.97$

Add 0.97 mL of *S. aureus* seed culture to 9.03 mL of MHB as the first dilution.

Sufficient volumes of the final inoculum cultures were prepared in pre-warmed MHB (37° C.) by diluting the standardized cultures to the required final concentration (*S. aureus* required a 108 dilution).

Assay Procedure (for 96-Well Microtitre Plates)

To each well of the 96-well microtitre plate was added 50 µL of liquid medium.

The peptoid compounds to be tested were dissolved in a 50% $MeOH/H_2O$ solution to give a concentration of 1 mg/mL 50 µL of test solution was added in triplicate to the top row of the microtitre plate (2 peptoid samples were tested per plate). A vancomycin control set (triplicate) and a compound negative control set (triplicate) were also included on each plate (FIG. 1).

The inoculated culture medium was incubated at 37° C. for 30 min, with shaking at 130 rpm.

Using a multichannel pipette, the contents of the first row were mixed before 50 µL was transferred to the second row. The pipette tips were changed and the process repeated by 50 µL of the mixed broth solutions in the second row being transferred to the third row. This process was repeated until the last row contained either the diluted test compound or a control (vancomycin or compound-negative). 50 µL was discarded from this final row so that each well contained 50 µL of liquid medium.

Using a multistepper pipette, 50 µL of the inoculum was added to each well of the plate except for the last row in the compound-negative control set, which received 50 µL of liquid broth.

The plates were incubated at 37° C. for 18 h, with shaking at 100 rpm in an environment of approximately 90% humidity.

The results were recorded as the highest dilution of test compound that prevented bacterial growth (MIC).

Antibacterial Testing of Compounds of Example 2

Introduction

The specific testing procedures and protocols are outlined in the section "Antibacterial Screening Methodology for the Compounds of Example 2". The antibacterial testing was performed on a vancomycin-susceptible strain of *S. aureus*, and compounds that showed promising activity were subsequently tested against a variety of vancomycin resistant and vancomycin sensitive enterococcal strains (*Enterococcus faecium*) (see Chapter 5).

Antibacterial Testing Results

The antibacterial activity results are measured by minimum inhibitory concentration (MIC), which is the lowest concentration of compound necessary to prevent bacterial growth. The activities ranged from MIC 7.8 µl/mL for compound 75 to MIC>125 µg/mL (inactive) for a number of compounds. Some testing was done in the earlier stages of the project at higher concentration ranges up to 500 µg/mL, while later testing was performed with an upper limit of 125 µg/mL. For consistency, activity values greater than 125 µl/mL have been designated inactive, whilst an activity of 125 µg/mL is considered weakly active. Vancomycin was used as the standard/control and typically had an MIC range of 1.25-2.5 µg/mL. The antibacterial testing results for *S. aureus* are tabulated in Table 1.

TABLE 1

Tabulated antibacterial testing results on *S. aureus*

| Compound | Antibacterial activity (MIC µg/mL) |
|---|---|
| 69 | 125 |
| 70 | 125 |
| 71 | 125 |
| 72 | 125 |
| 73 | 31.3 |
| 74 | 15.6 |
| 75 | 7.8 |
| 76 | 15.6 |
| 77 | 125 |
| 83 | 125 |
| 12 | 62.5 |
| 43 | 125 |
| 48 | 125 |
| 32 | 62.5 |
| 37 | 125 |

TABLE 1-continued

Tabulated antibacterial testing results on *S. aureus*

| Compound | Antibacterial activity (MIC μg/mL) |
|---|---|
| 65 | 15.6 |
| 56 | 125 |

Antibacterial Testing of Linear Cationic Peptides of Example 2

Introduction

The antibacterial testing was performed using the same protocols as those used previously described in the section "Antibacterial Testing of compounds of Example 2", using a vancomycin-susceptible strain of *S. aureus*, and an additional three strains of vancomycin-sensitive or partially sensitive enterococci (E.f243, E.f449 and E.f987: vancomycin MIC 1.95, 62.5 and <0.98 μg/mL respectively) and one fully vancomycin-resistant *Enterrococci faecium* strain (E.f820: vancomycin MIC>125 μg/mL).

Antibacterial Testing Results

The testing results again are measured by minimum inhibitory concentration (MIC), on a scale from 0.98 μg/mL to 125 μg/mL. Vancomycin was used as the standard/control. The antibacterial testing results for the linear cationic peptides are described in Tables 2 and 3

TABLE 2

| | Antibacterial activity μg/mL | | | | |
|---|---|---|---|---|---|
| Compound | S.a | E.f243 | E.f449 | E.f820 | E.f987 |
| Vancomycin | 1.95 | 1.95 | 62.5 | >125 | <0.98 |
| 118 | 31.3 | >125 | >125 | >125 | >125 |
| 119 | 15.6 | >125 | >125 | >125 | >125 |
| 120 | 3.9 | 62.5 | 62.5 | 62.5 | 62.5 |
| 121 | 7.8 | 125 | 125 | 125 | >125 |
| 132 | 3.9 | 31.3 | 31.3 | 31.3 | 62.5 |
| 90 | 1.95 | 31.3 | 31.3 | 31.3 | 31.3 |
| 134 | 3.9 | 62.5 | 62.5 | 62.5 | 125 |
| 135 | 7.8 | 125 | 62.5 | 62.5 | 125 |
| 136 | 7.8 | 125 | 62.5 | 62.5 | 125 |
| 137 | 3.9 | 62.5 | 31.3 | 31.3 | 62.5 |
| 138 | 3.9 | 31.3 | 15.6 | 15.6 | 31.3 |
| 139 | 15.6 | >125 | >125 | >125 | >125 |
| 140 | 7.8 | >125 | >125 | >125 | >125 |
| 141 | 3.9 | 31.3 | 31.3 | 31.25 | 62.5 |

TABLE 3

| | Antibacterial activity μg/mL | | | | |
|---|---|---|---|---|---|
| Compound | S.a | E.f243 | E.f449 | E.f820 | E.f987 |
| 155 | 7.8 | >125 | 125 | 125 | >125 |
| 156 | 3.9 | 125 | 125 | 62.5 | 62.5 |
| 157 | 15.6 | >125 | 125 | 125 | >125 |
| 158 | 7.8 | 62.5 | 62.5 | 31.3 | 62.5 |
| 159 | 62.5 | 125 | 125 | 62.5 | >125 |
| 160 | 7.8 | 62.5 | 62.5 | 62.5 | 125 |
| 161 | 15.6 | — | — | 62.5 | — |
| 162 | 3.9 | >125 | >125 | >125 | >125 |
| 163 | 15.6 | >125 | >125 | >125 | >125 |
| 164 | 7.8 | >125 | >125 | >125 | >125 |

Testing of Compounds of Example 2 Against the HIV Integrase Enzyme

HIV Integrase Initial Screening Results

Compounds synthesized in Example 2 were additionally included in a random database screening strategy against the HIV integrase enzyme.

The compounds that were chosen to be tested against HIV integrase were 78, 81, 88 and 89 and the results are represented in Table 4.

TABLE 4

| Compound | Conc. (μg/mL) | % Inhibition |
|---|---|---|
| 78 | 50 | 15% |
| 81 | 50 | 70% |
| 88 | 50 | 95% |
| 89 | 50 | 4% |

These results represent promising hits as the compounds are significantly different in structure from previously known HIV integrase inhibitors. These results formed a preliminary set of structure activity relationships (SAR's) with regard to the stereochemistry of the amino acid residues and the length and functionality of the basic side-chain.

Testing Against the HIV Integrase Enzyme

The results for the screening of the four target molecules 165-168 against the HIV integrase enzyme yielded some encouraging results which supported the proposed mechanism of binding in the active binding trench of the HIV integrase enzyme. The testing procedure for the four target compounds differed from the original screening protocols employed. The original screening measured inhibition against the 3' processing function of the enzyme at the fixed concentration of 50 μg/mL, whereas the four target molecules were tested in an assay adapted from a literature procedure,[107] which measures inhibition against the 3' strand transfer function of the enzyme. This allows a result to be obtained as an inhibition constant ($IC_{50}$) concentration, which is the standard measurement of inhibition within the literature. Along with the four target molecules, 88 was also re-tested in the 3' strand transfer assay to determine the $IC_{50}$ for direct comparison with the literature. The results for the testing of the four target molecules and the re-testing of 88 against HIV integrase are summarized in Table 5.

TABLE 5

Compound

88

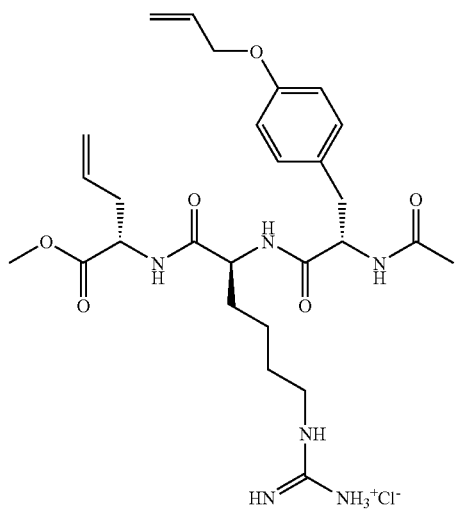

$IC_{50}$ 12 μM
eb;normal

165

TABLE 5-continued

Compound

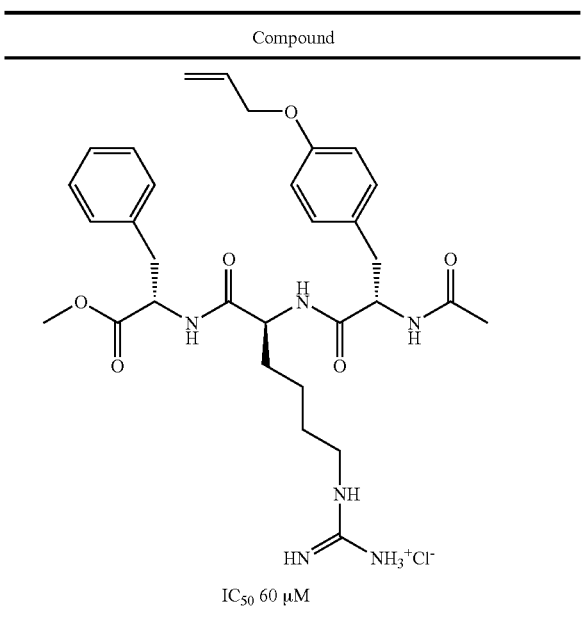

IC$_{50}$ 60 µM

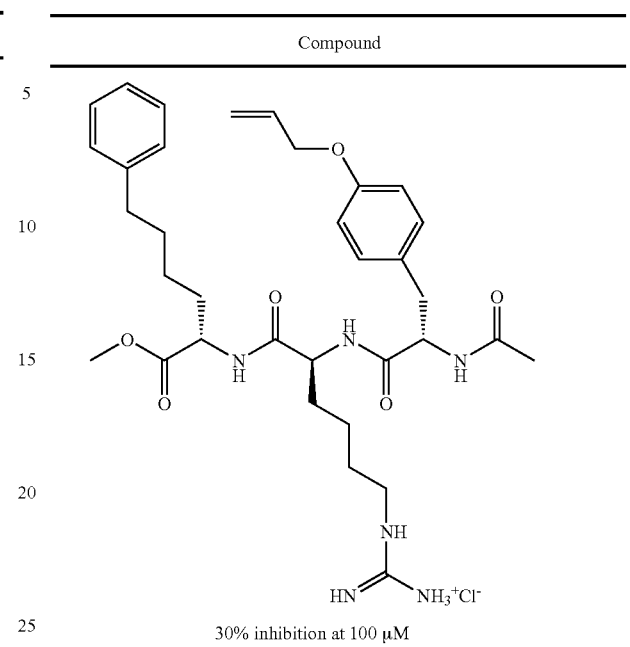

30% inhibition at 100 µM

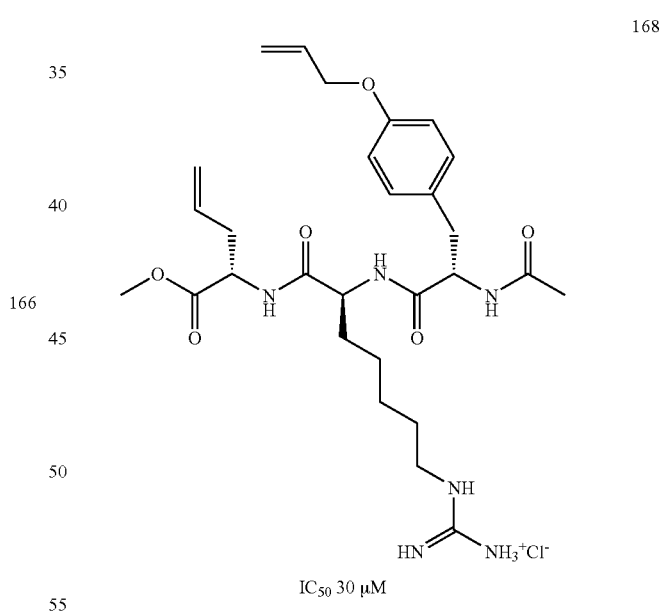

168

IC$_{50}$ 30 µM

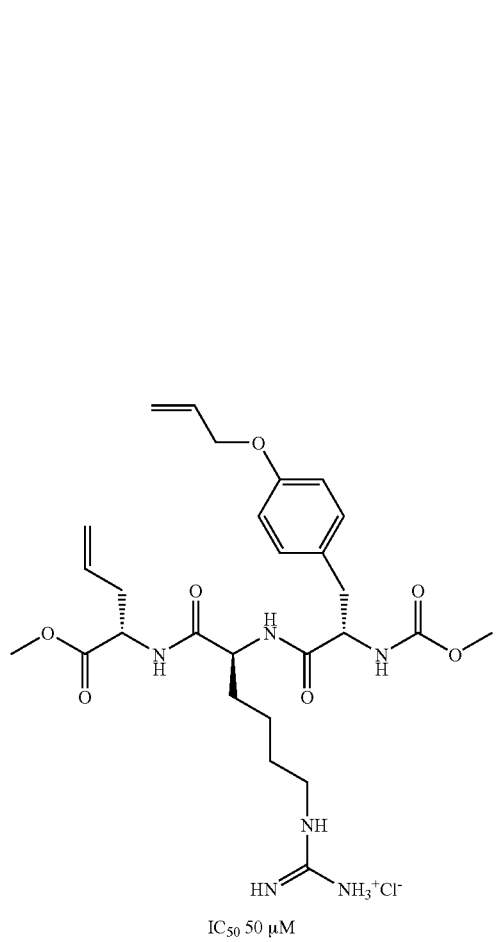

IC$_{50}$ 50 µM

167

After these compounds and the computer modelling studies had become established, all compounds that were sent for screening in the antibacterial assay were then also cross tested for their ability to inhibit the HIV integrase enzyme. Several compounds are active with moderate levels of inhibition and compound 163, one of the hydroxamic acid binaphthyl derivatives, appears to be almost as active as the original lead 88, and is again structurally unique with the large hydrophobic binaphthyl moiety. The results of these compounds are summarized in Table 6.

TABLE 6
Compound
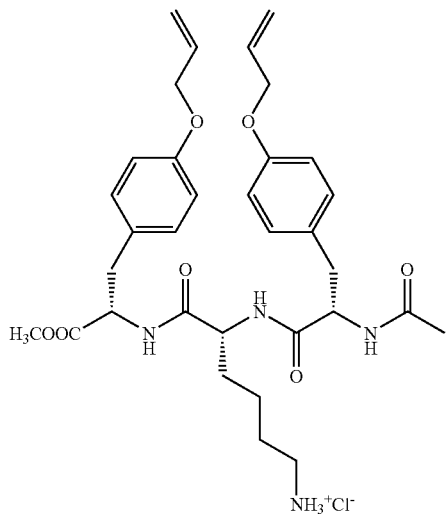
83
$IC_{50}$ 55 μM
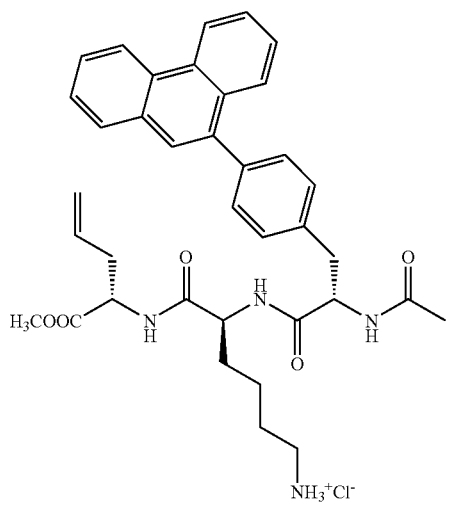
119
$IC_{50}$ 41 μM
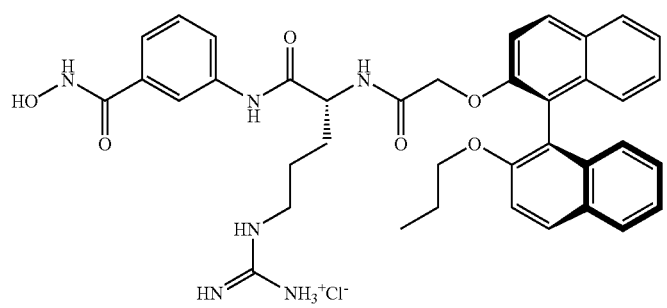
164
$IC_{50}$ 25 μM TABLE 6-continued Compound

163

IC$_{50}$ 15 µM

158

IC$_{50}$ 95 µM

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed anywhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES (1) Dineen, P.; Homan, W. P.; Grafe, W. R. *Annals of Surgery* 1976, 184, 717-22.
(2) Neu, H. C. *Science* 1992, 257, 1064-72.
(3) Nicolaou, K. C.; Boddy, C. N. C. *Sci. Am.* 2001, 284, 54-61.
(4) Noble, W. C.; Virani, Z.; Cree, R. G. A. *FEMS Microbiol. Lett.* 1992, 93, 195-8.
(5) Guiot, H. F.; Peetermans, W. E.; Sebens, F. W. *Eur. J. Clin. Microbiol. Infect. Dis.* 1991, 10, 32-4.
(6) Handwerger, S.; Raucher, B.; Altarac, D.; Monka, J.; Marchione, S.; Singh, K. V.; Murray, B. E.; Wolff, J.; Walters, B. *Clin. Infect. Dis.* 1993, 16, 750-5.
(7) Sievert, D. M. *Morbid. Mortal. Wkly Rep.* 2002, 51, 565-7.
(8) Daly, J. S.; Eliopoulos, G. M.; Willey, S.; Moellering, R. C., Jr. *Antimicrob. Agents Chemother.* 1988, 32, 1341-6.
(9) Tsiodras, S.; Gold, H. S.; Sakoulas, G.; Eliopoulos, G. M.; Wennersten, C.; Venkataraman, L.; Moellering, R. C.; Ferraro, M. J. *Lancet* 2001, 358, 207-8.
(10) Gonzales, R. D.; Schreckenberger, P. C.; Graham, M. B.; Kelkar, S.; DenBesten, K.; Quinn, J. P. *Lancet* 2001, 357, 1179.
(11) Halls, G. *The Complete Guide to Anti-infectives*; PJB Publications: Richmond Surrey UK, 1999.
(12) Stover, C. K.; Pham, X. Q.; Erwin, A. L.; Mizoguchi, S. D.; Warrener, P.; Hickey, M. J.; Brinkman, F. S.; Hufnagle, W. O.; Kowalik, D. J.; Lagrou, M.; Garber, R. L.; Goltry, L.; Tolentino, E.; Westbrock-Wadman, S.; Yuan, Y.; Brody, L. L.; Coulter, S. N.; Folger, K. R.; Kas, A.; Larbig, K.; Lim, R.; Smith, K.; Spencer, D.; Wong, G. K.; Wu, Z.; Paulsen, I. T.; Reizer, J.; Saieri, M. H.; Hancock, R. E.; Lory, S.; Olson, M. V. *Nature* 2000, 406, 959-64.
(13) Perna, N. T.; Plunkett, G., 3rd; Burland, V.; Mau, B.; Glasner, J. D.; Rose, D. J.; Mayhew, G. F.; Evans, P. S.; Gregor, J.; Kirkpatrick, H. A.; Posfai, G.; Hackett, J.; Klink, S.; Boutin, A.; Shao, Y.; Miller, L.; Grotbeck, E. J.; Davis, N. W.; Lim, A.; Dimalanta, E. T.; Potamousis, K. D.; Apodaca, J.; Anantharaman, T. S.; Lin, J.; Yen, G.; Schwartz, D. C.; Welch, R. A.; Blattner, F. R. *Nature* 2001, 409, 529-33.
(14) Kuroda, M.; Ohta, T.; Uchiyama, I.; Baba, T.; Yuzawa, H.; Kobayashi, I.; Cui, L.; Oguchi, A.; Aoki, K.; Nagai, Y.; Lian, J.; Ito, T.; Kanamori, M.; Matsumaru, H.; Maruyama, A.; Murakami, H.; Hosoyama, A.; Mizutani-Ui, Y.; Takahashi, N. K.; Sawano, T.; Inoue, R.; Kaito, C.; Sekimizu, K.; Hirakawa, H.; Kuhara, S.; Goto, S.; Yabuzaki, J.; Kanehisa, M.; Yamashita, A.; Oshima, K.; Furuya, K.; Yoshino, C.; Shiba, T.; Hattori, M.; Ogasawara, N.; Hayashi, H.; Hiramatsu, K. *Lancet* 2001, 357, 1225-40.
(15) Payne, D. J.; Wallis, N. G.; Gentry, D. R.; Rosenberg, M. *Curr. Opin. Drug Discovery & Development* 2000, 3, 177-90.
(16) Searls, D. B. *Drug Discovery Today* 2000, 5, 135-143.
(17) Moir, D. T.; Shaw, K. J.; Hare, R. S.; Vovis, G. F. *Antimicrob. Agents Chemother.* 1999, 43, 439-46.
(18) Loferer, H. *Mol. Med. Today* 2000, 6, 470-4.
(19) Dessen, A.; Mouz, N.; Gordon, E.; Hopkins, J.; Dideberg, O. *J. Biol. Chem.* 2001, 276, 45106-12.
(20) Dowson, C. G.; Hutchison, A.; Brannigan, J. A.; George, R. C.; Hansman, D.; Linares, J.; Tomasz, A.; Smith, J. M.; Spratt, B. G. *Proc. Natl. Acad. Sci. USA* 1989, 86, 8842-6.
(21) Severin, A.; Figueiredo, A. M. S.; Tomasz, A. *J. Bacteriol.* 1996, 178, 1788-92.
(22) Bush, K.; Jacoby, G. A.; Medeiros, A. A. *Antimicrob. Agents Chemother.* 1995, 39, 1211-33.
(23) Swaren, P.; Golemi, D.; Cabantous, S.; Bulychev, A.; Maveyraud, L.; Mobashery, S.; Samama, J. P. *Biochemistry* 1999, 38, 9570-6.
(24) Blanpain, P. C.; Nagy, J. B.; Laurent, G. H.; Durant, F. V. *J. Med. Chem.* 1980, 23, 1283-92.
(25) Lee, W.; McDonough, M. A.; Kotra, L. P.; Li, Z.-H.; Silvaggi, N. R.; Takeda, Y.; Kelly, J. A.; Mobashery, S. *Proc. Natl. Acad. Sci. USA* 2001, 98, 1427-31.
(26) McCormick, M., Stark, W. M., Pittenger, G. E., Pittenger, R. C. and McGuire, J. M.; Welch, H. a. M.-I., F., Ed.; Medical Encyclopedia: New York, 1956, p 606-11.
(27) Griffith, R. S. a. P., F. GB.; Welsh, H. a. M.-I., F., Ed.; Medical Encyclopedia: New York, 1956, p 619-22.
(28) Anderson, R. C., Worth, H. M., Harris, P. N., and Chen, K. K.; Welch, H. a. M.-I., F., Ed.; Medical Encyclopedia: New York, 1957, p 75-81.
(29) Harris, C. M.; Harris, T. M. *J. Am. Chem. Soc.* 1982, 104, 4293-5.
(30) Marshall, F. J. *J. Med. Chem.* 1965, 8, 18-22.
(31) Williams, D. H.; Kalman, J. *J. Am. Chem. Soc.* 1977, 99, 2768-74.
(32) Sheldrick, G. M.; Jones, P. G.; Kennard, O.; Williams, D. H.; Smith, G. A. *Nature* 1978, 271, 223-5.
(33) Kaplan, J.; Korty, B. D.; Axelsen, P. H.; Loll, P. J. *J. Med. Chem.* 2001, 44, 1837-40.
(34) Ge, M.; Chen, Z.; Onishi, H. R.; Kohler, J.; Silver, L. L.; Kerns, R.; Fukuzawa, S.; Thompson, C.; Kahne, D. *Science* 1999, 284, 507-11.
(35) Williams, D. H., Westwell, M. S., Beauregard, D. A., Sharman, G. J., Dancer, R. J., Try, A. C., and Bardsley, B. in *Anti-infectives. Recent Advances in Chemistry and Structure Activity Relationships* (Bently, P. H.; O'HAnlon, P. J.) Royal Society of Chem., Cambridge., 1997, p 3-14.
(36) Williams, D. H.; Williamson, M. P.; Butcher, D. W.; Hammond, S. J. *J. Am. Chem. Soc.* 1983, 105, 1332-9.
(37) Gale, T. F.; Gorlitzer, J.; O'Brien, S. W.; Williams, D. H. *J. Chem. Soc., Perkin Trans.* 1 1999, 2267-70.
(38) Wright, G. D.; Walsh, C. T. *Acc. Chem. Res.* 1992, 25, 468-73.
(39) Gold, H. S.; Moellering, R. C., Jr. *New Engl. J. Med.* 1996, 335, 1445-53.
(40) Sussmuth, R. D. *Chem Bio Chem* 2002, 3, 295-8.
(41) Beauregard, D. A.; Williams, D. H.; Gwynn, M. N.; Knowles, D. J. *Antimicrob. Agents Chemother.* 1995, 39, 781-5.
(42) Westwell, M. S.; Gerhard, U.; Williams, D. H. *J. Antibiot.* 1995, 48, 1292-8.
(43) Slee, A. M.; Wuonola, M. A.; McRipley, R. J.; Zajac, I.; Zawada, M. J.; Bartholomew, P. T.; Gregory, W. A.; Forbes, M. *Antimicrob. Agents Chemother.* 1987, 31, 1791-7.
(44) Nicas, T. I.; Zeckel, M. L.; Braun, D. K. *Trends Microbiol.* 1997, 5, 240-9.
(45) Eliopoulos, G. M.; Wennersten, C. B.; Gold, H. S.; Moellering, R. C., Jr. *Antimicrob. Agents Chemother.* 1996, 40, 1745-7.
(46) Ford, C. W.; Hamel, J. C.; Stapert, D.; Moerman, J. K.; Hutchinson, D. K.; Barbachyn, M. R.; Zurenko, G. E. *Trends Microbiol.* 1997, 5, 196-200.
(47) Ford, C. W.; Hamel, J. C.; Wilson, D. M.; Moerman, J. K.; Stapert, D.; Yancey, R. J., Jr.; Hutchinson, D. K.; Barbachyn, M. R.; Brickner, S. J. *Antimicrob. Agents Chemother.* 1996, 40, 1508-13. 2416-9.
(51) Jones, R. N.; Barrett, M. S.; Erwin, M. E. *Antimicrob. Agents Chemother.* 1997, 41, 488-93.
(52) Zelenitsky, S. A.; Karlowsky, J. A.; Zhanel, G. G.; Hoban, D. J.; Nicas, T. *Antimicrob. Agents Chemother.* 1997, 41, 1407-8.
(53) Baltch, A. L.; Smith, R. P.; Ritz, W. J.; Bopp, L. H. *Antimicrob. Agents Chemother.* 1998, 42, 2564-8.
(54) Kems, R.; Dong, S. D.; Fukuzawa, S.; Carbeck, J.; Kohler, J.; Silver, L.; Kahne, D. *J. Am. Chem. Soc.* 2000, 122, 12608-9.
(55) Ge, M.; Chen, Z.; Onishi, H. R.; Kohler, J.; Silver, L. L.; Kems, R.; Fukuzawa, S.; Thompson, C.; Kahne, D. *Science* 1999, 284, 507-11.
(56) Van Heijenoort, J. *Glycobiol.* 2001, 11, 25R-36R.
(57) Wang, Q. M.; Peery, R. B.; Johnson, R. B.; Albom, W. E.; Yeh, W. K.; Skatrud, P. L. *J. Bacteriol.* 2001, 183, 4779-85.
(58) Sundram, U. N.; Griffin, J. H.; Nicas, T. I. *J. Am. Chem. Soc.* 1996, 118, 13107-8.
(59) Hinzen, B.; Seiler, P.; Diederich, F. *Helv. Chim. Acta.* 1996, 79, 942-60.
(60) Xu, R.; Greiveldinger, G.; Marenus, L. E.; Cooper, A.; Ellman, J. A. *J. Am. Chem. Soc.* 1999, 121, 4898-9.
(61) Miller, C. T.; Weragoda, R.; Izbicka, E.; Iverson, B. L. *Bioorg. Med. Chem.* 2001, 9, 2015-24.
(62) Monnee, M. C. F.; Brouwer, A. J.; Verbeek, L. M.; van Wageningen, A. M. A.; Liskamp, R. M. J. *Bioorg. Med. Chem. Lett.* 2001, 11, 1521-5.
(63) Chiosis, G.; Boneca, I. G. *Science* 2001, 293, 1484-7.
(64) Hoffmann, J. A.; Kafatos, F. C.; Janeway, C. A.; Ezekowitz, R. A. *Science* 1999, 284, 1313-8.
(65) Thennarasu, S.; Nagaraj, R. *Biochem. Biophys. Res. Commun.* 1999, 254, 281-283.
(66) Saido-Sakanaka, H.; Ishibashi, J.; Sagisaka, A.; Momotani, E.; Yamakawa, M. *Biochem. J.* 1999, 338, 29-33.
(67) Tossi, A.; Tarantino, C.; Romeo, D. *Eur. J. Biochem.* 1997, 250, 549-58.
(68) Strom, M. B.; Rekdal, O.; Svendsen, J. S. *J. Pept. Res.* 2000, 56, 265-74.
(69) Haug, B. E.; Svendsen, J. S. *J. Pept. Sci.* 2001, 7, 190-6.
(70) Haug, B. E.; Skar, M. L.; Svendsen, J. S. *J. Pept. Sci.* 2001, 7, 425-32.
(71) Strom, M. B.; Rekdal, O.; Svendsen, J. S. *J. Pept. Sci.* 2002, 8, 431-7.
(72) Strom, M. B.; Haug, B. E.; Skar, M. L.; Stensen, W.; Stiberg, T.; Svendsen, J. S. *J. Med. Chem.* 2003, 46, 1567-70.
(73) Mosca, D. A.; Hurst, M. A.; So, W.; Viajar, B. S.; Fujii, C. A.; Falla, T. J. *Antimicrob. Agents Chemother.* 2000, 44, 1803-8.
(74) Toney, J. H. *Cur. Opin. Invest. Drugs* 2002, 3, 225-8.
(75) Oh, H.-S.; Kim, S.; Cho, H.; Lee, K.-H. *Bioorg. Med. Chem. Lett.* 2004, 14, 1109-13.

(76) Houghten, R. A.; Pinilla, C.; Blondelle, S. E.; Appel, J. R.; Dooley, C. T.; Cuervo, J. H. *Nature* 1991, 354, 84-6.
(77) Abiraj, K.; Prakasha Gowda, A. S.; Channe Gowda, D. *Lett. Pept. Sci.* 2003, 9, 283-90.
(78) Bremner, J. B.; Coates, J. A.; Coghlan, D. R.; David, D. M.; Keller, P. A.; Pyne, S. G. *N. J. Chem.* 2002, 26, 1549-51.
(79) Bremner, J. B.; Coates, J. A.; Keller, P. A.; Pyne, S. G.; Witchard, H. M. *Synlett* 2002, 219-22.
(80) Bremner, J. B.; Coates, J. A.; Keller, P. A.; Pyne, S. G.; Witchard, H. M. *Tetrahedron* 2003, 59, 8741-55.
(81) Bremner, J. B.; Pyne, S. G.; Keller, P. A.; Coghlan, D. R., *Personal Communication.*
(82) McGrady, K. A. W.; Overberger, C. G. *Polymer J.* 1987, 19, 539-55.
(83) Gamet, J. P.; Jacquier, R.; Verducci, J. *Tetrahedron* 1984, 40, 1995-2001.
(84) Luening, B.; Norberg, T.; Tejbrant, J. *Chem. Commun.* 1989, 1267-8.
(85) Schuster, M.; Blechert, S. *Angew. Chem. Int. Ed.* 1997, 36, 2037-56.
(86) Trnka, T. M.; Grubbs, R. H. *Acc. Chem. Res.* 2001, 34, 18-29.
(87) Brummer, O.; Ruckert, A.; Blechert, S. *Chem. Europ. J.* 1997, 3, 441-6.
(88) Grubbs, R. H.; Miller, S. J.; Blackwell, H. E.; (California Institute of Technology, USA). Application: US, 1998, 21 pp.
(89) Miller, S. J.; Blackwell, H. E.; Grubbs, R. H. *J. Am. Chem. Soc.* 1996, 118, 9606-14.
(90) Miller, S. J.; Grubbs, R. H. *J. Am. Chem. Soc.* 1995, 117, 5855-6.
(91) Feichtinger, K.; Zapf, C.; Sings, H. L.; Goodman, M. *J. Org. Chem.* 1998, 63, 3804-5.
(92) Weerapana, E.; Imperiali, B. *Org. Biomol. Chem.* 2003, 1, 93-9.
(93) Lei, H.; Stoakes, M. S.; Schwabacher, A. W.; Herath, K. P. B.; Lee, J. *J. Org. Chem.* 1994, 59, 4206-10.
(94) Morera, E.; Ortar, G. *Synlett* 1997, 1403-5.
(95) Wilbur, D. S.; Hamlin, D. K.; Srivastava, R. R.; Burns, H. D. *Biocon. Chem.* 1993, 4, 574-80.
(96) Stille, J. K. *Angew. Chem.* 1986, 98, 504-19.
(97) Burke, T. R., Jr.; Fesen, M. R.; Mazumder, A.; Wang, J.; Carothers, A. M.; Grunberger, D.; Driscoll, J.; Kohn, K.; Pommier, Y. *J. Med. Chem.* 1995, 38, 4171-8.
(98) Yi, J.; Arthur, J. W.; Dunbrack, R. L., Jr.; Skalka, A. M. *J. Biol. Chem.* 2000, 275, 38739-48.
(99) Andrake, M. D.; Skalka, A. M. *J. Biol. Chem.* 1996, 271, 19633-6.
(100) O'Brien, C. *Science* 1994, 266, 1946.
(101) Hickman, A. B.; Palmer, I.; Engelman, A.; Craigie, R.; Wingfield, P. *J. Biol. Chem.* 1994, 269, 29279-87.
(102) Goldgur, Y.; Craigie, R.; Cohen, G. H.; Fujiwara, T.; Yoshinaga, T.; Fujishita, T.; Sugimoto, H.; Endo, T.; Murai, H.; Davies, D. R. *Proc. Natl. Acad. Sci. USA* 1999, 96, 13040-3.
(103) Modelling studies were performed by AMRAD in collaboration with the Victorian College of Pharmacy. For experimental details and docking procedures see: Wielens, J. PhD Thesis, Victorian College of Pharmacy (Monash University), 2004.
(104) van Benthem, R. A. T. M.; Michels, J. J.; Hiemstra, H.; Speckamp, W. N. *Synlett* 1994, 368-70.
(105) Beaulieu, P. L.; Schiller, P. W. *Tetrahedron Lett.* 1988, 29, 2019-22.
(106) Dong, Z. *Tetrahedron Lett.* 1992, 33, 7725-6.
(107) Hwang, Y.; Rhodes, D.; Bushman, F. *Nucl. Acids Res.* 2000, 28, 4884-92.
(108) Nieto, M.; Perkins, H. R. *Biochem. J.* 1971, 123, 789-803.
(109) Mackay, J. P.; Gerhard, U.; Beauregard, D. A.; Williams, D. H.; Westwell, M. S.; Searle, M. S. *J. Am. Chem. Soc.* 1994, 116, 4581-90.
(110) Linsdell, H.; Toiron, C.; Bruix, M.; Rivas, G.; Menendez, M. *J. Antibiot.* 1996, 49, 181-93.
(111) Searle, M. S.; Sharman, G. J.; Groves, P.; Benhamu, B.; Beauregard, D. A.; Westwell, M. S.; Dancer, R. J.; Maguire, A. J.; Try, A. C.; Williams, D. H. *J. Chem. Soc., Perkin Trans.* 1 1996, 2781-6.
(112) Dancer, R. J.; Try, A. C.; Sharman, G. J.; Williams, D. H. *Chem. Commun.* 1996, 1445-6.
(113) Allen, N. E.; LeTourneau, D. L.; Hobbs, J. N., Jr. *Antimicrob. Agents Chemother.* 1997, 41, 66-71.
(114) Barna, J. C. J.; Williams, D. H.; Williamson, M. P. *Chem. Commun.* 1985, 254-6.
(115) Williamson, M. P.; Williams, D. H.; Hammond, S. J. *Tetrahedron* 1984, 40, 569-77.
(116) Rodriguez-Tebar, A.; Vazquez, D.; Perez Velazquez, J. L.; Laynez, J.; Wadso, I. *J. Antibiot.* 1986, 39, 1578-83.
(117) Jorgensen, T. J. D.; Staroske, T.; Roepstorff, P.; Williams, D. H.; Heck, A. J. R. *J. Chem. Soc., Perkin Trans.* 2 1999, 1859-63.
(118) Jorgensen, T. J. D.; Roepstorff, P.; Heck, A. J. R. *Anal. Chem.* 1998, 70, 4427-32.
(119) Van de Kerk-Van Hoof, A.; Heck, A. J. R. *J. Antimicrob. Chemother.* 1999, 44, 593-9.
(120) Perrin, D. D. A., W. L. F. *Purification of Laboratory Chemicals;* 3rd ed.; Pergamon Press Ltd.: Oxford, 1988.
(121) Hellwinkel, D. *Systematic Nomenclature of Organic Chemistry;* 1st ed.; Springer: Berlin, 2001.
(122) Tous, G.; Bush, A.; Tous, A.; Jordan, F. *J. Med. Chem.* 1990, 33, 1620-34.
(123) Meyer, L.; Poirier, J.-M.; Duhamel, P.; Duhamel, L. *J. Org. Chem.* 1998, 63, 8094-5.
(124) Pearson, A. J.; Bruhn, P. R. *J. Org. Chem.* 1991, 56, 7092-7.
(125) Pirrung, M. C.; Shuey, S. W. *J. Org. Chem.* 1994, 59, 3890-7.
(126) Erickson, S. D.; Simon, J. A.; Still, W. C. *J. Org. Chem.* 1993, 58, 1305-8.
(127) Ma, D.; Tang, W.; Kozikowski, A. P.; Lewin, N. E.; Blumberg, P. M. *J. Org. Chem.* 1999, 64, 6366-73.
(128) Abbott, S. D.; Lane-Bell, P.; Sidhu, K. P. S.; Vederas, J. C. *J. Am. Chem. Soc.* 1994, 116, 6513-20.

The invention claimed is:
1. A compound of formula Ia

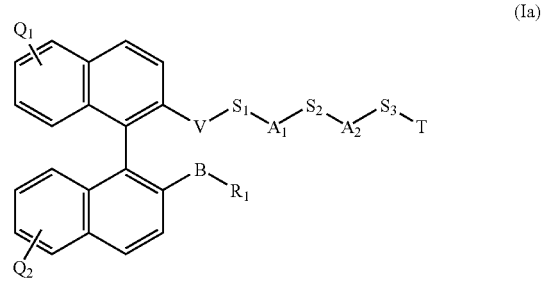

or a pharmaceutically acceptable salt thereof, wherein $Q_1$ and $Q_2$ are each independently selected from hydrogen, $C_1$-$C_{12}$alkyl, $C_3$-$C_6$cycloalkyl, $C_1$-$C_{12}$alkyloxy, nitro, halogen, hydroxyl, amino, mono or dialkylamino, carboxylic acid or a salt or ester thereof, sulphonic acid or a salt or ester thereof, phosphoric acid or a salt or ester thereof, carboxamide, sulphonamide and phosphoramide wherein each $C_1$-$C_{12}$alkyl, $C_3$-$C_6$cycloalkyl, or $C_1$-$C_{12}$alkyloxy is optionally substituted with hydroxyl, amino, carboxylic acid or a salt or ester thereof, sulphonic acid or a salt or ester thereof, phosphoric acid or a salt or ester thereof, or carboxamide, sulphonamide or phosphoramide;

B is selected from —O—, —S—, —S(O)—, —S(O)$_2$—, —NH—, and —N($C_1$-$C_6$alkyl)-;

$R_1$ is selected from hydrogen, $C_1$-$C_{12}$alkyl, $C_1$-$C_6$alkyl$C_3$-$C_6$cycloalkyl, $C_1$-$C_6$alkyl$C_6$-$C_{10}$aryl, $C_2$-$C_6$alkenyl, $C_2$-$C_6$alkynyl, a polyoxyalkylene having from 2 to 6 carbon atoms, and when B is —S—, —S(O)—, —S(O)$_2$—, —NH— or —N($C_1$-$C_6$alkyl)- then $R_1$ may be hydroxyl;

V is a linker group selected from —O—, —O-L-C(O), —O-L-N$R_6$—, —C(O)—, —N$R_6$—, —S(O)—, —S(O)$_2$—, —O-L-S(O)—, —S(O)$_2$-L-C(O)—, —S(O)$_2$-L-N$R_6$—, P(O)$_2$O—;

wherein L is selected from $C_1$-$C_{12}$alkyl, $C_2$-$C_8$ alkenyl, $C_3$-$C_6$cycloalkyl, polyoxyalkylene having from 2 to 6 carbon atoms, $C_6$-$C_{10}$aryl and $C_1$-$C_6$alkyl$C_6$-$C_{10}$aryl; and wherein $R_6$ is selected from H and $C_1$-$C_{12}$alkyl;

$S_1$ and $S_2$ are absent;

$A_1$ is lysine or ornithine;

$A_2$ is arginine;

$S_3$ is an amino acid; and

T is absent or is selected from —C(O)$R_8$, —C(O)O$R_8$, —O$R_8$, —NH$R_8$, NHO$R_8$, —NH—$C_6$aryl-CO—$R_8$, —NH—$C_6$aryl-CO—NH$R_8$, —NH—$C_6$aryl-CONHO$R_8$, —NH—$C_6$aryl-CONHOH, —C(O)NH$R_8$, —(NH)—SO$_2$$C_6$aryl, and —(NH)CO$R_8$, or T forms a carboxylate isostere, optionally substituted with $R_8$, which replaces the carboxylic acid group of the amino acid to which T is connected;

wherein $R_8$ is selected from hydrogen, $C_1$-$C_{12}$alkyl, $C_1$-$C_6$alkyl$C_6$-$C_{10}$aryl, $C_1$-$C_6$alkyl$C_3$-$C_6$cycloalkyl, $C_2$-$C_6$alkenyl and $C_2$-$C_6$alkynyl; and wherein when T is connected to the C-terminus of an amino acid residue then the carbonyl group of the amino acid residue may be reduced to methylene.

2. A compound of formula Ib

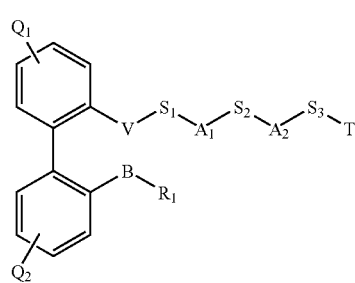

(1b)

or a pharmaceutically acceptable salt thereof, wherein $Q_1$ and $Q_2$ are each independently selected from hydrogen, $C_1$-$C_{12}$alkyl, $C_3$-$C_6$cycloalkyl, $C_1$-$C_{12}$alkyloxy, nitro, halogen, hydroxyl, amino, mono or dialkylamino, carboxylic acid or a salt or ester thereof, sulphonic acid or a salt or ester thereof, phosphoric acid or a salt or ester thereof, carboxamide, sulphonamide and phosphoramide wherein each $C_1$-$C_{12}$alkyl, $C_3$-$C_6$cycloalkyl, or $C_1$-$C_{12}$alkyloxy is optionally substituted with hydroxyl, amino, carboxylic acid or a salt or ester thereof, sulphonic acid or a salt or ester thereof, phosphoric acid or a salt or ester thereof, or carboxamide, sulphonamide or phosphoramide;

B is selected from —O—, —S—, —S(O)—, —S(O)$_2$—, —NH—, and —N($C_1$-$C_6$alkyl)-;

$R_1$ is selected from hydrogen, $C_1$-$C_{12}$alkyl, $C_1$-$C_6$alkyl$C_3$-$C_6$cycloalkyl, $C_1$-$C_6$alkyl$C_6$-$C_{10}$aryl, $C_2$-$C_6$alkenyl, $C_2$-$C_6$alkynyl, a polyoxyalkylene having from 2 to 6 carbon atoms, and when B is —S—, —S(O)—, —S(O)$_2$—, —NH— or —N($C_1$-$C_6$alkyl)- then $R_1$ may be hydroxyl;

V is a linker group selected from —O—, —O-L-C(O), —O-L-N$R_6$—, —C(O)—, —N$R_6$—, —S(O)—, —S(O)$_2$—, —O-L-S(O)—, —S(O)$_2$-L-C(O)—, —S(O)$_2$-L-N$R_6$—, P(O)$_2$O—;

wherein L is selected from $C_1$-$C_{12}$alkyl, $C_2$-$C_8$ alkenyl, $C_3$-$C_6$cycloalkyl, polyoxyalkylene having from 2 to 6 carbon atoms, $C_6$-$C_{10}$aryl and $C_1$-$C_6$alkyl$C_6$-$C_{10}$aryl; and wherein $R_6$ is selected from H and $C_1$-$C_{12}$alkyl;

$S_1$ and $S_2$ are absent;

$A_1$ is lysine or ornithine;

$A_2$ is arginine;

$S_3$ is an amino acid; and

T is absent or is selected from —C(O)$R_8$, —C(O)O$R_8$, —O$R_8$, —NH$R_8$, NHO$R_8$, —NH—$C_6$aryl-CO—$R_8$, —NH—$C_6$aryl-CO—NH$R_8$, —NH—$C_6$aryl-CONHO$R_8$, —NH—$C_6$aryl-CONHOH, —C(O)NH$R_8$, —(NH)—SO$_2$$C_6$aryl, and —(NH)CO$R_8$, or T forms a carboxylate isostere, optionally substituted with $R_g$, which replaces the carboxylic acid group of the amino acid to which T is connected;

wherein $R_8$ is selected from hydrogen, $C_1$-$C_{12}$alkyl, $C_1$-$C_6$alkyl$C_6$-$C_{10}$aryl, $C_1$-$C_6$alkyl$C_3$-$C_6$cycloalkyl, $C_2$-$C_6$alkenyl and $C_2$-$C_6$alkynyl; and wherein when T is connected to the C-terminus of an amino acid residue then the carbonyl group of the amino acid residue may be reduced to methylene.

3. A compound selected from the group consisting of compounds 1-30, or a pharmaceutically acceptable salt thereof, wherein compounds 1-30 are as follows:
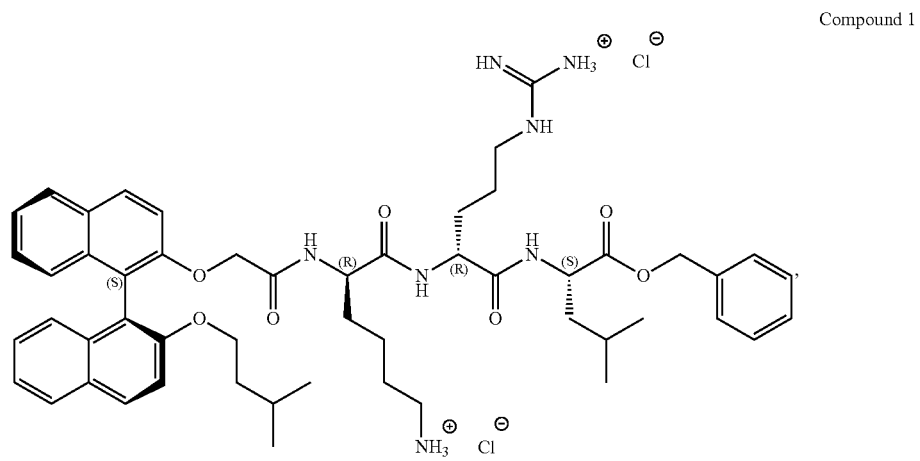
Compound 1
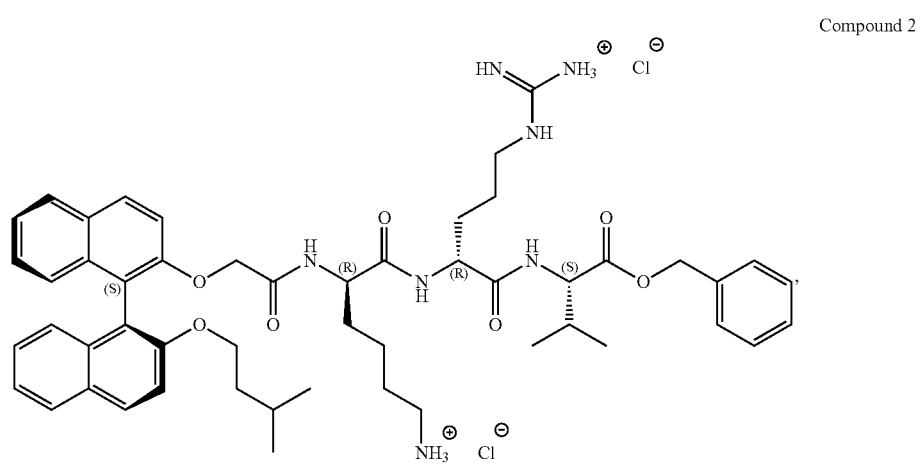
Compound 2
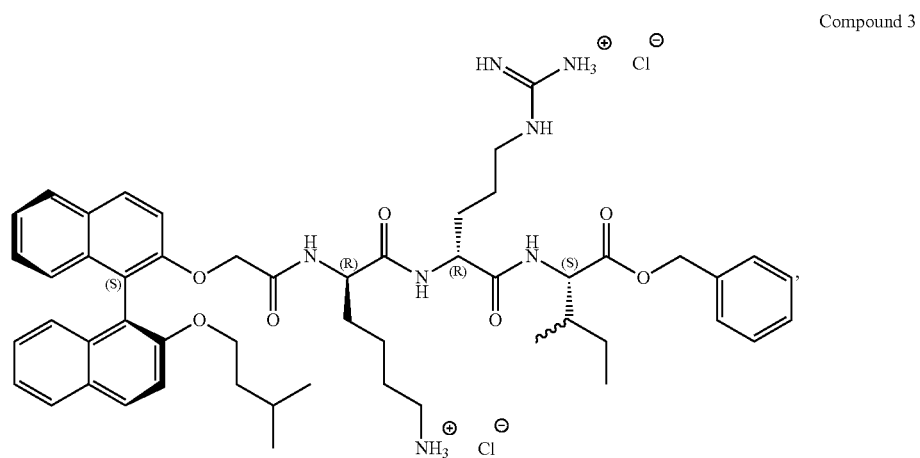
Compound 3

Compound 4
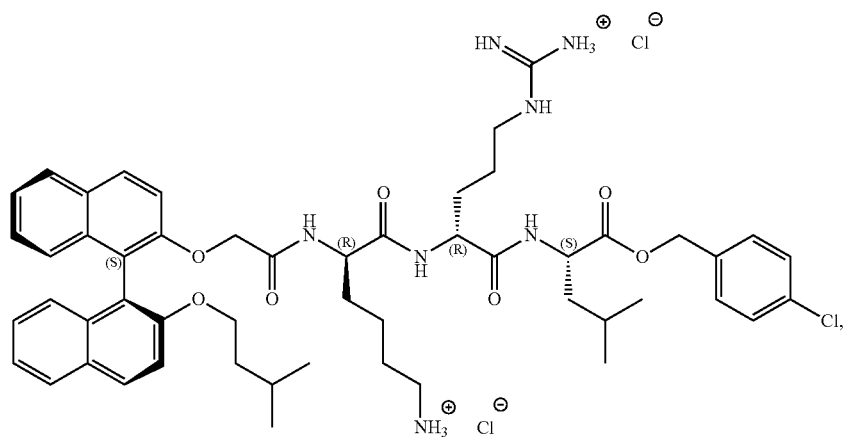
Compound 5
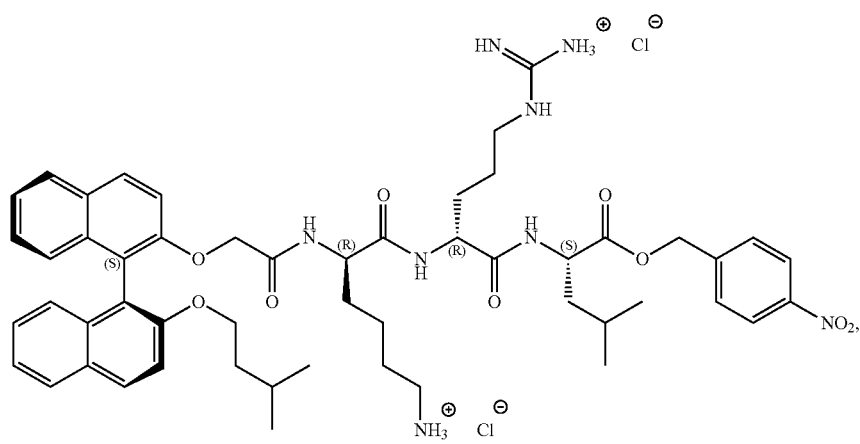
Compound 6
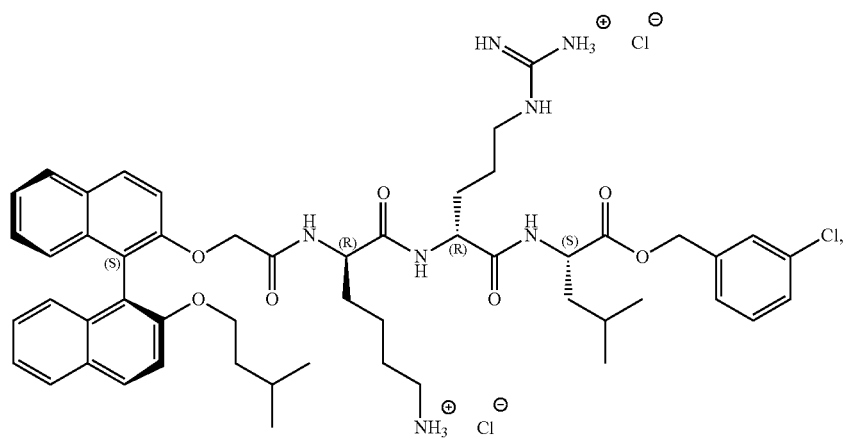

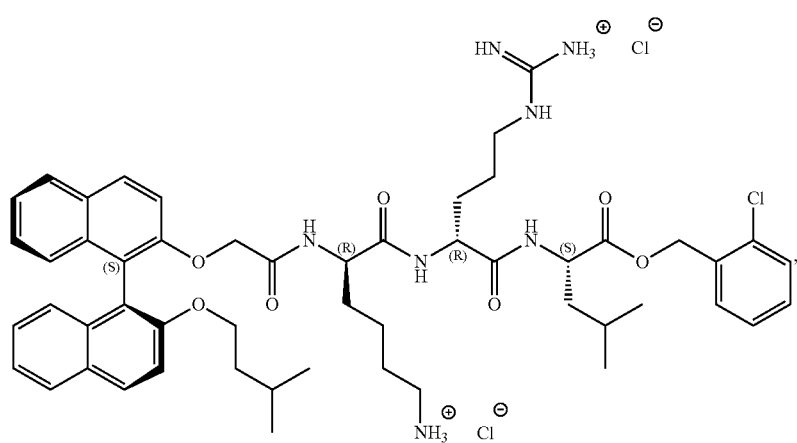
Compound 7
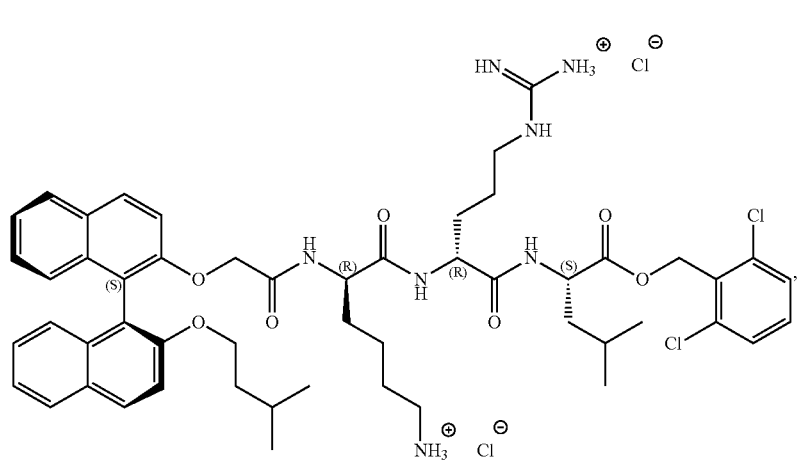
Compound 8
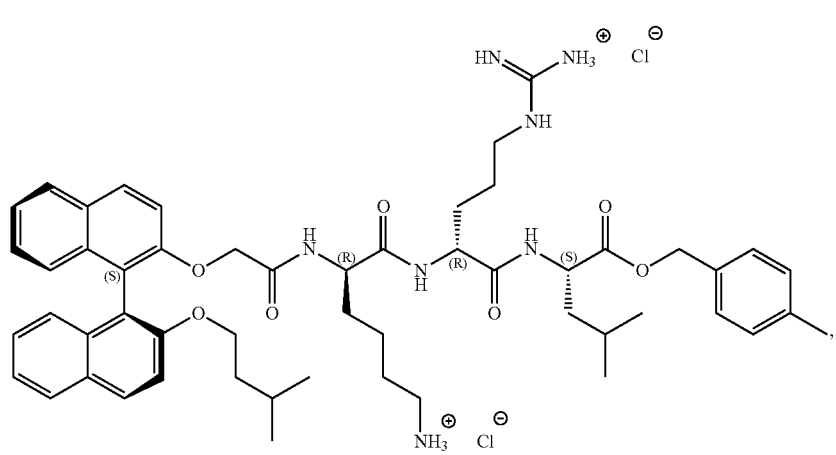
Compound 9

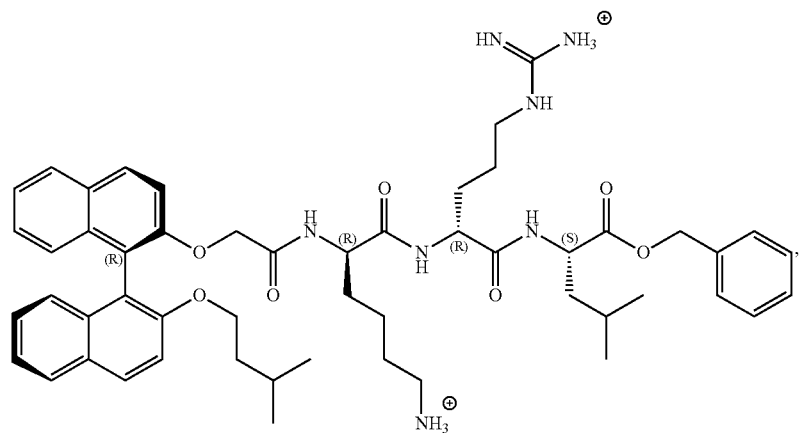
Compound 10
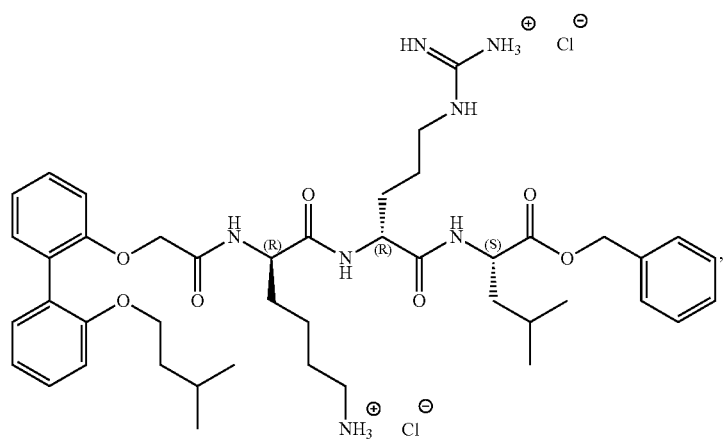
Compound 11
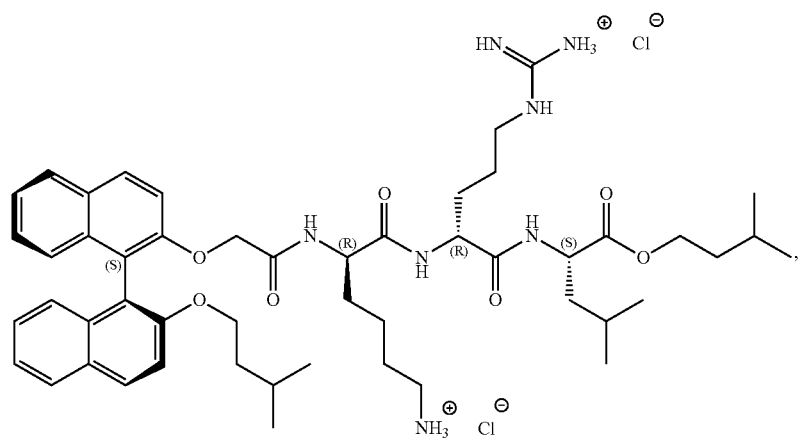
Compound 12

-continued
Compound 13
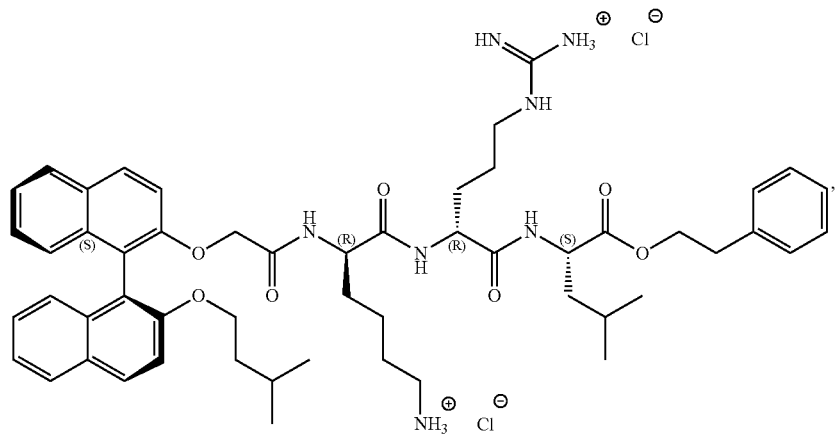
Compound 14
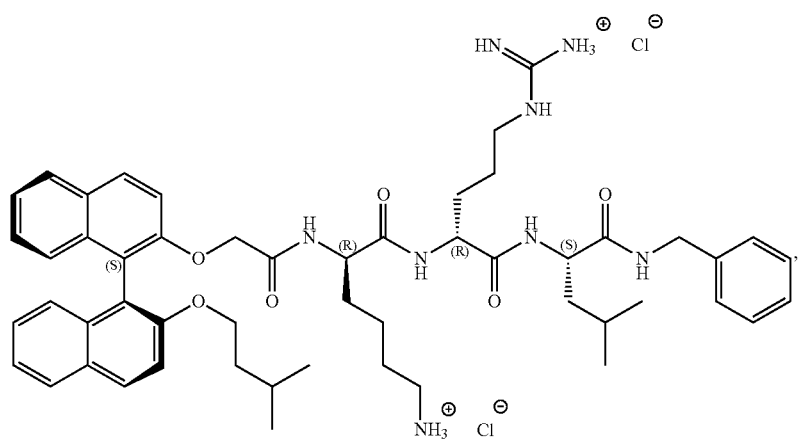
Compound 15
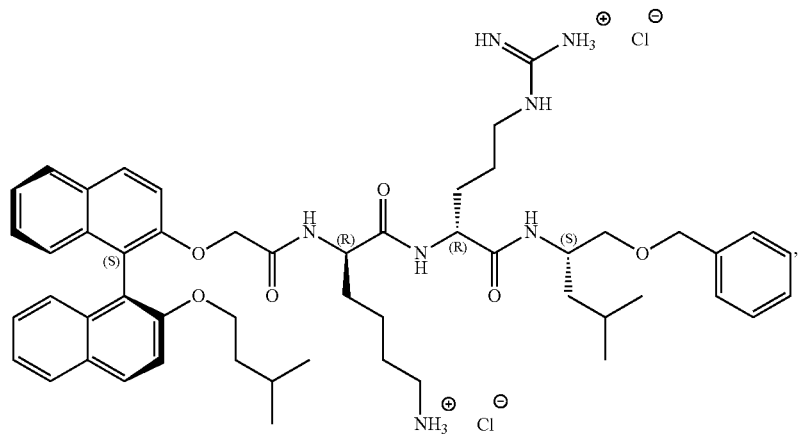

Compound 16
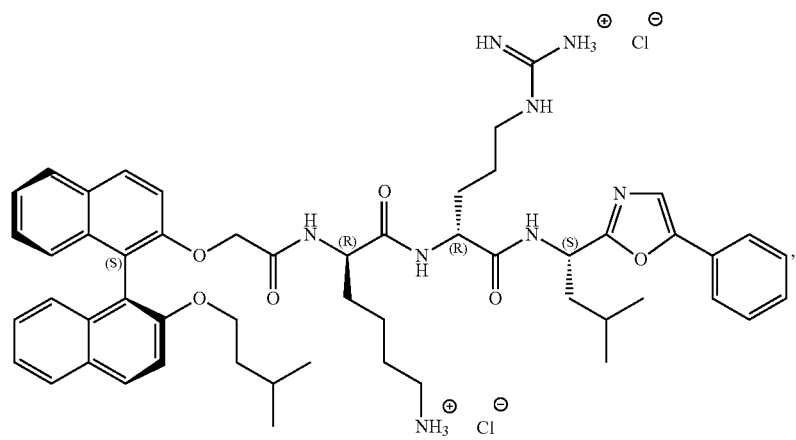
Compound 17
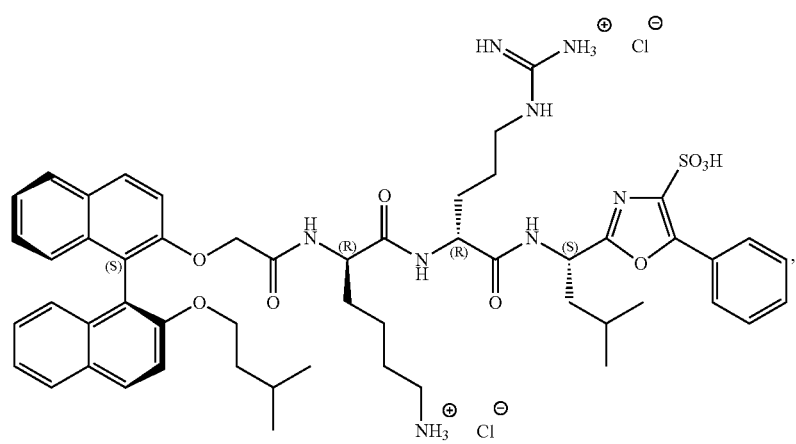
Compound 18
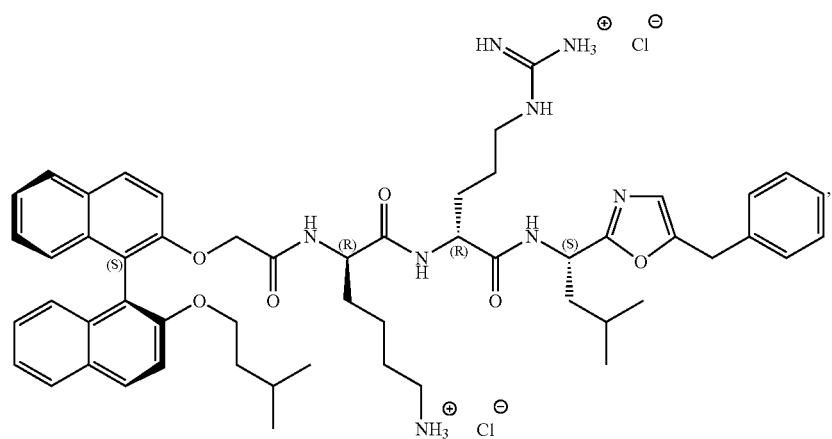

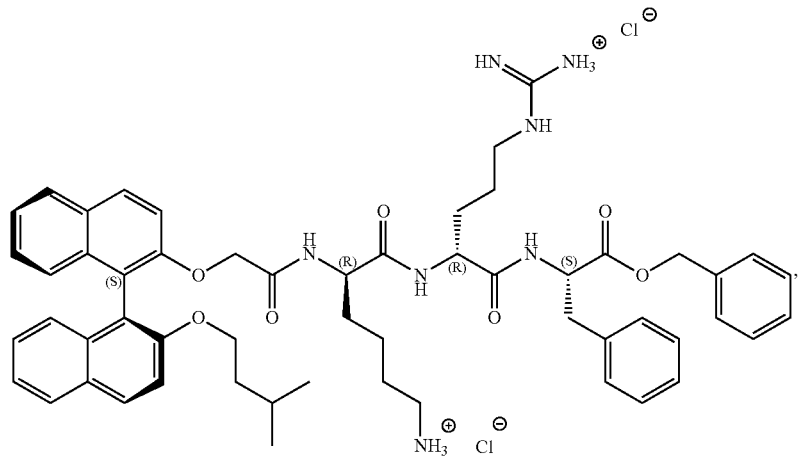
Compound 19
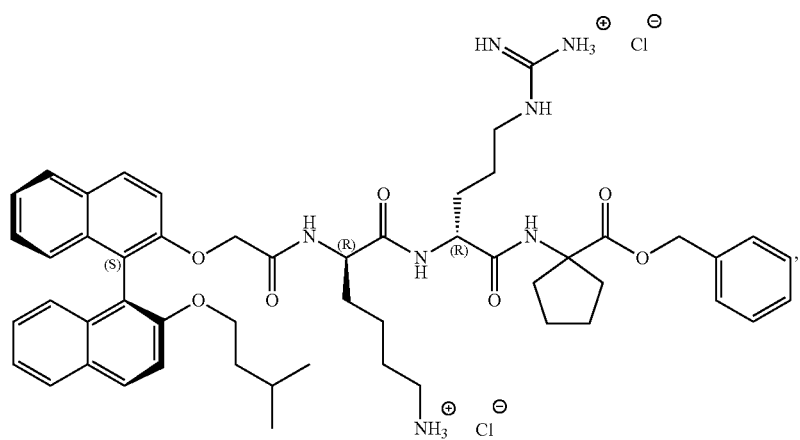
Compound 20
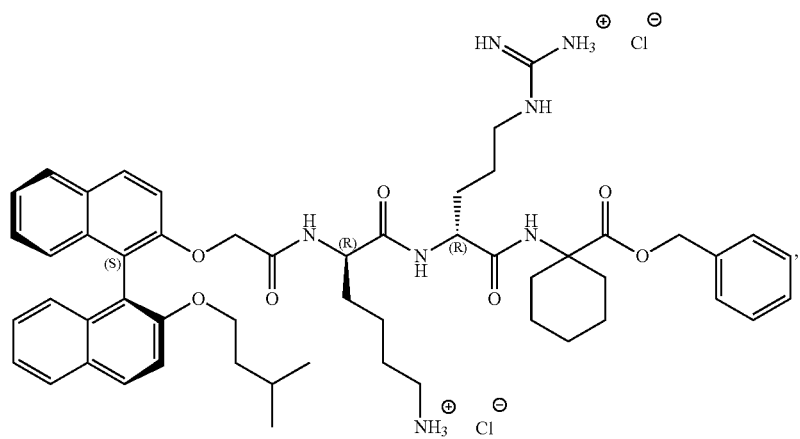
Compound 21

-continued
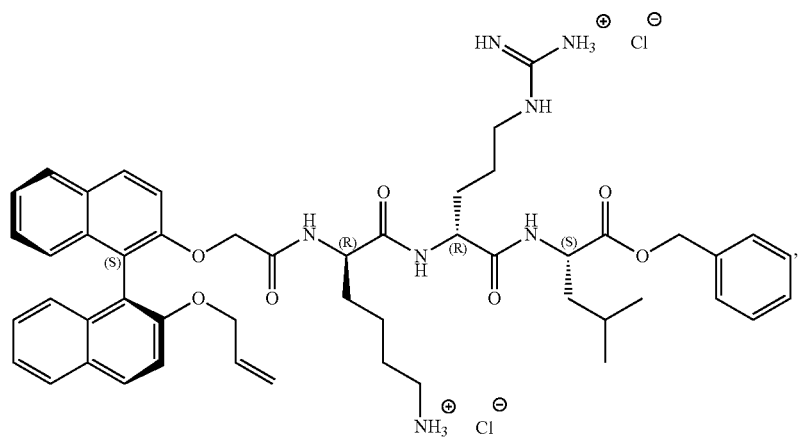
Compound 22
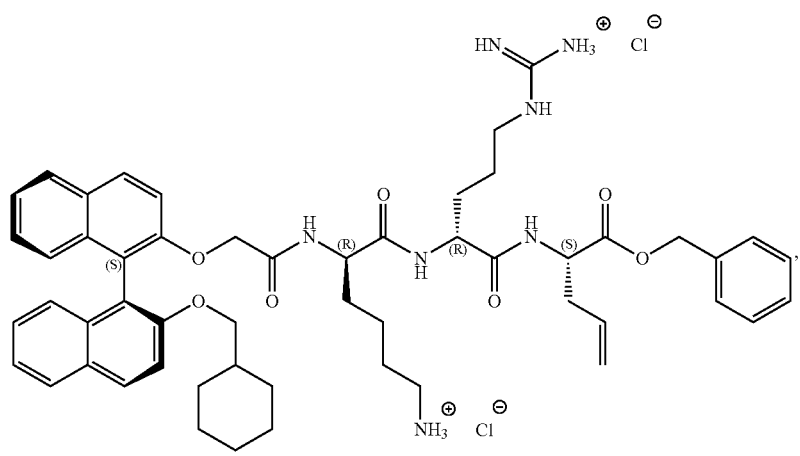
Compound 23
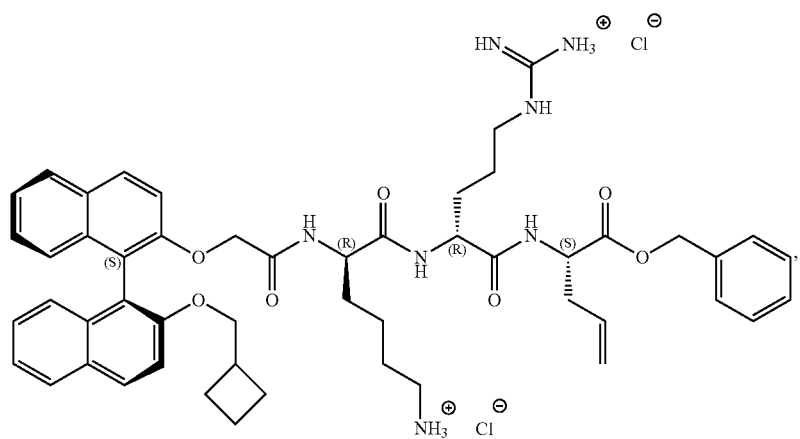
Compound 24

-continued
Compound 25
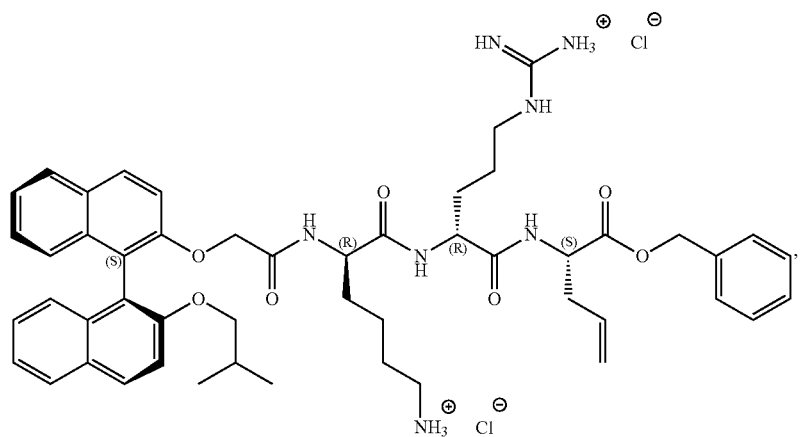
Compound 26
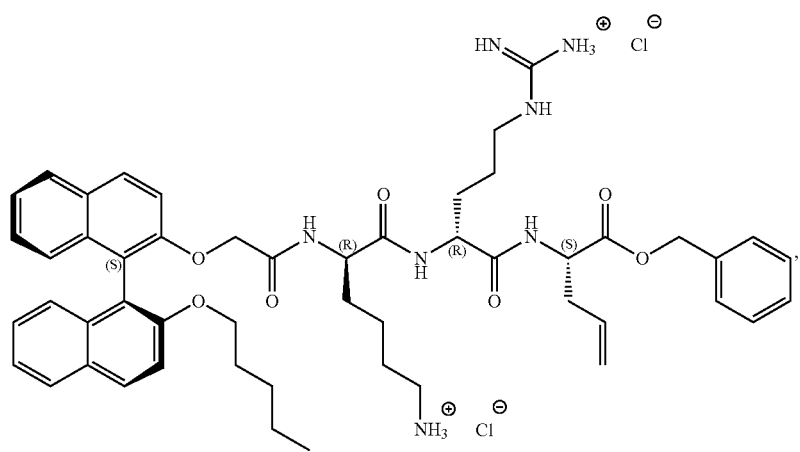
Compound 27
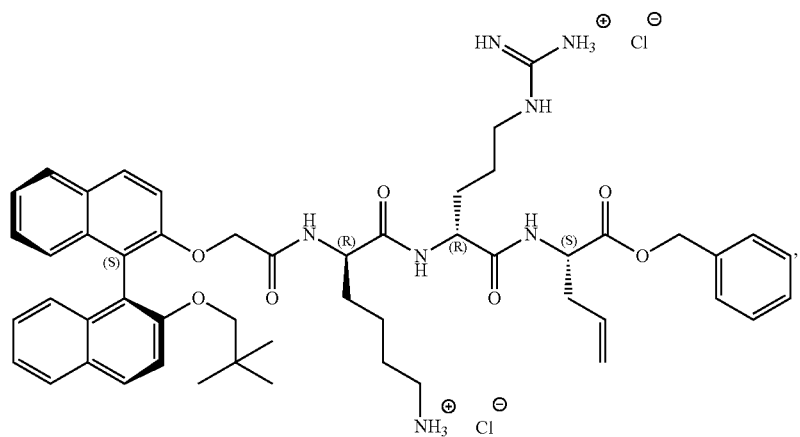

-continued

Compound 28

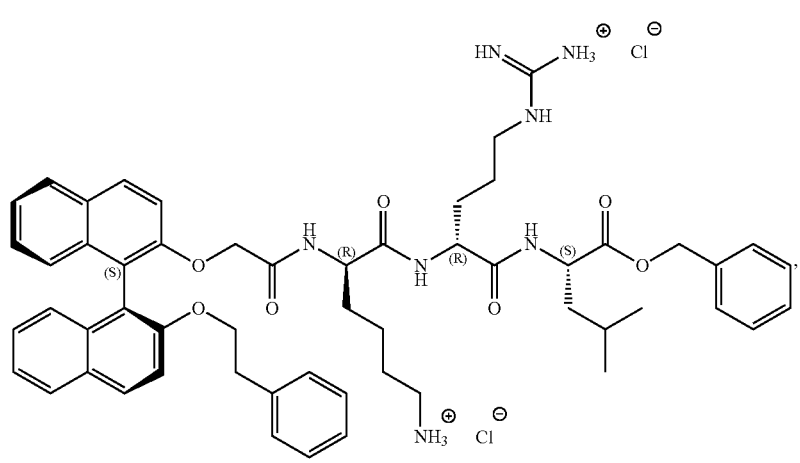

Compound 29

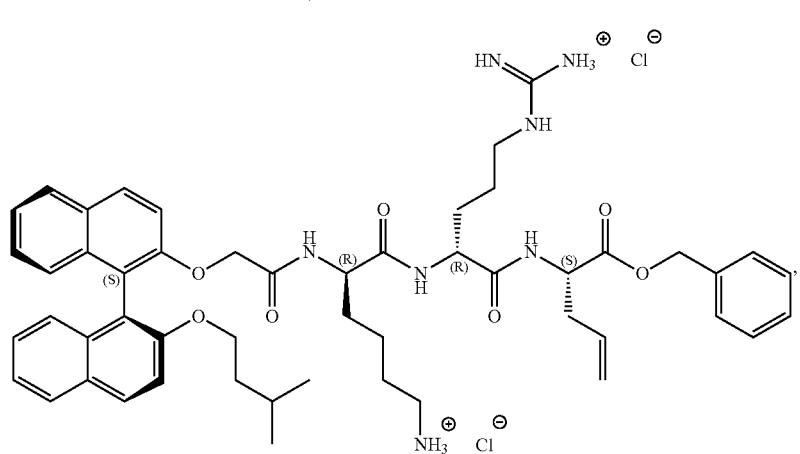

Compound 30

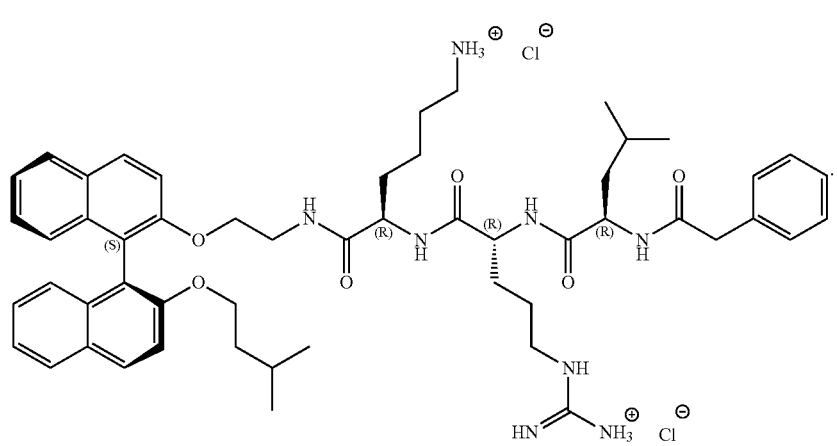

4. A composition comprising a compound of claim 1 or a pharmaceutically acceptable salt thereof, and a pharmaceutically acceptable carrier or adjuvant.

5. A composition comprising a compound of claim 2 or a pharmaceutically acceptable salt thereof, and a pharmaceutically acceptable carrier or adjuvant.

6. A composition comprising a compound of claim 3 or a pharmaceutically acceptable salt thereof, and a pharmaceutically acceptable carrier or adjuvant.

* * * * *